(12) United States Patent
Gallagher et al.

(10) Patent No.: US 8,916,552 B2
(45) Date of Patent: *Dec. 23, 2014

(54) PHARMACEUTICAL COMBINATIONS

(75) Inventors: Neil James Gallagher, Basel (CH);
John Francis Lyons, Cambridge (GB);
Neil Thomas Thompson, Cambridge
(GB); Stephen Murray Yule,
Cambridge (GB); **Christopher William
Murray**, Cambridge (GB)

(73) Assignee: Astex Therapeutics Limited,
Cambridge (GB)

( * ) Notice: Subject to any disclaimer, the term of this patent is extended or adjusted under 35 U.S.C. 154(b) by 1420 days.

This patent is subject to a terminal disclaimer.

(21) Appl. No.: 12/445,180

(22) PCT Filed: Oct. 12, 2007

(86) PCT No.: PCT/GB2007/003879
§ 371 (c)(1),
(2), (4) Date: Mar. 16, 2010

(87) PCT Pub. No.: WO2008/044041
PCT Pub. Date: Apr. 17, 2008

(65) Prior Publication Data
US 2010/0179145 A1    Jul. 15, 2010

Related U.S. Application Data

(60) Provisional application No. 60/829,196, filed on Oct. 12, 2006.

(51) Int. Cl.
| | |
|---|---|
| A61K 31/535 | (2006.01) |
| A61K 31/497 | (2006.01) |
| A01N 43/40 | (2006.01) |
| A61K 31/435 | (2006.01) |
| A61K 31/445 | (2006.01) |
| A01N 43/56 | (2006.01) |
| A61K 31/415 | (2006.01) |
| A01N 43/38 | (2006.01) |
| A61K 31/40 | (2006.01) |
| C07D 209/44 | (2006.01) |
| A61K 45/06 | (2006.01) |
| A61K 31/4035 | (2006.01) |
| A61K 31/403 | (2006.01) |

(52) U.S. Cl.
CPC .............. *A61K 31/403* (2013.01); *A61K 45/06* (2013.01); *A61K 31/4035* (2013.01)
USPC ................... 514/235.2; 514/254.08; 514/277; 514/315; 514/317; 514/326; 514/406; 514/416; 548/470

(58) Field of Classification Search
None
See application file for complete search history.

(56) References Cited

U.S. PATENT DOCUMENTS

| 4,582,909 A | 4/1986 | Butler et al. |
| 4,760,064 A | 7/1988 | Tominaga et al. |
| 5,310,951 A | 5/1994 | Djuric et al. |
| 5,332,735 A | 7/1994 | Rault et al. |
| 6,469,024 B2 | 10/2002 | Li et al. |

(Continued)

FOREIGN PATENT DOCUMENTS

| DE | 19955283 | 5/2001 |
| DE | 10 2004 049 078 | 4/2006 |

(Continued)

OTHER PUBLICATIONS

Hunter et al., "Cdc37: a protein kinase chaperone?" Trends in Cell Biology, vol. 7, Issue 4, Apr. 1997, pp. 157-161.*

(Continued)

*Primary Examiner* — Jeffrey S. Lundgren
*Assistant Examiner* — William Lee
(74) *Attorney, Agent, or Firm* — Vedder Price P.C.; Thomas J. Kowalski; Pooja Varshneya

(57) ABSTRACT

The invention provides combinations comprising (or consisting essentially of) one or more ancillary compound(s) and a compound of the formula (I):

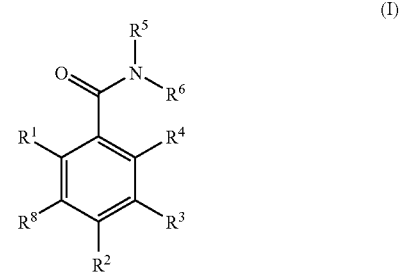

or salts, tautomers, solvates and N-oxides thereof; wherein $R^1$ is hydroxy or hydrogen; $R^2$ is hydroxy; methoxy or hydrogen; provided that at least one of $R^1$ and $R^2$ is hydroxy; $R^3$ is selected from hydrogen; halogen; cyano; optionally substituted $C_{1-5}$ hydrocarbyl and optionally substituted $C_{1-5}$ hydrocarbyloxy; $R^4$ is selected from hydrogen; a group —(O)$_n$—$R^7$ where n is 0 or 1 and $R^7$ is an optionally substituted acyclic $C_{1-5}$ hydrocarbyl group or a monocyclic carbocyclic or heterocyclic group having 3 to 7 ring members; halogen; cyano; hydroxy; amino; and optionally substituted mono- or di-$C_{1-5}$ hydrocarbyl-amino; or $R^3$ and $R^4$ together form a monocyclic carbocyclic or heterocyclic ring of 5 to 7 ring members; and $NR^5R^6$ forms an optionally substituted bicyclic heterocyclic group having 8 to 12 ring members of which up to 5 ring members are heteroatoms selected from oxygen, nitrogen and sulphur. The combinations have activity as Hsp90 and/or glycogen synthase kinase-3 and/or cyclin dependent kinase inhibitors.

4 Claims, 7 Drawing Sheets

(56) References Cited

U.S. PATENT DOCUMENTS

| | | | |
|---|---|---|---|
| 7,208,630 B2 | 4/2007 | Blagg et al. | |
| 7,229,986 B2 | 6/2007 | Ishihara et al. | |
| 7,385,059 B2 * | 6/2008 | Berdini et al. | 546/188 |
| 7,425,633 B2 | 9/2008 | Jiaang | |
| 7,577,114 B2 | 8/2009 | Hsieh | |
| 7,700,625 B2 | 4/2010 | Chessari et al. | |
| 7,754,725 B2 | 7/2010 | Chessari et al. | |
| 8,101,648 B2 | 1/2012 | Chessari | |
| 8,106,057 B2 | 1/2012 | Chessari et al. | |
| 8,277,807 B2 * | 10/2012 | Gallagher et al. | 424/141.1 |
| 8,530,469 B2 * | 9/2013 | Chessari et al. | 514/235.2 |
| 2003/0158177 A1 | 8/2003 | Ishihara et al. | |
| 2003/0203898 A1 | 10/2003 | Haning et al. | |
| 2004/0039038 A1 | 2/2004 | Bernardon et al. | |
| 2004/0253228 A1 | 12/2004 | Srivastava et al. | |
| 2004/0259877 A1 | 12/2004 | Muto et al. | |
| 2005/0037922 A1 | 2/2005 | Bickers et al. | |
| 2006/0019958 A1 | 1/2006 | Muto et al. | |
| 2006/0019961 A1 | 1/2006 | Mahaney | |
| 2006/0084647 A1 | 4/2006 | Wang et al. | |
| 2006/0089495 A1 | 4/2006 | Blagg et al. | |
| 2006/0100257 A1 | 5/2006 | Muto et al. | |
| 2006/0111409 A1 | 5/2006 | Muto et al. | |
| 2006/0122243 A1 | 6/2006 | Muto et al. | |
| 2006/0173188 A1 | 8/2006 | Seki et al. | |
| 2006/0178381 A1 | 8/2006 | Jolidon et al. | |
| 2006/0183902 A1 | 8/2006 | Baxter et al. | |
| 2006/0194843 A1 * | 8/2006 | Berdini et al. | 514/326 |
| 2007/0042997 A1 | 2/2007 | Ital et al. | |
| 2007/0184516 A1 | 8/2007 | Marahiel et al. | |
| 2007/0185059 A1 | 8/2007 | Muto et al. | |
| 2007/0259871 A1 | 11/2007 | Chessari et al. | |
| 2007/0265268 A1 | 11/2007 | Kitamura et al. | |
| 2008/0090880 A1 | 4/2008 | Eggenweiler et al. | |
| 2008/0306054 A1 | 12/2008 | Chessari | |
| 2009/0215742 A1 | 8/2009 | Funk et al. | |
| 2009/0215772 A1 * | 8/2009 | Chessari et al. | 514/235.2 |
| 2010/0152184 A1 | 6/2010 | Congreve et al. | |

FOREIGN PATENT DOCUMENTS

| | | |
|---|---|---|
| EP | 347168 | 12/1989 |
| EP | 353753 | 2/1990 |
| EP | 0474403 | 3/1992 |
| EP | 0486386 | 5/1992 |
| EP | 0500336 | 8/1992 |
| EP | 0722723 | 7/1996 |
| EP | 1283199 | 2/2003 |
| EP | 1352650 | 10/2003 |
| EP | 1510207 | 3/2005 |
| EP | 1510210 | 3/2005 |
| EP | 1512396 | 3/2005 |
| EP | 1514544 | 3/2005 |
| EP | 1642880 | 4/2006 |
| EP | 1704856 | 9/2006 |
| EP | 1852112 | 11/2007 |
| JP | 49010506 | 1/1974 |
| JP | 09194450 | 7/1997 |
| WO | WO 91/08205 | 6/1991 |
| WO | WO 92/17467 | 10/1992 |
| WO | WO 97/26884 | 7/1997 |
| WO | WO 97/35999 | 10/1997 |
| WO | WO 97/36876 | 10/1997 |
| WO | WO 97/39750 | 10/1997 |
| WO | WO 97/47270 | 12/1997 |
| WO | WO 98/40385 | 9/1998 |
| WO | WO 98/45255 | 10/1998 |
| WO | WO 98/47885 | 10/1998 |
| WO | WO 98/50036 | 11/1998 |
| WO | WO 99/21422 | 5/1999 |
| WO | WO 99/29705 | 6/1999 |
| WO | WO 00/59867 | 10/2000 |
| WO | WO 01/36351 | 5/2001 |
| WO | WO 01/60369 | 8/2001 |
| WO | WO 01/87834 | 11/2001 |
| WO | WO 01/87887 | 11/2001 |
| WO | WO 01/90053 | 11/2001 |
| WO | WO 02/12210 | 2/2002 |
| WO | WO 02/18319 | 3/2002 |
| WO | WO 03/051877 | 6/2003 |
| WO | WO 03/053366 | 7/2003 |
| WO | WO 03/055860 | 7/2003 |
| WO | WO 03/086282 | 10/2003 |
| WO | WO 03/103665 | 12/2003 |
| WO | WO 2004/005295 | 1/2004 |
| WO | WO 2004/007501 | 1/2004 |
| WO | WO 2004/035571 | 4/2004 |
| WO | WO 2004/072051 | 8/2004 |
| WO | WO 2004/074283 | 9/2004 |
| WO | WO 2004/096757 | 11/2004 |
| WO | WO 2005/000300 | 1/2005 |
| WO | WO 2005/000839 | 1/2005 |
| WO | WO 2005/007151 | 1/2005 |
| WO | WO 2005/009940 | 2/2005 |
| WO | WO 2005/012256 * | 2/2005 |
| WO | WO 2005/012297 | 2/2005 |
| WO | WO 2005/012541 | 2/2005 |
| WO | WO 2005/016889 | 2/2005 |
| WO | WO 2005/023818 | 3/2005 |
| WO | WO 2005/037214 | 4/2005 |
| WO | WO 2005/047249 | 5/2005 |
| WO | WO 2005/000778 | 6/2005 |
| WO | WO 2005/063222 | 7/2005 |
| WO | WO 2006/015123 | 2/2006 |
| WO | WO 2006/023778 | 3/2006 |
| WO | WO 2006/047740 | 5/2006 |
| WO | WO 2006/051808 | 5/2006 |
| WO | WO 2006/055760 | 5/2006 |
| WO | WO 2006/070195 | 7/2006 |
| WO | WO 2006/077426 * | 7/2006 |
| WO | WO 2006/082001 | 8/2006 |
| WO | WO 2006/088193 | 8/2006 |
| WO | WO 2006/109085 | 10/2006 |
| WO | WO 2006/117669 | 11/2006 |
| WO | WO 2006/125119 | 11/2006 |
| WO | WO 2007/050124 | 5/2007 |
| WO | WO 2008/044027 | 4/2008 |
| WO | WO 2008/044029 | 4/2008 |
| WO | WO 2008/044034 | 4/2008 |
| WO | WO 2008/044041 | 4/2008 |
| WO | WO 2008/044045 | 4/2008 |
| WO | WO 2008/044054 | 4/2008 |
| WO | WO 2008/053319 | 5/2008 |

OTHER PUBLICATIONS

UK Patent Office Search Report for GB 0604111.5, Mar. 6, 2006.
International Search Report for PCT/GB2006/001382, Jan. 9, 2006.
Brown, Michael E. "Chapter 5: Thermoptometry", *Introduction to Thermal Analysis: Techniques and Applications, Second Edition*, Netherlands, 2001.
UK Patent Office Search Report for GB 0507474.5, Jul. 18, 2005.
Bryn et al., Solid State Chemistry of Drugs, 2nd edition, 1999, pp. 233-247.
Chemical Abstracts, Accession No. 81:120448 (Abstract of JP 49010506, Mar. 11, 1994).
Y. Otani et al., "An Evaluation of Amide Group Planarity in 7-azabicyclo[2.2.1]Heptane Amids. Low Amide Bond Barrier in Solution." *J. Amer. Chem. Soc.*, 125(49), 15191-15199, 1983.
Golub et al., Molecular Classification of Cancer: Class Discovery and Class Prediction by Gene Expression Monitoring. Science. Oct. 15, 1999;286(5439):531-7.
Lala et al., Role of Nitric Oxide in Tumor Progression: Lessons From Experimental Tumors. Cancer Metastasis Rev. Mar. 1998:17(1):91-106.
Mahaney et al., Synthesis and Activity of a New Class of Pathway-Selective Estrogen Receptor Ligands: Hydroxybenzoyl-3,4-dihydroquinoxalin-2(1H)-ones. Bioorg Med Chem. May 15, 2006;14(10):3455-66.
Madsen et al., Glucose-6-Phosphatase Catalytic Enzyme Inhibitors: Synthesis and In Vitro Evaluation of Novel 4,5,6,7-tetrahydrothieno[3,2-c]-and [2,3c]pyridines. Bioorg Med Chem. Sep. 2000;8(9):2277-89.

(56) References Cited

OTHER PUBLICATIONS

Vippagunta et al., Adv. Drug Delivery Reviews (2001) vol. 48, p. 3-26.
Dymock, et al., Expert Opin. Ther. Patents (2004) vol. 14, p. 837-847.
Kubinyi et al., 3D QSAR in Drug Design: Ligand-Protein. Interactions and Molecular Similarity, Springer (988) vol. 2-3, 800 pages, TOC and pp. 243-244 provided, (1998).
Bohonowych et al., Journal of Oncology, vol. 2010, pp. 1-17 (2010).
Stephen Neidle Ed,. Cancer Drug Design and Discovery, Elsevier/Academic Press, 2008, pp. 427-431.
Gura, Science, Nov. 7, 1997, vol. 278, No. 5340, pp. 1041-1042.
Roberts et al, JAMA, 292(17): 2130-2140 (2004).
Ju huai-qiang et al: "Synthesis and in vitro anti-HSV-1 activity of a novel Hsp90 inhibitor BJ-B11.", Bioorganic & Medicinal Chemistry Letters Mar. 15, 2011, vol. 21, No. 6, p. 1675-1677.
Galam, et al. Bioog. Med. Chem. (2007) vol. 15, p. 1939-1946.
Wermuth, The Practice of Medicinal Chemistry, 2d ed. (2003) 768 pages, Chapters 9-10 provided.
U.S. Appl. No. 13/271,678, filed Oct. 12, 2011, and, Preliminary Amendment therefor, Oct. 12, 2011.
Abstract: JP 9-221476: Hidenori, et al, Preparation and Formulation of Benzazepine Derivatives and analogs as Pharmaceuticals With Affinity for Vasopressin Receptors, STN Database Accession No. 127.248027, 1997.

\* cited by examiner

PHARMACEUTICAL COMBINATIONS

This application is a National Stage filing under 35 U.S.C. §371 of PCT Application No. PCT/GB2007/003879, filed Oct. 12, 2007, and published as WO 2008/044041 on Apr. 17, 2008, which claims priority to provisional application U.S. Ser. No. 60/829,196, filed Oct. 12, 2006.

TECHNICAL FIELD

This invention relates to combinations of compounds that inhibit or modulate the activity of the heat shock protein Hsp90 with one or more ancillary compounds (e.g. of the formula (0) or (I') as herein defined), to the use of the combinations in the treatment or prophylaxis of disease states or conditions mediated by Hsp90, and to combinations comprising compounds having Hsp90 inhibitory or modulating activity. The combinations of the invention are useful in the prophylaxis or treatment of a range of disease states or conditions mediated by Hsp90 and/or cyclin dependent kinases and/or glycogen synthase kinase-3.

BACKGROUND OF THE INVENTION

In response to cellular stresses including heat, toxins, radiation, infection, inflammation, and oxidants, all cells produce a common set of heat shock proteins (Hsps) (Macario & de Macario 2000). Most heat shock proteins act as molecular chaperones. Chaperones bind and stabilize proteins at intermediate stages of folding and allow proteins to fold to their functional states. Hsp90 is the most abundant cytosolic Hsp under normal conditions. There are two human isoforms of Hsp90, a major inducible form Hsp90α and minor constitutively expressed form Hsp90β and two other closely related chaperones which are restricted in their intracellular location (Endoplasmic reticulum GP96/GRP94; mitochondrial TRAP1). The term HSP90 as used here includes all these analogues unless stated. Hsp90 binds proteins at a late stage of folding and is distinguished from other Hsps in that most of its protein substrates are involved in signal transduction. Hsp90 has a distinct ATP binding site, including a Bergerat fold characteristic of bacterial gyrase, topoisomerases and histidine kinases. It has been shown that ATP bound at the N-terminal pocket of Hsp90 is hydrolysed. This ATPase activity results in a conformational change in Hsp90 that is required to enable conformational changes in the client protein.

A dimerization domain and a second ATP binding site, which may regulate ATPase activity, is found near the c-terminus of Hsp90. Dimerization of HSP90 appears critical for ATP hydrolysis. Activation of Hsp90 is further regulated through interactions with a variety of other chaperone proteins and can be isolated in complex with other chaperones including Hsp70, Hip, Hop, p23, and p50cdc37. Many other co-chaperone proteins have also been demonstrated to bind HSP90. A simplified model has emerged in which ATP binding to the amino terminal pocket alters Hsp90 conformation to allow association with a multichaperone complex. First the client protein is bound to an Hsp70/Hsp40 complex. This complex then associates with Hsp90 via Hop. When ADP is replaced by ATP, the conformation of Hsp90 is altered, Hop and Hsp70 are released and a different set of co-chaperones is recruited including p50cdc37 and p23. ATP hydrolysis results in the release of these co-chaperones and the client protein from the mature complex. Ansamycin antibiotics herbimycin, geldanamycin (GA) and 17-allylamino-17-desmethoxygeldanamycin (17-AAG) are ATP binding site inhibitors that block the binding of ATP and prevent conversion to the mature complex (Grenert et. al., 1997. J Biol Chem., 272: 23834-23850).

Despite Hsp90 being ubiquitously expressed, GA has a higher binding affinity for Hsp90 derived from tumour vs. normal cell lines (Kamal et. al., Nature 2003; 425: 407-410). GA also shows more potent cytotoxic activity in tumour cells and is sequestered at higher concentrations within tumours in xenograft mouse models (Brazidec *J. Med. Chem.* 2004, 47, 3865-3873). Furthermore the ATP-ase activity of Hsp90 is elevated in cancer cells and is an indication of the increased level of stress in these cells. Hsp90 gene amplification has also been reported to occur in the later stages of cancer (Jolly and Morimoto JNCI Vol. 92, No. 19, 1564-1572, 2000).

Increased genetic instability associated with the cancer phenotype leads to an increase in the production of non-native or mutant proteins. The ubiquitin pathway also serves to protect the cell from non-native or misfolded proteins, by targeting these proteins for proteasomal degradation. Mutant proteins are by their nature not native and therefore have the potential to show structural instability and an increased requirement for the chaperone system. (Giannini et al., Mol Cell Biol. 2004; 24(13):5667-76).

There is some evidence that Hsp90 is found primarily within "activated" multichaperone complexes in the tumour cells as opposed to "latent" complexes in normal cells. One component of the multichaperone complex is the cdc37 co-chaperone. Cdc37 binds Hsp90 at the base of the ATP binding site and could affect the off rates of inhibitors bound to Hsp90 in the "activated" state (Roe et. al., *Cell* 116, (2004), pp. 87-98). The client protein bound to the Hsp90-Hsp70 form of the chaperone complex is believed to be more susceptible to ubiquitination and targeting to the proteasome for degradation. E3 ubiquitin ligases have been identified with chaperone interacting motifs and one of these (CHIP) was shown to promote the ubiquitination and degradation of Hsp90 client proteins (Connell et al., 2001. Xu et al., 2002).

Hsp90 Client Proteins

The number of reported Hsp90 client proteins now exceeds 100. Since many of its client proteins are involved in cell signalling proliferation and survival, Hsp90 has received major interest as an oncology target. Two groups of client proteins, cell signalling protein kinases and transcription factors, in particular suggest Hsp90 regulation may have potential benefit as an anticancer therapy.

Hsp90 protein kinase client proteins implicated in cell proliferation and survival include the following:

c-Src

Cellular Src (c-Src) is a receptor tyrosine kinase, required for mitogenesis initiated by multiple growth factor receptors, including the receptors for epidermal growth factor receptor (EGFR), platelet-derived growth factor receptor (PDGFR), colony stimulating factor-1 (CSF-1R), and the basic fibroblast growth factor (bFGFR). C-Src is also overexpressed and activated in many of the same human carcinomas that overexpress EGFR and ErbB2. Src is also required for the maintenance of normal bone homeostasis through its regulation of osteoclast function.

p185erbB2

ErbB2 (Her2/neu) is a receptor tyrosine kinase overexpressed in a variety of malignancies including breast, ovarian, prostate, and gastric cancers. ErbB2 was originally identified as an oncogene and inhibition of Hsp90 results in the poly-ubiquitination and degradation of erbB2.

Polo Mitotic Kinase

Polo-like kinases (Plks) are important regulators of cell cycle progression during M-phase. Plks are involved in the assembly of the mitotic spindle apparatus and in the activation of CDK/cyclin complexes. Plk1 regulates tyrosine dephosphorylation of CDKs through phosphorylation and activation of Cdc25C. CDK1 activation in turn leads to spindle formation and entry into M phase.

Akt (PKB)

Akt is involved in pathways that regulate cell growth by stimulating cell proliferation and suppressing apoptosis. Hsp90 inhibition by ansamycins results in a reduction in the Akt half life through ubiquitination and proteasomal degradation. Binding of cdc37 to Hsp90 is also required for the down-regulation of Akt. Following ansamycin treatment cancer cells arrest in the G2/M phase of the cell cycle 24 hours after treatment and proceed to apoptosis 24-48 hours later. Normal cells also arrest 24 hours after ansamycin treatment, but do not proceed on to apoptosis.

c-Raf, B-RAF, Mek

The RAS-RAF-MEK-ERK-MAP kinase pathway mediates cellular responses to growth signals. RAS is mutated to an oncogenic form in approximately 15% of human cancers. The three RAF genes are serine/threonine kinases that are regulated by binding RAS.

EGFR

The epidermal growth factor receptor (EGFR) is implicated in cell growth, differentiation, proliferation, survival, apoptosis, and migration. Overexpression of EGFR has been found in many different cancers and activating mutations of its kinase domain appear to be pathogenic in a subset of adenocarcinoams of the lung.

Flt3

FMS-like tyrosine kinase 3 (FLT3) is a receptor tyrosine kinase involved in cell proliferation, differentiation and apoptosis. Flt3 activation also leads to the activation of phosphatidylinositol 3-kinase (PI3K) and RAS signal-transduction cascades.

c-Met c-met is a receptor tyrosine kinase which binds hepatocyte growth factor (HGF) and regulates both cell motility and cell growth. c-met is overexpressed in tumours, including thyroid, stomach, pancreatic and colon cancer. HGF is also detected around the tumours, including liver metastases. This suggests that c-met and HGF play an important role in invasion and metastasis.

Cdk1, Cdk2, Cdk4, Cdk6

Cdk1, Cdk2, Cdk4, and Cdk6 drive the cell cycle. The activity of CDKs is regulated by their binding to specific subunits such as cyclins, inhibitory and assembly factors. The substrate specificity and timing of CDK activities is dictated by their interaction with specific cyclins. Cdk4/cyclin D and Cdk6/cyclin D are active in the G1 phase, Cdk2/cyclin E and Cdk2/cyclin A in S phase, and Cdc2/cyclin A and Cdc2/cyclin B in G2/M phase.

Cyclin-dependent kinase type 4 (CDK4), plays a key role in allowing cells to traverse G1 to S-phase transition of the cell cycle and is constitutively activated in many human cancers. The CDK4 activator, cyclin D1, is overexpressed and a CDK4 inhibitor, p16, is deleted in a variety of human tumours.

Cdk1/Cdk2 inhibitors have been developed which reversibly block normal cells in either the G1/S-phase or at the G2/M border. G2/M arrest is generally less well tolerated by the cells and consequently, they undergo apoptotic cell death. Since Hsp90 also is known to affect cell survival pathways this effect may be further amplified with an Hsp90 inhibitor.

Wee-1

The Wee-1 protein kinase carries out the inhibitory phosphorylation of CDC2 on tyrosine 15 (Tyr15).

This is required for activation of the G2-phase checkpoint in response to DNA damage.

Hsp90 transcription factors implicated in cell proliferation and survival include the following:

Mutant p53

P53 is a tumour suppressor protein that causes cell cycle arrest and induces apoptosis. P53 is mutated in approximately half of all cancers. Mutant p53 associates with Hsp90 and is down-regulated in cancer lines treated with Hsp90 inhibitors, while wild type p53 levels were unaffected.

Progesterone Receptor/Estrogen Receptor/Androgen Receptor

Approximately 70% of post-menopausal women who develop breast cancer have tumours that express the estrogen receptor. The first line treatment of these patients is directed at preventing signalling through this pathway and thus inhibiting tumour growth. This can be done by ovarian ablation, treatment with gonadotrophin releasing hormone agonists, aromatase inhibition or treatment with specific agonists which bind to the estrogen receptor but prevent further signalling. Ultimately patients develop resistance to these interventions often as a consequence of crosstalk between the estrogen receptor and growth factor receptors located on the cell membrane. In the unliganded state estrogen receptors are complexed with Hsp90 which facilitates hormone binding. Following binding to the mature receptor Hsp90 complex the liganded receptor can bind to hormone-response elements (HREs) within the regulatory regions of target genes involved in maintaining cell proliferation. Inhibition of Hsp90 initiates proteosomal degradation of the estrogen receptor thus preventing further growth signalling via this pathway. Prostate cancers are hormone-dependent malignancies that respond to therapeutic interventions which reduce circulating levels of testosterone or prevent testosterone binding to the androgen receptor. Although patients initially respond to these treatments most subsequently develop resistance via restoration of signalling via the androgen receptor. Prior to ligand binding the androgen receptor exists in a complex with Hsp90 and other co-chaperones including p23 and immunophilins. This interaction maintains the androgen receptor in a high-affinity ligand binding conformation. Inhibition of Hsp90 leads to proteosomal degradation of the androgen receptor and other co-chaperones which may sensitise the tumour to further hormonal therapies.

Mutated steroid hormone receptors that have arisen for example during anti-hormone therapy and which might be resistant to such therapies are likely to have a greater dependence on HSP90 for their stability and hormone binding function.

Hif-1a

Hypoxia inducible factor-1a (HIF-1a) is a transcription factor that controls the expression of genes which play a role in angiogenesis. HIF-1a is expressed in the majority of metastases and is known to associate with Hsp90. Ansamycin treatment of renal carcinoma cell lines leads to the ubiquitination and proteasomal degradation of HIF-1a.

Hsp90 inhibitors are capable of affecting a large number of targets significant to signal transduction in tumour cell proliferation. Signal transduction inhibitors which regulate the activities of a single target, may not be as efficacious due to signalling pathway redundancy and the rapid development of resistance.

By regulating multiple targets involved in cell signalling and cell proliferation HSP90 inhibitors may prove beneficial in the treatment of a wide spectrum of proliferative disorders.

ZAP70

ZAP-70, a member of the Syk-ZAP-70 protein tyrosine kinase family, is normally expressed in T cells and natural killer cells and has a critical role in the initiation of T-cell signaling. However, it is also expressed aberrantly in approximately 50% of cases of CLL, usually in those cases with unmutated B-cell receptor genes. The mutational status of immunoglobulin heavy-chain variable-region ($IgV_H$) genes in the leukemic cells of chronic lymphocytic leukemia (CLL) is an important prognostic factor. The expression of ZAP-70 in CLL cells correlates with $IgV_H$ mutational status, disease progression, and survival. ZAP-70 positive CLL is more aggressive than ZAP-70 negative CLL indicating that ZAP-70 may be a key driver of malignancy in this disease. ZAP-70 is physically associated with HSP90 in B-CLL lymphoblasts thus the inhibition of Hsp90 may sensitise these cells to existing chemotherapy or monoclonal antibody therapy.

hERG

In the late 1990s a number of drugs, approved by the US FDA, had to be withdrawn from sale in the US when it was discovered they were implicated in deaths caused by heart malfunction. It was subsequently found that a side effect of these drugs was the development of arrhythmias caused by the blocking of hERG channels in heart cells. The hERG channel is one of a family of potassium ion channels the first member of which was identified in the late 1980s in a mutant *Drosophila melanogaster* fruitfly (see Jan, L. Y. and Jan, Y. N. (1990). A Superfamily of Ion Channels. Nature, 345(6277): 672). The biophysical properties of the hERG potassium ion channel are described in Sanguinetti, M. C., Jiang, C., Curran, M. E., and Keating, M. T. (1995). A Mechanistic Link Between an Inherited and an Acquired Cardiac Arrhythmia: HERG encodes the Ikr potassium channel. Cell, 81:299-307, and Trudeau, M. C., Warmke, J. W., Ganetzky, B., and Robertson, G. A. (1995). HERG, a Human Inward Rectifier in the Voltage-Gated Potassium Channel Family. Science, 269:92-95.

The elimination of hERG blocking activity remains an important consideration in the development of any new drug.

Heat Shock Proteins and Antitumour Drug Resistance

It has long been recognized that the native tertiary conformation of any given polypeptide is determined by its primary (amino acid) sequence. However, as explained above, it is now clear that the proper folding of many proteins in vivo requires the assistance of heat-shock proteins (Hsps) acting as molecular chaperones. While this chaperone function is important to normal cellular function under all conditions, it becomes crucial in cells which are stressed (for example by heat, hypoxia or acidosis).

Such conditions typically prevail in tumour cells, which exist in a hostile host environment. The upregulation of Hsps often seen in such cells is therefore likely to represent a mechanism by which malignant cells maintain the integrity of their proteomes under conditions which compromise protein folding. Thus, modulators or inhibitors of stress proteins in general (and Hsp90 in particular) represent a class of chemotherapeutics with the unique ability to inhibit multiple aberrant signaling pathways simultaneously. They can therefore exert antitumour effects whilst eliminating (or reducing the incidence of) resistance relative to other treatment paradigms.

Moreover, therapeutic anticancer interventions of all types necessarily increase the stresses imposed on the target tumour cells. In mitigating the deleterious effects of such stresses, Hsps are directly implicated in resisting the effects of cancer drugs and treatment regimens. Thus, modulators or inhibitors of stress protein function in general (and Hsp90 in particular) represent a class of chemotherapeutics with the potential for:

(i) sensitizing malignant cells to anticancer drugs and/or treatments; (ii) alleviating or reducing the incidence of resistance to anticancer drugs and/or treatments; (iii) reversing resistance to anticancer drugs and/or treatments; (iv) potentiating the activity of anticancer drugs and/or treatments; (v) delaying or preventing the onset of resistance to anticancer drugs and/or treatments.

HSP90 Inhibitors and the Treatment of Hepatitis C and Other Viral Diseases

Infection of a host cell with viral RNA/DNA results in a substantial redirection of cellular protein synthesis towards key viral proteins encoded by the viral nucleic acid. The increased protein synthetic burden places a stress on the cell as a consequence of increased demand for energy and synthetic precursors. Upregulation of heat shock proteins is frequently a consequence of viral infection at least in part due to this stress. One function of the HSP induction may be to assist in the stabilization and folding of the high levels of 'foreign' protein generated in preparation for virus replication. In particular recent work has suggested that HSP90 is required for stable production of functional NS2/3 protease in Hepatitis C (HCV) replicon infected cells. HSP 90 inhibitors have also been demonstrated to block viral replication in in vitro systems. (Nagkagawa, S, Umehara T, Matsuda C, et al Biochem. Biophys. Res Commun. 353 (2007) 882-888; Waxman L, Witney, M et al PNAS 98 (2001) 13931-13935).

Glycogen Synthase Kinase

Glycogen Synthase Kinase-3 (GSK3) is a serine-threonine kinase that occurs as two ubiquitously expressed isoforms in humans (GSK3α & beta GSK3β). GSK3 has been implicated as having roles in embryonic development, protein synthesis, cell proliferation, cell differentiation, microtubule dynamics, cell motility and cellular apoptosis. As such GSK3 has been implicated in the progression of disease states such as diabetes, cancer, Alzheimer's disease, stroke, epilepsy, motor neuron disease and/or head trauma. Phylogenetically GSK3 is most closely related to the cyclin dependent kinases (CDKs).

The consensus peptide substrate sequence recognised by GSK3 is (Ser/Thr)-X-X-X-(pSer/pThr), where X is any amino acid (at positions (n+1), (n+2), (n+3)) and pSer and pThr are phospho-serine and phospho-threonine respectively (n+4). GSK3 phosphorylates the first serine, or threonine, at position (n). Phospho-serine, or phospho-threonine, at the (n+4) position appear necessary for priming GSK3 to give maximal substrate turnover. Phosphorylation of GSK3α at Ser21, or GSK3β at Ser9, leads to inhibition of GSK3. Mutagenesis and peptide competition studies have led to the model that the phosphorylated N-terminus of GSK3 is able to compete with phospho-peptide substrate (S/TXXXpS/pT) via an autoinhibitory mechanism. There are also data suggesting that GSK3α and GSK3β may be subtly regulated by phosphorylation of tyrosines 279 and 216 respectively. Mutation of these residues to a Phe caused a reduction in in vivo kinase activity. The X-ray crystallographic structure of GSK3β has helped to shed light on all aspects of GSK3 activation and regulation.

GSK3 forms part of the mammalian insulin response pathway and is able to phosphorylate, and thereby inactivate, glycogen synthase. Upregulation of glycogen synthase activity, and thereby glycogen synthesis, through inhibition of GSK3, has thus been considered a potential means of combating type II, or non-insulin-dependent diabetes mellitus (NIDDM): a condition in which body tissues become resistant to insulin stimulation. The cellular insulin response in liver, adipose, or muscle tissues, is triggered by insulin binding to an extracellular insulin receptor. This causes the phosphorylation, and subsequent recruitment to the plasma membrane, of the insulin receptor substrate (IRS) proteins. Further phosphorylation of the IRS proteins initiates recruitment of phosphoinositide-3 kinase (PI3K) to the plasma membrane where it is able to liberate the second messenger phosphatidylinosityl 3,4,5-trisphosphate (PIP3). This facilitates co-localisation of 3-phosphoinositide-dependent protein kinase 1 (PDK1) and protein kinase B (PKB or Akt) to the membrane, where PDK1 activates PKB. PKB is able to phosphorylate, and thereby inhibit, GSK3α and/or GSK3β through phosphorylation of Ser9, or ser21, respectively. The inhibition of GSK3 then triggers upregulation of glycogen synthase activity. Therapeutic agents able to inhibit GSK3 may thus be able to induce cellular responses akin to those seen on insulin stimulation. A further in vivo substrate of GSK3 is the eukaryotic protein synthesis initiation factor 2B (eIF2B). eIF2B is inactivated via phosphorylation and is thus able to suppress protein biosynthesis. Inhibition of GSK3, e.g. by inactivation of the "mammalian target of rapamycin" protein (mTOR), can thus upregulate protein biosynthesis. Finally there is some evidence for regulation of GSK3 activity via the mitogen activated protein kinase (MAPK) pathway through phosphorylation of GSK3 by kinases such as mitogen activated protein kinase activated protein kinase 1 (MAPKAP-K1 or RSK). These data suggest that GSK3 activity may be modulated by mitogenic, insulin and/or amino acid stimulii.

It has also been shown that GSK3β is a key component in the vertebrate Wnt signalling pathway. This biochemical pathway has been shown to be critical for normal embryonic development and regulates cell proliferation in normal tissues. GSK3 becomes inhibited in response to Wnt stimulii. This can lead to the de-phosphorylation of GSK3 substrates such as Axin, the adenomatous polyposis coli (APC) gene product and β-catenin. Aberrant regulation of the Wnt pathway has been associated with many cancers. Mutations in APC, and/or β-catenin, are common in colorectal cancer and other tumours. β-catenin has also been shown to be of importance in cell adhesion. Thus GSK3 may also modulate cellular adhesion processes to some degree. Apart from the biochemical pathways already described there are also data implicating GSK3 in the regulation of cell division via phosphorylation of cyclin-D1, in the phosphorylation of transcription factors such as c-Jun, CCAAT/enhancer binding protein α (C/EBPα), c-Myc and/or other substrates such as Nuclear Factor of Activated T-cells (NFATc), Heat Shock Factor-1 (HSF-1) and the c-AMP response element binding protein (CREB). GSK3 also appears to play a role, albeit tissue specific, in regulating cellular apoptosis. The role of GSK3 in modulating cellular apoptosis, via a pro-apoptotic mechanism, may be of particular relevance to medical conditions in which neuronal apoptosis can occur. Examples of these are head trauma, stroke, epilepsy, Alzheimer's and motor neuron diseases, progressive supranuclear palsy, corticobasal degeneration, and Pick's disease. In vitro it has been shown that GSK3 is able to hyper-phosphorylate the microtubule associated protein Tau. Hyperphosphorylation of Tau disrupts its normal binding to microtubules and may also lead to the formation of intra-cellular Tau filaments. It is believed that the progressive accumulation of these filaments leads to eventual neuronal dysfunction and degeneration. Inhibition of Tau phosphorylation, through inhibition of GSK3, may thus provide a means of limiting and/or preventing neurodegenerative effects.

Cyclin Dependent Kinases

The process of eukaryotic cell division may be broadly divided into a series of sequential phases termed G1, S, G2 and M. Correct progression through the various phases of the cell cycle has been shown to be critically dependent upon the spatial and temporal regulation of a family of proteins known as cyclin dependent kinases (cdks) and a diverse set of their cognate protein partners termed cyclins. Cdks are cdc2 (also known as cdk1) homologous serine-threonine kinase proteins that are able to utilise ATP as a substrate in the phosphorylation of diverse polypeptides in a sequence dependent context. Cyclins are a family of proteins characterised by a homology region, containing approximately 100 amino acids, termed the "cyclin box" which is used in binding to, and defining selectivity for, specific cdk partner proteins.

Modulation of the expression levels, degradation rates, and activation levels of various cdks and cyclins throughout the cell cycle leads to the cyclical formation of a series of cdk/cyclin complexes, in which the cdks are enzymatically active. The formation of these complexes controls passage through discrete cell cycle checkpoints and thereby enables the process of cell division to continue. Failure to satisfy the prerequisite biochemical criteria at a given cell cycle checkpoint, i.e. failure to form a required cdk/cyclin complex, can lead to cell cycle arrest and/or cellular apoptosis. Aberrant cellular proliferation, as manifested in cancer, can often be attributed to loss of correct cell cycle control. Inhibition of cdk enzymatic activity therefore provides a means by which abnormally dividing cells can have their division arrested and/or be killed. The diversity of cdks, and cdk complexes, and their critical roles in mediating the cell cycle, provides a broad spectrum of potential therapeutic targets selected on the basis of a defined biochemical rationale.

Progression from the G1 phase to the S phase of the cell cycle is primarily regulated by cdk2, cdk3, cdk4 and cdk6 via association with members of the D and E type cyclins. The D-type cyclins appear instrumental in enabling passage beyond the G1 restriction point, where as the cdk2/cyclin E complex is key to the transition from the G1 to S phase. Subsequent progression through S phase and entry into G2 is thought to require the cdk2/cyclin A complex. Both mitosis, and the G2 to M phase transition which triggers it, are regulated by complexes of cdk1 and the A and B type cyclins.

During G1 phase Retinoblastoma protein (Rb), and related pocket proteins such as p130, are substrates for cdk(2, 4, & 6)/cyclin complexes. Progression through G1 is in part facilitated by hyperphosphorylation, and thus inactivation, of Rb and p130 by the cdk(4/6)/cyclin-D complexes. Hyperphosphorylation of Rb and p130 causes the release of transcription factors, such as E2F, and thus the expression of genes necessary for progression through G1 and for entry into S-phase, such as the gene for cyclin E. Expression of cyclin E facilitates formation of the cdk2/cyclin E complex which amplifies, or maintains, E2F levels via further phosphorylation of Rb. The cdk2/cyclin E complex also phosphorylates other proteins necessary for DNA replication, such as NPAT, which has been implicated in histone biosynthesis. G1 progression and the G1/S transition are also regulated via the mitogen stimulated Myc pathway, which feeds into the cdk2/cyclin E pathway. Cdk2 is also connected to the p53 mediated DNA damage response pathway via p53 regulation of p21 levels. p21 is a protein inhibitor of cdk2/cyclin E and is thus capable of blocking, or delaying, the G1/S transition. The cdk2/cyclin E complex may thus represent a point at which biochemical stimuli from the Rb, Myc and p53 pathways are to some degree integrated. Cdk2 and/or the cdk2/cyclin E complex therefore represent good targets for therapeutics designed at arresting, or recovering control of, the cell cycle in aberrantly dividing cells.

The exact role of cdk3 in the cell cycle is not clear. As yet no cognate cyclin partner has been identified, but a dominant negative form of cdk3 delayed cells in G1, thereby suggesting that cdk3 has a role in regulating the G1/S transition.

Although most cdks have been implicated in regulation of the cell cycle there is evidence that certain members of the cdk family are involved in other biochemical processes. This is exemplified by cdk5 which is necessary for correct neuronal development and which has also been implicated in the phosphorylation of several neuronal proteins such as Tau, NUDE-1, synapsin1, DARPP32 and the Munc18/Syntaxin1A complex. Neuronal cdk5 is conventionally activated by binding to the p35/p39 proteins. Cdk5 activity can, however, be deregulated by the binding of p25, a truncated version of p35. Conversion of p35 to p25, and subsequent deregulation of cdk5 activity, can be induced by ischemia, excitotoxicity, and β-amyloid peptide. Consequently p25 has been implicated in the pathogenesis of neurodegenerative diseases, such as Alzheimer's, and is therefore of interest as a target for therapeutics directed against these diseases.

Cdk7 is a nuclear protein that has cdc2 CAK activity and binds to cyclin H. Cdk7 has been identified as component of the TFIIH transcriptional complex which has RNA polymerase II C-terminal domain (CTD) activity. This has been associated with the regulation of HIV-1 transcription via a Tat-mediated biochemical pathway. Cdk8 binds cyclin C and has been implicated in the phosphorylation of the CTD of RNA polymerase II. Similarly the cdk9/cyclin-T1 complex (P-TEFb complex) has been implicated in elongation control of RNA polymerase II. PTEF-b is also required for activation of transcription of the HIV-1 genome by the viral transactivator Tat through its interaction with cyclin T1. Cdk7, cdk8, cdk9 and the P-TEFb complex are therefore potential targets for anti-viral therapeutics.

At a molecular level mediation of cdk/cyclin complex activity requires a series of stimulatory and inhibitory phosphorylation, or dephosphorylation, events. Cdk phosphorylation is performed by a group of cdk activating kinases (CAKs) and/or kinases such as wee 1, Myt1 and Mik1. Dephosphorylation is performed by phosphatases such as cdc25(a & c), pp2a, or KAP.

Cdk/cyclin complex activity may be further regulated by two families of endogenous cellular proteinaceous inhibitors: the Kip/Cip family, or the INK family. The INK proteins specifically bind cdk4 and cdk6. p16$^{ink4}$ (also known as MTS1) is a potential tumour suppressor gene that is mutated, or deleted, in a large number of primary cancers. The Kip/Cip family contains proteins such as p21$^{Cip1,Waf1}$, p27$^{Kip1}$ and p57$^{kip2}$. As discussed previously p21 is induced by p53 and is able to inactivate the cdk2/cyclin(E/A) and cdk4/cyclin(D1/D2/D3) complexes. Atypically low levels of p27 expression have been observed in breast, colon and prostate cancers. Conversely over expression of cyclin E in solid tumours has been shown to correlate with poor patient prognosis. Over expression of cyclin D1 has been associated with oesophageal, breast, squamous, and non-small cell lung carcinomas.

The pivotal roles of cdks, and their associated proteins, in co-ordinating and driving the cell cycle in proliferating cells have been outlined above. Some of the biochemical pathways in which cdks play a key role have also been described. The development of monotherapies for the treatment of proliferative disorders, such as cancers, using therapeutics targeted generically at cdks, or at specific cdks, is therefore potentially highly desirable. Cdk inhibitors could conceivably also be used to treat other conditions such as viral infections, autoimmune diseases and neuro-degenerative diseases, amongst others. Cdk targeted therapeutics may also provide clinical benefits in the treatment of the previously described diseases when used in combination therapy with either existing, or new, therapeutic agents. Cdk targeted anticancer therapies could potentially have advantages over many current antitumour agents as they would not directly interact with DNA and should therefore reduce the risk of secondary tumour development.

Ancillary Compounds

A wide variety of ancillary compounds find application in the combinations of the invention, as described in detail below.

In one embodiment, the ancillary compounds for use in the combinations of the invention have the general formula (0) below:

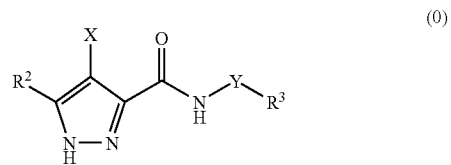

or salts or tautomers or N-oxides or solvates thereof;
wherein
X is a group $R^1$-A-$NR^4$— or a 5- or 6-membered carbocyclic or heterocyclic ring;
A is a bond, $SO_2$, C=O, $NR^g$(C=O) or O(C=O) wherein $R^g$ is hydrogen or $C_{1-4}$ hydrocarbyl optionally substituted by hydroxy or $C_{1-4}$ alkoxy;
Y is a bond or an alkylene chain of 1, 2 or 3 carbon atoms in length;
$R^1$ is hydrogen; a carbocyclic or heterocyclic group having from 3 to 12 ring members; or a $C_{1-8}$ hydrocarbyl group optionally substituted by one or more substituents selected from halogen (e.g. fluorine), hydroxy, $C_{1-4}$ hydrocarbyloxy, amino, mono- or di-$C_{1-4}$ hydrocarbylamino, and carbocyclic or heterocyclic groups having from 3 to 12 ring members, and wherein 1 or 2 of the carbon atoms of the hydrocarbyl group may optionally be replaced by an atom or group selected from O, S, NH, SO, $SO_2$;
$R^2$ is hydrogen; halogen; $C_{1-4}$ alkoxy (e.g. methoxy); or a $C_{1-4}$ hydrocarbyl group optionally substituted by halogen (e.g. fluorine), hydroxyl or $C_{1-4}$ alkoxy (e.g. methoxy);
$R^3$ is selected from hydrogen and carbocyclic and heterocyclic groups having from 3 to 12 ring members; and
$R^4$ is hydrogen or a $C_{1-4}$ hydrocarbyl group optionally substituted by halogen (e.g. fluorine), hydroxyl or $C_{1-4}$ alkoxy (e.g. methoxy);
wherein the compounds correspond to formula (0) in WO 2005/012256 (PCT/GB2004/003179) and various possible substituents, sub-groups, embodiments and examples thereof as therein defined.

In another embodiment, the ancillary compounds for use in the combinations of the invention have the general formula (I') below:

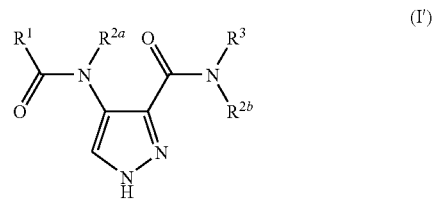

In formula (I) of WO 2006/077416 (i.e. formula (I') herein):
$R^1$ is 2,6-dichlorophenyl;
$R^{2a}$ and $R^{2b}$ are both hydrogen;
and $R^3$ is a group:

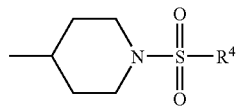

where $R^4$ is $C_{1-4}$ alkyl.

The compounds of formula (I') correspond to formula (I) in WO 2006/077416 (the contents of which are incorporated herein by reference) or salts, tautomers, solvates and N-oxides thereof and various possible substituents, sub-groups, embodiments and examples thereof as therein defined.

A preferred compound within formula (I) of WO 2006/077416 (i.e. formula (I') herein) is 4-(2,6-dichloro-benzoylamino)-1H-pyrazole-3-carboxylic acid (1-methanesulphonyl-piperidin-4-yl)-amide.

Auxiliary Compounds

A wide variety of optional auxiliary compounds may be further combined with the combinations of the invention, as described in detail below. The optional auxiliary compounds may be anti-cancer agents.

WO 99/29705 (Glycomed et al) disclose a class of glycomimetic compounds having a number of possible uses including the treatment of cancer. One compound specifically disclosed in WO 99/29705 is the compound 2-(2-hydroxybenzoyl)-1,2,3,4-tetrahydro-isoquinoline-3-carboxylic acid.

Our earlier International application PCT/GB2006/001382 discloses hydroxybenzoic acid amides as Hsp90 inhibitors.

SUMMARY OF THE INVENTION

Figure 1:
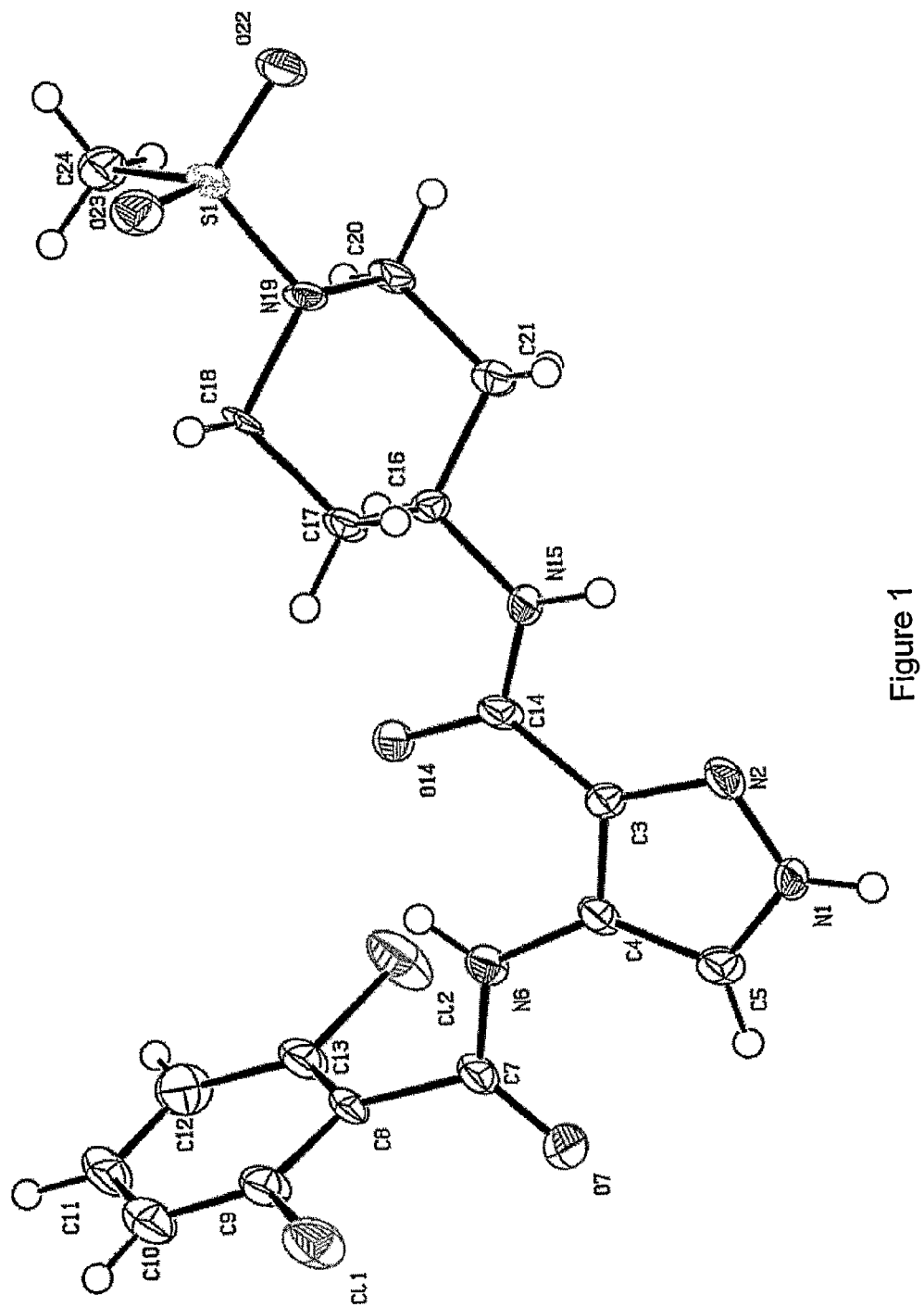
FIG. 1 shows the crystal structure of the methanesulfonic acid salt of 4-(2,6-dichlorobenzoylamino)-1H-pyrazole-3-carboxylic acid piperidin-4-ylamide mesylate

Combinations according to the invention include a compound of formula (I), (II), (III), (IV), (V), (VI), (VIa), (VII), (VIIa) or (VIIb) (including acid addition salts, particularly the L-lactate, and crystalline forms thereof) or any sub-groups or examples thereof as defined herein (and in particular compounds of formula (VI)).

The invention provides combinations of one or more ancillary compounds with compounds that have Hsp90 inhibiting or modulating activity and which will be useful in preventing or treating disease states or conditions mediated by Hsp90 and/or glycogen synthase kinase-3 and/or cyclin dependent kinases.

Thus, for example, the combinations of the invention will be useful in alleviating or reducing the incidence of cancer.

In a first aspect, the invention provides a combination comprising (or consisting essentially of) one or more ancillary compounds and a compound of the formula (I):

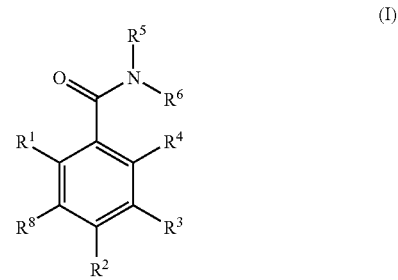

(I)

or salts, tautomers, solvates and N-oxides thereof; wherein:

$R^1$ is hydroxy or hydrogen;

$R^2$ is hydroxy; methoxy or hydrogen; provided that at least one of $R^1$ and $R^2$ is hydroxy;

$R^3$ is selected from hydrogen; halogen; cyano; $C_{1-5}$ hydrocarbyl and $C_{1-5}$ hydrocarbyloxy; wherein the $C_{1-5}$ hydrocarbyl and $C_{1-5}$ hydrocarbyloxy moieties are each optionally substituted by one or more substituents selected from hydroxy, halogen, $C_{1-2}$ alkoxy, amino, mono- and di-$C_{1-2}$ alkylamino, and aryl and heteroaryl groups of 5 to 12 ring members;

$R^4$ is selected from hydrogen; a group —$(O)_n$—$R^7$ where n is 0 or 1 and $R^7$ is an acyclic $C_{1-5}$ hydrocarbyl group or a monocyclic carbocyclic or heterocyclic group having 3 to 7 ring members; halogen; cyano; hydroxy; amino; and mono- or di-$C_{1-5}$ hydrocarbyl-amino, wherein the acyclic $C_{1-5}$ hydrocarbyl group and the mono and di-$C_{1-5}$ hydrocarbylamino moieties in each instance are optionally substituted by one or more substituents selected from hydroxy, halogen, $C_{1-2}$ alkoxy, amino, mono- and di-$C_{1-2}$ alkylamino, and aryl and heteroaryl groups of 5 to 12 ring members;

or $R^3$ and $R^4$ together form a monocyclic carbocyclic or heterocyclic ring of 5 to 7 ring members;

$R^5$ and $R^6$ together with the nitrogen atom to which they are attached form a bicyclic heterocyclic group having 8 to 12 ring members of which up to 5 ring members are heteroatoms selected from oxygen, nitrogen and sulphur; wherein the bicyclic heterocyclic group is optionally substituted by one or more substituents $R^{10}$;

$R^8$ is selected from hydrogen and fluorine; and $R^{10}$ is selected from:
halogen;
hydroxy;
trifluoromethyl;
cyano;
nitro;
carboxy;
amino;

mono- or di-$C_{1-4}$ hydrocarbylamino;
carbocyclic and heterocyclic groups having from 3 to 12 ring members; and
a group $R^a$-$R^b$; wherein:
$R^a$ is a bond, O, CO, $X^1C(X^2)$, $C(X^2)X^1$, $X^1C(X^2)X^1$, S, SO, $SO_2$, $NR^c$, $SO_2NR^c$ or $NR^cSO_2$; and
$R^b$ is selected from hydrogen; carbocyclic and heterocyclic groups having from 3 to 12 ring members; and $C_{1-12}$ hydrocarbyl (such as $C_{1-10}$ hydrocarbyl) optionally substituted by one or more substituents selected from hydroxy, oxo, halogen, cyano, nitro, carboxy, amino, mono- or di-$C_{1-8}$ non-aromatic hydrocarbylamino (e.g. mono- or di-$C_{1-4}$ hydrocarbylamino), and carbocyclic and heterocyclic groups having from 3 to 12 ring members and wherein one or more carbon atoms of the $C_{1-12}$ hydrocarbyl group (or $C_{1-10}$ hydrocarbyl group) may optionally be replaced by O, S, SO, $SO_2$, $NR^c$, $X^1C(X^2)$, $C(X^2)X^1$ or $X^1C(X^2)X^1$;
$R^c$ is selected from $R^b$, hydrogen and $C_{1-4}$ hydrocarbyl; and $X^1$ is O, S or $NR^c$ and $X^2$ is =O, =S or =$NR^c$;
optionally excluding the compound 2-(2-hydroxy-benzoyl)-1,2,3,4-tetrahydro-isoquinoline-3-carboxylic acid.

The invention also provides inter alia:

A combination comprising (or consisting essentially of) one or more ancillary compounds and a compound of the formula (I), (II), (III), (IV), (V), (VI), (Via), (VII), (VIIa) or (VIIb) or any sub-groups or examples thereof as defined herein for use in the prophylaxis or treatment of a disease state or condition mediated by Hsp90 and/or glycogen synthase kinase-3 and/or cyclin dependent kinases.

The use of a combination comprising (or consisting essentially of) one or more ancillary compounds and a compound of the formula (I), (II), (III), (IV), (V), (VI), (VIa), (VII), (VIIa) or (VIIb) or any sub-groups or examples thereof as defined herein for the manufacture of a medicament for the prophylaxis or treatment of a disease state or condition mediated by Hsp90 and/or glycogen synthase kinase-3 and/or cyclin dependent kinases.

A method for the prophylaxis or treatment of a disease state or condition mediated by Hsp90 and/or glycogen synthase kinase-3 and/or cyclin dependent kinases, which method comprises administering to a subject in need thereof a combination comprising (or consisting essentially of) one or more ancillary compounds and a compound of the formula (I), (II), (III), (IV), (V), (VI), (Via), (VII), (VIIa) or (VIIb) or any sub-groups or examples thereof as defined herein.

A combination comprising (or consisting essentially of) one or more ancillary compounds and a compound of the formula (I), (II), (III), (IV), (V), (VI), (VIa), (VII), (VIIa) or (VIIb) or any sub-groups or examples thereof as defined herein for use in alleviating or reducing the incidence of a disease state or condition mediated by Hsp90 and/or glycogen synthase kinase-3 and/or cyclin dependent kinases.

The use of a combination comprising (or consisting essentially of) one or more ancillary compounds and a compound of the formula (I), (II), (III), (IV), (V), (VI), (VIa), (VII), (VIIa) or (VIIb) or any sub-groups or examples thereof as defined herein for the manufacture of a medicament for alleviating or reducing the incidence of a disease state or condition mediated by Hsp90 and/or glycogen synthase kinase-3 and/or cyclin dependent kinases.

A method for alleviating or reducing the incidence of a disease state or condition mediated by Hsp90 and/or glycogen synthase kinase-3 and/or cyclin dependent kinases, which method comprises administering to a subject in need thereof a combination comprising (or consisting essentially of) one or more ancillary compounds and a compound of the formula (I), (II), (III), (IV), (V), (VI), (VIa), (VII), (VIIa) or (VIIb) or any sub-groups or examples thereof as defined herein.

A combination comprising (or consisting essentially of) one or more ancillary compounds and a compound of the formula (I), (II), (III), (IV), (V), (VI), (VIa), (VII), (VIIa) or (VIIb) or any sub-groups or examples thereof as defined herein for use in treating a disease or condition comprising or arising from abnormal cell growth in a mammal.

The use of a combination comprising (or consisting essentially of) one or more ancillary compounds and a compound of the formula (I), (II), (III), (IV), (V), (VI), (VIa), (VII), (VIIa) or (VIIb) or any sub-groups or examples thereof as defined herein for the manufacture of a medicament for treating a disease or condition comprising or arising from abnormal cell growth in a mammal.

A method for treating a disease or condition comprising or arising from abnormal cell growth in a mammal, which method comprises administering to the mammal a combination comprising (or consisting essentially of) one or more ancillary compounds and a compound of the formula (I), (II), (III), (IV), (V), (VI), (VIa), (VII), (VIIa) or (VIIb) or any sub-groups or examples thereof as defined herein in an amount effective in inhibiting abnormal cell growth.

A combination comprising (or consisting essentially of) one or more ancillary compounds and a compound of the formula (I), (II), (III), (IV), (V), (VI), (VIa), (VII), (VIIa) or (VIIb) or any sub-groups or examples thereof as defined herein for use in alleviating or reducing the incidence of a disease or condition comprising or arising from abnormal cell growth in a mammal.

The use of a combination comprising (or consisting essentially of) one or more ancillary compounds and a compound of the formula (I), (II), (III), (IV), (V), (VI), (VIa), (VII), (VIIa) or (VIIb) or any sub-groups or examples thereof as defined herein for the manufacture of a medicament for alleviating or reducing the incidence of a disease or condition comprising or arising from abnormal cell growth in a mammal.

A method for alleviating or reducing the incidence of a disease or condition comprising or arising from abnormal cell growth in a mammal, which method comprises administering to the mammal a combination comprising (or consisting essentially of) one or more ancillary compounds and a compound of the formula (I), (II), (III), (IV), (V), (VI), (VIa), (VII), (VIIa) or (VIIb) or any sub-groups or examples thereof as defined herein in an amount effective in inhibiting abnormal cell growth.

A method for treating a disease or condition comprising or arising from abnormal cell growth in a mammal, the method comprising administering to the mammal a combination comprising (or consisting essentially of) one or more ancillary compounds and a compound of the formula (I), (II), (III), (IV), (V), (VI), (VIa), (VII), (VIIa) or (VIIb) or any sub-groups or examples thereof as defined herein in an amount effective to inhibit Hsp90 and/or glycogen synthase kinase-3 and/or cyclin dependent kinase activity.

A method for alleviating or reducing the incidence of a disease or condition comprising or arising from abnormal cell growth in a mammal, the method comprising administering to the mammal a combination comprising (or consisting essentially of) one or more ancillary compounds and a compound of the formula (I), (II), (III), (IV), (V), (VI), (VIa), (VII), (VIIa) or (VIIb) or any sub-groups or examples thereof as defined herein in an amount effective to inhibit Hsp90 and/or glycogen synthase kinase-3 and/or cyclin dependent kinase activity.

A combination comprising (or consisting essentially of) one or more ancillary compounds and a compound of the formula (I), (II), (III), (IV), (V), (VI), (VIa), (VII), (VIIa) or (VIIb) or any sub-groups or examples thereof as defined herein for use as an inhibitor of Hsp90 and/or glycogen synthase kinase-3 and/or cyclin dependent kinase.

A method of inhibiting Hsp90 and/or glycogen synthase kinase-3 and/or cyclin dependent kinase, which method comprises contacting the Hsp90 and/or glycogen synthase kinase-3 and/or cyclin dependent kinase with an Hsp90 and/or glycogen synthase kinase-3 and/or cyclin dependent kinase-inhibiting combination comprising (or consisting essentially of) one or more ancillary compounds and a compound of the formula (I), (II), (III), (IV), (V), (VI), (VIa), (VII), (VIIa) or (VIIb) or any sub-groups or examples thereof as defined herein.

A combination comprising (or consisting essentially of) one or more ancillary compounds and a compound of the formula (I), (II), (III), (IV), (V), (VI), (VIa), (VII), (VIIa) or (VIIb) or any sub-groups or examples thereof as defined herein for use in modulating a cellular process (for example cell division) by inhibiting the activity of Hsp90 and/or glycogen synthase kinase-3 and/or cyclin dependent kinase.

A method of modulating a cellular process (for example cell division) by inhibiting the activity of Hsp90 and/or glycogen synthase kinase-3 and/or cyclin dependent kinase using a combination comprising (or consisting essentially of) one or more ancillary compounds and a compound of the formula (I), (II), (III), (IV), (V), (VI), (VIa), (VII), (VIIa) or (VIIb) or any sub-groups or examples thereof as defined herein.

A combination comprising (or consisting essentially of) one or more ancillary compounds and a compound of the formula (I), (II), (III), (IV), (V), (VI), (VIa), (VII), (VIIa) or (VIIb) or any sub-groups or examples thereof as defined herein for use in the prophylaxis or treatment of a disease state as described herein.

The use of a combination comprising (or consisting essentially of) one or more ancillary compounds and a compound of the formula (I), (II), (III), (IV), (V), (VI), (VIa), (VII), (VIIa) or (VIIb) or any sub-groups or examples thereof as defined herein for the manufacture of a medicament, wherein the medicament is for any one or more of the uses defined herein.

A pharmaceutical composition comprising a combination comprising (or consisting essentially of) one or more ancillary compounds and a compound of the formula (I), (II), (III), (IV), (V), (VI), (VIa), (VII), (VIIa) or (VIIb) or any sub-groups or examples thereof as defined herein and a pharmaceutically acceptable carrier.

A pharmaceutical composition comprising a combination comprising (or consisting essentially of) one or more ancillary compounds and a compound of the formula (I), (II), (III), (IV), (V), (VI), (VIa), (VII), (VIIa) or (VIIb) or any sub-groups or examples thereof as defined herein and a pharmaceutically acceptable carrier in a form suitable for oral administration.

A pharmaceutical composition comprising a combination comprising (or consisting essentially of) one or more ancillary compounds and a compound of the formula (I), (II), (III), (IV), (V), (VI), (VIa), (VII), (VIIa) or (VIIb) or any sub-groups or examples thereof as defined herein and a pharmaceutically acceptable carrier in a form suitable for parenteral administration, for example by intravenous (i.v.) administration.

A pharmaceutical composition comprising combination comprising (or consisting essentially of) one or more ancillary compounds and a compound of the formula (I), (II), (III), (IV), (V), (VI), (VIa), (VII), (VIIa) or (VIIb) or any sub-groups or examples thereof as defined herein and a pharmaceutically acceptable carrier in a form suitable for intravenous (i.v.) administration by injection or infusion.

A combination comprising (or consisting essentially of) one or more ancillary compounds and a compound of the formula (I), (II), (III), (IV), (V), (VI), (VIa), (VII), (VIIa) or (VIIb) or any sub-groups or examples thereof as defined herein for use in medicine.

A combination comprising (or consisting essentially of) one or more ancillary compounds and a compound as defined herein for any of the uses and methods set forth above, and as described elsewhere herein.

A combination comprising (or consisting essentially of) one or more ancillary compounds and a compound of the formula (I), (II), (III), (IV), (V), (VI), (VIa), (VII), (VIIa) or (VIIb) or any sub-groups or examples thereof as defined herein for use in treatment or prophylaxis of a disease state or condition in a patient who has been screened and has been determined as suffering from, or being at risk of suffering from, a disease or condition which would be susceptible to treatment with a compound having activity against Hsp90 and/or glycogen synthase kinase-3 and/or cyclin dependent kinase.

The use of a combination comprising (or consisting essentially of) one or more ancillary compounds and a compound of the formula (I), (II), (III), (IV), (V), (VI), (VIa), (VII), (VIIa) or (VIIb) or any sub-groups or examples thereof as defined herein for the manufacture of a medicament for the treatment or prophylaxis of a disease state or condition in a patient who has been screened and has been determined as suffering from, or being at risk of suffering from, a disease or condition which would be susceptible to treatment with a compound having activity against Hsp90 and/or glycogen synthase kinase-3 and/or cyclin dependent kinase.

A method for the diagnosis and treatment of a disease state or condition mediated by Hsp90 and/or glycogen synthase kinase-3 and/or cyclin dependent kinase, which method comprises (i) screening a patient to determine whether a disease or condition from which the patient is or may be suffering is one which would be susceptible to treatment with a compound having activity against Hsp90 and/or glycogen synthase kinase-3 and/or cyclin dependent kinase; and (ii) where it is indicated that the disease or condition from which the patient is thus susceptible, thereafter administering to the patient a combination comprising (or consisting essentially of) one or more ancillary compounds and a compound of the formula (I), (II), (III), (IV), (V), (VI), (VIa), (VII), (VIIa) or (VIIb) or any sub-groups or examples thereof as defined herein.

A combination comprising (or consisting essentially of) one or more ancillary compounds and a compound of the formula (I), (II), (III), (IV), (V), (VI), (VIa), (VII), (VIIa) or (VIIb) or any sub-groups or examples thereof as defined herein wherein the ancillary compound and compound of formula (I), (II), (III), (IV), (V), (VI), (VIa), (VII), (VIIa) or (VIIb) or any sub-groups or examples thereof as defined herein are physically associated.

A combination comprising (or consisting essentially of) one or more ancillary compounds and a compound of the formula (I), (II), (III), (IV), (V), (VI), (VIa), (VII), (VIIa) or (VIIb) or any sub-groups or examples thereof as defined herein wherein the ancillary compound and compound of formula (I), (II), (III), (IV), (V), (VI), (VIa), (VII), (VIIa) or (VIIb) or any sub-groups or examples thereof as defined herein are non-physically associated.

A combination comprising (or consisting essentially of) one or more ancillary compounds and a compound of the formula (I), (II), (III), (IV), (V), (VI), (VIa), (VII), (VIIa) or (VIIb) or any sub-groups or examples thereof as defined herein in the form of a pharmaceutical pack, kit or patient pack.

A compound of the formula (I), (II), (III), (IV), (V), (VI), (VIa), (VII), (VIIa) or (VIIb) or any sub-groups or examples thereof as defined herein for use in the prophylaxis or treatment of a disease state or condition mediated by Hsp90 and/or glycogen synthase kinase-3 and/or cyclin dependent kinase in a subject undergoing treatment with one or more ancillary compounds.

The use of a compound of the formula (I), (II), (III), (IV), (V), (VI), (VIa), (VII), (VIIa) or (VIIb) or any sub-groups or examples thereof as defined herein for the manufacture of a medicament for the prophylaxis or treatment of a disease state or condition mediated by Hsp90 and/or glycogen synthase kinase-3 and/or cyclin dependent kinase in a subject undergoing treatment with one or more ancillary compounds.

A method for the prophylaxis or treatment of a disease state or condition mediated by Hsp90 and/or glycogen synthase kinase-3 and/or cyclin dependent kinase, which method comprises administering to a subject in need thereof a compound of the formula (I), (II), (III), (IV), (V), (VI), (VIa), (VII), (VIIa) or (VIIb) or any sub-groups or examples thereof as defined herein, wherein the subject is undergoing treatment with one or more ancillary compounds.

A compound of the formula (I), (II), (III), (IV), (V), (VI), (VIa), (VII), (VIIa) or (VIIb) or any sub-groups or examples thereof as defined herein for use in alleviating or reducing the incidence of a disease state or condition mediated by Hsp90 and/or glycogen synthase kinase-3 and/or cyclin dependent kinase in a subject undergoing treatment with one or more ancillary compounds.

The use of a compound of the formula (I), (II), (III), (IV), (V), (VI), (VIa), (VII), (VIIa) or (VIIb) or any sub-groups or examples thereof as defined herein for the manufacture of a medicament for alleviating or reducing the incidence of a disease state or condition mediated by Hsp90 and/or glycogen synthase kinase-3 and/or cyclin dependent kinase in a subject undergoing treatment with one or more ancillary compounds.

A method for alleviating or reducing the incidence of a disease state or condition mediated by Hsp90 and/or glycogen synthase kinase-3 and/or cyclin dependent kinase, which method comprises administering to a subject in need thereof a compound of the formula (I), (II), (III), (IV), (V), (VI), (VIa), (VII), (VIIa) or (VIIb) or any sub-groups or examples thereof as defined herein, wherein the subject is undergoing treatment with one or more ancillary compounds.

A compound of the formula (I), (II), (III), (IV), (V), (VI), (VIa), (VII), (VIIa) or (VIIb) or any sub-groups or examples thereof as defined herein for use in treating a disease or condition comprising or arising from abnormal cell growth in a mammal in a subject undergoing treatment with one or more ancillary compounds.

The use of a compound of the formula (I), (II), (III), (IV), (V), (VI), (VIa), (VII), (VIIa) or (VIIb) or any sub-groups or examples thereof as defined herein for the manufacture of a medicament for treating a disease or condition comprising or arising from abnormal cell growth in a mammal in a subject undergoing treatment with one or more ancillary compounds.

A method for treating a disease or condition comprising or arising from abnormal cell growth in a mammal, which method comprises administering to the mammal a compound of the formula (I), (II), (III), (IV), (V), (VI), (VIa), (VII), (VIIa) or (VIIb) or any sub-groups or examples thereof as defined herein in an amount effective in inhibiting abnormal cell growth, wherein the mammal is undergoing treatment with one or more ancillary compounds.

A compound of the formula (I), (II), (III), (IV), (V), (VI), (VIa), (VII), (VIIa) or (VIIb) or any sub-groups or examples thereof as defined herein for use in alleviating or reducing the incidence of a disease or condition comprising or arising from abnormal cell growth in a mammal in a subject undergoing treatment with one or more ancillary compounds.

The use of a compound of the formula (I), (II), (III), (IV), (V), (VI), (VIa), (VII), (VIIa) or (VIIb) or any sub-groups or examples thereof as defined herein for the manufacture of a medicament for alleviating or reducing the incidence of a disease or condition comprising or arising from abnormal cell growth in a mammal in a subject undergoing treatment with one or more ancillary compounds.

A method for alleviating or reducing the incidence of a disease or condition comprising or arising from abnormal cell growth in a mammal, which method comprises administering to the mammal a compound of the formula (I), (II), (III), (IV), (V), (VI), (VIa), (VII), (VIIa) or (VIIb) or any sub-groups or examples thereof as defined herein in an amount effective in inhibiting abnormal cell growth, wherein the mammal is undergoing treatment with one or more ancillary compounds.

A method for treating a disease or condition comprising or arising from abnormal cell growth in a mammal, the method comprising administering to the mammal a compound of the formula (I), (II), (III), (IV), (V), (VI), (VIa), (VII), (VIIa) or (VIIb) or any sub-groups or examples thereof as defined herein in an amount effective to inhibit Hsp90 and/or glycogen synthase kinase-3 and/or cyclin dependent kinase activity, wherein the mammal is undergoing treatment with one or more ancillary compounds.

A method for alleviating or reducing the incidence of a disease or condition comprising or arising from abnormal cell growth in a mammal, the method comprising administering to the mammal a compound of the formula (I), (II), (III), (IV), (V), (VI), (VIa), (VII), (VIIa) or (VIIb) or any sub-groups or examples thereof as defined herein in an amount effective to inhibit Hsp90 and/or glycogen synthase kinase-3 and/or cyclin dependent kinase activity, wherein the mammal is undergoing treatment with one or more ancillary compounds.

A compound of the formula (I), (II), (III), (IV), (V), (VI), (VIa), (VII), (VIIa) or (VIIb) or any sub-groups or examples thereof as defined herein for use as an inhibitor of Hsp90 and/or glycogen synthase kinase-3 and/or cyclin dependent kinase in a subject undergoing treatment with one or more ancillary compounds.

A method of inhibiting Hsp90 in a subject undergoing treatment with one or more ancillary compounds, which method comprises contacting the Hsp90 with an Hsp90-inhibiting compound of the formula (I), (II), (III), (IV), (V), (VI), (VIa), (VII), (VIIa) or (VIIb) or any sub-groups or examples thereof as defined herein.

A compound of the formula (I), (II), (III), (IV), (V), (VI), (VIa), (VII), (VIIa) or (VIIb) or any sub-groups or examples thereof as defined herein for use in modulating a cellular process (for example cell division) by inhibiting the activity of Hsp90 in a subject undergoing treatment with one or more ancillary compounds.

A method of modulating a cellular process (for example cell division) in a subject undergoing treatment with one or more ancillary compounds by inhibiting the activity of Hsp90 using a compound of the formula (I), (II), (III), (IV), (V), (VI), (VIa), (VII), (VIIa) or (VIIb) or any sub-groups or examples thereof as defined herein.

A compound of the formula (I), (II), (III), (IV), (V), (VI), (VIa), (VII), (VIIa) or (VIIb) or any sub-groups or examples thereof as defined herein for use in the prophylaxis or treatment of a disease state as described herein in a subject undergoing treatment with one or more ancillary compounds.

The use of a compound of the formula (I), (II), (III), (IV), (V), (VI), (VIa), (VII), (VIIa) or (VIIb) or any sub-groups or examples thereof as defined herein for the manufacture of a medicament, wherein the medicament is for any one or more of the uses defined herein in a subject undergoing treatment with one or more ancillary compounds.

A compound of the formula (I), (II), (III), (IV), (V), (VI), (VIa), (VII), (VIIa) or (VIIb) or any sub-groups or examples thereof as defined herein for use in treatment or prophylaxis of a disease state or condition in a patient who has been screened and has been determined as suffering from, or being at risk of suffering from, a disease or condition which would be susceptible to treatment with a compound having activity against Hsp90 and which patient is undergoing treatment with one or more ancillary compounds.

The use of a compound of the formula (I), (II), (III), (IV), (V), (VI), (VIa), (VII), (VIIa) or (VIIb) or any sub-groups or examples thereof as defined herein for the manufacture of a medicament for the treatment or prophylaxis of a disease state or condition in a patient who has been screened and has been determined as suffering from, or being at risk of suffering from, a disease or condition which would be susceptible to treatment with a compound having activity against Hsp90 and which patient is undergoing treatment with one or more ancillary compounds.

A method for the diagnosis and treatment of a disease state or condition mediated by Hsp90, which method comprises (i) screening a patient to determine whether a disease or condition from which the patient is or may be suffering is one which would be susceptible to treatment with a compound having activity against Hsp90; and (ii) where it is indicated that the disease or condition from which the patient is thus susceptible, thereafter administering to the patient a compound of the formula (I), (II), (III), (IV), (V), (VI), (VIa), (VII), (VIIa) or (VIIb) or any sub-groups or examples thereof as defined herein, wherein the patient is undergoing treatment with one or more ancillary compounds.

One or more ancillary compounds (e.g. one or more ancillary compounds selected from any of the ancillary compounds disclosed herein) for use in combination therapy with a compound of the formula (I), (II), (III), (IV), (V), (VI), (VIa), (VII), (VIIa) or (VIIb) or any sub-groups or examples thereof as defined herein.

A compound of the formula (I), (II), (III), (IV), (V), (VI), (VIa), (VII), (VIIa) or (VIIb) or any sub-groups or examples thereof as defined herein for use in combination therapy with one or more ancillary compounds (e.g. one or more ancillary compounds selected from any of the ancillary compounds disclosed herein).

Use of one or more ancillary compounds (e.g. one or more ancillary compounds selected from any of the ancillary compounds disclosed herein) for the manufacture of a medicament for use in the treatment or prophylaxis of a patient undergoing treatment with a compound of the formula (I), (II), (III), (IV), (V), (VI), (VIa), (VII), (VIIa) or (VIIb) or any sub-groups or examples thereof as defined herein.

Use of a compound of the formula (I), (II), (III), (IV), (V), (VI), (VIa), (VII), (VIIa) or (VIIb) or any sub-groups or examples thereof as defined herein for the manufacture of a medicament for use in the treatment or prophylaxis of a patient undergoing treatment with one or more ancillary compounds (e.g. one or more ancillary compounds selected from any of the ancillary compounds disclosed herein).

A method for the treatment of a cancer in a warm-blooded animal such as a human, which comprises administering to said animal an effective amount of one or more ancillary compounds (e.g. one or more ancillary compounds selected from any of the ancillary compounds disclosed herein) sequentially e.g. before or after, or simultaneously with an effective amount of a compound of the formula (I), (II), (III), (IV), (V), (VI), (VIa), (VII), (VIIa) or (VIIb) or any sub-groups or examples thereof as defined herein.

A method of combination cancer therapy in a mammal comprising administering a therapeutically effective amount of one or more ancillary compounds (e.g. one or more ancillary compounds selected from any of the ancillary compounds disclosed herein) and a therapeutically effective amount of a compound of the formula (I), (II), (III), (IV), (V), (VI), (VIa), (VII), (VIIa) or (VIIb) or any sub-groups or examples thereof as defined herein.

A compound of the formula (I), (II), (III), (IV), (V), (VI), (VIa), (VII), (VIIa) or (VIIb) or any sub-groups or examples thereof as defined herein for use in combination therapy with one or more ancillary compounds (e.g. one or more ancillary compounds selected from any of the ancillary compounds disclosed herein) to alleviate or reduce the incidence of a disease or condition comprising or arising from abnormal cell growth in a mammal.

A compound of the formula (I), (II), (III), (IV), (V), (VI), (VIa), (VII), (VIIa) or (VIIb) or any sub-groups or examples thereof as defined herein for use in combination therapy with one or more ancillary compounds (e.g. one or more ancillary compounds selected from any of the ancillary compounds disclosed herein) to inhibit tumour growth in a mammal.

A compound of the formula (I), (II), (III), (IV), (V), (VI), (VIa), (VII), (VIIa) or (VIIb) or any sub-groups or examples thereof as defined herein for use in combination therapy with one or more ancillary compounds (e.g. one or more ancillary compounds selected from any of the ancillary compounds disclosed herein) to prevent, treat or manage cancer in a patient in need thereof.

A compound of the formula (I), (II), (III), (IV), (V), (VI), (VIa), (VII), (VIIa) or (VIIb) or any sub-groups or examples thereof as defined herein for use in enhancing or potentiating the response rate in a patient suffering from a cancer where the patient is being treated with one or more ancillary compounds (e.g. one or more ancillary compounds selected from any of the ancillary compounds disclosed herein).

A method of enhancing or potentiating the response rate in a patient suffering from a cancer where the patient is being treated with one or more ancillary compounds (e.g. one or more ancillary compounds selected from any of the ancillary compounds disclosed herein), which method comprises administering to the patient, in combination with the ancillary compound, a compound of the formula (I), (II), (III), (IV), (V), (VI), (VIa), (VII), (VIIa) or (VIIb) or any sub-groups or examples thereof as defined herein.

A method for the prophylaxis or treatment (or alleviation or reduction of the incidence) of a disease state or condition mediated by Hsp90, which method comprises administering to a subject in need thereof a combination of the invention, wherein the disease state or condition mediated by Hsp90 is the development of resistance to a cancer drug (for example to one or more of the ancillary compounds described herein).

A method for: (i) sensitizing malignant cells to an anticancer drug; (ii) alleviating or reducing the incidence of resistance to an anticancer drug; (iii) reversing resistance to an anticancer drug; (iv) potentiating the activity of an anticancer drug; (v) delaying or preventing the onset of resistance to an anticancer drug, which method comprises administering to a subject in need thereof a combination of the invention (wherein the anticancer drug is for example one or more of the ancillary compounds described herein).

A method for the treatment of a cancer which method comprises administering to a subject in need thereof a combination of the invention, which method is characterized by the absence of drug resistance.

A method for the prophylaxis or treatment (or alleviation or reduction of the incidence) of a disease state or condition mediated by Hsp90 in a subject undergoing treatment with one or more ancillary compounds (e.g. one or more ancillary compounds selected from any of the ancillary compounds disclosed herein), which method comprises administering to the subject a compound of the formula (I), (II), (III), (IV), (V), (VI), (VIa), (VII), (VIIa) or (VIIb) or any sub-groups or examples thereof as defined herein, wherein the disease state or condition mediated by Hsp90 is the development of resistance to said ancillary compound.

A method for: (i) sensitizing malignant cells to one or more ancillary compounds; (ii) alleviating or reducing the incidence of resistance to one or more ancillary compounds; (iii) reversing resistance to one or more ancillary compounds; (iv) potentiating the activity of an one or more ancillary compounds; (v) delaying or preventing the onset of resistance to one or more ancillary compounds, which method comprises administering to a subject undergoing treatment with said ancillary compound a compound of the formula (I), (II), (III), (IV), (V), (VI), (VIa), (VII), (VIIa) or (VIIb) or any sub-groups or examples thereof as defined herein (wherein the ancillary compound is for example selected from one or more of the ancillary compounds described herein).

A method for the treatment of a cancer in a subject undergoing treatment with one or more ancillary compounds (e.g. one or more ancillary compounds selected from one or more of the ancillary compounds described herein), which method comprises administering to a subject in need thereof compound of the formula (I), (II), (III), (IV), (V), (VI), (VIa), (VII), (VIIa) or (VIIb) or any sub-groups or examples thereof as defined herein, which method is characterized by the absence of drug resistance (e.g. to said ancillary compound).

Combinations, compounds, methods, uses and other embodiments of the invention comprising one or more optional auxiliary compounds (as herein described).

In the combinations, methods, uses etc. listed above, the compounds of the formula (I), (II), (III), (IV), (V), (VI), (VIa), (VII), (VIIa) or (VIIb) include subgroups thereof, acid addition salts (particularly the L-lactate) and crystalline forms thereof.

GENERAL PREFERENCES AND DEFINITIONS

As used herein, the term "modulation", as applied to the activity of the heat shock protein Hsp90, to the activity of cyclin dependent kinase (CDK) and/or glycogen synthase kinase (GSK, e.g. GSK-3) and/or any other kinase as described herein, is intended to define a change in the level of biological activity of the heat shock protein and/or kinase. Thus, modulation encompasses physiological changes which effect an increase or decrease in the relevant heat shock protein/kinase activity. In the latter case, the modulation may be described as "inhibition". The modulation may arise directly or indirectly, and may be mediated by any mechanism and at any physiological level, including for example at the level of gene expression (including for example transcription, translation and/or post-translational modification), at the level of expression of genes encoding regulatory elements which act directly or indirectly on the levels of heat shock protein/kinase activity. Thus, modulation may imply elevated/suppressed expression or over- or under-expression of the heat shock protein/kinase, including gene amplification (i.e. multiple gene copies) and/or increased or decreased expression by a transcriptional effect, as well as hyper- (or hypo-)activity and (de)activation of the heat shock protein/kinase (including (de)activation) by mutation(s). The terms "modulated", "modulating" and "modulate" are to be interpreted accordingly.

As used herein, the term "mediated", as used e.g. in conjunction with the heat shock protein, cyclin dependent kinase (CDK) and/or glycogen synthase kinase (GSK, e.g. GSK-3) and/or any other kinase as described herein (and applied for example to various physiological processes, diseases, states, conditions, therapies, treatments or interventions) is intended to operate limitatively so that the various processes, diseases, states, conditions, treatments and interventions to which the term is applied are those in which heat shock protein Hsp90 and/or the kinase plays a biological role. In cases where the term is applied to a disease, state or condition, the biological role played by heat shock protein Hsp90 and/or the kinase may be direct or indirect and may be necessary and/or sufficient for the manifestation of the symptoms of the disease, state or condition (or its aetiology or progression). Thus, heat shock protein Hsp90/kinase activity (and in particular aberrant levels of heat shock protein Hsp90/kinase activity, e.g. Hsp90/kinase over-expression) need not necessarily be the proximal cause of the disease, state or condition: rather, it is contemplated that the heat shock protein Hsp90/kinase mediated diseases, states or conditions include those having multifactorial aetiologies and complex progressions in which Hsp90 and/or the kinase is only partially involved. In cases where the term is applied to treatment, prophylaxis or intervention (e.g. in the "Hsp90-mediated treatments" and "Hsp90-mediated prophylaxis" of the invention), the role played by Hsp90/kinase may be direct or indirect and may be necessary and/or sufficient for the operation of the treatment, prophylaxis or outcome of the intervention. Thus, a disease state or condition mediated by Hsp90 includes the development of resistance to any particular cancer drug or treatment (including in particular resistance to one or more of the ancillary compounds described herein).

The term "intervention" is a term of art used herein to define any agency which effects a physiological change at any level. Thus, the intervention may comprises the induction or repression of any physiological process, event, biochemical pathway or cellular/biochemical event. The interventions of the invention typically effect (or contribute to) the therapy, treatment or prophylaxis of a disease or condition.

The combinations of the invention may produce a therapeutically efficacious effect relative to the therapeutic effect of the individual compounds when administered separately.

The term 'efficacious' includes advantageous effects such as additivity, synergism, reduced side effects, reduced toxicity, increased time to disease progression, increased time of survival, sensitization or resensitization of one agent to another, or improved response rate.

Advantageously, an efficacious effect may allow for lower doses of each or either component to be administered to a patient, thereby decreasing the toxicity of chemotherapy, whilst producing and/or maintaining the same therapeutic effect.

A "synergistic" effect in the present context refers to a therapeutic effect produced by the combination which is larger than the sum of the therapeutic effects of the components of the combination when presented individually.

An "additive" effect in the present context refers to a therapeutic effect produced by the combination which is larger than the therapeutic effect of any of the components of the combination when presented individually.

The term "response rate" as used herein refers, in the case of a solid tumour, to the extent of reduction in the size of the tumour at a given time point, for example 12 weeks. Thus, for example, a 50% response rate means a reduction in tumour size of 50%. References herein to a "clinical response" refer to response rates of 50% or greater. A "partial response" is defined herein as being a response rate of less than 50%.

As used herein, the term "combination", as applied to two or more compounds and/or agents (also referred to herein as the components), is intended tomay define material in which the two or more compounds/agents are associated. The terms "combined" and "combining" in this context are to be interpreted accordingly.

The association of the two or more compounds/agents in a combination may be physical or non-physical. Examples of physically associated combined compounds/agents include:

compositions (e.g. unitary formulations) comprising the two or more compounds/agents in admixture (for example within the same unit dose);

compositions comprising material in which the two or more compounds/agents are chemically/physicochemically linked (for example by crosslinking, molecular agglomeration or binding to a common vehicle moiety);

compositions comprising material in which the two or more compounds/agents are chemically/physicochemically co-packaged (for example, disposed on or within lipid vesicles, particles (e.g. micro- or nanoparticles) or emulsion droplets);

pharmaceutical kits, pharmaceutical packs or patient packs in which the two or more compounds/agents are co-packaged or co-presented (e.g. as part of an array of unit doses);

Examples of non-physically associated combined compounds/agents include:

material (e.g. a non-unitary formulation) comprising at least one of the two or more compounds/agents together with instructions for the extemporaneous association of the at least one compound to form a physical association of the two or more compounds/agents;

material (e.g. a non-unitary formulation) comprising at least one of the two or more compounds/agents together with instructions for combination therapy with the two or more compounds/agents;

material comprising at least one of the two or more compounds/agents together with instructions for administration to a patient population in which the other(s) of the two or more compounds/agents have been (or are being) administered;

material comprising at least one of the two or more compounds/agents in an amount or in a form which is specifically adapted for use in combination with the other(s) of the two or more compounds/agents.

As used herein, the term "combination therapy" is intended to define therapies which comprise the use of a combination of two or more compounds/agents (as defined above). Thus, references to "combination therapy", "combinations" and the use of compounds/agents "in combination" in this application may refer to compounds/agents that are administered as part of the same overall treatment regimen. As such, the posology of each of the two or more compounds/agents may differ: each may be administered at the same time or at different times. It will therefore be appreciated that the compounds/agents of the combination may be administered sequentially (e.g. before or after) or simultaneously, either in the same pharmaceutical formulation (i.e. together), or in different pharmaceutical formulations (i.e. separately). Simultaneously in the same formulation is as a unitary formulation whereas simultaneously in different pharmaceutical formulations is non-unitary.

The posologies of each of the two or more compounds/agents in a combination therapy may also differ with respect to the route of administration.

As used herein, the term "pharmaceutical kit" defines an array of one or more unit doses of a pharmaceutical composition together with dosing means (e.g. measuring device) and/or delivery means (e.g. inhaler or syringe), optionally all contained within common outer packaging. In pharmaceutical kits comprising a combination of two or more compounds/agents, the individual compounds/agents may unitary or non-unitary formulations. The unit dose(s) may be contained within a blister pack. The pharmaceutical kit may optionally further comprise instructions for use.

As used herein, the term "pharmaceutical pack" defines an array of one or more unit doses of a pharmaceutical composition, optionally contained within common outer packaging. In pharmaceutical packs comprising a combination of two or more compounds/agents, the individual compounds/agents may unitary or non-unitary formulations. The unit dose(s) may be contained within a blister pack. The pharmaceutical pack may optionally further comprise instructions for use.

As used herein, the term "patient pack" defines a package, prescribed to a patient, which contains pharmaceutical compositions for the whole course of treatment. Patient packs usually contain one or more blister pack(s). Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

The combinations of the invention may produce a therapeutically efficacious effect relative to the therapeutic effect of the individual compounds/agents when administered separately.

The term "ancillary compound" as used herein may define a compound which yields an efficacious combination (as herein defined) when combined with a compound of the formula (I), (II), (III), (IV), (V), (VI), (VIa), (VII), (VIIa) or (VIIb) or any sub-groups or examples thereof as defined herein (including acid addition salts, particularly the L-lactate, and crystalline forms thereof). The ancillary compound may therefore act as an adjunct to the compound of the formula (I), (II), (III), (IV), (V), (VI), (VIa), (VII), (VIIa) or (VIIb) or any sub-groups or examples thereof as defined herein (including acid addition salts, particularly the L-lactate, and crystalline forms thereof), or may otherwise contribute to the efficacy of the combination (for example, by producing a synergistic or additive effect or improving the response rate, as herein defined).

Compounds of Formula (I)

In this section, as in all other sections of this application, unless the context indicates otherwise, references to a compound of formula (I) includes all subgroups of formula (I) as defined herein, including formulae (II), (III), (IV), (V), (VI), (VIa), (VII), (VIIa) and (VIIb) (particularly formula (VI)) and the term 'subgroups' includes all preferences, embodiments, examples and particular compounds defined herein.

Moreover, a reference to a particular compound (including inter alia any of the compounds of formula (I), (II), (III), (IV), (V), (VI), (VIa), (VII), (VIIa) or (VIIb) (particularly formula (VI)) or any sub-groups or examples thereof as defined herein or to the ancillary compounds described herein) includes ionic forms, salts, solvates, isomers, tautomers, N-oxides, esters, prodrugs, isotopes and protected forms thereof, as discussed below: —preferably, the salts or tautomers or isomers or N-oxides or solvates thereof: —and more preferably, the salts or tautomers or N-oxides or solvates thereof.

The following general preferences and definitions shall apply to each of $R^1$ to $R^8$, $R^{10}$, $R^a$, $R^b$, $R^c$, $X^1$ and $X^2$ and their various sub-groups, sub-definitions, examples and embodiments unless the context indicates otherwise.

Any references to formula (I) herein shall also be taken to refer to and any sub-group of compounds within formula (I) and any preferences and examples thereof unless the context requires otherwise.

References to "carbocyclic" and "heterocyclic" groups as used herein shall, unless the context indicates otherwise, include both aromatic and non-aromatic ring systems. Thus, for example, the term "carbocyclic and heterocyclic groups" includes within its scope aromatic, non-aromatic, unsaturated, partially saturated and fully saturated carbocyclic and heterocyclic ring systems. In general, such groups may be monocyclic or bicyclic and may contain, for example, 3 to 12 ring members, more usually 5 to 10 ring members. Examples of monocyclic groups are groups containing 3, 4, 5, 6, 7, and 8 ring members, more usually 3 to 7, for example 5 to 7, and preferably 5 or 6 ring members. Examples of bicyclic groups are those containing 8, 9, 10, 11 and 12 ring members, and more usually 9 or 10 ring members.

The term "bicyclic" as used herein refers to groups that have two rings joined together in such as way that at least one ring member is shared by both rings. Thus, the bicyclic group can be a fused ring (two ring members shared by both rings), spirocyclic (one ring member shared by both rings) or a bridged ring (three or more ring members shared by both rings).

The carbocyclic or heterocyclic groups can be aryl or heteroaryl groups having from 5 to 12 ring members, more usually from 5 to 10 ring members. The term "aryl" as used herein refers to a carbocyclic group having aromatic character and the term "heteroaryl" is used herein to denote a heterocyclic group having aromatic character. The terms "aryl" and "heteroaryl" embrace polycyclic (e.g. bicyclic) ring systems wherein one or more rings are non-aromatic, provided that at least one ring is aromatic. In such polycyclic systems, the group may be attached by the aromatic ring, or by a non-aromatic ring. The aryl or heteroaryl groups can be monocyclic or bicyclic groups and can be unsubstituted or substituted with one or more substituents, for example one or more groups $R^{10}$ as defined herein.

The term "non-aromatic group" embraces unsaturated ring systems without aromatic character, partially saturated and fully saturated carbocyclic and heterocyclic ring systems. The terms "unsaturated" and "partially saturated" refer to rings wherein the ring structure(s) contains atoms sharing more than one valence bond i.e. the ring contains at least one multiple bond e.g. a C=C, C≡C or N=C bond. The terms "fully saturated" and "saturated" refer to rings where there are no multiple bonds between ring atoms. Saturated carbocyclic groups include cycloalkyl groups as defined below. Partially saturated carbocyclic groups include cycloalkenyl groups as defined below, for example cyclopentenyl, cycloheptenyl and cyclooctenyl. A further example of a cycloalkenyl group is cyclohexenyl.

Examples of heteroaryl groups are monocyclic and bicyclic groups containing from five to twelve ring members, and more usually from five to ten ring members. The heteroaryl group can be, for example, a five membered or six membered monocyclic ring or a bicyclic structure formed from fused five and six membered rings or two fused six membered rings or, by way of a further example, two fused five membered rings. Each ring may contain up to about four heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of five membered heteroaryl groups include but are not limited to pyrrole, furan, thiophene, imidazole, furazan, oxazole, oxadiazole, oxatriazole, isoxazole, thiazole, isothiazole, pyrazole, triazole and tetrazole groups.

Examples of six membered heteroaryl groups include but are not limited to pyridine, pyrazine, pyridazine, pyrimidine and triazine.

A bicyclic heteroaryl group may be, for example, a group selected from:

a) a benzene ring fused to a 5- or 6-membered ring containing 1, 2 or 3 ring heteroatoms;
b) a pyridine ring fused to a 5- or 6-membered ring containing 1, 2 or 3 ring heteroatoms;
c) a pyrimidine ring fused to a 5- or 6-membered ring containing 1 or 2 ring heteroatoms;
d) a pyrrole ring fused to a 5- or 6-membered ring containing 1, 2 or 3 ring heteroatoms;
e) a pyrazole ring fused to a 5- or 6-membered ring containing 1 or 2 ring heteroatoms;
f) a pyrazine ring fused to a 5- or 6-membered ring containing 1 or 2 ring heteroatoms;
g) an imidazole ring fused to a 5- or 6-membered ring containing 1 or 2 ring heteroatoms;
h) an oxazole ring fused to a 5- or 6-membered ring containing 1 or 2 ring heteroatoms;
i) an isoxazole ring fused to a 5- or 6-membered ring containing 1 or 2 ring heteroatoms;
j) a thiazole ring fused to a 5- or 6-membered ring containing 1 or 2 ring heteroatoms;
k) an isothiazole ring fused to a 5- or 6-membered ring containing 1 or 2 ring heteroatoms;
l) a thiophene ring fused to a 5- or 6-membered ring containing 1, 2 or 3 ring heteroatoms;
m) a furan ring fused to a 5- or 6-membered ring containing 1, 2 or 3 ring heteroatoms;
n) a cyclohexyl ring fused to a 5- or 6-membered ring containing 1, 2 or 3 ring heteroatoms; and
o) a cyclopentyl ring fused to a 5- or 6-membered ring containing 1, 2 or 3 ring heteroatoms.

One sub-group of bicyclic heteroaryl groups consists of groups (a) to (e) and (g) to (o) above.

Particular examples of bicyclic heteroaryl groups containing a five membered ring fused to another five membered ring include but are not limited to imidazothiazole (e.g. imidazo[2,1-b]thiazole) and imidazoimidazole (e.g. imidazo[1,2-a]imidazole).

Particular examples of bicyclic heteroaryl groups containing a six membered ring fused to a five membered ring include but are not limited to benzfuran, benzthiophene, benzimidazole, benzoxazole, isobenzoxazole, benzisoxazole, benzthiazole, benzisothiazole, isobenzofuran, indole, isoindole, indolizine, indoline, isoindoline, purine (e.g., adenine, guanine), indazole, pyrazolopyrimidine (e.g. pyrazolo[1,5-a]pyrimidine), triazolopyrimidine (e.g. [1,2,4]triazolo[1,5-a]pyrimidine), benzodioxole and pyrazolopyridine (e.g. pyrazolo[1,5-a]pyridine) groups.

Particular examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups.

One sub-group of heteroaryl groups comprises pyridyl, pyrrolyl, furanyl, thienyl, imidazolyl, oxazolyl, oxadiazolyl, oxatriazolyl, isoxazolyl, thiazolyl, isothiazolyl, pyrazolyl, pyrazinyl, pyridazinyl, pyrimidinyl, triazinyl, triazolyl, tetrazolyl, quinolinyl, isoquinolinyl, benzfuranyl, benzthienyl, chromanyl, thiochromanyl, benzimidazolyl, benzoxazolyl, benzisoxazole, benzthiazolyl and benzisothiazole, isobenzofuranyl, indolyl, isoindolyl, indolizinyl, indolinyl, isoindolinyl, purinyl (e.g., adenine, guanine), indazolyl, benzodioxolyl, chromenyl, isochromenyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl and pteridinyl groups.

Examples of polycyclic aryl and heteroaryl groups containing an aromatic ring and a non-aromatic ring include tetrahydronaphthalene, tetrahydroisoquinoline, tetrahydroquinoline, dihydrobenzthiene, dihydrobenzfuran, 2,3-dihydro-benzo[1,4]dioxine, benzo[1,3]dioxole, 4,5,6,7-tetrahydrobenzofuran, indoline and indane groups.

Examples of carbocyclic aryl groups include phenyl, naphthyl, indenyl, and tetrahydronaphthyl groups.

Examples of non-aromatic heterocyclic groups include unsubstituted or substituted (by one or more groups $R^{10}$) heterocyclic groups having from 3 to 12 ring members, typically 4 to 12 ring members, and more usually from 5 to 10 ring members. Such groups can be monocyclic or bicyclic, for example, and typically have from 1 to 5 heteroatom ring members (more usually 1,2,3 or 4 heteroatom ring members) typically selected from nitrogen, oxygen and sulphur.

When sulphur is present, it may, where the nature of the adjacent atoms and groups permits, exist as —S—, —S(O)— or —S(O)$_2$—.

The heterocyclic groups can contain, for example, cyclic ether moieties (e.g. as in tetrahydrofuran and dioxane), cyclic thioether moieties (e.g. as in tetrahydrothiophene and dithiane), cyclic amine moieties (e.g. as in pyrrolidine), cyclic amide moieties (e.g. as in pyrrolidone), cyclic thioamides, cyclic thioesters, cyclic ester moieties (e.g. as in butyrolactone), cyclic sulphones (e.g. as in sulpholane and sulpholene), cyclic sulphoxides, cyclic sulphonamides and combinations thereof (e.g. morpholine and thiomorpholine and its S-oxide and S,S-dioxide). Further examples of heterocyclic groups are those containing a cyclic urea moiety (e.g. as in imidazolidin-2-one), In one sub-set of heterocyclic groups, the heterocyclic groups contain cyclic ether moieties (e.g as in tetrahydrofuran and dioxane), cyclic thioether moieties (e.g. as in tetrahydrothiophene and dithiane), cyclic amine moieties (e.g. as in pyrrolidine), cyclic sulphones (e.g. as in sulpholane and sulpholene), cyclic sulphoxides, cyclic sulphonamides and combinations thereof (e.g. thiomorpholine).

Examples of monocyclic non-aromatic heterocyclic groups include 5-, 6- and 7-membered monocyclic heterocyclic groups. Particular examples include morpholine, piperidine (e.g. 1-piperidinyl, 2-piperidinyl, 3-piperidinyl and 4-piperidinyl), pyrrolidine (e.g. 1-pyrrolidinyl, 2-pyrrolidinyl and 3-pyrrolidinyl), pyrrolidone, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazine, and N-alkyl piperazines such as N-methyl piperazine. Further examples include thiomorpholine and its S-oxide and S,S-dioxide (particularly thiomorpholine). Still further examples include azetidine, piperidone, piperazone, and N-alkyl piperidines such as N-methyl piperidine.

One preferred sub-set of non-aromatic heterocyclic groups consists of saturated groups such as azetidine, pyrrolidine, piperidine, morpholine, thiomorpholine, thiomorpholine S,S-dioxide, piperazine, N-alkyl piperazines, and N-alkyl piperidines.

Another sub-set of non-aromatic heterocyclic groups consists of pyrrolidine, piperidine, morpholine, thiomorpholine, thiomorpholine S,S-dioxide, piperazine and N-alkyl piperazines such as N-methyl piperazine.

One particular sub-set of heterocyclic groups consists of pyrrolidine, piperidine, morpholine and N-alkyl piperazines (e.g. N-methyl piperazine), and optionally thiomorpholine.

Examples of non-aromatic carbocyclic groups include cycloalkane groups such as cyclohexyl and cyclopentyl, cycloalkenyl groups such as cyclopentenyl, cyclohexenyl, cycloheptenyl and cyclooctenyl, as well as cyclohexadienyl, cyclooctatetraene, tetrahydronaphthenyl and decalinyl.

Preferred non-aromatic carbocyclic groups are monocyclic rings and most preferably saturated monocyclic rings.

Typical examples are three, four, five and six membered saturated carbocyclic rings, e.g. optionally substituted cyclopentyl and cyclohexyl rings.

One sub-set of non-aromatic carboyclic groups includes unsubstituted or substituted (by one or more groups $R^{10}$) monocyclic groups and particularly saturated monocyclic groups, e.g. cycloalkyl groups. Examples of such cycloalkyl groups include cyclopropyl, cyclobutyl, cyclopentyl, cyclohexyl and cycloheptyl; more typically cyclopropyl, cyclobutyl, cyclopentyl and cyclohexyl, particularly cyclohexyl.

Further examples of non-aromatic cyclic groups include bridged ring systems such as bicycloalkanes and azabicycloalkanes although such bridged ring systems are generally less preferred. By "bridged ring systems" is meant ring systems in which two rings share more than two atoms, see for example *Advanced Organic Chemistry*, by Jerry March, 4th Edition, Wiley Interscience, pages 131-133, 1992. Examples of bridged ring systems include bicyclo[2.2.1]heptane, azabicyclo[2.2.1]heptane, bicyclo[2.2.2]octane, aza-bicyclo [2.2.2]octane, bicyclo[3.2.1]octane and aza-bicyclo[3.2.1] octane. A particular example of a bridged ring system is the 1-aza-bicyclo[2.2.2]octan-3-yl group.

Where reference is made herein to carbocyclic and heterocyclic groups, the carbocyclic or heterocyclic ring can, unless the context indicates otherwise, be unsubstituted or substituted by one or more substituent groups $R^{10}$ selected from halogen, hydroxy, trifluoromethyl, cyano, nitro, carboxy, amino, mono- or di-$C_{1-4}$ hydrocarbylamino, carbocyclic and heterocyclic groups having from 3 to 12 ring members; a group $R^a$-$R^b$ wherein $R^a$ is a bond, O, CO, $X^1C(X^2)$, $C(X^2)$ $X^1$, $X^1C(X^2)X^1$, S, SO, $SO_2$, $NR^c$, $SO_2NR^c$ or $NR^cSO_2$; and $R^b$ is selected from hydrogen, carbocyclic and heterocyclic groups having from 3 to 12 ring members, and a $C_{1-12}$ hydrocarbyl group (such as a $C_{1-10}$ hydrocarbyl group) optionally substituted by one or more substituents selected from hydroxy, oxo, halogen, cyano, nitro, carboxy, amino, mono- or di-$C_{1-8}$ non-aromatic hydrocarbylamino (e.g. mono- or di-$C_{1-4}$ hydrocarbylamino), carbocyclic and heterocyclic groups having from 3 to 12 ring members and wherein one or more carbon atoms of the $C_{1-12}$ hydrocarbyl group (or $C_{1-10}$ hydrocarbyl group) may optionally be replaced by O, S, SO, $SO_2$, $NR^c$, $X^1C(X^2)$, $C(X^2)X^1$ or $X^1C(X^2)X^1$;

$R^c$ is selected from $R^b$, hydrogen and $C_{1-4}$ hydrocarbyl; and $X^1$ is O, S or $NR^c$ and $X^2$ is $=$O, $=$S or $=NR^c$.

Where the substituent group $R^{10}$ comprises or includes a carbocyclic or heterocyclic group, the said carbocyclic or heterocyclic group may be unsubstituted or may itself be substituted with one or more further substituent groups $R^{10}$. In one sub-group of compounds of the formula (I), such further substituent groups $R^{10}$ may include carbocyclic or heterocyclic groups, which are typically not themselves further substituted. In another sub-group of compounds of the formula (I), the said further substituents do not include carbocyclic or heterocyclic groups but are otherwise selected from the groups listed above in the definition of $R^{10}$.

The substituents $R^{10}$ may be selected such that they contain no more than 20 non-hydrogen atoms, for example, no more than 15 non-hydrogen atoms, e.g. no more than 12, or 11, or 10, or 9, or 8, or 7, or 6, or 5 non-hydrogen atoms.

Where the carbocyclic and heterocyclic groups have a pair of substituents on the same or adjacent ring atoms, the two substituents may be linked so as to form a cyclic group. Thus, two adjacent groups $R^{10}$, together with the carbon atoms or heteroatoms to which they are attached may form a 5-membered heteroaryl ring or a 5- or 6-membered non-aromatic carbocyclic or heterocyclic ring, wherein the said heteroaryl and heterocyclic groups contain up to 3 heteroatom ring members selected from N, O and S. For example, an adjacent pair of substituents on adjacent carbon atoms of a ring may be linked via one or more heteroatoms and optionally substituted alkylene groups to form a fused oxa-, dioxa-, aza-, diaza- or oxa-aza-cycloalkyl group.

Examples of such linked substituent groups include:

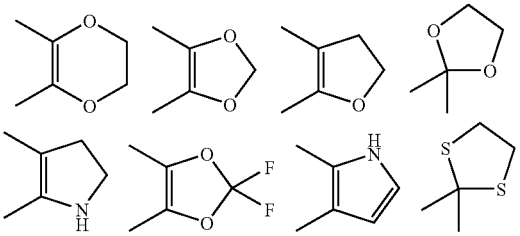

Examples of halogen substituents include fluorine, chlorine, bromine and iodine. Fluorine and chlorine are particularly preferred.

In the definition of the compounds of the formula (I) above and as used hereinafter, the term "hydrocarbyl" is a generic term encompassing aliphatic, alicyclic and aromatic groups having an all-carbon backbone and consisting of carbon and hydrogen atoms, except where otherwise stated.

In certain cases, as defined herein, one or more of the carbon atoms making up the carbon backbone may be replaced by a specified atom or group of atoms.

Examples of hydrocarbyl groups include alkyl, cycloalkyl, cycloalkenyl, carbocyclic aryl, alkenyl, alkynyl, cycloalkylalkyl, cycloalkenylalkyl, and carbocyclic aralkyl, aralkenyl and aralkynyl groups. Such groups can be unsubstituted or, where stated, substituted by one or more substituents as defined herein. The examples and preferences expressed below apply to each of the hydrocarbyl substituent groups or hydrocarbyl-containing substituent groups referred to in the various definitions of substituents for compounds of the formula (I) unless the context indicates otherwise.

The prefix "$C_{x-y}$" (where x and y are integers) as used herein refers to the number of carbon atoms in a given group. Thus, a $C_{1-4}$ hydrocarbyl group contains from 1 to 4 carbon atoms, and a $C_{3-6}$ cycloalkyl group contains from 3 to 6 carbon atoms, and so on.

The term "acyclic hydrocarbyl" (e.g. as in "acyclic $C_{1-5}$ hydrocarbyl") as used herein refers to non-cyclic hydrocarbyl groups and in particular to alkyl, alkenyl and alkynyl groups as defined herein.

The term "mono- or di-$C_{1-5}$ hydrocarbylamino" as used herein refers to a monosubstituted or disubstituted amine group bearing either one or two hydrocarbyl substituent groups that each contain from 1 to 5 carbon atoms.

Preferred non-aromatic hydrocarbyl groups are saturated groups such as alkyl and cycloalkyl groups.

Generally by way of example, the hydrocarbyl groups can have up to ten carbon atoms (and more typically up to eight carbon atoms), unless the context requires otherwise. Within the sub-set of hydrocarbyl groups having 1 to 10 carbon atoms, particular examples are $C_{1-8}$ hydrocarbyl groups or $C_{1-6}$ hydrocarbyl groups, such as $C_{1-4}$ hydrocarbyl groups (e.g. $C_{1-3}$ hydrocarbyl groups or $C_{1-2}$ hydrocarbyl groups or $C_{2-3}$ hydrocarbyl groups or $C_{2-4}$ hydrocarbyl groups), specific examples being any individual value or combination of values selected from $C_1$, $C_2$, $C_3$, $C_4$, $C_5$, $C_6$, $C_7$, $C_8$, $C_9$ and $C_{10}$ hydrocarbyl groups.

The term "alkyl" covers both straight chain and branched chain alkyl groups. Examples of alkyl groups include methyl, ethyl, propyl, isopropyl, n-butyl, isobutyl, tert-butyl, n-pentyl, 2-pentyl, 3-pentyl, 2-methyl butyl, 3-methyl butyl, and n-hexyl and its isomers. Within the sub-set of alkyl groups having 1 to 8 carbon atoms, particular examples are $C_{1-6}$ alkyl groups, such as $C_{1-4}$ alkyl groups (e.g. $C_{1-3}$ alkyl groups or $C_{1-2}$ alkyl groups or $C_{2-3}$ alkyl groups or $C_{2-4}$ alkyl groups).

Examples of cycloalkyl groups are those derived from cyclopropane, cyclobutane, cyclopentane, cyclohexane and cycloheptane. Within the sub-set of cycloalkyl groups the cycloalkyl group will have from 3 to 10 carbon atoms, more typically 3 to 8 carbon atoms, particular examples being $C_{3-6}$ cycloalkyl groups.

Examples of alkenyl groups include, but are not limited to, ethenyl (vinyl), 1-propenyl, 2-propenyl (allyl), isopropenyl, butenyl, buta-1,4-dienyl, pentenyl, and hexenyl. Within the sub-set of alkenyl groups the alkenyl group will have 2 to 10 carbon atoms, more typically 2 to 8 carbon atoms, particular examples being $C_{2-6}$ alkenyl groups, such as $C_{2-4}$ alkenyl groups.

Examples of cycloalkenyl groups include, but are not limited to, cyclopropenyl, cyclobutenyl, cyclopentenyl, cyclopentadienyl and cyclohexenyl. Within the sub-set of cycloalkenyl groups the cycloalkenyl groups have from 3 to 10 carbon atoms, more typically 3 to 8 carbon atoms, and particular examples are $C_{3-6}$ cycloalkenyl groups.

Examples of alkynyl groups include, but are not limited to, ethynyl and 2-propynyl (propargyl) groups. Within the sub-set of alkynyl groups having 2 to 10 carbon atoms, more typically 2 to 8 carbon atoms, particular examples are $C_{2-6}$ alkynyl groups, such as $C_{2-4}$ alkynyl groups.

Examples of carbocyclic aryl groups include substituted and unsubstituted phenyl groups.

Examples of cycloalkylalkyl, cycloalkenylalkyl, carbocyclic aralkyl, aralkenyl and aralkynyl groups include phenethyl, benzyl, styryl, phenylethynyl, cyclohexylmethyl, cyclopentylmethyl, cyclobutylmethyl, cyclopropylmethyl and cyclopentenylmethyl groups.

The terms $C_{1-12}$ hydrocarbyl, $C_{1-10}$ hydrocarbyl and $C_{1-8}$ hydrocarbyl as used herein encompasses alkyl, alkenyl, alkynyl, cycloalkyl, cycloalkenyl, phenyl, benzyl and phenylethyl groups wherein the preferences for and examples of each of the aforesaid groups are as defined above. Within this definition, particular hydrocarbyl groups are alkyl, cycloalkyl, phenyl, benzyl and phenylethyl (e.g. 1-phenylethyl or 2-phenylethyl) groups, one subset of hydrocarbyl groups consisting of alkyl and cycloalkyl groups and in particular $C_{1-4}$ alkyl and cycloalkyl groups such as methyl, ethyl, n-propyl, isopropyl, n-butyl, isobutyl, tert-butyl, cyclopropyl and cyclobutyl.

The term $C_{1-5}$ hydrocarbyl as used herein encompasses alkyl, alkenyl, alkynyl, cycloalkyl and cycloalkenyl groups wherein the preferences for and examples of the aforesaid groups are as defined above. Within this definition, particular saturated $C_{1-5}$ hydrocarbyl groups are saturated $C_{1-5}$ hydrocarbyl groups, namely alkyl and cycloalkyl groups, such as methyl, ethyl, n-propyl, isopropyl, n-butyl, isobutyl, tert-butyl, n-pentyl, 3-methylbutyl, 2-methyl butyl, pent-2-yl, pent-3-yl, 3-methylbut-2-yl, 2,2-dimethylpropyl, cyclopropyl, cyclobutyl, cyclopentyl, cyclopropylmethyl, cyclopropylethyl, cyclobutylmethyl, methylcyclopropyl, ethylcyclopropyl, di methylcyclopropyl, methylcyclobutyl.

Also within the scope of the term $C_{1-5}$ hydrocarbyl as used herein are unsaturated $C_{1-5}$ hydrocarbyl groups, i.e. alkene, cycloalkene and alkyne groups such as vinyl, 1-propenyl, isopropenyl, 1-butenyl, 2-butenyl, 1-pentenyl, 2-pentenyl, allyl, methylallyl, dimethylallyl, acetylenyl, propargyl, cyclobutenyl and cyclopentenyl.

The term $C_{1-4}$ hydrocarbyl as used herein encompasses alkyl, alkenyl, alkynyl, cycloalkyl and cycloalkenyl groups wherein the preferences for and examples of the aforesaid groups are as defined above. Within this definition, particular C1-4 hydrocarbyl groups are alkyl and cycloalkyl groups, such as methyl, ethyl, n-propyl, isopropyl, n-butyl, isobutyl, tert-butyl, cyclopropyl and cyclobutyl.

When present, and where stated, a hydrocarbyl group can be optionally substituted by one or more substituents selected from hydroxy, oxo, alkoxy, carboxy, halogen, cyano, nitro, amino, mono- or di-$C_{1-4}$ hydrocarbylamino, and monocyclic or bicyclic carbocyclic and heterocyclic groups having from 3 to 12 (typically 3 to 10 and more usually 5 to 10) ring members. Preferred substituents include halogen such as fluorine. Thus, for example, the substituted hydrocarbyl group can be a partially fluorinated or perfluorinated group such as difluoromethyl or trifluoromethyl. In one embodiment preferred substituents include monocyclic carbocyclic and heterocyclic groups having 3-7 ring members, more usually 3, 4, 5 or 6 ring members.

Where stated, one or more carbon atoms of a hydrocarbyl group may optionally be replaced by O, S, SO, $SO_2$, $NR^c$, $X^1C(X^2)$, $C(X^2)X^1$ or $X^1C(X^2)X^1$ (or a sub-group thereof) wherein $X^1$ and $X^2$ are as hereinbefore defined, provided that at least one carbon atom of the hydrocarbyl group remains. For example, 1, 2, 3 or 4 carbon atoms of the hydrocarbyl group may be replaced by one of the atoms or groups listed, and the replacing atoms or groups may be the same or different. In general, the number of linear or backbone carbon atoms replaced will correspond to the number of linear or backbone atoms in the group replacing them. Examples of groups in which one or more carbon atom of the hydrocarbyl group have been replaced by a replacement atom or group as defined above include ethers and thioethers (C replaced by O or S), amides, esters, thioamides and thioesters (C—C replaced by $X^1C(X^2)$ or $C(X^2)X^1$), sulphones and sulphoxides (C replaced by SO or $SO_2$), amines (C replaced by $NR^c$). Further examples include ureas, carbonates and carbamates (C—C—C replaced by $X^1C(X^2)X^1$).

Where an amino group has two hydrocarbyl substituents, they may, together with the nitrogen atom to which they are attached, and optionally with another heteroatom such as nitrogen, sulphur, or oxygen, link to form a ring structure of 4 to 7 ring members, more usually 5 to 6 ring members.

The term "aza-cycloalkyl" as used herein refers to a cycloalkyl group in which one of the carbon ring members has been replaced by a nitrogen atom. Thus examples of aza-cycloalkyl groups include piperidine and pyrrolidine. The term "oxa-cycloalkyl" as used herein refers to a cycloalkyl group in which one of the carbon ring members has been replaced by an oxygen atom. Thus examples of oxa-cycloalkyl groups include tetrahydrofuran and tetrahydropyran. In an analogous manner, the terms "diaza-cycloalkyl", "dioxa-cycloalkyl" and "aza-oxa-cycloalkyl" refer respectively to cycloalkyl groups in which two carbon ring members have been replaced by two nitrogen atoms, or by two oxygen atoms, or by one nitrogen atom and one oxygen atom. Thus, in an oxa-$C_{4-6}$cycloalkyl group, there will be from 3 to 5 carbon ring members and an oxygen ring member. For example, an oxa-cyclohexyl group is a tetrahydropyranyl group.

The definition "$R^a$-$R^b$" as used herein, either with regard to substituents present on a carbocyclic or heterocyclic moiety, or with regard to other substituents present at other locations on the compounds of the formula (I), includes inter alia compounds wherein $R^a$ is selected from a bond, O, CO, OC(O), SC(O), $NR^cC(O)$, OC(S), SC(S), $NR^cC(S)$, $OC(NR^c)$, $SC(NR^c)$, $NR^cC(NR^c)$, C(O)O, C(O)S, $C(O)NR^c$, C(S)O, C(S)S, C(S) $NR^c$, $C(NR^c)O$, $C(NR^c)S$, $C(NR^c)NR^c$, OC(O) O, SC(O)O, $NR^cC(O)O$, OC(S)O, SC(S)O, $NR^cC(S)O$, $OC(NR^c)O$, $SC(NR^c)O$, $NR^cC(NR^c)O$, OC(O)S, SC(O)S, $NR^cC(O)S$, OC(S)S, SC(S)S, $NR^cC(S)S$, $OC(NR^c)S$, SC(N-$R^c$)S, $NR^cC(NR^c)S$, $OC(O)NR^c$, $SC(O)NR^c$, $NR^cC(O)$ $NR^c$, $OC(S)NR^c$, SC(S) $NR^c$, $NR^cC(S)NR^c$, $OC(NR^c)NR^c$, SC(N-$R^c$)$NR^c$, $NR^cC(NR^cNR^c$, S, SO, $SO_2$, $NR^c$, $SO_2NR^c$ and $NR^cSO_2$ wherein $R^c$ is as hereinbefore defined.

The moiety $R^b$ can be hydrogen or it can be a group selected from carbocyclic and heterocyclic groups having from 3 to 12 ring members (typically 3 to 10 and more usually from 5 to 10), and a $C_{1-8}$ hydrocarbyl group optionally substituted as hereinbefore defined. Examples of hydrocarbyl, carbocyclic and heterocyclic groups are as set out above.

When $R^a$ is O and $R^b$ is a $C_{1-10}$ hydrocarbyl group, $R^a$ and $R^b$ together form a hydrocarbyloxy group. Preferred hydrocarbyloxy groups include saturated hydrocarbyloxy such as alkoxy (e.g. $C_{1-6}$ alkoxy, more usually $C_{1-4}$ alkoxy such as ethoxy and methoxy, particularly methoxy), cycloalkoxy (e.g. $C_{3-6}$ cycloalkoxy such as cyclopropyloxy, cyclobutyloxy, cyclopentyloxy and cyclohexyloxy) and cycloalkylalkoxy (e.g. $C_{3-6}$ cycloalkyl-$C_{1-2}$ alkoxy such as cyclopropylmethoxy).

The hydrocarbyloxy groups can be substituted by various substituents as defined herein. For example, the alkoxy groups can be substituted by halogen (e.g. as in difluoromethoxy and trifluoromethoxy), hydroxy (e.g. as in hydroxyethoxy), $C_{1-2}$ alkoxy (e.g. as in methoxyethoxy), hydroxy-$C_{1-2}$ alkyl (as in hydroxyethoxyethoxy) or a cyclic group (e.g. a cycloalkyl group or non-aromatic heterocyclic group as hereinbefore defined). Examples of alkoxy groups bearing a non-aromatic heterocyclic group as a substituent are those in which the heterocyclic group is a saturated cyclic amine such as morpholine, piperidine, pyrrolidine, piperazine, $C_{1-4}$-alkyl-piperazines, $C_{3-7}$-cycloalkyl-piperazines, tetrahydropyran or tetrahydrofuran and the alkoxy group is a $C_{1-4}$ alkoxy group, more typically a $C_{1-3}$ alkoxy group such as methoxy, ethoxy or n-propoxy.

Alkoxy groups may be substituted by a monocyclic group such as pyrrolidine, piperidine, morpholine and piperazine and N-substituted derivatives thereof such as N-benzyl, N—$C_{1-4}$ acyl and N—$C_{1-4}$ alkoxycarbonyl. Particular examples include pyrrolidinoethoxy, piperidinoethoxy and piperazinoethoxy.

When $R^a$ is a bond and $R^b$ is a $C_{1-10}$ hydrocarbyl group, examples of hydrocarbyl groups $R^a$-$R^b$ are as hereinbefore defined. The hydrocarbyl groups may be saturated groups such as cycloalkyl and alkyl and particular examples of such groups include methyl, ethyl and cyclopropyl. The hydrocarbyl (e.g. alkyl) groups can be substituted by various groups and atoms as defined herein. Examples of substituted alkyl groups include alkyl groups substituted by one or more halogen atoms such as fluorine and chlorine (particular examples including bromoethyl, chloroethyl and trifluoromethyl), or hydroxy (e.g. hydroxymethyl and hydroxyethyl), $C_{1-10}$ acyloxy (e.g. acetoxymethyl and benzyloxymethyl), amino and mono- and dialkylamino (e.g. aminoethyl, methylaminoethyl, dimethylaminomethyl, dimethylaminoethyl and tert-butylaminomethyl), alkoxy (e.g. $C_{1-2}$ alkoxy such as methoxy—as in methoxyethyl), and cyclic groups such as cycloalkyl groups, aryl groups, heteroaryl groups and non-aromatic heterocyclic groups as hereinbefore defined).

Particular examples of alkyl groups substituted by a cyclic group are those wherein the cyclic group is a saturated cyclic amine such as morpholine, piperidine, pyrrolidine, piperazine, $C_{1-4}$-alkyl-piperazines, $C_{3-7}$-cycloalkyl-piperazines, tetrahydropyran or tetrahydrofuran and the alkyl group is a $C_{1-4}$ alkyl group, more typically a $C_{1-3}$ alkyl group such as methyl, ethyl or n-propyl. Specific examples of alkyl groups substituted by a cyclic group include pyrrolidinomethyl, pyrrolidinopropyl, morpholinomethyl, morpholinoethyl, morpholinopropyl, piperidinylmethyl, piperazinomethyl and N-substituted forms thereof as defined herein.

Particular examples of alkyl groups substituted by aryl groups and heteroaryl groups include benzyl and pyridylmethyl groups.

When $R^a$ is $SO_2NR^c$, $R^b$ can be, for example, hydrogen or an optionally substituted $C_{1-8}$ hydrocarbyl group, or a carbocyclic or heterocyclic group. Examples of $R^a$-$R^b$ where $R^a$ is $SO_2NR^c$ include aminosulphonyl, $C_{1-4}$alkylaminosulphonyl and di-$C_{1-4}$ alkylaminosulphonyl groups, and sulphonamides formed from a cyclic amino group such as piperidine, morpholine, pyrrolidine, or an optionally N-substituted piperazine such as N-methyl piperazine.

Examples of groups $R^a$-$R^b$ where $R^a$ is $SO_2$ include alkylsulphonyl, heteroarylsulphonyl and arylsulphonyl groups, particularly monocyclic aryl and heteroaryl sulphonyl groups. Particular examples include methylsulphonyl, phenylsulphonyl and toluenesulphonyl.

When $R^a$ is $NR^c$, $R^b$ can be, for example, hydrogen or an optionally substituted $C_{1-10}$ hydrocarbyl group, or a carbocyclic or heterocyclic group. Examples of $R^a$-$R^b$ where $R^a$ is $NR^c$ include amino, $C_{1-4}$ alkylamino (e.g. methylamino, ethylamino, propylamino, isopropylamino, tert-butylamino), di-$C_{1-4}$ alkylamino (e.g. dimethylamino and diethylamino) and cycloalkylamino (e.g. cyclopropylamino, cyclopentylamino and cyclohexylamino).

Specific Embodiments of and Preferences for $R^1$ to $R^{10}$
$R^1$ & $R^2$
$R^1$ is hydroxy or hydrogen; and $R^2$ is hydroxy, methoxy or hydrogen; provided that at least one of $R^1$ and $R^2$ is hydroxy.

Preferably, $R^1$ is hydroxy or hydrogen; and $R^2$ is hydroxy or hydrogen; provided that at least one of $R^1$ and $R^2$ is hydroxy.

In one embodiment, $R^1$ is hydroxy and $R^2$ is hydrogen or methoxy, preferably hydrogen.

In another embodiment, $R^1$ is hydrogen and $R^2$ is hydroxy.
In a further embodiment, $R^1$ is hydroxy and $R^2$ is hydroxy or methoxy.

In a preferred embodiment, $R^1$ and $R^2$ are both hydroxy.
$R^8$
$R^8$ is selected from hydrogen and fluorine. Preferably $R^8$ is hydrogen.
$R^3$
$R^3$ is selected from hydrogen, halogen, cyano, $C_{1-5}$ hydrocarbyl and $C_{1-5}$ hydrocarbyloxy; wherein the $C_{1-5}$ hydrocarbyl and $C_{1-5}$ hydrocarbyloxy moieties are each optionally substituted by one or more substituents selected from hydroxy, halogen, $C_{1-2}$ alkoxy, amino, mono- and di-$C_{1-2}$ alkylamino, and aryl and heteroaryl groups of 5 to 12 ring members.

In one sub-group of compounds, $R^3$ is selected from hydrogen, halogen, cyano, $C_{1-5}$ hydrocarbyl and $C_{1-5}$ hydrocarbyloxy; wherein the $C_{1-5}$ hydrocarbyl moiety in each instance is optionally substituted by one or more substituents selected from hydroxy, halogen, $C_{1-2}$ alkoxy and amino.

In another sub-group of compounds, $R^3$ is selected from halogen (e.g. chlorine or bromine), $C_{1-5}$ alkyl and $C_{3-4}$ cycloalkyl.

More typically, $R^3$ is selected from hydrogen, chlorine, $C_{1-5}$ hydrocarbyl and $C_{1-5}$ hydrocarbyloxy.

Particular groups $R^3$ include hydrogen, $C_{1-5}$ alkyl, $C_{2-5}$ alkenyl and $C_{3-4}$ cycloalkyl groups, preferably secondary alkyl and alkenyl groups such as isopropyl, sec-butyl, tert-butyl, 1,2-dimethylallyl and 1,2-dimethylpropyl, or cycloalkyl groups such as cyclopropyl.

A further sub-group of substituents $R^3$ consists of $C_{1-5}$ alkyl, $C_{2-5}$ alkenyl and $C_{3-4}$ cycloalkyl groups, preferably secondary alkyl and alkenyl groups such as isopropyl, sec-butyl, tert-butyl, 1,2-dimethylallyl and 1,2-dimethylpropyl, or cycloalkyl groups such as cyclopropyl.

When only one of $R^1$ and $R^2$ is hydroxy, $R^3$ may be other than hydrogen.

In one particular embodiment, $R^1$ and $R^2$ are both hydroxy and $R^3$ is hydrogen.

In a further particular embodiment, $R^3$ is selected from isopropyl and tert-butyl.

In one general embodiment, $R^3$ is other than halogen.

In another general embodiment, $R^3$ may be other than fluorine.

In a further general embodiment, $R^3$ may be other than fluorine or methoxy.

$R^4$

In one embodiment, $R^4$ is selected from hydrogen; a group $—(O)_n—R^7$ where n is 0 or 1 and $R^7$ is an acyclic $C_{1-5}$ hydrocarbyl group or a monocyclic carbocyclic or heterocyclic group having 3 to 7 ring members; halogen; cyano; hydroxy; amino; and mono- or di-$C_{1-5}$ hydrocarbylamino, wherein the acyclic $C_{1-5}$ hydrocarbyl group and the mono and di-$C_{1-5}$ hydrocarbylamino moieties in each instance are optionally substituted by one or more substituents selected from hydroxy, halogen, $C_{1-2}$ alkoxy, amino, mono- and di-$C_{1-2}$ alkylamino, and aryl and heteroaryl groups of 5 to 12 ring members.

In one sub-group of compounds, $R^4$ is selected from hydrogen; a group $—(O)_n—R^7$ where n is 0 or 1 and $R^7$ is an acyclic $C_{1-5}$ hydrocarbyl group or a monocyclic carbocyclic or heterocyclic group having 3 to 7 ring members; halogen; cyano; hydroxy; amino; and mono- or di-$C_{1-5}$ hydrocarbylamino, wherein the $C_{1-5}$ hydrocarbyl moiety in each instance is optionally substituted by one or more substituents selected from hydroxy, halogen, $C_{1-2}$ alkoxy and amino.

Within this sub-group, $R^4$ is more typically selected from hydrogen, methoxy, halogen (e.g. fluorine or chlorine), cyano; hydroxy; amino and $C_{3-6}$ cycloalkyl.

More particularly, $R^4$ can be selected from a sub-set $R^{4a}$ wherein the sub-set $R^{4a}$ consists of hydrogen, methoxy, fluorine and chlorine.

Preferably $R^4$ is hydrogen.

In another embodiment, $R^3$ and $R^4$ together form a carbocyclic or heterocyclic ring of 5 to 7 ring members. The carbocyclic and heterocyclic groups can be any of the groups listed above in General Definitions and Preferences section but one particular group is a group wherein $R^3$ and $R^4$ together with the phenyl ring form a dihydrobenzofuran group.

Particular examples of the phenyl ring containing the moieties $R^1$, $R^2$, $R^3$ and $R^4$ are as set out in Table 1. The point of attachment to the carbonyl group is indicated by means of an asterisk.

TABLE 1

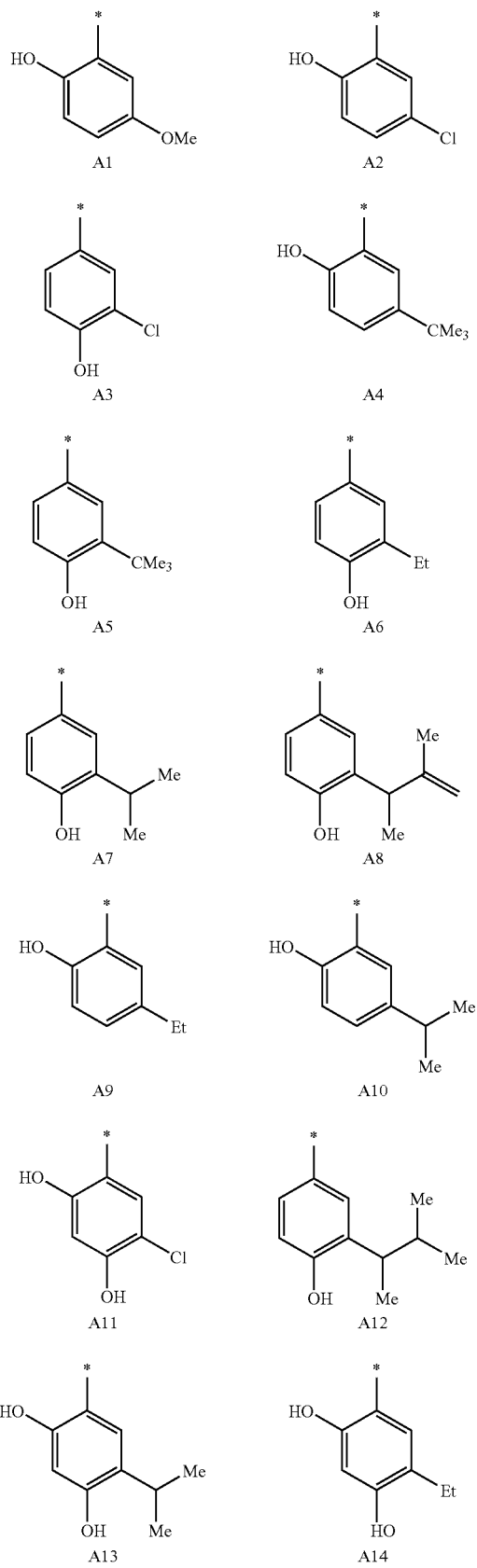

TABLE 1-continued

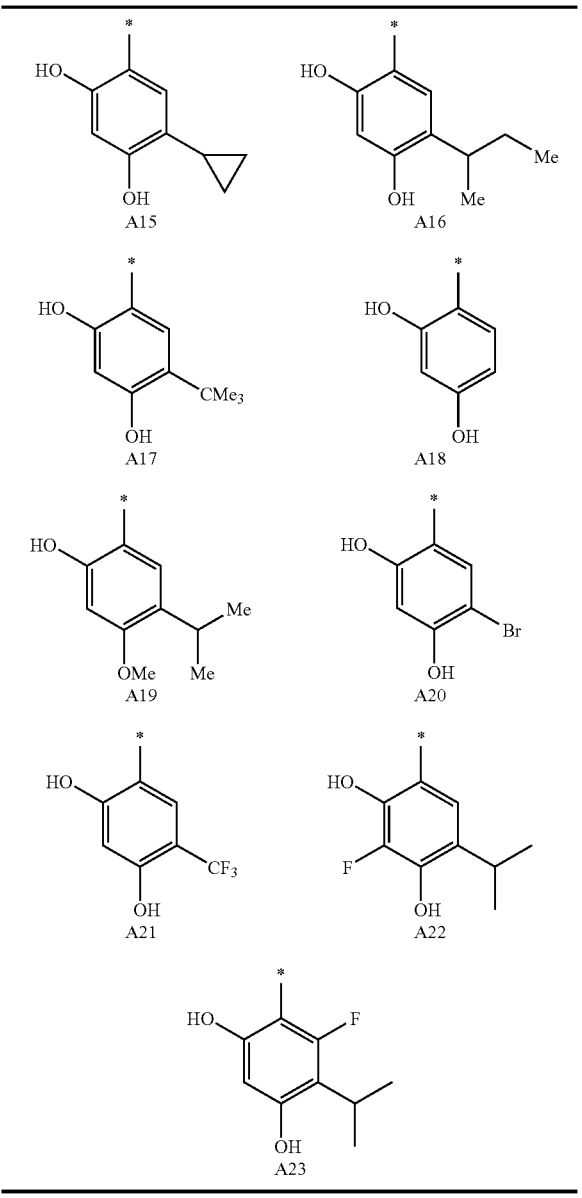

In one embodiment, the phenyl moiety is selected from groups A1 to A21.

In another embodiment, the phenyl moiety is selected from groups A1 to A18.

Preferred phenyl moieties include groups A5, A7, A11, A13, A14, A15, A16, A17 and A18.

Particularly preferred phenyl moieties are A5, A7, A13, A14 and A17.

Particularly preferred phenyl moieties are A11 and A13.
One particularly preferred phenyl moiety is group A13.

$R^5$ & $R^6$ $R^5$ and $R^6$ together with the nitrogen atom to which they are attached form a bicyclic heterocyclic group having up to 12 ring members of which up to 5 ring members are heteroatoms selected from oxygen, nitrogen and sulphur.

The bicyclic groups can be any of the groups listed above in the General Preferences and Definitions section or listed below in the Particular and Preferred Sub-groups section, and such groups may be unsubstituted or substituted by one or more substituents $R^{10}$ as defined herein.

The bicyclic heterocyclic group is typically a fused ring bicyclic group or a spirocylic group and more typically is a fused ring bicyclic group. Particular fused ring systems of interest in the context of the invention are 5.6 and 6.6 fused ring systems. In the bicyclic heterocyclic groups, one of the rings may be a heterocyclic ring and the other may be a carbocyclic ring, or both rings may be heterocyclic.

In one sub-group of compounds, one of the rings of the bicyclic heterocyclic group is non-aromatic and other is aromatic. Preferably the nitrogen atom of the group $NR^5R^6$ forms part of the non-aromatic ring. Particular examples of such groups are dihydroindole, dihydroisoindole, tetrahydroquinoline and tetrahydroisoquinoline groups.

More particular examples of such groups are dihydroindole, dihydroisoindole, tetrahydroquinoline and tetrahydroisoquinoline groups, but wherein the tetrahydroisoquinoline group bears no substituent groups on the non-aromatic ring thereof.

The bicyclic heterocyclic rings are optionally substituted by one or more substituent groups $R^{10}$ as defined herein.

In one embodiment, the bicyclic heterocyclic ring is substituted by 1, 2 or 3 substituent groups $R^{10}$ as defined herein.

In another embodiment, the bicyclic heterocyclic ring is substituted by 1 or 2 substituent groups $R^{10}$ as defined herein.

The substituent group or groups $R^{10}$ may be attached to either or both of the two rings making up the bicyclic heterocyclic group. In one embodiment, the ring containing the nitrogen atom of the group $NR^5R^6$ does not bear any substituents $R^{10}$. In another embodiment, the ring containing the nitrogen atom of the group $NR^5R^6$ bears a substituent $R^{10}$ but the substituent is other than a carboxylic acid group.

In one sub-group of compounds, the bicyclic heterocyclic group is unsubstituted or is substituted by one, two or three (preferably one or two) substituents selected from a group $R^{10a}$ consisting of halogen, hydroxy, amino and a group $R^a$-$R^b$ where $R^a$ is selected from a bond, O, CO, C(O)O, C(O)$NR^c$, $NR^cC(O)$, $NR^cC(O)O$, $NR^c$, SO, $SO_2$, $SONR^c$, and $SO_2NR^c$; and $R^b$ is selected from hydrogen; carbocyclic and heterocyclic groups having 5 or 6 ring members; and $C_{1-10}$ hydrocarbyl (e.g. $C_{1-8}$ hydrocarbyl such as $C_{1-8}$ alkyl or $C_{3-7}$ cycloalkyl) optionally substituted by one or more substituents selected from hydroxy, oxo, amino, mono- or di-$C_{1-8}$ non-aromatic hydrocarbylamino, (e.g. mono- or di-$C_{1-4}$ hydrocarbylamino), carboxy, and carbocyclic and heterocyclic groups having from 3 to 7 ring members, and wherein one or more of the carbon atoms of the $C_{1-8}$ hydrocarbyl group may optionally be replaced by O, S, C(O)O, C(O)$NR^c$ or $NR^c$.

Within this sub-group of compounds and sub-groups, preferences and examples thereof, where it is stated that one or more of the carbon atoms of the $C_{1-8}$ hydrocarbyl group may optionally be replaced by O, S, C(O)O, C(O)$NR^c$ or $NR^C$, the orientation of the ester and amide groups may be in either direction unless indicated to the contrary.

In the above sub-groups, when $R^b$ is a carbocyclic or heterocyclic group, the carbocyclic or heterocyclic group may be substituted by one or more substituents $R^{10}$ as defined herein. For example, when $R^b$ is a carbocyclic or heterocyclic group, the carbocyclic or heterocyclic group may be substituted by one or more substituents selected from $CO_2R^{14}$ wherein $R^{14}$ is hydrogen or $C_{1-8}$ alkyl;

$C_{1-4}$ alkyl optionally substituted by hydroxy or $C_{1-2}$ alkoxy;

$C_{1-4}$ alkoxy optionally substituted by hydroxy or $C_{1-2}$ alkoxy; or a group [sol], $CH_2$[sol], C(O)[sol], $OCH_2CH_2$[sol] or $OCH_2CH_2CH_2$[sol] where [sol] is as defined below.

In a more particular sub-group, the bicyclic heterocyclic group is unsubstituted or is substituted by one, two or three (preferably one or two) substituents selected from a group $R^{10b}$ consisting of halogen, OH, $NH_2$, $CH_2OH$, $CH_2NH_2$, $O-C_{1-6}$-alkyl, $NH-C_{1-6}$ alkyl, aryl, heteroaryl, $C_{3-7}$cycloalkyl, heterocyclyl, O-heteroaryl, $O-C_{3-7}$cycloalkyl, O-heterocycloalkyl, $C(=O)C_{1-6}$ alkyl, $C(=O)OC_{1-6}$ alkyl, $C(=O)NH_2$, $C(=O)NHC_{1-6}$alkyl, $C(=O)N(C_{1-6}$alkyl$)_2$, $NH(C_{1-6}$alkyl), $N(C_{1-6}$alkyl$)_2$, $NC(=O)C_{1-6}$alkyl, $C_6$ aryl, $OC_6$ aryl, $C(=O)C_6$aryl, $C(=O)OC_6$aryl, $C(=O)NH_2$, $C(=O)NHC_6$aryl, $C(=O)N(C_6$aryl$)_2$, $NH(C_6$aryl), $N(C_6$aryl$)_2$, $NC(=O)C_6$aryl, $C_{5-6}$ heterocyclyl, $OC_{5-6}$ heterocyclyl, $C(=O)C_{5-6}$ heterocyclyl, $C(=O)OC_{5-6}$ heterocyclyl, $C(=O)NHC_{5-6}$heterocyclyl, $C(=O)N(C_{5-6}$ heterocyclyl$)_2$, $NH(C_{5-6}$ heterocyclyl), $N(C_{5-6}$ heterocyclyl$)_2$, $NC(=O)C_{5-6}$ heterocyclyl, $C(=O)NHC_{1-6}$ alkyl, $C_{5-6}$ aryl, $S(=O)C_{1-6}$ alkyl, $S(=O)N-C_{1-6}$alkyl and $SO_2N-C_{1-6}$alkyl; and a group [sol], $CH_2$[sol] or $OCH_2CH_2$[sol] where [sol] is selected from the following groups

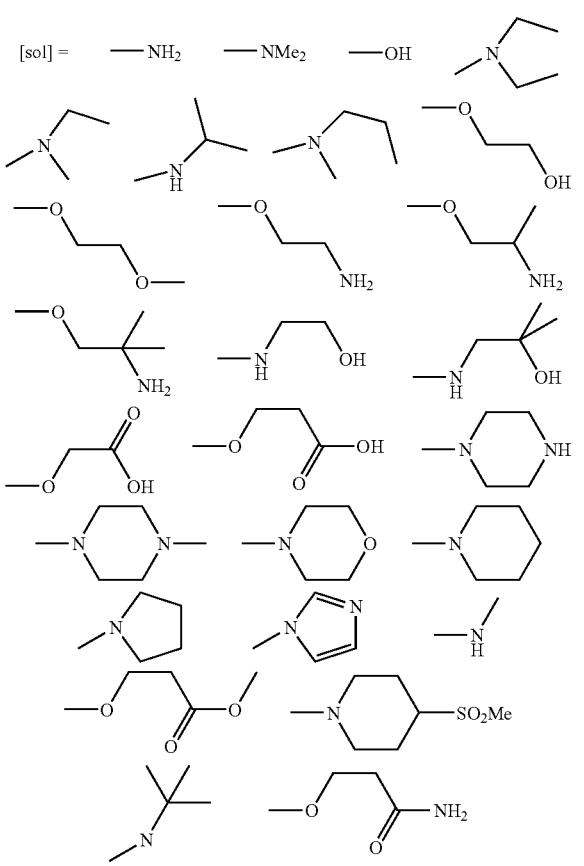

and wherein (i) $R^{10c}$ is optionally further selected from a group $OCH_2CH_2CH_2$[sol] and/or (ii) [sol] is further selected from $NHR^{11}$ wherein $R^{11}$ is $COR^{12}$ or $R^{12}$ and $R^{12}$ is $C_{1-4}$ alkyl, aryl or aryl-$C_{1-4}$ alkyl.

In another sub-group of compounds, the bicyclic ring is unsubstituted or is substituted by one or two substituents $R^{10cc}$ where $R^{10cc}$ is selected from:

halogen;

$CO_2R^{14}$ wherein $R^{14}$ is hydrogen or $C_{1-6}$ alkyl;

$C_{1-4}$ alkyl optionally substituted by hydroxy or $C_{1-2}$ alkoxy;

$C_{1-4}$ alkoxy optionally substituted by hydroxy or $C_{1-2}$ alkoxy; or a group [sol], $CH_2$[sol], $C(O)$[sol], $OCH_2CH_2$[sol] or $OCH_2CH_2CH_2$[sol] where [sol] is selected from the following groups

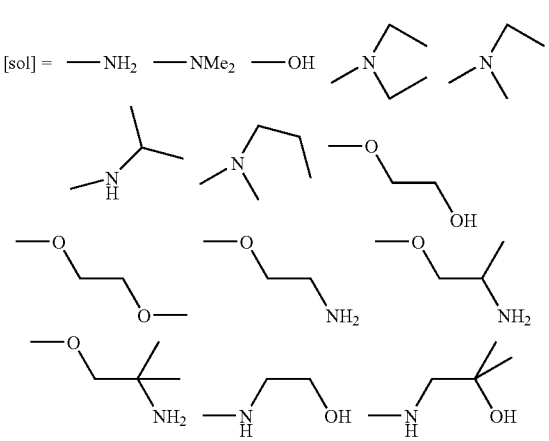

In another sub-group of compounds, the bicyclic ring is unsubstituted or is substituted by 1, 2 or 3 (e.g. 1 or 2, for example 1) groups $R^{10c}$ where $R^{10c}$ is a group [sol], $CH_2$[sol] or $OCH_2CH_2$[sol] where [sol] is selected from the following groups

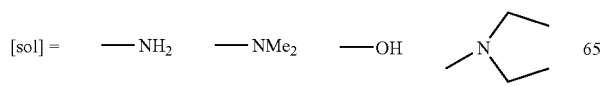

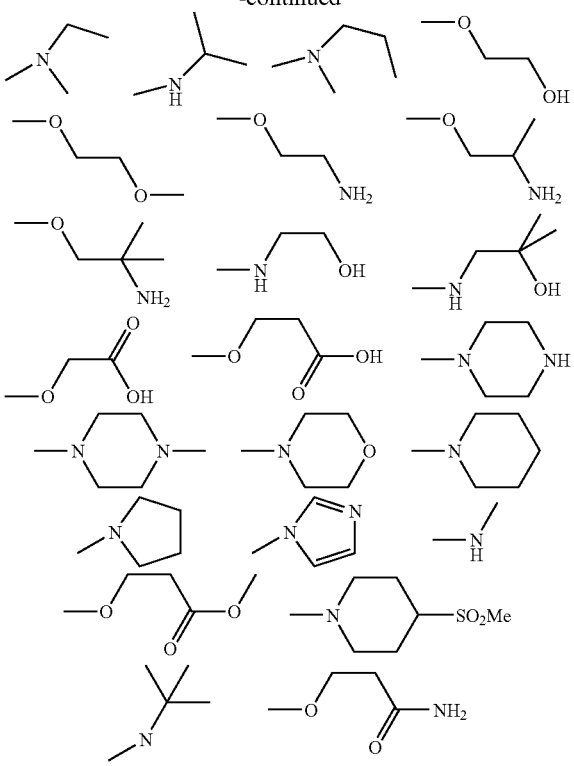

-continued

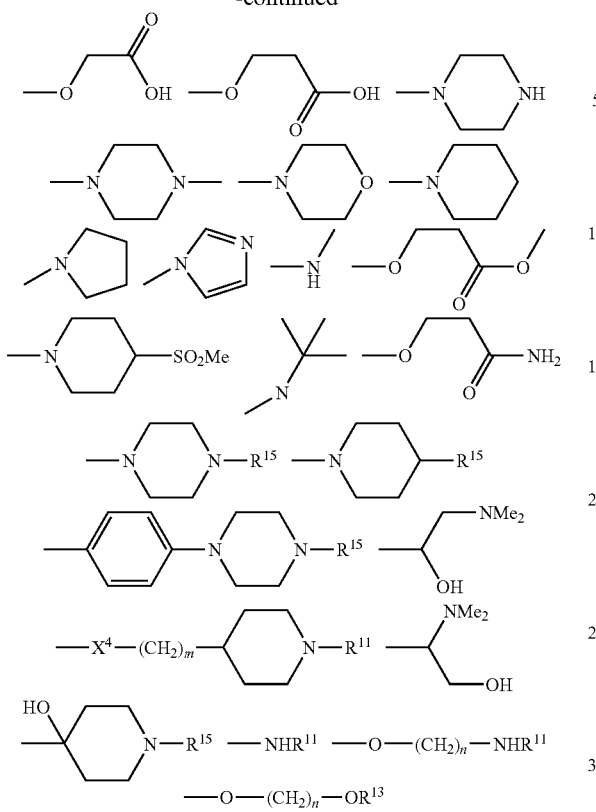

wherein $X^4$ is NH or O, m is 0 or 1, n is 1, 2 or 3, $R^{11}$ is hydrogen, $COR^{12}$, $C(O)OR^{12}$ or $R^{12}$; $R^{12}$ is $C_{1-6}$ alkyl, $C_{3-6}$ cycloalkyl, aryl, aryl-$C_{1-6}$ alkyl or $CH_2R^{15}$; and $R^{15}$ is selected from hydrogen, $C_{1-6}$ alkyl, $C_{3-6}$ cycloalkyl, hydroxy-$C_{1-6}$ alkyl, piperidine, N—$C_{1-6}$alkylpiperazine, piperazine, morpholine, $COR^{13}$ or $C(O)OR^{13}$; and $R^{13}$ is $C_{1-6}$ alkyl.

In a further sub-group of compounds, the bicyclic ring is unsubstituted or is substituted by one or two substituents $R^{10ccc}$ where $R^{10ccc}$ is selected from:

a group [sol] or $CH_2$[sol] where [sol] is selected from the following groups:

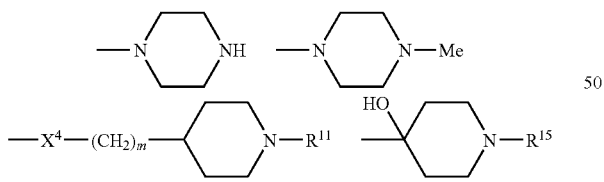

wherein $X^4$ is NH or O, m is 0 or 1, n is 1, 2 or 3, $R^{11}$ is hydrogen, $COR^{12}$, $C(O)OR^{12}$ or $R^{12}$; $R^{12}$ is $C_{1-6}$ alkyl, $C_{3-6}$ cycloalkyl, aryl, aryl-$C_{1-6}$ alkyl or $CH_2R^{15}$; and $R^{15}$ is selected from hydrogen, $C_{1-6}$ alkyl, $C_{3-6}$ cycloalkyl, hydroxy-$C_{1-6}$ alkyl, piperidine, N—$C_{1-6}$alkylpiperazine, piperazine, morpholine, $COR^{13}$ or $C(O)OR^{13}$; and $R^{13}$ is $C_{1-6}$ alkyl.

In another sub-group of compounds, where $R^{10b}$ or $R^{10c}$ or $R^{10cc}$ is a group [sol], $CH_2$[sol], $OCH_2CH_2$[sol] or $OCH_2CH_2CH_2$[sol] and [sol] contains a primary or secondary amine group, the primary or secondary amine group can be derivatised to form an acyl derivative such as an amide, carbamate or urea. For example, the amine group can be derivatised to form a carbamate such as a $C_{1-4}$alkyloxycarbonylamino group, or a benzyloxycarbonylamino group.

In one sub-group of compounds, $R^5$ and $R^6$ together with the nitrogen atom to which they are attached form an optionally substituted dihydroisoindole group wherein the optional substituents are selected from groups $R^{10}$, $R^{10a}$, $R^{10b}$, $R^{10c}$ and $R^{10cc}$ and sub-groups and examples thereof as defined herein.

Particular examples of the group $NR^5R^6$ are shown in Table 2. The point of attachment to the carbonyl group is shown by means of an asterisk.

TABLE 2

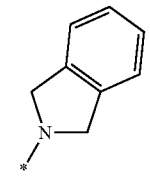

B8

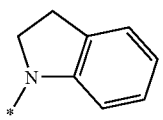

B13

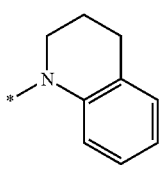

B14

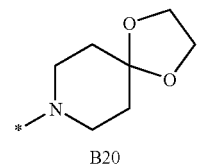 [SMILES: "B20" ; *N1CCC2(CC1)OCCO2]

B20

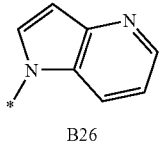

B26

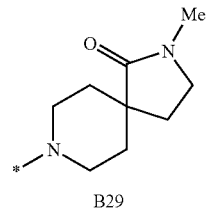 [SMILES: "B29" ; *N1CCC2(CC1)CCN(C)C2=O]

B29

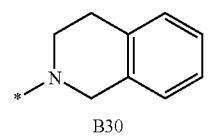 [SMILES: "B30" ; *N1CCc2ccccc2C1]

B30

TABLE 2-continued
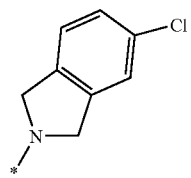
B35
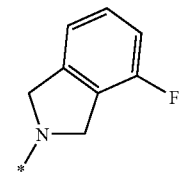
B36
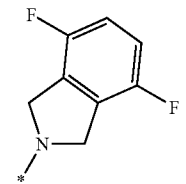
B37
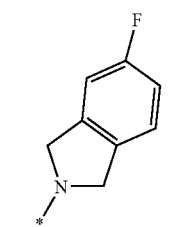
B38
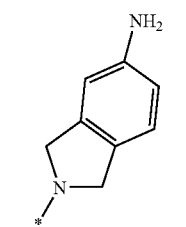
B39
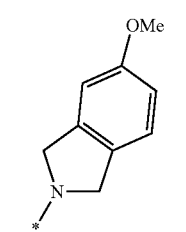
B40
TABLE 2-continued
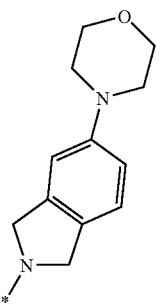
B41
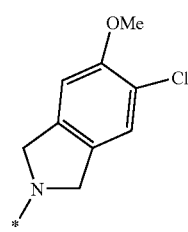
B42
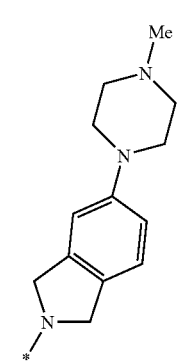
B43
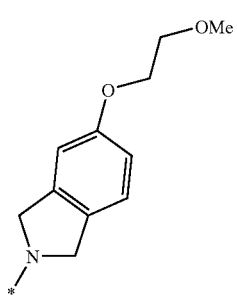
B45

TABLE 2-continued
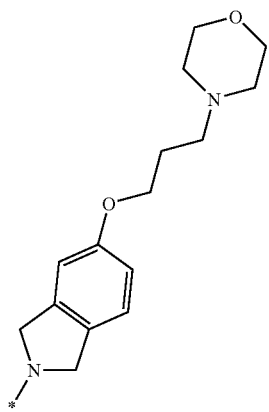
B46
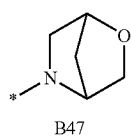
B47
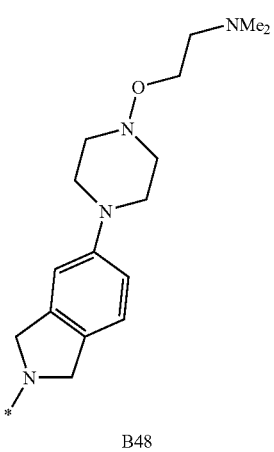 [SMILES: "B48" ; *N1Cc2ccc(N3CCN(OCCN(C)C)CC3)cc2C1]
B48
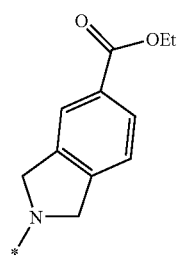
B53
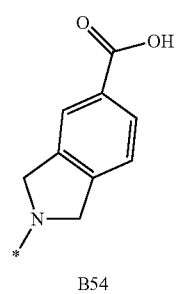 [SMILES: "B54" ; *N1Cc2ccc(C(=O)O)cc2C1]
B54
TABLE 2-continued
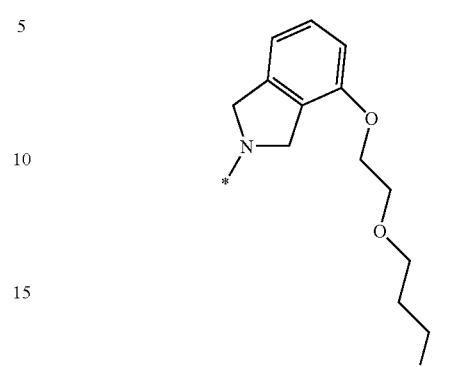
B55
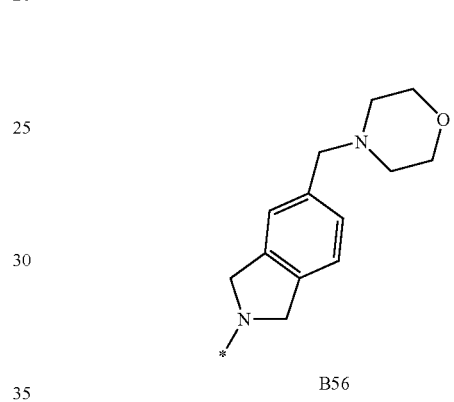
B56
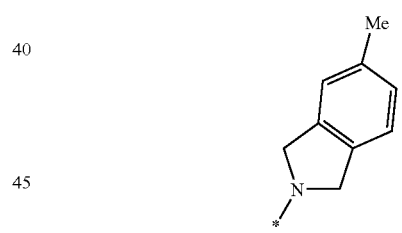
B57
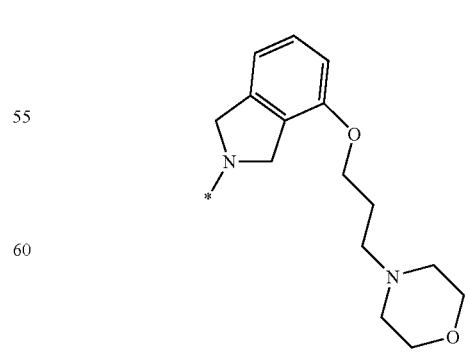
B58

TABLE 2-continued
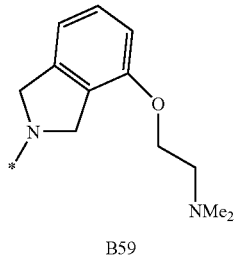 [SMILES: "B59" ; *N1Cc2cccc(OCCN(C)C)c2C1]
B59
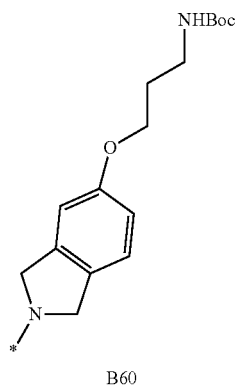 [SMILES: "B60" ; *N1Cc2ccc(OCCCNC(=O)OC(C)(C)C)cc2C1]
B60
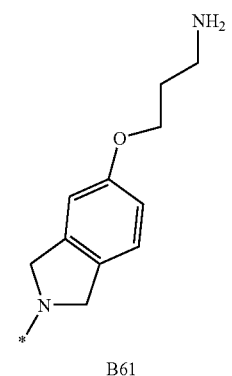 [SMILES: "B61" ; *N1Cc2ccc(OCCCN)cc2C1]
B61
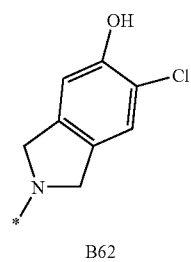 [SMILES: "B62" ; *N1Cc2cc(O)c(Cl)cc2C1]
B62
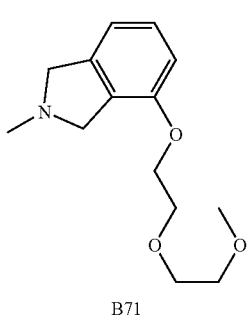 [SMILES: "B71" ; COCCOCCOc1cccc2c1CN(C)C2]
B71
TABLE 2-continued
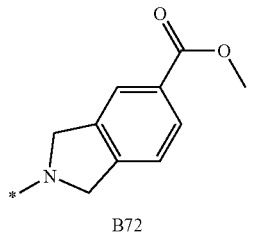 [SMILES: "B72" ; *N1Cc2ccc(C(=O)OC)cc2C1]
B72
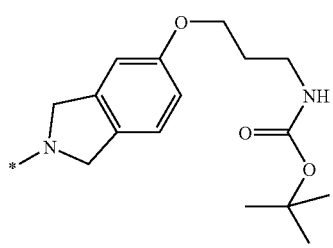
B73
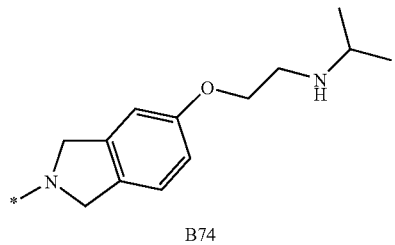 [SMILES: "B74" ; *N1Cc2ccc(OCCNC(C)C)cc2C1]
B74
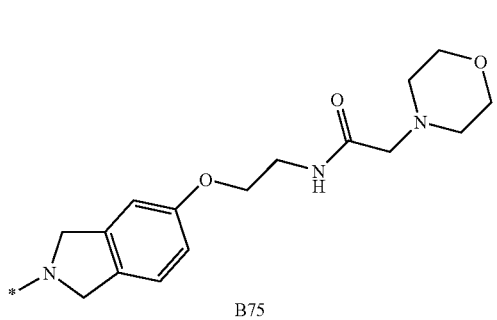 [SMILES: "B75" ; *N1Cc2ccc(OCCNC(=O)CN3CCOCC3)cc2C1]
B75
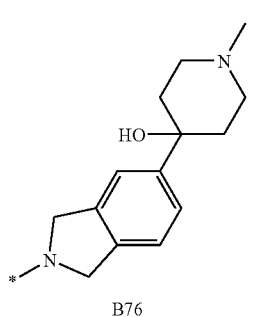 [SMILES: "B76" ; *N1Cc2ccc(C3(O)CCN(C)CC3)cc2C1]
B76

TABLE 2-continued
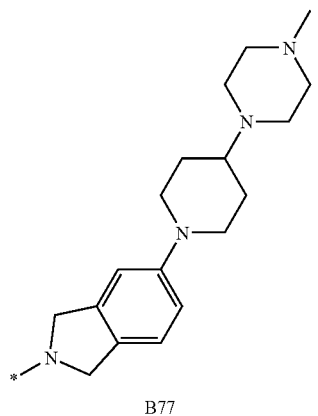 [SMILES: "B77" ; *N1Cc2ccc(N3CCC(N4CCN(C)CC4)CC3)cc2C1]
B77
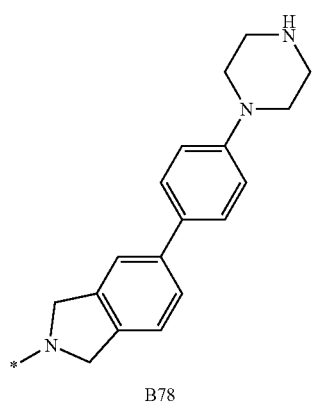 [SMILES: "B78" ; *N1Cc2ccc(-c3ccc(N4CCNCC4)cc3)cc2C1]
B78
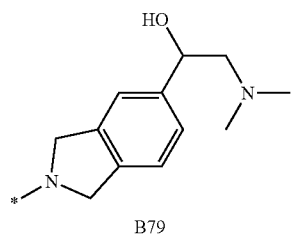 [SMILES: "B79" ; *N1Cc2ccc(C(O)CN(C)C)cc2C1]
B79
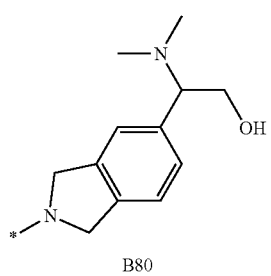 [SMILES: "B80" ; *N1Cc2ccc(C(CO)N(C)C)cc2C1]
B80
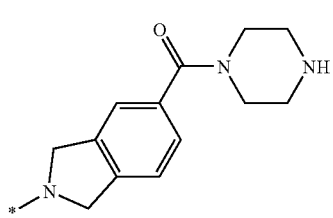
B81
TABLE 2-continued
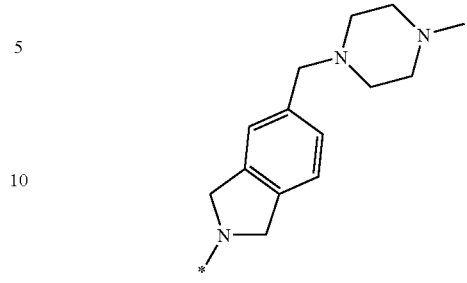
B82
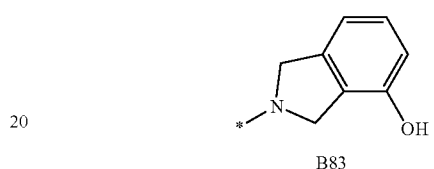
B83
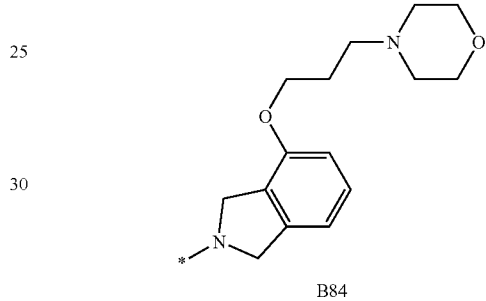
B84
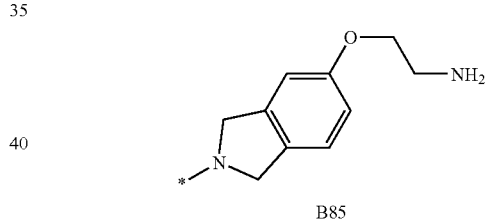
B85
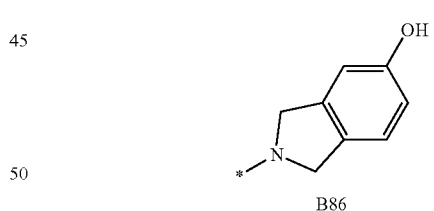
B86
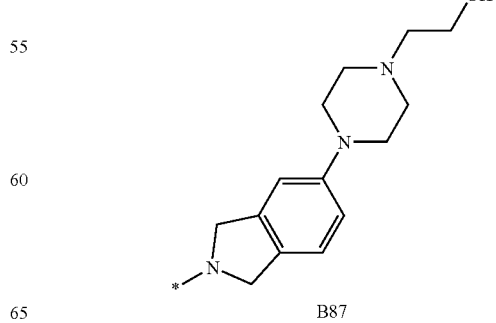
B87

TABLE 2-continued
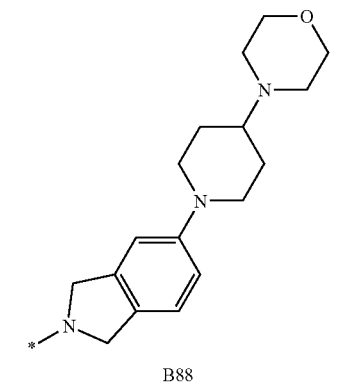 [SMILES: "B88" ; *N1Cc2ccc(N3CCC(N4CCOCC4)CC3)cc2C1]
B88
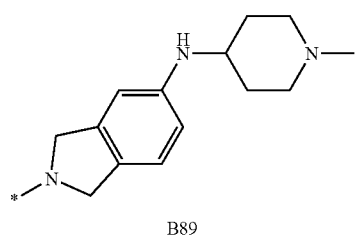 [SMILES: "B89" ; *N1Cc2ccc(NC3CCN(C)CC3)cc2C1]
B89
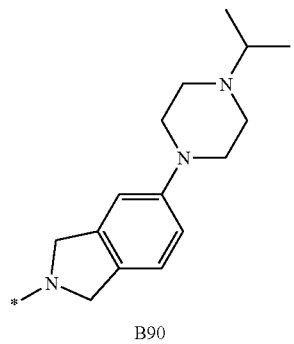 [SMILES: "B90" ; *N1Cc2ccc(N3CCN(C(C)C)CC3)cc2C1]
B90
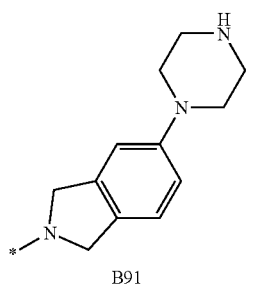 [SMILES: "B91" ; *N1Cc2ccc(N3CCNCC3)cc2C1]
B91
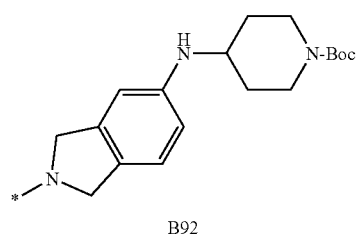
B92
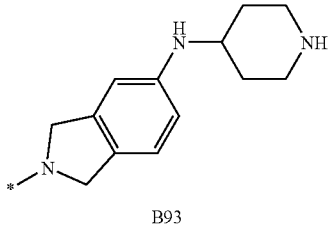 [SMILES: "B93" ; *N1Cc2ccc(NC3CCNCC3)cc2C1]
B93
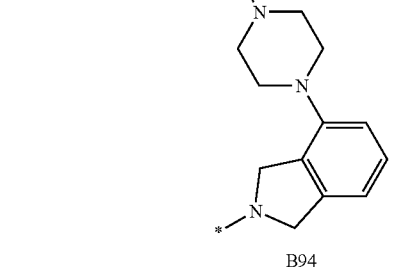
B94
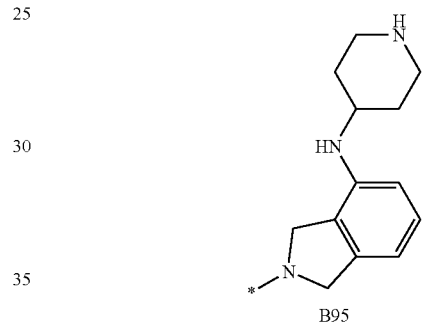
B95
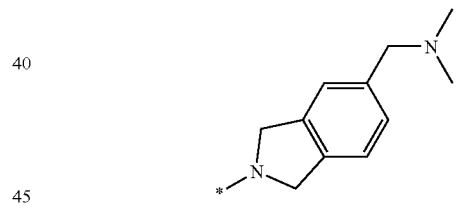
B96
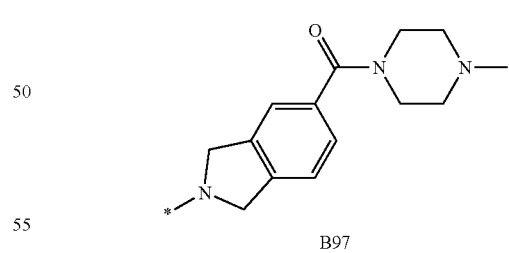
B97
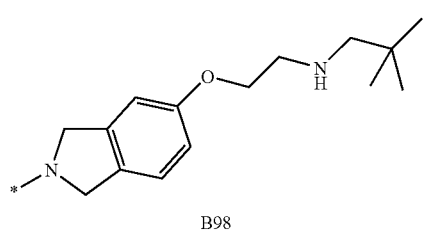 [SMILES: "B98" ; *N1Cc2ccc(OCCNCC(C)(C)C)cc2C1]
B98

TABLE 2-continued

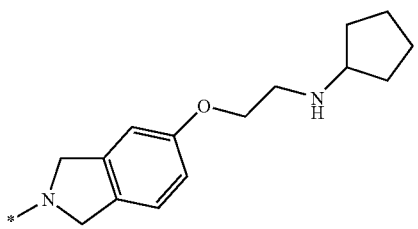

B99

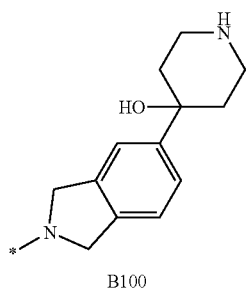 [SMILES: "B100" ; *N1Cc2ccc(C3(O)CCNCC3)cc2C1]

B100

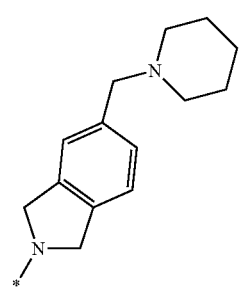

B101

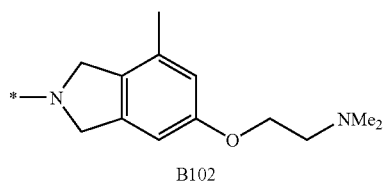 [SMILES: "B102" ; *N1Cc2cc(OCCN(C)C)cc(C)c2C1]

B102

One set of preferred groups $NR^5R^6$ consists of or includes groups B8 and B30.

Another preferred group $NR^5R^6$ is group B8.

A further set of preferred groups $NR^5R^6$ consists of groups B8, B35, B36, B37, B38, B39, B40, B41, B42, B43, B45, B46, B48, B53, B54, B55, B55, B57, B58, B59, B60, B61 and B62.

A further set of preferred groups $NR^5R^6$ consists of groups B8, B35, B36, B37, B38, B39, B40, B41, B42, B43, B45, B46, B48, B53, B54, B55, B56, B57, B58, B59, B60, B61 and B62

Another set of preferred groups consists of B8, B35, B36, B37, B38, B39, B40, B41, B42, B43, B45, B46, B48, B53, B54, B55, B56, B57, B58, B59, B60, B61, B62, B71, B72, B74, B75, B76, B77, B78, B79, B80, B81, B82, B83, B85, B86, B87, B93, B94, B95, B97, B98, B99, B100 and B101.

A further sub-set of groups $NR^5R^6$ consists of B43, B46, B48, B76, B82, B89, B91 and B96. Within this sub-set, more preferred groups are groups B43, B46, B48, B76, B82, B89 and B91, with B76, B82 and B89 being particularly preferred.

Particular and Preferred Sub-Groups

One sub-group of compounds for use according to the invention can be represented by the general formula (II):

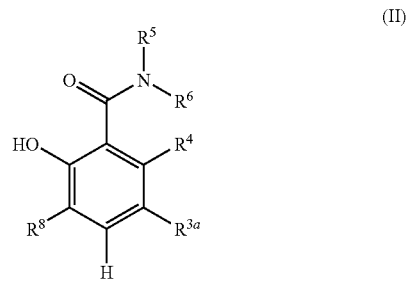

(II)

or salts, tautomers, solvates and N-oxides thereof; wherein:
$R^{3a}$ is selected from hydrogen, halogen, cyano, $C_{1-5}$ hydrocarbyl and $C_{1-5}$ hydrocarbyloxy; wherein the $C_{1-5}$ hydrocarbyl and $C_{1-5}$ hydrocarbyloxy moieties are each optionally substituted by one or more substituents selected from hydroxy, halogen, $C_{1-2}$ alkoxy, amino, mono- and di-$C_{1-2}$ alkylamino, and aryl and heteroaryl groups of 5 to 12 ring members;

$R^4$ is selected from hydrogen; a group $—(O)_n—R^7$ where n is 0 or 1 and $R^7$ is an acyclic $C_{1-5}$ hydrocarbyl group or a monocyclic carbocyclic or heterocyclic group having 3 to 7 ring members; halogen; cyano; hydroxy; amino; and mono- or di-$C_{1-5}$ hydrocarbyl-amino, wherein the acyclic $C_{1-5}$ hydrocarbyl group and the mono and di-$C_{1-5}$ hydrocarbylamino moieties in each instance are optionally substituted by one or more substituents selected from hydroxy, halogen, $C_{1-2}$ alkoxy, amino, mono- and di-$C_{1-2}$ alkylamino, and aryl and heteroaryl groups of 5 to 12 ring members;

or $R^{3a}$ and $R^4$ together form a monocyclic carbocyclic or heterocyclic ring of 5 to 7 ring members;

$R^5$ and $R^6$ together with the nitrogen atom to which they are attached form a bicyclic group having up to 12 ring members (e.g 8-12 ring members or 9-10 ring members) of which up to 5 ring members are heteroatoms selected from oxygen, nitrogen and sulphur; and $R^8$ is selected from hydrogen and fluorine.

Another sub-group of compounds for use according to the invention can be represented by the formula (III):

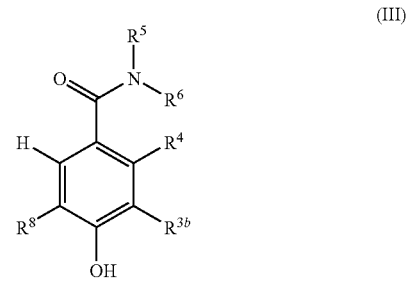

(III)

or salts, tautomers, solvates and N-oxides thereof; wherein:
$R^{3b}$ is selected from hydrogen, halogen, cyano, $C_{1-5}$ hydrocarbyl and $C_{1-5}$ hydrocarbyloxy; wherein the $C_{1-5}$ hydrocarbyl and $C_{1-5}$ hydrocarbyloxy moieties are each optionally substituted by one or more substituents selected from hydroxy, halogen, $C_{1-2}$ alkoxy, amino, mono- and di-$C_{1-2}$ alkylamino, and aryl and heteroaryl groups of 5 to 12 ring members;

$R^4$ is selected from hydrogen; a group —$(O)_n$—$R^7$ where n is 0 or 1 and $R^7$ is an acyclic $C_{1-5}$ hydrocarbyl group or a monocyclic carbocyclic or heterocyclic group having 3 to 7 ring members; halogen; cyano; hydroxy; amino; and mono- or di-$C_{1-5}$ hydrocarbyl-amino, wherein the acyclic $C_{1-5}$ hydrocarbyl group and the mono and di-$C_{1-5}$ hydrocarbylamino moieties in each instance are optionally substituted by one or more substituents selected from hydroxy, halogen, $C_{1-2}$ alkoxy, amino, mono- and di-$C_{1-2}$ alkylamino, and aryl and heteroaryl groups of 5 to 12 ring members;

or $R^{3b}$ and $R^4$ together form a monocyclic carbocyclic or heterocyclic ring of 5 to 7 ring members;

$R^5$ and $R^6$ together with the nitrogen atom to which they are attached form a bicyclic group having from up to 12 ring members (e.g. 8-12 ring members or 9-10 ring members) of which up to 5 ring members are heteroatoms selected from oxygen, nitrogen and sulphur; and $R^8$ is selected from hydrogen and fluorine.

A further sub-group of compounds for use according to the invention can be represented by the formula (IV):

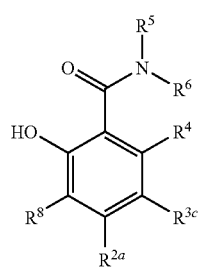

(IV)

or salts, tautomers, solvates and N-oxides thereof; wherein:

$R^{2a}$ is selected from hydroxy and methoxy (and is preferably hydroxy);

$R^{3c}$ is selected from hydrogen, halogen, cyano, $C_{1-5}$ hydrocarbyl and $C_{1-5}$ hydrocarbyloxy; wherein the $C_{1-5}$ hydrocarbyl and $C_{1-5}$ hydrocarbyloxy moieties are each optionally substituted by one or more substituents selected from hydroxy, halogen, $C_{1-2}$ alkoxy, amino, mono- and di-$C_{1-2}$ alkylamino, and aryl and heteroaryl groups of 5 to 12 ring members;

$R^4$ is selected from hydrogen; a group —$(O)_n$—$R^7$ where n is 0 or 1 and $R^7$ is an acyclic $C_{1-5}$ hydrocarbyl group or a monocyclic carbocyclic or heterocyclic group having 3 to 7 ring members; halogen; cyano; hydroxy; amino; and mono- or di-$C_{1-5}$ hydrocarbyl-amino, wherein the acyclic $C_{1-5}$ hydrocarbyl group and the mono and di-$C_{1-5}$ hydrocarbylamino moieties in each instance are optionally substituted by one or more substituents selected from hydroxy, halogen, $C_{1-2}$ alkoxy, amino, mono- and di-$C_{1-2}$ alkylamino, and aryl and heteroaryl groups of 5 to 12 ring members;

or $R^{3c}$ and $R^4$ together form a monocyclic carbocyclic or heterocyclic ring of 5 to 7 ring members;

$R^5$ and $R^6$ together with the nitrogen atom to which they are attached form a bicyclic group having up to 12 ring members (e.g. 8-12 ring members or 9-10 ring members) of which up to 5 ring members are heteroatoms selected from oxygen, nitrogen and sulphur; and $R^8$ is selected from hydrogen and fluorine.

Within formulae (II), (III) and (IV), particular sub-groups of compounds are those wherein $NR^5R^6$ forms a bicyclic ring of up 10 ring members (e.g. 9 or 10 ring members, preferably 9 ring members) of which up to 5 ring members are heteroatoms selected from O, N and S, the monocyclic or bicyclic ring being optionally substituted by up to three substituent groups $R^{10}$, $R^{10a}$, $R^{10b}$, $R^{10c}$ and $R^{10cc}$ as defined herein, more typically up to two substituents, for example up to one substituent.

More particular substituents for the bicyclic heterocyclic group $NR^5R^6$ are those forming part of a sub-group $R^{10d}$ which consists of the members of sub-group $R^{10c}$ and fluoro, chloro, bromo, trifluoromethyl, difluoromethoxy, trifluoromethoxy, cyano, methyl, ethyl, cyclopropyl, hydroxy, methylsulphonyl, amino, methylamino, dimethylamino, methoxy, ethoxy, hydroxymethyl, hydroxyethyl, ethoxycarbonyl, methoxycarbonyl, aminocarbonyl, oxo, methoxymethyl, carboxy, phenyl, alkoxycarbonyl, aminocarbonyl, acetyl, methylsulphonyl and pyridyl. Within this sub-group, one sub-set of substituents includes methyl, ethyl, chloro, fluoro, hydroxy, methylsulphonyl, amino, methylamino, dimethylamino, cyano, methoxy, ethoxy, hydroxymethyl, cyclopropyl, hydroxyethyl, ethoxycarbonyl, methoxycarbonyl, aminocarbonyl, oxo, methoxymethyl and acetyl.

For example, $NR^5R^6$ can form a 5.6 or 6.6 fused bicyclic ring of 9 or ten ring members of which 1 to 3 are heteroatoms, the bicyclic ring being optionally substituted by one or more substituents $R^{10}$ or $R^{10a}$ or $R^{10b}$ or $R^{10c}$ or $R^{10cc}$ or $R^{10d}$ and sub-groups (sub-sets) and examples thereof as defined herein.

Within this sub-group, examples of fused bicyclic rings are those in which a non-aromatic ring such as a pyrrolidine, piperidine, piperazine or morpholine ring is fused to a 6-membered aryl or heteroaryl ring such as a benzene or pyridine ring, and wherein a nitrogen atom present in the non-aromatic ring is bonded to the carbonyl group in formulae (II), (III) or (IV).

Particular fused bicyclic rings include dihydroindole, dihydroisoindole, tetrahydroquinoline and tetrahydroisoquinoline, and aza-analogues thereof in which one or two carbon ring members in the aromatic ring are replaced by nitrogen.

One sub-group of bicyclic heterocyclic groups formed by $NR^5R^6$ consists of dihydroisoindole optionally substituted by one or more (e.g. 1, 2 or 3) optional substituents selected from groups $R^{10}$, $R^{10a}$, $R^{10b}$ and $R^{10c}$ or $R^{10cc}$ and or $R^{10d}$ and sub-groups (sub-sets) and examples thereof as defined herein.

Preferred compounds are those wherein the group $R^{3a}$ or $R^{3b}$ or $R^{3c}$ is selected from hydrogen, halogen and $C_{1-5}$ alkyl; wherein the $C_{1-5}$ alkyl moiety in each instance is optionally substituted by one or more substituents selected from hydroxy, halogen, $C_{1-2}$ alkoxy and amino.

More preferably, the group $R^{3a}$ or $R^{3b}$ or $R^{3c}$ is hydrogen or a $C_{3-5}$ alkyl group optionally substituted by one or more substituents selected from hydroxy, halogen, $C_{1-2}$ alkoxy and amino. In particular, the group $R^{3a}$ or $R^{3b}$ or $R^{3c}$ is selected from hydrogen and isopropyl, sec-butyl, tert-butyl and 1,2-dimethylpropyl groups.

Another sub-group of compounds for use according to the invention is represented by formula (V):

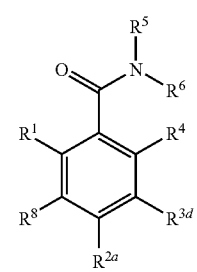

(V)

or salts, tautomers, solvates and N-oxides thereof;

wherein $R^1$ is hydrogen or hydroxy; $R^{2a}$ is hydroxy or methoxy; provided that at least one of $R^1$ and $R^{2a}$ is hydroxy; $R^{3d}$ is selected from ethyl and secondary and tertiary alkyl groups of 3 to 6 carbon atoms; $R^{4a}$ is selected from hydrogen, fluorine, chlorine and methoxy; and $R^5$, $R^6$ and $R^6$ are as defined herein; provided that when $R^1$ and $R^2$ are both hydroxy, then $R^{3d}$ can additionally be selected from hydrogen.

In one embodiment, when $R^1$ and $R^2$ are both hydroxy, $R^{3d}$ is hydrogen.

In another embodiment, $R^{3d}$ is ethyl or a secondary or tertiary alkyl group. Particularly preferred alkyl groups $R^{3d}$ are ethyl, isopropyl and tert-butyl, and in particular isopropyl.

Within formulae (II) to (V), preferred groups $NR^5R^6$ are dihydroisoindole groups which may be substituted or unsubstituted by one, two or three groups $R^{10}$, $R^{10a}$ or $R^{10b}$ or $R^{10c}$ or $R^{10cc}$ or $R^{10d}$ and sub-groups (sub-sets) and examples thereof as defined herein but, in one particular embodiment, are unsubstituted.

Another preferred sub-set of compounds can be represented by formula (VI):

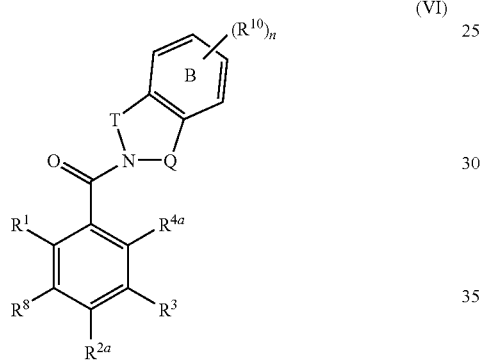

(VI)

or salts, tautomers, solvates and N-oxides thereof;

wherein $R^1$ is hydroxy or hydrogen; $R^{2a}$ is hydroxy or methoxy (preferably hydroxy) provided that at least one of $R^1$ and $R^{2a}$ is hydroxy, ring B is an aromatic ring containing up to two (and preferably 0 or 1) nitrogen heteroatom ring members; T is a group $(CHR^{10})_j$ and Q is a group $(CHR^{10})_k$ where j and k are each 0, 1, 2 or 3 provided that the sum of j and k is 2 or 3; n is 0, 1, 2 or 3 and $R^3$, $R^{4a}$, $R^8$ and $R^{10}$ are as defined herein.

Another preferred sub-set of compounds can be represented by formula (VIa):

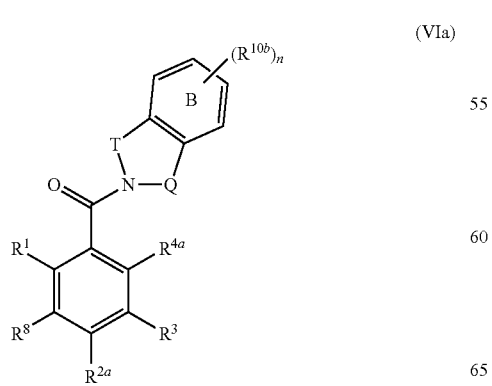

(VIa)

or salts, tautomers, solvates and N-oxides thereof;

wherein $R^1$ is hydroxy or hydrogen; $R^{2a}$ is hydroxy or methoxy (preferably hydroxy) provided that at least one of $R^1$ and $R^{2a}$ is hydroxy, ring B is an aromatic ring containing up to two (and preferably 0 or 1) nitrogen heteroatom ring members; T is a group $(CHR^{10b})_j$ and Q is a group $(CHR^{10b})_k$ where j and k are each 0, 1, 2 or 3 provided that the sum of j and k is 2 or 3; n is 0, 1, 2 or 3 and $R^3$, $R^{4a}$, $R^8$ and $R^{10b}$ are as defined herein.

In one sub-group of compounds within formula (VI) or formula (VIa), $R^1$ is hydrogen.

In another subgroup of compounds within formula (VI) or formula (VIa), $R^1$ is hydroxy.

In formula (VI), examples of the bicyclic group:

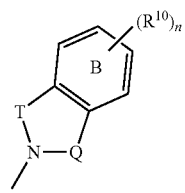

include the groups C1 to C6 below.

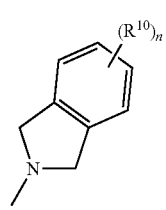

C1

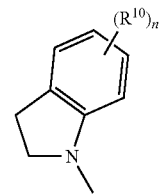

C2

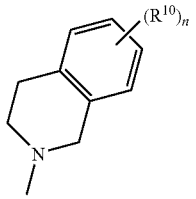

C3

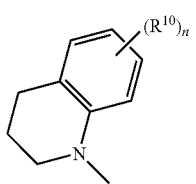

C4

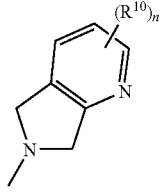
C5

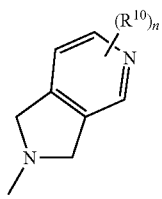
C6

Preferred groups are groups C1, C5 and C6

In the groups C1 to C6, the moiety $R^{10}$ can be a group $R^{10}$ as hereinbefore defined or can be a group $R^{10b}$, $R^{10c}$, $R^{10cc}$ or $R^{10ccc}$ as defined herein. In each case, n is preferably 1, 2 or 3, and more preferably is 1 or 2, e.g. 1.

A currently preferred group is group C1.

Within formula (VI), one particular group of compounds can be represented by the formula (VII):

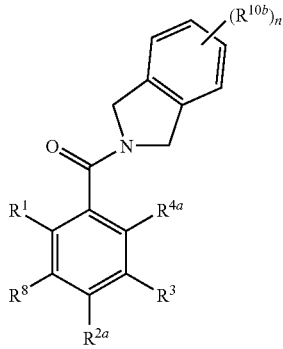
(VII)

or salts, tautomers, solvates and N-oxides thereof;

wherein $R^1$, $R^{2a}$, $R^3$ $R^{4a}$, $R^8$ and $R^{10b}$ are as defined herein and n is 0, 1 2 or 3 (more preferably 0, 1 or 2, e.g. 0 or 1), and provided that at least one of $R^1$ and $R^{2a}$ is hydroxy.

Within formulae (VI) and (VII), the substituent $R^3$ is preferably a group $R^{3d}$ as defined herein and/or the substituent $R^{10b}$ is either absent (n=0) or is selected from groups $R^{10c}$ and $R^{10d}$ and sub-groups (sub-sets) and examples thereof as defined herein. Preferably $R^1$ and $R^{2a}$ are both hydroxy.

One particular group of compounds for use according to the invention within formula (VII) is represented by the formula (VIIa):

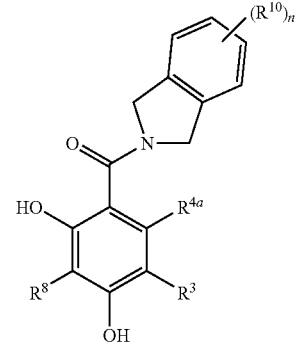
(VIIa)

or salts, tautomers, solvates and N-oxides thereof;

wherein $R^3$ is selected from hydrogen, halogen, $C_{1-5}$ alkyl, $C_{2-5}$ alkenyl and $C_{3-4}$ cycloalkyl groups;

$R^{4a}$ is selected from hydrogen, fluorine, chlorine and methoxy; $R^8$ is hydrogen or fluorine; n is 0, 1 2 or 3; and $R^{10}$ is as defined herein.

Within formula (VIIa), $R^{10}$ can be selected from, for example, one, two or three groups $R^{10a}$ or $R^{10b}$ or $R^{10c}$ or $R^{10cc}$ or $R^{10d}$ and sub-groups (sub-sets) and examples thereof as defined herein.

One preferred group of compounds for use according to the invention within formula (VII) is represented by the formula (VIIb):

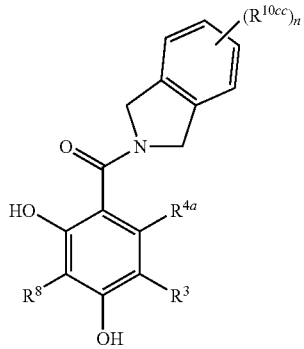
(VIIb)

or salts, tautomers, solvates and N-oxides thereof;

wherein $R^3$ is selected from hydrogen, halogen, $C_{1-5}$ alkyl, $C_{2-5}$ alkenyl and $C_{3-4}$ cycloalkyl groups;

$R^{4a}$ is selected from hydrogen, fluorine, chlorine and methoxy; $R^8$ is hydrogen or fluorine; n is 0, 1 2 or 3; and $R^{10cc}$ is selected from:

halogen;

$CO_2R^{14}$ wherein $R^{14}$ is hydrogen or $C_{1-6}$ alkyl;

$C_{1-4}$ alkyl optionally substituted by hydroxy or $C_{1-2}$ alkoxy;

$C_{1-4}$ alkoxy optionally substituted by hydroxy or $C_{1-2}$ alkoxy; or a group [sol], $CH_2$[sol], $C(O)$[sol], $OCH_2CH_2$[sol] or $OCH_2CH_2CH_2$[sol] where [sol] is selected from the following groups

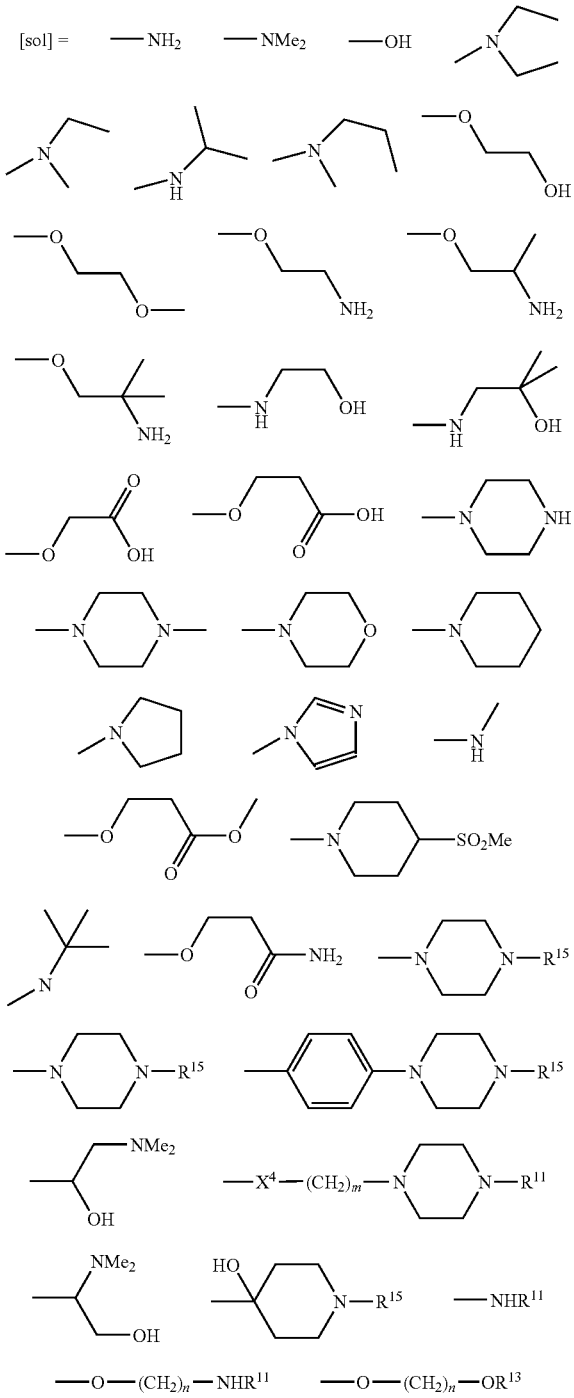

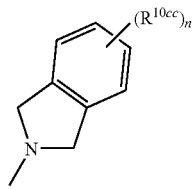

For example, the group:

in the compound of formula (VIIa) may be replaced by:

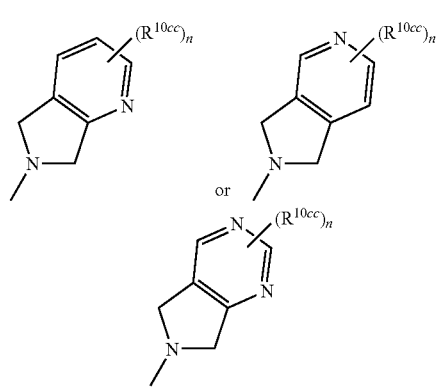

or or

In each of formulae (VI), (VIa), (VII), (VIIa) and (VIIb) and sub-groups thereof as defined herein, n is preferably 1, 2 or 3, and more preferably is 1 or 2. In one embodiment, n is 1.

Specific compounds for use according to the invention include:
(5-chloro-2-hydroxy-phenyl)-(1,3-dihydro-isoindol-2-yl)-methanone;
(3-tert-butyl-4-hydroxy-phenyl)-(2,3-dihydro-indol-1-yl)-methanone;
(3-tert-butyl-4-hydroxy-phenyl)-(3,4-dihydro-2H-quinolin-1-yl)-methanone;
(3,4-dihydro-1H-isoquinolin-2-yl)-(4-hydroxy-3-isopropyl-phenyl)-methanone;
(1,3-dihydro-isoindol-2-yl)-(2,4-dihydroxy-5-isopropyl-phenyl)-methanone;
(3-tert-butyl-4-hydroxy-phenyl)-(1,4-dioxa-8-aza-spiro[4.5]dec-8-yl)-methanone;
(3-tert-butyl-4-hydroxy-phenyl)-(1,3-dihydro-isoindol-2-yl)-methanone;
(3-tert-butyl-4-hydroxy-phenyl)-pyrrolo[3,2-b]pyridin-1-yl-methanone;
8-(3-tert-butyl-4-hydroxy-benzoyl)-2-methyl-2,8-diaza-spiro[4.5]decan-1-one;
(1,3-dihydro-isoindol-2-yl)-(4-hydroxy-3-isopropyl-phenyl)-methanone;
(3-tert-butyl-4-hydroxy-phenyl)-(3,4-dihydro-1H-isoquinolin-2-yl)-methanone;
(1,3-dihydro-isoindol-2-yl)-(5-ethyl-2,4-dihydroxy-phenyl)-methanone;
(5-cyclopropyl-2,4-dihydroxy-phenyl)-(1,3-dihydro-isoindol-2-yl)-methanone;
(5-sec-butyl-2,4-dihydroxy-phenyl)-(1,3-dihydro-isoindol-2-yl)-methanone;
(1,3-dihydro-isoindol-2-yl)-(2,4-dihydroxy-phenyl)-methanone;
(5-chloro-1,3-dihydro-isoindol-2-yl)-(2,4-dihydroxy-5-isopropyl-phenyl)-methanone;

wherein $X^4$ is NH or O, m is 0 or 1, n is 1, 2 or 3, $R^{11}$ is hydrogen, $COR^{12}$, $C(O)OR^{12}$ or $R^{12}$; $R^{12}$ is $C_{1-6}$ alkyl, $C_{3-6}$ cycloalkyl, aryl, aryl-$C_{1-6}$ alkyl or $CH_2R^{15}$; and $R^{15}$ is selected from hydrogen, $C_{1-6}$ alkyl, $C_{3-6}$ cycloalkyl, hydroxy-$C_{1-6}$ alkyl, piperidine, N—$C_{1-6}$alkylpiperazine, piperazine, morpholine, $COR^{13}$ or $C(O)OR^{13}$; and $R^{13}$ is $C_{1-6}$ alkyl.

In a further embodiment, the compound can be an aza- or diaza-analogue of the compounds of formulae (VI), (VII) and (VIIa) as defined herein wherein one or two of the carbon atoms of the benzene ring attached to the five membered ring is replaced by nitrogen.

[5-(3-amino-propoxy)-1,3-dihydro-isoindol-2-yl]-(2,4-dihydroxy-5-isopropyl-phenyl)-methanone;
(5-Bromo-2,4-dihydroxy-phenyl)-(1,3-dihydro-isoindol-2-yl)-methanone;
(1,3-Dihydro-isoindol-2-yl)-(2,4-dihydroxy-5-trifluoromethyl-phenyl)-methanone;
(2,4-Dihydroxy-5-isopropyl-phenyl)-{4-[2-(2-methoxy-ethoxy)-ethoxy]-1,3-dihydro-isoindol-2-yl}methanone;
(2,4-Dihydroxy-5-isopropyl-phenyl)-[4-(2-dimethylamino-ethoxy)-1,3-dihydro-isoindol-2-yl]-methanone;
(2,4-Dihydroxy-5-isopropyl-phenyl)-[4-(3-morpholin-4-yl-propoxy)-1,3-dihydro-isoindol-2-yl]methanone;
(3-sec-Butyl-4-hydroxy-phenyl)-(1,3-dihydro-isoindol-2-yl)-methanone;
(5-tert-Butyl-2,4-dihydroxy-phenyl)-(1,3-dihydro-isoindol-2-yl)-methanone;
(5-Chloro-2,4-dihydroxy-phenyl)-(1,3-dihydro-isoindol-2-yl)-methanone;
(1,3-Dihydro-isoindol-2-yl)-(2-hydroxy-5-isopropyl-4-methoxy-phenyl)-methanone;
(4,7-difluoro-1,3-dihydro-isoindol-2-yl)-(2,4-dihydroxy-5-isopropyl-phenyl)-methanone;
(2,4-dihydroxy-5-isopropyl-phenyl)-(5-fluoro-1,3-dihydro-isoindol-2-yl)-methanone;
(1,3-dihydro-isoindol-2-yl)-(3-fluoro-2,4-dihydroxy-5-isopropyl-phenyl)-methanone;
(1,3-dihydro-isoindol-2-yl)-(2-fluoro-4,6-dihydroxy-3-isopropyl-phenyl)-methanone;
(2,4-dihydroxy-5-isopropyl-phenyl)-(4-fluoro-1,3-dihydro-isoindol-2-yl)-methanone hydrochloride;
(5-chloro-6-methoxy-1,3-dihydro-iso-indol-2-yl)-(2,4-dihydroxy-5-isopropyl-phenyl)-methanone;
(2,4-dihydroxy-5-isopropyl-phenyl)-[5-(2-methoxy-ethoxy)-1,3-dihydro-isoindol-2-yl]-methanone;
(2,4-dihydroxy-5-isopropyl-phenyl)-[5-(3-morpholin-4-yl-propoxy)-1,3-dihydro-isoindol-2-yl]-methanone;
(2,4-dihydroxy-5-isopropyl-phenyl)-[5-(2-dimethylamino-ethoxy)-1,3-dihydro-isoindol-2-yl]-methanone;
(2,4-dihydroxy-5-isopropyl-phenyl)-(2-oxa-5-aza-bicyclo[2.2.1]hept-5-yl)-methanone;
(3,4-dihydro-1H-isoquinolin-2-yl)-(2,4-dihydroxy-5-isopropyl-phenyl)-methanone;
(5-amino-1,3-dihydro-isoindol-2-yl)-(2,4-dihydroxy-5-isopropyl-phenyl)-methanone;
(2,4-dihydroxy-5-isopropyl-phenyl)-(5-methoxy-1,3-dihydro-isoindol-2-yl)-methanone;
(2,4-dihydroxy-5-isopropyl-phenyl)-(5-morpholin-4-yl-1,3-dihydro-isoindol-2-yl)-methanone;
(2,4-dihydroxy-5-isopropyl-phenyl)-[5-(4-methyl-piperazin-1-yl)-1,3-dihydro-isoindol-2-yl]-methanone;
2-(2,4-dihydroxy-5-isopropyl-benzoyl)-2,3-dihydro-1H-isoindole-5-carboxylic acid methyl ester;
2-(2,4-dihydroxy-5-isopropyl-benzoyl)-2,3-dihydro-1H-isoindole-5-carboxylic acid;
(2,4-dihydroxy-5-isopropyl-phenyl)-(5-morpholin-4-ylmethyl-1,3-dihydro-isoindol-2-yl)-methanone;
{3-[2-(2,4-dihydroxy-5-isopropyl-benzoyl)-2,3-dihydro-1H-isoindol-5-yloxy]-propyl}-carbamic acid tert-butyl ester;
(2,4-dihydroxy-5-isopropyl-phenyl)-(5-methyl-1,3-dihydro-isoindol-2-yl)-methanone;
(2,4-dihydroxy-5-isopropyl-phenyl)-[5-(2-isopropylamino-ethoxy)-1,3-dihydro-isoindol-2-yl]-methanone;
N-{2-[2-(2,4-dihydroxy-5-isopropyl-benzoyl)-2,3-dihydro-1H-isoindol-5-yloxy]-ethyl}-2-morpholin-4-yl-acetamide;
(2,4-dihydroxy-5-isopropyl-phenyl)-[5-(4-hydroxy-1-methyl-piperidin-4-yl)-1,3-dihydro-isoindol-2-yl]-methanone;
(2,4-dihydroxy-5-isopropyl-phenyl)-{5-[4-(4-methyl-piperazin-1-yl)-piperidin-1-yl]-1,3-dihydro-isoindol-2-yl}-methanone;
(2,4-dihydroxy-5-isopropyl-phenyl)-[5-(4-piperazin-1-yl-phenyl)-1,3-dihydro-isoindol-2-yl]-methanone;
2,4-dihydroxy-5-isopropyl-phenyl)-[5-(1-dimethylamino-2-hydroxy-ethyl)-1,3-dihydro-isoindol-2-yl]-methanone;
dihydroxy-5-isopropyl-phenyl)-[5-(2-dimethylamino-1-hydroxy-ethyl)-1,3-dihydro-isoindol-2-yl]-methanone;
(2,4-dihydroxy-5-isopropyl-phenyl)-[5-(piperazine-1-carbonyl)-1,3-dihydro-isoindol-2-yl]-methanone hydrochloride;
(2,4-dihydroxy-5-isopropyl-phenyl)-[5-(4-methyl-piperazin-1-ylmethyl)-1,3-dihydro-isoindol-2-yl]-methanone;
(2,4-dihydroxy-5-isopropyl-phenyl)-[4-(3-morpholin-4-yl-propoxy)-1,3-dihydro-isoindol-2-yl]methanone;
[5-(2-Amino-ethoxy)-1,3-dihydro-isoindol-2-yl]-(2,4-dihydroxy-5-isopropyl-phenyl)-methanone;
(2,4-Dihydroxy-5-isopropyl-phenyl)-(5-hydroxy-1,3-dihydro-isoindol-2-yl)-methanone;
(2,4-Dihydroxy-5-isopropyl-phenyl)-{5-[4-(2-hydroxy-ethyl)-piperazin-1-yl]-1,3-dihydro-isoindol-2-yl}-methanone;
(2,4-Dihydroxy-5-isopropyl-phenyl)-[5-(4-morpholin-4-yl-piperidin-1-yl)-1,3-dihydro-isoindol-2-yl]-methanone;
(2,4-Dihydroxy-5-isopropyl-phenyl)-[5-(1-methyl-piperidin-4-ylamino)-1,3-dihydro-isoindol-2-yl]-methanone;
(2,4-Dihydroxy-5-isopropyl-phenyl)-[5-(4-isopropyl-piperazin-1-yl)-1,3-dihydro-isoindol-2-yl]-methanone;
(2,4-Dihydroxy-5-isopropyl-phenyl)-(5-piperazin-1-yl-1,3-dihydro-isoindol-2-yl)-methanone;
4-[2-(2,4-Dihydroxy-5-isopropyl-benzoyl)-2,3-dihydro-1H-isoindol-5-ylamino]-piperidine-1-carboxylic acid tert-butyl ester;
(2,4-dihydroxy-5-isopropyl-phenyl)-[5-(piperidin-4-ylamino)-1,3-dihydro-isoindol-2-yl]-methanone;
(2,4-dihydroxy-5-isopropyl-phenyl)-[4-(4-methyl-piperazin-1-yl)-1,3-dihydro-isoindol-2-yl]-methanone;
(2,4-dihydroxy-5-isopropyl-phenyl)-[4-(piperidin-4-ylamino)-1,3-dihydro-isoindol-2-yl]-methanone;
(2,4-Dihydroxy-5-isopropyl-phenyl)-(5-dimethylaminomethyl-1,3dihydroisoindol-2-yl)-methanone;
(2,4-Dihydroxy-5-isopropyl-phenyl)-[5-(4-methyl-piperazine-1-carbonyl)-1,3-dihydro-isoindol-2-yl]-methanone;
(2,4-Dihydroxy-5-isopropyl-phenyl)-{5-[2-(2,2-dimethyl-propylamino)-ethoxy]-1,3-dihydro-isoindol-2-yl}-methanone;
[5-(2-Cyclopentylamino-ethoxy)-1,3-dihydro-isoindol-2-yl]-(2,4-dihydroxy-5-isopropyl-phenyl)-methanone;
(2,4-Dihydroxy-5-isopropyl-phenyl)-(5-piperidin-1-ylmethyl-1,3-dihydro-isoindol-2-yl)-methanone;
(2,4-Dihydroxy-5-isopropyl-phenyl)-[5-(4-hydroxypiperidin-4-yl)-1,3-dihydro-isoindol-2-yl]-methanone;
(5-Chloro-2,4-dihydroxy-phenyl)-[5-(4-methyl-piperazin-1-yl)-1,3-dihydro-isoindol-2-yl]methanone; and
(5-chloro-6-hydroxy-1,3-dihydro-isoindol-2-yl)-(2,4-dihydroxy-5-isopropyl-phenyl)-methanone;
(2,4-dihydroxy-5-isopropyl-phenyl)-[5-(4-methyl-piperazin-1-yl)-1,3-dihydro-isoindol-2-yl]-methanone;
(5-chloro-2,4-dihydroxy-phenyl)-[5-(4-methyl-piperazin-1-yl)-1,3-dihydro-isoindol-2-yl]methanone;
(2,4-dihydroxy-5-isopropyl-phenyl)-[5-(2-dimethylamino-ethoxy)-7-methyl-1,3-dihydro-isoindol-2-yl]-methanone;
and salts, solvates, N-oxides and tautomers thereof.

Preferred individual compounds of the formula (I) are:
(2,4-dihydroxy-5-isopropyl-phenyl)-[5-(2-dimethylamino-ethoxy)-1,3-dihydro-isoindol-2-yl]-methanone;
(2,4-dihydroxy-5-isopropyl-phenyl)-[5-(4-methyl-piperazin-1-yl)-1,3-dihydro-isoindol-2-yl]-methanone;
(2,4-dihydroxy-5-isopropyl-phenyl)-[5-(4-hydroxy-1-methyl-piperidin-4-yl)-1,3-dihydro-isoindol-2-yl]-methanone;
(2,4-dihydroxy-5-isopropyl-phenyl)-[5-(4-methyl-piperazin-1-ylmethyl)-1,3-dihydro-isoindol-2-yl]-methanone;
(2,4-dihydroxy-5-isopropyl-phenyl)-[5-(1-methyl-piperidin-4-ylamino)-1,3-dihydro-isoindol-2-yl]-methanone;
(2,4-dihydroxy-5-isopropyl-phenyl)-(5-piperazin-1-yl-1,3-dihydro-isoindol-2-yl)-methanone;
(2,4-dihydroxy-5-isopropyl-phenyl)-(5-dimethylaminomethyl-1,3dihydroisoindol-2-yl)-methanone;
or salts, solvates, N-oxides and tautomers thereof.

A particularly preferred set of individual compounds consists of:
(2,4-dihydroxy-5-isopropyl-phenyl)-[5-(4-hydroxy-1-methyl-piperidin-4-yl)-1,3-dihydro-isoindol-2-yl]-methanone;
(2,4-dihydroxy-5-isopropyl-phenyl)-[5-(4-methyl-piperazin-1-ylmethyl)-1,3-dihydro-isoindol-2-yl]-methanone; and
(2,4-dihydroxy-5-isopropyl-phenyl)-[5-(1-methyl-piperidin-4-ylamino)-1,3-dihydro-isoindol-2-yl]-methanone;
or salts, solvates or tautomers thereof.

For the avoidance of doubt, it is to be understood that each general and specific preference, embodiment and example of the group $R^1$ may be combined with each general and specific preference, embodiment and example of the groups $R^2$ and/or $R^3$ and/or $R^4$ and/or $R^4$ and/or $R^5$ and/or $R^6$ and/or $R^{10}$ and/or Q and/or T and/or sub-groups thereof as defined herein and that all such combinations are embraced by this application.

The various functional groups and substituents making up the compounds of the formula (I) are typically chosen such that the molecular weight of the compound of the formula (I) does not exceed 1000. More usually, the molecular weight of the compound will be less than 750, for example less than 700, or less than 650, or less than 600, or less than 550. More preferably, the molecular weight is less than 525 and, for example, is 500 or less.

One preferred compound of the formula (I) is the compound of formula (1):

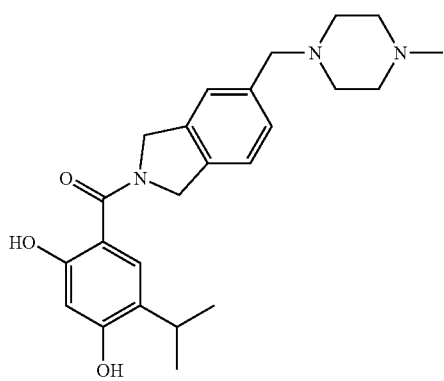

(1)

which has the chemical name (2,4-dihydroxy-5-isopropyl-phenyl)-[5-(4-methyl-piperazin-1-ylmethyl)-1,3-dihydro-isoindol-2-yl]-methanone (including acid addition salts, particularly the L-lactate, and crystalline forms thereof).

Acid Addition Salts of 2,4-dihydroxy-5-isopropyl-phenyl)-[5-(4-methyl-piperazin-1-ylmethyl)-1,3-dihydro-isoindol-2-yl]-methanone The 2,4-dihydroxy-5-isopropyl-phenyl)-[5-(4-methyl-piperazin-1-ylmethyl)-1,3-dihydro-isoindol-2-yl]-methanone may be presented in the form of an acid addition salt.

Acid addition salts may be formed with a wide variety of acids, both inorganic and organic. Examples of acid addition salts include salts formed with an acid selected from the group consisting of acetic, 2,2-dichloroacetic, adipic, alginic, ascorbic (e.g. L-ascorbic), aspartic (e.g. L-aspartic), benzenesulphonic, benzoic, 4-acetamidobenzoic, butanoic, camphoric (e.g. (+) camphoric), camphor-sulphonic, (+)-(1S)-camphor-10-sulphonic, capric, caproic, caprylic, carbonic, cinnamic, citric, cyclamic, dodecanoic, dodecylsulphuric, ethane-1,2-disulphonic, ethanesulphonic, 2-hydroxyethanesulphonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrobromic, hydrochloric, hydriodic, isethionic, isobutyric, lactic (e.g. (+)-L-lactic [which may be referred to elsewhere herein simply as L-lactic acid] and (±)-DL-lactic), laurylsulphonic, lactobionic, maleic, malic, (−)-L-malic, malonic, (±)-DL-mandelic, methanesulphonic, mucic, naphthalenesulphonic (e.g. naphthalene-2-sulphonic and naphthalene-1,5-disulphonic), 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulphuric, tannic, tartaric (e.g. (+)-L-tartaric), thiocyanic, toluenesulphonic (e.g. p-toluenesulphonic), undecylenic, valeric acids and xinafoic acids.

Particular acid addition salts are the salts formed with hydrochloric acid, lactic acid (e.g. L-lactic acid) or sulphuric acid.

A preferred salt is the salt formed with lactic acid, i.e. the lactate salt and in particular the L-lactate salt.

The acid addition salts are typically pharmaceutically acceptable salts, and examples of pharmaceutically acceptable salts are discussed in Berge et al., 1977, "Pharmaceutically Acceptable Salts," J. Pharm. Sci., Vol. 66, pp. 1-19.

In the solid state, the acid addition salts can be crystalline or amorphous or a mixture thereof.

In one embodiment, the salts are amorphous.

In an amorphous solid, the three dimensional structure that normally exists in a crystalline form does not exist and the positions of the molecules relative to one another in the amorphous form are essentially random, see for example Hancock et al. J. Pharm. Sci. (1997), 86, 1).

In another embodiment, the acid addition salts are substantially crystalline.

The acid addition salts can be synthesized from the parent compound by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free base form of the compound of formula (1) with the appropriate acid in water or in an organic solvent, or in a mixture of the two.

For example, the acid addition salt can be prepared by forming a solution of (2,4-dihydroxy-5-isopropyl-phenyl)-[5-(4-methyl-piperazin-1-ylmethyl)-1,3-dihydro-isoindol-2-yl]-methanone free base in a solvent (typically an organic solvent) or mixture of solvents, and treating the solution with an acid to form a precipitate of the acid addition salt.

The acid may be added as a solution in a solvent which is miscible with the solvent in which the free base is dissolved. The solvent in which the free base is initially dissolved may be one in which the acid addition salt thereof is insoluble. Alternatively, the solvent in which the free base is initially dissolved may be one in which the acid addition salt is at least partially soluble, a different solvent in which the acid addition salt is less soluble subsequently being added such that the salt precipitates out of solution.

In an alternative method of forming an acid addition salt, (2,4-dihydroxy-5-isopropyl-phenyl)-[5-(4-methyl-piperazin-1-ylmethyl)-1,3-dihydro-isoindol-2-yl]-methanone is dissolved in a solvent comprising a volatile acid and optionally a co-solvent, thereby to form a solution of the acid addition salt with the volatile acid, and the resulting solution is then concentrated or evaporated to isolate the salt. An example of an acid addition salt that can be made in this way is the acetate salt.

The salt is typically precipitated from the organic solvent as it is formed and hence can be isolated by separation of the solid from the solution, e.g. by filtration.

One acid salt can be converted to the free base and optionally to another acid addition salt by methods well known to the skilled person. For example, the free base can be formed by passing the salt solution through a column containing an amine stationary phase (e.g. a Strata-NH2 column). Alternatively, a solution of the acid addition salt in water can be treated with sodium bicarbonate to decompose the salt and precipitate out the free base. The free base may then be combined with another acid by one of the methods described above or elsewhere herein.

Acid addition salts have a number of advantages over the corresponding free base. For example, they will enjoy one or more of the following advantages over the free base in that they:

will be more soluble and hence will be better for i.v. administration (e.g. by infusion)
will have better stability (e.g. improved shelf life);
will have better thermal stability;
will be less basic and therefore better for i.v. administration;
will have advantages for production;
will have improved solubility in aqueous solution;
will have better physicochemical properties;
may have improved anti-cancer activity; and
may have an improved therapeutic index.

Particular advantages of the L-lactate salt of the compound of formula (1) are that it:

is not hydrated and therefore is easier to formulate;
has fewer polymorphic forms than the free base and other salt forms tested (i.e. the salts formed with hydrochloric acid and sulphuric acid);
is non-hygroscopic; and
has a better rate of solubility than the free base and other salts tested.

The term 'stable' or 'stability' as used herein includes chemical stability and solid state (physical) stability. The term 'chemical stability' means that the compound can be stored in an isolated form, or in the form of a formulation in which it is provided in admixture with for example, pharmaceutically acceptable carriers, diluents or adjuvants as described herein, under normal storage conditions, with little or no chemical degradation or decomposition' for example for a period of six months or more, more usually twelve months or more, for example eighteen months or more.

'Solid-state stability' means the compound can be stored in an isolated solid form, or the form of a solid formulation in which it is provided in admixture with, for example, pharmaceutically acceptable carriers, diluents or adjuvants as described herein, under normal storage conditions, with little or no solid-state transformation (e.g. hydration, dehydration, solvatisation, desolvatisation, crystallisation, recrystallisation or solid-state phase transition).

The terms "non-hygroscopic" and "non-hygroscopicity" and related terms as used herein refer to substances that absorb less than 5% by weight (relative to their own weight) of water when exposed to conditions of high relative humidity, for example 90% relative humidity, and/or do not undergo changes in crystalline form in conditions of high humidity and/or do not absorb water into the body of the crystal (internal water) in conditions of high relative humidity.

Crystalline Forms of 2,4-dihydroxy-5-isopropyl-phenyl)-[5-(4-methyl-piperazin-1-ylmethyl)-1,3-dihydro-isoindol-2-yl]-methanone In another preferred embodiment, the compound of formula (1) i.e. (2,4-dihydroxy-5-isopropyl-phenyl)-[5-(4-methyl-piperazin-1-ylmethyl)-1,3-dihydro-isoindol-2-yl]-methanone, or an acid addition salt thereof, is presented in substantially crystalline form.

By "substantially crystalline" is meant that the compound of formula (1) or its acid addition salt are from 50% to 100% crystalline, and more particularly the compound of formula (1) or its acid addition salts may be at least 50% crystalline, or at least 60% crystalline, or at least 70% crystalline, or at least 80% crystalline, or at least 90% crystalline, or at least 95% crystalline, or at least 98% crystalline, or at least 99% crystalline, or at least 99.5% crystalline, or at least 99.9% crystalline, for example 100% crystalline.

More preferably the compound of formula (1) or its acid addition salts are those (or may be selected from the group consisting of those) that are 95% to 100% crystalline, for example at least 98% crystalline, or at least 99% crystalline, or at least 99.5% crystalline, or at least 99.6% crystalline or at least 99.7% crystalline or at least 99.8% crystalline or at least 99.9% crystalline, for example 100% crystalline.

The crystalline forms, in the solid state, can be solvated (e.g. hydrated) or non-solvated (e.g. anhydrous).

In one embodiment, the crystalline forms are non-solvated (e.g. anhydrous).

The term "anhydrous" as used herein does not exclude the possibility of the presence of some water on or in the salt (e.g a crystal of the salt). For example, there may be some water present on the surface of the salt (e.g. salt crystal), or minor amounts within the body of the salt (e.g. crystal). Typically, an anhydrous form contains fewer than 0.4 molecules of water per molecule of compound, and more preferably contains fewer than 0.1 molecules of water per molecule of compound, for example 0 molecules of water.

In another embodiment, the crystalline forms are solvated. Where the crystalline forms are hydrated, they can contain, for example, up to three molecules of water of crystallisation, more usually up to two molecules of water, e.g. one molecule of water or two molecules of water. Non-stoichiometric hydrates may also be formed in which the number of molecules of water present is less than one or is otherwise a non-integer. For example, where there is less than one molecule of water present, there may be for example 0.4, or 0.5, or 0.6, or 0.7, or 0.8, or 0.9 molecules of water present per molecule of compound.

Other solvates include alcoholates such as ethanolates and isopropanolates.

The crystalline forms described herein, individual crystals thereof and their crystal structures form further aspects of the invention.

The crystalline forms and their crystal structures can be characterised using a number of techniques including single crystal X-ray crystallography, X-ray powder diffraction (XRPD), differential scanning calorimetry (DSC) and infra red spectroscopy, e.g. Fourier Transform infra-red spectroscopy (FTIR). The behaviour of the crystals under conditions of varying humidity can be analysed by gravimetric vapour sorption studies and also by XRPD.

Determination of the crystal structure of a compound can be performed by X-ray crystallography which can be carried out according to conventional methods, such as those described herein and in Fundamentals of Crystallography, C. Giacovazzo, H. L. Monaco, D. Viterbo, F. Scordari, G. Gilli, G. Zanotti and M. Catti, (International Union of Crystallography/Oxford University Press, 1992 ISBN 0-19-855578-4 (p/b), 0-19-85579-2 (h/b)). This technique involves the analysis and interpretation of the X-ray diffraction of single crystal.

Alternatively, the crystalline structure of a compound can be analysed by the solid state technique of X-ray Powder Diffraction (XRPD). XRPD can be carried out according to conventional methods such as those described herein and in Introduction to X-ray Powder Diffraction, Ron Jenkins and Robert L. Snyder (John Wiley & Sons, New York, 1996). The presence of defined peaks (as opposed to random background noise) in an XRPD diffractogram indicates that the compound has a degree of crystallinity.

A compound's X-ray powder pattern is characterised by the diffraction angle ($2\theta$) and interplanar spacing (d) parameters of an X-ray diffraction spectrum. These are related by Bragg's equation, $n\lambda = 2d \sin\theta$, (where $n=1$; $\lambda$=wavelength of the cathode used; d=interplanar spacing; and $\theta$=diffraction angle). Herein, interplanar spacings, diffraction angle and overall pattern are important for identification of crystal in the X-ray powder diffraction, due to the characteristics of the data. The relative intensity should not be strictly interpreted since it may be varied depending on the direction of crystal growth, particle sizes and measurement conditions. In addition, the diffraction angles usually mean ones which coincide in the range of $2\theta \pm 0.2°$. The peaks mean main peaks and include peaks not larger than medium at diffraction angles other than those stated above.

The compound of formula (1) and its acid addition salts exist in a number of different crystalline forms and these are described in more detail in our co-pending GB 0620259.2 and U.S. provisional patent application Ser. No. 60/829,243, both filed on 12 Oct. 2006.

Particular crystalline salts of interest are the L-lactate salts described below.

Crystalline forms of the salts formed between (2,4-dihydroxy-5-isopropyl-phenyl)-[5-(4-methyl-piperazin-1-ylmethyl)-1,3-dihydro-isoindol-2-yl]-methanone and L-lactic acid The lactic acid salts of the compound of formula (1) exist in one unstable form (FL3) and two stable forms (FL1 and FL2).

Form FL1

In another embodiment, the combination of the invention comprises (2,4-dihydroxy-5-isopropyl-phenyl)-[5-(4-methyl-piperazin-1-ylmethyl)-1,3-dihydro-isoindol-2-yl]-methanone L-lactate salt in a crystalline form characterised by an XRPD pattern having a diffraction angle ($2\theta/°$) peak at 16.81.

Preferably, the XRPD pattern also exhibits diffraction angle ($2\theta/°$) peaks at 6.53, 13.10, 14.13, 14.40, 17.22, 18.65, 19.52, 19.82, 22.33, 22.84 and 23.09.

More preferably, the XRPD pattern further exhibits diffraction angle ($2\theta/°$) peaks at 6.18, 8.39, 11.08, 15.21, 16.21, 20.49, 20.76, 21.13, 22.02, 23.94, 25.19, 26.41, 26.95 and 27.81.

Figure 4:
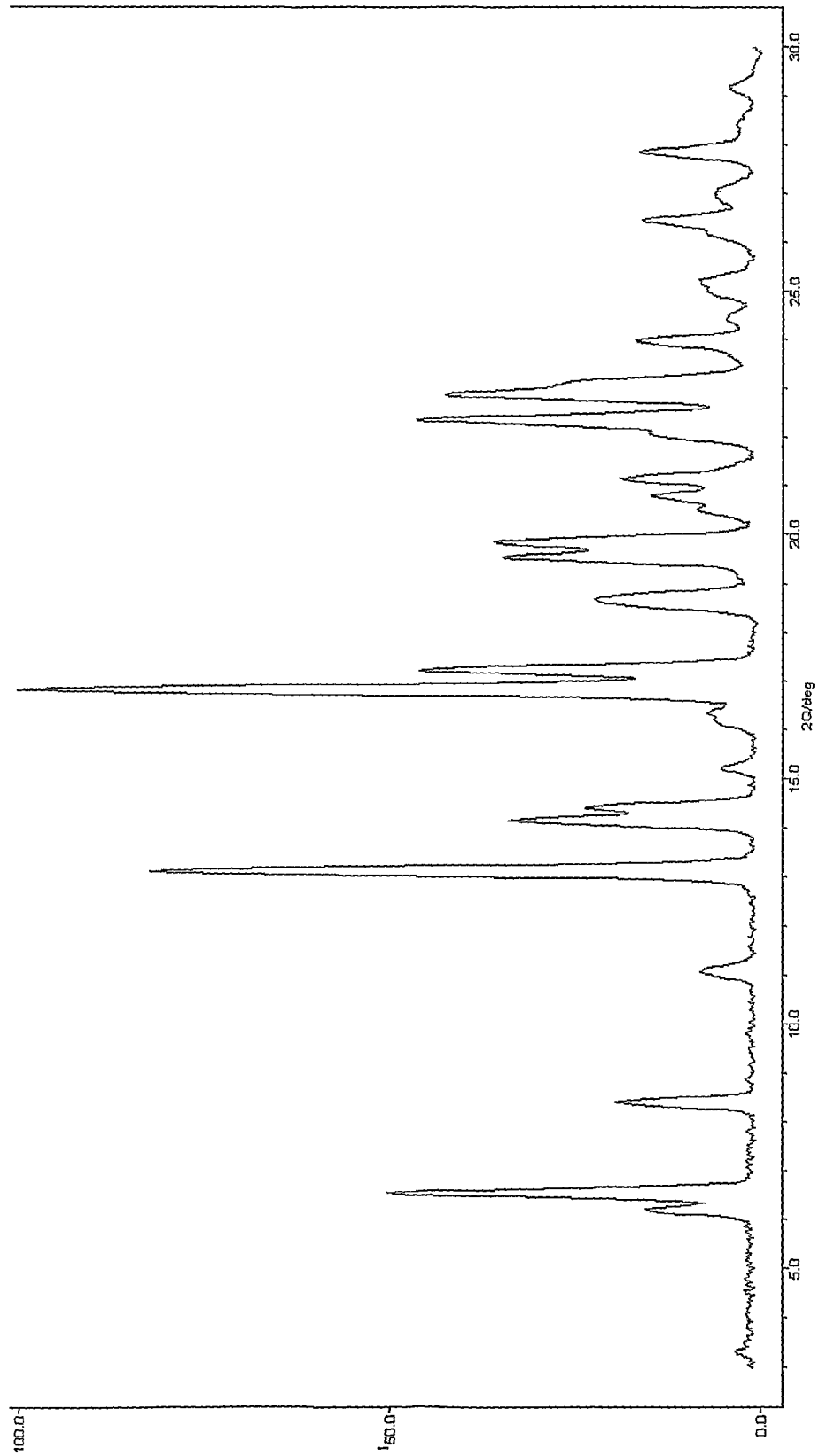
FIG. 4 shows the XRPD pattern for form FL1 of (2,4-dihydroxy-5-isopropyl-phenyl)-[5-(4-methyl-piperazin-1-ylmethyl)-1,3-dihydro-isoindol-2-yl]-methanone L-lactate.

Most preferably, the XRPD pattern is substantially as shown in FIG. 4 herein.

Form FL1 can be prepared by suspending (2,4-dihydroxy-5-isopropyl-phenyl)-[5-(4-methyl-piperazin-1-ylmethyl)-1,3-dihydro-isoindol-2-yl]-methanone free base in a mixture of ethanol and EtOAc (e.g. in a volume ratio of 3:5); adding L-lactic acid to the mixture (e.g. wherein the L-lactic acid is in the form of a solution in ethanol); clarifying the mixture (e.g. by heating until clear and/or filtering off any remaining solid); stirring the clarified mixture with seeding and removing crystallised form FL1, e.g. by filtration.

Form FL2

In another embodiment, the combination of the invention comprises (2,4-dihydroxy-5-isopropyl-phenyl)-[5-(4-methyl-piperazin-1-ylmethyl)-1,3-dihydro-isoindol-2-yl]-methanone L-lactate salt in a crystalline form characterised by an XRPD pattern having a diffraction angle)($2\theta/°$) peak at 22.34.

Preferably, the XRPD pattern also exhibits diffraction angle)($2\theta/°$) peaks at 8.03, 10.71, 11.98, 13.13, 15.39, 16.09, 16.61, 17.26, 18.17, 18.82, 20.40, 21.01, 21.53, 22.34, 22.56, 23.71 and 27.70.

More preferably, the XRPD pattern further exhibits diffraction angle)($2\theta/°$) peaks at 24.30, 24.65, 26.56 and 28.29.

Figure 5:
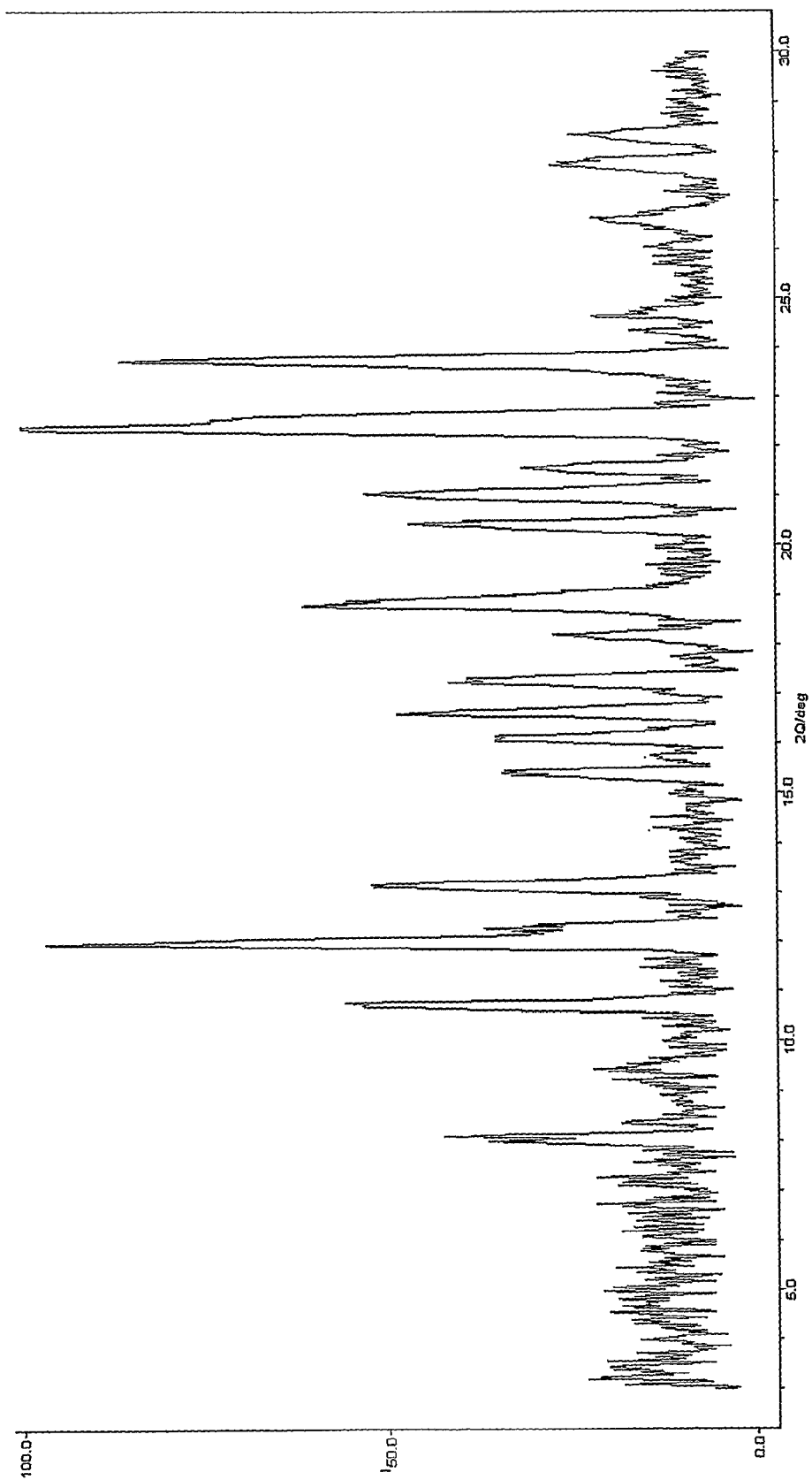
FIG. 5 shows shows the XRPD pattern for form FL2 of (2,4-dihydroxy-5-isopropyl-phenyl)-[5-(4-methyl-piperazin-1-ylmethyl)-1,3-dihydro-isoindol-2-yl]-methanone L-lactate.

Most preferably, the XRPD pattern is substantially as shown in FIG. 5 herein.

From X-ray crystallography studies, it has been found that form FL2 has a crystal structure that belongs belong to the monoclinic space group $P2_1$ and has crystal lattice parameters at 293 K a=5.8 b=16.6, c=14.9 Å, $\beta=98$ $\alpha=\gamma=90°$. The crystal packing diagram for FL2 is shown in FIG. 6 herein.

Figure 6:
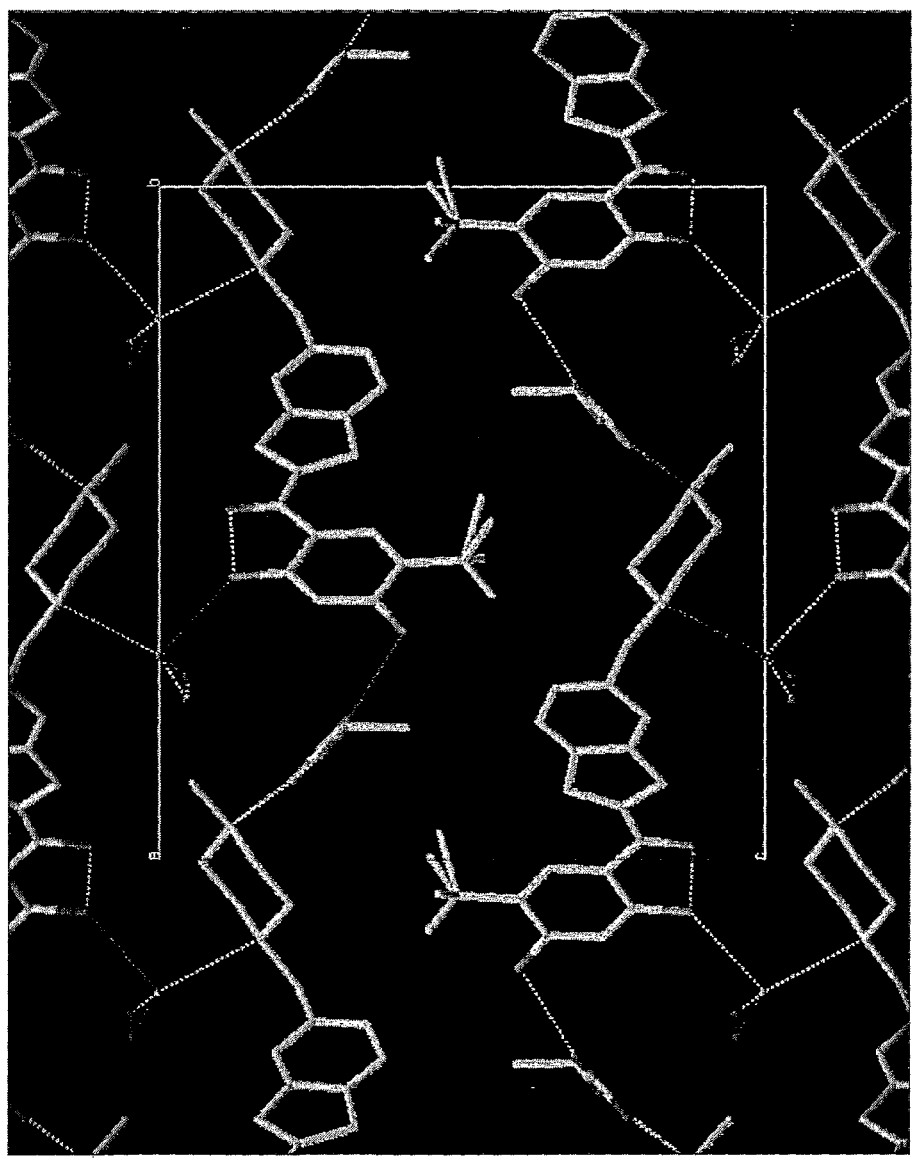
FIG. 6 is the crystal packing diagram for FL2.

Accordingly, in another embodiment, the combination of the invention comprises (2,4-dihydroxy-5-isopropyl-phenyl)-[5-(4-methyl-piperazin-1-ylmethyl)-1,3-dihydro-isoindol-2-yl]-methanone L-lactate which is crystalline and:

(a) has a crystal structure as set out in FIG. 6; and/or (b) has a crystal structure as defined by the coordinates in Table EX84B(ii) herein; and/or (c) has crystal lattice parameters at 293 K a=5.8 b=16.6, c=14.9 Å, $\beta=98$ $\alpha=\gamma=90°$; and/or (d) has a crystal structure that belongs belong to a monoclinic space group such as $P2_1$.

Crystalline form FL2 is a stable hydrate which is nominally a trihydrate since there are three crystal; water positions in the asymmetric unit but they are not 100% occupied at room temperature and humidity. Form FL2 may be used for the preparation of solid pharmaceutical compositions. Accordingly, in another aspect, the invention provides combinations comprising a solid pharmaceutical composition containing 2,4-dihydroxy-5-isopropyl-phenyl)-[5-(4-methyl-piperazin-1-ylmethyl)-1,3-dihydro-isoindol-2-yl]-methanone L-lactate in crystalline form FL2 as defined herein.

Form FL2 can be prepared by precipitation from a saturated aqueous methanolic solution using acetone as the antisolvent. More particularly, crystalline form FL2 can be prepared by a method which comprises forming saturated solution of form FL1 in methanol:water (preferably in a 9:1 ratio) and then adding acetone to precipitate form FL2.

Form FL3

In another embodiment, the combination of the invention comprises (2,4-dihydroxy-5-isopropyl-phenyl)-[5-(4-methyl-piperazin-1-ylmethyl)-1,3-dihydro-isoindol-2-yl]-methanone L-lactate salt in a crystalline form characterised by an XRPD pattern having a diffraction angle$(2\theta/°)$ peak at 5.53.

Preferably, the XRPD pattern also exhibits diffraction angle$(2\theta/°)$ peaks at 11.07, 13.16, 16.69, 17.17, 18.00, 18.49, 19.28, 21.05, 22.47 and 22.84.

More preferably, the XRPD pattern further exhibits diffraction angle$(2\theta/°)$ peaks at 8.36, 13.85, 19.79, 20.34, 21.47, 21.93, 24.56, 26.28, 27.06, 27.47 and 29.11.

Figure 7:
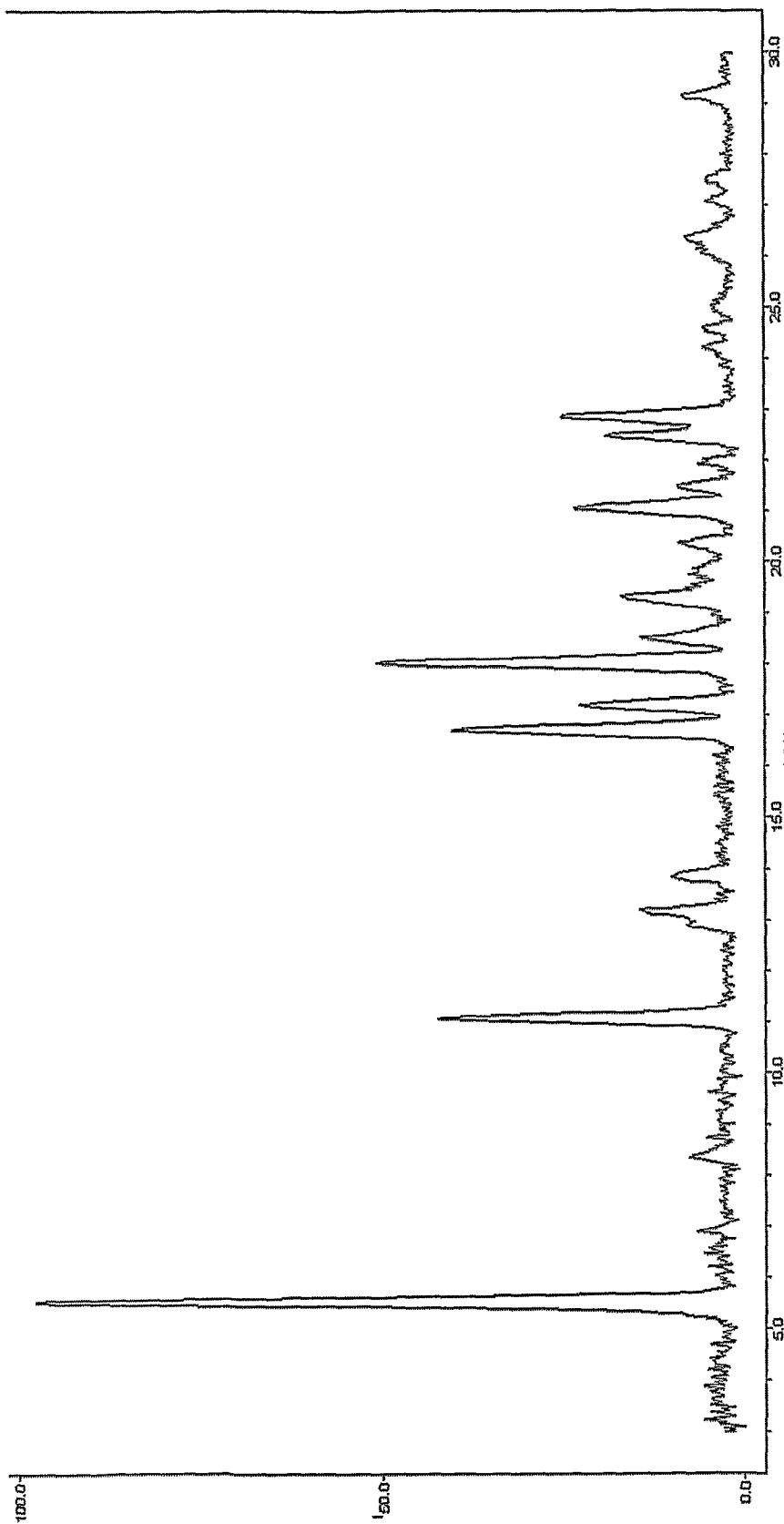
FIG. 7 shows the XRPD pattern of a fresh sample of form FL3 of (2,4-dihydroxy-5-isopropyl-phenyl)-[5-(4-methyl-piperazin-1-ylmethyl)-1,3-dihydro-isoindol-2-yl]-methanone L-lactate.

Most preferably, the XRPD pattern is substantially as shown in FIG. 7 herein.

Form FL3 is an unstable form that can be made by precipitation from a saturated THF solution using heptane as the anti-solvent. Accordingly, in another aspect, the invention provides a method for preparing crystalline form FL3, which method comprises forming a saturated solution of form FL1 in THF and then adding heptane to precipitate form FL3.

Pharmaceutical Uses of the Acid Addition Salts and Crystalline Forms of Compound (1)

In other aspects, the invention provides:

- A combination as defined herein comprising an acid addition salt (e.g. an L-lactate salt) of a compound of the formula (1) as defined herein, or a crystalline form of a compound of the formula (1) or an acid addition salt (e.g. an L-lactate salt) thereof as defined herein, for use in the prophylaxis or treatment of a disease state or condition mediated by Hsp90.
- The use of a combination as defined herein comprising an acid addition salt (e.g. an L-lactate salt) of a compound of the formula (1) as defined herein, or a crystalline form of a compound of the formula (1) or an acid addition salt (e.g. an L-lactate salt) thereof as defined herein, for the manufacture of a medicament for the prophylaxis or treatment of a disease state or condition mediated by Hsp90.
- A method for the prophylaxis or treatment of a disease state or condition mediated by Hsp90, which method comprises administering to a subject in need thereof a combination as defined herein comprising an acid addition salt (e.g. an L-lactate salt) of a compound of the formula (1) as defined herein, or a crystalline form of a compound of the formula (1) or an acid addition salt (e.g. an L-lactate salt) thereof as defined herein.
- A combination as defined herein comprising an acid addition salt (e.g. an L-lactate salt) of a compound of the formula (1) as defined herein, or a crystalline form of a compound of the formula (1) or an acid addition salt (e.g. an L-lactate salt) thereof as defined herein, for use in alleviating or reducing the incidence of a disease state or condition mediated by Hsp90.
- The use of a combination as defined herein comprising an acid addition salt (e.g. an L-lactate salt) of a compound of the formula (1) as defined herein, or a crystalline form of a compound of the formula (1) or an acid addition salt (e.g. an L-lactate salt) thereof as defined herein, for the manufacture of a medicament for alleviating or reducing the incidence of a disease state or condition mediated by Hsp90.
- A method for alleviating or reducing the incidence of a disease state or condition mediated by Hsp90, which method comprises administering to a subject in need thereof a combination as defined herein comprising an acid addition salt (e.g. an L-lactate salt) of a compound of the formula (1) as defined herein, or a crystalline form of a compound of the formula (1) or an acid addition salt (e.g. an L-lactate salt) thereof as defined herein.
- A combination as defined herein comprising an acid addition salt (e.g. an L-lactate salt) of a compound of the formula (1) as defined herein, or a crystalline form of a compound of the formula (1) or an acid addition salt (e.g. an L-lactate salt) thereof as defined herein, for use in treating a disease or condition comprising or arising from abnormal cell growth in a mammal.
- The use of a combination as defined herein comprising an acid addition salt (e.g. an L-lactate salt) of a compound of the formula (1) as defined herein, or a crystalline form of a compound of the formula (1) or an acid addition salt (e.g. an L-lactate salt) thereof as defined herein, for the manufacture of a medicament for treating a disease or condition comprising or arising from abnormal cell growth in a mammal.
- A method for treating a disease or condition comprising or arising from abnormal cell growth in a mammal, which method comprises administering to the mammal a combination as defined herein comprising an acid addition salt (e.g. an L-lactate salt) of a compound of the formula (1) as defined herein, or a crystalline form of a compound of the formula (1) or an acid addition salt (e.g. an L-lactate salt) thereof as defined herein, in an amount effective in inhibiting abnormal cell growth.
- A combination as defined herein comprising an acid addition salt (e.g. an L-lactate salt) of a compound of the formula (1) as defined herein, or a crystalline form of a compound of the formula (1) or an acid addition salt (e.g. an L-lactate salt) thereof as defined herein, for use in alleviating or reducing the incidence of a disease or condition comprising or arising from abnormal cell growth in a mammal.
- The use of a combination as defined herein comprising an acid addition salt (e.g. an L-lactate salt) of a compound of the formula (1) as defined herein, or a crystalline form of a compound of the formula (1) or an acid addition salt (e.g. an L-lactate salt) thereof as defined herein, as defined herein for the manufacture of a medicament for alleviating or reducing the incidence of a disease or condition comprising or arising from abnormal cell growth in a mammal.
- A method for alleviating or reducing the incidence of a disease or condition comprising or arising from abnormal cell growth in a mammal, which method comprises administering to the mammal a combination as defined herein comprising an acid addition salt (e.g. an L-lactate salt) of a compound of the formula (1) as defined herein, or a crystalline form of a compound of the formula (1) or an acid addition salt (e.g. an L-lactate salt) thereof as defined herein, in an amount effective in inhibiting abnormal cell growth.
- A method for treating a disease or condition comprising or arising from abnormal cell growth in a mammal, the method comprising administering to the mammal a combination as defined herein comprising an acid addition salt (e.g. an L-lactate salt) of a compound of the formula (1) as defined herein, or a crystalline form of a compound of the formula (1) or an acid addition salt (e.g. an L-lactate salt) thereof as defined herein, in an amount effective to inhibit Hsp90 activity.
- A method for alleviating or reducing the incidence of a disease or condition comprising or arising from abnormal cell growth in a mammal, the method comprising administering to the mammal a combination as defined herein comprising an acid addition salt (e.g. an L-lactate salt) of a compound of the formula (1) as defined herein, or a crystalline form of a compound of the formula (1) or an acid addition salt (e.g. an L-lactate salt) thereof as defined herein, an amount effective to inhibit Hsp90 activity.

A combination as defined herein comprising an acid addition salt (e.g. an L-lactate salt) of a compound of the formula (1) as defined herein, or a crystalline form of a compound of the formula (1) or an acid addition salt (e.g. an L-lactate salt) thereof as defined herein, for use in the prophylaxis or treatment of a disease state as described herein.

The use of a combination as defined herein comprising an acid addition salt (e.g. an L-lactate salt) of a compound of the formula (1) as defined herein, or a crystalline form of a compound of the formula (1) or an acid addition salt (e.g. an L-lactate salt) thereof as defined herein, for the manufacture of a medicament, wherein the medicament is for any one or more of the uses defined herein.

A pharmaceutical composition comprising a combination as defined herein, wherein the combination comprises an acid addition salt (e.g. an L-lactate salt) of a compound of the formula (1) as defined herein, or a crystalline form of a compound of the formula (1) or an acid addition salt (e.g. an L-lactate salt) thereof as defined herein, and a pharmaceutically acceptable carrier.

A pharmaceutical composition comprising a combination as defined herein, wherein the combination comprises an acid addition salt (e.g. an L-lactate salt) of a compound of the formula (1) as defined herein, or a crystalline form of a compound of the formula (1) or an acid addition salt (e.g. an L-lactate salt) thereof as defined herein, and a pharmaceutically acceptable carrier in a form suitable for oral administration.

A pharmaceutical composition comprising a combination as defined herein, wherein the combination comprises an acid addition salt (e.g. an L-lactate salt) of a compound of the formula (1) as defined herein, or a crystalline form of a compound of the formula (1) or an acid addition salt (e.g. an L-lactate salt) thereof as defined herein, and a pharmaceutically acceptable carrier in a form suitable for parenteral administration, for example by intravenous (i.v.) administration.

A pharmaceutical composition comprising a combination as defined herein, wherein the combination comprises an acid addition salt (e.g. an L-lactate salt) of a compound of the formula (1) as defined herein, or a crystalline form of a compound of the formula (1) or an acid addition salt (e.g. an L-lactate salt) thereof as defined herein, and a pharmaceutically acceptable carrier in a form suitable for intravenous (i.v.) administration by injection or infusion.

A combination as defined herein comprising an acid addition salt (e.g. an L-lactate salt) of a compound of the formula (1) as defined herein, or a crystalline form of a compound of the formula (1) or an acid addition salt (e.g. an L-lactate salt) thereof as defined herein, for use in medicine.

A combination as defined herein comprising an acid addition salt (e.g. an L-lactate salt) of a compound of the formula (1) as defined herein, or a crystalline form of a compound of the formula (1) or an acid addition salt (e.g. an L-lactate salt) thereof as defined herein, compound as defined herein for any of the uses and methods set forth above, and as described elsewhere herein.

A combination as defined herein comprising an acid addition salt (e.g. an L-lactate salt) of a compound of the formula (1) as defined herein, or a crystalline form of a compound of the formula (1) or an acid addition salt (e.g. an L-lactate salt) thereof as defined herein, for use in treatment or prophylaxis of a disease state or condition in a patient who has been screened and has been determined as suffering from, or being at risk of suffering from, a disease or condition which would be susceptible to treatment with a compound having activity against Hsp90.

The use of a combination as defined herein comprising an acid addition salt (e.g. an L-lactate salt) of a compound of the formula (1) as defined herein, or a crystalline form of a compound of the formula (1) or an acid addition salt (e.g. an L-lactate salt) thereof as defined herein, for the manufacture of a medicament for the treatment or prophylaxis of a disease state or condition in a patient who has been screened and has been determined as suffering from, or being at risk of suffering from, a disease or condition which would be susceptible to treatment with a compound having activity against Hsp90.

A method for the diagnosis and treatment of a disease state or condition mediated by Hsp90, which method comprises (i) screening a patient to determine whether a disease or condition from which the patient is or may be suffering is one which would be susceptible to treatment with a compound having activity against Hsp90; and (ii) where it is indicated that the disease or condition from which the patient is thus susceptible, thereafter administering to the patient a combination as defined herein comprising an acid addition salt (e.g. an L-lactate salt) of a compound of the formula (1) as defined herein, or a crystalline form of a compound of the formula (1) or an acid addition salt (e.g. an L-lactate salt) thereof as defined herein.

Biological Activity and Therapeutic Uses

Compounds of the formula (I), (II), (III), (IV), (V), (VI), (VIa), (VII), (VIIa) or (VIIb), subgroups thereof, acid addition salts (particularly the L-lactate) and crystalline forms thereof for use in the combinations of the invention are inhibitors of Hsp90 and consequently are beneficial in the treatment of wide spectrum of proliferative disorders. Examples of such proliferative disorders are not limited to, but can be selected from, a carcinoma, for example a carcinoma of the bladder, breast, colon (e.g. colorectal carcinomas such as colon adenocarcinoma and colon adenoma), kidney, epidermis, liver, lung, for example adenocarcinoma, small cell lung cancer and non-small cell lung carcinomas, oesophagus, gall bladder, ovary, pancreas e.g. exocrine pancreatic carcinoma, stomach, cervix, thyroid, prostate, gastrointestinal system, e.g. gastrointestinal stromal tumours, or skin, for example squamous cell carcinoma; a hematopoieitic tumour of lymphoid lineage, for example leukaemia, acute lymphocytic leukaemia, chronic lymphocytic leukaemia, B-cell lymphoma (such as diffuse large B cell lymphoma), T-cell lymphoma, Hodgkin's lymphoma, non-Hodgkin's lymphoma, hairy cell lymphoma, or Burkitt's lymphoma; a hematopoieitic tumour of myeloid lineage, including acute myeloid leukaemia, chronic myeloid leukaemias, myelogenous leukaemias, and Imatinib sensitive and refractory chronic myelogenous leukaemias, myelodysplastic syndrome, Bortezomib sensitive and refractory multiple myeloma, myeloproliferative disease or promyelocytic leukaemia; thyroid follicular cancer; a tumour of mesenchymal origin, for example fibrosarcoma or habdomyosarcoma; a tumour of the central or peripheral nervous system, for example astrocytoma, neuroblastoma, glioma or schwannoma; melanoma; seminoma; teratocarcinoma; osteosarcoma; xeroderma pigmentosum; keratoacanthoma; thyroid follicular cancer; or Kaposi's sarcoma. A further example of a tumour of mesenchymal origin is Ewing's sarcoma.

The cancers may be cancers which are sensitive to Hsp90 inhibition, and such cancers may be determined by a method as set out in the section headed "Methods of Diagnosis".

One group of cancers includes human breast cancers (e.g. primary breast tumours, node-negative breast cancer, invasive duct adenocarcinomas of the breast, non-endometrioid breast cancers); and mantle cell lymphomas. In addition, other cancers are colorectal and endometrial cancers.

Another sub-set of cancers includes hematopoietic tumours of both lymphoid and myeloid lineage, for example acute lymphoblastic leukemia, chronic lymphocytic leukaemia (Both T and B cell), acute myeloid leukaemia, chronic myeloid leukaemia, mantle cell lymphoma and B-cell lymphoma (such as diffuse large B cell lymphoma) and optionally further includes chronic myelogenous leukaemia and multiple myeloma.

A preferred sub-set of cancers consists of ErbB2-positive breast, prostate, lung, and gastric cancer; chronic myeloid leukemia; androgen receptor dependent prostate cancer; Flt3-dependent acute myeloid leukaemia; melanoma associated with Braf mutation; multiple myeloma; velcade refractory multiple myeloma; and gastrointestinal stromal tumours (GIST).

Of these, particularly preferred cancers are multiple myelomas and velcade refractory tumour types as defined herein.

Another preferred sub-set of cancers consists of hormone refractory prostate cancer, metastatic melanoma, HER2 positive breast cancer, mutant EGFR positive non-small cell lung carcinoma and Gleevec resistant gastrointestinal stromal tumours.

The combinations of the invention can also be used to treat other conditions such as viral infections, parasitic disease, autoimmune diseases (e.g. multiple sclerosis and lupus erythematosus), neuro-degenerative disorders (e.g. Alzheimer's disease), inflammation, Type I and II diabetes, atherosclerosis and cardiac disease.

The combinations of the invention can also have clinical benefit in transplantation and immunosuppression.

The combinations of the invention can also have clinical benefit in the previously described diseases when used in combination with existing or new therapeutic agents.

Based on the activities of Hsp90 client proteins and experimental evidence, the invention finds particular application in the treatment of the following disorders.

ErbB2-Positive Breast, Prostate, Lung, and Gastric Cancer

Overexpression of ErbB2 (HER-2) occurs in approximately 30% of breast cancers and ErbB2 receptor downregulation by herceptin sensitized cells to Taxol. ErbB2 overexpression is linked to poor prognosis and drug resistance (Tsugawa et. al., 1993. Oncology 1993; 50: 418).

Mutant EGFR in Lung Cancer

Somatic mutations in the kinase domain of the epidermal growth factor receptor (EGFR), including L858R and exon 19 deletions, underlie responsiveness to gefitinib and erlotinib in non-small cell lung cancer (NSCLC). Acquired resistance to these tyrosine kinase inhibitors is in some cases mediated by a second mutation, T790M. Ansamycin antibiotics, such as geldanamycin, potently inhibit heat shock protein 90 (Hsp90), promoting ubiquitin-mediated degradation of oncogenic kinases that require the chaperone for proper conformational folding. Exposure of EGFR-mutant cell lines to geldanamycin induced marked depletion of phospho-Akt and cyclin D1 as well as apoptosis. These data suggest mutational activation of EGFR is associated with dependence on Hsp90 for stability and that Hsp90 inhibition may represent a novel strategy for the treatment of EGFR-mutant NSCLC.

Chronic Myeloid Leukemia

The aberrant BCR-Abl protein is created through a chromosomal translocation and results in a constitutively active Abl kinase domain. This translocation event has been shown to be causal for CML. P210BcrAbl is a known client protein for Hsp90. Treatment of the BCR-Abl positive cell line K562 with an hsp90 inhibitor induced apoptosis. The Bcr-Abl inhibitor Gleevec® also induces apoptosis in K562 cells; however Gleevec® resistant K562 cells still retain sensitivity towards Hsp90 inhibitors (Gorre et. al. 2002, Blood 100: 3041-3044).

Androgen Receptor Dependent Prostate Cancer

The androgen receptor kinase is an Hsp90 client protein. Hormone replacement therapy is usually adopted where surgery does not resolve the cancer. The cancer may become refractory to hormone manipulation through receptor mutation. Hsp90 regulation of the receptor would still be viable post-mutation.

The same would apply to estrogen-dependent breast cancers.

Flt3-Dependent Acute Myeloid Leukaemia

Internal duplication of the tyrosine kinase receptor Flt3 leads to its constitutive activation and oncogenesis. These internal duplications are observed in 20% of all reported cases of AML and are an indication of poor prognosis. Much like the activation of the ABL kinase in CML, this represents another example of a single genetic lesion giving rise to a malignancy. Hsp90 inhibitors are predicted to be of clinical benefit to these patients as Flt3 is an Hsp90 client protein (Bali et. al., 2004 Cancer Res. 64(10):3645-52).

Melanoma Associated with Braf Mutation

Braf encodes for a serine/threonine kinase which is mutated in 70% of all melanomas. 80% of these represent a single V599E point mutation that confers elevated kinase activity to BRAF. This mutation is also transforming in NIH3T3 cells (Bignell et. al., 2002 Nature. 417(6892):949-54).

Multiple Myeloma

The Hsp90 inhibitor 17-AAG potently inhibits proliferation of Bortezomib refractory multiple myeloma cell lines. Cell surface levels of IGF-1R and IL-6R were also diminished in 17-aag treated MM-1 cells (Mitsiades et. al., Blood 107:1092-1100, 2006). Autocrine stimulation of multiple myeloma cells, as well as paracrine stimulation of bone marrow stromal cells with IL-6 is also diminished through downregulation of the Hsp90 client IKK.

Velcade Refractory Multiple Myeloma

The combinations of the invention can be used in the treatment of velcade refractory tumour types including treatment of patients with second line mantle cell lymphoma, indolent non-Hodgkin's lymphoma, stage IIIB and IV Bronchioloalveolar carcinoma, advanced non-small cell lung cancer, breast, prostate and ovarian cancers and non-Hodgkin's lymphoma.

Gastrointestinal Stromal Tumours (GIST)

GIST disease particularly disease dependent on growth factor activation or overexpression (e.g. c-kit).

B-CLL

ZAP-70 is an Hsp90 client protein and the requirement for Hsp90 by ZAP-70 is limited to CLL cells and is not observed in T cells where this kinase is normally expressed. Hence, ZAP-70 is unique among identified Hsp90 clients as its chaperone dependency is conditional on the type of cell in which it is expressed.

Other conditions or disorders for which an Hsp90 inhibitor may be of clinical benefit include, but are not limited to:

Neurodegenerative Disorders

Huntington's disease (HD) is a progressive neurodegenerative disorder with no effective treatment. GA inhibition of Hsp90 and the resulting up-regulation of Hsps are effective in preventing huntington protein aggregation in neuronal cells. (Sittler et. al., 2001, Human Molecular Genetics, Vol. 10, No. 12 1307-1315). Up-regulation of HSP may also be of clinical benefit in other diseases of protein misfolding e.g., CJD and Alzheimer's.

Inflammatory Disease, Including Rheumatoid Arthritis, Asthma, Chronic Obstructive Pulmonary Disease, and Inflammatory Bowel Disease GA has been shown to dissociate HSF-1 from Hsp90 leading to the activation and nuclear translocation of HSF-1. HSF-1 subsequently acts as a transcription factor to induce HSP90 and Hsp70. The induction of Hsp70 has been implicated in the resolution of inflammation in an induced mouse model of edema (Ianaro et al., 2004 Human Molecular Genetics, 2001, Vol. 10, No. 12 1307-1315). Additionally GA treatment inhibited IkappaB kinase (IKK) activation by TNF-a or PMA. IkBa is a regulator of Nf-kB and Ap-1. (Broemer et. al. 2004). Ap-1 and Nf-kB is a major transcription factor leading to the production of pro-inflammatory cytokines (Yeo et. al., 2004 *Biochem Biophys Res Commun.* 30; 320(3):816-24). The stability of pro-inflammatory cytokine transcripts is also regulated through inhibition of p38 MapK (Wax et. al., 2003. *Rheumatism Vol.* 48, No. 2, pp 541-550).

Atherosclerosis

It is known that inflammatory and immune cells play a central role in the initiation and progression of human atherosclerosis (Riganò et al., *Ann. N.Y. Acad. Sci.*, 2007, 1107:1-10) and it has been proposed that Hsp90 acts as an autoantigen in carotid atherosclerosis. Riganò et al. found specific antibodies and cells against Hsp90 in the sera of 60% of patients tested who were suffering from carotid atherosclerotic plaques but no specific antibodies and T cells against Hsp90 in the sera of healthy patients. Therefore, The combinations of the invention are useful in the treatment or prevention of atherosclerosis.

Angiogenesis Related Disease, Including but not Limited to: Tumour Angiogenesis, Psoriasis, Rheumatoid Arthritis, and Diabetic Retinopathy Induction of angiogenesis is regulated by Hsp90 client proteins eNOS and Akt in endothelial cells (Sun and Liao, 2004 *Arterioscler Thromb Vasc Biol.* 24(12):2238-44). Suppression of hypoxia-inducible factor (HIF)-1a can also impair the growth, angiogenesis and vessel maturation of gastric tumours in a mouse model. (Stoeltzing et. al., 2004 *J Natl Cancer Inst;* 96:946-956).

Type I and Type II Diabetes

Hsp90 inhibition has a profound effect on Akt signalling as well as e-nos. These are two key regulators in high glucose induced endothelial cell apoptosis in type I diabetes (Lin et. al., 2005 J Cell Biochem. 1; 94(1):194-201) and the development of hypertension in type II diabetes (Kobayashi et. al., 2004 *Hypertension.* 44(6):956-62).

Immunosuppression and Transplantation

Hsp90 inhibition has been shown to down regulate Lck, a T-cell specific tyrosine kinase required for T-cell activation. (Yorgin et. al., 2000 *J Immunol.* 15; 164(6):2915-23.)

Cardiac Disease

Cardiac ischemic is the most common cause of death in the western world. Hsps, and notably Hsp70 (induced by radicicol treatment) have demonstrated cardioprotective activity in rat cardiomyocytes (Griffin et. al., 2004). Inhibition of Hsp90 results in the release of HSF-1 from the chaperone complex and its subsequent activation of Hsp genes. Inhibition of Hsp90 also leads to the down-regulation of HIF-1, which has been implicated in the pathogenesis of ischemic heart disease and stroke.

Infectious Disease and Anti-Viral Activity

Hepatitis C viral NS2/3 protease is an Hsp90 client protein and Hsp90 activity is required for viral processing and replication (Whitney et. al., 2001. *Proc Natl Acad Sci USA.* 20; 98(24):13931-5).

As discussed above in the introductory sections of this application, infection of a host cell with viral RNA/DNA results in a substantial redirection of cellular protein synthesis towards key viral proteins encoded by the viral nucleic acid, and this frequently gives rise to upregulation of heat shock proteins. It is believed that one function of the HSP induction may be to assist in the stabilization and folding of the high levels of 'foreign' protein generated in preparation for virus replication and it has been shown (Nagkagawa et al.) that HSP 90 inhibitors can block viral replication. Accordingly, the compounds of the invention are useful in combatting viral infections, for example by blocking or inhibiting viral replication.

Therefore, in another aspect, the invention provides a combination of the invention as defined herein for use in the prophylaxis or treatment of a viral infection (or viral disease).

In further aspects, the invention provides:

The use of a combination of the invention as defined herein for the manufacture of a medicament for the prophylaxis or treatment of a viral infection (or viral disease).

A method for the prophylaxis or treatment of a viral infection (or viral disease), which method comprises administering to a subject in need thereof a combination of the invention as defined herein.

A combination of the invention as defined herein for use in blocking or inhibiting viral replication in a host organism (e.g. an animal such as a mammal (e.g. human)).

The use of a combination of the invention as defined herein for the manufacture of a medicament for use in blocking or inhibiting viral replication in a host organism (e.g. an animal such as a mammal (e.g. human)).

A method of blocking or inhibiting viral replication in a host organism (e.g. an animal such as a mammal (e.g. human)), which method comprises administering to the host organism a combination of the invention as defined herein.

Examples of viral infections that may be treated with the compounds of the invention include infections due to any one or more of the following viruses:

Picornaviruses such as rhinoviruses (common cold virus), Coxsackie virus (e.g. Coxsackie B virus); and foot and mouth disease virus;

Hepatitis viruses such as hepatitis A virus (HAV), hepatitis B virus (HBV), hepatitis C virus (HCV), hepatitis D virus (HDV) and hepatitis E virus (HEV), Coronaviruses (e.g. common cold virus and Severe acute respiratory syndrome (SARS) virus)

Adenoviruses such as Human Adenoviruses (a cause of respiratory and conjunctival infections);

Astroviruses (a cause of flu-like symptoms);

Flaviviruses such as the Yellow Fever virus;

Orthomyxoviruses such as influenza viruses (e.g. influenza A, B and C viruses);

Parainfluenza viruses;
Respiratory syncytial virus;
Enteroviruses such as Poliovirus (Poliomyelitis virus);
Paramyxoviruses such as the Measles (rubeola) virus, mumps virus, respiratory syncytial virus (RSV) and canine distemper virus (CDV);
Togaviruses such as the Rubella (German Measles) virus and Sindbis virus;
Herpes viruses such as:
Herpes simplex virus (HSV), for example HSV-1 which causes fever blisters (cold sores), gingivostomatitis, herpes keratitis, eczema herpeticum and HSV encephalitis); and HSV-2 which causes genital lesions, neonatal infections, HSV meningitis, HSV proctitis;
Varicella zoster virus (VZV), which causes chickenpox, congenital varicella syndrome and shingles;
Epstein-Barr Virus (EBV), which causes infectious mononucleosis, Burkitt's lymphoma and nasopharyngeal cancer;
Cytomegalovirus (CMV), e.g. human cytomegalovirus (HCMV);
Human herpes virus 6 (HHV-6), which causes exanthum subitum or roseola infantum
Human herpes virus 8 (HHV-8) or Kaposi's sarcoma-associated herpes virus (KSHV), which is found in the saliva of many AIDS patients and associated with Kaposi's sarcoma;
Papovaviridae such as polyoma virus and human papilloma virus (HPV);
Parvoviruses;
Poxviruses such as Variola virus (human smallpox virus);
Rhabdoviruses such as rabies virus and vesicular stomatitis virus (VSV); and
Retroviruses such as Human immunodefficiency virus (HIV) which is responsible for acquired immune deficiency syndrome (AIDS); and Human T-lymphotrophic virus (HTLV).

Particular viral infections against which the compounds of the invention may be used include herpes virus, pox virus, Epstein-Barr virus, Sindbis virus, adenovirus, HIV (for prevention of AIDS development in HIV-infected individuals), HPV, HCV and HCMV viruses.

The viral infection may be other than an infection with hepatitis C virus (HCV).

The activity of the compounds of the invention as agents for blocking or preventing viral replication in host organisms or host cells can be determined in accordance with standard procedures well known to the skilled person.

The compounds of the invention may be used as the sole antiviral agent or they may be used in conjunction with other anti-viral agents such as acyclovir, ganciclovir, oseltamivir (Tamiflu®) and zanamavir (Relenza®), amantidine, rimantadine, adefovir dipivoxil, interferons (e.g. interferon alfa-2b and pegylated interferon alfa-2a), lamivudine, entecavir, ribavirin, famciclovir, valcicylovir, valacyclovir, azidothymidine (AZT—Retrovir®), atazanavir, fosamprenavir, lamivudine, lamivudine+abacavir, tenofovir disoproxil fumarate, tenofovir disoproxil fumarate+emtricitabine, tipranavir, nelfinavir, indinavir, raltegravir, ritonavir, lopinavir+ritonavir, darunavir, amprenavir, enfuvirtide, saquinavir, hydroxyurea, VGV-1 and anti-viral vaccines.

Accordingly, the invention further provides:
A combination as defined herein with an ancillary compound which is an antiviral agent.
A pharmaceutical composition comprising a combination as defined herein with an ancillary compound which is an antiviral agent.

Parasitic Disease

GA has reported antimalarial activity against an Hsp90 ortholog of Plasmodium falciparum. Plasmodium growth was inhibited with GA at an $IC_{50}$ similar to that observed with chloroquine. GA was also effective against chloroquine resistant strains of Plasmodium falciparum (Kamar et. al., 2003. Malar J. 15; 2(1):30).

The biological activity of the compounds for use in the invention, e.g. as inhibitors of Hsp90, can be measured using the assays set forth in the examples below, for example the isothermal titration calorimetry (ITC) experiments described in Example 80 and the anti-proliferative activity assays described in Example 81. The level of activity exhibited by a given compound in the ITC assay can be defined in terms of the $K_d$ value, and preferred compounds for use in the present invention are compounds having a $K_d$ value of less than 1 micromolar, more preferably less than 0.1 micromolar. In the anti-proliferative activity assays, the level of activity exhibited by a given compound in an assay can be defined in terms of the $IC_{50}$ value, and preferred compounds for use in the present invention are compounds having an $IC_{50}$ value of less than 1 micromolar, more preferably less than 0.1 micromolar.

hERG

In the late 1990s a number of drugs, approved by the US FDA, had to be withdrawn from sale in the US when it was discovered they were implicated in deaths caused by heart malfunction. It was subsequently found that a side effect of these drugs was the development of arrhythmias caused by the blocking of hERG channels in heart cells. The hERG channel is one of a family of potassium ion channels the first member of which was identified in the late 1980s in a mutant *Drosophila melanogaster* fruitfly (see Jan, L. Y. and Jan, Y. N. (1990). A Superfamily of Ion Channels. Nature, 345(6277): 672). The biophysical properties of the hERG potassium ion channel are described in Sanguinetti, M. C., Jiang, C., Curran, M. E., and Keating, M. T. (1995). A Mechanistic Link Between an Inherited and an Acquired Cardiac Arrhythmia: HERG encodes the Ikr potassium channel. Cell, 81:299-307, and Trudeau, M. C., Warmke, J. W., Ganetzky, B., and Robertson, G. A. (1995). HERG, a Human Inward Rectifier in the Voltage-Gated Potassium Channel Family. Science, 269:92-95.

The elimination of hERG blocking activity remains an important consideration in the development of any new drug.

It has also been found that many compounds of the formula (I) have low hERG activity and a good separation between Hsp90 inhibitory activity and hERG activity.

Preferred compounds of the formula (I) have mean $IC_{50}$ values against hERG that are greater than 30 times, or greater than 40 times, or greater than 50 times the $IC_{50}$ values of the compounds in cellular proliferation assays. Preferred compounds of the formula (I) have mean $IC_{50}$ values against hERG that are greater than 5 µM, more particularly greater than 10 µM, and more preferably greater than 15 µM. Some compounds for use according to the invention have mean $IC_{50}$ values against hERG that are greater than 50 µM.

Compounds for use in the invention have advantageous ADME properties and in particular better tumour distribution.

Hsps and Antitumour Drug Resistance

Therapeutic anticancer interventions of all types necessarily increase the stresses imposed on the target tumour cells. In mitigating the deleterious effects of such stresses, Hsps are directly implicated in resisting the effects of cancer drugs and treatment regimens. Thus, modulators or inhibitors of stress protein function in general (and Hsp90 in particular) represent a class of chemotherapeutics with the potential for: (i)

sensitizing malignant cells to anticancer drugs and/or treatments; (ii) alleviating or reducing the incidence of resistance to anticancer drugs and/or treatments; (iii) reversing resistance to anticancer drugs and/or treatments; (iv) potentiating the activity of anticancer drugs and/or treatments; (v) delaying or preventing the onset of resistance to anticancer drugs and/or treatments.

Methods for the Preparation of Compounds of the Formula (I)

In this section, as in all other sections of this application unless the context indicates otherwise, references to Formula (I) also include all sub-groups and examples thereof as defined herein. Where a reference is made to a group $R^1$, $R^2$, $R^3$, $R^4$, $R^5$, $R^6$, $R^{10}$ or any other "R" group, the definition of the group in question is as set out above and as set out in the following sections of this application unless the context requires otherwise.

Compounds of the formula (I) can be prepared in accordance with synthetic methods well known to the skilled person. For example, compounds of the formula (I) can be prepared by the reaction of a compound of the formula (X):

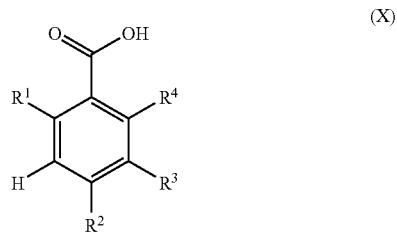

(X)

or an activated and/or protected form thereof, with an amine of the formula $HNR^5R^6$ under conditions suitable for forming an amide bond, and thereafter where necessary removing any protecting groups and optionally converting one compound of the formula (I) to another compound of the formula (I).

The amines of the formula $HNR^5R^6$ are either commercially available or can be made using methods well known to the skilled person, see for example, *Advanced Organic Chemistry*, by Jerry March, 4th edition, 119, Wiley Interscience, New York; *Fiesers' Reagents for Organic Synthesis*, Volumes 1-17, John Wiley, edited by Mary Fieser (ISBN: 0-471-58283-2); and *Organic Syntheses*, Volumes 1-8, John Wiley, edited by Jeremiah P. Freeman (ISBN: 0-471-31192-8).

The carboxylic acid (X) can be converted to an amide of the formula (I) by first forming an acid chloride by treatment of the carboxylic acid with thionyl chloride, or by reaction with oxalyl chloride in the presence of a catalytic amount of dimethyl formamide, or by reaction of a potassium salt of the acid with oxalyl chloride. The acid chloride can then be reacted with the amine $HNR^5R^6$ in the presence of a non-interfering base such as triethylamine. The reaction may be carried out at around room temperature in a polar solvent such as dioxan.

As an alternative to using the acid chloride method described above, the carboxylic acid (X) can be converted to the amide (I) by reaction with the amine $HNR^5R^6$ in the presence of amide coupling reagents of the type commonly used in the formation of peptide linkages. Examples of such reagents include 1,3-dicyclohexylcarbodiimide (DCC) (Sheehan et al, *J. Amer. Chem Soc.* 1955, 77, 1067), 1-ethyl-3-(3'-dimethylaminopropyl)-carbodiimide (referred to herein either as EDC or EDAC but also known in the art as EDCI and WSCDI) (Sheehan et al, *J. Org. Chem.*, 1961, 26, 2525), uronium-based coupling agents such as O-(7-azabenzotriazol-1-yl)-N,N,N',N'-tetramethyluronium hexafluorophosphate (HATU) and phosphonium-based coupling agents such as 1-benzo-triazolyloxytris-(pyrrolidino)phosphonium hexafluorophosphate (PyBOP) (Castro et al, *Tetrahedron Letters*, 1990, 31, 205). Carbodiimide-based coupling agents are advantageously used in combination with 1-hydroxy-7-azabenzotriazole (HOAt) (L. A. Carpino, *J. Amer. Chem. Soc.*, 1993, 115, 4397) or 1-hydroxybenzotriazole (HOBt) (Konig et al, *Chem. Ber.*, 103, 708, 2024-2034). Preferred coupling reagents include EDC (EDAC) and DCC in combination with HOAt or HOBt.

The coupling reaction is typically carried out in a non-aqueous, non-protic solvent such as acetonitrile, dioxan, dimethylsulphoxide, dichloromethane, dimethylformamide or N-methylpyrrolidine, or in an aqueous solvent optionally together with one or more miscible co-solvents. The reaction can be carried out at room temperature or, where the reactants are less reactive (for example in the case of electron-poor anilines bearing electron withdrawing groups such as sulphonamide groups) at an appropriately elevated temperature. The reaction may be carried out in the presence of a non-interfering base, for example a tertiary amine such as triethylamine or N,N-diisopropylethylamine.

Illustrative routes to the compounds of formula (I) are described in more detail below.

Compounds of the formula (I) in which the benzoyl moiety is derived from a 2-hydroxy-5-substituted benzoic acid can be prepared by the sequence of reactions shown in Scheme 1.

The starting material for the synthetic route shown in Scheme 1 is 5-chloro-2-hydroxy benzoic acid, which can be obtained commercially. Conversion to the acid chloride is carried out by heating with thionyl chloride. The acid chloride may be used either in situ and reacted with various amines, or can be isolated as a stable white solid. Other simple 2-hydroxy-5-substituted benzoic acids may be used in this procedure to synthesise other amides of 2-hydroxy-5-substituted benzoic acids.

Scheme 1: 5-Chloro-2-hydroxybenzoic acid amides

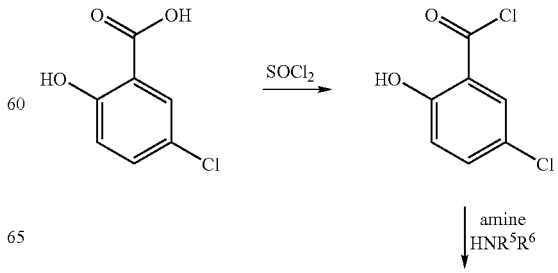

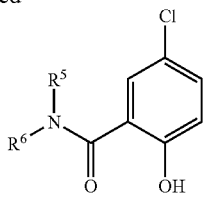

Compounds of formula (I) can also be made according to the method shown in Scheme 2. The starting material for the synthetic route shown in Scheme 2 is 4-ethyl anisole, which can be obtained commercially. Conversion to the carboxylic acid can be carried out by lithiation at low temperature, followed by quenching of the resulting anion with solid carbon dioxide. The carboxylic acid may be coupled with various amines, using standard amide coupling reagents of the type commonly used in the formation of peptide linkages as described above.

Deprotection of the methyl ether can be effected using boron tribromide (e.g. by the method described in *Synthesis* 1991, 469) to give the compound of formula (I). The method illustrated in Scheme 2 can be used to prepare other simple 2-hydroxy-5-substituted benzoic acids which can then be coupled to an appropriate amine to give the compounds of formula (I). The process of coupling intermediates acids with amines, anilines or amino-heterocyclic compounds, followed by removal of any protecting groups, is straightforward and is suitable for the synthesis of large combinatorial libraries of molecules, useful for this invention. Examples of combinatorial libraries are described in *Solid-Phase Synthesis and Combinatorial Technologies* by Pierfausto Seneci. Wiley-Interscience, New York. 2000. xii+637 pp. ISBN 0471331953).

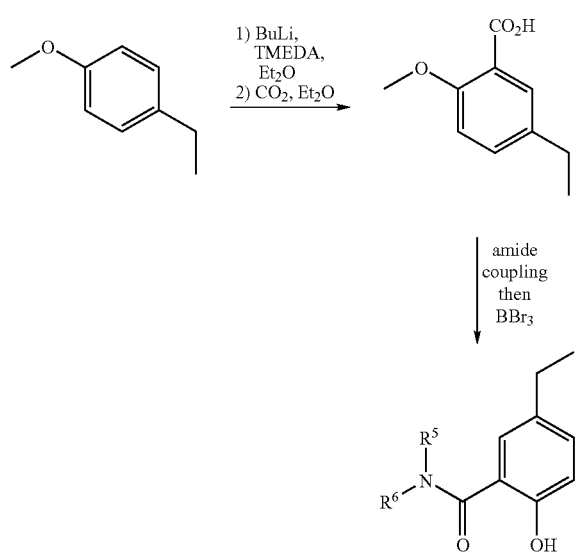

Compounds of the Formula (I) can also be made according to the methods described in Scheme 3. The starting material 3-tert-butyl-4-hydroxybenzoic acid (X=tert-butyl) is commercially available and can be coupled using the amide coupling agents (as outlined above) with a broad range of amines of the formula $HNR^5R^6$ to give compounds for use according to the invention. The other starting material illustrated in Scheme 3, 3-isopropyl-4-hydroxybenzoic acid (X=isopropyl), can be prepared according to a modification of a literature procedure using carbon tetrachloride and copper powder in a Friedel-Crafts type reaction, in which the intermediate species is hydrolysed to the carboxylic acid (*J Chem Soc, Chem Commun* 1985, 1134). The Friedel Crafts method can be used to prepare other simple 2-hydroxy-3-substituted benzoic acids.

Scheme 3: 3-Alkyl-4-hydroxybenzoic acid amides

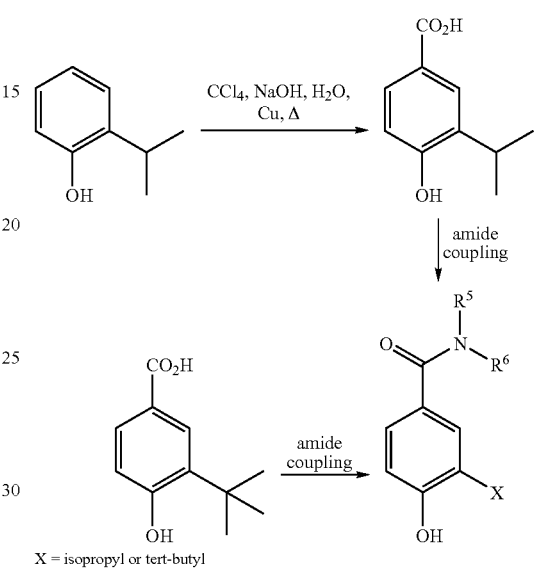

X = isopropyl or tert-butyl

Compounds of the formula (I) can also be made according to the method described in Scheme 4. 2,4-Dihydroxy-5-isopropyl-benzoic acid amides can be prepared by amide coupling using coupling reagents (as outlined above) from a bi-benzyl ether protected intermediate, shown in the scheme, followed by catalytic hydrogenation using hydrogen gas and palladium on carbon. The benzoic acid intermediate itself is made by Friedel-Crafts acylation of 2,4-dihydroxybenzoic acid methyl ester (from commercial sources) using a literature procedure (*J. Ind. Chem. Soc.*, 1953, 30, 269). Typically, Friedel-Crafts acylation of a phenol is carried out by treatment of the phenol with an acylating agent (such as an acid chloride or acid anhydride) in the presence of a Lewis acid catalyst (such as boron trifluoride or aluminium chloride) either at room temperature or at more elevated temperatures (60-120° C.). Benzyl protection of the phenol groups, the Wittig reaction of the ketone to the olefin and ester hydrolysis (saponification) can be carried out under standard conditions, well known to those skilled in the art of organic synthesis (for example see, *Advanced Organic Chemistry*, by Jerry March, 4th edition, 119, Wiley Interscience, New York; Fiesers' *Reagents for Organic Synthesis*, Volumes 1-17, John Wiley, edited by Mary Fieser (ISBN: 0-471-58283-2); and *Organic Syntheses*, Volumes 1-8, John Wiley, edited by Jeremiah P. Freeman (ISBN: 0-471-31192-8). For example, the Wittig reaction can be carried out in an inert polar solvent (such as tetrahydrofuran) and can involve treatment of an aldehyde or ketone with a phosphorus ylide species that may be prepared by the reaction of a phosphonium salt with a base (such as butyl lithium or potassium tert-butoxide). The ester hydrolysis to the carboxylic acid is usually carried out by treatment with an aqueous alkali metal hydroxide such sodium hydroxide. The saponification reaction may be carried out using an organic co-solvent such as an alcohol (e.g. methanol) and the reaction mixture is typically heated to a non-extreme temperature, for example up to about 50-60° C.

It is to be understood that other 2,4-dihydroxy-5-substituted benzoic acids could be made using this procedure to synthesise different examples of compounds of formula 1 not specifically exemplified herein.

In Scheme 4, as an alternative to the use of the Wittig reagent MePPH$_3$Br to form the olefin (XXVI), the ketone (XXV) can be reacted with methyl magnesium bromide under standard Grignard reaction conditions to give an intermediate hydroxy compound which is then dehydrated to the olefin by reaction with a suitable reagent such as sodium acetate and acetic acid.

The intermediate compound 2,4-bis-benzyloxy-5-isopropenyl-benzoic acid (XXVII) and its precursor compounds (XXV) and (XXVI) shown in Scheme 4 are believed to be novel and, as such, each of the compounds represents a further aspect of the invention.

The 2,4-bis-benzyloxy-5-isopropenyl-benzoic acid amides (XXVIII) are also believed to be novel and also form a further aspect of the invention.

Scheme 4: 2,4-Dihydroxy-5-isopropyl-benzoic acid amides

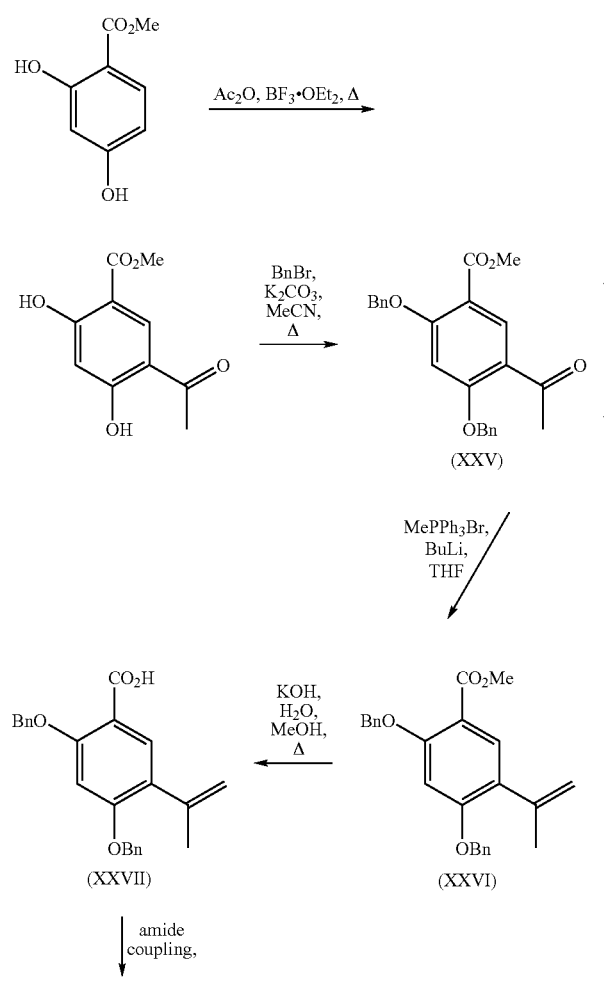

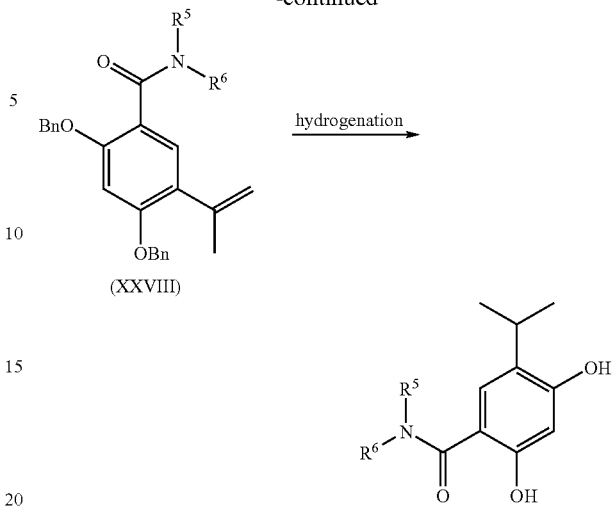

The intermediate compound 2,4-bis-benzyloxy-5-isopropenyl-benzoic acid (XXVII) in Scheme 4 can be made using a variety of methods well known to the skilled person. For example, compound (XXVII) can be made by the synthetic route illustrated in Scheme 4A.

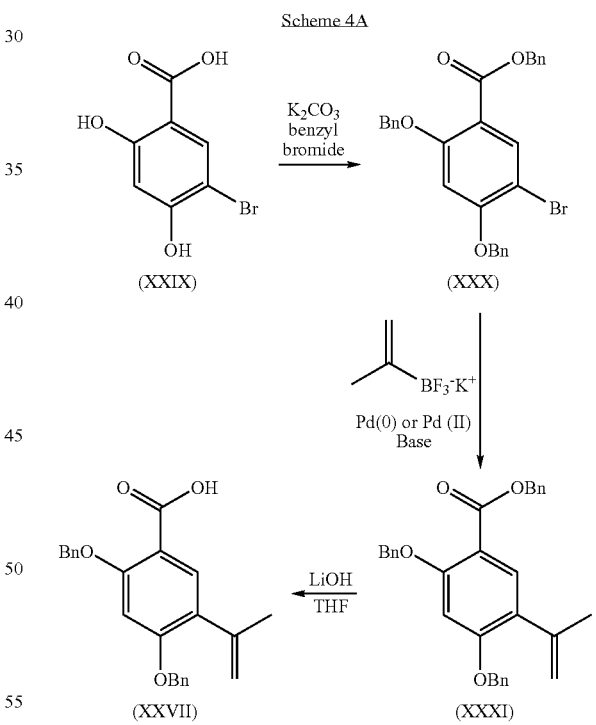

As shown in Scheme 4A, 5-bromo-2,4-dihydroxybenzoic acid is benzylated using benzyl bromide in the presence of a base such as potassium carbonate to give the bis-benzyloxy-bromobenzoic acid benzyl ester (XXX). The ester (XXX) is then reacted with potassium isoprenyl trifluoroborate in the presence of a palladium (0) or palladium (II) compound and a base to give the isopropenyl-bis benzyl ester (XXXI). The palladium compound can be a palladium (0) compound such as Pd(PPh$_3$)$_4$ or a palladium (II) compound such as [1,1'-bis(diphenyl-phosphino)ferrocene]dichloropalladium(II). The base can be an organic base such as n-butylamine or an inorganic base such as a metal carbonate, e.g. caesium carbonate. The reaction with potassium isoprenyl trifluoroborate is typically carried out at reflux temperature for a prolonged period, for example 15 hours or more. The resulting isopropenyl bis-benzyloxy ester (XXXI) is then hydrolysed to give the carboxylic acid (XXVII) using, for example, an alkali metal hydroxide such as lithium hydroxide, typically with heating to a non-extreme temperature.

Compounds of the formula (I) can also be made according to the route illustrated in Scheme 5. 4-Hydroxy-3-(1',2'-dimethyl-propyl)-benzoic acid amides can be prepared by amide coupling using standard coupling agents (as outlined above) from the alkyl substituted acid. The olefinic acid itself can be prepared by Claisen rearrangement of a precursor ether, as shown in the scheme, by thermal rearrangement in anisole, followed by saponification, which in this case can yield more than one isomer of the olefin, the major one being shown in the scheme. Such Claisen reactions are well known in the literature, e.g. see *J. Chem. Soc, Perkin Trans* 1 1981, 897. The ether itself can be prepared by simple alkylation of commercially available 4-hydroxy benzoic acid ethyl ester. The alkylation and saponification reactions are simple modifications that can be carried out under various conditions (for example see, *Advanced Organic Chemistry*, by Jerry March, 4$^{th}$ edition, 119, Wiley Interscience, New York; *Fiesers' Reagents for Organic Synthesis*, Volumes 1-17, John Wiley, edited by Mary Fieser (ISBN: 0-471-58283-2); and *Organic Syntheses*, Volumes 1-8, John Wiley, edited by Jeremiah P. Freeman (ISBN: 0-471-31192-8)). It is to be understood that other 4-hydroxy-3-substituted benzoic acids could be made using this procedure to synthesise different examples of compounds of formula 1 not specifically exemplified herein.

Scheme 5: 4-Hydroxy-3-(1',2'-dimethyl-propyl)-benzoic acid amides

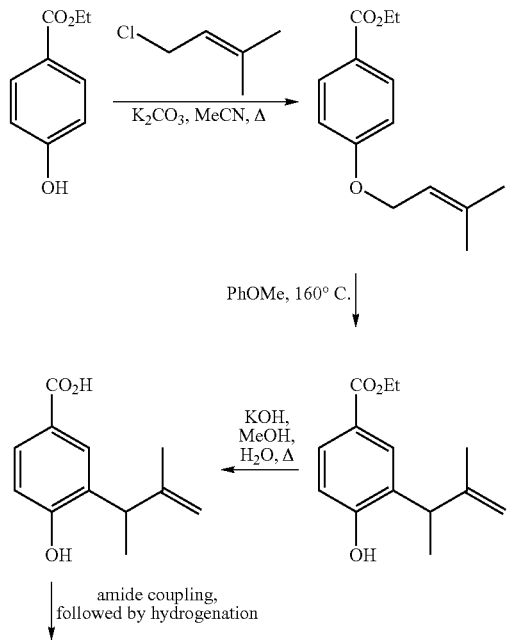

-continued

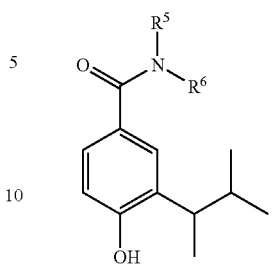

Compounds of the formula (I) can also be made according to the method shown in Scheme 6. 2,4-Dihydroxy-5-bromobenzoic acid is used as the starting material, which is commercially available. Simple protection and deprotection gives the benzoic acid precursor (for example see, *Advanced Organic Chemistry*, by Jerry March, 4$^{th}$ edition, 119, Wiley Interscience, New York; *Fiesers' Reagents for Organic Synthesis*, Volumes 1-17, John Wiley, edited by Mary Fieser (ISBN: 0-471-58283-2); and *Organic Syntheses*, Volumes 1-8, John Wiley, edited by Jeremiah P. Freeman (ISBN: 0-471-31192-8)), which can be used in amide coupling reactions with a range of amines (as outlined above). These precursor amides can be subjected to Suzuki cross coupling procedures to make alkyl substituted compounds. A broad range of Suzuki coupling conditions are described in the literature, and the ones used here were taken from *J. Am. Chem. Soc.* 2003, 11148. Suzuki coupling chemistry is also broadly applicable to synthesis of alkyl-aryl and aryl-aryl compounds. The Suzuki reaction is typically carried out in the presence of a palladium catalyst such as bis(tri-t-butylphosphine)-palladium and a base (e.g. a carbonate such as potassium carbonate). The reaction may be carried out in an aqueous solvent system, for example aqueous ethanol, and the reaction mixture is typically subjected to heating, for example to a temperature in excess of 100° C. Many boronates suitable for use in preparing compounds for use according to the invention are commercially available, for example from Boron Molecular Limited of Noble Park, Australia, or from Combi-Blocks Inc, of San Diego, USA. Where the boronates are not commercially available, they can be prepared by methods known in the art, for example as described in the review article by N. Miyaura and A. Suzuki, *Chem. Rev.* 1995, 95, 2457. Thus, boronates can be prepared by reacting the corresponding bromo-compound with an alkyl lithium such as butyl lithium and then reacting with a borate ester. The resulting boronate ester derivative can, if desired, be hydrolysed to give the corresponding boronic acid. The final products of the reaction sequence illustrated in Scheme 6 are formed by catalytic hydrogenation (as outlined above) to remove the benzyl protecting groups and to reduce the olefin, formed in the Suzuki reaction to the alkyl substituent. It is to be understood that other 2,4-dihydroxy-5-substituted benzoic acids could be made using this procedure to synthesise different examples of compounds of formula I not specifically exemplified herein.

Scheme 6: 2,4-Dihydroxy-5-(alkyl)-benzoic acid amides

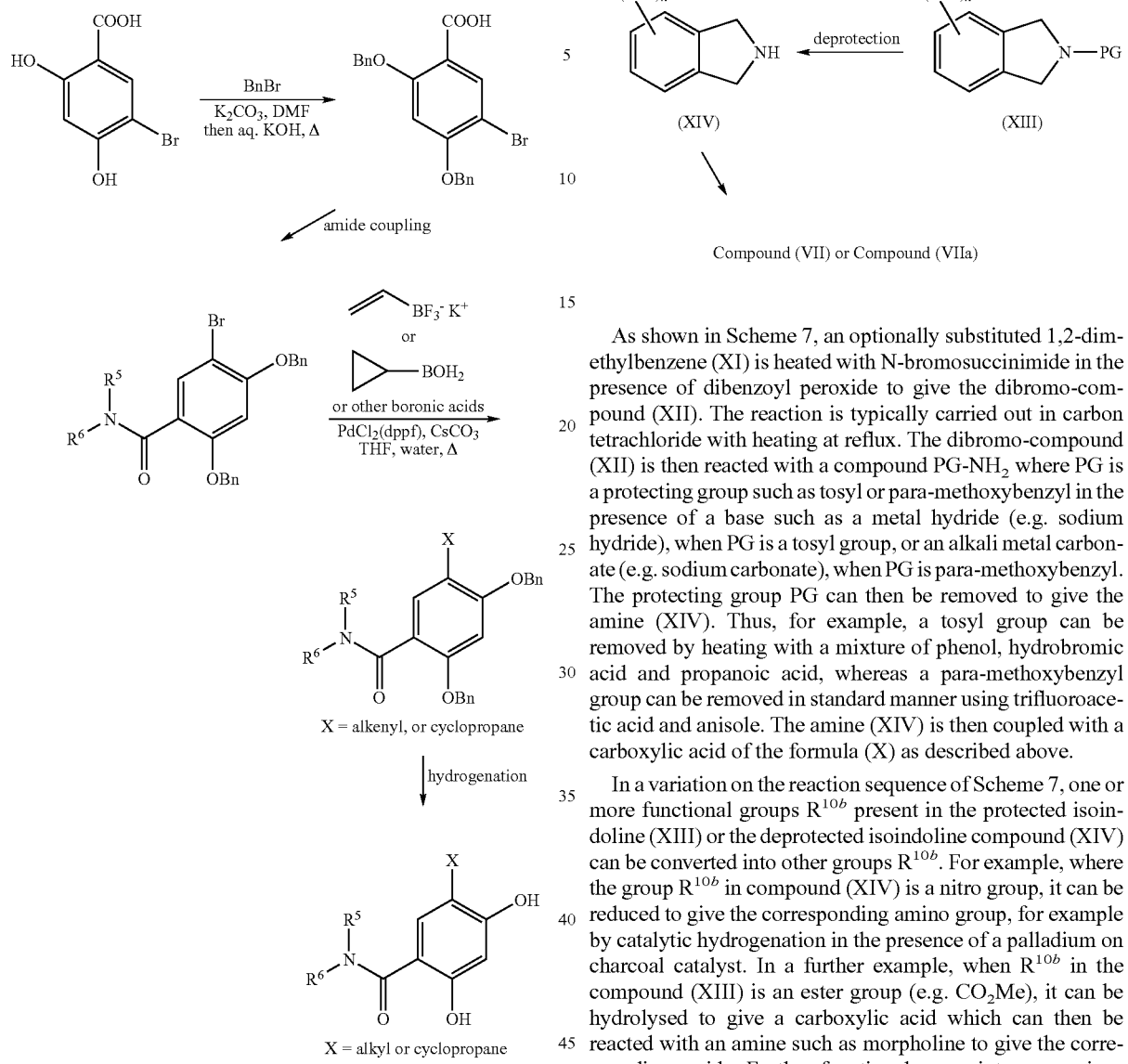

Compound (VII) or Compound (VIIa)

As shown in Scheme 7, an optionally substituted 1,2-dimethylbenzene (XI) is heated with N-bromosuccinimide in the presence of dibenzoyl peroxide to give the dibromo-compound (XII). The reaction is typically carried out in carbon tetrachloride with heating at reflux. The dibromo-compound (XII) is then reacted with a compound PG-NH$_2$ where PG is a protecting group such as tosyl or para-methoxybenzyl in the presence of a base such as a metal hydride (e.g. sodium hydride), when PG is a tosyl group, or an alkali metal carbonate (e.g. sodium carbonate), when PG is para-methoxybenzyl. The protecting group PG can then be removed to give the amine (XIV). Thus, for example, a tosyl group can be removed by heating with a mixture of phenol, hydrobromic acid and propanoic acid, whereas a para-methoxybenzyl group can be removed in standard manner using trifluoroacetic acid and anisole. The amine (XIV) is then coupled with a carboxylic acid of the formula (X) as described above.

In a variation on the reaction sequence of Scheme 7, one or more functional groups $R^{10b}$ present in the protected isoindoline (XIII) or the deprotected isoindoline compound (XIV) can be converted into other groups $R^{10b}$. For example, where the group $R^{10b}$ in compound (XIV) is a nitro group, it can be reduced to give the corresponding amino group, for example by catalytic hydrogenation in the presence of a palladium on charcoal catalyst. In a further example, when $R^{10b}$ in the compound (XIII) is an ester group (e.g. CO$_2$Me), it can be hydrolysed to give a carboxylic acid which can then be reacted with an amine such as morpholine to give the corresponding amide. Further functional group interconversions may subsequently be carried out (for example reduction of the amide to the corresponding aminomethyl compound with lithium aluminium hydride) before removal of the protecting group PG.

Compounds of the formula (I) wherein NR$^5$R$^6$ is an optionally substituted isoindoline group, for example as in compounds of the formulae (VII) and (VIIa), can be prepared by the methods illustrated in Scheme 7, or methods analogous thereto.

An alternative synthesis of the isoindoline compound (XIV) is shown in Scheme 8.

Scheme 7

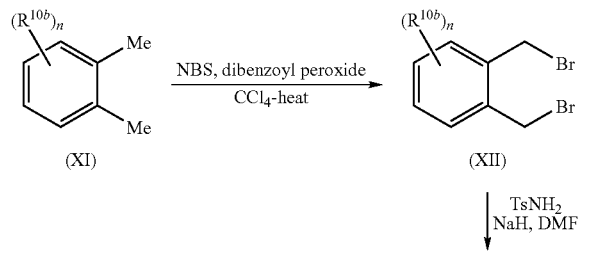

Scheme 8

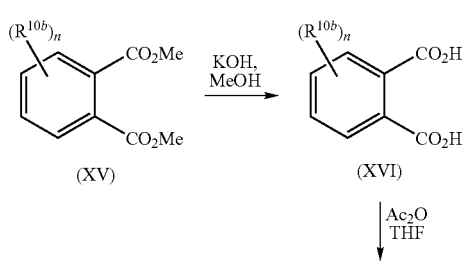

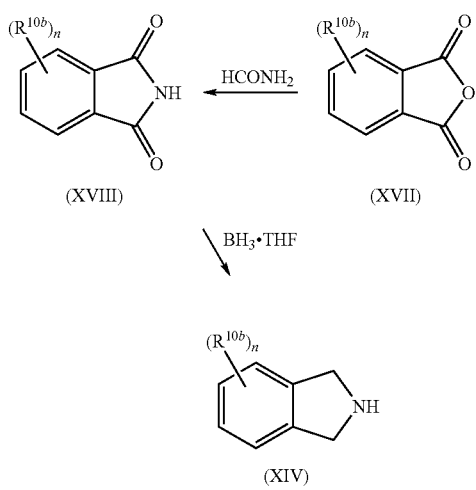

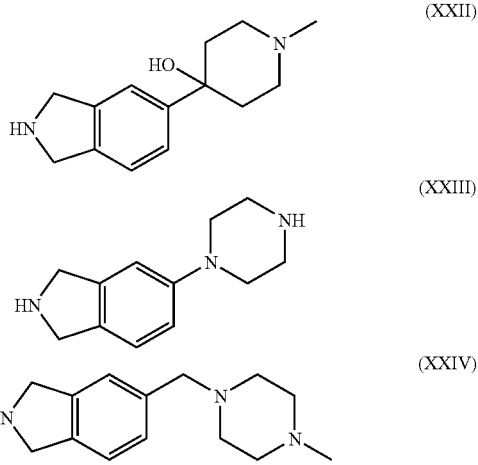

wherein n is 0 or 1; M is N or CHOH and $R^{25}$ is hydrogen or methyl; provided that when n is 0 and $R^{25}$ is methyl, then M is CHOH.

Particular intermediates within formula (XXI) are the compounds (XXII), (XXIII) and (XXIV) below.

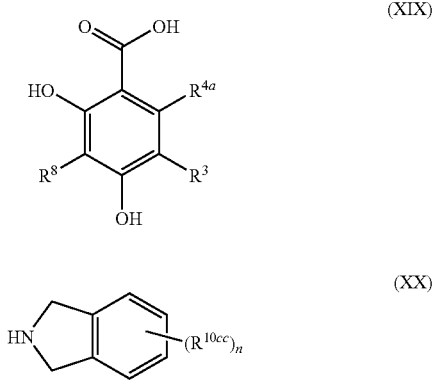

The starting material for Scheme 8 is the ortho diester (XV) which is hydrolysed to the corresponding dicarboxylic acid (XVI) using an alkali metal hydroxide such as potassium hydroxide before being subjected to cyclisation to the phthalic anhydride (XVII) by reaction with acetic anhydride. The phthalic anhydride (XVII) can be converted to the corresponding phthalimide (XVIII) by reaction with formamide at an elevated temperature (e.g. approximately 210° C.). The phthalimide (XVIII) can then be reduced to the isoindoline (XIV) using a suitable reducing agent such as borane in tetrahydrofuran.

Compounds of the formula (VIIb) as defined herein can be prepared by the reaction of a compound of the formula (XIX) or a protected derivative thereof with a compound of the formula (XX):

wherein n, $R^3$, $R^{4a}$, $R^8$ and $R^{10cc}$ are as defined herein, under amide forming conditions as described above and in the examples.

Many of the compounds of formula (XX) are novel and, as such, form another aspect of the invention. Thus, in another aspect, the invention provides a compound of the formula (XX) but excluding any and all compounds known per se in the prior art.

Within formula (XX), particular intermediates can be represented by the formula (XXI):

The intermediates of formula (XXI) can be made by methods well known to the skilled person or methods analogous thereto. For example, intermediate XXII can be prepared by lithium-halogen exchange of a suitably N-protected 5-bromoisoindoline, quenching with 1-methyl-4-piperidone and subsequent deprotection. Intermediate XXII can be prepared by Buchwald palladium coupling of 4-BOC-piperazine and a suitably N-protected 5-bromoisoindoline followed by subsequent deprotection. One method of preparation for intermediate XXIV is from a suitably N-protected isoindoline-5-carboxylic acid, Weinreb amide formation, reduction to the aldehyde, followed by reductive amination and subsequent deprotection.

Once formed, where the substituent groups permit, one compound of the formula (I), or a protected form thereof, can be converted into another compound of the formula (I).

For example, when $R^1$ and $R^2$ are both protected hydroxy groups (e.g. benzyloxy groups), and $R^3$ is bromine, the bromine atom can be replaced by trifluoromethyl by reaction with a trifluoroacetate salt (e.g. sodium trifluoroacetate), and copper (I) iodide in a polar solvent such as dimethylformamide.

In another procedure, compounds of the formula (I) wherein $R^8$ is fluorine can be prepared from compounds of the formula (I) where $R^8$ is hydrogen by electrophilic fluorination. Electrophilic fluorination can be carried out using a fluorinating agent such as 1-(chloromethyl)-4-fluoro-1,4-diazoniabicyclo[2.2.2]octane bis(tetrafluoroborate) or similar N-fluoro-diazonia compounds.

In a further procedure, compounds of the formula (I) wherein $R^1$ and $R^2$ are both hydroxy groups can be monomethylated to give a compound where one of $R^1$ and $R^2$ is a methoxy group by reaction with one equivalent of a methylating agent such as dimethylsulphate. The methylation reaction is typically carried out in a polar solvent such as acetonitrile in the presence of a base, for example an alkali metal carbonate such as potassium carbonate. Analogous methylation reactions may also be carried out on intermediate compounds containing two phenolic hydroxy groups.

Many of the procedures described below and used in this synthesis are well known to those skilled in the art, and examples of alkylations, acylations, functional group interconversions and reagents and conditions for carrying out such conversions can be found in, for example, *Advanced Organic Chemistry*, by Jerry March, $4^{th}$ edition, 119, Wiley Interscience, New York; *Fiesers' Reagents for Organic Synthesis*, Volumes 1-17, John Wiley, edited by Mary Fieser (ISBN: 0-471-58283-2); and *Organic Syntheses*, Volumes 1-8, John Wiley, edited by Jeremiah P. Freeman (ISBN: 0-471-31192-8).

As well as the specific examples, and the methods of preparation outlined below, it is understood that modification to the routes described would allow synthesis of many further examples of compounds claimed in Formula 1. For example, alternative benzoic acid starting materials with differing or additional substitution patterns could be prepared.

In many of the reactions described above, it may be necessary to protect one or more groups to prevent reaction from taking place at an undesirable location on the molecule. Examples of protecting groups, and methods of protecting and deprotecting functional groups, can be found in *Protective Groups in Organic Synthesis* (T. Green and P. Wuts; 3rd Edition; John Wiley and Sons, 1999).

A hydroxy group may be protected, for example, as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(=O)CH$_3$, —OAc). When the hydroxy group is a phenolic hydroxy group, for example in compounds of the formula (I) wherein $R^1$ and/or $R^2$ are hydroxy, a preferred protecting group is a benzyl group.

An aldehyde or ketone group may be protected, for example, as an acetal (R—CH(OR)$_2$) or ketal (R$_2$C(OR)$_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid. An amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH—Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), or as a 2(-phenylsulphonyl)ethyloxy amide (—NH-Psec). Other protecting groups for amines, such as cyclic amines and heterocyclic N—H groups, include toluenesulphonyl (tosyl) and methanesulphonyl (mesyl) groups and benzyl groups such as a para-methoxybenzyl (PMB) group. A carboxylic acid group may be protected as an ester for example, as: an $C_{1-7}$ alkyl ester (e.g., a methyl ester; a t-butyl ester); a $C_{1-7}$ haloalkyl ester (e.g., a $C_{1-7}$trihaloalkyl ester); a triC$_{1-7}$alkylsilyl-C$_{1-7}$ alkyl ester; or a C$_{5-20}$ aryl-C$_{1-7}$alkyl ester (e.g., a benzyl ester; a nitrobenzyl ester); or as an amide, for example as a methyl amide. A thiol group may be protected, for example, as a thioether (—SR), for example, as: a benzyl thioether; an acetamidomethyl ether (—S—CH$_2$NHC(=O)CH$_3$).

Methods of Purification of the Compounds of Formula (I)

The compounds may be isolated and purified by a number of methods well known to those skilled in the art and examples of such methods include chromatographic techniques such as column chromatography (e.g. flash chromatography) and HPLC. Preparative LC-MS is a standard and effective method used for the purification of small organic molecules such as the compounds described herein. The methods for the liquid chromatography (LC) and mass spectrometry (MS) can be varied to provide better separation of the crude materials and improved detection of the samples by MS. Optimisation of the preparative gradient LC method will involve varying columns, volatile eluents and modifiers, and gradients. Methods are well known in the art for optimising preparative LC-MS methods and then using them to purify compounds. Such methods are described in Rosentreter U, Huber U.; Optimal fraction collecting in preparative LC/MS; *J Comb Chem.*; 2004; 6(2), 159-64 and Leister W, Strauss K, Wisnoski D, Zhao Z, Lindsley C., Development of a custom high-throughput preparative liquid chromatography/mass spectrometer platform for the preparative purification and analytical analysis of compound libraries; *J Comb Chem.*; 2003; 5(3); 322-9.

Alternatively, normal phase preparative LC based methods might be used in place of reverse phase methods. Most preparative LC-MS systems utilise reverse phase LC and volatile acidic modifiers, since the approach is very effective for the purification of small molecules and because the eluents are compatible with positive ion electrospray mass spectrometry. Employing other chromatographic solutions e.g. normal phase LC, alternatively buffered mobile phase, basic modifiers etc as outlined in the analytical methods described above could alternatively be used to purify the compounds.

Ancillary Compounds for use According to the Invention

The invention provides a combination comprising (or consisting essentially of) a compound of the formula (I) and one or more ancillary compounds.

Any of a wide variety of ancillary compounds may be used in the combinations of the invention, including those of formula (0) and (I'), as herein defined.

In one embodiment, the combination comprises one or more compounds of formula (0) as ancillary compound(s). In such embodiments, the combination may comprise one compound of formula (0).

In another embodiment, the combination comprises one or more compounds of formula (I') as ancillary compound(s). In such embodiments, the combination may comprise one compound of formula (I').

In another embodiment the combination comprises one or more compounds of formula (0) and one or more compounds of formula (I') as ancillary compounds. In such embodiments, the combination may comprise one compound of formula (0) and one compound of formula (I').

Thus, the combinations of the invention may comprise (or consist essentially of) one or more compound(s) of formula (I) and (a) one or more compound(s) of formula (0) and/or (a) one or more compound(s) of formula (I').

The appropriate dose of the ancillary compound(s) for use according to the invention may be determined by reference to the teachings of WO 2005/012256 and WO 2006/077426 (in the case of ancillary compounds of formula (0)) and WO 2006/077416 (in the case of ancillary compounds of formula (I')), which disclosure is hereby incorporated herein by reference. Those skilled in the art will be able to readily determine the appropriate dose on the basis of the aforementioned teachings in the light of the compounds selected for any particular combination, the particular use to which they are to be put and the patient to be treated. For example, combinations comprising two or more ancillary agents of formula (0) and formula (I') may permit dose-sparing of one or more of the ancillary compounds (or of the compound of formula (I)).

General Preferences and Definitions for Ancillary Compounds of Formula (0)

A wide variety of compounds of the formula (0) find application in the combinations of the invention, as described in detail below. The compounds of formula (0) for use in the combinations of the invention correspond to those of formula (0) in WO 2005/012256 (the contents of which are incorporated herein by reference) and various possible substituents, sub-groups, embodiments and examples thereof as therein defined. The content of WO 2005/012256 describing the various possible substituents, subgroups, embodiments and examples of compounds of formula (0) is hereby incorporated herein by reference.

The formula (0) of WO 2005/012256 (PCT/GB2004/003179) is herein also referred to as formula (0) and references to formula (0) herein are to be interpreted accordingly.

Thus, the compound of formula (0) for use in the combinations of the invention has the formula:

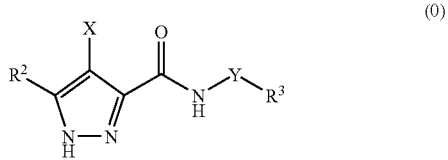

(0)

or are salts or tautomers or N-oxides or solvates thereof;
wherein
X is a group $R^1$-A-$NR^4$— or a 5- or 6-membered carbocyclic or heterocyclic ring;
A is a bond, $SO_2$, C=O, $NR^g$(C=O) or O(C=O) wherein $R^g$ is hydrogen or $C_{1-4}$ hydrocarbyl optionally substituted by hydroxy or $C_{1-4}$ alkoxy;
Y is a bond or an alkylene chain of 1, 2 or 3 carbon atoms in length;
$R^1$ is hydrogen; a carbocyclic or heterocyclic group having from 3 to 12 ring members; or a $C_{1-8}$ hydrocarbyl group optionally substituted by one or more substituents selected from halogen (e.g. fluorine), hydroxy, $C_{1-4}$ hydrocarbyloxy, amino, mono- or di-$C_{1-4}$ hydrocarbylamino, and carbocyclic or heterocyclic groups having from 3 to 12 ring members, and wherein 1 or 2 of the carbon atoms of the hydrocarbyl group may optionally be replaced by an atom or group selected from O, S, NH, SO, $SO_2$;
$R^2$ is hydrogen; halogen; $C_{1-4}$ alkoxy (e.g. methoxy); or a $C_{1-4}$ hydrocarbyl group optionally substituted by halogen (e.g. fluorine), hydroxyl or $C_{1-4}$ alkoxy (e.g. methoxy);
$R^3$ is selected from hydrogen and carbocyclic and heterocyclic groups having from 3 to 12 ring members; and
$R^4$ is hydrogen or a $C_{1-4}$ hydrocarbyl group optionally substituted by halogen (e.g. fluorine), hydroxyl or $C_{1-4}$ alkoxy (e.g. methoxy),
so corresponding to formula (0) in WO 2005/012256 (PCT/GB2004/003179) and including the various possible substituents, subgroups, embodiments and examples thereof as defined in WO 2005/012256 (PCT/GB2004/003179), so that the general preferences and definitions defined in WO 2005/012256 (PCT/GB2004/003179) shall apply to each of the moieties X, Y, $R^g$, $R^1$ to $R^4$ and any substituent, moieties, sub-definition, sub-group or embodiment thereof, unless the context indicates otherwise.

In particular the carbocyclic and heterocyclic groups forming part of X, $R^1$ and $R^3$ may be optionally substituted as defined in WO 2005/012256.

Particular compounds of the formula (0) are those defined in, for example, the compounds of formulae ($I^0$), (I), (Ia), (Ib), (II), (III), (IV), (IVa), (Va), (Vb), (VIa), (VIb), (VII) or (VIII), and any sub-groups thereof in PCT/GB2004/003179 (WO 2005/012256), the compounds listed in PCT/GB2004/003179 (WO 2005/012256) and the compounds exemplified in the Examples section of PCT/GB2004/003179 (WO 2005/012256), the aforementioned sections of PCT/GB2004/003179 (WO 2005/012256) being hereby incorporated by reference.

A preferred sub-group of CDK inhibitor compounds within WO 2005/012256 is represented by the formula (Va):

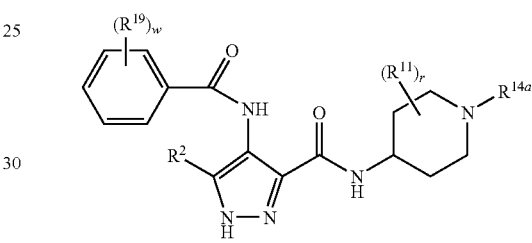

(Va)

or salts or tautomers or N-oxides or solvates thereof;
wherein $R^{14a}$ is selected from hydrogen, $C_{1-4}$ alkyl optionally substituted by fluoro (e.g. methyl, ethyl, n-propyl, i-propyl, butyl and 2,2,2-trifluoroethyl), cyclopropylmethyl, phenyl-$C_{1-2}$ alkyl (e.g. benzyl), $C_{1-4}$ alkoxycarbonyl (e.g. ethoxycarbonyl and t-butyloxycarbonyl), phenyl-$C_{1-2}$ alkoxycarbonyl (e.g. benzyloxycarbonyl), $C_{1-2}$-alkoxy-$C_{1-2}$ alkyl (e.g. methoxymethyl and methoxyethyl), and $C_{1-4}$ alkylsulphonyl (e.g. methanesulphonyl), wherein the phenyl moieties when present are optionally substituted by one to three substituents selected from fluorine, chlorine, $C_{1-4}$ alkoxy optionally substituted by fluoro or $C_{1-2}$-alkoxy, and $C_{1-4}$ alkyl optionally substituted by fluoro or $C_{1-2}$-alkoxy;
w is 0, 1, 2 or 3;
$R^2$ is hydrogen or methyl, most preferably hydrogen;
r is 0, 1 or 2;
$R^{11}$ is selected from hydrogen and $C_{1-3}$ alkyl (and more preferably is selected from hydrogen and methyl and most preferably is hydrogen); and
$R^{19}$ is selected from fluorine; chlorine; $C_{1-4}$ alkoxy optionally substituted by fluoro or $C_{1-2}$-alkoxy; and $C_{1-4}$ alkyl optionally substituted by fluoro or $C_{1-2}$-alkoxy.

Particular compounds within formula (VIb) of WO 2005/012256 include:
4-(2,6-difluoro-benzoylamino)-1H-pyrazole-3-carboxylic acid piperidin-4-ylamide;
4-(2,6-difluoro-benzoylamino)-1H-pyrazole-3-carboxylic acid (1-methyl-piperidin-4-yl)-amide;
4-(2,6-dichloro-benzoylamino)-1H-pyrazole-3-carboxylic acid piperidin-4-ylamide; and
4-(2-fluoro-6-methoxy-benzoylamino)-1H-pyrazole-3-carboxylic acid piperidin-4-ylamide;
or salts or tautomers or N-oxides or solvates thereof.

The compound 4-(2,6-dichloro-benzoylamino)-1H-pyrazole-3-carboxylic acid piperidin-4-ylamide may be present in the form of an acid addition salt which may be a salt formed with hydrochloric acid or a salt as described in WO 2006/077426, the contents of which are incorporated herein by reference.

For example, the acid addition salt may be selected from salts formed with an acid selected from the group consisting of acetic, adipic, alginic, ascorbic (e.g. L-ascorbic), aspartic (e.g. L-aspartic), benzenesulphonic, benzoic, camphoric (e.g. (+) camphoric), capric, caprylic, carbonic, citric, cyclamic, dodecanoate, dodecylsulphuric, ethane-1,2-disulphonic, ethanesulphonic, fumaric, galactaric, gentisic, glucoheptonic, D-gluconic, glucuronic (e.g. D-glucuronic), glutamic (e.g. L-glutamic), α-oxoglutaric, glycolic, hippuric, isethionic, isobutyric, lactic (e.g. (+)-L-lactic and (±)-DL-lactic), lactobionic, laurylsulphonic, maleic, malic, (−)-L-malic, malonic, methanesulphonic, mucic, naphthalenesulphonic (e.g. naphthalene-2-sulphonic), naphthalene-1,5-disulphonic, nicotinic, oleic, orotic, oxalic, palmitic, pamoic, phosphoric, propionic, sebacic, stearic, succinic, sulphuric, tartaric (e.g. (+)-L-tartaric), thiocyanic, toluenesulphonic (e.g. p-toluenesulphonic), valeric and xinafoic acids.

One sub-group of acid addition salts includes salts formed with an acid selected from the group consisting of acetic, adipic, ascorbic (e.g. L-ascorbic), aspartic (e.g. L-aspartic), caproic, carbonic, citric, dodecanoic, fumaric, galactaric, glucoheptonic, gluconic (e.g. D-gluconic), glucuronic (e.g. D-glucuronic), glutamic (e.g. L-glutamic), glycolic, hippuric, lactic (e.g. (+)-L-lactic and (±)-DL-lactic), maleic, palmitic, phosphoric, sebacic, stearic, succinic, sulphuric, tartaric (e.g. (+)-L-tartaric) and thiocyanic acids.

More particularly the salts are acid addition salts formed with an acid selected from methanesulphonic acid and acetic acid, and mixtures thereof.

In one embodiment, the salt is an acid addition salt formed with methanesulphonic acid.

In another embodiment, the salt is an acid addition salt formed with acetic acid.

The salts may be prepared from 4-(2,6-dichloro-benzoylamino)-1H-pyrazole-3-carboxylic acid piperidin-4-ylamide by the methods described in WO 2006/077426.

The salts may be substantially crystalline; i.e. they are from 50% to 100% crystalline, and more particularly they may be at least 50% crystalline, or at least 60% crystalline, or at least 70% crystalline, or at least 80% crystalline, or at least 90% crystalline, or at least 95% crystalline, or at least 98% crystalline, or at least 99% crystalline, or at least 99.5% crystalline, or at least 99.9% crystalline, for example 100% crystalline.

More preferably the salts may be those (or may be selected from the group consisting of those) that are 95% to 100% crystalline, for example at least 98% crystalline, or at least 99% crystalline, or at least 99.5% crystalline, or at least 99.6% crystalline or at least 99.7% crystalline or at least 99.8% crystalline or at least 99.9% crystalline, for example 100% crystalline.

One example of a substantially crystalline salt is a crystalline salt formed with methanesulphonic acid. Another example of a substantially crystalline salt is a crystalline salt formed with acetic acid.

The salts of the invention, in the solid state, can be solvated (e.g. hydrated) or non-solvated (e.g. anhydrous).

In one embodiment, the salts are non-solvated (e.g. anhydrous). An example of a non-solvated salt is the crystalline salt formed with methanesulphonic acid.

Figure 2:
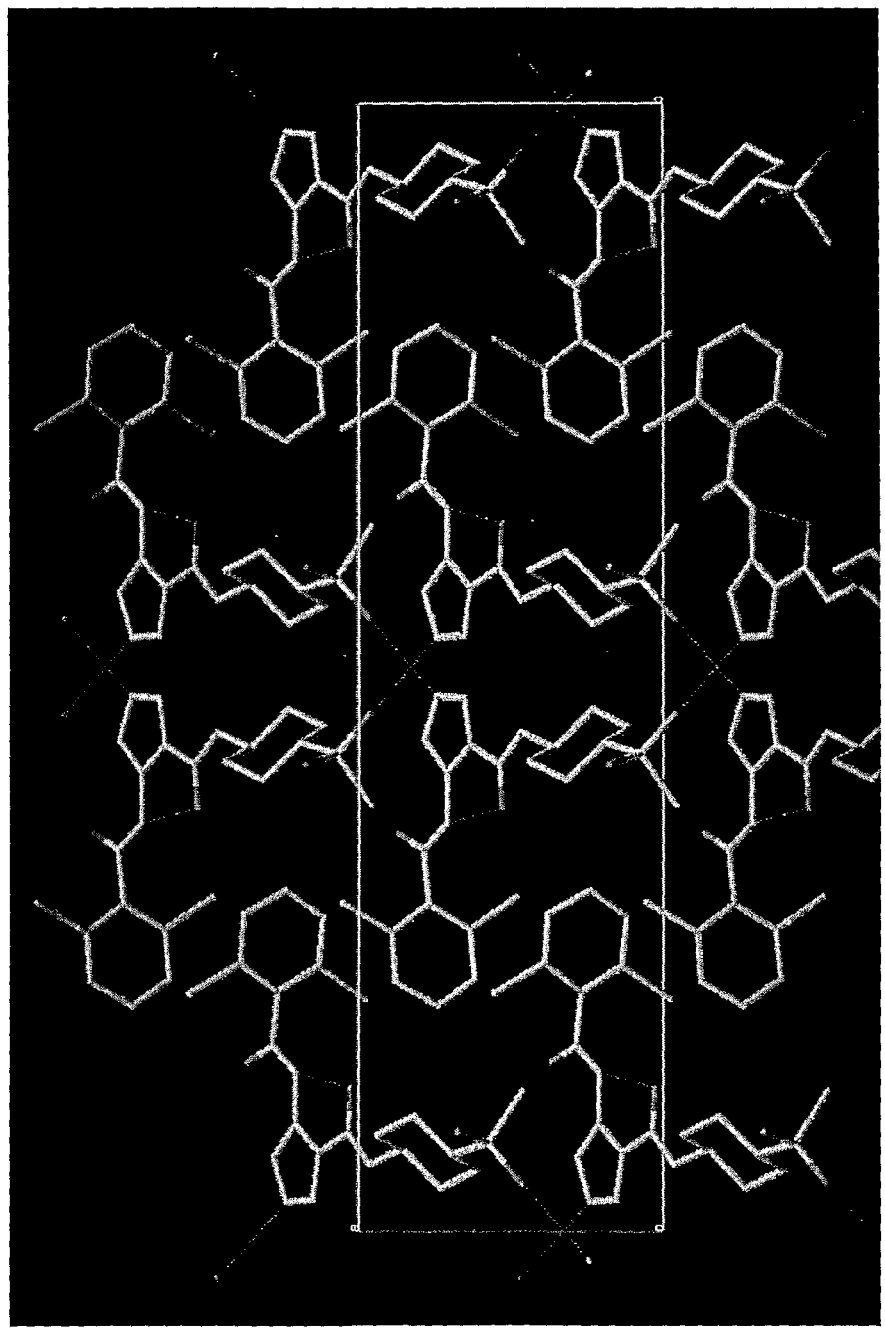
FIG. 2 shows the crystal structure of the methanesulfonic acid salt of 4-(2,6-dichlorobenzoylamino)-1H-pyrazole-3-carboxylic acid piperidin-4-ylamide mesylate
Figure 3:
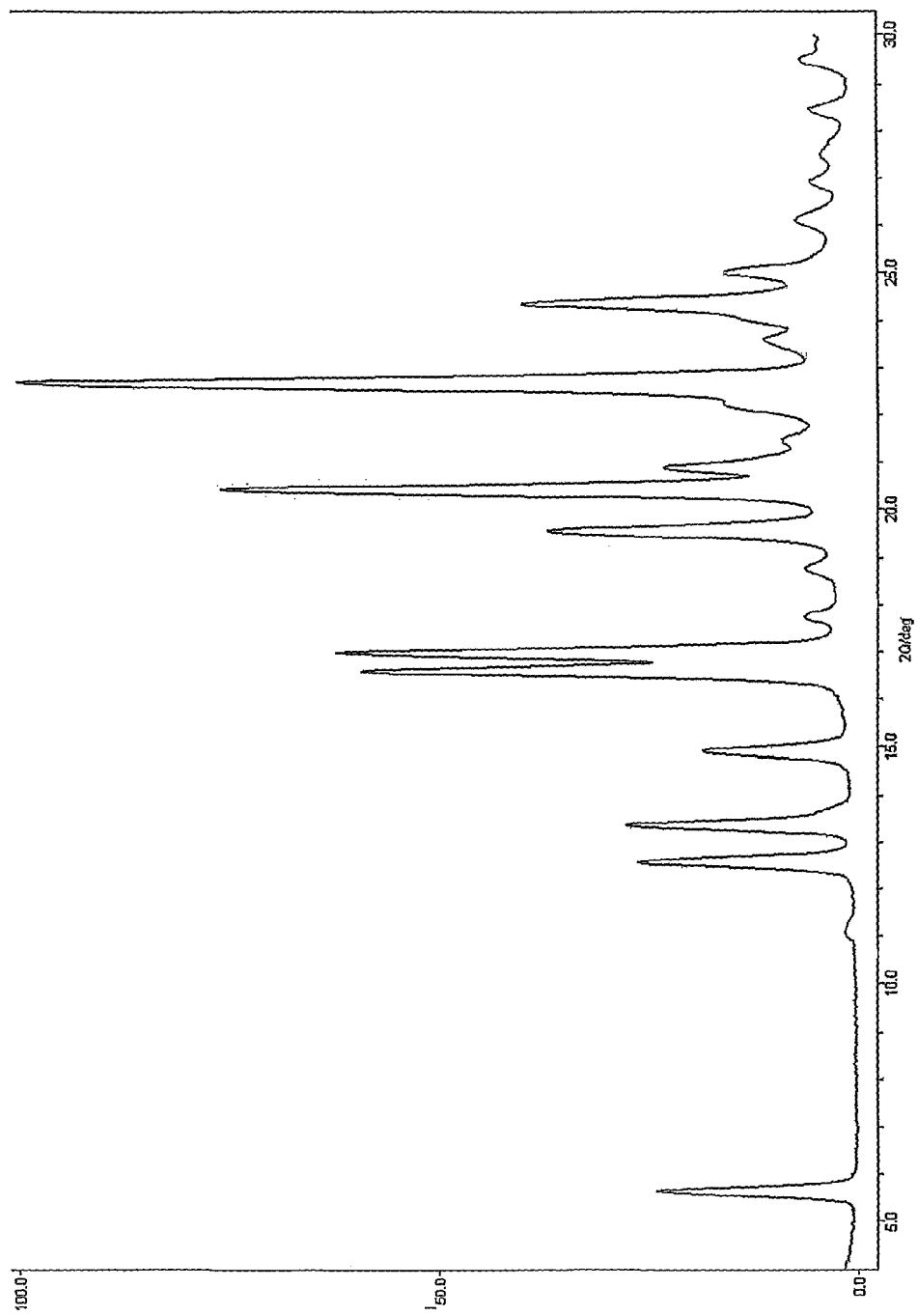
FIG. 3 shows shows the XRPD pattern for 4-(2,6-dichlorobenzoylamino)-1H-pyrazole-3-carboxylic acid piperidin-4-ylamide mesylate methanesulfonic acid

In one embodiment, the salt is a methanesulphonic acid salt of 4-(2,6-dichlorobenzoylamino)-1H-pyrazole-3-carboxylic acid piperidin-4-ylamide mesylate salt which is crystalline and is characterised by any one or more (in any combination) or all of the following parameters, namely that the salt:

(a) has a crystal structure as set out in FIGS. 1 and 2 of WO 2006/077426; and/or (b) has a crystal structure as defined by the coordinates in Example 2 of WO 2006/077426; and/or (c) has crystal lattice parameters at 93 K a=8.90(10), b=12.44(10), c=38.49(4) Å, α=β=γ=90°; and/or (d) has a crystal structure that belongs belong to an orthorhombic space group such as Pbca (#61); and/or (e) has an X-ray powder diffraction pattern characterised by the presence of major peaks at the diffraction angles (2θ) and interplanar spacings (d) set forth in Table A below, and optionally Table B below; for example wherein the X-ray powder diffraction pattern is characterised by the presence of major peaks at the diffraction angles (2θ), interplanar spacings (d) and intensities set forth in Table C below; and/or (f) exhibits peaks at the same diffraction angles as those of the X-ray powder diffraction pattern shown in FIG. 3 of WO 2006/077426 and optionally wherein the peaks have the same relative intensity as the peaks in FIG. 3 of WO 2006/077426; and/or (g) has an X-ray powder diffraction pattern substantially as shown in FIG. 3 of WO 2006/077426; and/or (h) is anhydrous and exhibits an endothermic peak at 379-380° C. e.g. 379.8° C. when subjected to DSC; and/or (i) exhibits an infra-red spectrum, when analysed using the KBr disc method, that contains characteristic peaks at 3233, 3002, 2829, 1679, 1632, 1560, 1430, 1198, 1037, 909 and 784 $cm^{-1}$.

Particular pharmaceutical compositions comprising an aqueous solution containing an acid addition salt of 4-(2,6-dichloro-benzoylamino)-1H-pyrazole-3-carboxylic acid piperidin-4-ylamide (such as the mesylate and acetate and mixtures thereof, and preferably the mesylate) are also described in WO 2006/077426.

Methods of Treatment using this compound are described in WO 2005/012256 and WO 2006/077426. Methods of Diagnosis of a patient to determine whether a disease or condition from which the patient is or may be suffering is one which would be susceptible to treatment with a compound having activity against CDK.

A preferred compound of the formula (0) is 4-(2,6-dichloro-benzoylamino)-1H-pyrazole-3-carboxylic acid piperidin-4-ylamide.

Accordingly, a preferred combination comprises (or consists essentially of) one or more ancillary compounds 4-(2,6-dichloro-benzoylamino)-1H-pyrazole-3-carboxylic acid piperidin-4-ylamide.

A further combination of the invention comprises (or consists essentially of) 4-(2,6-dichloro-benzoylamino)-1H-pyrazole-3-carboxylic acid piperidin-4-ylamide in the form of a salt selected from the acid addition salts formed with hydrochloric acid, methanesulphonic acid and/or acetic acid as one or more ancillary compounds.

In addition combination of the invention comprises (or consists essentially of) the methane sulphonic acid salt of 4-(2,6-dichloro-benzoylamino)-1H-pyrazole-3-carboxylic acid piperidin-4-ylamide as one or more ancillary compounds.

In addition combination of the invention comprises (or consists essentially of) methane sulphonic acid salt of 4-(2, 6-dichloro-benzoylamino)-1H-pyrazole-3-carboxylic acid piperidin-4-ylamide is in crystalline form as one or more ancillary compounds.

Methods for the Preparation of Compounds of the Formula (0) are as described in WO 2005/012256, WO 2006/077416 and WO 2006/077426, the contents of which are incorporated herein by reference. In particular, the contents of WO 2005/012256 which relate to the relevant processes at pages 91 to 101 are hereby incorporated herein by reference. In particular, the contents of WO 2006/074416 which relate to the relevant processes at pages 33 to 39 are hereby incorporated herein by reference. In particular, the contents of WO 2006/077426 which relate to the relevant processes at pages 30 to 36 are hereby incorporated herein by reference.

The Biological Activity of the compounds of formula (0) are described at pages 88 to 91 of WO 2005/012256 and at pages 39 to 49 of WO 2006/077426, which disclosure is hereby incorporated herein by reference.

Thus, combinations comprising one or more ancillary compounds of formula (0) are inhibitors of cyclin dependent kinases, and in particular cyclin dependent kinases selected from CDK1, CDK2, CDK3, CDK4, CDK5 and CDK6. Preferred combinations comprising compounds of formula (0) inhibit one or more CDK kinases selected from CDK1, CDK2, CDK4 and CDK5, for example CDK1 and/or CDK2. The combinations comprising compounds of formula (0) of the invention are also considered to be inhibitors of glycogen synthase kinase-3 (GSK3).

As a consequence of their activity in modulating or inhibiting CDK and glycogen synthase kinase, combinations comprising one or more ancillary compounds of formula (0) are useful in providing a means of arresting, or recovering control of, the cell cycle in abnormally dividing cells. It is therefore anticipated that they will prove useful in treating or preventing proliferative disorders such as cancers. It is also envisaged that they will be useful in treating conditions such as viral infections, type II or non-insulin dependent diabetes mellitus, autoimmune diseases, head trauma, stroke, epilepsy, neurodegenerative diseases such as Alzheimer's, motor neurone disease, progressive supranuclear palsy, corticobasal degeneration and Pick's disease for example autoimmune diseases and neurodegenerative diseases for example.

One sub-group of disease states and conditions where it is envisaged that the salts of the invention will be useful consists of viral infections, autoimmune diseases and neurodegenerative diseases.

CDKs play a role in the regulation of the cell cycle, apoptosis, transcription, differentiation and CNS function. Therefore, CDK inhibitors could be useful in the treatment of diseases in which there is a disorder of proliferation, apoptosis or differentiation such as cancer. In particular RB+ve tumours may be particularly sensitive to CDK inhibitors. RB−ve tumours may also be sensitive to CDK inhibitors.

Examples of cancers which may be inhibited include, but are not limited to, a carcinoma, for example a carcinoma of the bladder, breast, colon (e.g. colorectal carcinomas such as colon adenocarcinoma and colon adenoma), kidney, epidermis, liver, lung, for example adenocarcinoma, small cell lung cancer and non-small cell lung carcinomas, oesophagus, gall bladder, ovary, pancreas e.g. exocrine pancreatic carcinoma, stomach, cervix, thyroid, prostate, or skin, for example squamous cell carcinoma; a hematopoietic tumour of lymphoid lineage, for example leukaemia, acute lymphocytic leukaemia, B-cell lymphoma, T-cell lymphoma, Hodgkin's lymphoma, non-Hodgkin's lymphoma, hairy cell lymphoma, or Burkett's lymphoma; a hematopoietic tumour of myeloid lineage, for example acute and chronic myelogenous Leukaemias, myelodysplastic syndrome, or promyelocyte leukaemia; thyroid follicular cancer; a tumour of mesenchymal origin, for example fibrosarcoma or habdomyosarcoma; a tumour of the central or peripheral nervous system, for example astrocytoma, neuroblastoma, glioma or schwannoma; melanoma; seminoma; teratocarcinoma; osteosarcoma; xeroderma pigmentosum; keratoctanthoma; thyroid follicular cancer; or Kaposi's sarcoma.

The cancers may be cancers which are sensitive to inhibition of any one or more cyclin dependent kinases selected from CDKI, CDK2, CDK4, CDK6 and CDK9, for example, one or more CDK kinases selected from CDKI, CDK2, CDK4 and CDK9, e.g. CDKI and/or CDK2.

Whether or not a particular cancer is one which is sensitive to inhibition by a cyclin dependent kinase may be determined by means of a cell growth assay as set out in the examples below or by a method as set out in the section headed "Methods of Diagnosis".

CDKs are also known to play a role in apoptosis, proliferation, differentiation and transcription and therefore CDK inhibitors could also be useful in the treatment of the following diseases other than cancer; viral infections, for example herpes virus, pox virus, Epstein-Barr virus, Sindbis virus, adenovirus, HIV, HPV, HCV and HCMV; prevention of AIDS development in HIV-infected individuals; chronic inflammatory diseases, for example systemic lupus erythematosus, autoimmune mediated glomerulonephritis, rheumatoid arthritis, psoriasis, inflammatory bowel disease, and autoimmune diabetes mellitus; cardiovascular diseases for example cardiac hypertrophy, restenosis, atherosclerosis; neurodegenerative disorders, for example Alzheimer's disease, AIDS-related dementia, Parkinson's disease, amyotropic lateral sclerosis, retinitis pigmentosa, spinal muscular atropy and cerebellar degeneration; glomerulonephritis; myelodysplastic syndromes, ischemic injury associated myocardial infarctions, stroke and reperfusion injury, arrhythmia, atherosclerosis, toxin-induced or alcohol related liver diseases, haematological diseases, for example, chronic anaemia and aplastic anaemia; degenerative diseases of the musculoskeletal system, for example, osteoporosis and arthritis, aspirin-sensitive rhinosinusitis, cystic fibrosis, multiple sclerosis, kidney diseases and cancer pain.

It has also been discovered that some cyclin-dependent kinase inhibitors can be used in combination with other anticancer agents. For example, the cyclin-dependent kinase inhibitor flavopiridol has been used with other anticancer agents in combination therapy.

Thus, in the pharmaceutical compositions, uses or methods of this invention for treating a disease or condition comprising abnormal cell growth, the disease or condition comprising abnormal cell growth in one embodiment is a cancer.

One group of cancers includes human breast cancers (e.g. primary breast tumours, node-negative breast cancer, invasive duct adenocarcinomas of the breast, non-endometrioid breast cancers); and mantle cell lymphomas. In addition, other cancers are colorectal and endometrial cancers.

Another sub-set of cancers includes hematopoietic tumours of lymphoid lineage, for example leukemia, chronic lymphocytic leukaemia, mantle cell lymphoma and B-cell lymphoma (such as diffuse large B cell lymphoma).

One particular cancer is chronic lymphocytic leukaemia.

Another particular cancer is mantle cell lymphoma.

Another particular cancer is diffuse large B cell lymphoma.

A further sub-set of cancers includes breast cancer, ovarian cancer, colon cancer, prostate cancer, oesophageal cancer, squamous cancer and non-small cell lung carcinomas.

The activity of the acid addition salts of the invention as inhibitors of cyclin dependent kinases and glycogen synthase kinase-3 can be measured using the assays set forth in the examples below and the level of activity exhibited can be defined in terms of the IC50 value.

Thus, for example, it is envisaged that the acid addition salts of the invention will be useful in alleviating or reducing the incidence of cancer.

Thus, the combinations of the invention comprising one or more ancillary compounds of formula (0) find application in the treatment of any of the diseases and disorders described above and at pages 88 to 91 of WO 2005/012256 and pages 39 to 49 of WO 2006/077426, which disclosure is hereby incorporated herein by reference.

General Preferences and Definitions for Ancillary Compounds of Formula (I')

A wide variety of compounds of the formula (I') find application in the combinations of the invention, as described in detail below. The compounds of formula (I') for use in the combinations of the invention correspond to those of formula (I) described in WO 2006/077416 and include the various possible substituents, sub-groups, embodiments and examples thereof as therein defined. The content of WO 2006/077416 describing the various possible substituents, sub-groups, embodiments and examples of compounds of formula (I) (i.e. formula (I') herein) is hereby incorporated herein by reference.

In this specification in general (and this section in particular), unless the context indicates otherwise, references to a compound of formula (I') includes all subgroups of formula (I') as defined herein and the term 'subgroups' includes all preferences, embodiments, examples and particular compounds defined herein. Any references to formula (I') herein shall also be taken to refer to and any sub-group of compounds within formula (I') and any preferences and examples thereof unless the context requires otherwise.

The formula (I) of WO 2006/077416 is herein referred to as formula (I') and references to formula (I') herein are to be interpreted accordingly.

As described infra, compounds of the formula (I') have the formula:

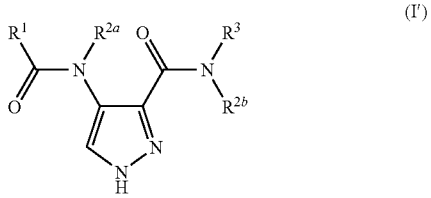

or salts, tautomers, solvates and N-oxides thereof;
wherein:
R$^1$ is 2,6-dichlorophenyl;
R$^{2a}$ and R$^{2b}$ are both hydrogen;
and R$^3$ is a group:

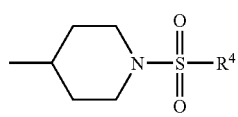

where R$^4$ is C$_{1-4}$ alkyl.

Within this genus are many 'subgroups', preferences, embodiments, examples and particular compounds and while any references to formula (I') herein shall also be taken to refer to and any sub-group of compounds within formula (I') and any preferences and examples thereof unless the context requires otherwise, the following sections describe certain general preferences and definitions in relation to compounds of the formula (I') for use in the combinations of the invention.

The C$_{1-4}$ alkyl group can be a C$_1$, C$_2$, C$_3$ or C$_4$ alkyl group.
Within the group of C$_{1-4}$ alkyl groups are the sub-groups of:
C$_{1-3}$ alkyl groups;
C$_{1-2}$ alkyl groups;
C$_{2-3}$ alkyl groups; and
C$_{2-4}$ alkyl groups.
One particular sub-group is C$_{1-3}$ alkyl.
Particular C$_{1-4}$ alkyl groups are methyl, ethyl, i-propyl, n-butyl, i-butyl and tert-butyl groups.
Another sub-group of C$_{1-4}$ alkyl groups consists of methyl, ethyl, i-propyl and n-propyl groups.
One preferred group is a methyl group.
Other particular groups R$^4$ are ethyl and isopropyl.

Accordingly, a preferred combination comprises (or consists essentially of) one or more ancillary compounds 4-(2,6-dichloro-benzoylamino)-1H-pyrazole-3-carboxylic acid (1-methanesulphonyl-piperidin-4-yl)-amide.

A further combination comprises (or consists essentially of) substantially crystalline 4-(2,6-dichloro-benzoylamino)-1H-pyrazole-3-carboxylic acid (1-methanesulphonyl-piperidin-4-yl)-amide or crystal form thereof as one or more ancillary compounds.

A further combination comprises (or consists essentially of) formulations comprising 4-(2,6-dichloro-benzoylamino)-1H-pyrazole-3-carboxylic acid (1-methanesulphonyl-piperidin-4-yl)-amide as one or more ancillary compounds.

In such embodiments, the ancillary compound may be 4-(2,6-dichloro-benzoylamino)-1H-pyrazole-3-carboxylic acid (1-methanesulphonyl-piperidin-4-yl)-amide (for example 4-(2,6-dichloro-benzoylamino)-1H-pyrazole-3-carboxylic acid (1-methanesulphonyl-piperidin-4-yl)-amide in crystalline form).

A preferred compound within formula (I') is 4-(2,6-dichloro-benzoylamino)-1H-pyrazole-3-carboxylic acid (1-methanesulphonyl-piperidin-4-yl)-amide.

The compound 4-(2,6-dichloro-benzoylamino)-1H-pyrazole-3-carboxylic acid (1-methanesulphonyl-piperidin-4-yl)-amide may be substantially crystalline; i.e. it is from 50% to 100% crystalline. Crystalline forms of 4-(2,6-dichloro-benzoylamino)-1H-pyrazole-3-carboxylic acid (1-methanesulphonyl-piperidin-4-yl)-amide are disclosed in our applications U.S. 60/746,541 and U.S. 60/830,967, the contents of each of which are incorporated herein by reference.

More particularly, the compound 4-(2,6-dichloro-benzoylamino)-1H-pyrazole-3-carboxylic acid (1-methanesulphonyl-piperidin-4-yl)-amide may be at least 55% crystalline, or at least 60% crystalline, or at least 65% crystalline, or at least 70% crystalline, or at least 75% crystalline, or at least 80% crystalline, or at least 85% crystalline, or at least 90% crystalline, or at least 95% crystalline, or at least 98% crystalline, or at least 99% crystalline, or at least 99.5% crystalline, or at least 99.9% crystalline, for example 100% crystalline.

The crystalline forms of the compound may be solvated (e.g. hydrated) or non-solvated (e.g. anhydrous). In one embodiment, the crystalline forms are solvated (e.g. hydrated). In another embodiment, the crystalline forms are non-solvated (e.g. anhydrous).

In one embodiment, the crystalline form of 4-(2,6-dichloro-benzoylamino)-1H-pyrazole-3-carboxylic acid (1-methanesulphonyl-piperidin-4-yl)-amide is a crystalline form which is characterised by any one or more (in any combination) or all of the following parameters, namely that the crystalline form:

- has a crystal structure as set out in FIGS. 1 and 2 herein (and as set forth in U.S. 60/746,541 and U.S. 60/830, 967); and/or
- has a crystal structure as defined by the coordinates in Table 1 herein (and as set forth in U.S. 60/746,541 and U.S. 60/830,967); and/or
- has crystal lattice parameters at a=9.15, b=31.32, c=7.93 Å, β=113.3°, α=γ=90°; and/or
- has a crystal structure that belongs belong to a monoclinic space group such as C2/c (#15); and/or
- has an X-ray powder diffraction pattern characterised by the presence of major peaks at the diffraction angles (2θ) and interplanar spacings (d) set forth in Table A:

TABLE A

| 2θ/° | d/Å | I |
|---|---|---|
| 16.57 | 5.35 | 59 |
| 16.95 | 5.23 | 62 |
| 20.42 | 4.35 | 76 |
| 22.66 | 3.92 | 100 |
| 24.33 | 3.66 | 40 | and optionally Table B:

TABLE B

| 2θ/° | d/Å | I |
|---|---|---|
| 5.63 | 15.70 | 24 |
| 12.56 | 7.05 | 26 |
| 13.35 | 6.63 | 27 |
| 14.89 | 5.95 | 18 |
| 19.53 | 4.55 | 37 |
| 20.88 | 4.25 | 23 |
| 24.99 | 3.56 | 16 | and/or
- exhibits peaks at the same diffraction angles as those of the X-ray powder diffraction pattern shown in FIG. 3 herein (and as set forth in U.S. 60/746,541 and U.S. 60/830, 967) and optionally wherein the peaks have the same relative intensity as the peaks in FIG. 3 herein (and as set forth in U.S. 60/746,541 and U.S. 60/830,967); and/or
- has an X-ray powder diffraction pattern substantially as shown in FIG. 3 herein (and as set forth in U.S. 60/746, 541 and U.S. 60/830,967); and/or
- is anhydrous and exhibits an endothermic peak at 293-296° C., for example 294.5-295° C., when subjected to DSC; and/or
- exhibits an infra-red spectrum, when analysed using the Universal Attenuated Total Reflectance (UATR) method, that contains characteristic peaks at containing characteristic peaks at 3362, 3019, 2843, 1677, 1577, 1547, 1533, 1326, 1150, 926, 781, 667 cm$^{-1}$.

TABLE 1 space group: C2/c (# 15)
unit cell at 104K with a, b & c having 5% s.u.:
a = 9.150
b = 31.320
c = 7.930
alpha = gamma = 90.00
beta = 113.30

TABLE 1-continued loop_
_atom_site_label
_atom_site_type_symbol
_atom_site_fract_x
_atom_site_fract_y
_atom_site_fract_z
_atom_site_U_iso_or_equiv
_atom_site_adp_type
_atom_site_occupancy
_atom_site_symmetry_multiplicity
_atom_site_calc_flag
_atom_site_refinement_flags
_atom_site_disorder_assembly
_atom_site_disorder_group
Cl1 Cl 1.55055(16) 0.20997(4) 1.6202(2) 0.0376(4) Uani 1 1 d . . .
Cl2 Cl 0.97743(17) 0.20548(4) 1.6837(3) 0.0447(5) Uani 1 1 d . . .
S1 S 0.57041(12) 0.07771(3) 0.25572(15) 0.0212(3) Uani 1 1 d . . .
O7 O 1.3597(5) 0.14890(12) 1.8380(5) 0.0376(10) Uani 1 1 d . . .
O14 O 1.0227(4) 0.12633(10) 1.1610(5) 0.0266(8) Uani 1 1 d . . .
O22 O 0.4600(4) 0.04232(10) 0.1911(5) 0.0285(9) Uani 1 1 d . . .
O23 O 0.6695(4) 0.08741(13) 0.1578(5) 0.0282(9) Uani 1 1 d . . .
N1 N 1.2370(5) 0.02604(12) 1.5929(6) 0.0215(9) Uani 1 1 d . . .
H1 H 1.2665 0.0019 1.6538 0.026 Uiso 1 1 calc . . .
N2 N 1.1481(5) 0.02788(12) 1.4095(6) 0.0241(10) Uani 1 1 d . . .
N6 N 1.2053(5) 0.13987(12) 1.5365(6) 0.0226(9) Uani 1 1 d . . .
H6 H 1.1513 0.1533 1.4330 0.027 Uiso 1 1 calc . . .
N15 N 0.9606(5) 0.05870(11) 1.0508(6) 0.0192(9) Uani 1 1 d . . .
H15 H 0.9804 0.0313 1.0720 0.023 Uiso 1 1 calc . . .
N19 N 0.6881(4) 0.06785(12) 0.4705(5) 0.0185(9) Uani 1 1 d . . .
C3 C 1.1279(5) 0.06988(14) 1.3718(7) 0.0196(10) Uani 1 1 d . . .
C4 C 1.2051(5) 0.09437(14) 1.5332(7) 0.0210(10) Uani 1 1 d . . .
C5 C 1.2765(6) 0.06537(16) 1.6738(8) 0.0240(11) Uani 1 1 d . . .
H5 H 1.3393 0.0714 1.7992 0.029 Uiso 1 1 calc . . .
C7 C 1.2811(6) 0.16340(14) 1.6846(7) 0.0243(11) Uani 1 1 d . . .
C8 C 1.2638(7) 0.21135(14) 1.6550(8) 0.0239(11) Uani 1 1 d . . .
C9 C 1.3834(6) 0.23627(16) 1.6278(7) 0.0260(11) Uani 1 1 d . . .
C10 C 1.3723(7) 0.27967(18) 1.6094(8) 0.0331(13) Uani 1 1 d . . .
H10 H 1.4564 0.2955 1.5978 0.040 Uiso 1 1 calc . . .
C11 C 1.2352(7) 0.30098(16) 1.6076(8) 0.0333(14) Uani 1 1 d . . .
H11 H 1.2266 0.3311 1.5928 0.040 Uiso 1 1 calc . . .
C12 C 1.1136(7) 0.27794(18) 1.6273(8) 0.0354(14) Uani 1 1 d . . .
H12 H 1.0207 0.2921 1.6242 0.043 Uiso 1 1 calc . . .
C13 C 1.1291(7) 0.23383(16) 1.6518(8) 0.0321(14) Uani 1 1 d . . .
C14 C 1.0327(5) 0.08684(14) 1.1863(7) 0.0218(11) Uani 1 1 d . . .
C16 C 0.8492(5) 0.07270(14) 0.8678(7) 0.0184(10) Uani 1 1 d . . .
H16 H 0.7916 0.0985 0.8838 0.022 Uiso 1 1 calc . . .
C17 C 0.9342(5) 0.08479(14) 0.7426(7) 0.0211(11) Uani 1 1 d . . .
H17A H 0.9903 0.0595 0.7223 0.025 Uiso 1 1 calc . . .
H17B H 1.0142 0.1073 0.8019 0.025 Uiso 1 1 calc . . .
C18 C 0.8119(5) 0.10120(15) 0.5567(7) 0.0225(10) Uani 1 1 d . . .
H18A H 0.7612 0.1276 0.5760 0.027 Uiso 1 1 calc . . .
H18B H 0.8665 0.1080 0.4743 0.027 Uiso 1 1 calc . . .
C20 C 0.6048(5) 0.05454(15) 0.5920(7) 0.0242(11) Uani 1 1 d . . .
H20A H 0.5265 0.0319 0.5305 0.029 Uiso 1 1 calc . . .
H20B H 0.5466 0.0792 0.6132 0.029 Uiso 1 1 calc . . .
C21 C 0.7264(6) 0.03785(14) 0.7776(7) 0.0234(11) Uani 1 1 d . . .
H21A H 0.6712 0.0302 0.8584 0.028 Uiso 1 1 calc . . .
H21B H 0.7798 0.0120 0.7578 0.028 Uiso 1 1 calc . . .
C24 C 0.4560(6) 0.12321(16) 0.2544(8) 0.0279(12) Uani 1 1 d . . .
H24A H 0.5263 0.1479 0.2999 0.042 Uiso 1 1 calc . . .
H24B H 0.3984 0.1181 0.3338 0.042 Uiso 1 1 calc . . .
H24C H 0.3796 0.1288 0.1288 0.042 Uiso 1 1 calc . . .

Pharmaceutical compositions comprising a compound of formula (I') and a pharmaceutically acceptable carrier in a form suitable for oral administration are described in WO 2006/077416.

In particular a pharmaceutical composition comprising a substantially amorphous solid solution, said solid solution comprising (a) a compound of the formula (I), for example the compound of Example 1; and (b) a polymer selected from the group consisting of:

polyvinylpyrrolidone (povidone), crosslinked polyvinylpyrrolidone (crospovidone), hydroxypropyl methylcellulose, hydroxypropylcellulose, polyethylene oxide, gelatin, crosslinked polyacrylic acid (carbomer), carboxymethylcellulose, crosslinked carboxymethylcellulose (croscarmellose), methylcellulose, methacrylic acid copolymer, methacrylate copolymer, and water soluble salts such as sodium and ammonium salts of methacrylic acid and methacrylate copolymers, cellulose acetate phthalate, hydroxypropylmethylcellulose phthalate and propylene glycol alginate;

wherein the ratio of said compound to said polymer is about 1:1 to about 1:6, for example a 1:3 ratio, spray dried from a mixture of one of chloroform or dichloromethane and one of methanol or ethanol, preferably dichloromethane/ethanol in a 1:1 ratio.

Further compositions are disclosed in our applications U.S. 60/746,541 and U.S. 60/830,967, the contents of each of which are incorporated herein by reference.

Methods of Treatment using this compound are described in WO 2006/077416. Methods of Diagnosis of a patient to determine whether a disease or condition from which the patient is or may be suffering is one which would be susceptible to treatment with a compound having activity against CDK.

Salts, Solvates, Tautomers, Isomers, N-Oxides, Esters, Prodrugs and Isotopes

A reference to a particular compound (including inter alia any of the compounds of formula (I), (0) and (I') or the ancillary compounds described herein) also includes ionic forms, salts, solvates, isomers, tautomers, N-oxides, esters, prodrugs, isotopes and protected forms thereof, for example, as discussed below; preferably, the salts or tautomers or isomers or N-oxides or solvates thereof; and more preferably, the salts or tautomers or N-oxides or solvates thereof.

Such salts, solvates, tautomers, isomers, N-oxides, esters, prodrugs and isotopes are described in WO 2006/077416 at pages 18 to 25 in relation to compounds of "formula (I)" therein (which correspond to the compounds of formula (I') herein, as explained above). This disclosure in WO 2006/077416 is hereby incorporated herein by reference, and the teachings relating to salts, solvates, tautomers, isomers, N-oxides, esters, prodrugs and isotopes of compounds of formula (I) are to be extended to the various compounds (including inter alia any of the compounds of formula (I'), (0), (I') or the ancillary compounds described herein).

Biological Activity of the Compounds of Formula (I')

These are described at pages 25 to 28 of WO 2006/077416, which disclosure is hereby incorporated herein by reference.

The combinations comprising ancillary compounds of the formulae (I') are inhibitors of cyclin dependent kinases. For example, compounds of the invention are inhibitors of cyclin dependent kinases, and in particular cyclin dependent kinases selected from CDKI, CDK2, CDK3, CDK4, CDK5, CDK6 and CDK9, and more particularly selected from CDKI, CDK2, CDK3, CDK4, CDK5 and CDK9. Preferred combinations comprise compounds that inhibit one or more CDK kinases selected from CDKI, CDK2, CDK4 and CDK9, for example CDKI and/or CDK2. The combinations comprising compounds of formula (I') also have activity against glycogen synthase kinase-3 (GSK-3).

As a consequence, the combinations of the invention comprising ancillary compounds of formula (I') have activity in modulating or inhibiting CDK and glycogen synthase kinase, and so are useful in providing a means of arresting, or recovering control of, the cell cycle in abnormally dividing cells. It is therefore anticipated that the combinations will prove useful in treating or preventing proliferative disorders such as cancers. It is also envisaged that the combinations of the invention will be useful in treating conditions such as viral infections, type II or non-insulin dependent diabetes mellitus, autoimmune diseases, head trauma, stroke, epilepsy, neurodegenerative diseases such as Alzheimer's, motor neurone disease, progressive supranuclear palsy, corticobasal degeneration and Pick's disease, for example autoimmune diseases and neurodegenerative diseases.

One sub-group of disease states and conditions where it is envisaged that the combinations of the invention will be useful consists of viral infections, autoimmune diseases and neurodegenerative diseases.

CDKs play a role in the regulation of the cell cycle, apoptosis, transcription, differentiation and CNS function. Therefore, CDK inhibitors could be useful in the treatment of diseases in which there is a disorder of proliferation, apoptosis or differentiation such as cancer. In particular RB+ve tumours may be particularly sensitive to CDK inhibitors. RB−ve tumours may also be sensitive to CDK inhibitors.

Examples of cancers which may be inhibited include, but are not limited to, a carcinoma, for example a carcinoma of the bladder, breast, colon (e.g. colorectal carcinomas such as colon adenocarcinoma and colon adenoma), kidney, epidermis, liver, lung, for example adenocarcinoma, small cell lung cancer and non-small cell lung carcinomas, oesophagus, gall bladder, ovary, pancreas e.g. exocrine pancreatic carcinoma, stomach, cervix, thyroid, prostate, or skin, for example squamous cell carcinoma; a hematopoietic tumour of lymphoid lineage, for example leukemia, acute lymphocytic leukemia, chronic lymphocytic leukaemia, B-cell lymphoma (such as diffuse large B cell lymphoma), T-cell lymphoma, Hodgkin's lymphoma, non-Hodgkin's lymphoma, hairy cell lymphoma, or Burkett's lymphoma; a hematopoietic tumour of myeloid lineage, for example acute and chronic myelogenous leukemias, myelodysplastic syndrome, or promyelocytic leukemia; thyroid follicular cancer; a tumour of mesenchymal origin, for example fibrosarcoma or habdomyosarcoma; a tumour of the central or peripheral nervous system, for example astrocytoma, neuroblastoma, glioma or schwannoma; melanoma; seminoma; teratocarcinoma; osteosarcoma; xeroderma pigmentosum; keratoctanthoma; thyroid follicular cancer; or Kaposi's sarcoma.

The cancers may be cancers which are sensitive to inhibition of any one or more cyclin dependent kinases selected from CDKI, CDK2, CDK3, CDK4, CDK5 and CDK6, for example, one or more CDK kinases selected from CDKI, CDK2, CDK4 and CDK5, e.g. CDKI and/or CDK2.

Whether or not a particular cancer is one which is sensitive to inhibition by a cyclin dependent kinase may be determined by means of a cell growth assay as set out in the examples below or by a method as set out in the section headed "Methods of Diagnosis".

CDKs are also known to play a role in apoptosis, proliferation, differentiation and transcription and therefore CDK inhibitors could also be useful in the treatment of the following diseases other than cancer; viral infections, for example herpes virus, pox virus, Epstein-Barr virus, Sindbis virus, adenovirus, HIV, HPV, HCV and HCMV; prevention of AIDS development in HIV-infected individuals; chronic inflammatory diseases, for example systemic lupus erythematosus, autoimmune mediated glomerulonephritis, rheumatoid arthritis, psoriasis, inflammatory bowel disease, and autoimmune diabetes mellitus; cardiovascular diseases for example cardiac hypertrophy, restenosis, atherosclerosis; neurodegenerative disorders, for example Alzheimer's disease, AIDS-related dementia, Parkinson's disease, amyotropic lateral sclerosis, retinitis pigmentosa, spinal muscular atropy and cerebellar degeneration; glomerulonephritis; myelodysplastic syndromes, ischemic injury associated myocardial infarctions, stroke and reperfusion injury, arrhythmia, atherosclerosis, toxin-induced or alcohol related liver diseases, haematological diseases, for example, chronic anemia and aplastic anemia; degenerative diseases of the musculoskeletal system, for example, osteoporosis and arthritis, aspirin-sensitive rhinosinusitis, cystic fibrosis, multiple sclerosis, kidney diseases and cancer pain.

It has also been discovered that some cyclin-dependent kinase inhibitors can be used in combination with other anticancer agents. For example, the cyclin-dependent kinase inhibitor flavopiridol has been used with other anticancer agents in combination therapy.

Thus, in the pharmaceutical compositions, uses or methods of this invention for treating a disease or condition comprising abnormal cell growth, the disease or condition comprising abnormal cell growth in one embodiment is a cancer.

One group of cancers includes human breast cancers (e.g. primary breast tumours, node-negative breast cancer, invasive duct adenocarcinomas of the breast, non-endometrioid breast cancers); and mantle cell lymphomas. In addition, other cancers are colorectal and endometrial cancers.

Another sub-set of cancers includes hematopoietic tumours of lymphoid lineage, for example leukemia, chronic lymphocytic leukaemia, mantle cell lymphoma and B-cell lymphoma (such as diffuse large B cell lymphoma).

One particular cancer is chronic lymphocytic leukaemia. Another particular cancer is mantle cell lymphoma. Another particular cancer is diffuse large B cell lymphoma Another sub-set of cancers includes breast cancer, ovarian cancer, colon cancer, prostate cancer, oesophageal cancer, squamous cancer and non-small cell lung carcinomas.

Thus, the combinations of the invention comprising one or more ancillary compounds of formula (I') find application in the treatment of any of the diseases and disorders described above and at pages 25 to 28 of WO 2006/077416, which disclosure is hereby incorporated herein by reference.

Advantages of the Compounds of Formula (I') as Components of the Combinations of the Invention These are described at pages 28 to 30 of WO 2006/077416, which disclosure is hereby incorporated herein by reference.

Methods for the Preparation of Compounds of the Formula (I')

These are described at pages 30 to 36 of WO 2006/077416, which disclosure is hereby incorporated herein by reference.

Methods of Purification of the Compounds of Formula (I')

These are described at pages 36 to 37 of WO 2006/077416, which disclosure is hereby incorporated herein by reference.

Salts, Solvates, Tautomers, Isomers, N-Oxides, Esters, Prodrugs and Isotopes

A reference to a particular compound (including inter alia any of the ancillary compounds or compounds of formula (I), (II), (III), (IV), (V), (VI), (VIa), (VII), (VIIa) or (VIIb) or any sub-groups or examples thereof as defined herein (including acid addition salts, particularly the L-lactate, and crystalline forms thereof) or to the ancillary compounds described herein) also includes ionic forms, salts, solvates, isomers, tautomers, N-oxides, esters, prodrugs, isotopes and protected forms thereof, for example, as discussed below; preferably, the salts or tautomers or isomers or N-oxides or solvates thereof; and more preferably, the salts or tautomers or N-oxides or solvates thereof Many compounds (including those of formula (I), (II), (III), (IV), (V), (VI), (VIa), (VII), (VIIa) or (VIIb) or any sub-groups or examples thereof as defined herein (including acid addition salts, particularly the L-lactate, and crystalline forms thereof) and many of the ancillary compounds described herein) can exist in the form of salts, for example acid addition salts or, in certain cases salts of organic and inorganic bases such as phenolate, carboxylate, sulphonate and phosphate salts. All such salts are within the scope of this invention, and references to compounds (e.g. of formula (I), (II), (III), (IV), (V), (VI), (VIa), (VII), (VIIa) or (VIIb) or any sub-groups or examples thereof as defined herein, including acid addition salts, particularly the L-lactate, and crystalline forms thereof) include the salt forms of the compounds.

The salts can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, non-aqueous media such as ether, ethyl acetate, ethanol, isopropanol, or acetonitrile are used.

Acid addition salts may be formed with a wide variety of acids, both inorganic and organic. Examples of acid addition salts include salts formed with an acid selected from the group consisting of acetic, 2,2-dichloroacetic, adipic, alginic, ascorbic (e.g. L-ascorbic), L-aspartic, benzenesulphonic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethanesulphonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrobromic, hydrochloric, hydriodic, isethionic, (+)-L-lactic, (±)-DL-lactic, lactobionic, maleic, malic, (−)-L-malic, malonic, (±)-DL-mandelic, methanesulphonic, naphthalene-2-sulphonic, naphthalene-1,5-disulphonic, 1-hydroxy-2-naphthoic, nicotinic, nitric, oleic, orotic, oxalic, palmitic, pamoic, phosphoric, propionic, L-pyroglutamic, salicylic, 4-aminosalicylic, sebacic, stearic, succinic, sulphuric, tannic, (+)-L-tartaric, thiocyanic, p-toluenesulphonic, undecylenic and valeric acids, as well as acylated amino acids and cation exchange resins.

If the compound is anionic, or has a functional group which may be anionic (e.g., —COOH may be —COO$^-$), then a salt may be formed with a suitable cation. Examples of suitable inorganic cations include, but are not limited to, alkali metal ions such as Na$^+$ and K$^+$, alkaline earth metal cations such as Ca$^{2+}$ and Mg$^{2+}$, and other cations such as Al$^{3+}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

Where the compounds contain an amine function, these may form quaternary ammonium salts, for example by reaction with an alkylating agent according to methods well known to the skilled person. Such quaternary ammonium compounds are within the scope of formula (I).

The salt forms of the compounds are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds, also form part of the invention.

Compounds (e.g. of the formula (I), (II), (III), (IV), (V), (VI), (VIa), (VII), (VIIa) or (VIIb) or any sub-groups or examples thereof as defined herein, including acid addition salts, particularly the L-lactate, and crystalline forms thereof) containing an amine function may also form N-oxides. A reference herein to such a compound that contains an amine function also includes the N-oxide.

Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle.

N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

Compounds comprised in the combinations of the invention (e.g. compounds of the formula (I), (II), (III), (IV), (V), (VI), (VIa), (VII), (VIIa) or (VIIb) or any sub-groups or examples thereof as defined herein, including acid addition salts, particularly the L-lactate, and crystalline forms thereof) may exist in a number of different geometric isomeric, and tautomeric forms and references to such compounds include all such forms. For the avoidance of doubt, where a compound can exist in one of several geometric isomeric or tautomeric forms and only one is specifically described or shown, all others are nevertheless contemplated (and are for example embraced by formula (I)).

Examples of tautomeric forms include, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

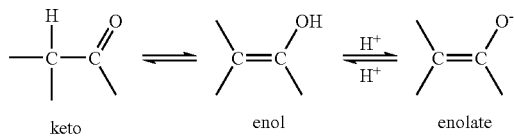

Where any constituent compound of the combination of the invention (e.g. compounds of the formula (I)) contain one or more chiral centres, and can exist in the form of two or more optical isomers, references to such compounds include all optical isomeric forms thereof (e.g. enantiomers, epimers and diastereoisomers), either as individual optical isomers, or mixtures (e.g. racemic mixtures) or two or more optical isomers, unless the context requires otherwise.

The optical isomers may be characterised and identified by their optical activity (i.e. as + and − isomers, or d and l isomers) or they may be characterised in terms of their absolute stereochemistry using the "R and S" nomenclature developed by Cahn, Ingold and Prelog, see *Advanced Organic Chemistry* by Jerry March, 4$^{th}$ Edition, John Wiley & Sons, New York, 1992, pages 109-114, and see also Cahn, Ingold & Prelog, *Angew. Chem. Int. Ed. Engl.*, 1966, 5, 385-415.

Optical isomers can be separated by a number of techniques including chiral chromatography (chromatography on a chiral support) and such techniques are well known to the person skilled in the art.

As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulphonic, separating the diastereoisomers by preferential crystallisation, and then dissociating the salts to give the individual enantiomer of the free base.

Where compounds (e.g. of the formula (I)) exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers. Accordingly, the invention provides compositions containing a compound of the formula (I) having one or more chiral centres, wherein at least 55% (e.g. at least 60%, 65%, 70%, 75%, 80%, 85%, 90% or 95%) of the compound of the formula (I) is present as a single optical isomer (e.g. enantiomer or diastereoisomer). In one general embodiment, 99% or more (e.g. substantially all) of the total amount of the compound of the formula (I) may be present as a single optical isomer (e.g. enantiomer or diastereoisomer).

The compounds include compounds with one or more isotopic substitutions, and a reference to a particular element includes within its scope all isotopes of the element. For example, a reference to hydrogen includes within its scope $^{1}$H, $^{2}$H (D), and $^{3}$H (T). Similarly, references to carbon and oxygen include within their scope respectively $^{12}$C, $^{13}$C and $^{14}$C and $^{16}$O and $^{18}$O.

The isotopes may be radioactive or non-radioactive. In one embodiment of the invention, the compounds contain no radioactive isotopes. Such compounds are preferred for therapeutic use. In another embodiment, however, the compound may contain one or more radioisotopes. Compounds containing such radioisotopes may be useful in a diagnostic context.

Esters such as carboxylic acid esters and acyloxy esters (e.g. of the compounds of formula (I)) bearing a carboxylic acid group or a hydroxyl group are also contemplated and are embraced by formula (I). Examples of esters are compounds containing the group —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Particular examples of ester groups include, but are not limited to, —C(=O)OCH$_3$, —C(=O)OCH$_2$CH$_3$, —C(=O)OC(CH$_3$)$_3$, and —C(=O)OPh. Examples of acyloxy (reverse ester) groups are represented by —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Particular examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

In one general embodiment, formula (I) and sub-formulae, sub-groups, preferences and examples thereof do not cover esters such as carboxylic acid esters and acyloxy esters.

In one particular embodiment, formula (I) and sub-formulae, sub-groups, preferences and examples thereof do not cover esters of hydroxy compounds wherein $R^2$ is hydroxy and the ester is formed with the hydroxy group $R^2$.

Also encompassed by formula (I) are any polymorphic forms of the compounds, solvates (e.g. hydrates), complexes (e.g. inclusion complexes or clathrates with compounds such as cyclodextrins, or complexes with metals) of the compounds, and pro-drugs of the compounds (e.g. the compounds of formula (I)). By "prodrugs" is meant for example any compound that is converted in vivo into a biologically active compound (e.g. into one or more ancillary compounds or into a compound of the formula (I)).

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Examples of such metabolically labile esters include those of the formula —C(=O)OR wherein R is:

$C_{1-7}$alkyl
(e.g., -Me, -Et, -nPr, -iPr, -nBu, -sBu, -iBu, -tBu);
$C_{1-7}$aminoalkyl
(e.g., aminoethyl; 2-(N,N-diethylamino)ethyl; 2-(4-morpholino)ethyl); and
acyloxy-$C_{1-7}$alkyl
(e.g., acyloxymethyl;
acyloxyethyl;
pivaloyloxymethyl;
acetoxymethyl;
1-acetoxyethyl;
1-(1-methoxy-1-methyl)ethyl-carbonxyloxyethyl;
1-(benzoyloxy)ethyl; isopropoxy-carbonyloxymethyl;
1-isopropoxy-carbonyloxyethyl; cyclohexyl-carbonyloxymethyl;
1-cyclohexyl-carbonyloxyethyl;
cyclohexyloxy-carbonyloxymethyl;
1-cyclohexyloxy-carbonyloxyethyl;
(4-tetrahydropyranyloxy)carbonyloxymethyl;
1-(4-tetrahydropyranyloxy)carbonyloxyethyl;
(4-tetrahydropyranyl)carbonyloxymethyl; and
1-(4-tetrahydropyranyl)carbonyloxyethyl).

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Optional Auxiliary Compounds and Treatments for Use According to the Invention

Any of a wide variety of auxiliary compounds may optionally be used as further constituents of the combinations of the invention. Such optional auxiliary compounds may be anti-cancer agents.

In this section, as in all other sections of this application, unless the context indicates otherwise, references to a compound of formula (I) includes all subgroups of formula (I) as defined herein, including formulae (II), (III), (IV), (V), (VI), (VIa), (VII), (VIIa) and (VIIb) (in particular formula (VI) and including acid addition salts, particularly the L-lactate, and crystalline forms thereof) and the term 'subgroups' includes all preferences, embodiments, examples and particular compounds defined herein.

Preferably, the optional auxiliary compounds for use in the combinations of the invention are selected from the following classes:

1. hormones, hormone agonists, hormone antagonists and hormone modulating agents (including corticosteroids, antiandrogens, antiestrogens and GNRAs);
2. cytokines and cytokine activating agents;
3. retinoids and rexinoids
4. monoclonal antibodies (including monoclonal antibodies to cell surface antigen(s));
5. *camptothecin* compounds and other topoisomerase I inhibitors;
6. antimetabolites;
7. *vinca* alkaloids and other tubulin targeting agents;
8. taxanes;
9. epothilones;
10. platinum compounds;
11. DNA binders and Topo II inhibitors (including anthracycline derivatives);
12. alkylating agents (including aziridine, nitrogen mustard and nitrosourea alkylating agents);
13. signalling inhibitors (including PKA/B inhibitors and PKB pathway inhibitors);
14. CDK inhibitors;
15. COX-2 inhibitors;
16. HDAC inhibitors;
17. Selective immunoresponse modulators;
18. DNA methyl transferase inhibitors;
19. proteasome inhibitors;
20. Aurora inhibitors;
21. Hsp90 inhibitors (including ancillary Hsp90 inhibitors);
22. Checkpoint targeting agents;
23. DNA repair inhibitors
24. Inhibitors of G-protein coupled receptor inhibitors
25. Other therapeutic or prophylactic agents; for example agents that reduce or alleviate some of the side effects associated with chemotherapy. Particular examples of such agents include anti-emetic agents and agents that prevent or decrease the duration of chemotherapy-associated neutropenia and prevent complications that arise from reduced levels of red blood cells or white blood cells, for example erythropoietin (EPO), granulocyte macrophage-colony stimulating factor (GM-CSF), and granulocyte-colony stimulating factor (G-CSF). Also included are agents that inhibit bone resorption such as bisphosphonate agents e.g. zoledronate, pamidronate and ibandronate, agents that suppress inflammatory responses (such as dexamethazone, prednisone, and prednisolone) and agents used to reduce blood levels of growth hormone and IGF-I in acromegaly patients such as synthetic forms of the brain hormone somatostatin, which includes octreotide acetate which is a long-acting octapeptide with pharmacologic properties mimicking those of the natural hormone somatostatin. Further included are agents such as leucovorin, which is used as an antidote to drugs that decrease levels of folic acid, or folinic acid it self and agents such as megestrol acetate which can be used for the treatment of side-effects including oedema and thromoembolic episodes.

In embodiments where the combination of the invention comprises one or more auxiliary compounds, the auxiliary compound(s) are preferably independently selected from the classes (1) (in particular corticosteroids), (4), (6), (7), (8), (10), (11), (12), (13), (17), (18), (19), (23) and (24) of list A (above). Most preferably, the one or more auxiliary compounds are independently selected from classes (1) in particular corticosteroids, (4), (6), (8), (10), (11), (12), (13), (18), (19), and (24) of the list above.

In embodiments where the combination of the invention comprises two or more auxiliary compounds, then the two or more auxiliary compounds are preferably independently selected from the classes (1) to (24) of the list set out above.

In embodiments where the combination of the invention comprises two or more auxiliary compounds, then the two or more auxiliary compounds are preferably independently selected from the classes (1) (in particular corticosteroids), (2), (3), (17), (22), (23) and (24) of the list set out above.

Each of the compounds present in the combinations of the invention may be given in individually varying dose schedules and via different routes.

The compound of the formula (I) and ancillary compound may be administered simultaneously or sequentially. When administered sequentially, they can be administered at closely spaced intervals (for example over a period of 5-10 minutes) or at longer intervals (for example 1, 2, 3, 4 or more hours apart, or even longer periods apart where required), the precise dosage regimen being commensurate with the properties of the therapeutic agent(s).

The combinations of the invention may also be administered in conjunction with non-chemotherapeutic treatments such as radiotherapy, photodynamic therapy, gene therapy; surgery and controlled diets.

For use in combination therapy with one or more ancillary compounds, the combination of the invention and one, two, three, four or more ancillary compounds can be, for example, formulated together in a dosage form containing two, three, four or more ancillary compounds. In an alternative, the constituent compounds of the combination of the invention may be formulated separately and presented together in the form of a kit, optionally with instructions for their use.

In embodiments where the combination of the invention comprises one or more auxiliary compounds, the auxiliary compound(s) are preferably independently selected from the classes (1) (in particular corticosteroids), (4), (6), (7), (8), (10), (11), (12), (13), (17), (18), (19), (23) and (24). Most preferably, the one or more auxiliary compounds are independently selected from classes (1) in particular corticosteroids, (4), (6), (8), (10), (11), (12), (13), (18), (19), and (24).

In embodiments where the combination of the invention comprises two or more auxiliary compounds, then the two or more auxiliary compounds are preferably independently selected from the classes (1) to (24) set out above.

Further embodiments of the invention where the combination of the invention comprises two or more auxiliary compounds include:
 a combination of lenolidamide and thalidomide;
 a combination of two or more of the foregoing classes independently selected from (1), preferably corticosteroids, (12) and (17), preferably lenolidamide or thalidomide;
 a combination of two or more of the foregoing classes independently selected from (1), preferably corticosteroids, (7) and (11);
 a combination of two of the foregoing classes (1), preferably corticosteroids and (19);
 a combination of two of the foregoing classes (18) and (23);
 a combination of two of the foregoing classes (10) and (23);
 a combination of two or more of the foregoing classes independently selected from (1), preferably corticosteroids, (4), (6), (7), (8), (10), (11), (12), (13), (17), (18), (19), (23) and/or (24);
 a combination of two or more of the foregoing classes independently selected from (1), preferably corticosteroids, (4), (6), (8), (10), (11), (12), (13), (18), (19) and/or (24); and
 a combination of two or more of the foregoing classes independently selected from (1), preferably corticosteroids, (11), (12), (17) and/or (19);

A reference to a particular auxiliary compound herein is intended to include ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof).

1. Hormones, Hormone Agonists, Hormone Antagonists and Hormone Modulating Agents Definition: The terms "corticosteroid", "antiandrogen", "antiestrogen", "antiandrogen agent" and "antiestrogen agent" as used herein refers to those described herein and analogues thereof, including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Biological activity: The hormones, hormone agonists, hormone antagonists and hormone modulating agents (including the antiandrogens and antiestrogen agents) working via one or more pharmacological actions as described herein have been identified as suitable anti-cancer agents. The term 'hormonal therapies' is used to collectively to refer to hormones, hormone agonists, hormone antagonists and hormone modulating agents.

Technical background: Hormonal therapy plays an important role in the treatment of certain types of cancer where tumours are formed in tissues that are sensitive to hormonal growth control such as the breast and prostate. Thus, for example, estrogen promotes growth of certain breast cancers and testosterone promotes growth of prostate cancers. Since the growth of such tumours is dependent on specific hormones, considerable research has been carried out to investigate whether it is possible to affect tumour growth by increasing or decreasing the levels of certain hormones in the body. Hormonal therapy attempts to control tumour growth in these hormone-sensitive tissues by manipulating the activity of the hormones.

Cancers which are derived from either lymphocyte precursors or mature lymphocytes such as certain types of leukemia, Hodgkin's disease and non-Hodgkin's lymphoma often retain the sensitivity to treatment with corticosteroids including prednisolone, predisone and dexamethasone exhibited by mature lymphophocytes. As a consequence treatment with one or more corticosteroids is often incorporated into the treatment of these diseases. Thus contemplated for use with the invention are corticosteroids.

With regard to breast cancer, tumour growth is stimulated by estrogen, and antiestrogen agents have therefore been proposed and widely used for the treatment of this type of cancer. One of the most widely used of such agents is tamoxifen which is a competitive inhibitor of estradiol binding to the estrogen receptor (ER). When bound to the ER, tamoxifen induces a change in the three-dimensional shape of the receptor, inhibiting its binding to the estrogen responsive element on DNA. Under normal physiological conditions, estrogen stimulation increases tumour cell production of transforming growth cell b (TGF-b), an autocrine inhibitor of tumour cell growth. By blocking these pathways, the net effect of tamoxifen treatment is to decrease the autocrine stimulation of breast cancer growth. In addition, tamoxifen decreases the local production of insulin-like growth factor (IGF-1) by surrounding tissues: IGF-I is a paracrine growth factor for the breast cancer cell (Jordan and Murphy, Endocr. Rev., 1990, 1

1; 578-610). An alternative approach to disease control is to reduce circulating levels of estradiol by inhibition of aromatase—an enzyme which is critical for its production. Both Tamoxifen and aromatase inhibitors including anastrazole, letrozole and examestane are widely used in the treatment of post-menopausal women with breast cancer both in the adjuvant and metatsatic setting (e.g. metastatic breast cancer). Tamoxifen is also used in pre-menopausal women with ER-positive tumours. There are various potential side-effects of long-term tamoxifen treatment, for example the possibility of endometrial cancer and the occurrence of thrombo-embolic events. Although aromatase inhibitors are generally better tolerated than tamoxifen patients often experience musculoskeletal pain and significant bone loss leading to osteoporosis.

Other estrogen receptor antagonists (or selective estrogen receptor modulators (SERMs)) with broadly similar action to tamoxifen include toremifene and raloxifene. Toremifene is a non-steroidal SERM, which has the chemical name 2-(4-[(Z)-4-chloro-1,2-diphenyl-1-butenyl]-phenoxy)-N,N-dimethylethylamine, and is used for the treatment of metastatic breast cancer, side-effects including hot flushes, nausea and dizziness. Raloxifene is a benzothiophene SERM, which has the chemical name [6-hydroxy-2-(4-hydroxyphenyl)benzo[b]thien-3-yl]-[4-[2-(1-piperidinyl)ethoxy]-phenyl]-methanone hydrochloride, and is being investigated for the treatment of breast cancer, side-effects including hot flushes and leg cramps.

Fulvestrant, which acts by reducing the expression of the ER in tumour tissue has the chemical name 7-α-[9-(4,4,5,5,5-pentafluoropentylsulphinyl)-nonyl]estra-1,3,5-(10)-triene-3,17-beta-diol, is often used following treatment with tamoxifen and an aromatase inhibitor (e.g. as a second line treatment of advanced breast cancer). Treatment may be accompanied by hot flushes and endometrial stimulation.

Prostate cancer cells almost invariably overexpress the androgen receptor, and thus antiandrogens are widely used in the treatment of the disease. Antiandrogens are androgen receptor antagonists which bind to the androgen receptor and prevent dihydrotestosterone from binding. Dihydrotestosterone stimulates new growth of prostate cells, including cancerous prostate cells. An example of an antiadrogen is bicalutamide, which has the chemical name (R,S)—N-(4-cyano-3-(4-fluorophenylsulfonyl)-2-hydroxy-2-methyl-3-(trifluoromethyl)propanamide, and has been approved for use in combination with luteinizing hormone-releasing hormone (LHRH) analogs for the treatment of advanced prostate cancer, side effects including hot flushes, bone pain, hematuria and gastro-intestinal symptoms. An alternative means of reducing circulating levels of dihydrotestosterone is to directly inhibit its production from testosterone using flutamide.

In one embodiment the hormonal therapies include fulvestrant, toremifene and raloxifene.

A further type of hormonal cancer treatment comprises the use of progestin analogs. Progestin is the synthetic form of progesterone, a hormone secreted by the ovaries and endometrial lining of the uterus. Acting with estrogen, progesterone promotes breast development and growth of endometrial cells during the menstrual cycle. It is believed that progestins may act by suppressing the production of estrogen from the adrenal glands (an alternate source particularly in post-menopausal women), lowering estrogen receptor levels, or altering tumour hormone metabolism.

Progestin analogs are used in the management of uterine cancer (e.g. advanced uterine cancer) or renal cancer. They can also be used for treating advanced breast cancer, although this use is less common, due to the numerous anti-estrogen treatment options available. Occasionally, progestin analogs are used as hormonal therapy for prostate cancer. An example of a progestin analog is megestrol acetate (a.k.a. megestrel acetate), which has the chemical name 17α-acetyloxy-6-methylpregna-4,6-diene-3,20-dione, and is a putative inhibitor of pituitary gonadotrophin production with a resultant decrease in estrogen secretion, The drug is used for the palliative treatment of advanced carcinoma of the breast or endometrium (i.e., recurrent, inoperable, or metastatic disease), side-effects including oedema and thromoembolic episodes.

Preferences and specific embodiments: A particularly preferred antiestrogen agent for use in accordance with the invention is tamoxifen. Tamoxifen is commercially available for example from AstraZeneca plc under the trade name Nolvadex, or may be prepared for example as described in U.K. patent specifications 1064629 and 1354939, or by processes analogous thereto.

Yet another preferred antiestrogen agent is droloxifene. Fulvestrant is commercially available for example from AstraZeneca plc under the trade name Faslodex, or may be prepared for example as described in European patent specification No. 138504, or by processes analogous thereto.

Raloxifene is commercially available for example from Eli Lilly and Company under the trade name Evista, or may be prepared for example as described in U.S. Pat. No. 4,418,068, or by processes analogous thereto. Toremifene is commercially available for example from Schering Corporation under the trade name Fareston, or may be prepared for example as described in U.S. Pat. No. 4,696,949, or by processes analogous thereto. The antiestrogen agent droloxifene, which may be prepared for example as described in U.S. Pat. No. 5,047,431, or by processes analogous thereto, can also be used in accordance with the invention.

A preferred antiandrogen for use in accordance with the invention is bicalutamide which is commercially available for example from AstraZeneca plc under the trade name Casodex, or may be prepared for example as described in European patent specification No. 100172, or by processes analogous thereto. Other preferred hormonal therapies for use in accordance with the invention include tamoxifen, fulvestrant, raloxifene, toremifene, droloxifene, letrazole, anastrazole, exemestane, bicalutamide, luprolide, megestrol/megestrel acetate, aminoglutethimide (alternatively spelt aminoglutethamide) and flutamide.

Other preferred hormonal therapies for use in accordance with the invention include tamoxifen, fulvestrant, raloxifene, toremifene, droloxifene, letrazole, anastrazole, exemestane, bicalutamide, luprolide, megestrol/megestrel acetate, aminoglutethimide and bexarotene.

A preferred progestin analog is megestrol/megestrel acetate which is commercially available for example from Bristol-Myers Squibb Corporation under the trade name Megace, or may be prepared for example as described in U.S. Pat. No. 2,891,079, or by processes analogous thereto.

Thus, specific embodiments of these anti-cancer agents for use in the combinations of the invention include: tamoxifen; toremifene; raloxifene; medroxyprogesterone; megestrol/megestrel; aminoglutethimide; letrozole; anastrozole; exemestane; goserelin; leuprolide; abarelix; fluoxymestrone; diethylstilbestrol; ketoconazole; fulvestrant; flutamide; bicalutimide; nilutamide; cyproterone and buserelin.

Thus, contemplated for use in the combinations of the invention are antiandrogens and antiestrogens.

In other embodiments, the hormone, hormone agonist, hormone antagonist or hormone modulating agent is fulvestrant, raloxifene, droloxifene, toremifene, megestrol/megestrel and flutamide.

In other embodiments, the hormone, hormone agonist, hormone antagonist or hormone modulating agent is fulvestrant, raloxifene, droloxifene, toremifene, megestrol/megestrel and bexarotene.

In one embodiment the hormones, hormone agonists, hormone antagonists and hormone modulating agents include corticosteroids, antiandrogens, antiestrogens and GNRAs. In another embodiment the hormones, hormone agonists, hormone antagonists and hormone modulating agents include antiandrogens, antiestrogens and GNRAs.

Posology: The antiandrogen or antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day (or 20 mg once a day), continuing the therapy for sufficient time to achieve and maintain a therapeutic effect.

With regard to the other preferred antiestrogen agents: fulvestrant is advantageously administered in the form of a 250 mg monthly injection (though doses of 250-750 mg per month may also be employed); toremifene is advantageously administered orally in a dosage of about 60 mg once a day, continuing the therapy for sufficient time to achieve and maintain a therapeutic effect; droloxifene is advantageously administered orally in a dosage of about 20-100 mg once a day; and raloxifene is advantageously administered orally in a dosage of about 60 mg once a day.

With regard to the preferred antiandrogen bicalutamide, this is generally administered in an oral dosage of 50 mg daily.

With regard to the preferred progestin analog megestrol/megestrel acetate, this is generally administered in an oral dosage of 40 mg four times daily.

The dosages noted above may generally be administered for example once, twice or more per course of treatment, which may be repeated for example daily or every 7, 14, 21 or 28 days in particular every 7, 14, 21 or 28 days.

Aromatase Inhibitors

Of the hormones, hormone agonists, hormone antagonists and hormone modulating agents for use in the combinations of the invention, preferred are aromatase inhibitors.

In post-menopausal women, the principal source of circulating estrogen is from conversion of adrenal androgens (androstenedione and testosterone) to estrogens (estrone and estradiol) by the aromatase enzyme in peripheral tissues. Estrogen deprivation through aromatase inhibition or inactivation is an effective and selective treatment for some post-menopausal patients with hormone-dependent breast cancer. Examples of such hormone modulating agents include aromatase inhibitors or inactivators, such as exemestane, anastrozole, letrozole and aminoglutethimide.

Exemestane, which has the chemical name 6-methylenandrosta-1,4-diene-3,17-dione, is used for the treatment of advanced breast cancer in post-menopausal women whose disease has progressed following tamoxifen therapy, side effects including hot flashes and nausea. Anastrozole, which has the chemical name, $\alpha,\alpha,\alpha',\alpha'$-tetramethyl-5-(1H-1,2,4-triazol-1-ylmethyl)-1,3-benzenediacetonitrile, is used for adjuvant treatment of post-menopausal women with hormone receptor-positive early breast cancer, and also for the first-line treatment of post-menopausal women with hormone receptor-positive or hormone receptor-unknown locally advanced or metastatic breast cancer, and for the treatment of advanced breast cancer in post-menopausal women with disease progression following tamoxifen therapy. Administration of anastrozole usually results in side-effects including gastrointestinal disturbances, musculoskeletal pain, rashes and headaches. Letrozole, which has the chemical name 4,4'-(1H-1,2,4-triazol-1-ylmethylene)-dibenzonitrile, is used for the adjuvant treatment of ER positive breast cancer, for first-line treatment of post-menopausal women with hormone receptor-positive or hormone receptor-unknown locally advanced or metastatic breast cancer, and for the treatment of advanced breast cancer in post-menopausal women with disease progression following antiestrogen therapy, possible side-effects including occasional transient thrombocytopenia and elevation of liver transaminases.

Aminoglutethimide which has the chemical name 3-(4-aminophenyl)-3-ethyl-2,6-piperidinedione, is also used for treating breast cancer but suffers from the side-effects of skin rashes and less commonly thrombocytopenia and leukopenia.

Preferred aromatase inhibitors include letrozole, anastrozole, exemestane and aminoglutethimide. Letrozole is commercially available for example from Novartis A.G. under the trade name Femara, or may be prepared for example as described in U.S. Pat. No. 4,978,672, or by processes analogous thereto. Anastrozole is commercially available for example from AstraZeneca plc under the trade name Arimidex, or may be prepared for example as described in U.S. Pat. No. 4,935,437, or by processes analogous thereto. Exemestane is commercially available for example from Pharmacia Corporation under the trade name Aromasin, or may be prepared for example as described in U.S. Pat. No. 4,978,672, or by processes analogous thereto. Aminoglutethimide is commercially available for example from Novartis A.G. under the trade name Cytadren, or may be prepared for example as described in U.S. Pat. No. 2,848,455, or by processes analogous thereto. The aromatase inhibitor vorozole, which may be prepared for example as described in European patent specification No. 293978, or by processes analogous thereto, can also be used in accordance with the invention.

With regard to the preferred aromatase inhibitors, these are generally administered in an oral daily dosage in the range 1 to 1000 mg, for example letrozole in a dosage of about 2.5 mg once a day; anastrozole in a dosage of about 1 mg once a day; exemestane in a dosage of about 25 mg once a day; and aminoglutethimide in a dosage of 250 mg 2-4 times daily.

Particularly preferred are aromatase inhibitors selected from the agents described herein, for example, letrozole, anastrozole, exemestane and aminoglutethimide.

GNRAs

Of the hormones, hormone agonists, hormone antagonists and hormone modulating agents for use in the combinations of the invention, preferred are agents of the GNRA class.

Definition: As used herein the term GNRA is intended to define gonadotropin-releasing hormone (GnRH) agonists and antagonists (including those described below), together with the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Technical background: When released from the hypothalamus in the brain, gonadotropin-releasing hormone (GnRH) agonists stimulate the pituitary gland to produce gonadotropins. Gonadotropins are hormones that stimulate androgen synthesis in the testes and estrogen synthesis in the ovaries. When GnRH agonists are first administered, they can cause an increase in gonadotropin release, but with continued administration, GnRH will block gonadotropin release, and therefore decrease the synthesis of androgen and estrogen.

GnRH analogs are used to treat metastatic prostate cancer. They have also been approved for treatment of metastatic breast cancer in pre-menopausal women. Examples of GnRH analogs include goserelin acetate and leuprolide acetate. In contrast GnRH antagonists such as aberelix cause no initial GnRH surge since they have no agonist effects. However, due to their narrow therapeutic index, their use is currently limited to advanced prostate cancer that is refractory to other hormonal treatment such as GnRH agonists and anti-androgens.

Goserelin acetate is a synthetic decapeptide analog of LHRH or GnRH, and has the chemical structure of pyro-Glu-His-Trp-Ser-Tyr-D-Ser(Bu)-Leu-Arg-Pro-Azgly-$NH_2$ acetate, and is used for the treatment of breast and prostate cancers and also endometriosis, side effects include hot flashes, bronchitis, arrhythmias, hypertension, anxiety and headaches. Leuprolide acetate is a synthetic nonapeptide analog of GnRH or LHRH, and has the chemical name 5-oxo-L-prolyl-L-histidyl-L-tryptophyl-L-seryl-L-tyrosyl-D-leucyl-L-leucyl-L-arginyl-N-ethyl-L-prolinamide acetate. Leuprolide acetate is used for the treatment of prostate cancer, endometriosis, and also breast cancer, side effects being similar to those of goserelin acetate.

Abarelix is a synthetic decapeptide Ala-Phe-Ala-Ser-Tyr-Asn-Leu-Lys-Pro-Ala, and has the chemical name N-Acetyl-3-(2-naphthalenyl)-D-alanyl-4-chloro-D-phenylalanyl-3-(3-pyridinyl)-D-alanyl-L-seryl-N-methyl-L-tyrosyl-D-asparaginyl-L-leucyl-N6-(1-methylethyl)-L-lysyl-L-prolyl-D-alaninamide. Abarelix can be prepared according to R. W. Roeske, WO9640757 (1996 to Indiana Univ. Found.).

Preferences and specific embodiments: Preferred GnRH agonists and antagonists for use in accordance with the invention include any of the GNRAs described herein, including in particular goserelin, leuprolide/leuporelin, triptorelin, buserelin, abarelix, goserelin acetate and leuprolide acetate. Particularly preferred are goserelin and leuprolide. Goserelin acetate is commercially available for example from AstraZeneca plc under the trade name Zoladex, or may be prepared for example as described in U.S. Pat. No. 5,510,460, or by processes analogous thereto. Leuprolide acetate is commercially available for example from TAP Pharmaceuticals Inc. under the trade name Lupron, or may be prepared for example as described in U.S. Pat. No. 3,914,412, or by processes analogous thereto. Goserelin is commercially available from AstraZeneca under the trade name Zoladex and may be prepared for example as described in ICI patent publication U.S. Pat. No. 4,100,274 or Hoechst patent publication EP475184 or by processes analagous thereto. Leuprolide is commercially available in the USA from TAP Pharmaceuticals Inc. under the trade name Lupron and in Europe from Wyeth under the trade name Prostap and may be prepared for example as described in Abbott patent publication U.S. Pat. No. 4,005,063 or by processes analogous thereto. Triptorelin is commercially available from Watson Pharma under the trade name Trelstar and may be prepared for example as described in Tulane patent publication U.S. Pat. No. 5,003,011 or by processes analagous thereto. Buserelin is commercially available under the trade name Suprefact and may be prepared for example as described in Hoechst patent publication U.S. Pat. No. 4,024,248 or by processes analogous thereto. Abarelix is commercially available from Praecis Pharmaceuticals (now part of GSK) under the trade name Plenaxis and may be prepared for example as described by Jiang et al., J Med Chem (2001), 44(3), 453-467 or Polypeptide Laboratories patent publication WO2003055900 or by processes analogous thereto.

Other GnRH agonists and antagonists for use in accordance with the invention include, but are not limited to, His-trelin from Ortho Pharmaceutical Corp, Nafarelin acetate from Roche, and Deslorelin from Shire Pharmaceuticals.

Posology: The GnRH agonists and antagonists are advantageously administered in dosages of 1.8 mg to 100 mg, for example 3.6 mg monthly or 10.8 mg every three months for goserelin or 7.5 mg monthly, 22.5 mg every three months or 30 mg every four months for leuprolide.

With regard to the preferred GnRH analogs, these are generally administered in the following dosages, namely goserelin acetate as a 3.6 mg subcutaneous implant every 4 weeks, and leuprolide as a 7.5 mg intramuscular depot every month.

2. Cytokines and Cytokine-Activating Agents

Definition: The term "cytokine" is a term of art, and references to cytokines herein is intended to cover the cytokine per se together with the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above. The term "cytokine-activating agent" is intended to cover any agent which (directly or indirectly) induces, potentiates, stimulates, activates or promotes endogenous cytokine production or the activity thereof in vivo, together with the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Technical background: Cytokines are a class of proteins or polypeptides predominantly produced by cells of the immune system which have the capacity to control the function of a second cell. In relation to anticancer therapy cytokines are used to control the growth or kill the cancer cells directly and to modulate the immune system more effectively to control the growth of tumours.

Cytokines, such as interferon (IFN) alpha and Interleukin-2, induce growth arrest or tumour cell death. IFN-alpha is used the treatment of malignant melanoma, chronic myelogenous leukemia (CML), hairy cell leukemia, and Kaposi's sarcoma. Interleukin-2 is used in the treatment of malignant melanoma and renal cell cancer either alone or in combination with IFN-alpha.

Cytokines exhibit antitumour activity through a variety of different mechanisms including the stimulation of immune cells to fight tumors For example, the T cell growth factor, IL-2 promotes T-cell and natural killer (NK) cell activation. Other cytokines such as the interferons and granulocyte-macrophage colony-stimulating factor (GM-CSF) act on antigen presenting cells to facilitate the activation of the key immune effector B cells and T cells.

Preferences and specific embodiments: Any of the cytokines and cytokine-modulating agents described herein may find application in the invention, including in particular interferons (such as interferon-γ and interferon α) and interleukins (e.g. interleukin 2). Interferon α-2b (recombinant) is available commercially under the trade name of INTRON® A from Schering Plough.

Other preferred interferons include Interferon α-2a which is available under the trade name of ROFERON from Roche.

A particularly preferred interleukin is PROLEUKIN® IL-2 (aldesleukin) which is available from Chiron Corp.

Posology: The interferons are administered by injection in a schedule which is dependent on that particular indication. For IntronA treatment of malignant melanoma preferably in a schedule that includes induction treatment on 5 consecutive days per week for 4 weeks as an intravenous (IV) infusion at a dose of 20 million IU/m2, followed by maintenance treatment three times per week for 48 weeks as a subcutaneous (SC) injection, at a dose of 10 million IU/m2. For Intron A treatment of non-Hodgkin's Lymphoma preferably in a schedule of 5 million IU subcutaneously three times per week for up to 18 months in conjunction with an anthracycline-containing chemotherapy regimen.

The recommended initial dose of Roferon-A for CML is 9 MIU daily administered as a subcutaneous or intramuscular injection. Based on clinical experience short-term tolerance may be improved by gradually increasing the dose of Roferon-A over the first week of administration from 3 MIU daily for 3 days to 6 MIU daily for 3 days to the target dose of 9 MIU daily for the duration of the treatment period. The induction dose of Roferon-A for Hairy cell leukaemia is 3 MIU daily for 16 to 24 weeks, administered as a subcutaneous or intramuscular injection. Subcutaneous administration is particularly suggested for, but not limited to, thrombocytopenic patients (platelet count <50,000) or for patients at risk for bleeding. The recommended maintenance dose is 3 MIU, three times a week (tiw).

For PROLEUKIN the following schedule has been used to treat adult patients with metastatic renal cell carcinoma (metastatic RCC) or metastatic melanoma (each course of treatment consists of two 5-day treatment cycles separated by a rest period): 600,000 IU/kg (0.037 mg/kg) dose administered every 8 hours by a 15-minute IV infusion for a maximum of 14 doses. Following 9 days of rest, the schedule is repeated for another 14 doses, for a maximum of 28 doses per course, as tolerated.

Cytokine-activating agents: Preferred cytokine-activating agents include: (a) Picibanil from Chugai Pharmaceuticals, an IFN-gamma-inducing molecule for carcinoma treatment; (b) Romurtide from Daiichi which activates the cytokine network by stimulation of colony stimulating factor release; (c) Sizofiran from Kaken Pharmaceutical, a beta1-3, beta1-6 D-glucan isolated from suehirotake mushroom, which stimulates production of IFN-gamma and IL-2 by mitogen-stimulated peripheral blood mononuclear cells, and is useful in uterine cervix tumour and lung tumour treatment; (d) Virulizin from Lorus Therapeutics Inc, a NK agonist and cytokine release modulator which stimulates IL-17 synthesis and IL-12 release for the treatment of sarcoma, melanoma, pancreas tumours, breast tumours, lung tumours, and Kaposis sarcoma (e) Thymosin alpha 1, a synthetic 28-amino acid peptide with multiple biological activities primarily directed towards immune response enhancement for increased production of Th1 cytokines, which is useful in the treatment of non-small-cell lung cancer, hepatocellular carcinoma, melanoma, carcinoma, and lung brain and renal tumours.

3. Retinoids and Rexinoids

Definition: The term "retinoid" is a term of art used herein in a broad sense to include not only the specific retinoids disclosed herein, but also the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above. The term 'rexinoids' refers to synthetic agents that bind specifically to retinoid X receptors.

Technical background: Tretinoin is an endogenous metabolite of retinol. It induces terminal differentiation in several hemopoietic precursor cell lines, including human myeloid cell lines. Acute Promyelocytic Leukemia (APL) is associated with a specific translocation between chromosomes 15 and 17; the retinoic acid receptor—α is located on chromosome 17. The translocation appears to inhibit differentiation and lead to carcinogenesis; tretinoin may overcome this when used in high doses. Tretinoin induces remissions in 64-100% of APL patients, with time to remission usually between 8 and 119 days of therapy. Acquired resistance during therapy is common especially with prolonged dosing (4-6 months). Alitretinoin is a 9-cis-retinoic acid derivative which appears to be selective for the RXR subfamily of retinoid receptors. This selectivity may preserve therapeutic antineoplastic effects while reducing significant side effects of retinoid therapy including birth defects at fetal exposure, irritation of skin and mucosal surfaces or skeletal abnormalities. Topical alitretinoin is approved in the US for the treatment of Kaposi's Sarcoma. Oral and gel (topical) formulations of bexarotene (Targretin; LGD-1069), a retinoid X receptor (RXR)-selective antitumor retinoid, are available for the treatment of cutaneous T-cell lymphoma (CTCL).

U.S. Pat. No. 6,127,382, WO 01/70668, WO 00/68191, WO 97/48672, WO 97/19052 and WO 97/19062 (all to Allergan) each describe compounds having retinoid-like activity for use in the treatment of various hyperproliferative diseases including cancers.

Preferences and specific embodiments: Preferred retinoids for use in accordance with the invention include any of the retinoids disclosed herein, including in particular tretinoin (all-trans retinoic acid), alitretinoin and bexarotene. Tretinoin (Retacnyl, Aknoten, Tretin M) is commercially available from Roche under the trade name Vesanoid and may be prepared for example as described in D. A. van Dorp, J. R. Arens, Rec. Tray. Chim. 65, 338 (1946); C. D. Robeson et al., J. Am. Chem. Soc. 77, 4111 (1955); R. Marbet, DE 2061507; U.S. Pat. No. 3,746,730 (1971, 1973 both to Hoffmann-La Roche), or by processes analogous thereto. Alitretinoin (9-cis-Tretinoin, Panrexin) is commercially available from Ligand Pharmaceuticals under the trade name Panretin and may be prepared for example as described in C. D. Robeson et al., J. Am. Chem. Soc. 77, 4111 (1955); M. Matsui et al., J. Vitaminol. 4, 178 (1958); M. F. Boehm et al., J. Med. Chem. 37, 408 (1994), or by processes analogous thereto. Bexarotene (Targrexin, Targret) is commercially available from Eisai Inc under the trade name Targretin and may be prepared for example as described in M. F. Boehm et al., WO 9321146 (1993 to Ligand Pharm.); M. L. Dawson et al., U.S. Pat. No. 5,466,861 (1995 to SRI Int.; La Jolla Cancer Res. Found.), or by processes analogous thereto.

Posology: Tretinoin is advantageously administered in dosages of 25 mg/m$^2$/day to 45 mg/m$^2$/day by mouth in two divided doses for 30 days after complete remission or up to a maximum of 90 days. Alitretinoin gel 0.1% is advantageously administered initially by application two (2) times a day to cutaneous KS lesions.

Bexarotene is advantageously administered initially as a single daily oral dose of 300 mg/m$^2$/day. The dose may be adjusted to 200 mg/m$^2$/day then to 100 mg/m$^2$/day, or temporarily suspended, if necessitated by toxicity. If there is no tumor response after eight weeks of treatment and if the initial dose of 300 mg/m2/day is well tolerated, the dose may be escalated to 400 mg/m$^2$/day with careful monitoring. Bexarotene gel is advantageously applied initially once every other day for the first week. The application frequency may be increased at weekly intervals to once daily, then twice daily, then three times daily and finally four times daily according to individual lesion tolerance.

4. Monoclonal Antibodies.

Any monoclonal antibody e.g. including but not limited to one or more cell surface antigen(s) may be used in the combinations of the invention. Antibody specificity may be assayed or determined using any of a wide variety of techniques well-known to those skilled in the art.

Definition: The term "monoclonal antibody" used herein refers to antibodies from any source, and so includes those that are fully human and also those which contain structural or specificity determining elements derived from other species (and which can be referred to as, for example, chimeric or humanized antibodies).

Technical background: The use of monoclonal antibodies is now widely accepted in anticancer chemotherapy as they are highly specific and can therefore bind and affect disease specific targets, thereby sparing normal cells and causing fewer side-effects than traditional chemotherapies.

One group of cells which have been investigated as targets for antibody chemotherapy for the treatment of various cancers are those bearing the cell-surface antigens comprising the cluster designation (CD) molecules which are over-expressed or aberrantly expressed in tumour cells, for example CD20, CD22, CD33 and CD52 which are over-expressed on the tumour cell surface, most notably in tumours of hematopoietic origin. Antibodies to these CD targets (anti-CD antibodies) include the monoclonal antibodies rituximab (a.k.a. rituxamab), tositumomab and gemtuzumab ozogamicin.

Rituximab/rituxamab is a mouse/human chimeric anti-CD20 monoclonal antibody which has been used extensively for the treatment of B-cell non-Hodgkin's lymphoma including relapsed, refractory low-grade or follicular lymphoma. The product is also being developed for various other indications including chronic lymphocytic leukaemia and rheumatoid arthritis. Side effects of rituximab/rituxamab may include hypoxia, pulmonary infiltrates, acute respiratory distress syndrome, myocardial infarction, ventricular fibrillation or cardiogenic shock. Tositumomab is a cell-specific anti-CD20 antibody labelled with iodine-131, for the treatment of non-Hodgkin's lymphoma and lymphocytic leukaemia. Possible side-effects of tositumomab include thrombocytopenia and neutropenia. Gemtuzumab ozogamicin is a cytotoxic drug (calicheamicin) linked to a human monoclonal antibody specific for CD33. Calicheamicin is a very potent antitumour agent, over 1,000 times more potent than adriamycin. Once released inside the cell, calicheamicin binds in a sequence-specific manner to the minor groove of DNA, undergoes rearrangement, and exposes free radicals, leading to breakage of double-stranded DNA, and resulting in cell apoptosis (programmed cell death). Gemtuzumab ozogamicin is used as a second-line treatment for acute myeloid leukaemia, possible side-effects including severe hypersensitivity reactions such as anaphylaxis, and also hepatotoxicity.

Alemtuzumab (Millennium Pharmaceuticals, also known as Campath) is a humanized monoclonal antibody against CD52 useful for the treatment of chronic lymphocytic leukaemia and Non-Hodgkin lymphoma which induces the secretion of TNF-alpha, IFN-gamma and IL-6.

Preferences: Preferred monoclonal antibodies for use according to the invention include anti-CD antibodies, including alemtuzumab, CD20, CD22 and CD33. Particularly preferred are monoclonal antibody to cell surface antigens, including anti-CD antibodies (for example, CD20, CD22, CD33) as described above. Other preferred monoclonal antibodies include those which target interleukin 6 (IL-6).

Specific embodiments: In one embodiment, the monoclonal antibody is an antibody to the cluster designation CD molecules, for example, CD20, CD22, CD33 and CD52. In another embodiment, the monoclonal antibody to cell surface antigen is selected from rituximab/rituxamab, tositumomab and gemtuzumab ozogamicin. Other monoclonal antibodies that may be used according to the invention include bevacizumab.

Exemplary formulations: Monoclonal antibodies to cell surface antigen(s) for use according to the invention include CD52 antibodies (e.g. alemtuzumab) and other anti-CD antibodies (for example, CD20, CD22 and CD33), as described herein. Preferred are therapeutic combinations comprising a monoclonal antibody to cell surface antigen(s), for example anti-CD antibodies (e.g. CD20, CD22 and CD33) which exhibit an advantageous efficacious effect, for example, against tumour cell growth, in comparison with the respective effects shown by the individual components of the combination.

CD52 selectivity has also been achieved through the combination of a specific ligand with diphtheria toxin which is released intracellularly (denileukin difitox; Ontak). This approach has been licensed for use in the treatment of cutaneous T-cell lymphoma and is under investigation for the treatment of other types of non-hodgkin's lymphoma.

In addition targeting structures other than tumour cells themselves have also been shown to be efficacious in cancer therapy. This approach has been most effective in inhibiting new blood vessel formation using bevacuzimab, a monoclonal antibody directed against circulating Vascular Endothelial Growth Factor. This approach may be useful in the treatment of a wide range of malignancies.

Preferred examples of monoclonal antibodies to cell surface antigens (anti-CD antibodies) include rituximab/rituxamab, tositumomab and gemtuzumab ozogamicin. Rituximab/rituxamab is commercially available from F Hoffman-La Roche Ltd under the trade name Mabthera, or may be obtained as described in PCT patent specification No. WO 94/11026. Tositumomab is commercially available from GlaxoSmithKline plc under the trade name Bexxar, or may be obtained as described in U.S. Pat. No. 5,595,721. Gemtuzumab ozogamicin is commercially available from Wyeth Research under the trade name Mylotarg, or may be obtained as described in U.S. Pat. No. 5,877,296.

Biological activity: Monoclonal antibodies (e.g. monoclonal antibodies to one or more cell surface antigen(s)) have been identified as suitable anti-cancer agents. Antibodies are effective through a variety of mechanisms. They can block essential cellular growth factors or receptors, directly induce apoptosis, bind to target cells or deliver cytotoxic payloads such as radioisotopes and toxins.

Posology: The anti-CD antibodies may be administered for example in dosages of 5 to 400 mg per square meter ($mg/m^2$) of body surface; in particular gemtuzumab ozogamicin may be administered for example in a dosage of about 9 $mg/m^2$ of body surface; rituximab/rituxamab may be administered for example in a dosage of about 375 $mg/m^2$ as an IV infusion once a week for four doses; the dosage for tositumomab must be individually quantified for each patient according to the usual clinical parameters such as age, weight, sex and condition of the patient to ensure appropriate delivery of the radioisotope.

These dosages may be administered for example once, twice or more per course of treatment, which may be repeated for example every 7, 14, 21 or 28 days.

5. *Camptothecin* Compounds

Definition: The term "*camptothecin* compound" as used herein refers to *camptothecin* per se or analogues of *camptothecin* as described herein, including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Technical background: *Camptothecin* compounds are compounds related to or derived from the parent compound *camptothecin* which is a water-insoluble alkaloid derived from the Chinese tree *Camptothecin acuminata* and the Indian tree *Nothapodytes foetida*. *Camptothecin* has a potent inhibitory activity against DNA biosynthesis and has shown high activity against tumour cell growth in various experimental systems. Its clinical use in anti-cancer therapy is, however, limited significantly by its high toxicity, and various analogues have been developed in attempts to reduce the toxicity of *camptothecin* while retaining the potency of its anti-tumour effect. Examples of such analogues include irinotecan and topotecan.

These compounds have been found to be specific inhibitors of DNA topoisomerase I. Topoisomerases are enzymes that are capable of altering DNA topology in eukaryotic cells. They are critical for important cellular functions and cell proliferation. There are two classes of topoisomerases in eukaryotic cells, namely type I and type II. Topoisomerase I is a monomeric enzyme having a molecular weight of approximately 100,000. The enzyme binds to DNA and introduces a transient single-strand break, unwinds the double helix (or allows it to unwind) and subsequently reseals the break before dissociating from the DNA strand.

Irinotecan, namely 7-ethyl-10-(4-(1-piperidino)-1-piperidino)carbonyloxy-(20S)-*camptothecin*, and its hydrochloride, also known as CPT 11, have been found to have improved potency and reduced toxicity, and superior water-solubility. Irinotecan has been found to have clinical efficacy in the treatment of various cancers especially colorectal cancer. Another important *camptothecin* compound is topotecan, namely (S)-9-dimethylaminomethyl-10-hydroxy-*camptothecin* which, in clinical trials, has shown efficacy against several solid tumours, particularly ovarian and cervical cancer and small cell lung cancer or alternatively ovarian cancer and non-small cell lung carcinoma.

Exemplary formulations: A parenteral pharmaceutical formulation for administration by injection and containing a *camptothecin* compound can be prepared by dissolving 100 mg of a water soluble salt of the *camptothecin* compound (for example a compound as described in EP 0321122 and in particular the examples therein) in 10 ml of sterile 0.9% saline and then sterilising the solution and filling the solution into a suitable container.

Biological activity: The *camptothecin* compounds of the combinations of the invention are specific inhibitors of DNA topoisomerase I are described above and have activity against various cancers.

Prior art references: WO 01/64194 (Janssen) discloses combinations of farnesyl transferase inhibitors and *camptothecin* compounds. EP 137145 (Rhone Poulenc Rorer) discloses *camptothecin* compounds including irinotecan. EP 321122 (SmithKline Beecham) discloses *camptothecin* compounds including topotecan.

Problems: Although *camptothecin* compounds are widely used as chemotherapeutic agents in humans, they are not therapeutically effective in all patients or against all types of tumours. There is therefore a need to increase the inhibitory efficacy of *camptothecin* compounds against tumour growth and also to provide a means for the use of lower dosages of *camptothecin* compounds to reduce the potential for adverse toxic side effects to the patient.

Preferences: Preferred *camptothecin* compounds for use in accordance with the invention include irinotecan and topotecan referred to above. Irinotecan is commercially available for example from Rhone-Poulenc Rorer under the trade name "Campto" and may be prepared for example as described in European patent specification No. 137145 or by processes analogous thereto. Topotecan is commercially available for example from SmithKline Beecham under the trade name "Hycamtin" and may be prepared for example as described in European patent number 321122 or by processes analogous thereto. Other *camptothecin* compounds may be prepared in conventional manner for example by processes analogous to those described above for irinotecan and topotecan.

Specific embodiments: In one embodiment, the *camptothecin* compound is irinotecan. In another embodiment, the *camptothecin* compound is a *camptothecin* compound other than irinotecan, for example a *camptothecin* compound such as topotecan.

Posology: The *camptothecin* compound is advantageously administered in a dosage of 0.1 to 400 mg per square meter (mg/m$^2$) of body surface area, for example 1 to 300 mg/m$^2$, particularly for irinotecan in a dosage of about 100 to 350 mg/m$^2$ and for topotecan in about 1 to 2 mg/m$^2$ per course of treatment. These dosages may be administered for example once, twice or more per course of treatment, which may be repeated daily or every 7, 14, 21 or 28 days in particular every 7, 14, 21 or 28 days.

6. Antimetabolites

Definition: The terms "antimetabolic compound" and "antimetabolite" are used as synonyms and define antimetabolic compounds or analogues of antimetabolic compounds as described herein, including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above. Thus, the antimetabolic compounds, otherwise known as antimetabolites, referred to herein constitute a large group of anticancer drugs that interfere with metabolic processes vital to the physiology and proliferation of cancer cells. Such compounds include nucleoside derivatives, either pyrimidine or purine nucleoside analogs, that inhibit DNA synthesis, and inhibitors of thymidylate synthase and/or dihydrofolate reductase enzymes.

Technical background: Antimetabolites (or antimetabolic compounds), constitute a large group of anticancer drugs that interfere with metabolic processes vital to the physiology and proliferation of cancer cells. Such compounds include nucleoside derivatives, either pyrimidine or purine nucleoside analogues, that inhibit DNA synthesis, and inhibitors of thymidylate synthase and/or dihydrofolate reductase enzymes. Anti-tumour nucleoside derivatives have been used for many years for the treatment of various cancers. Among the oldest and most widely used of these derivatives is 5-fluorouracil (5-FU) which has been used to treat a number of cancers such as colorectal, breast, hepatic and head and neck tumours.

In order to enhance the cytotoxic effect of 5-FU, leucovorin has been used to stabilise the resulting thymidylate synthase/5-FU complex thus further increasing its inhibition. However, various factors limit the use of 5-FU, for example tumour resistance, toxicities, including gastrointestinal and haematological effects, and the need for intravenous administration. Various approaches have been taken to overcome these disadvantages including proposals to overcome the poor bioavailability of 5-FU and also to increase the therapeutic index of 5-FU, either by reducing systemic toxicity or by increasing the amount of active drug reaching the tumour.

One such compound which provides an improved therapeutic advantage over 5-FU is capecitabine, which has the chemical name [1-(5-deoxy-β-D-ribofuranosyl)-5-fluoro-1,2-dihydro-2-oxo-4-pyrimidinyl]-carbamic acid pentyl ester.

Capecitabine is a pro-drug of 5-FU which is well absorbed after oral dosing and delivers pharmacologically-active concentrations of 5-FU to tumours. As well as offering potentially superior activity to 5-FU, it can also be used for oral therapy with prolonged administration.

Gemcitabine is a nucleoside analogue which has the chemical name 2'-deoxy-2',2'-difluoro-cytidine, and which has been used in the treatment of various cancers including non-small cell lung cancer, breast, ovarian and pancreatic cancer in particular non-small cell lung cancer and pancreatic cancer. Further anti-tumour nucleosides include cytarabine and fludarabine. Cytarabine, also known as ara-C, which has the chemical name 1-β-D-arabinofuranosylcytosine, has been found useful in the treatment of acute leukemia, chronic myelocytic leukemia and erythroleukemia. Cytarabine, also known as ara-C, which has the chemical name 1-β-D-arabinofuranosylcytosine, has been found useful in the treatment of acute myelocytic leukemia, chronic myelocytic leukemia (blast phase), acute lymphocytic leukemia and erythroleukemia. Fludarabine is a DNA synthesis inhibitor, which has the chemical name 9-β-D-arabinofuranosyl-2-fluoro-adenine, and is used for the treatment of refractory B-cell chronic lymphocytic leukaemia. Other anti-folate antimetabolites used in anticancer chemotherapy include the enzyme inhibitors raltitrexed, pemetrexed, and methotrexate. Raltitrexed is a folate-based thymidylate synthase inhibitor, which has the chemical name N-[5-[N-[(3,4-dihydro-2-methyl-4-oxo-6-quinazolinyl)-methyl-N-methylamino]-2-thenoyl]-L-glutamic acid, and is used in the treatment of advanced colorectal cancer. Pemetrexed is a thymidylate synthase and transferase inhibitor, which has the chemical name N-[4-[2-(2-amino-4,7-dihydro-4-oxo-1H-pyrrolo[2,3-d]pyrimidin-5-yl)ethyl]benzoyl]-L-glutamic acid, disodium salt, and is used for the treatment of mesothelioma and locally advanced or metastatic non-small-cell lung cancer (SCLC) in previously treated patients. Methotrexate is an antimetabolite which interrupts cell division by inhibiting DNA replication through dihydrofolate reductase inhibition, resulting in cell death, and has the chemical name is N-[4-[[(2,4-diamino-6-pteridinyl)methyl]-ethylamino]benzoyl]-L-glutamic acid, and is used for the treatment of acute lymphocytic leukemia, and also in the treatment of breast cancer, epidermoid cancers of the head and neck, and lung cancer, particularly squamous cell and small cell types, and advanced stage non-Hodgkin's lymphomas, in particular in the treatment of breast cancer, epidermoid cancers of the head and neck, and advanced stage non-Hodgkin's lymphomas.

Biological activity: The antimetabolic compounds of the combinations of the invention interfere with metabolic processes vital to the physiology and proliferation of cancer cells as described above and have activity against various cancers.

Problems: These anticancer agents have a number of side-effects especially myelosuppression and in some cases nausea and diarrhoea. There is therefore a need to provide a means for the use of lower dosages to reduce the potential of adverse toxic side effects to the patient.

Preferences: Preferred antimetabolic compounds for use in accordance with the invention include anti-tumour nucleosides such as 5-fluorouracil, gemcitabine, capecitabine, cytarabine and fludarabine and enzyme inhibitors such as raltitrexed, pemetrexed and methotrexate referred to herein. Thus, preferred antimetabolic compounds for use in accordance with the invention are anti-tumour nucleoside derivatives including 5-fluorouracil, gemcitabine, capecitabine, cytarabine and fludarabine referred to herein. Other preferred antimetabolic compounds for use in accordance with the invention are enzyme inhibitors including ralitrexed, pemetrexed and methotrexate.

5-Fluorouracil is widely available commercially, or may be prepared for example as described in U.S. Pat. No. 2,802,005. Gemcitabine is commercially available for example from Eli Lilly and Company under the trade name Gemzar, or may be prepared for example as described in European patent specification No. 122707, or by processes analogous thereto. Capecitabine is commercially available for example from Hoffman-La Roche Inc under the trade name Xeloda, or may be prepared for example as described in European patent specification No. 698611, or by processes analogous thereto. Cytarabine is commercially available for example from Pharmacia and Upjohn Co under the trade name Cytosar, or may be prepared for example as described in U.S. Pat. No. 3,116,282, or by processes analogous thereto. Fludarabine is commercially available for example from Schering AG under the trade name Fludara, or may be prepared for example as described in U.S. Pat. No. 4,357,324, or by processes analogous thereto. Ralitrexed is commercially available for example from AstraZeneca plc under the trade name Tomudex, or may be prepared for example as described in European patent specification No. 239632, or by processes analogous thereto. Pemetrexed is commercially available for example from Eli Lilly and Company under the trade name Alimta, or may be prepared for example as described in European patent specification No. 432677, or by processes analogous thereto. Methotrexate is commercially available for example from Lederle Laboraories under the trade name Methotrexate-Lederle, or may be prepared for example as described in U.S. Pat. No. 2,512,572, or by processes analogous thereto. Other antimetabolites for use in the combinations of the invention include 6-mercaptopurine, 6-thioguanine, cladribine, 2'-deoxycoformycin and hydroxyurea.

Specific embodiments: In one embodiment, the antimetabolic compound is gemcitabine. In another embodiment, the antimetabolic compound is a antimetabolic compound other than 5-fluorouracil or fludarabine, for example an antimetabolic compound such as gemcitabine, capecitabine, cytarabine, ralitrexed, pemetrexed or methotrexate.

Posology: The antimetabolite compound will be administered in a dosage that will depend on the factors noted above. Examples of dosages for particular preferred antimetabolites are given below by way of example. With regard to anti-tumour nucleosides, these are advantageously administered in a daily dosage of 10 to 2500 mg per square meter (mg/m$^2$) of body surface area, for example 700 to 1500 mg/m$^2$, particularly for 5-FU in a dosage of 200 to 500 mg/m$^2$, for gemcitabine in a dosage of 800 to 1200 mg/m$^2$, for capecitabine in a dosage of 1000 to 1200 mg/m$^2$, for cytarabine in a dosage of 100-200 mg/m$^2$ and for fludarabine in a dosage of 10 to 50 mg/m$^2$.

For the following enzyme inhibitors, examples are given of possible doses. Thus, raltitrexed can be administered in a dosage of about 3 mg/m$^2$, pemetrexed in a dosage of 500 mg/m$^2$ and methotrexate in a dosage of 30-40 mg/m$^2$.

The dosages noted above may generally be administered for example once, twice or more per course of treatment, which may be repeated for example every 7, 14, 21 or 28 days.

7. *Vinca* Alkaloids

Definition: The term "*vinca* alkaloid" as used herein refers to *vinca* alkaloid compounds or analogues of *vinca* alkaloid compounds as described herein, including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Technical background: The *vinca* alkaloids for use in the combinations of the invention are anti-tumour *vinca* alkaloids related to or derived from extracts of the periwinkle plant (*Vinca rosea*). Among these compounds, vinblastine and vincristine are important clinical agents for the treatment of leukaemias, lymphomas and testicular cancer, and vinorelbine has activity against lung cancer and breast cancer.

Biological activity: The *vinca* alkaloid compounds of the combinations of the invention are tubulin targeting agents and have activity against various cancers.

Problems: Treatment with *Vinca* alkaloids is accompanied by significant toxicities. For example, vinblastine causes leukopenia which reaches a nadir in 7 to 10 days following drug administration, after which recovery ensues within 7 days, while vincristine demonstrates some neurological toxicity for example numbness and trembling of the extremities, loss of deep tendon reflexes and weakness of distal limb musculature. Vinorelbine has some toxicity in the form of granulocytopenia but with only modest thrombocytopenia and less neurotoxicity than other *vinca* alkaloids. There is therefore a need to increase the inhibitory efficacy of anti-tumour *vinca* alkaloids against tumour growth and also to provide a means for the use of lower dosages of anti-tumour *vinca* alkaloids to reduce the potential of adverse toxic side effects to the patient.

Preferences: Preferred anti-tumour *vinca* alkaloids for use in accordance with the invention include vindesine, vinvesir, vinblastine, vincristine and vinorelbine. Particularly preferred anti-tumour *vinca* alkaloids for use in accordance with the invention include vinblastine, vincristine and vinorelbine referred to above. Vinblastine is commercially available for example as the sulphate salt for injection from Eli Lilly and Co under the trade name Velban, and may be prepared for example as described in German patent specification No. 2124023 or by processes analogous thereto. Vincristine is commercially available for example as the sulphate salt for injection from Eli Lilly and Co under the trade name Oncovin and may be prepared for example as described in the above German patent specification No. 2124023 or by processes analogous thereto. Vincristine is also available as a liposomal formulation under the name Onco-TCS™. Vinorelbine is commercially available for example as the tartrate salt for injection from Glaxo Wellcome under the trade name Navelbine and may be prepared for example as described in U.S. Pat. No. 4,307,100, or by processes analogous thereto. Other anti-tumour *vinca* alkaloids may be prepared in conventional manner for example by processes analogous to those described above for vinoblastine, vincristine and vinorelbine.

Another preferred *vinca* alkaloid is vindesine. Vindesine is a synthetic derivative of the dimeric catharanthus alkaloid vinblastine, is available from Lilly under the tradename Eldisine and from Shionogi under the tradename Fildesin. Details of the synthesis of Vindesine are described in Lilly patent DE2415980 (1974) and by C. J. Burnett et al., J. Med. Chem. 21, 88 (1978).

Specific embodiments: In one embodiment, the *vinca* alkaloid compound is selected from vinoblastine, vincristine and vinorelbine. In another embodiment, the *vinca* alkaloid compound is vinoblastine.

Posology: The anti-tumour *vinca* alkaloid is advantageously administered in a dosage of 2 to 30 mg per square meter (mg/m$^2$) of body surface area, particularly for vinblastine in a dosage of about 3 to 12 mg/m$^2$, for vincristine in a dosage of about 1 to 2 mg/m$^2$, and for vinorelbine in dosage of about 10 to 30 mg/m$^2$ per course of treatment. These dosages may be administered for example once, twice or more per course of treatment, which may be repeated for example every 1, 14, 21 or 28 days.

8. Taxanes (Taxoids)

Definition: The term "taxane compound" as used herein refers to taxane compounds or analogues of taxane compounds as described herein, including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Technical background: The taxanes are a class of compounds having the taxane ring system and related to or derived from extracts from certain species of yew (*Taxus*) trees. These compounds have been found to have activity against tumour cell growth and certain compounds in this class have been used in the clinic for the treatment of various cancers. Thus, for example, paclitaxel is a diterpene isolated from the bark of the yew tree, *Taxus brevifolia*, and can be produced by partial synthesis from 10-acetylbacctin, a precursor obtained from yew needles and twigs or by total synthesis, see Holton et al, J. Am. Chem. Soc. 116; 1597-1601 (1994) and Nicholau et al, Nature 367:630 (1994). Paclitaxel has shown anti-neoplastic activity and more recently it has been established that its antitumour activity is due to the promotion of microtubule polymerisation, Kumar N. J., Biol. Chem. 256: 1035-1041 (1981); Rowinsky et al, J. Natl. Cancer Inst. 82: 1247-1259 (1990); and Schiff et al, Nature 277: 655-667 (1979). Paclitaxel has now demonstrated efficacy in several human tumours in clinical trials, McGuire et al, Ann. Int. Med., 111:273-279 (1989); Holmes et al, J. Natl. Cancer Inst. 83: 1797-1805 (1991); Kohn et al J. Natl. Cancer Inst. 86: 18-24 (1994); and Kohn et al, American Society for Clinical Oncology, 12 (1993). Paclitaxel is used for the treatment of ovarian, breast and lung cancer, in particular has for example been used for the treatment of ovarian cancer and also breast cancer.

More recently a nanomolar formulation of paclitaxel complexed with albumin has been shown to be at least as efficacious and less myelosuppressive than paclitaxel alone. (APP; Abraxane). Paclitaxel mconjugates with glutamic acid are also in development.

Another taxane compound which has been used in the clinic is docetaxel which has been shown to have particular efficacy in the treatment of advanced breast cancer. Docetaxel has shown a better solubility in excipient systems than paclitaxel, therefore increasing the ease with which it can be handled and used in pharmaceutical compositions.

Biological activity: The taxane compounds of the combinations of the invention are tubulin targeting agents and have activity against various cancers.

Problems: Clinical use of taxanes has demonstrated a narrow therapeutic index with many patients unable to tolerate the side effects associated with its use. There is therefore a need to increase the inhibitory efficacy of taxane compounds against tumour growth and also to provide a means for the use of lower dosages of taxane compounds to reduce the potential of adverse toxic side effects to the patient. The development of taxanes with increased solubility in aqueous solutions would also be desirable.

Preferences: Preferred taxane compounds for use in accordance with the invention include paclitaxel Abraxane or docetaxel referred to herein. Paclitaxel is available commercially for example under the trade name Taxol from Bristol Myers Squibb and docetaxel is available commercially under the trade name Taxotere from Sanofi-Aventis (previously Rhone- Poulenc Rorer). Both compounds and other taxane compounds may be prepared in conventional manner for example as described in EP 253738, EP 253739 and WO 92/09589 or by processes analogous thereto.

Specific embodiments: In one embodiment, the taxane compound is paclitaxel. In another embodiment, the taxane compound is docetaxel.

Posology: The taxane compound is advantageously administered in a dosage of 50 to 400 mg per square meter (mg/m$^2$) of body surface area, for example 75 to 250 mg/m$^2$, particularly for paclitaxel in a dosage of about 175 to 250 mg/m$^2$ and for docetaxel in about 75 to 150 mg/m$^2$ per course of treatment. These dosages may be administered for example once, twice or more per course of treatment, which may be repeated for example every 7, 14, 21 or 28 days.

9. Epothilones

Definition: As used herein, the term "epothilone" is used to define a class of cytotoxic macrolides with a similar mechanism of action to paclitaxel but with the potential advantage of activity in taxane-resistant settings in preclinical models. The epothilones ixabepilone, patupilone, BMS-310705, KOS-862 and ZK-EPO are in early clinical trials for cancer treatment. Phase I studies have shown that dose-limiting toxicities of epothilones are generally neurotoxicity and neutropenia although initial studies with patupilone indicated that diarrhoea was dose limiting. Neuropathy induced by ixabepilone may be schedule dependent. Response rates in taxane-refractory metastatic breast cancer are relatively modest, but ixabepilone and patupilone have shown promising efficacy in hormone-refractory metastatic prostate cancer and in taxane-refractory ovarian cancer.

Technical Background; Epothilones A and B were originally isolated as anti-fungal fermentation products of the myxobacteria *Sorangium cellulosum*. Shortly thereafter these agents were demonstrated to stabilize microtubules and induce mitotic arrest. Though their cytotoxic activity relies on the same mechanism as that of the taxanes, the epothilones have a couple of key advantages. Firstly they are not substrates for the multi-drug resistance pump P-gylycoprotein. Secondly they are easier both to produce (because of their bacterial origin) and to manipulate. Chemical syntheses, either total or partial, of these molecules and their analogs allows for modification to enhance their efficacy Mani et al. Anticancer Drugs 2004; 15(6):553-8). Several epothilones or epothilone-derivatives have been shown effective against cell lines and tumor xenografts and are now in clinical trials (Goodin et al. J Clin Oncol 2004; 22(10): 2015-25). An unexpected source for the identification of microtubule stabilizing agents has been marine organisms. Laulimalide and isolaulimalide are natural products of the marine sponge *Cacospongia mycofijiensis* with strong paclitaxel-like activity, even against P-gp expressing cell lines. Eluetherobin, similar in both respects, is a product of the *Eleutherobia* species of soft coral.

Biological Activity; Formation of microtubules involves polymerization of heterodimeric α/β-tubulin subunits with multiple isoforms of both α- and β-tubulin present in human cells. Intact microtubule function is required for formation and functioning of the mitotic spindle, and cells treated with agents that bind either tubulin subunits or polymerized microtubules exhibit alterations in spindle formation, as well as arrest at the G2/M phase of the cell cycle, which is associated with induction of apoptosis. Compounds that target microtubules are potent cytotoxic agents, exemplified by the convergent evolution of microtubule-targeting compounds by a variety of plant and marine species. Published studies of three epothilones in current clinical development, epothilone B, aza-epothilone B, and desoxyepothilone B, indicate that these compounds exhibit broad spectrum antitumor activity in cell culture models and in xenografts. Furthermore, epothilones are generally more cytotoxic than paclitaxel in cell culture studies, with IC$_{50}$ values in the sub- or low nanomolar range in a variety of tumor cell lines (Bollag et al. Cancer Res 55:2325-2333, 1995; Lee et al. Clin Cancer Res 7:1429-1437, 2001; Chou et al. Proc Natl Acad Sci USA 95:9642-9647, 1998; Newman et al. Cancer Chemother Pharmacol 48:319-326, 2001). Preclinical studies also demonstrated important differences with regard to drug resistance mechanisms between epothilones and taxanes. In particular, overexpression of P-glycoprotein minimally affects the cytotoxicity of epothilone B, aza-epothilone B, and desoxyepothilones in cell culture models. Comparison of the cytotoxic effects of epothilone B, aza-epothilone B, and desoxyepothilone B among P-glycoprotein-overexpressing cell lines suggests that desoxyepothilone B is least affected, whereas aza-epothilone B is most affected by P-glycoprotein expression. However, it should be noted that differences among the IC$_{50}$s of these compounds in P-glycoprotein-overexpressing cell lines are small compared with the differences between these values and IC$_{50}$s for paclitaxel in these cell lines. Although the significance of P-glycoprotein expression in clinical resistance to taxanes remains uncertain, these results suggest that epothilones may be more active than taxanes in patients with malignancies characterized by high levels of P-glycoprotein expression. In vivo studies indicate that epothilones are active in paclitaxel-sensitive and -resistant tumor models using a variety of schedules. When administered intravenously to mice using intermittent daily or weekly schedules, aza-epothilone B is highly active in ovarian, colon, and breast xenografts and induces cures in an ovarian xenograft model (Pat-7) that is resistant to paclitaxel. Notably, unlike paclitaxel, aza-epothilone B is effective when administered orally in preclinical models. This phenomenon likely relates to the expression of P-glycoprotein in intestinal mucosa, resulting in poor absorption of paclitaxel but not epothilones.

Problems; Sensory neuropathy and myelosuppression has been documented with epothilones Preferences; Existing structure-activity data provide some insight into the interaction between epothilones and microtubules. Results from several groups indicate that modifications at or near the C12-13 epoxide can affect microtubule-stabilizing activity (Wartmann and Altmann, Curr Med Chem Anti-Canc Agents 2:123-148, 2002). For example, addition of a methyl group to epothilone A at position C12 yields epothilone B, which is approximately twice as potent as epothilone A or paclitaxel in inducing tubulin polymerization in vitro (Kowalski et al. J Biol Chem 272: 2534-2541, 1997; Nicolaou et al. Nature 387:268-272, 1997, abstr 428). In addition, it is clear that an epoxide at C12-13 is not required for microtubule-binding, because desoxyepothilone B (also known as epothilone D or KOS-862) lacks the C12-13 epoxide and is a more potent microtubule stabilizer in vitro than epothilone A or B. Less data are available regarding the effects of modifying other regions of epothilone. Despite attempts to improve microtubule binding by altering the C9-C12 region (on the basis of molecular modeling), alterations in this area resulted in loss of cytotoxic activity. By contrast, replacement of the lactone oxygen of epothilone B with a lactam (aza-epothilone B, also known as BMS-247550) does not impair microtubule-polymerizing activity or cytotoxicity. Although a variety of other epothilone analogs have been synthesized, it should be noted that increasing microtubule-stabilizing activity does not always result in increased cytotoxicity, presumably because of the importance of other variables such as cellular accumulation and metabolic stability (Wartmann and Altmann, Curr Med Chem Anti-Canc Agents 2:123-148, 2002). Indeed, replacement of the methyl group at C12 position of desoxyepothilone B with a propanol group results in a compound that is as effective as desoxyepothilone B against the leukemic cell line CCRF-CEM but is significantly less active against a P-glycoprotein-overexpressing subline ($IC_{50}$ of 17 nmol/L for desoxyepothilone B v 167 nmol/L for the propanol derivative) (Chou et al. Proc Natl Acad Sci USA 95:9642-9647, 1998). Additional modifications of naturally occurring epothilones have been made in an effort to improve solubility, such as BMS-310705, which is a C-21-substituted derivative of epothilone B (Lee et al. Proc Am Assoc Cancer Res 43:a3928, 2002).

Specific embodiments: In one embodiment, the epothilone compound is BMS-247550. In another embodiment, the epothilone compound is Desoxyeopthilone and in another embodiment the epothilone compound is BMS-310705

Posology: BMS-247550 is dosed either 40 mg/m² over 3 hours every 21 days or 6 mg/m² administered over 1 hour daily times 5 days every 3 weeks. Because of the frequency of mucositis and neutropenia in the first 18 patients on the single-dose every-3-week schedule, the dose was reduced to 32 mg/m². EPO906 is dosed either at 2.5 mg/m² weekly for 3 weeks followed by 1 week of rest in one trial, and 6 mg/m² once every 3 weeks. KOS-862 is scheduled at either a single dose every 3 weeks, a daily dose times 3 every 3 weeks, a fixed rate dose every 3 weeks, and a weekly dose for 3 weeks with 1 week rest.

10. Platinum Compounds

Definition: The term "platinum compounds" as used herein refers to any tumour cell growth inhibiting platinum compound including platinum coordination compounds, compounds which provide platinum in the form of an ion and analogues of platinum compounds as described herein, including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Technical background: In the chemotherapeutic treatment of cancers, cisplatin (cis-diaminodichloroplatinum (II)) has been used successfully for many years in the treatment of various human solid malignant tumours for example testicular cancer, ovarian cancer and cancers of the head and neck, bladder, oesophagus and lung.

More recently, other diamino-platinum complexes, for example carboplatin (diamino(1,1-cyclobutane-dicarboxylato)platinum (II)), have also shown efficacy as chemotherapeutic agents in the treatment of various human solid malignant tumours, carboplatin being approved for the treatment of ovarian and small cell lung cancer in particular in the treatment of ovarian cancer. A further antitumour platinum compound is oxaliplatin (L-OHP), a third generation diaminocyclohexane platinum-based cytotoxic drug, which has the chemical name (1,2-diaminocyclohexane)oxalato-platinum (II). Oxaliplatin is used, for example, for the treatment of metastatic colorectal cancer, based on its lack of renal toxicity and higher efficacy in preclinical models of cancer in comparison to cisplatin.

Oxaliplatin is used in combination with 5-FU, for the treatment of metastatic colorectal cancer and is under investigation in the treatment of upper gastrointestinal cancer. An oral platinum derivative is under investigation for the treatment of prostate cancer.

Biological activity: The platinum compounds of the combinations of the invention have activity against various cancers.

Problems: Although cisplatin and other platinum compounds have been widely used as chemotherapeutic agents in humans, they are not therapeutically effective in all patients or against all types of tumours. Moreover, such compounds need to be administered at relatively high dosage levels which can lead to toxicity problems such as kidney damage, myelosuppression and neuropathy. Also, and especially with cisplatin, the compounds cause nausea and vomiting in patients to a varying extent, as well as leucopenia, anemia and thrombocytopenia. There is therefore a need to increase efficacy and also to provide a means for the use of lower dosages to reduce the potential of adverse toxic side effects to the patient.

Preferences: Preferred platinum compounds for use in accordance with the invention include cisplatin, carboplatin and oxaliplatin. Other platinum compounds include chloro (diethylenediamino)-platinum (II) chloride; dichloro(ethylenediamino)-platinum (II); spiroplatin; iproplatin; diamino (2-ethylmalonato)platinum (II); (1,2-diaminocyclohexane) malonatoplatinum (II); (4-carboxyphthalo)-(1,2-diaminocyclohexane)platinum (II); (1,2-diaminocyclohexane)-(isocitrato)platinum (II); (1,2-diaminocyclohexane)-cis-(pyruvato)platinum (II); onnaplatin; and tetraplatin. Cisplatin is commercially available for example under the trade name Platinol from Bristol-Myers Squibb Corporation as a powder for constitution with water, sterile saline or other suitable vehicle. Cisplatin may also be prepared for example as described by G. B. Kauffman and D. O. Cowan, Inorg. Synth. 7, 239 (1963), or by processes analogous thereto. Carboplatin is commercially available for example from Bristol-Myers Squibb Corporation under the trade name Paraplatin, or may be prepared for example as described in U.S. Pat. No. 4,140,707, or by processes analogous thereto. Oxaliplatin is commercially available for example from Sanofi-Synthelabo Inc under the trade name Eloxatin, or may be prepared for example as described in U.S. Pat. No. 4,169,846, or by processes analogous thereto. Other platinum compounds and their pharmaceutical compositions are commercially available and/or can be prepared by conventional techniques.

Specific embodiments: In one embodiment, the platinum compound is selected from chloro(diethylenediamino)-platinum (II) chloride; dichloro(ethylenediamino)-platinum (II); spiroplatin; iproplatin; diamino(2-ethylmalonato)platinum (II); (1,2-diaminocyclohexane)malonatoplatinum (II); (4-carboxyphthalo)-(1,2-diaminocyclohexane)platinum (II); (1,2-diaminocyclohexane)-(isocitrato)platinum (II); (1,2-diaminocyclohexane)-cis-(pyruvato)platinum (II); onnaplatin; tetraplatin, cisplatin, carboplatin and oxaliplatin. In another embodiment, the platinum compound is a platinum compound other than cisplatin, for example a platinum compound such as chloro(diethylenediamino)-platinum (II) chloride; dichloro(ethylenediamino)-platinum (II); spiroplatin; iproplatin; diamino(2-ethylmalonato)platinum (II); (1,2-diaminocyclohexane)malonatoplatinum (II); (4-carboxyphthalo)-(1,2-diaminocyclohexane)platinum (II); (1,2-diaminocyclohexane)-(isocitrato)platinum (II); (1,2-diaminocyclohexane)-cis-(pyruvato)platinum (II); onnaplatin; tetraplatin, carboplatin or oxaliplatin, preferably selected from carboplatin and oxaliplatin.

Posology: The platinum coordination compound is advantageously administered in a dosage of 1 to 500 mg per square meter (mg/m²) of body surface area, for example 50 to 400 mg/m² or 500 mg/m² (e.g. 50 to 400 mg/m²) particularly for cisplatin in a dosage of about 75 mg/m², for carboplatin in about 300-500 mg/m² e.g. 300 mg/m², and for oxaliplatin in about 50-100 mg/m². These dosages may be administered for example once, twice or more per course of treatment, which may be repeated for example every 7, 14, 21 or 28 days.

11. Topoisomerase 2 Inhibitors

Definition: The term "topoisomerase 2 inhibitor" as used herein refers to topoisomerase 2 inhibitor or analogues of topoisomerase 2 inhibitor as described above, including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Technical background: An important class of anticancer drugs are the inhibitors of the enzyme topoisomerase 2 which causes double-strand breaks to release stress build-up during DNA transcription and translation. Compounds that inhibit the function of this enzyme are therefore cytotoxic and useful as anti-cancer agents.

Among the topoisomerase 2 inhibitors which have been developed and used in cancer chemotherapy are the podophyllotoxins. These drugs act by a mechanism of action which involves the induction of DNA strand breaks by an interaction with DNA topoisomerase 2 or the formation of free radicals. Podophyllotoxin, which is extracted from the mandrake plant, is the parent compound from which two glycosides have been developed which show significant therapeutic activity in several human neoplasms, including pediatric leukemia, small cell carcinomas of the lung, testicular tumours, Hodgkin's disease, and non-Hodgkin's lymphomas. Podophyllotoxin has activity in pediatric leukemia, small cell carcinomas of the lung, testicular tumours, Hodgkin's disease, and large cell lymphomas. These derivatives are etoposide (VP-16), which has the chemical name 4'-demethylepipodophyllotoxin 9-[4,6-O—(R)-ethylidene-β-D-glucopyranoside], and teniposide (VM-26), which has the chemical name 4'-demethylepipodophyllotoxin 9-[4,6-0-(R)-2-thenylidene-β-D-glucopyranoside].

Both etoposide and teniposide, however, suffer from certain toxic side-effects especially myelosuppression. Another important class of topoisomerase 2 inhibitors are the anthracycline derivatives which are important anti-tumour agents and comprise antibiotics obtained from the fungus *Streptomyces peuticus* var. *caesius* and their derivatives, characterized by having a tetracycline ring structure with an unusual sugar, daunosamine, attached by a glycosidic linkage. Among these compounds, the most widely used include daunorubicin, which has the chemical name 7-(3-amino-2,3,6-trideoxy-L-lyxohexosyloxy)-9-acetyl-7,8,9,10-tetrahydro-6,9,11-trihydroxy-4-methoxy-5,12-naphthacenequinone, doxorubicin, which has the chemical name 10-[(3-amino-2,3,6-trideoxy-α-L-lyxohexopyranosyl)oxy]-7,8,9,10-tetrahydro-6,8,11-trihydroxy-8-(hydroxylacetyl)-I-methoxy-5,12-naphthacenedione, and idarubicin (Zavedos™), which has the chemical name 9-acetyl-[(3-amino-2,3,6-trideoxy-α-L-lyxohexopyranosyl)oxy]-7,8,9,10-tetrahydro-6,9,11-trihydroxy-5,12-naphthacenedione.

Daunorubicin and idarubicin have been used primarily for the treatment of acute leukaemias whereas doxorubicin has been more widely tested against solid tumours particularly breast cancer. Another anthracycline derivative which is useful in cancer chemotherapy is epirubicin. Epirubicin, which has the chemical name (8S-cis)-10-[(3-amino-2,3,6-trideoxy-α-L-arabino-hexopyranosyl)oxy]-7,8,9,10-tetrahydro-6,8,11-trihydroxy-8-(hydroxyacetyl)-1-methoxy-5,12-naphthacenedione, is a doxorubicin analog having a catabolic pathway that involves glucuronidation, by uridine diphosphate-glucuronosyl transferase in the liver (unlike that for doxorubicin), which is believed to account for its shorter half-life and reduced cardiotoxicity. The compound has been used for the treatment of various cancers including cervical cancer, endometrial cancer, advanced breast cancer and carcinoma of the bladder but suffers from the side-effects of myelosuppression and cardiotoxicity. The latter side-effect is typical of anthracycline derivatives which generally display a serious cardiomyopathy at higher cumulative doses. A further type of topoisomerase 2 inhibitor is represented by mitoxantrone, which has the chemical name 1,4-dihydroxy-5,8-bis [[2-[(2-hydroxyethyl)amino]ethyl]amino]-9,10-anthracenedione, and is used for the treatment of multiple sclerosis, non-Hodgkin's lymphoma, acute myelogenous leukaemia, and breast, prostate and liver tumours. Others include losoxantrone and actinomycin D (the latter agent also known as Dactinomycin and Cosmegen Lyovac®).

Side-effects from administration of mitoxantrone include myelosuppression, nausea, vomiting, stomatitis and alopecia Biological activity: The topoisomerase 2 inhibitors of the combinations of the invention have activity against various cancers as described above.

Problems: This class of cytotoxic compound is associated with side effects, as mentioned above. Thus, there is a need to provide a means for the use of lower dosages to reduce the potential of adverse toxic side effects to the patient.

Preferences: Preferred topoisomerase 2 inhibitor compounds for use in accordance with the invention include anthracycline derivatives, mitoxantrone and podophyllotoxin derivatives as defined to herein.

Preferred anti-tumour anthracycline derivatives for use in accordance with the invention include daunorubicin, doxorubicin, idarubicin and epirubicin referred to above. Daunorubicin is commercially available for example as the hydrochloride salt from Bedford Laboratories under the trade name Cerubidine, or may be prepared for example as described in U.S. Pat. No. 4,020,270, or by processes analogous thereto. The therapeutic index of daunorubicin in acute myeloid leukemia may be improved by encapsulating the molecule in a liposome (Daunoxome; Gilead/Diatos). Doxorubicin is commercially available for example from Pharmacia and Upjohn Co under the trade name Adriamycin, or may be prepared for example as described in U.S. Pat. No. 3,803,124, or by processes analogous thereto. Doxorubicin derivatives include pegylated doxorubicin hydrochloride and liposome-encapsulated doxorubicin citrate. Pegylated doxorubicin hydrochloride is commercially available from Schering-Plough Pharmaceuticals under the trade name Caeylx; non-pegylated liposome-encapsulated doxorubicin citrate is commercially available for example from Cephalon Europe under the trade name Myocet. Idarubicin is commercially available for example as the hydrochloride salt from Pharmacia & Upjohn under the trade name Idamycin, or may be prepared for example as described in U.S. Pat. No. 4,046,878, or by processes analogous thereto. Epirubicin is commercially available for example from Pharmacia and Upjohn Co under the trade name Pharmorubicin, or may be prepared for example as described in U.S. Pat. No. 4,058,519, or by processes analogous thereto. Mitoxantrone is commercially available for example from OSI Pharmaceuticals, under the trade name Novantrone, or may be prepared for example as described in U.S. Pat. No. 4,197,249, or by processes analogous thereto.

Other anti-tumour anthracycline derivatives may be prepared in conventional manner for example by processes analogous to those described above for the specific anthracycline derivatives.

Preferred anti-tumour podophyllotoxin derivatives for use in accordance with the invention include etoposide and teniposide referred to above. Etoposide is commercially available for example from Bristol-Myers Squibb Co under the trade name VePesid, or may be prepared for example as described in European patent specification No 111058, or by processes analogous thereto. Teniposide is commercially available for example from Bristol-Myers Squibb Co under the trade name Vumon, or may be prepared for example as described in PCT patent specification No. WO 93/02094, or by processes analogous thereto. Other anti-tumour podophyllotoxin derivatives may be prepared in conventional manner for example by processes analogous to those described above for etoposide and teniposide.

Specific embodiments: In one embodiment, the topoisomerase 2 inhibitor is an anthracycline derivative, mitoxantrone or a podophyllotoxin derivative. In another embodiment, the topoisomerase 2 inhibitor is selected from daunorubicin, doxorubicin, idarubicin and epirubicin. In a further embodiment, the topoisomerase 2 inhibitor is selected from etoposide and teniposide. Thus, in a preferred embodiment, the topoisomerase 2 inhibitor is etoposide. In another embodiment, the topoisomerase 2 inhibitor is an anthracycline derivative other than doxorubicin, for example a topoisomerase 2 inhibitor such as daunorubicin, idarubicin and epirubicin.

Posology: The anti-tumour anthracycline derivative is advantageously administered in a dosage of 10 to 150 mg per square meter ($mg/m^2$) of body surface area, for example 15 to 60 $mg/m^2$, particularly for doxorubicin in a dosage of about 40 to 75 $mg/m^2$, for daunorubicin in a dosage of about 25 to 45 $mg/m^2$, for idarubicin in a dosage of about 10 to 15 $mg/m^2$ and for epirubicin in a dosage of about 100-120 $mg/m^2$.

Mitoxantrone is advantageously administered in a dosage of about 12 to 14 $mg/m^2$ as a short intravenous infusion about every 21 days.

The anti-tumour podophyllotoxin derivative is advantageously administered in a dosage of 30 to 300 $mg/m^2$ of body surface area, for example 50 to 250 mg/m particularly for etoposide in a dosage of about 35 to 100 mg/m, and for teniposide in about 50 to 250 $mg/m^2$.

The dosages noted above may generally be administered for example once, twice or more per course of treatment, which may be repeated for example every 7, 14, 21 or 28 days.

12. Alkylating Agents

Definition: The term "alkylating agent" or "alkylating agents" as used herein refers to alkylating agents or analogues of alkylating agents as described herein, including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Technical background: Alkylating agents used in cancer chemotherapy encompass a diverse group of chemicals that have the common feature that they have the capacity to contribute, under physiological conditions, alkyl groups to biologically vital macromolecules such as DNA. With most of the more important agents such as the nitrogen mustards and the nitrosoureas, the active alkylating moieties are generated in vivo after complex degradative reactions, some of which are enzymatic. The most important pharmacological actions of the alkylating agents are those that disturb the fundamental mechanisms concerned with cell proliferation, in particular DNA synthesis and cell division. The capacity of alkylating agents to interfere with DNA function and integrity in rapidly proliferating tissues provides the basis for their therapeutic applications and for many of their toxic properties. Alkylating agents as a class have therefore been investigated for their anti-tumour activity and certain of these compounds have been widely used in anti-cancer therapy although they tend to have in common a propensity to cause dose-limiting toxicity to bone marrow elements and to a lesser extent the intestinal mucosa.

Among the alkylating agents, the nitrogen mustards represent an important group of anti-tumour compounds which are characterised by the presence of a bis-(2-chloroethyl) grouping and include cyclophosphamide, which has the chemical name 2-[bis(2-chloroethyl)amino]tetrahydro-2H-1,3,2-oxazaphospholine oxide, and chlorambucil, which has the chemical name 4-[bis(2-chloroethyl)amino]-benzenebutoic acid. Cyclophosphamide has a broad spectrum of clinical activity and is used as a component of many effective drug combinations for non-Hodgkin's lymphoma, Hodgkin's disease, Burkitt's lymphoma and breast cancer. Cyclophosphamide has also been used as a component of combinations for malignant lymphomas.

Ifosfamide (a.k.a. ifosphamide) is a structural analogue of cyclophosphamide and its mechanism of action is presumed to be identical. It has the chemical name 3-(2-chloroethyl)-2-[(2-chloroethyl)amino]tetrahydro-2H-1,3,2-oxazaphosphorin-2-oxide, and is used for the treatment of cervical cancer, sarcoma, and testicular cancer but may have severe urotoxic effects. Chlorambucil has been used for treating chronic lymphocytic leukaemia and non-Hodgkin's lymphoma.

Chlorambucil has also been used for treating CLL and malignant lymphomas including lymphosarcoma.

Another important class of alkylating agents are the nitrosoureas which are characterised by the capacity to undergo spontaneous non-enzymatic degradation with the formation of the 2-chloroethyl carbonium ion. Examples of such nitrosourea compounds include carmustine (BiCNU® or BCNU) which has the chemical name 1,3-bis(2-chloroethyl)-I-nitrosourea, and lomustine (CCNU) which has the chemical name 1-(2-chloroethyl)cyclohexyl-I-nitrosourea. Carmustine and lomustine each have an important therapeutic role in the treatment of brain tumours and gastrointestinal neoplasms although these compounds cause profound, cumulative myelosuppression that restricts their therapeutic value.

Another class of alkylating agent is represented by the bifunctional alkylating agents having a bis-alkanesulfonate group and represented by the compound busulfan which has the chemical name 1,4-butanediol dimethanesulfonate, and is used for the treatment of chronic myelogenous (myeloid, myelocytic or granulocytic) leukaemia. However, it can induce severe bone marrow failure resulting in severe pancytopenia. This property has led to its widespread usage as a conditioning agent prior to hematological stem cell transplantation.

Another class of alkylating agent are the aziridine compounds containing a three-membered nitrogen-containing ring which act as anti-tumour agents by binding to DNA, leading to cross-linking and inhibition of DNA synthesis and function. An example of such an agent is mitomycin, an antibiotic isolated from *Streptomyces caespitosus*, and having the chemical name 7-amino-9α-methoxymitosane.

Mitomycin is used to treat adenocarcinoma of stomach, pancreas, colon and breast, small cell and non-small cell lung cancer, and, in combination with radiation, head and neck cancer, side-effects including myelosuppression, nephrotoxicity, interstitial pneumonitis, nausea and vomiting.

Biological activity: One of the most important pharmacological actions of the alkylating agent in combination with the invention is its ability to disturb the fundamental mechanisms concerned with cell proliferation as herein before defined. This capacity to interfere with DNA function and integrity in rapidly proliferating tissues provides the basis for their therapeutic application against various cancers.

Problems: This class of cytotoxic compound is associated with side effects, as mentioned above. Thus, there is a need to provide a means for the use of lower dosages to reduce the potential of adverse toxic side effects to the patient.

Preferences: Preferred alkylating agents for use in accordance with the invention include the nitrogen mustard compounds cyclophosphamide, ifosfamide/ifosphamide and chlorambucil and the nitrosourea compounds carmustine and lomustine referred to above. Preferred nitrogen mustard compounds for use in accordance with the invention include cyclophosphamide, ifosfamide/ifosphamide and chlorambucil referred to above. Cyclophosphamide is commercially available for example from Bristol-Myers Squibb Corporation under the trade name Cytoxan, or may be prepared for example as described in U.K. patent specification No. 1235022, or by processes analogous thereto. Chlorambucil is commercially available for example from GlaxoSmithKline plc under the trade name Leukeran, or may be prepared for example as described in U.S. Pat. No. 3,046,301, or by processes analogous thereto. Ifosfamide/ifosphamide is commercially available for example from Baxter Oncology under the trade name Mitoxana, or may be prepared for example as described in U.S. Pat. No. 3,732,340, or by processes analogous thereto. Preferred nitrosourea compounds for use in accordance with the invention include carmustine and lomustine referred to above. Carmustine is commercially available for example from Bristol-Myers Squibb Corporation under the trade name BiCNU, or may be prepared for example as described in European patent specification No. 902015, or by processes analogous thereto. Lomustine is commercially available for example from Bristol-Myers Squibb Corporation under the trade name CeeNU, or may be prepared for example as described in U.S. Pat. No. 4,377,687, or by processes analogous thereto. Busulfan is commercially available for example from GlaxoSmithKline plc under the trade name Myleran, or may be prepared for example as described in U.S. Pat. No. 2,917,432, or by processes analogous thereto. Mitomycin is commercially available for example from Bristol-Myers Squibb Corporation under the trade name Mutamycin. Others include estramustine, mechlorethamine, melphalan, bischloroethylnitrosurea, cyclohexylchloroethylnitrosurea, methylcyclohexylchloroethylnitrosurea, nimustine, procarbazine, dacarbazine, temozolimide and thiotepa.

Specific embodiments: In one embodiment, the alkylating agent is a nitrogen mustard compound selected from cyclophosphamide, ifosfamide/ifosphamide and chlorambucil. In another embodiment, the alkylating agent is a nitrosurea selected from carmustine and lomustine. The alkylating agents further include Busulfan. In one embodiment, the alkylating agents are as herein before defined other than mitomycin C or cyclophosphamide.

Posology: The nitrogen mustard or nitrosourea alkylating agent is advantageously administered in a dosage of 100 to 9000 e.g. 100 to 2500 mg per square meter ($mg/m^2$) of body surface area, for example 100 to 5000, 100 to 2500 or 120 to 500 $mg/m^2$, particularly for cyclophosphamide in a dosage of about 100 to 5000 e.g. 100 to 500 $mg/m^2$, for ifosfamide/ifosphamide in a dosage of 500-9000 $mg/m^2$ e.g. 500-2500 $mg/m^2$, for chlorambucil in a dosage of about 0.1 to 0.2 mg/kg, for carmustine in a dosage of about 150 to 200 $mg/m^2$ and for lomustine in a dosage of about 100 to 150 $mg/m^2$. For bis-alkanesulfonate compounds such as busulphan a typical dose may be 1-2 $mg/m^2$, e.g. about 1.8 $mg/m^2$.

Aziridine alkylating agents such as mitomycin can be administered for example in a dosage of 15 to 25 $mg/m^2$ preferably about 20 $mg/m^2$.

The dosages noted above may be administered for example once, twice or more per course of treatment, which may be repeated for example every 7, 14, 21 or 28 days.

13. Signalling Inhibitors for Use According to the Invention

Definition: The term "signalling inhibitor" (or "signal transduction inhibitor") as used herein refers to signalling inhibitors or analogues of signalling inhibitors as described herein, including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Technical background: A malignant tumour is the product of uncontrolled cell proliferation. Cell growth is controlled by a delicate balance between growth-promoting and growth-inhibiting factors. In normal tissue the production and activity of these factors results in differentiated cells growing in a controlled and regulated manner that maintains the normal integrity and functioning of the organ. The malignant cell has evaded this control; the natural balance is disturbed (via a variety of mechanisms) and unregulated, aberrant cell growth occurs.

One driver for growth is the epidermal growth factor (EGF), and the receptor for EGF (EGFR) has been implicated in the development and progression of a number of human solid tumours including those of the lung, breast, prostate, colon, ovary, head and neck. EGFR is a member of a family of four receptors, namely EGFR (HER1 or ErbB1), ErbB2 (HER2/neu), ErbB3 (HER3), and ErbB4 (HER4). These receptors are large proteins that reside in the cell membrane, each having a specific external ligand binding domain, a transmembrane domain and an internal domain which has tyrosine kinase enzyme activity. When EGF attaches to EGFR, it activates the tyrosine kinase, triggering reactions that cause the cells to grow and multiply. EGFR is found at abnormally high levels on the surface of many types of cancer cells, which may divide excessively in the presence of EGF. Inhibition of EGFR activity has therefore been a target for chemotherapeutic research in the treatment of cancer. Such inhibition can be effected by direct interference with the target EGFR on the cell surface, for example by the use of antibodies, or by inhibiting the subsequent tyrosine kinase activity.

Examples of antibodies which target EGFR are the monoclonal antibodies trastuzumab and cetuximab. Amplification of the human epidermal growth factor receptor 2 protein (HER 2) in primary breast carcinomas has been shown to correlate with a poor clinical prognosis for certain patients. Trastuzumab is a highly purified recombinant DNA-derived humanized monoclonal IgG1 kappa antibody that binds with high affinity and specificity to the extracellular domain of the HER2 receptor. In vitro and in vivo preclinical studies have shown that administration of trastuzumab alone or in combination with paclitaxel or carboplatin significantly inhibits the growth of breast tumour-derived cell lines that over-express the HER2 gene product. In clinical studies trastuzumab has been shown to have clinical activity in the treatment of breast cancer. The most common adverse effects of trastuzumab are fever and chills, pain, asthenia, nausea, vomiting, diarrhea, headache, dyspnea, rhinitis, and insomnia. Particularly troublesome is the onset of cardiomyopathy which may be reversible in the majority of patients. Trastuzumab has been approved for the treatment of early and metastatic breast cancer, in particular metastic breast cancer, exhibiting over-expression of the HER2 protein Cetuximab has been used for the treatment of irinotecan-refractory colorectal cancer (CRC) and in combination with radiotherapy in the treatment of head and neck cancer. It is also being evaluated both as a single agent and in combination with other agents for use in the treatment of a variety of other cancers including metastatic pancreatic carcinoma, and non-small-cell lung cancer. The administration of cetuximab can cause serious side effects, which may include difficulty in breathing and low blood pressure.

Another suitable monoclonal antibody for use in the combinations of the invention is panitumumab. Amgen Inc (formerly Immunex and Abgenix Inc) is developing panitumumab (ABX-EGF), a fully human monoclonal antibody against the EGF receptor, for the potential treatment of cancer, such as monotherapy for renal cancer, non-small-cell lung cancer, and CRC in combination with standard chemotherapy as first-line treatment, as third-line monotherapy in advanced CRC, in particular to treat metastatic colorectal cancer (MCC) and in patients who failed standard chemotherapy. Thus ABX-EGF can be administered as a monotherapy or in association with chemotherapy and radiotherapy in order to complement independent approaches for the treatment of cancer.

ABX-EGF is a fully humanized IgG2 monoclonal antibody against the human EGFR.

Fully humanized monoclonal antibodies such as ABX-EGF have several advantages over chimeric antibodies, which contain significant amounts of mouse protein. They do not generate human anti-mouse antibodies (HAMA); the risk of inducing hypersensitivity reactions in patients is therefore reduced and the antibodies should demonstrate an increased in vivo lifetime. Such considerations may be important for long-term administration.

It can be prepared as described in WO98/50433 and process analogous thereto.

Panitumumab may be dosed ranging from 0.01 to 5.0 mg/kg once per week, 6.0 mg/kg once every two weeks or 9.0 mg/kg once every three weeks administered by intravenous infusion.

In a Phase 3 pivotal study examining panitumumab as third-line monotherapy in colorectal cancer patients, patients received panitumumab every two weeks.

The farnesyltransferase inhibitor tipifarnib prevents signaling thru ras-mediated pathways and is under investigation for the treatment of myeloid leukemias.

Examples of agents which target EGFR tyrosine kinase activity include the tyrosine kinase inhibitors gefitinib and erlotinib. Gefitinib which has the chemical name 4-(3-chloro-4-fluoroanilino)-7-methoxy-6-(3-morpholinopropoxy) quinazoline, is used for the treatment of non-small-cell lung cancer. It has also been studied for other solid tumours that over-express EGF receptors such as breast and colorectal cancer. It has been found that patients receiving gefitinib may develop interstitial lung disease and eye irritation Erlotinib, which has the chemical name N-(3-ethynyl-phenyl)-6,7-bis (2-methoxyethoxy)-4-quinazoline, has also been used for the treatment of non-small-cell lung cancer, and is being developed for the treatment of various other solid tumours such as pancreatic cancer, the most common side effects being rash, loss of appetite and fatigue; a more serious side effect which has been reported is interstitial lung disease.

Another growth factor which has received attention as a target for anticancer research is the vascular endothelial growth factor (VEGF). VEGF is a key regulator of vasculogenesis during angiogenic processes including wound healing, retinopathy, psoriasis, inflammatory disorders, tumour growth and metastasis. Studies have shown that over-expression of VEGF is strongly associated with invasion and metastasis in human malignant disease.

An example of an antibody that targets the VEGF antigen on the surface of a cell is the monoclonal antibody bevacizumab which is a recombinant humanised monoclonal IgG1 antibody that binds to and inhibits VEGF. Bevacizumab has been used for the treatment of colorectal cancer, for example in combination with chemotherapy e.g. 5-fluorouracil. Bevacizumab also being developed as a potential treatment for other solid tumours such as metastatic breast cancer, metastatic non-small-cell lung cancer and renal cell carcinoma. The most serious adverse events associated with bevacizumab include gastrointestinal perforations, hypertensive crises, nephrotic syndrome and congestive heart failure. Other therapeutic agents in development which target the action of VEGF at alternate points in the signal transduction cascade initiated by this growth factor include sunitinib which is marketed under the trade name Sutent by Sugen/Pfizer and inhibits the kinase activity of the VEGF receptor. Sutent has demonstrated efficacy in Phase III trials in gastrointestinal stromal tumours and has regulatory approval for the treatment of renal cancer.

Another growth factor of importance in tumour development is the platelet-derived growth factor (PDGF) that comprises a family of peptide growth factors that signal through cell surface tyrosine kinase receptors (PDGFR) and stimulate various cellular functions including growth, proliferation, and differentiation. PDGF expression has been demonstrated in a number of different solid tumours including glioblastomas and prostate carcinomas. The tyrosine kinase inhibitor imatinib mesylate, which has the chemical name 4-[(4-methyl-1-piperazinyl)methyl]-N-[4-methyl-3-[[4-(3-pyridinyl)-2-ylpyridinyl]amino]-phenyl]benzamide methanesulfonate, blocks activity of the Bcr-Abl oncoprotein and the cell surface tyrosine kinase receptor c-Kit, and as such is approved for the treatment on chronic myeloid leukemia and gastrointestinal stromal tumours. Imatinib mesylate is also a potent inhibitor of PDGFR kinase and is currently being evaluated for the treatment of chronic myelomonocytic leukemia and glioblastoma multiforme, based upon evidence in these diseases of activating mutations in PDGFR. The most frequently reported drug-related adverse events were edema, nausea, vomiting, cramps and musculosketetal pain.

A further growth factor target for cancer chemotherapy is inhibition of Raf which is a key enzyme in the chain reaction of the body's chemistry that triggers cell growth. Abnormal activation of this pathway is a common factor in the development of most cancers, including two-thirds of melanomas. By blocking the action of Raf kinase, it may be possible to reverse the progression of these tumours. One such inhibitor is sorafenib (a.k.a. BAY 43-9006 and Nexavar) which has the chemical name 4-(4-(3-(4-chloro-3-(trifluoromethyl)phenyl) ureido)phenoxy)-N2-methylpyridine-2-carboxamide. Sorafenib targets both the Raf signalling pathway to inhibit cell proliferation and the VEGFR/PDGFR signalling cascades to inhibit tumour angiogenesis. Raf kinase is a specific enzyme in the Ras pathway. Mutations in the Ras gene occur in approximately 20 percent of all human cancers, including 90 percent of pancreatic cancers, 50 percent of colon cancers and 30 percent of non-small cell lung cancers. Sorafenib is being investigated for the treatment of a number of cancers including liver and kidney cancer. The most common side effects of sorafenib are pain, swelling, redness of the hands and/or feet, and also rash, fatigue and diarrhea.

Biological activity: The signalling inhibitors of the combinations of the invention are specific inhibitors of cell signalling proteins as described above and have activity against various cancers. Combinations of compounds of formula I with signalling inhibitors may be beneficial in the treatment and diagnosis of many types of cancer. Combination with a molecularly targeted agent such as a signalling inhibitor (e.g. Iressa, Avastin, herceptin, or Gleevec™) would find particular application in relation to cancers which express or have activated the relevant molecular target such as EGF receptor, VEGF receptor, ErbB2, BCRabl, c-kit, PDGF. Diagnosis of such tumours could be performed using techniques known to a person skilled in the art and as described herein such as RTPCR and FISH.

Problems: There is a need to increase the inhibitory efficacy of signalling inhibitors against tumour growth and also to provide a means for the use of lower dosages of signaling inhibitors to reduce the potential for adverse toxic side effects to the patient.

Preferences: Preferred signalling inhibitors for use in accordance with the invention include antibodies targeting EGFR such as monoclonal antibodies trastuzumab and cetuximab, EGFR tyrosine kinase inhibitors such as gefitinib and erlotinib, VEGF targeting antibody such as pantumab and bevacizumab, PDGFR inhibitor such as imatinib mesylate and Raf inhibitor such as sorafenib referred to herein.

Preferred antibodies targeting EGFR include the monoclonal antibodies trastuzumab and cetuximab. Trastuzumab is commercially available from Genentech Inc under the trade name Herceptin, or may be obtained as described in U.S. Pat. No. 5,821,337. Cetuximab is commercially available from Bristol-Myers Squibb Corporation under the trade name Erbitux, or may be obtained as described in PCT patent specification No. WO 96/40210.

Preferred EGFR tyrosine kinase inhibitors include gefitinib and erlotinib. Gefitinib is commercially available from AstraZeneca plc under the trade name Iressa, or may be obtained as described in PCT patent specification No. WO 96/33980. Erlotinib is commercially available from Genentech/Roche under the trade name Tarceva, or may be obtained as described in PCT patent specification No. WO 96/30347.

A preferred antibody targeting VEGF is bevacizumab which is commercially available from Genentech Inc under the trade name Avastin, or may be obtained as described in PCT patent specification No. WO 94/10202.

Also preferred is sorafenib and sunitinib.

A preferred PDGFR inhibitor is imatinib mesylate which is commercially available from Novartis AG under the trade name Gleevec™ (a.k.a. Glivec®), or may be obtained as described in European patent specification No 564409.

A preferred Raf inhibitor is sorafenib which is available from Bayer AG, or may be obtained as described in PCT patent specification No. WO 00/42012.

Specific embodiments: In one embodiment, the signalling inhibitor is gefitinib (Iressa). In other embodiments the signalling inhibitor is selected from trastuzumab, cetuximab, gefitinib, erlotinib, bevacizumab, imatinib mesylate and sorafenib.

Further combinations of the invention include the following signalling inhibitors: dasatinib, lapatinib, nilotinib, vandetanib, vatalanib and CHIR-258, in particular dasatinib, lapatinib, nilotinib, vandetanib and vatalinib.

BMS is developing dasatinib (Sprycel or BMS-354825) an oral multitargeted kinase inhibitor, for the potential twice-daily treatment of chronic myelogenous leukemia (CML), Philadelphia chromosome-positive (Ph+) acute lymphoblastic leukemia (ALL) and solid tumors. The drug is also under investigation for multiple myeloma (MM) and other hematologic malignancies. Dasatanib has proved effective in Ph+ CML and AML in clinical trials given twice daily at 50-90 mg and also in imatinib resistant patients. Thrombocytopenia and neutropenia were amongst the side effects observed during clinical evaluation of dasatinib.

The structure of dasatinib, a Src/Abl kinase inhibitor is below:

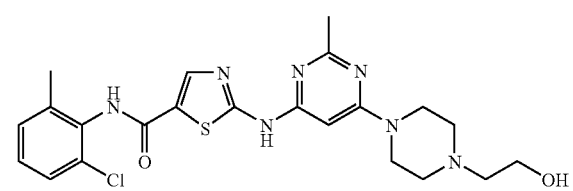 [SMILES: Cc1nc(Nc2ncc(C(=O)Nc3c(C)cccc3Cl)s2)cc(N2CCN(CCO)CC2)n1]

Dasatinib can be prepared by processes described in or analogous to WO 00/062778, WO 2005/076990 and WO 2005/077945.

Novartis is developing nilotinib (AMN-107), an orally available signal transduction inhibitor that targets BCR-ABL, c-kit and PDGF, for the potential treatment of leukemias. The compound is being investigated for chronic myeloid leukemia (CML) and relapsed or refractory acute lymphoblastic leukemia (ALL), systemic mastocytosis or chronic eosinophilic leukemia (hypereosinophilic syndrome), refractory gastrointestinal stromal tumor (GIST). Adverse events included hematological adverse events, headache, fatigue, muscle spasms, and nausea and vomiting. In early clinical studies doses of the order of 400 mg given twice daily have proved effective in treating CML, AML and ALL The structure of nilotinib is shown below. It can be prepared as described in or analogous to as described in WO 2004/005281 and WO 2005/049032.

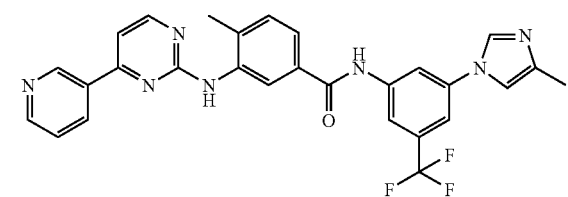 [SMILES: Cc1cn(-c2cc(NC(=O)c3ccc(C)c(Nc4nccc(-c5cccnc5)n4)c3)cc(C(F)(F)F)c2)cn1]

Vatalanib (PTK787/ZK222584) is a VEGF receptor tyrosine kinase angiogenesis inhibitor, under development by Novartis AG (formerly Ciba-Geigy) and Schering AG, for the potential treatment of colorectal cancer. The compound entered trials for colorectal cancer, the first- and second-line treatment of metastatic colorectal cancer (untreated and pre-treated metastatic colorectal patients). Schering and Novartis are also investigating vatalanib in other solid tumors e.g. non-small cell lung cancer (NSCLC), as a second-line monotherapy in patients with stage IIIb/IV disease who had relapsed or were refractory to first-line therapy, renal cell cancer and glioblastoma, and potentially prostate, ovarian, breast, pancreas and small cell lung cancers. In addition vatalanib is also investigated for wet age-related macular degeneration (AMD). Vatalanib has been evaluated at doses up to 1,250 mg daily in clinical studies. Adverse events include nausea/vomiting, fatigue, ataxia, lethargy, hypertension, headache, dizziness, diarrhoea, hypertension as well as syncope and neurotoxicity.

Vatalinib (structure shown below) can be prepared as described in or analogues to as described in WO 98/35958

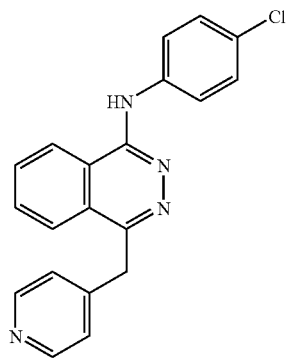 [SMILES: Clc1ccc(Nc2nnc(Cc3ccncc3)c3ccccc23)cc1]

Lapatinib ditosylate (Tykerb or GW2016/572016), an ErbB2 and EGFR dual tyrosine kinase inhibitor, is being developed by GlaxoSmithKline plc (GSK) for the potential treatment of solid tumors.

It is under investigation for various tumors including breast, lung, stomach, bladder and head and neck cancers, in particular for the treatment of patients with refractory advanced or metastatic breast cancer whose tumours express HER-2 and who have failed previous therapies both as a single agent and in combination with other therapies including capecitabine and paclitaxel. The compound had also entered trials for renal cell cancer, advanced and metastatic non-small cell lung cancer (NSCLC) and in the treatment of brain metastases associated with breast cancer. In early clinical evaluation Lapatinib has been evaluated on a twice daily and once daily schedule at doses over the range 500-1500 mg and at doses of 750-1250 mg given twice daily. Side effects include gastrointestinal gaseous symptoms, rash, headache and abnormal liver function tests.

Quinazoline compounds, and ditosylate salts, anhydrate or hydrate forms such as of the structure shown below (lapatinib) can be synthesised using the process described in WO 00/202552 and WO 99/35146 or process analogues thereto.

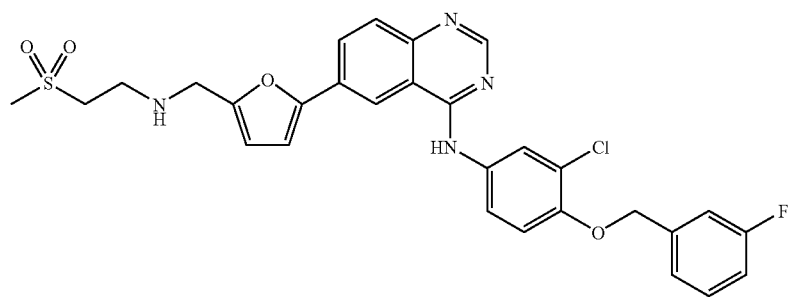 [SMILES: CS(=O)(=O)CCNCc1ccc(-c2ccc3ncnc(Nc4ccc(OCc5cccc(F)c5)c(Cl)c4)c3c2)o1]

Vandetanib (ZD-6474; Zactima; formerly AZD-6474) is under development by AstraZeneca for the potential once-daily oral treatment of solid and haematological tumors including thyroid, lung, breast, head and neck, brain (i.e. glioma) and multiple myeloma. It is one of a series of inhibitors of vascular endothelial growth factor (VEGF) receptor tyrosine kinase) that also has activity against the EGF and RET receptor tyrosine kinases. Clinical studies have investigated doses of vandetanib in the region of 100-300 mg daily as monotherapy and in combinations. Common adverse effects observed were rash, fatigue, nausea, diarrhea, asymptomatic QTc prolongation

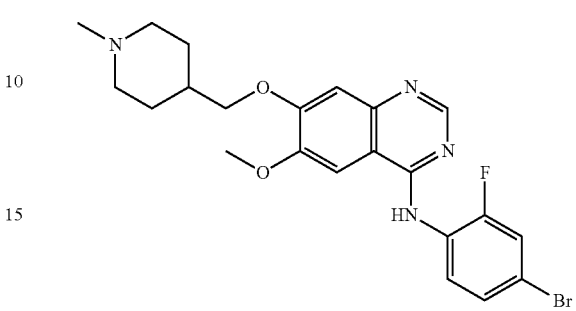

ZD-6474 can be prepared as described in WO 01/32651 and processes analogous therein.

CHIR-258 (GFKI-258; structure shown), is a potent VEGF, FGF and PDGF receptor kinase inhibitor, for the potential oral treatment of various types of cancer. Novartis (formerly Chiron), had initiated a study in acute myelogenous leukemia (AML) patients and multiple myeloma (MM).

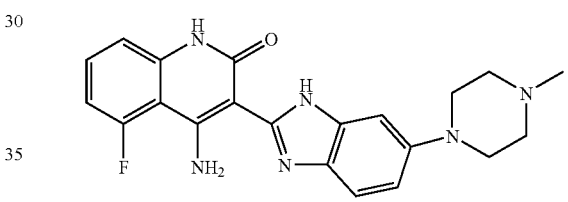

CHIR-258 can be prepared as described in WO 02/22598 and WO 2005/046590 and processes analogous therein.

Another suitable signalling inhibitor for use in the combinations of the invention is axitinib (AG-013736). Pfizer is developing axitinib (AG-13736, AG-013736), an oral inhibitor of the VEGF, PDGF and CSF-1 receptor tyrosine kinases which was discovered by Pfizer's wholly-owned subsidiary Agouron Pharmaceuticals, as an anti-angiogenic agent for the potential treatment of cancer. It is being studied for breast cancer, renal cell carcinoma (RCC), non-small cell lung cancer (NSCLC), melanoma, and carcinomas. The compound has also being investigated for the treatment of acute myeloid leukemia and myelodysplastic syndrome (MDS).

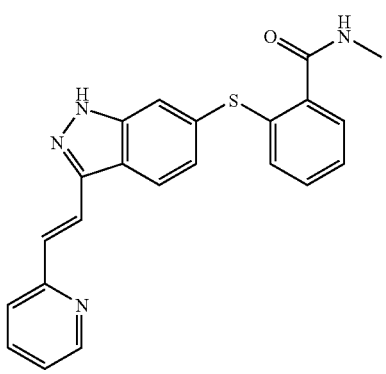 [SMILES: CNC(=O)c1ccccc1Sc1ccc2c(/C=C/c3ccccn3)n[nH]c2c1]

It can be prepared as described in WO 2004/087152, WO 2006/048746 and WO 2006/048745 and process analogous thereto. Axitinib may be dosed at 5 mg PO BID.

Posology: With regard to the EGFR antibodies, these are generally administered in a dosage of 1 to 500 mg per square meter (mg/m$^2$) of body surface area, trastuzumab being advantageously administered in a dosage of 1 to 5 mg/m$^2$ of body surface area, particularly 2 to 4 mg/m$^2$; cetuximab is advantageously administered in a dosage of about 200 to 400 mg/m$^2$, preferably about 250 mg/m$^2$.

With regard to the EGFR tyrosine kinase inhibitors, these are generally administered in a daily oral dosage of 100 to 500 mg, for example gefitinib in a dosage of about 250 mg and erlotinib in a dosage of about 150 mg.

With regard to the VEGF monoclonal antibody bevacizumab, this is generally administered in a dosage of about 1 to 10 mg/kg for example about 5 mg/kg.

With regard to the PDGF inhibitor imatinib, this is generally administered in a dosage of about 400 to 800 mg per day preferably about 400 mg per day.

With regard to the Raf inhibitor sorafenib, this is administered at a dose of 800 mg daily.

These dosages may be administered for example once, twice or more per course of treatment, which may be repeated for example every 7, 14, 21 or 28 days.

PKA/B Inhibitors and PKB Pathway Inhibitors

Another preferred class of signaling inhibitor for use in the combinations of the invention are PKA/B inhibitors and PKB pathway inhibitors.

PKB pathway inhibitors are those that inhibit the activation of PKB, the activity of the kinase itself or modulate downstream targets, blocking the proliferative and cell survival effects of the pathway. Target enzymes in the pathway include phosphatidyl inositol-3 kinase (PI3K), PKB itself, mammalian target of rapamycin (MTOR), PDK-1 and p70 S6 kinase and forkhead translocation factor. Several components of the PI 3-kinase/PKB/PTEN pathway are implicated in oncogenesis. In addition to growth factor receptor tyrosine kinases, integrin-dependent cell adhesion and G-protein coupled receptors activate PI 3-kinase both directly and indirectly through adaptor molecules. Functional loss of PTEN (the most commonly mutated tumour-suppressor gene in cancer after p53), oncogenic mutations in PI 3-kinase, amplification of PI 3-kinase and overexpression of PKB have been established in many malignancies. In addition, persistent signaling through the PI 3-kinase/PKB pathway by stimulation of the insulin-like growth factor receptor is a mechanism of resistance to epidermal growth factor receptor inhibitors.

The discovery of non-random, somatic mutations in the gene encoding p110α in a range of human tumours suggests an oncogenic role for the mutated PI 3-kinase enzyme (Samuels, et al., Science, 304 554, April 2004). Mutations in p110α have since been detected in the following human tumours: colon (32%), hepatocellular (36%) and endometroid and clear cell cancer (20%). p110α is now the most commonly mutated gene in breast tumours (25-40%). Forkhead family translocations often occur in acute leukemia.

The PI 3-kinase/PKB/PTEN pathway is thus an attractive target for cancer drug development since such agents would be expected to inhibit proliferation and surmount resistance to cytotoxic agents in cancer cells.

Examples of PKB pathway inhibitors include PI3K Inhibitors such as Semaphore, SF1126 and MTOR inhibitors such as Rapamycin Analogues. RAD 001 (everolimus) from Novartis is an orally available derivative of the compound rapamycin. The compound is a novel macrolide, which is being developed as an antiproliferative drug with applications as an immunosuppressant and anticancer agent. RAD001 exerts its activity on growth-factor dependent proliferation of cells through its high affinity for an intracellular receptor protein, FKBP-12. The resulting FKBP-12/RAD001 complex then binds with mTOR to inhibit downstream signaling events. The compound is currently in clinical development for a wide variety of oncology indications. CCI 779 (temsirolemus) from Wyeth Pharmaceuticals and AP23573 from Ariad Pharmaceuticals are also rapamycin analogues. AP23841 and AP23573 from Ariad Pharmaceutical also target mTOR. Calmodulin inhibitors from Harvard are forkhead translocation inhibitors. (Nature Reviews drug discovery, Exploiting the PI3K/AKT Pathway for Cancer Drug Discovery; Bryan T. Hennessy, Debra L. Smith, Prahlad T. Ram, Yiling Lu and Gordon B. Mills; December 2005, Volume 4; pages 988-1004).

Definitions: The term "PKA/B inhibitor" is used herein to define a compound which has protein kinase B (PKB) and/or protein kinase A (PKA) inhibiting or modulating activity ity, including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

The term "PKB pathway inhibitor" is used herein to define a compound which inhibits the activation of PKB, the activity of the kinase itself or modulate downstream targets, blocking the proliferative and cell survival effects of the pathway (including one or more of the target enzymes in the pathway as described herein, including phosphatidyl inositol-3 kinase (PI3K), PKB itself, mammalian target of rapamycin (MTOR), PDK-1 and p70 S6 kinase and forkhead translocation).

Technical background: KRX-0401 (Perifosine/NSC 639966) is a synthetic substituted heterocyclic alkylphosphocholine that acts primarily at the cell membrane targeting signal transduction pathways, including inhibition of PKB phosphorylation. KRX-0401 has been evaluated in phase 1 studies as a potential oral anticancer drug. Dose limiting toxicities included nausea, vomiting and fatigue. Gastrointestinal toxicities increased at higher doses. A phase II trial in refractory sarcoma is planned.

API-2/TCN is a small molecule inhibitor of PKB signaling pathway in tumour cells. Phase I and II clinical trials of API-2/TCN have been conducted on advanced tumours. API-2/TCN exhibited some side effects, which include hepatotoxicity, hypertriglyceridemia, thrombocytopenia, and hyperglycemia.

RX-0201 is being developed as an AKT protein kinase inhibitor for the treatment of solid tumours. In July 2004, a phase I trial was initiated in patients with advanced malignancies. Data from this showed RX-0201 inhibited overexpression of Akt and suppressed cancer growth in brain, breast, cervix, liver, lung, ovary, prostate and stomach tumours, and was well tolerated. By March 2005, US Orphan Drug status had been granted to RX-0201 for several solid tumour types.

Enzastaurin HCl (LY317615) suppresses angiogenesis and was advanced for clinical development based upon anti-angiogenic activity. It is described as a selective PKCβ inhibitor. It also has a direct anti-tumour effect, and suppresses GSK3β phosphorylation. It is currently being investigated for the treatment of glioma and non-Hodgkin's lymphoma.

SR-13668 is claimed to be an orally active specific AKT inhibitor that significantly inhibits phospho-AKT in breast cancer cells both in vitro and in vivo. In vivo assessment in mice showed no adverse effects at doses 10 times more than were needed for antitumour activity.

PX-316 is a D-3-deoxy-phosphatidyl-myo-inositol that binds to the PH domain of PKB, trapping it in the cytoplasm and thus preventing PKB activation. Anti-tumour activity was seen in early xenografts and was well tolerated.

Allosteric, selective inhibitors of PKB based on a 2,3-diphenylquinoxaline core or a 5,6-diphenylpyrazin-2(1H)-one core have been developed (Merck).

KRX-0401: In a Phase I weekly dosing study conducted in Europe, the recommended Phase II dose was 600/mg/week. Subsequent studies conducted in the U.S. have shown that much higher doses are well tolerated when the doses are divided and administered at 4 to 6 hour intervals. In addition, it has been shown that KRX-0401 has a very long half-life in the range of 100 hours. This makes the possibility of a relative non-toxic, intermittent dosing schedule very plausible.

A phase I trial of API-2 was conducted using a 5-day continuous infusion schedule. Dose levels ranged from 10 mg/sq m/day×5 days to 40 mg/sq m/day×5 days. Initially, courses were repeated every 3 to 4 weeks. As cumulative toxicity became manifested, the interval between courses was changed to every 6 weeks. Recommended schedule for Phase II studies is 20 mg/sq m/day for 5 days every 6 weeks. A Phase II trial of TCN-P was conducted in metastatic or recurrent squamous cell carcinoma of the cervix using a 5-day continuous infusion schedule. The starting dose was 35 mg/m$^2$×5 days and courses were repeated every 6 weeks.

Further PKB inhibitors include Perifosine from Keryx Biopharmaceuticals. Perifosine is an oral Akt inhibitor which exerts a marked cytotoxic effect on human tumour cell lines, and is currently being tested in several phase II trials for treatment of major human cancers. KRX-0401 (Perifosine/NSC 639966) has the structure:

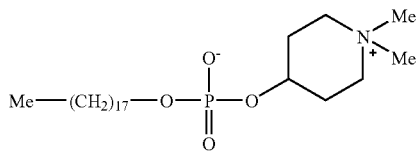

It can be prepared according to Aste Medica patent publication DE4222910 or Xenoport patent publication US2003171303.

API-2/TCN (Triciribine) has the structure:

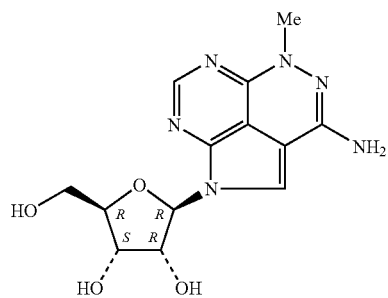

It can be prepared according to Bodor patent publication WO9200988 or Ribapharm patent publication WO2003061385.

Enzastaurin hydrochloride has the structure:

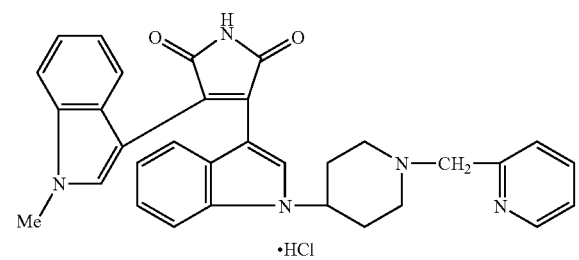 [SMILES: Cn1cc(C2=C(c3cn(C4CCN(Cc5ccccn5)CC4)c4ccccc34)C(=O)NC2=O)c2ccccc21 ; Cl]

It can be prepared according to Eli Lilly patent publication WO2004006928.

SR 13668 has the structure:

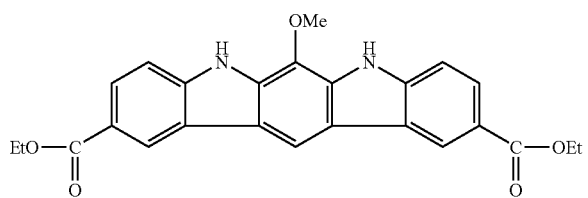 [SMILES: CCOC(=O)c1ccc2[nH]c3c(OC)c4[nH]c5ccc(C(=O)OCC)cc5c4cc3c2c1]

It can be prepared according to SRI International patent publication US2004043965.

NL-71-101 has the structure:

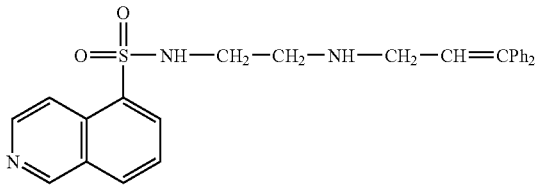

It can be prepared according to Biochemistry (2002), 41(32), 10304-10314 or Peptor patent publication WO2001091754.

DeveloGen (formerly Peptor) is investigating NL-71-101, a protein kinase B (PKB) inhibitor, for the potential treatment of cancer [466579], [539004]. At the beginning of 2003, the compound was undergoing lead optimization [495463]. By February 2004, the company was seeking to outlicense certain development rights to its protein kinase B program [523638].

In 2002, data were published showing that NL-71-101 inhibited the activity of PKB over PKA, PKG and PKC with IC50 values of 3.7, 9, 36 and 104 microM, respectively. NL-71-101 induced apoptosis in OVCAR-3 tumour cells, in which PKB is amplified at concentrations of 50 and 100 microM [466579]. This compound has the structure:

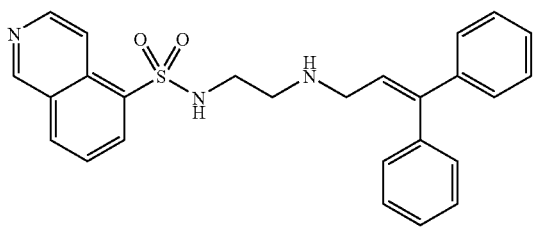 [SMILES: O=S(=O)(NCCNCC=C(c1ccccc1)c1ccccc1)c1cccc2cnccc12]

Specific embodiments: Embodiments contemplated include combinations in which the anti-cancer agent is a PKB inhibitor selected from one or more of the specific compounds described above.

14. CDK Inhibitors

Definition: The term "CDK inhibitor" as used herein refers to compounds that inhibit or modulate the activity of cyclin dependent kinases (CDK), including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Technical background: CDKs play a role in the regulation of the cell cycle, apoptosis, transcription, differentiation and CNS function. Therefore, CDK inhibitors may find application in the treatment of diseases in which there is a disorder of proliferation, apoptosis or differentiation such as cancer. In particular RB+ve tumours may be particularly sensitive to CDK inhibitors. RB−ve tumours may also be sensitive to CDK inhibitors.

Examples of CDK inhibitors which may be used in combinations according to the invention include seliciclib, alvocidib, 7-hydroxy-staurosporine, JNJ-7706621, BMS-387032 (a.k.a. SNS-032), PHA533533, PD332991, ZK-304709, and AZD-5438.

Seliciclib, which is the R isomer of roscovitine, and otherwise known as CYC 202, has the chemical name (2R)-2-[[9-(1-methylethyl)-6-[(phenylmethyl)-amino]-9H-purin-2-yl]amino]-1-butanol. It is being evaluated in clinical trials for the potential treatment of various cancers including lymphoid leukaemia, non-small-cell lung cancer, glomerulonephritis, mantle cell lymphoma, multiple myeloma, and breast cancer. Observed toxicities in clinical trials include nausea/vomiting and asthenia, skin rash and hypokalemia. Other toxicities included reversible renal impairment and transaminitis, and emesis.

Alvocidib, which is otherwise known as flavopiridol, HMR 1275 or L 86-8275, and which has the chemical name 5,7-dihydroxy-8-(4-N-methyl-2-hydroxypyridyl)-6'-chloroflavone, is being investigated in clinical trials for the potential treatment of various cancers including cancer of the esophagus, stomach, prostate, lung and colon, and also chronic lymphocytic leukaemia, and multiple myeloma, lymphoma; the most common toxicities observed were diarrhea, tumour pain, anemia, dyspnea and fatigue.

7-Hydroxystaurosporine, which is otherwise known as UCN-01 is being evaluated in clinical trials for the potential treatment of various cancers including chronic lymphocytic leukaemia, pancreas tumours and renal tumours; adverse events observed included nausea, headache and hyperglycemia.

JNJ-7706621, which has the chemical name N3-[4-(aminosulfonyl)-phenyl]-1-(2,6-difluorobenzoyl)-1H-1,2,4-triazole-3,5-diamine, is the subject of pre-clinical testing for the potential treatment of melanoma and prostate cancer. BMS-387032 which has the chemical name N-[5-[[[5-(1,1-dimethylethyl)-2-oxazolyl]-methyl]thio]-2-thiazolyl]-4-piperidinecarboxamide, has been evaluated in phase I studies as a potential anticancer drug for patients with metastatic solid tumours such as renal cell carcinomas, non-small-cell lung cancer, head and neck cancers and leiomyosarcoma The drug was well tolerated with transient neutropenia noted as the primary toxicity. Other side-effects included transient liver aminase elevations, gastrointestinal toxicity, nausea, vomiting, diarrhea and anorexia. PHA533533, which has the chemical name (αS)—N-(5-cyclopropyl-1H-pyrazol-3-yl)-α-methyl-4-(2-oxo-1-pyrrolidinyl)-benzene-acetamide, is the subject of pre-clinical testing for the potential treatment of various cancers such as tumours of the prostate, colon and ovary. PD332991, which has the chemical name 8-cyclohexyl-2-[[4-(4-methyl-1-piperazinyl)phenyl]amino]-pyrido[2,3-d]pyrimidin-7(8H)-one, is the subject of pre-clinical testing for the potential treatment of various cancers. Pre-clinical data suggests that it is a highly selective and potent CDK4 inhibitor, demonstrating marked tumour regression in vivo models.

ZK-304709 is an oral dual specificity CDK and VEGFR kinase inhibitor, described in PCT patent specification No. WO 02/096888, and is the subject of pre-clinical testing for the potential treatment of various cancers. AZD-5438 is a selective cyclin-dependent kinase (CDK) inhibitor, which is in pre-clinical development for the treatment of solid cancers. Seliciclib may be prepared for example as described in PCT patent specification No. WO 97/20842, or by processes analogous thereto. Alvocidib, may be prepared for example as described in U.S. Pat. No. 4,900,727 or by processes analogous thereto. 7-Hydroxystaurosporine may be prepared for example as described in U.S. Pat. No. 4,935,415, or by processes analogous thereto. JNJ-7706621 may be prepared for example as described in PCT patent specification No. WO 02/057240, or by processes analogous thereto. BMS-387032 may be prepared for example as described in PCT patent specification No. WO 01/44242, or by processes analogous thereto. PHA533533 may be prepared for example as described in U.S. Pat. No. 6,455,559, or by processes analogous thereto. PD332991, may be prepared for example as described in PCT patent specification No. WO 98/33798, or by processes analogous thereto. ZK-304709 may be prepared for example as described in PCT patent specification No. WO 02/096888, or by processes analogous thereto.

Preferences and specific embodiments: Embodiments contemplated include combinations in which the anti-cancer agent is a CDK inhibitor selected from one or more of the specific compounds described above. Thus, preferred CDK inhibitors for use in combinations according to the invention include seliciclib, alvocidib, 7-hydroxystaurosporine, JNJ-7706621, BMS-387032, PHA533533, PD332991 and ZK-304709. Particular CDK inhibitors for use in combinations according to the invention include seliciclib, alvocidib, 7-hydroxystaurosporine, JNJ-7706621, BMS-387032, PHA533533, PD332991 and ZK-304709.

Posology: The CDK inhibitor may be administered for example in a daily dosage of for example 0.5 to 2500 mg, more preferably 10 to 1000 mg, or alternatively 0.001 to 300 mg/kg, more preferably 0.01 to 100 mg/kg, particularly for seliciclib, in a dosage of 10 to 50 mg; for alvocidib, in a dosage in accordance with the above-mentioned U.S. Pat. No. 4,900,727; for 7-hydroxystaurosporine in a dosage of 0.01 to 20 mg/kg; for JNJ-7706621 in a dosage of 0.001 to 300 mg/kg; for BMS-387032 in a dosage of 0.001 to 100 mg/kg more preferably 0.01 to 50 mg/kg, and most preferably 0.01 to 20 mg/kg; for PHA533533 in a dosage of 10 to 2500 mg; for PD332991 in a dosage of 1 to 100 mg/kg; and for ZK-304709 in a dosage of 0.5 to 1000 mg preferably 50 to 200 mg.

These dosages may be administered for example once, twice or more per course of treatment, which may be repeated for example every 7, 14, 21 or 28 days.

15. COX-2 Inhibitors

Definition: The term "COX-2 inhibitor" is used herein to define compounds which inhibit or modulate the activity of the cyclo-oxygenase-2 (COX-2) enzyme, including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Biological activity: The COX-2 inhibitors working via one or more pharmacological actions as described herein have been identified as suitable anti-cancer agents.

Technical background: Recently, research in cancer chemotherapy has focused on the role of the cyclo-oxygenase-2 (COX-2) enzyme in the aetiology of cancer. Epidemiological studies have shown that people who regularly take non-steroidal anti-inflammatory drugs (NSAIDs), for example aspirin and ibuprofen to treat conditions such as arthritis, have lower rates of colorectal polyps, colorectal cancer, and death due to colorectal cancer. NSAIDs block cyclooxygenase enzymes, which are produced by the body in inflammatory processes, and which are also produced by pre-cancerous tissues. For example in colon cancers, a dramatic increase of COX-2 levels is observed. One of the key factors for tumour growth is the supply of blood to support its increased size. Many tumours can harness chemical pathways that prompt the body to create a web of new blood vessels around the cancer, a process called angiogenesis. COX-2 is believed to have a role in this process. It has therefore been concluded that inhibition of COX-2 may be effective for treating cancer, and COX-2 inhibitors have been developed for this purpose. For example celecoxib, which has the chemical name 4-[5-(4-methylphenyl)-3-(trifluoromethyl)-1H-pyrazol-1-yl]benzenesulfonamide, is a selective COX-2 inhibitor that is being investigated for the treatment of various cancers including bladder and esophageal cancer, renal cell carcinoma, cervical cancer, breast cancer, pancreatic cancer non-Hodgkin's lymphoma and non-small cell lung cancer.

Posology: The COX-2 inhibitor (for example celecoxib) can be administered in a dosage such as 100 to 200 mg e.g. daily.

These dosages may also be administered for example once, twice or more per course of treatment, which may be repeated for example every 7, 14, 21 or 28 days.

Problems: The most common adverse effects are headache, abdominal pain, dyspepsia, diarrhea, nausea, flatulence and insomnia. There is a need to provide a means for the use of lower dosages of COX-2 inhibitors to reduce the potential for adverse toxic side effects to the patient.

Preferences and specific embodiments: In one embodiment the COX-2 inhibitor is celecoxib. Celecoxib is commercially available for example from Pfizer Inc under the trade name Celebrex, or may be prepared for example as described in PCT patent specification No. WO 95/15316, or by processes analogous thereto.

Two other commercially available COX-2 inhibitors are Arcoxia (etoricoxib from Merck) and Novartis Cox-2 inhibitor lumiracoxib (Prexige).

16. HDAC Inhibitors

Definition: The term "HDAC inhibitor" is used herein to define compounds which inhibit or modulate the activity of histone deacetylases (HDAC), including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Biological activity: The HDAC inhibitors working via one or more pharmacological actions as described herein have been identified as suitable anti-cancer agents.

Technical background: Reversible acetylation of histones is a major regulator of gene expression that acts by altering accessibility of transcription factors to DNA. In normal cells, histone deacetylase (HDAC) and histone acetyltrasferase (HDA) together control the level of acetylation of histones to maintain a balance. Inhibition of HDA results in the accumulation of hyperacetylated histones, which results in a variety of cellular responses. Inhibitors of HDA (HDAI) have been studied for their therapeutic effects on cancer cells. Recent developments in the field of HDAI research have provided active compounds, that are suitable for treating tumours.

Accruing evidence suggests that HDAI are more efficacious when used in combination with other chemotherapeutic agents. There are both synergistic and additive advantages, both for efficacy and safety. Therapeutic effects of combinations of chemotherapeutic agents with HDAI can result in lower safe dosage ranges of each component in the combination.

The study of inhibitors of histone deacetylases (HDAC) indicate that these enzymes play an important role in cell proliferation and differentiation. The inhibitor Trichostatin A (TSA) causes cell cycle arrest at both G1 and G2 phases, reverts the transformed phenotype of different cell lines, and induces differentiation of Friend leukaemia cells and others. TSA (and suberoylanilide hydroxamic acid SAHA) have been reported to inhibit cell growth, induce terminal differentiation, and prevent the formation of tumours in mice (Finnin et al., Nature, 401:188-193, 1999).

Trichostatin A has also been reported to be useful in the treatment of fibrosis, e.g. liver fibrosis and liver chirrhosis. (Geerts et al., European Patent Application EPO 827 742, published 11 Mar. 1998).

Preferences and specific embodiments: Preferred HDAC inhibitors for use in accordance with the invention are selected from TSA, SAHA, JNJ-16241199, LAQ-824, MGCD-0103 and PXD-101 (referred to above).

Thus, synthetic inhibitors of histone deacetylases (HDAC) which are suitable for use in the present invention include JNJ-16241199 from Johnson and Johnson Inc, LAQ-824 from Novartis, MGCD-0103 from MethylGene, and PXD-101 from Prolifix.

JNJ-16241199 has the following structure:

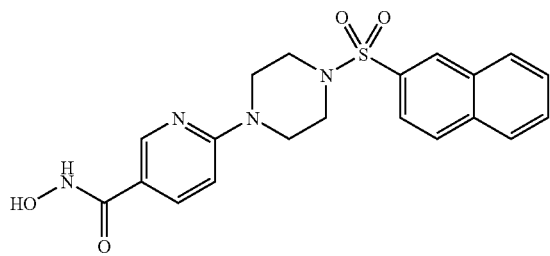 [SMILES: O=C(NO)c1ccc(N2CCN(S(=O)(=O)c3ccc4ccccc4c3)CC2)nc1]

MGCD-0103 has the structure:

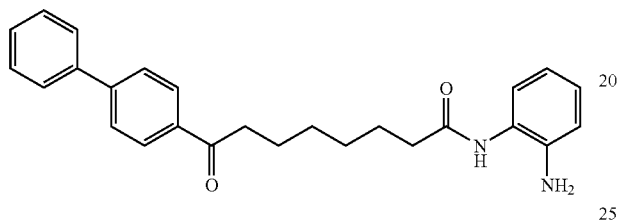

LAQ-824 has the structure:

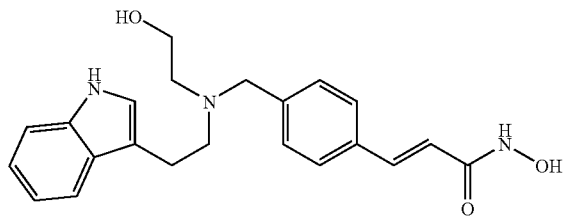 [SMILES: O=C(/C=C/c1ccc(CN(CCO)CCc2c[nH]c3ccccc23)cc1)NO]

Other inhibitors of histone deacetylases (HDAC) which are suitable for use in the present invention include, but are not limited to, the peptide chlamydocin, and A-173, also from Abbott Laboratories.

A-173 is a succinimide macrocyclic compound with the following structure:

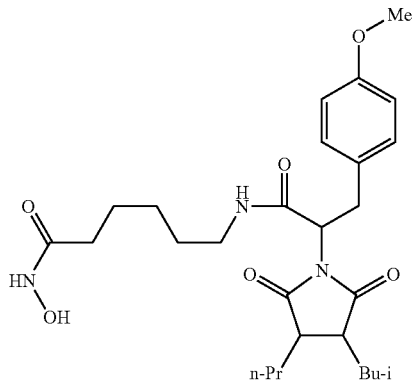

Posology: In general, for HDAC inhibitors it is contemplated that a therapeutically effective amount would be from 0.005 mg/kg to 100 mg/kg body weight, and in particular from 0.005 mg/kg to 10 mg/kg body weight. It may be appropriate to administer the required dose as two, three, four or more sub-doses at appropriate intervals throughout the day. Said sub-doses may be formulated as unit dosage forms, for example, containing 0.5 to 500 mg, and in particular 10 mg to 500 mg of active ingredient per unit dosage form.

17. Selective Immunoresponse Modulators

Selective immunoresponse modulators include Lenalidomide and Thalidomide.

Lenalidomide (Revlimid) is an oral thalidomide derivative developed by Celgene which is a potent inhibitor of TNF-alpha and interleukin-1 beta which is being developed for the treatment of 5q-myelodysplastic syndrome multiple myeloma, chronic lymphocytic leukaemia gliomas, cutaneous T-cell lymphoma and epithelial ovarian cancer.

Lenalidomide (3-(4-amino-1-oxoisoindolin-2-yl)piperidine-2,6-dione) has the following structure:

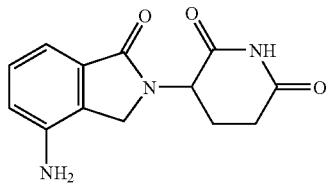 [SMILES: Nc1cccc2c1CN(C1CCC(=O)NC1=O)C2=O]

Thalidomide is a sedative and anti-emetic that became widely recognized as a result of reports of its teratogenic effects, most notably limb deformities in up to 12,000 children born to women who had received thalidomide in Europe and Canada during the 1960s. Celgene has developed and launched thalidomide as an oral TNF-alpha inhibitor (Sold to Pharmion). Extensive clinical evidence has accumulated with regard to the potential antitumor activity of thalidomide in several types of neoplasias, with notable activity in relapsed/refractory multiple myeloma, Waldenstrom's macroglobulinemia (WM) and myelodysplastic syndromes (MDS). There is also evidence of biological activity in acute myeloid leukemia, myelofibrosis with myeloid metaplasia, renal cell carcinoma, malignant gliomas, prostate cancer, Kaposi's sarcoma and colorectal carcinoma.

Thalidomide (1,3-dioxo-2-(2,6-dioxopiperidin-3-yl)isoindoline) has the following structure:

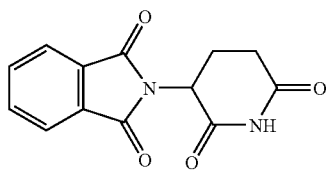 [SMILES: O=C1CCC(N2C(=O)c3ccccc3C2=O)C(=O)N1]

Posology: Thalidomide may be advantageously administered in dosages of 100 to 800 mg/day continuously as tolerated. Lenalidomide may be advantageously administered in 5- to 40-mg doses continuously as tolerated.

18. DNA Methylase Inhibitors

Definition: The term "DNA methylase inhibitor" or "DNA methyltransferase inhibitor" as used herein refers to a compound which directly or indirectly perturbs, disrupts, blocks, modulates or inhibits the methylation of DNA, including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above. They are also referred to as "hypomethylating agents".

Biological activity: The DNA methylase inhibitors working via one or more pharmacological actions as described herein have been identified as suitable anti-cancer agents.

Technical background: One target for cancer chemotherapy is DNA synthesis, which may depend on appropriate methylation of tumour DNA. Compounds which directly or indirectly perturb, disrupt, block, modulate or inhibit the methylation of DNA may therefore be useful anticancer drugs.

The DNA methylase inhibitor temozolomide is used for the treatment of glioblastoma multiforme, and first-line treatment of patients with advanced metastatic malignant melanoma (such as first-line treatment of patients with advanced metastatic malignant melanoma) and has also being investigated and used for the treatment of malignant glioma at first relapse. This compound undergoes rapid chemical conversion at physiological pH to the active compound, monomethyl triazeno imidazole carboxamide (MTIC) which is responsible for the methylation of DNA at the $O^6$ position of guanine residues (which appears to lead to a suppression in expression of DNA methyltransferase and so produce hypomethylation).

Problems: The most common side effects associated with temozolomide therapy are nausea, vomiting, headache, fatigue, thrombocytopenia and constipation. There is a need to increase the inhibitory efficacy of DNA\methylase inhibitors and to provide a means for the use of lower dosages of signaling inhibitors to reduce the potential for adverse toxic side effects to the patient.

Preferences and specific embodiments: In one embodiment, the DNA methylase inhibitor is temozolomide (3,4-dihydro-3-methyl-4-oxoimidazo[5,1-d]-as-tetrazine-8-carboxamide). Temozolomide is commercially available for example from Schering Corporation under the trade name Temodar, or may be prepared for example as described in German patent specification No. 3231255, or by processes analogous thereto.

A further DNA methyltransferase inhibitor for use in the combinations of the invention is Decitabine (a.k.a. Dacogen) having the structure shown below:

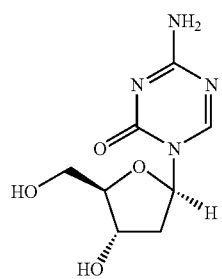 [SMILES: Nc1ncn([C@H]2C[C@H](O)[C@@H](CO)O2)c(=O)n1]

SuperGen Inc and MGI Pharma Inc have developed decitabine (Dacogen), an inhibitor of DNA methyltransferase, preventing methylation of cytosine residues on DNA and leading to hypomethylation of gene promoters, thereby reactivating silenced genes. Decitabine/Dacogen is cytotoxic to a broad range of malignant cells in vitro. It shows significant activity against acute myeloid leukemia (AML), chronic myeloid leukemia (CML) and myelodysplastic syndromes (MDS). Decitabine/Dacogen is indicated for the treatment of myelodysplastic syndromes (MDS) and secondary MDS (including chronic myelomonocytic leukemia, refractory anemia, refractory anemia with ringed sideroblasts, refractory anemia with excess blasts and refractory anemia with excess blasts in transformation).

Decitabine/Dacogen is an analog of deoxycytidine (beta-D-anomer of 2'-deoxy-5-azacytidine). It differs from deoxycytidine by substitution at position 5 of the pyrimidine ring with nitrogen. Decitabine contains deoxyribose, in contrast to the related analog, Pharmion Corp's 5-azacytidine (Vidaza), which contains a ribose sugar. Decitabine is, therefore, a deoxynucleoside and is incorporated into DNA, but not RNA, in contrast to 5-azacytidine which is incorporated into RNA. Decitabine and 5-azacytidine differ from other pyrimidine analogs, such as cytosine arabinoside and gemcitabine, by modification at position 5 of the pyrimidine ring. This distinctive feature, which is not present in these latter drugs, is responsible for inhibition of DNA methyltransferase. Pseudoisocytidine and 5-fluoro-2'-deoxycytidine, further analogs with modifications of the 5 position of the pyrimidine ring, also inhibit demethylation.

Decitabine/Dacogen is dosed at 15 mg/m2 over a three hour period every 8 hours for 3 days every 6 weeks as a cycle of therapy or on a daily dosing schedule with a one hour infusion usually delivered at 20 mg/m2 per day either for one week or two weeks every 6 weeks as a cycle At toxic doses decitabine/Dacogen produces leukopenia, thrombocytopenia and weight loss. The major toxicity of decitabine is myelosuppression, which is proportional to dose and duration of therapy. The effects are pronounced at high doses (>200 mg/m2/day), and myelosuppression is enhanced by concomitant administration of other cytotoxic drugs. Neutropenic infection and other complications of myelosuppression have proved fatal. Non-hematological side effects include nausea, vomiting, mucositis and alopecia.

Decitabine/Dacogen and other analogues thereof can be made as outlined in U.S. Pat. No. 3,432,549 and further discussed on WO 006/017278 and WO 2006/037024 to SuperGen Inc.

A further DNA methyltransferase inhibitor for use in the combinations of the invention is azacytidine (a.k.a. 5-azacitidine, 5-azacytidine or Vidaza) a sc administered hypomethylating agent and DNA methyltransferase inhibitor. It is indicated for the treatment of all myelodysplastic syndrome (MDS) subtypes, including refractory anemia (RA) or RA with ringed sideroblasts, RA with excess blasts, RA with excess blasts in transformation and chronic myelomonocytic leukemia.

5-azacitidine (Vidaza) can be administered twice-daily subcutaneously or via the iv route administration for MDS treatment.

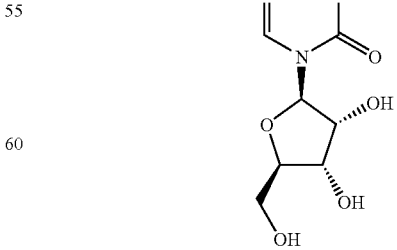

It can be prepared as described in DE 1922702, GB 1227691 and FR 2008048 from Ceskoslovenska Akademie Ved and WO 2004082618, WO 2004082619 and WO 2004082822 from Pharmion and process analogous thereto.

Posology: The DNA methylating agent (for example temozolomide) can be administered in a dosage such as 0.5 to 2.5 mg per square meter (mg/m$^2$) of body surface area, particularly about 1.3 mg/m$^2$. These dosages may be administered for example once, twice or more per course of treatment, which may be repeated for example every 7, 14, 21 or 28 days.

19. Proteasome Inhibitors

Definition: The term "proteasome inhibitor" as used herein refers to compounds which directly or indirectly perturb, disrupt, block, modulate or inhibit the half-life of many short-lived biological processes, such as those involved in the cell cycle. The term therefore embraces compounds which block the action of proteasomes (large protein complexes that are involved in the turnover of other cellular proteins). The term also embraces the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Biological activity: The proteasome inhibitors working via one or more pharmacological actions as described herein have been identified as suitable anti-cancer agents.

Technical background: Another class of anticancer agents are the proteasome inhibitors. Proteasomes control the half-life of many short-lived biological processes, such as those involved in the cell cycle. Therefore, proteasome malfunction can lead to abnormal regulation of the cell cycle and uncontrolled cell growth.

The cell cycle is controlled by both positive and negative signals. In a normal cell, proteasomes break down proteins that inhibit the cell cycle, such as cyclin-dependent kinase inhibitors. Inhibition of proteasome function causes cell cycle arrest and cell death. Tumour cells are more susceptible to these effects than normal cells, in part because they divide more rapidly and in part because many of their normal regulatory pathways are disrupted. The mechanism for the differential response of normal and cancer cells to proteasome inhibition is not fully understood. Overall, cancer cells are more susceptible to proteasome inhibitors and, as a result, these inhibitors may be an effective treatment for certain cancers.

One such proteasome inhibitor is bortezimib, which has the chemical name [(1R)-3-methyl-1-[[(2S)-1-oxo-3-phenyl-2-[(pyrazinylcarbonyl)amino]propyl]amino]butyl]-boronic acid. Bortezimib specifically interacts with a key amino acid, namely threonine, within the catalytic site of the proteasome. Bortezimib is being used for the treatment of multiple myeloma and also for a number of other cancers, including leukemia and lymphoma, and prostate, pancreatic and colorectal carcinoma. In addition Velcade is useful for the treatment of non-Hodgkin's lymphoma.

Problems: The most common side effects with bortezimib are nausea, tiredness, diarrhea, constipation, decreased platelet blood count, fever, vomiting, and decreased appetite. Bortezimib can also cause peripheral neuropathy.

Thus, there is a need to provide a means for the use of lower dosages to reduce the potential of adverse toxic side effects to the patient.

Preferences and specific embodiments: Preferred proteasome inhibitors for use in accordance with the invention include bortezimib. Bortezimib is commercially available for example from Millennium Pharmaceuticals Inc under the trade name Velcade, or may be prepared for example as described in PCT patent specification No. WO 96/13266, or by processes analogous thereto.

Posology: The proteasome inhibitor (such as bortezimib) can be administered in a dosage such as 100 to 200 mg/m$^2$. These dosages may be administered for example once, twice or more per course of treatment, which may be repeated for example every 7, 14, 21 or 28 days.

The antibiotic bleomycin may also be used as a cytotoxic agent as an anti-cancer agent according to the invention.

20. Aurora Inhibitors

In one embodiment of the invention, the ancillary compound is an Aurora kinase inhibitor or modulator. Such Aurora inhibitors or modulators may be selected from the various Aurora inhibitors described herein and preferred ancillary Aurora inhibitors are discussed in more detail below.

Definition: The term "Aurora kinase inhibitor" (or simply "Aurora inhibitor") as used herein refers to compounds that inhibit or modulate the activity of any of the Aurora kinase isoforms A, B and/or C as described herein, including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Technical Background: Aurora kinases play a role in regulating the cell cycle and in particular in the process of cellular mitosis (they have an important role in the mitotic phase of the cell cycle). Therefore, Aurora kinase inhibitors may find application in the treatment of diseases in which there is a disorder of proliferation, cell division, differentiation such as cancer. In particular tumours with mitotic and or spindle defects may be particularly sensitive to CDK inhibitors.

Inhibition of the Aurora kinases has been shown to substantially disrupt the mitotic process leading to early mitotic effects from inhibition of Aurora A and late abnormalities of cytokinesis by inhibition of Aurora B. Combining Aurora kinase inhibitors with agents that activate, interfere with or modulate the mitotic or cell cycle checkpoint sensitises cells to the cytotoxic effects and a beneficial combination effect is observed (Anand S, Penrhyn-Lowe S, Venkitaraman A R. Cancer Cell. 2003 January; 3(1):51-62). In this context a combination of Aurora kinase inhibitors with the taxanes, epothilones or *vinca* alkaloids are beneficial. Particular taxanes, epothilones and *vinca* alkaloids are described herein.

Examples of auxiliary Aurora kinase inhibitors include AZD1152, MK0457 (VX680), PHA-739358, MLN-8054, MP-235 in particular MK0457 (VX680), PHA-739358, MLN-8054, MP-235. AZD1152 is undergoing clinical evaluation. AZD1152 is a pro-drug which is converted rapidly to the active moiety AZD1152-HQPA in the plasma (AZD-1152 hydroxy-QPA, structure shown below). In early studies in patients with advanced solid malignancies, AZD1152 given in a 2 hr infusion weekly, induces p53 independent cellular multinucleation and polyploidy, resulting in apoptosis. These early studies indicate neutropenia is the dose-limiting toxicology (ASCO 2006).

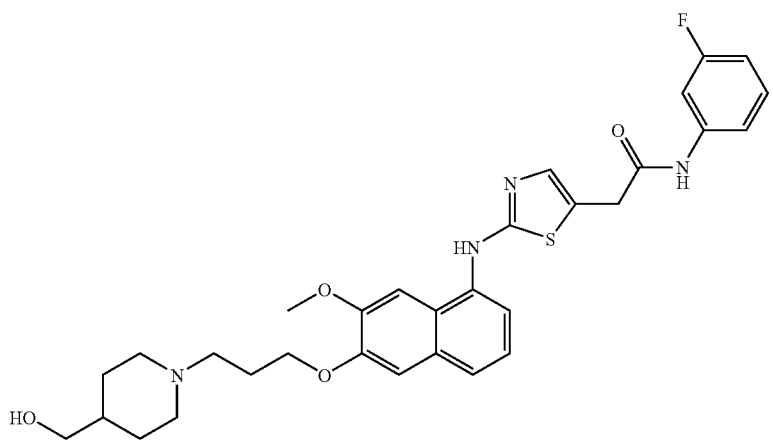 [SMILES: COc1cc2c(Nc3ncc(CC(=O)Nc4cccc(F)c4)s3)cccc2cc1OCCCN1CCC(CO)CC1]

AZD1152 and AZD1152-HQPA can be synthesized as described in WO 02/00649 or by processes analogous thereto.

MK0457 (VX-680) is undergoing clinical evaluation. MK0457 has been given to patients with refractory malignancies in a continuous 5 day infusion every 28 days. These early studies indicate neutropenia is the dose-limiting toxicology (ASCO 2006).

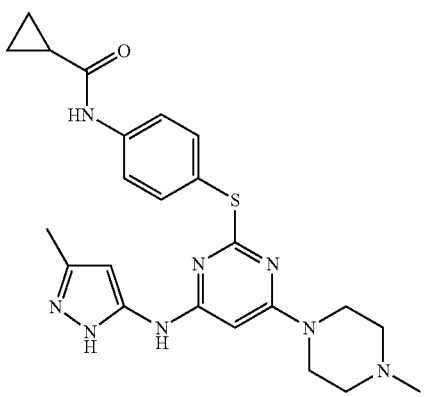 [SMILES: Cc1cc(Nc2cc(N3CCN(C)CC3)nc(Sc3ccc(NC(=O)C4CC4)cc3)n2)[nH]n1]

MK0457 can be synthesised as described in Harrington et al, *Nat Med.* 2004 March; 10(3):262-7 and WO 02/057259, WO 02/059111, WO 02/059112, WO 02/062789, WO 02/068415, WO 02/066461, WO 02/050065, WO 02/050066 and in particular WO 2004/000833, and by processes analogous thereto.

PHA-739358, the structure of which is shown below, is currently being evaluated by Nerviano Medical Sciences Srl in a multicenter phase 1 dose escalation clinical trials.

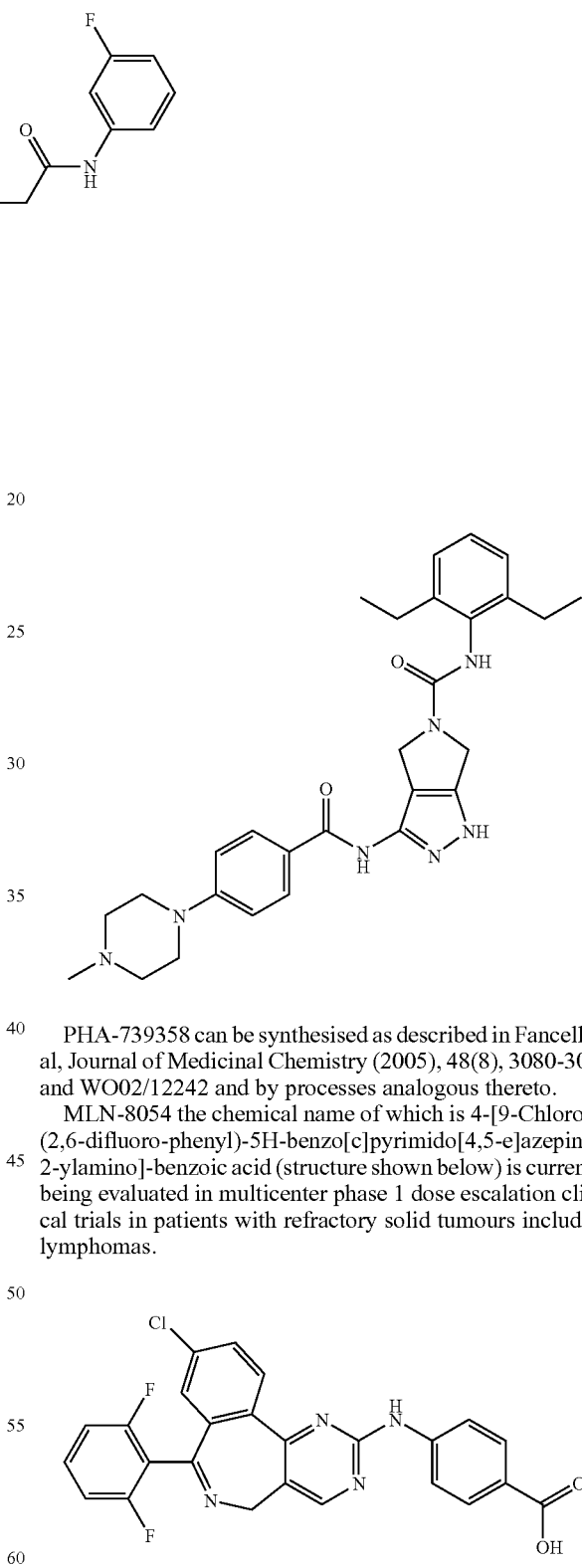

PHA-739358 can be synthesised as described in Fancelli et al, Journal of Medicinal Chemistry (2005), 48(8), 3080-3084 and WO02/12242 and by processes analogous thereto.

MLN-8054 the chemical name of which is 4-[9-Chloro-7-(2,6-difluoro-phenyl)-5H-benzo[c]pyrimido[4,5-e]azepin-2-ylamino]-benzoic acid (structure shown below) is currently being evaluated in multicenter phase 1 dose escalation clinical trials in patients with refractory solid tumours including lymphomas.

MLN-8054 can be synthesised as described in WO 2005/111039, and by processes analogous thereto.

SuperGen, following the acquisition of Montigen in April 2006, is investigating a series of small molecule Aurora-2 kinase inhibitors that induce apoptosis and inhibit cell division, including MP-235 (HPK-62) (4-(6,7-Dimethoxy-9H-1, 3,9-triaza-fluoren-4-yl)-piperazine-1-carbothioic acid [4-(pyrimidin-2-ylsulfamoyl)-phenyl]-amide, structure shown), for the potential treatment of various cancers, including pancreatic cancer. MP-235 can be synthesised as described in WO 2005/037825 and by processes analogous thereto

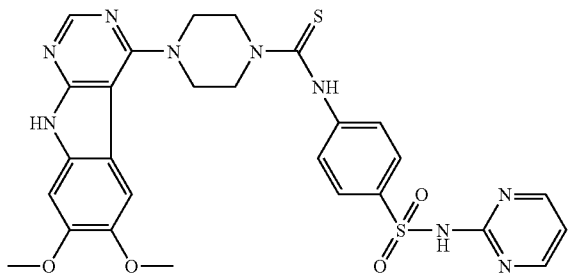 [SMILES: COc1cc2[nH]c3ncnc(N4CCN(C(=S)Nc5ccc(S(=O)(=O)Nc6ncccn6)cc5)CC4)c3c2cc1OC]

Further Aurora compounds include those described herein, including an additional compound of formula (I'), a further compound of the formula (I") and also includes those described in Formula (I) of WO2005/002552 (PCT/GB2004/002824). WO 2005/002552 is incorporated herein by reference and relates to compounds of Formula (I) as laid out therein.

21. Hsp90 Inhibitors

In one embodiment of the invention, the ancillary agent is an inhibitor of Hsp90.

Preferred Hsp90 inhibitors for use as ancillary agents in the combinations of the invention are compounds of formula (I) as defined herein. However, Hsp90 inhibitors for use in the combinations of the invention also include the ancillary Hsp90 inhibitors described in more detail below that have Hsp90 inhibiting or modulating activity. Thus, the combinations of the present invention may comprise (or consist essentially of) two or more compounds of formula (I) as defined herein.

In addition to the Hsp90 inhibitors of formula I herein, the combinations of the present invention may include one or more ancillary Hsp90 inhibitors or modulators. Such ancillary Hsp90 inhibitors or modulators may be selected from the various Hsp90 inhibitors described herein and preferred ancillary Hsp90 inhibitors are discussed in more detail below.

Definition: The term Hsp90 inhibitor as used herein refers to compounds that inhibit or modulate the activity of Heat Shock Protein 90 as described herein.

The term "ancillary Hsp90 inhibitor" as used herein refers to compounds that inhibit or modulate the activity of Heat Shock Protein 90 and which does not conform to the structure of formula (I) as defined herein, including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Technical Background: In response to cellular stresses including heat, toxins, radiation, infection, inflammation, and oxidants, all cells produce a common set of heat shock proteins (Hsps) (Macario & de Macario 2000). Most heat shock proteins act as molecular chaperones. Chaperones bind and stabilize proteins at intermediate stages of folding and allow proteins to fold to their functional states. Hsp90 is the most abundant cytosolic Hsp under normal conditions. There are two human isoforms of Hsp90, a major form Hsp90α and minor form Hsp90β. Hsp90 binds proteins at a late stage of folding and is distinguished from other Hsps in that most of its protein substrates are involved in signal transduction. It has been shown that ATP bound at the N-terminal pocket of Hsp90 is hydrolysed. This ATPase activity results in a conformational change in Hsp90 that is required to enable conformational changes in the client protein.

Activation of Hsp90 is further regulated through interactions with a variety of other chaperone proteins and can be isolated in complex with other chaperones including Hsp70, Hip, Hop, p23, and p50cdc37. Many other co-chaperone proteins have also been demonstrated to bind Hsp90. There is some evidence that Hsp90 is found primarily within "activated" multichaperone complexes in the tumour cells as opposed to "latent" complexes in normal cells.

Increased genetic instability associated with the cancer phenotype leads to an increase in the production of non-native or mutant proteins. The ubiquitin pathway also serves to protect the cell from non-native or misfolded proteins, by targeting these proteins for proteasomal degradation. Mutant proteins are by their nature not native and therefore have the potential to show structural instability and an increased requirement for the chaperone system. (Giannini et al., Mol Cell Biol. 2004; 24(13):5667-76).

The number of reported Hsp90 client proteins now exceeds 100. Since many of its client proteins are involved in cell signalling proliferation and survival, Hsp90 has received major interest as an oncology target. Hsp90 protein kinase client proteins implicated in cell proliferation and survival include the following; Cellular Src (c-Src), ErbB2 (Her2/neu), Polo-like kinases (Plks), Akt (PKB), c-Raf, B-RAF, Mek, epidermal growth factor receptor (EGFR), FMS-like tyrosine kinase 3 (FLT3), c-met, Cdk1, Cdk2, Cdk4, and Cdk6, Wee-1, Mutant p53, Hypoxia inducible factor-1a (HIF-1a)

Examples of Hsp90 inhibitors include herbimycin, geldanamycin (GA), 17-AAG e.g. Kos-953 and CNF-1010, 17-DMAG (Kos-1022), CNF-2024 (an oral purine), and IPI-504, in particular 17-AAG e.g. Kos-953 and CNF-1010, 17-DMAG (Kos-1022), CNF-2024, and IPI-504. Preferred compounds are geldanamycin analogs such as 17-AAG e.g. Kos-953 and CNF-1010, 17-DMAG (Kos-1022), and IPI-504.

Ansamycin antibiotics herbimycin, geldanamycin (GA) and 17-allylamino-17-desmethoxygeldanamycin (17-AAG) are ATP binding site inhibitors that block the binding of ATP and prevent conversion to the mature complex (Grenert et. al., 1997. J Biol Chem., 272:23834-23850). Despite Hsp90 being ubiquitously expressed, GA and its analogues have a higher binding affinity for Hsp90 derived from tumour vs. normal cell lines (Kamal et. al., Nature 2003; 425: 407-410). GA also shows more potent cytotoxic activity in tumour cells and is sequestered at higher concentrations within tumours in xenograft mouse models (Brazidec J. Med. Chem. 2004, 47, 3865-3873). Furthermore the ATP-ase activity of Hsp90 is elevated in cancer cells and is an indication of the increased level of stress in these cells. Hsp90 gene amplification has also been reported to occur in the later stages of cancer (Jolly and Morimoto JNCI Vol. 92, No. 19, 1564-1572, 2000).

17-AAG (NSC-330507, 17-allylaminogeldanamycin) is an injectable semisynthetic derivative of geldanamycin and a polyketide inhibitor of Hsp90 identified at the University of Maryland under development by Kosan Biosciences, in collaboration with the National Cancer Institute (NCI) and the UK Institute of Cancer Research, for the potential treatment of cancer. Studies of 17-AAG have been initiated in melanoma, multiple myeloma, non-Hodgkin's lymphoma (NHL)

and Hodgkin's lymphoma (HL) and as a combination therapy with imatinib (qv) for chronic myelogenous leukemia (CML).

The structure of 17-AAG is outlined below. It can be prepared as described in WO 02/36574 and processes analogous those described therein.

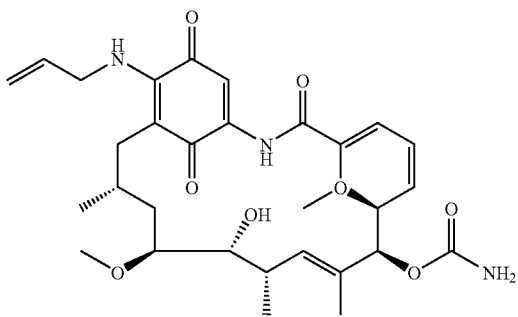

KOS-953 is a 17-AAG formulation developed by Kosan that replaces the DMSO-egg lecithin vehicle used in the original formulation, with the aim of improving patient tolerability and providing greater stability. This can be prepared as described in WO 2005/110398 and processes analogous those described therein.

Conforma is developing CNF-1010, an organic solvent-free lipid-based formulation of 17-AAG (qv) for the potential iv treatment of cancer. This can be prepared as described in WO 03/026571, WO 02/069900 and WO 2006/050333 and processes analogous those described therein. An oral formulation of 17-AAG is described by Conforma in U.S. 2006/0067953.

17-DMAG (17-dimethylaminoethylamino-17-demethoxygeldanamycin hydrochloride, NSC-707545; structure shown) is an analog of 17-AAG (qv). It is a water-soluble geldanamycin derivative and it is being investigated for advanced solid tumors. Kosan, under license from the National Cancer Institute (NCI), is developing an iv formulation of KOS-1022 (17-DMAG), for the potential treatment of solid tumors. Kosan is also developing an oral formulation of KOS-1022 (qv) for the same indication.

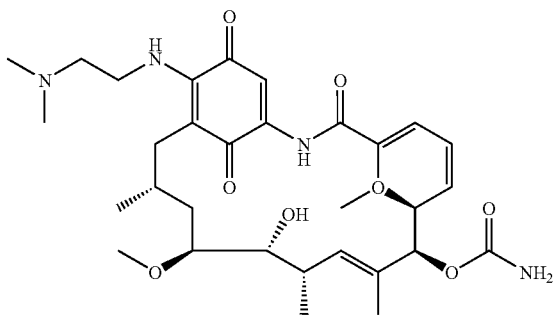

It can be prepared as described in WO 03/013430 and processes analogous to those described therein.

Infinity is developing the Hsp90 inhibitor IPI-504, a further analog of 17-AAG (qv) that is soluble in aqueous formulations for iv administration, for the potential treatment of cancer. Infinity started studies of IPI-504 in multiple myeloma (MM), and gastrointestinal stromal tumors (GIST), and the compound has potential for other haematological cancers and solid tumors.

The structure of IPI-504, a reduced form of 17-AAG called 18,21-didehydro-17-demethoxy-18,21-dideoxo-18,21-dihydroxy-17-(2-propenylamino)-geldanamycin monohydrochloride, is shown below. It can be prepared as described in WO 2005/063714 and processes analogous those described therein.

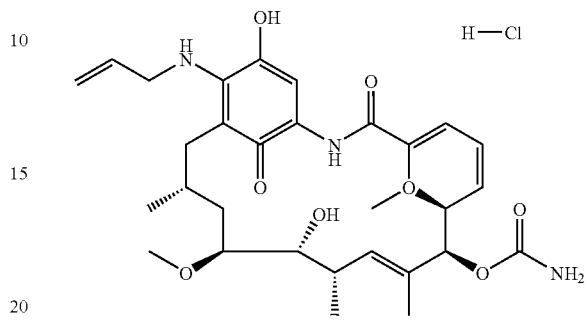

Conforma Therapeutics is developing CNF-2024, a synthetic oral Hsp 90 inhibitor, for the potential treatment of cancer. CNF-2024 is an oral purine analogue.

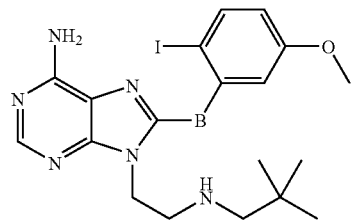

It can be prepared as described in J Med Chem (2006) 49: 817-828.

22. Checkpoint Targeting Agents

The cell proliferation cycle is a complex process during which the cell first replicates its chromosomes and then undergoes cell division or cytokinesis. At various stages of the cycle, mechanisms exist to prevent further progression through the cycle until all appropriate events have occurred. This ensures the integrity of the DNA of the cell as it progresses through the cycle in the required sequential manner. One such checkpoint is known to occur in mitosis. This is variously referred to as the mitotic or spindle checkpoint. Cells are held at this checkpoint until all chromosomes are appropriately attached to the mitotic spindle via their centrosomes. Defects in this checkpoint lead to either aneuploid phenotypes, typical of cancer cells or an imbalance of chromosomes in daughter cells. Some cancer therapies are known to act by disruption of this checkpoint causing chromosome mis-alignment or premature cytokinesis leading to activation of a checkpoint that results in preferential death of the tumour cell. For example the taxanes and epothilones are classes of agents which cause stabilisation of spindle microtubules preventing the normal spindle contraction process. The *vinca* alkaloids are another class of agents which act to prevent spindle formation via an action on tubulin the principal protein in the microtubules. Agents which cause DNA damage or disrupt DNA replication including platinum compounds and nucleoside analogues such as 5-FU lead to cell arrest at checkpoints and subsequent cell death. They thus require a functional checkpoint for their therapeutic action.

The Aurora kinases have an important role in the mitotic phase of the cell cycle. Inhibition of the Aurora kinases has been shown to substantially disrupt the mitotic process leading to early mitotic effects from inhibition of Aurora A and late abnormalities of cytokinesis by inhibition of Aurora B. It is believed that combining Aurora kinase inhibitors with agents that activate, interfere with or modulate the mitotic or cell cycle checkpoint could sensitise cells to the cytotoxic effects and a beneficial combination effect could be observed (Anand S, Penrhyn-Lowe S, Venkitaraman A R. Cancer Cell. 2003 January; 3(1):51-62). In this context a combination of Aurora kinase inhibitors with the taxanes, epothilones or *vinca* alkaloids would be expected to be beneficial. Particular taxanes, epothilones and *vinca* alkaloids are described herein.

Further checkpoint targeting agents are those that cause DNA damage or disrupt DNA replication including platinum compounds such as cisplatin and nucleoside analogues such as 5-FU leading to cell arrest at checkpoints and subsequent cell death. In this context a combination of Aurora kinase inhibitors with the platinum compounds and nucleoside analogues would be expected to be beneficial as they could sensitise cells to the cytotoxic effects. Particular platinum compounds and nucleoside analogues are described herein.

Further checkpoint targeting agents that activate, interfere with or modulate the cell cycle checkpoints which would also be expected to be particularly beneficial for use in combination with the Aurora inhibitors of the invention include polo-like kinase inhibitors (Plks), CHK kinase inhibitors, inhibitors of the BUB kinase family and kinesin inhibitors. Polo-like kinases are important regulators of cell cycle progression during M-phase. Plks are involved in the assembly of the mitotic spindle apparatus and in the activation of CDK/cyclin complexes. Plk1 regulates tyrosine dephosphorylation of CDKs through phosphorylation and activation of Cdc25C. CDK1 activation in turn leads to spindle formation and entry into M phase. The importance of Checkpoint kinases such as Chk1 and Chk2 is described herein.

Thus other agents in development which act to disrupt the mitotic checkpoint and therefore could be combined beneficially with the compounds of the invention include polo-like kinase inhibitors (e.g. BI-2536), CHK kinase inhibitors (e.g. Irofulven (a CHK2 inhibitor), 7-hydroxystaurosporine (UCN-01, an inhibitor of both CHK1 and PKC) and PD-321852), inhibitors of the BUB kinase family, and kinesin inhibitors (also known as mitotic kinesin spindle protein (KSP) inhibitors) such as CK0106023, CK-0060339 and SB-743921 (structures shown below).

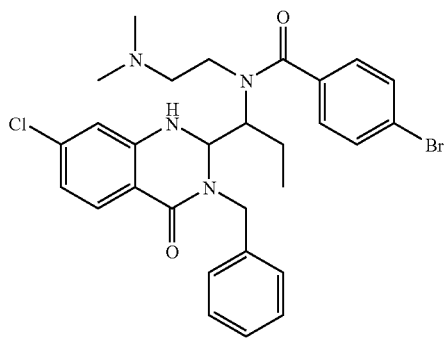

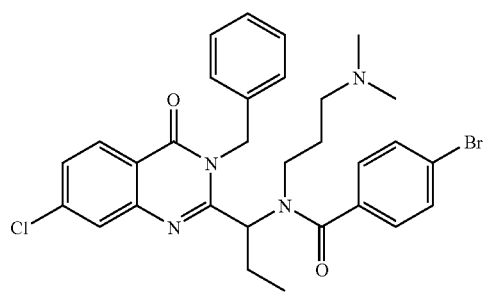

CK0106023, CK-0060339 and SB-743921 can be prepared and used as described in WO 01/30768 and WO 01/98278 and processes analogous thereto.

CHK kinase inhibitors include irofulven, UCN-01 and PD-321852. Irofulven (structure shown) is a semisynthetic compound derived from illudin S, a toxin from the *Omphalotus illudens* mushroom, for the potential treatment of refractory and relapsed tumors, including ovarian, prostate, hepatocellular, breast, lung and colon cancers, and gliomas. This can be synthesised as described in WO 98/05669 or processes analogous thereto.

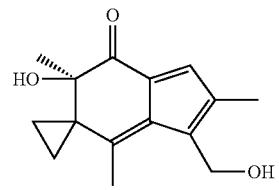 [SMILES: CC1=C(CO)C2=C(C)C3(CC3)[C@@](C)(O)C(=O)C2=C1]

PD-321852, a checkpoint kinase Chk I inhibitor, (structure shown), is being investigated by Pfizer for the potential treatment of cancer.

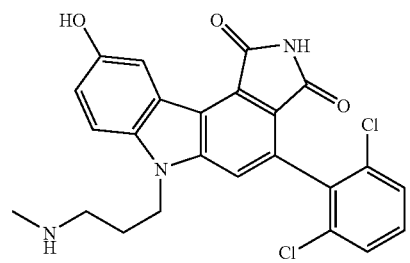 [SMILES: CNCCCn1c2ccc(O)cc2c2c3c(c(-c4c(Cl)cccc4Cl)cc21)C(=O)NC3=O]

It can be prepared and used as described in WO 01/53274, WO 01/53268 and in particular WO 03/091255 or processes analogous thereto.

BI-2536 (structure shown below) an inhibitor of the serine-threonine kinase polo-like kinase-1 (PLK-1), for the potential treatment of solid tumors. It can be prepared and used as described in WO2004/076454, WO 2006/018220, WO 2006/018221 and WO 2006/018222 or processes analogous thereto.

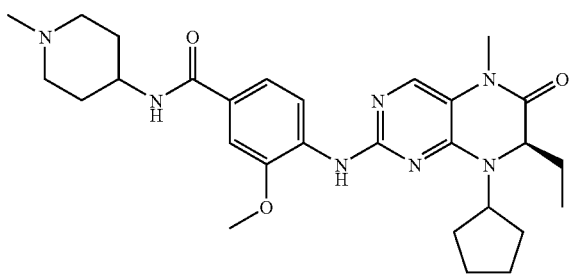 [SMILES: CC[C@@H]1C(=O)N(C)c2cnc(Nc3ccc(C(=O)NC4CCN(C)CC4)cc3OC)nc2N1C1CCCC1]

In addition, checkpoint targeting agents that arrest cells in G2/M phase could also be combined with the Aurora kinase inhibitors of the invention to have a similar beneficial effect. Therefore Platinum compounds and CDK inhibitors would be therefore be expected to be beneficial in combination with the combinations of the invention and are thus further Checkpoint Targeting Agents. Particular Platinum compounds and CDK inhibitors are described herein.

Thus, examples of Checkpoint Targeting Agents for use according to the invention include Platinum compounds, nucleoside analogues, CDK inhibitors, Taxanes, *Vinca* alkaloids, polo-like kinase inhibitors, CHK kinase inhibitors, inhibitors of the BUB kinase family and kinesin inhibitors, in particular Platinum compounds, nucleoside analogues, Taxanes and *Vinca* alkaloids more particularly checkpoint targeting agents which target the mititoic checkpoint such as Taxanes and *Vinca* alkaloids. Particular combinations of the invention include cisplatin or vinblastine or taxol or 5FU, in particular taxol.

23. DNA Repair Inhibitors

DNA repair inhibitors include PARP inhibitors.

Definition: The term "PARP inhibitor" is used herein to define compounds which inhibit or modulate the activity of the family of Poly adenosine diphosphate rbose (poly(ADP-Ribose)) nuclear enzymes, including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above. They may also be referred to as "DNA repair inhibitors".

Biological activity: PARP inhibitors have a role as chemosensitizing agents (for example by preventing DNA repair after anticancer therapy) and may have a role in enhancing overall patient response to anti-cancer treatments. PARP inhibitors may also act in isolation as anti cancer agents in patients whose tumours have intrinsic deficiencies in DNA repair.

Technical background: The PARP enzyme synthesizes poly(ADP-ribose), a branched polymer that can consists of over 200 ADP-ribose units. The protein acceptors of poly (ADP-ribose) are directly or indirectly involved in maintaining DNA integrity. They include histones, topoisomerases, DNA and RNA polymerases, DNA ligases, and Ca 2'- and Mg 2, -dependent endonucleases. PARP protein is expressed at a high level in many tissues, most notably in the immune system, heart, brain and germ-line cells. Under normal physiological conditions, there is minimal PARP activity. However, DNA damage causes an immediate activation of PARP by up to 500-fold.

PARP is activated by damaged DNA fragments and, once activated, catalyzes the attachment of up to 100 ADP-ribose units to a variety of nuclear proteins, including histones and PARP itself. It is also known that PARP inhibitors, such as 3-amino benzamide, affect overall DNA repair in response, for example, to hydrogen peroxide or ionizing radiation. The pivotal role of PARP in the repair of DNA strand breaks is well established, especially when caused directly by ionizing radiation or, indirectly after enzymatic repair of DNA lesions induced by methylating agents, especially temozolamide, topoisomerases I inhibitors and other chemotherapeutic agents as cisplatin and bleomycin. A variety of studies using knockout mice, trans-dominant inhibition models (over-expression of the DNA-binding domain), antisense and small molecular weight inhibitors have demonstrated the role of PARP in repair and cell survival after induction of DNA damage. The inhibition of PARP enzymatic activity should lead to an enhanced sensitivity of tumor cells towards DNA damaging treatments.

PARP inhibitors have been reported to be effective in radiosensitizing (hypoxic) tumor cells and effective in preventing tumor cells from recovering from potentially lethal and sublethal damage of DNA after radiation therapy, presumably by their ability to prevent DNA strand break rejoining and by affecting several DNA damage signaling pathways. PARP inhibitors have been used to treat cancer. A recent comprehensive review of the state of the art has been published by Li and Zhang in IDrugs 2001, 4(7): 804.

Preferences and specific embodiments: Preferred PARP inhibitors for use in accordance with the invention are selected from Bendamustine (5-[Bis(2-chloroethyl)amino]-1-methyl-2-benzimidazolebutyric acid or α-[1-Methyl-5-[bis(.beta.-chloroethyl)amino]-2-benzimidazolyl]butyric acid), available from Bayer, INO-1001 (Pardex) from Inotek Pharmaceuticals, BSI-201 from BiPar Sciences, AG-014699 from Pfizer, and ONO-2231 (N-[3-(3,4-dihydro-4-oxo-1-phthalazinyl)phenyl]-4-morpholinebutanamide methanesulfonate) from Ono Pharmaceutical.

Posology: The PARP inhibitors are advantageously administered in daily dosages of 20-100 mg, for example 80-120 mg/m2 iv over a 30 to 60 min infusion over a 21 day cycle for Bendamustine. —The key PARP inhibitor is a Pfizer product which is in phase III combination trials in metastatic melanoma. It is administered intravenously on days one thru five of a twenty-one day cycle dose?

24. Inhibitors of G-Protein Coupled Receptors (GPCR)

A preferred GPCR is Atrasentan (3-Pyrrolidinecarboxylic acid, 4-(1,3-benzodioxol-5-yl)-1-[2-(dibutylamino)-2-oxoethyl]-2-(4-methoxyphenyl)-, [2R-(2.alpha.,3.beta.,4.alpha.)]-). Atrasentan, from Abbott Laboratories, is a potent and selective endothelin A receptor antagonist for the treatment of prostate tumors. There is also evidence of biological activity in other cancer types such as glioma, breast tumor, lung tumor, brain tumor, ovary tumor, colorectal tumor and renal tumor.

Posology: Atrasentan may be advantageously administered orally in dosages of e.g. 10 mg daily.

Anti-Cancer Agent Combinations

The combinations of the invention may be used for treating any of the diseases and disorders described herein.

The combinations of the invention may comprise two or more auxiliary compounds. In such embodiments, the auxiliary compounds may be anti-cancer agents. In such embodiments, the two or more anticancer agents may be independently selected from carboplatin, cisplatin, taxol, taxotere, gemcitabine, and vinorelbine. Preferably the two or more further anti-cancer agents are carboplatin, taxol and vinorelbine, or carboplatin and taxol.

Combinations with platinum agents, taxol, taxotere, gemcitabine, pemetrexed, mitomycin, ifosfamide, vinorelbine, erlotinib and bevacizumab or combinations of compounds of formula (I) with carboplatin and taxol or cisplatin and gemcitabine are particularly suitable for treating Non-Small cell lung cancer.

In one embodiment, the two or more anti-cancer agents are independently selected from 5-FU, leucovorin, oxaliplatin, CPT 11, bevacizumab, cetuximab and pantumab (Vectabix). Preferably, the two or more anti-cancer agents are 5-FU, leucovorin and CPT 11 or 5-FU, leucovorin and oxaliplatin, CPT 11 and cetuximab.

Combinations with 5-FU, leucovorin and CPT 11 or a combination of compounds of formula (I) with 5-FU, leucovorin and oxaliplatin, each with bevacizumab are particularly suitable for treating colon cancer.

In one embodiment, the two or more anti-cancer agents are independently selected from methotrexate, taxanes, anthracyclines e.g. doxorubicin, herceptin, lapatinib, bevacizumab, mitozantrone, epothilones, 5-FU, and cyclophosphamide. In one embodiment, the two or more anti-cancer agents are independently selected from taxanes, anthracyclines e.g. doxorubicin, herceptin, 5-FU, and cyclophosphamide. In one embodiment, the two or more anti-cancer agents are independently selected from 5-FU, methotrexate, cyclophosphamide and doxorubicin. Preferably the two or more anti-cancer agents are 5-FU, methotrexate and cyclophosphamide or 5-FU, doxorubicin and cyclophosphamide or doxorubicin and cyclophosphamide.

Combinations with 5-FU, methotrexate and cyclophosphamide, or combinations with 5-FU, doxorubicin and cyclophosphamide, or combinations with doxorubicin and cyclophosphamide, are particularly suitable for treating breast cancer.

In one embodiment, the two or more anti-cancer agents are independently selected from cyclophosphamide, doxorubicin (hydroxydaunorubicin), vincristine, bortezomib, rituximab and prednisone. Preferably the two or more anti-cancer agents are cyclophosphamide, doxorubicin (hydroxydaunorubicin), vincristine and prednisone, or cyclophosphamide, vincristine and prednisone with or without rituximab.

Combinations with cyclophosphamide, doxorubicin (hydroxydaunorubicin), vincristine, rituximab and prednisone are particularly suitable for treating non Hodgkin's lymphoma (and in particular high grade non Hodgkin's lymphoma). Combinations with cyclophosphamide, vincristine, rituximab and prednisone are particularly suitable for treating non Hodgkin's lymphoma (and in particular low grade non Hodgkin's lymphoma).

In one embodiment, the two or more anti-cancer agents are independently selected from vincristine, thalidomide, doxorubicin, bortezomib and dexamethasone. Preferably the two or more anti-cancer agents are vincristine, doxorubicin and dexamethasone.

Combinations with vincristine, doxorubicin, thalidomide and dexamethasone are particularly suitable for treating multiple myeloma.

In one embodiment, the two or more anti-cancer agents are independently selected from fludarabine, almentuzamab and rituxamab. Preferably the two or more anti-cancer agents are fludarabine and rituxamab.

Combinations with fludarabine and rituxamab are particularly suitable for treating chronic lymphocytic leukemia.

In one embodiment the combination of the invention optionally excludes combination of two or more of the following anti-cancer agents selected from a topoisomerase inhibitor, an alkylating agent, a antimetabolite, DNA binders, monoclonal antibodies, signal transduction inhibitors and microtubule inhibitors (tubulin targeting agents), such as cisplatin, cyclophosphamide, doxorubicin, irinotecan, fludarabine, 5FU, taxanes and mitomycin C.

In one embodiment the combination of the invention includes at least one anti-cancer agent selected from an anti-androgen, a histone deacetylase inhibitor (HDAC), cylcooxygenase-2 (COX-2) inhibitor, proteasome inhibitor, DNA methylation inhibitor and a CDK inhibitor.

Disease-Specific Anti-Cancer Agent Combinations

Multiple Myeloma

Particularly suitable for treating multiple myeloma are combinations of the invention with auxiliary compounds selected from: (a) monoclonal antibodies (e.g. those targeting Interleukin 6); (b) proteasome inhibitors (e.g. bortezomib); (c) proteasome inhibitors and corticosteroids (e.g. velcade and dexamethasone); and (d) corticosteroids, alkylating agents and lenolidamide/thalidomide (e.g. prednisolone, melphalan and thalidomide).

Melanoma

Particularly suitable for treating melanoma are combinations of the invention with auxiliary compounds selected from: (a) DNA methylase inhibitors/hypomethylating agents (e.g. temozolamide); (b) alkylating agents (e.g. dacarbazine or fotemustine); and (c) DNA methylase inhibitors/hypomethylating agents (e.g. temozolamide) and DNA repair inhibitors/PARP inhibitors.

Breast Cancer

Particularly suitable for treating breast cancer are combinations of the invention with auxiliary compounds selected from: (a) monoclonal antibodies (e.g. trastuzumab and bevicizamab); (b) monoclonal antibodies (e.g. trastuzumab and bevicizamab) and taxanes; and (c) antimetabolites (e.g. capecitabine) and signalling inhibitors (e.g. lapatinib).

Prostate Cancer

Particularly suitable for treating prostate cancer are combinations of the invention with auxiliary compounds selected from hormones and G-protein coupled receptor inhibitors.

Non Small Cell Lung Cancer (NSCLC)

Particularly suitable for treating NSCLC are combinations of the invention with auxiliary compounds selected from: (a) platinum compounds and taxanes; and (b) platinum compounds and antimetabolites.

Specific Combinations of the Invention

Particular combinations according to the invention include the following two or more anti-cancer agents:

For cancer (and in particular acute myeloid leukemia) treatment, two or more anti-cancer agents independently selected from two or more of anthracycline, Ara C (a.k.a. Cytarabine), 6-mercaptopurine, thiopurine, methotrexate, mitoxantrone, daunorubicin, idarubicin, gemtuzumab ozogamicin and granulocyte colony stimulating factors. Alternatively, the two or more anti-cancer agents may be independently selected from two or more of anthracycline, Ara C (a.k.a. Cytarabine), daunorubicin, idarubicin, gemtuzumab ozogamicin and granulocyte colony stimulating factors.

For cancer (and in particular breast cancer) treatment, two or more anti-cancer agents independently selected from bevacizumab, taxanes, methotrexate, paclitaxel, docetaxel, gemcitabine, anastrozole, exemestane, letrozole, tamoxifen, doxorubicin, herceptin, 5-fluorouracil, cyclophosphamide, epirubicin and capecitabine, particularly 5-FU, methotrexate and cyclophosphamide; 5FU, doxorubicin and cyclophosphamide; or doxorubicin and cyclophosphamide. Preferably, for cancer (and in particular breast cancer) treatment, the two or more anti-cancer agents may also be independently selected from taxanes, methotrexate, paclitaxel, docetaxel, gemcitabine, anastrozole, exemestane, letrozole, tamoxifen, doxorubicin, herceptin, 5-fluorouracil, cyclophosphamide, epirubicin and capecitabine, particularly 5-FU, methotrexate and cyclophosphamide; 5FU, doxorubicin and cyclophosphamide; or doxorubicin and cyclophosphamide.

Typical dosing regimens include:
Cyclophosphamide at 100 mg/m$^2$ PO Daily×14 days, Doxorubicin at 30 mg/m$^2$ IV Day 1 & day 8 and fluorouracil at 500 mg/m$^2$ IV Day 1 & day 8, repeated every 28 days
Cyclophosphamide at 600 mg/m$^2$ IV Day 1 and Doxorubicin at 60 mg/m$^2$ IV Day 1, repeated every 21 days For cancer (and in particular chronic lymphocytic leukemia (CLL)) treatment, two or more anti-cancer agents independently selected from alemtuzumab, chlorambucil, cyclophosphamide, almentuzumab, vincristine, predinisolone, fludarabine, mitoxantrone and rituximab/rituxamab, particularly fludarabine and rituxamab. Preferably, for cancer (and in particular chronic lymphocytic leukemia (CLL)) treatment, the two or more anti-cancer agents are independently selected from chlorambucil, cyclophosphamide, vincristine, predinisolone, fludarabine, mitoxantrone and rituximab/rituxamab, particularly fludarabine and rituxamab.

For cancer (and in particular chronic myeloid leukemia (CML)) treatment, two or more anti-cancer agents independently selected from hydroxyurea, cytarabine, desatinib, nilotinib and imatinib.

For cancer (and in particular Colon Cancer treatment), two or more anti-cancer agents independently selected from cetuximab, 5-Fluorouracil, pantumab, leucovorin, irinotecan, oxaliplatin, raltirexed, capecitabine, bevacizumab, oxaliplatin, CPT 11, particularly 5-Fluorouracil, Leucovorin and CPT 11 or Fluorouracil, Leucovorin and Oxaliplatin.

Alternatively, for cancer (and in particular Colon Cancer treatment), two or more anti-cancer agents independently selected from 5-Fluorouracil, leucovorin, irinotecan, oxaliplatin, raltirexed, capecitabine, bevacizumab, oxaliplatin, CPT 11 and particularly 5-Fluorouracil, Leucovorin and CPT 11 or Fluorouracil, Leucovorin and Oxaliplatin.

Typical dosing regimens include:
Fluorouracil at 400-425 mg/m$^2$ IV Days 1 to 5 and Leucovorin at 20 mg/m$^2$ IV Days 1 to 5, repeated every 28 days
Irinotecan at 100-125 mg/m$^2$ IV over 90 minutes Days 1, 8, 15 & 22, Folinic acid at 20 mg/m2 IV Days 1, 8, 15 & 22, and Fluorouracil at 400-500 mg/m2 IV Days 1, 8, 15 & 22, repeated every 42 days until disease progression
Oxaliplatin at 85 mg/m2 IV in 500 mL of D5W over 120 minutes Day 1, Folinic acid at 200 mg/m2 IV over 120 minutes Days 1 & 2, Fluorouracil at 400 mg/m2 IV bolus, after Folinic Acid, Days 1 & 2, then Fluorouracil at 600 mg/m2 CIV over 22 hours Days 1 & 2, repeated every 12 days for up to 12 cycles For cancer (and in particular multiple myeloma treatment), two or more anti-cancer agents independently selected from vincristine, doxorubicin, dexamethasone, melphalan, prednisone, cyclophosphaimde, etoposide, pamidronate, thalidomide, zoledronate and bortezomib, particularly vincristine, doxorubicin and dexamethasone.

For cancer (and in particular Non-Hodgkin's lymphoma treatment), two or more anti-cancer agents independently selected from cyclophosphamide, doxorubicin/hydroxydaunorubicin, vincristine/Onco-TCS (V/O), prednisolone, methotrexate, cytarabine, bleomycin, etoposide, rituximab/rituxamab, fludarabine, cisplatin, and ifosphamide, particularly cyclophosphamide, doxorubicin (hydroxydaunorubicin), vincristine and prednisone for high grade NHL or cyclophosphamide, vincristine and prednisone for low grade NHL.

For cancer (and in particular Non Small Cell Lung Cancer (NSCLC)) treatment, two or more anti-cancer agents may be independently selected from bevacizumab, gefitinib, erlotinib, cisplatin, carboplatin, mitomycin, vinblastine, paclitaxel, docetaxel, gemcitabine and vinorelbine, especially taxol and carboplatin or gemcitabine and cisplatin.

Typical dosing regimens include:
Gemcitabine at 1000 mg/m$^2$ IV Days 1, 8 & 15, and Cisplatin at 75-100 mg/m$^2$ IV Day 1, repeated every 28 days for 4-6 cycles
Paclitaxel at 135-225 mg/m$^2$ IV over 3 hrs Day 1 and Carboplatin at AUC 6.0 IV Day 1, repeated every 21 days for 4-6 cycles
Docetaxel at 75 mg/m$^2$ IV Day 1, and Carboplatin at AUC 5 or 6 IV Day 1, repeated every 21 days for 4-6 cycles
Docetaxel at 75 mg/m$^2$ IV Day 1, and Cisplatin at 75 mg/m$^2$ IV Day 1, repeated every 21 days for 4-6 cycles For cancer (and in particular ovarian cancer) treatment, two or more anti-cancer agents independently selected from platinum compounds (for example Cisplatin, Carboplatin), doxorubicin, liposomal doxorubicin, paclitaxel, docetaxel, gemcitabine, melphalan and mitoxantrone.

For cancer (and in particular prostate cancer) treatment, two or more anti-cancer agents independently selected from mitoxantrone, prednisone, buserelin, goserelin, bicalutamide, nilutamide, flutamide, cyproterone acetate, megestrol/megestrel, diethylstilboestrol, docetaxel, paclitaxel, zoledronic acid, prednisolone and taxotere.

Pharmaceutical Formulations

While it is possible for the active compounds of the combinations of the invention to be administered alone, it is preferable to present it as a pharmaceutical composition (e.g. formulation) comprising at least one active compound of the combinations of the invention together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents; for example agents that reduce or alleviate some of the side effects associated with chemotherapy. Particular examples of such agents include anti-emetic agents and agents that prevent or decrease the duration of chemotherapy-associated neutropenia and prevent complications that arise from reduced levels of red blood cells or white blood cells, for example erythropoietin (EPO), granulocyte macrophage-colony stimulating factor (GM-CSF), and granulocyte-colony stimulating factor (G-CSF).

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilizers, or other materials, as described herein.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Accordingly, in a further aspect, the invention provides combinations as defined herein in the form of pharmaceutical compositions.

The pharmaceutical compositions can be in any form suitable for oral, parenteral, topical, intranasal, ophthalmic, otic, rectal, intra-vaginal, or transdermal administration. Where the compositions are intended for parenteral administration, they can be formulated for intravenous, intramuscular, intra-peritoneal, subcutaneous administration or for direct delivery into a target organ or tissue by injection, infusion or other means of delivery. The delivery can be by bolus injection, short term infusion or longer term infusion and can be via passive delivery or through the utilisation of a suitable infusion pump.

Pharmaceutical formulations adapted for parenteral administration include aqueous and non-aqueous sterile injection solutions which may contain anti-oxidants, buffers, bacteriostats, co-solvents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, inter alia, stabilising the active ingredient in a soluble form and rendering the formulation isotonic with the blood of the intended recipient. Pharmaceutical formulations for parenteral administration may also take the form of aqueous and non-aqueous sterile suspensions which may include suspending agents and thickening agents (R. G. Strickly, Solubilizing Excipients in oral and injectable formulations, Pharmaceutical Research, Vol 21(2) 2004, p 201-230).

A drug molecule that is ionizable can be solubilized to the desired concentration by pH adjustment if the drug's $pK_a$ is sufficiently away from the formulation pH value. The acceptable range is pH 2-12 for intravenous and intramuscular administration, but subcutaneously the range is pH 2.7-9.0. The solution pH is controlled by either the salt form of the drug, strong acids/bases such as hydrochloric acid or sodium hydroxide, or by solutions of buffers which include but are not limited to buffering solutions formed from glycine, citrate, acetate, maleate, succinate, histidine, phosphate, tris (hydroxymethyl)-aminomethane (TRIS), or carbonate.

The combination of an aqueous solution and a water-soluble organic solvent/surfactant (i.e., a cosolvent) is often used in injectable formulations. The water-soluble organic solvents and surfactants used in injectable formulations include but are not limited to propylene glycol, ethanol, polyethylene glycol 300, polyethylene glycol 400, glycerin, dimethylacetamide (DMA), N-methyl-2-pyrrolidone (NMP; Pharmasolve), dimethylsulphoxide (DMSO), Solutol HS 15, Cremophor EL, Cremophor RH 60, and polysorbate 80. Such formulations can usually be, but are not always, diluted prior to injection.

Propylene glycol, PEG 300, ethanol, Cremophor EL, Cremophor RH 60, and polysorbate 80 are the entirely organic water-miscible solvents and surfactants used in commercially available injectable formulations and can be used in combinations with each other. The resulting organic formulations are usually diluted at least 2-fold prior to IV bolus or IV infusion.

Alternatively increased water solubility can be achieved through molecular complexation with cyclodextrins.

Liposomes are closed spherical vesicles composed of outer lipid bilayer membranes and an inner aqueous core and with an overall diameter of <100 μm. Depending on the level of hydrophobicity, moderately hydrophobic drugs can be solubilized by liposomes if the drug becomes encapsulated or intercalated within the liposome. Hydrophobic drugs can also be solubilized by liposomes if the drug molecule becomes an integral part of the lipid bilayer membrane, and in this case, the hydrophobic drug is dissolved in the lipid portion of the lipid bilayer. A typical liposome formulation contains water with phospholipid at 5-20 mg/ml, an isotonicifier, a pH 5-8 buffer, and optionally cholesterol.

The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use.

The pharmaceutical formulation can be prepared by lyophilising one or more of the constituent component(s) (or salt thereof) of the combination. Lyophilisation refers to the procedure of freeze-drying a composition. Freeze-drying and lyophilisation are therefore used herein as synonyms. A typical process is to solubilise the compound(s) and the resulting formulation is clarified, sterile filtered and aseptically transferred to containers appropriate for lyophilisation (e.g. vials). In the case of vials, they are partially stoppered with lyo-stoppers. The formulation can be cooled to freezing and subjected to lyophilisation under standard conditions and then hermetically capped forming a stable, dry lyophile formulation. The composition will typically have a low residual water content, e.g. less than 5% e.g. less than 1% by weight based on weight of the lyophile.

The lyophilisation formulation may contain other excipients for example, thickening agents, dispersing agents, buffers, antioxidants, preservatives, and tonicity adjusters. Typical buffers include phosphate, acetate, citrate and glycine. Examples of antioxidants include ascorbic acid, sodium bisulphite, sodium metabisulphite, monothioglycerol, thiourea, butylated hydroxytoluene, butylated hydroxyl anisole, and ethylenediaminetetraacetic acid salts. Preservatives may include benzoic acid and its salts, sorbic acid and its salts, alkyl esters of para-hydroxybenzoic acid, phenol, chlorobutanol, benzyl alcohol, thimerosal, benzalkonium chloride and cetylpyridinium chloride. The buffers mentioned previously, as well as dextrose and sodium chloride, can be used for tonicity adjustment if necessary.

Bulking agents are generally used in lyophilisation technology for facilitating the process and/or providing bulk and/or mechanical integrity to the lyophilized cake. Bulking agent means a freely water soluble, solid particulate diluent that when co-lyophilised with the compound or salt thereof, provides a physically stable lyophilized cake, a more optimal freeze-drying process and rapid and complete reconstitution. The bulking agent may also be utilised to make the solution isotonic.

The water-soluble bulking agent can be any of the pharmaceutically acceptable inert solid materials typically used for lyophilisation. Such bulking agents include, for example, sugars such as glucose, maltose, sucrose, and lactose; polyalcohols such as sorbitol or mannitol; amino acids such as glycine; polymers such as polyvinylpyrrolidine; and polysaccharides such as dextran.

The ratio of the weight of the bulking agent to the weight of active compound is typically within the range from about 1 to about 5, for example of about 1 to about 3, e.g. in the range of about 1 to 2.

Alternatively they can be provided in a solution form which may be concentrated and sealed in a suitable vial. Sterilisation of dosage forms may be via filtration or by autoclaving of the vials and their contents at appropriate stages of the formulation process. The supplied formulation may require further dilution or preparation before delivery for example dilution into suitable sterile infusion packs.

Extemporaneous injection solutions and suspensions may be prepared from sterile powders, granules and tablets.

In one preferred embodiment of the invention, the pharmaceutical composition is in a form suitable for i.v. administration, for example by injection or infusion.

In another preferred embodiment, the pharmaceutical composition is in a form suitable for sub-cutaneous (s.c.) administration.

Pharmaceutical dosage forms suitable for oral administration include tablets, capsules, caplets, pills, lozenges, syrups, solutions, powders, granules, elixirs and suspensions, sublingual tablets, wafers or patches and buccal patches.

Pharmaceutical compositions of the invention can be formulated in accordance with known techniques, see for example, Remington's Pharmaceutical Sciences, Mack Publishing Company, Easton, Pa., USA.

Thus, tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (eg; tablets, capsules etc.) can be coated or un-coated, but typically have a coating, for example a protective film coating (e.g. a wax or varnish) or a release controlling coating. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum or duodenum. Alternatively or additionally, the coating can be used as a taste masking agent to mask unpleasant tastes such as bitter tasting drugs. The coating may contain sugar or other agents that assist in masking unpleasant tastes.

Instead of, or in addition to, a coating, the drug can be presented in a solid matrix comprising a release controlling agent, for example a release delaying agent which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. As a further alternative, the active compound can be formulated in a delivery system that provides osmotic control of the release of the compound. Osmotic release and other delayed release or sustained release formulations may be prepared in accordance with methods well known to those skilled in the art.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

Compositions for topical use include ointments, creams, sprays, patches, gels, liquid drops and inserts (for example intraocular inserts). Such compositions can be formulated in accordance with known methods.

Compositions for parenteral administration are typically presented as sterile aqueous or oily solutions or fine suspensions, or may be provided in finely divided sterile powder form for making up extemporaneously with sterile water for injection.

Examples of formulations for rectal or intra-vaginal administration include pessaries and suppositories which may be, for example, formed from a shaped mouldable or waxy material containing the active compound. Thus, unit-dose suppositories or pessaries may be prepared by admixture of the active ingredient with one or more conventional solid carriers, for example coca butter, and shaping the resulting mixture. Further examples of mouldable waxy materials include polymers such as high molecular weight polyalkylene glycols, e.g. high molecular weight polyethylene glycols.

Alternatively, in the case of vaginal administration, the formulation may be presented as a tampon impregnated with the active ingredients and optionally one or more excipients or diluents. Other formulations suitable for rectal and vaginal administration include creams, gels, foams, pastes and sprays.

Further examples of topical compositions include dressings such as bandages and adhesive plasters impregnated with active ingredients and optionally one or more excipients or diluents. Carriers which may be used include e.g. polyhydric alcohols such as polyethylene glycols, propylene glycol or glycerol. Suitable excipients are those known in the art to be appropriate.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The combination of the invention and/or its constituent compounds will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within this range, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired therapeutic effect.

Methods of Treatment

The combinations of the invention will be useful in the prophylaxis or treatment of a range of disease states or conditions mediated by Hsp90 client proteins and/or glycogen synthase kinase-3 and/or cyclin dependent kinase(s). Examples of such disease states and conditions are set out above.

The combinations are generally administered to a subject in need of such administration, for example a human or animal patient, preferably a human.

The combination will typically be administered in amounts that are therapeutically or prophylactically useful and which generally are non-toxic. However, in certain situations (for example in the case of life threatening diseases), the benefits of administering a combination of the invention may outweigh the disadvantages of any toxic effects or side effects, in which case it may be considered desirable to administer the combinations in amounts that are associated with a degree of toxicity.

The combinations may be administered over a prolonged term to maintain beneficial therapeutic effects or may be administered for a short period only. Alternatively they may be administered in a continuous manner or in a manner that provides persistent intermittent dosing (e.g. a pulsatile manner).

A typical daily dose can be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams, and more typically 1 microgram per kilogram to 20 milligrams per kilogram, for example 1 microgram to 10 milligrams per kilogram) per kilogram of bodyweight although higher or lower doses may be administered where required. Administration can be on a daily basis or on a repeat basis every 2, or 3, or 4, or 5, or 6, or 7, or 10 or 14, or 21, or 28 days for example.

In one particular dosing schedule, a patient will be given an infusion for periods of one hour to 4 hours daily for up to ten days in particular up to two days for one week, every two weeks in three, and the treatment repeated at a desired interval such as three to six weeks, in particular every three weeks.

More particularly, a patient may be given an infusion for periods of one hour daily twice a week for two weeks in three weeks and the treatment repeated every three weeks.

Alternatively, a patient may be given an infusion for periods of one hour daily twice a week for three weeks in four weeks and the treatment repeated every four weeks.

In another particular dosing schedule, a patient will be given an infusion for periods of one hour daily for up to ten days in particular up to five days for one week, and the treatment repeated at a desired interval such as two to four weeks, in particular every three weeks.

More particularly, a patient may be given an infusion for periods of one hour daily for 5 days and the treatment repeated every three weeks.

In another particular dosing schedule, a patient is given an infusion over 30 minutes to 1 hour followed by maintenance infusions of variable duration, for example 1 to 5 hours, e.g. 3 hours.

In a further particular dosing schedule, a patient is given a continuous infusion for a period of 12 hours to 5 days, an in particular a continuous infusion of 24 hours to 72 hours.

Ultimately, however, the quantity administered and the type of composition used will be commensurate with the nature of the disease or physiological condition being treated and will be at the discretion of the physician.

The combinations as defined herein can be administered as the sole therapeutic agent or they can be administered in combination therapy with one of more other compounds for treatment of a particular disease state, for example a neoplastic disease such as a cancer as hereinbefore defined. Examples of such compounds are set out in the section headed "optional auxiliary compounds for use according to the invention", above.

Examples of other therapeutic agents or treatments that may be administered together (whether concurrently or at different time intervals) with the combinations of the invention include but are not limited to:

Topoisomerase I inhibitors
Antimetabolites
Tubulin targeting agents
DNA binder and topoisomerase II inhibitors
Alkylating Agents
Monoclonal Antibodies.
Anti-Hormones
Signal Transduction Inhibitors
Proteasome Inhibitors
DNA methyl transferases
Cytokines and retinoids
Chromatin targeted therapies, e.g. HDAC or HAT modulators
Radiotherapy; and
Other therapeutic or prophylactic agents; for example agents that reduce or alleviate some of the side effects associated with chemotherapy. Particular examples of such agents include anti-emetic agents and agents that prevent or decrease the duration of chemotherapy-associated neutropenia and prevent complications that arise from reduced levels of red blood cells or white blood cells, for example erythropoietin (EPO), granulocyte macrophage-colony stimulating factor (GM-CSF), and granulocyte-colony stimulating factor (G-CSF). Also included are agents that inhibit bone resorption such as bisphosphonate agents e.g. zoledronate, pamidronate and ibandronate, agents that suppress inflammatory responses (such as dexamethazone, prednisone, and prednisolone) and agents used to reduce blood levels of growth hormone and IGF-I in acromegaly patients such as synthetic forms of the brain hormone somatostatin, which includes octreotide acetate which is a long-acting octapeptide with pharmacologic properties mimicking those of the natural hormone somatostatin. Further included are agents such as leucovorin, which is used as an antidote to drugs that decrease levels of folic acid, or folinic acid itself and agents such as megestrol acetate which can be used for the treatment of side-effects including oedema and thromboembolic episodes.

For the case of combinations of the invention further combined with other therapies, the two or more treatments may be given in individually varying dose schedules and via different routes.

Where the combination is administered with one, two, three, four or more other therapeutic agents (preferably one or two, more preferably one), the components can be administered simultaneously or sequentially. When administered sequentially, they can be administered at closely spaced intervals (for example over a period of 5-10 minutes) or at longer intervals (for example 1, 2, 3, 4 or more hours apart, or even longer periods apart where required), the precise dosage regimen being commensurate with the properties of the therapeutic agent(s).

The combinations of the invention may also be administered in conjunction with non-chemotherapeutic treatments such as radiotherapy, photodynamic therapy, gene therapy; surgery and controlled diets.

For use in combination therapy with another chemotherapeutic agent, the combination and one, two, three, four or more other therapeutic agents can be, for example, formulated together in a dosage form containing two, three, four or more therapeutic agents. In an alternative, the individual therapeutic agents may be formulated separately and presented together in the form of a kit, optionally with instructions for their use.

A person skilled in the art would know through his or her common general knowledge the dosing regimes and combination therapies to use.

Methods of Diagnosis

Prior to administration of a combination of the invention, a patient may be screened to determine whether a disease or condition from which the patient is or may be suffering is one which would be susceptible to treatment with a combination comprising a compound having activity against Hsp90 and/or glycogen synthase kinase-3 and/or cyclin dependent kinase.

In the case of screens to determine whether a disease or condition from which the patient is or may be suffering is one which would be susceptible to treatment with a combination comprising a compound having activity against glycogen synthase kinase-3 and/or cyclin dependent kinase, the relevant methods of diagnosis are described in WO 2005/012256 at pages 107-111 and WO 2006/077426 at pages 62-65 (in the case of combinations comprising ancillary compounds of formula (0)) and WO 2006/077416 at pages 52-56 (in the case of ancillary compounds of formula (I')), which disclosure is hereby incorporated herein by reference.

In the case of screens to determine whether a disease or condition from which the patient is or may be suffering is one which would be susceptible to treatment with a combination comprising a compound having activity against Hsp90, prior to administration of a combination of the invention, a patient may be screened to determine whether a disease or condition from which the patient is or may be suffering is one which would be susceptible to treatment with a compound having activity against Hsp90. In this case, a biological sample taken from a patient may be analysed to determine whether a condition or disease, such as cancer, that the patient is or may be suffering from is one which is characterised by a genetic abnormality or abnormal protein expression which leads to the mutation or over-activation of an Hsp90 client protein. Examples of such abnormalities that result in activation of Hsp90 client proteins include; Bcr-ABL translocation, Flt-3 internal duplication, and mutation of Braf, or over-expression of ErbB2.

Thus, the patient may be subjected to a diagnostic test to detect a marker characteristic of up-regulation. The term diagnosis includes screening. By marker we include genetic markers including, for example, the measurement of DNA composition to identify mutations of Braf, BCR-abl, and Flt3 or other affected client proteins. The term marker also includes proteins such as ErbB2, including levels or concentrations of the protein or some fragments or degradation product and for enzymes the enzymic activity. The protein (e.g. phosphorylated or not) and mRNA levels of the aforementioned proteins could also be assessed to characterise a change in activity. For example the level of phosphorylated AKT can be an indicator of sensitivity to HSP90 inhibitors The diagnostic tests are typically conducted on a biological sample selected from for example tumour biopsy samples, blood samples (isolation and enrichment of shed tumour cells), stool biopsies, sputum, chromosome analysis, pleural fluid, peritoneal fluid, buccal spears or biopsy or from urine.

The screening process will typically involve direct sequencing, oligonucleotide or protein microarray analysis, proteomic analysis by mass spectrometry, immunohistochemical techniques or detection using a specific antibody.

Methods of identification and analysis of mutations and up-regulation of proteins are well known to a person skilled in the art. Screening methods could include, but are not limited to, standard methods such as reverse-transcriptase polymerase chain reaction (RT-PCR), in-situ hybridisation or immunoblotting.

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. Current Protocols in Molecular Biology, 2004, John Wiley & Sons Inc., or Innis, M. A. et-al., eds. PCR Protocols: a guide to methods and applications, 1990, Academic Press, San Diego. Reactions and manipulations involving nucleic acid techniques are also described in Sambrook et al., 2001, 3rd Ed, Molecular Cloning: A Laboratory Manual, Cold Spring Harbor Laboratory Press. Alternatively a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference.

An example of an in-situ hybridisation technique for assessing mRNA expression would be fluorescence in-situ hybridisation (FISH) (see Angerer, 1987 Meth. Enzymol., 152: 649).

Generally, in situ hybridization comprises the following major steps: (1) fixation of tissue to be analyzed; (2) prehybridization treatment of the sample to increase accessibility of target nucleic acid, and to reduce non-specific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labelled, for example, with radioisotopes or fluorescent reporters. Preferred probes are sufficiently long, for example, from about 50, 100, or 200 nucleotides to about 1000 or more nucleotides, to enable specific hybridization with the target nucleic acid(s) under stringent conditions. Commercially available FISH probes also exist for cytogenetic detection of chromosome rearrangements, which can be used to detect Flt3 and Bcr-Abl translocations within leukemia cell populations. Standard methods for carrying out FISH are described in Ausubel, F. M. et al., eds. Current Protocols in Molecular Biology, 2004, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Methods for gene expression profiling are described by (DePrimo et al., *BMC Cancer* 2003, 3:3). Briefly, the protocol is as follows: double-stranded cDNA is synthesized from total RNA Using a (dT)24 oligomer for priming first-strand cDNA synthesis, followed by second strand cDNA synthesis with random hexamer primers. The double-stranded cDNA is used as a template for in vitro transcription of cRNA using biotinylated ribonucleotides. cRNA is chemically fragmented according to protocols described by Affymetrix (Santa Clara, Calif., USA), and then hybridized overnight on Human Genome Arrays.

Alternatively, the protein products expressed from the mRNAs may be assayed by immunohistochemistry of tumour samples, solid phase immunoassay with microtiter plates, Western blotting, 2-dimensional SDS-polyacrylamide gel electrophoresis, ELISA, flow cytometry and other methods known in the art for detection of specific proteins. Detection methods would include the use of site specific antibodies. The skilled person will recognize that all such well-known techniques for detection of the "philadelphia chromosome" indicative of BCR-ABL translocation.

Therefore, all of these techniques could also be used to identify tumours particularly suitable for treatment with the combinations of the invention.

EXAMPLES

The invention will now be illustrated, but not limited, by reference to the specific embodiments described in the following examples.

In the examples, the following abbreviations may be used.
AcOH acetic acid
BOC tert-butyloxycarbonyl
Bn benzyl
CDI 1,1-carbonyldiimidazole
DMAW90 Solvent mixture: DCM: MeOH, AcOH, $H_2O$ (90:18:3:2)
DMAW120 Solvent mixture: DCM: MeOH, AcOH, $H_2O$ (120:18:3:2)
DMAW240 Solvent mixture: DCM: MeOH, AcOH, $H_2O$ (240:20:3:2)
DCM dichloromethane
DMF dimethylformamide
DMSO dimethyl sulphoxide
EDC 1-ethyl-3-(3'-dimethylaminopropyl)-carbodiimide
$Et_3N$ triethylamine
EtOAc ethyl acetate
$Et_2O$ diethyl ether
h hour(s)
HOAt 1-hydroxyazabenzotriazole
HOBt 1-hydroxybenzotriazole
MeCN acetonitrile
MeOH methanol
min. minutes
P.E. petroleum ether
r.t. room temperature
$SiO_2$ silica
TBTU N,N,N',N'-tetramethyl-O-(benzotriazol-1-yl)uronium tetrafluoroborate
THF tetrahydrofuran Proton magnetic resonance ($^1H$ NMR) spectra were recorded on a Bruker AV400 instrument operating at 400.13 MHz, in DMSO-$d_6$ or MeOH-$d_4$ (as indicated) at 27° C., unless otherwise stated and are reported as follows: chemical shift δ/ppm (number of protons, multiplicity where s=singlet, d=doublet, t=triplet, q=quartet, m=multiplet, br=broad). The residual protic solvent was used as the internal reference.

In the examples, the compounds prepared were characterised by liquid chromatography and mass spectroscopy using the system and operating conditions set out below. Where atoms with different isotopes are present and a single mass quoted, the mass quoted for the compound is the monoisotopic mass (i.e. $^{35}Cl$; $^{79}Br$ etc.). Different systems were used, as described below, and these were equipped with, and were set up to run under, closely similar operating conditions. The operating conditions used are also described below.
System Description:
System 1 (Analytical System):
HPLC System: Waters 2795
Mass Spec Detector: Micromass Platform LC
PDA Detector: Waters 2996 PDA
System 2 (Preparative and Analytical System):
HPLC System: Waters Fractionlynx system
Mass Spec Detector: Waters ZQ
PDA Detector: Waters 2996 PDA
System 3 (Preparative and Analytical System):
HPLC System: Agilent 1100 system
Mass Spec Detector: LC/MSD
UV Detector: Agilent MWD
Operating Conditions:
Acidic Analytical Conditions:
Eluent A: $H_2O$ (0.1% Formic Acid)
Eluent B: $CH_3CN$ (0.1% Formic Acid)
Gradient: 5-95% eluent B over 3.5 minutes (over 15 minutes w/column 2)
Flow: 0.8 ml/min
Column 1: Phenomenex Synergi 4μ MAX-RP 80A, 2.0×50 mm
Column 2: Phenomenex Synergi 4μ MAX-RP 80A, 2.0× 150 mm
Basic Analytical Conditions:
Eluent A: $H_2O$ (10 mM $NH_4HCO_3$ buffer adjusted to pH=9.2 with $NH_4OH$)
Eluent B: $CH_3CN$
Gradient: 5-95% eluent B over 3.5 minutes
Flow: 0.8 ml/min
Column: Phenomenex Gemini 5μ 2.0×50 mm
MS Conditions (Waters Systems):
Capillary voltage: 3.6 kV (3.40 kV on ES negative)
Cone voltage: 25 V
Source Temperature: 120° C.
Scan Range: 125-800 amu
Ionisation Mode: ElectroSpray Positive, Negative or Positive & Negative
MS Conditions (Aqilent Systems):
Capillary voltage: 4000 V (3500 V on ES Negative)
Fragmentor/Gain: 150/1
Drying gas Temp/flow: 350° C./13.0 $Lmin^{-1}$
Nebuliser pressure: 50 psig
Scan Range: 125-800 amu
Ionisation Mode: ElectroSpray Positive or Negative The starting materials for each of the Examples are commercially available unless otherwise specified.

A. General Synthetic Methods

In the following general methods, the volumes stated may vary according to the scale of the reaction, as will be apparent to the skilled person.

Method A1

Amide Coupling (Acid Chloride Method)

A mixture of a carboxylic acid (1 equivalent) and thionyl chloride (1.5 equivalents) in benzene (or toluene) was stirred and held at reflux for 2 hours. Excess amine was added dropwise to the hot solution and the mixture stirred at room temperature for 15 minutes. Alternatively, the acid chloride could be isolated by evaporation and then re-dissolved in a 9:1 mixture of dichloromethane: triethylamine and the amine then added and the mixture stirred under nitrogen at room temperature for 1-18 hours. In either case, the mixture was diluted with ethyl acetate and extracted successively with water, saturated aqueous sodium bicarbonate and 2M hydrochloric acid. The organic layer was reduced to dryness in vacuo and the pure products were obtained either by trituration with ethyl acetate or by column chromatography on silica (eluting with mixtures of ethyl acetate in petroleum ether) or in a few cases by preparative HPLC/MS.

Method A2

Amide Coupling (EDC, HOBt Method)

A stirred solution of the acid (1 equivalent) in dichloromethane (10 ml) was treated successively with N-ethyl-N'-(3-dimethylaminopropyl)carbodiimide hydrochloride (1.2 equivalents), 1-hydroxybenzotriazole (1.2 equivalents) and the amine (1.5 equivalents) and the mixture was stirred at room temperature overnight. The mixture was washed successively with 2M hydrochloric acid and 2M sodium hydroxide, the organic layer was separated and the solvent removed in vacuo to afford the products. The products were either obtained pure or were purified by column chromatography on silica (eluting with mixtures of ethyl acetate in petroleum ether or methanol in ethyl acetate as appropriate).

Method A3

Anisole or Benzyl Ether Dealkylation (BBr$_3$ Method)

A stirred solution of the anisole or benzyl ether (1 equivalent) in dichloromethane at 0° C. was treated dropwise with a 1M solution of boron tribromide in dichloromethane (1.5 equivalents per group to be deprotected) and the mixture was stirred for 2 hours. The reaction was quenched by the addition of water and saturated aqueous sodium bicarbonate, the organic layer was separated and the solvent was removed in vacuo. The pure products were obtained either by trituration with diethyl ether or ethyl acetate or by column chromatography on silica (eluting with mixtures of ethyl acetate in petroleum ether).

Method A4

Amide Coupling (EDC, HOAt Method)

A stirred solution of the acid (1 equivalent) in dimethylformamide (5 ml) was treated successively with N-ethyl-N'-(3-dimethylaminopropyl)carbodiimide hydrochloride (1.2 equivalents), 1-hydroxy-7-aza-benzotriazole (1.2 equivalents) and the amine (1.5 equivalents) and the mixture was stirred at room temperature overnight. DMF was evaporated and crude dissolved in EtOAc and was washed successively with saturated sodium bicarbonate, the organic layer was separated and the solvent removed in vacuo. The products were either obtained pure or were purified by column chromatography on silica (eluting with mixtures of ethyl acetate in petroleum ether or methanol in ethyl acetate as appropriate).

Method A5

Hydrogenation

A stirred solution of protected derivative (1 equivalent) and a catalytic amount of 10% palladium on carbon (typically 30-50 mg) in ethanol (5-10 ml), methanol (5-10 ml) or methanol/DCM (3 ml/3 ml) was stirred at room temperature under an atmosphere of hydrogen for 2-16 hours. The catalyst was removed by filtration, washed with methanol (5 ml) and the solvent removed in vacuo to afford the products. Some required purification by flash chromatography, eluting typically with ether.

Method A6

Suzuki Coupling

The aryl bromide (1 equivalent, typically 0.5 mmol), boronic acid or potassium vinyl trifluoroborate derivative (1.2 equivalents) and caesium carbonate (3 equivalents) were dissolved in THF (10 ml) under nitrogen. 1,1'-Bis(diphenylphosphino)ferrocene]palladium(II) dichloride (0.1 equivalent) was added and then water (1 ml). The mixture begins to darken until black. The mixture was then heated at reflux under nitrogen until the reaction is complete (8-45 hrs). The mixture was cooled, diluted with DCM and magnesium sulphate added. The mixture was filtered and the solvent evaporated. The resulting residues were purified by flash chromatography in pet. ether/ether mixtures, and generally gave product in good yield (~60-80%).

Method A7

Resorcinol Mono-O-Methylation

Dimethyl sulphate (1 equivalent) was added to a stirred solution of the resorcinol (1 equivalent) and potassium carbonate (2.2 equivalents) in acetonitrile (10 ml per mmol of substrate) and the mixture was stirred at room temperature for 16 hours. The solvent was removed in vacuo, the residue partitioned between dichloromethane and water, the organic layer separated and the solvent removed in vacuo. The pure products were obtained either after column chromatography on silica (eluting with mixtures of petroleum ether and ethyl acetate) or by preparative HPLC/MS.

Method A8

Electrophilic Aromatic Fluorination 1-(Chloromethyl)-4-fluoro-1,4-diazoniabicyclo[2.2.2]octane bis(tetrafluoroborate) (1 equivalent) was added to a solution of the substrate (1 equivalent) in acetonitrile (15 ml per mmol of substrate) and the mixture was stirred at room temperature for 16 hours. The solvent was removed in vacuo and the residue was partitioned between ethyl acetate and water. The organic layer was separated and reduced to dryness in vacuo. The pure products were obtained either after column chromatography on silica (eluting with mixtures of petroleum ether and ethyl acetate) or by preparative HPLC/MS.

B. Synthesis of Carboxylic Acid Intermediates

Preparation B1

4-Hydroxy-3-isopropylbenzoic acid

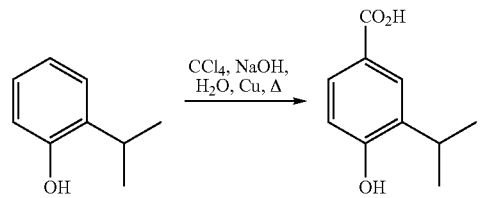

Carbon tetrachloride (28 ml, 0.26 mol) and copper powder (1.0 g) were added to a stirred solution of 2-isopropylphenol (27.2 g, 0.2 mol) in 50% aqueous sodium hydroxide (120 ml) and the mixture was held at reflux for 16 hours. Upon cooling the mixture was acidified to pH 2 or below by the addition of concentrated hydrochloric acid and was extracted with ethyl acetate. The organic layer was extracted with a saturated aqueous solution of sodium bicarbonate and the aqueous layer acidified to pH 2 or below by the very careful addition of concentrated hydrochloric acid. The solution was extracted with ethyl acetate, the organic layer was washed with water, separated and the solvent removed in vacuo to afford 4-hydroxy-3-isopropylbenzoic acid (12.5 g, 35%) as a bright red solid that was used without further purification. $^1$H NMR (DMSO-d$_6$) 12.36 (1H, br s), 10.13 (1H, br s), 7.73 (1H, d), 7.63 (1H, dd), 6.85 (1H, d), 3.22 (1H, m), 1.19 (6H, d). MS: [M–H]$^+$ 179.

Alternatively, if required, the crude product may be purified using a three step procedure involving di-benzylation [according to the conditions outlined below in Preparation B5 for the synthesis of methyl 5-acetyl-2,4-bis-benzyloxybenzoate (BnBr, K$_2$CO$_3$, MeCN, reflux)], column chromatography on silica to remove highly coloured impurities (eluting with 3-5% ethyl acetate in petroleum ether) and catalytic hydrogenation [according to Method A5 outlined above (10% Pd/C, EtOH, H$_2$)] to afford 4-hydroxy-3-isopropylbenzoic acid as a colourless solid.

Preparation B2

5-Ethyl-2-methoxybenzoic acid

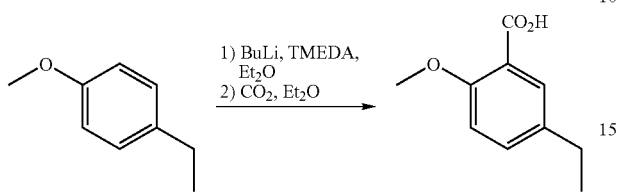

n-Butyl lithium (2.5M in hexanes, 38.5 ml, 100.0 mmol) was added dropwise under a nitrogen atmosphere to a stirred solution of 4-ethylanisole (11.7 g, 86.0 mmol) and N,N,N',N'-tetramethylethylenediamine (10 ml, 88.0 mmol) in anhydrous diethyl ether (100 ml) and the mixture was stirred and held at 30° C. for 16 hours. The mixture was cooled and poured slowly in to a mixture of excess solid carbon dioxide in anhydrous diethyl ether. Upon warming to room temperature the mixture was made basic by the addition of 2M sodium hydroxide, the aqueous layer was separated and acidified to pH 2 or below by the addition of concentrated hydrochloric acid. The mixture was extracted with diethyl ether, the organic layer separated and the solvent removed in vacuo to afford 5-ethyl-2-methoxybenzoic acid (5.7 g, 37%) as a pale yellow oil. $^1$H NMR (DMSO-d$_6$) 12.50 (1H, br s), 7.48 (1H, d), 7.33 (1H, dd), 7.03 (1H, d), 2.56 (2H, q), 1.17 (3H, q). MS: [M+H]$^+$ 181.

Preparation B3

2,4-Bis-benzyloxy-5-chloro-benzoic acid

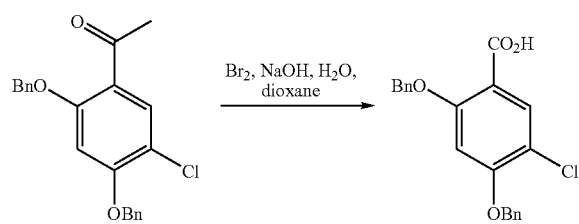

WO 2004/050087

1-(2,4-Bis-benzyloxy-5-chloro-phenyl)-ethanone [prepared as per WO 2004/0500087] (1.10 g, 3.0 mmol) was added to a stirred solution of sodium hydroxide (1.20 g, 30.0 mmol) in water (10 ml) and dioxane (10 ml). Bromine (1.44 g, 9.0 mmol) was added dropwise and the mixture stirred at room temperature for 3 hours. The dioxane was removed by evaporation in vacuo and the mixture acidified to pH 2 or below by the addition of 2M hydrochloric acid. The mixture was extracted with ethyl acetate, the organic layer separated and the solvent removed in vacuo to afford 2,4-bis-benzyloxy-5-chloro-benzoic acid (900 mg, 81%) as a pale yellow solid. $^1$H NMR (DMSO-d$_6$) 12.58 (1H, br s), 7.77 (1H, s), 7.55-7.30 (10H, m), 7.11 (1H, s), 5.31 (2H, s), 5.27 (2H, s). MS: [M+H]$^+$ 369.

Preparation B4

3-(1,2-Dimethyl-allyl)-4-hydroxy-benzoic acid

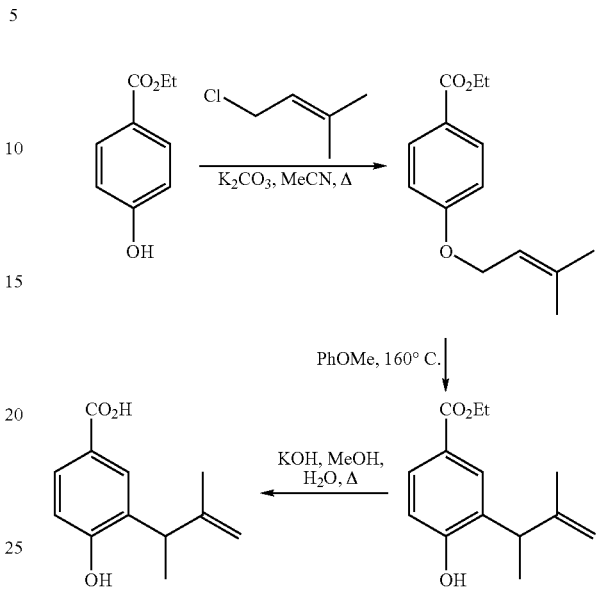

Ethyl 4-hydroxybenzoate (1.66 g, 10.0 mmol) and anhydrous potassium carbonate (2.07 g, 15.0 mmol) in acetonitrile (30 ml) was treated with 3-methyl-2-butenyl chloride (1.35 ml, 12.0 mmol) and the mixture was stirred and held at reflux for 3 hours. Upon cooling the solvent was removed in vacuo and the mixture partitioned between dichloromethane and water. The organics were separated and the solvent removed in vacuo to afford ethyl 4-(3-methyl-but-2-enyloxy)-benzoate (2.23 g, 95%) as a pale yellow liquid which was used without further purification. $^1$H NMR (DMSO-d$_6$) 7.89 (2H, d), 7.04 (2H, d), 5.44 (1H, t), 4.62 (2H, d), 4.28 (2H, q), 1.77 (3H, s), 1.73 (3H, s), 1.31 (3H, t). MS: [M+H]$^+$ 235.

Ethyl 4-(3-methyl-but-2-enyloxy)-benzoate (2.23 g, 9.53 mmol) was dissolved in anisole (8 ml) and the mixture stirred and held at reflux for 4 days. The solvent was removed in vacuo and the residue subjected to column chromatography on silica. Elution with 20% ethyl acetate in petroleum ether afforded ethyl 3-(1,2-dimethyl-allyl)-4-hydroxy-benzoate (600 mg, 27%) as a colorless solid. $^1$H NMR (DMSO-d$_6$) 10.32 (1H, br s), 7.67 (1H, dd), 7.62 (1H, s), 6.90 (1H, d), 4.90 (1H, s), 4.85 (1H, s), 4.25 (2H, q), 3.75 (1H, q), 1.61 (3H, s), 1.30 (3H, t), 1.26 (3H, d). MS: [M+H]$^+$ 235.

Ethyl 3-(1,2-dimethyl-allyl)-4-hydroxy-benzoate (600 mg, 2.56 mmol) was dissolved in methanol (20 ml), a solution of potassium hydroxide (560 mg, 10.0 mmol) in water (10 ml) was added and the mixture was stirred and held at reflux for 16 hours. Upon cooling the methanol was removed in vacuo and the solution acidified to pH 2 or below by the addition of 2M hydrochloric acid. The solution was extracted with dichloromethane, the organic layer was separated and the solvent was removed in vacuo to afford 3-(1,2-dimethyl-allyl)-4-hydroxy-benzoic acid (270 mg, 51%) as a colourless gum. $^1$H NMR (DMSO-d$_6$) 12.38 (1H, br s), 10.22 (1H, br s), 7.63 (2H, m), 6.88 (1H, d), 4.90 (1H, s), 4.87 (1H, s), 3.75 (1H, q), 1.60 (3H, s), 1.28 (3H, d). MS: [M–H]$^+$ 205.

Preparation B5

2,4-Bis-benzyloxy-5-isopropenyl-benzoic acid

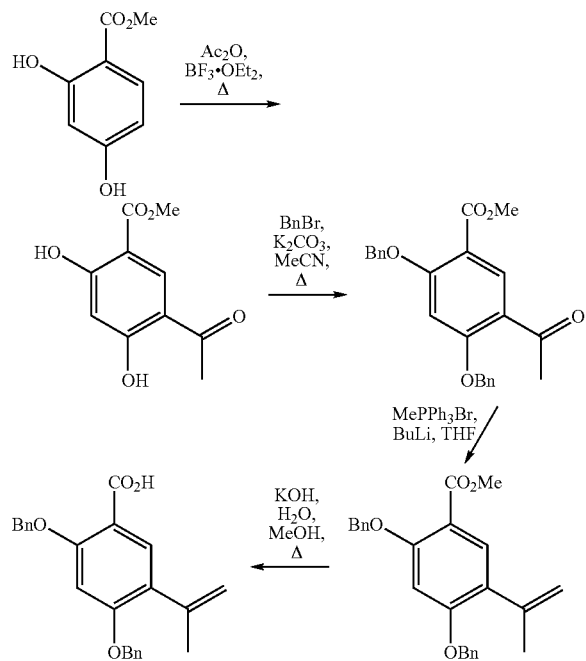

Acetic anhydride (3.06 g, 30.0 mmol) was added to methyl 2,4-dihydroxybenzoate (5.04 g, 30.0 mmol) in boron trifluoride diethyl etherate (7.6 ml) and the mixture was stirred and held at reflux for 3 hours and then allowed to cool to room temperature. Water (80 ml) was added and the mixture stirred at room temperature for 30 minutes. The resulting yellow solid was removed by filtration and sucked as dry as possible under vacuum. The solid was dissolved in dichloromethane and was washed with water, the organic layer was separated and the solvent removed in vacuo to afford methyl 5-acetyl-2,4-dihydroxybenzoate as a bright yellow solid (2.62 g, 42%) which was used without further purification. $^1$H NMR (DMSO-$d_6$) 12.58 (1H, s), 11.22 (1H, s), 8.33 (1H, s), 6.45 (1H, s), 3.90 (3H, s), 2.62 (3H, s). MS: [M+H]$^+$ 211.

Methyl 5-acetyl-2,4-dihydroxybenzoate (2.62 g, 12.48 mmol) was dissolved in acetonitrile (40 ml), anhydrous potassium carbonate (4.93 g, 35.7 mmol) was added and the stirred mixture was treated with benzyl bromide (5.09 g, 29.75 mmol) and held at reflux for 3 hours. Upon cooling the solvent was removed in vacuo and the mixture partitioned between water and dichloromethane. The organic layer was separated and the solvent removed in vacuo to afford methyl 5-acetyl-2,4-bis-benzyloxybenzoate (3.48 g, 71%) as a colourless solid which was dried at 50° C. in a vacuum oven and used without further purification. $^1$H NMR (DMSO-$d_6$) 8.21 (1H, s), 7.55 (4H, m), 7.43 (4H, m), 7.37 (2H, m), 7.04 (1H, s), 5.38 (4H, s), 3.79 (3H, s), 2.48 (3H, s). MS: [M+H]$^+$ 391.

A stirred suspension of methyltriphenylphosphonium bromide (1.96 g, 5.5 mmol) in anhydrous tetrahydrofuran (20 ml) at 0° C. under a nitrogen atmosphere was treated dropwise with n-butyl lithium (1.6 M in hexanes, 3.5 ml, 5.5 mmol) and the resulting bright yellow solution was stirred at 0° C. for 30 minutes. A solution of methyl 5-acetyl-2,4-bis-benzyloxybenzoate (1.95 g, 5.00 mmol) in anhydrous tetrahydrofuran (20 ml) was added dropwise and the resulting mixture was allowed to warm to room temperature and was stirred for 16 hours. Methanol (10 ml) was added and the solvent was removed in vacuo. The residues were partitioned between dichloromethane and water, the organic layer was separated and the solvent removed in vacuo to afford a brown gum that was purified by column chromatography on silica. Elution with 7% ethyl acetate in petroleum ether afforded methyl 2,4-bis-benzyloxy-5-isopropenyl-benzoate as a colourless solid (700 mg, 36%). $^1$H NMR (DMSO-$d_6$) 7.59 (1H, s), 7.52 (2H, d), 7.64-7.32 (8H, m), 6.97 (1H, s), 5.28 (2H, s), 5.22 (2H, s), 5.09 (1H, s), 5.04 (1H, s), 3.76 (3H, s), 2.02 (3H, s). MS: [M+H]$^+$ 389.

Methyl 2,4-bis-benzyloxy-5-isopropenyl-benzoate (700 mg, 1.80 mmol) was dissolved in methanol (20 ml), a solution of potassium hydroxide (286 mg, 5.1 mmol) in water (4 ml) was added and the mixture was stirred and held at reflux for 3 hours. Upon cooling the solvent was removed in vacuo and the mixture acidified to pH 2 or below by the addition of 2M hydrochloric acid. The mixture was extracted with dichloromethane, the organic layer was separated and the solvent removed in vacuo to afford 2,4-bis-benzyloxy-5-isopropenyl-benzoic acid (600 mg, 89%) as a colourless solid. $^1$H NMR (DMSO-$d_6$) 7.52 (2H, d), 7.47-7.29 (9H, m), 6.82 (1H, s), 5.20 (2H, s), 5.17 (2H, s), 5.06 (1H, s), 5.04 (1H, s), 2.03 (3H, s). MS: [M+H]$^+$ 375.

Preparation B6

2,4-Bis-benzyloxy-5-bromo-benzoic acid

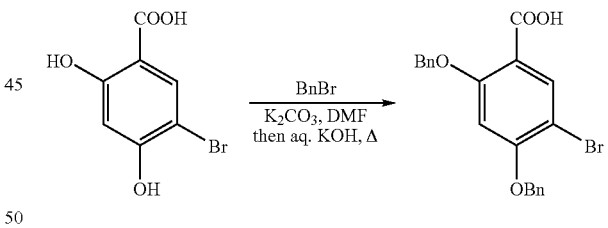

2,4-dihydroxy-5-bromobenzoic acid (5.16 g, 22.15 mmol) was dissolved in DMF (40 ml) and potassium carbonate (12.2 g) and benzyl bromide (8 ml) were sequentially added. The mixture was stirred at room temperature for 18 hours under nitrogen. An aqueous solution of potassium hydroxide (2 g) in water (25 ml) was then added, followed by methanol (50 ml) and the mixture heated to reflux with vigorous stirring for 24 hours. The mixture was then allowed to cool, was poured into 1N HCl (250 ml) and was then extracted with ether and then DCM. The combined organic layers were dried over magnesium sulphate and the solvent evaporated in vacuo. The resulting solid material was washed with P.E. and then Et$_2$O (3×50 ml) to yield pure product (5.2 g, 56%). $^1$H NMR (MeOH-$d_4$) 8.06 (1H, s), 7.51-7.30 (10H, m), 6.85 (1H, s), 5.22 (2H, s), 5.20 (2H, s). MS: [M+H]$^+$ 413.

Preparation B7

Synthesis of (Z)-4-benzyloxy-3-(1-methyl-propenyl)-benzoic acid

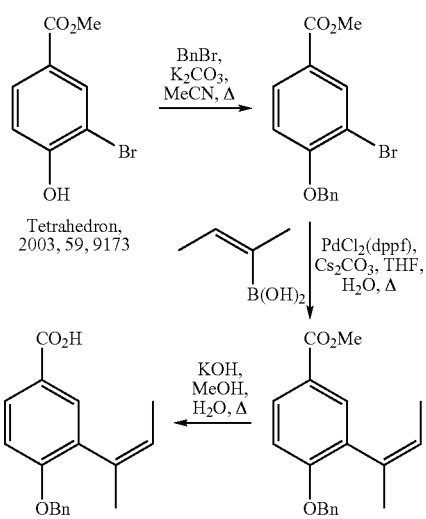

Methyl 3-bromo-4-hydroxybenzoate [prepared as per *Tetrahedron*, 2003, 59, 9173] (3.47 g, 15.0 mmol) was dissolved in acetonitrile (50 ml), anhydrous potassium carbonate (3.11 g, 22.5 mmol) was added and the stirred mixture was treated with benzyl bromide (3.08 g, 18.0 mmol) and held at reflux for 5 hours. Upon cooling the solvent was removed in vacuo and the mixture partitioned between water and dichloromethane. The organic layer was separated, the solvent removed in vacuo and the residue subjected to column chromatography on silica. Elution with 10% ethyl acetate in petroleum ether afforded methyl 4-benzyloxy-3-bromobenzoate (3.6 g, 75%) as a colourless solid. $^1$H NMR (DMSO-$d_6$) 8.12 (1H, d), 7.96 (1H, dd), 7.51 (2H, m), 7.43 (2H, t), 7.35 (2H, m), 5.32 (2H, s), 3.84 (3H, s).

Methyl 4-benzyloxy-3-bromobenzoate (1.61 g, 5.0 mmol), caesium carbonate (4.89 g, 15.0 mmol), (E)-2-buten-2-yl boronic acid (600 mg, 6.0 mmol) and [1,1'-bis(diphenylphosphino)ferrocenyl]palladium (II) chloride (204 mg, 0.25 mmol) were dissolved in anhydrous tetrahydrofuran (100 ml), water (10 ml) was added and the mixture was stirred and held at reflux under an atmosphere of nitrogen for 16 hours. Upon cooling the solvent was removed in vacuo and the mixture partitioned between dichloromethane and water. The organic layer was separated, the solvent removed in vacuo and the residue subjected to column chromatography on silica. Elution with 5% ethyl acetate in petroleum ether afforded methyl (Z)-4-benzyloxy-3-(1-methyl-propenyl)-benzoate (600 mg, 41%) as a colourless solid. $^1$H NMR (DMSO-$d_6$) 7.88 (1H, dd), 7.59 (1H, d), 7.40 (4H, m), 7.34 (1H, m), 7.23 (1H, d), 5.57 (1H, q), 5.21 (2H, s), 3.82 (3H, s), 1.94 (3H, s), 1.38 (3H, d).

Methyl (Z)-4-benzyloxy-3-(1-methyl-propenyl)-benzoate (592 mg, 2.0 mmol) was dissolved in methanol (20 ml), a solution of potassium hydroxide (336 mg, 6.0 mmol) in water (7 ml) was added and the mixture was stirred and held at reflux for 3 hours. Upon cooling the solvent was removed in vacuo and the mixture acidified to pH 2 or below by the addition of 2M hydrochloric acid. The mixture was extracted with dichloromethane, the organic layer was separated and the solvent removed in vacuo to afford (Z)-4-benzyloxy-3-(1-methyl-propenyl)-benzoic acid (460 mg, 82%) as a colourless solid. $^1$H NMR (DMSO-$d_6$) 7.85 (1H, dd), 7.57 (1H, d), 7.40 (4H, m), 7.34 (1H, m), 7.18 (1H, d), 5.57 (1H, q), 5.21 (2H, s), 1.96 (3H, s), 1.40 (3H, d). MS: [M+H]$^+$ 283.

Preparation B8

Synthesis of 2,4-bis-benzyloxy-5-tert-butyl-benzoic acid

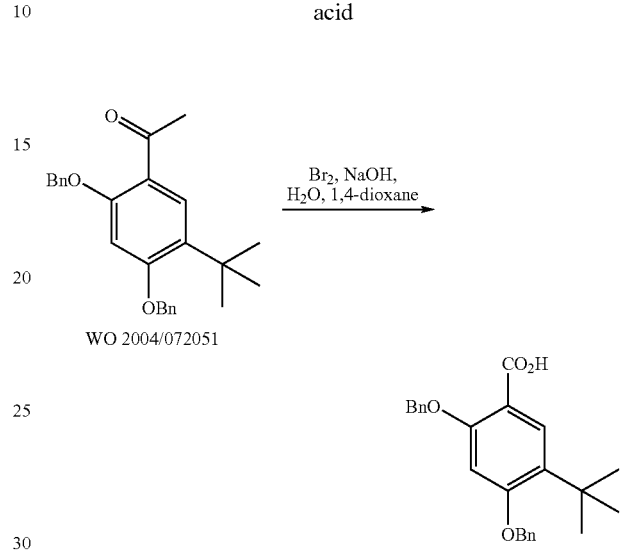

1-(2,4-Bis-benzyloxy-5-tert-butyl-phenyl)-ethanone [prepared as per WO 2004/072051] (2.02 g, 5.2 mmol) was dissolved in 1,4-dioxane (30 ml), a solution of sodium hydroxide (2.08 g, 52.0 mmol) in water (30 ml) was added and the mixture was stirred and treated dropwise with bromine (0.8 ml, 15.6 mmol). The resulting mixture was stirred at room temperature for 16 hours. The 1,4-dioxane was removed in vacuo and the mixture acidified to pH 2 or below by the addition of 2M hydrochloric acid. The mixture was extracted with ethyl acetate, the organic layer was separated, the solvent removed in vacuo and the residue subjected to column chromatography on silica. Elution with 30% ethyl acetate in petroleum ether afforded 2,4-bis-benzyloxy-5-tert-butyl-benzoic acid (1.6 g, 79%) as a pale yellow oil. $^1$H NMR (DMSO-$d_6$) 12.18 (1H, br s), 7.69 (1H, s), 7.52 (4H, t), 7.45-7.33 (6H, m), 6.93 (1H, s), 5.24 (2H, s), 5.23 (2H, s), 1.32 (9H, s). MS: [M+H]$^+$ 391.

Preparation B9

Synthesis of 2,4-bis-benzyloxy-5-isopropenyl-benzoic acid (Alternative Synthesis)

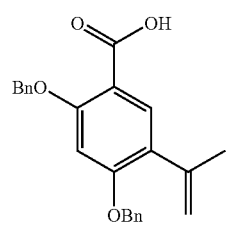 [SMILES: C=C(C)c1cc(C(=O)O)c(OCc2ccccc2)cc1OCc1ccccc1]

193

Step 1: Synthesis of 2,4-bis-benzyloxy-5-bromo-benzoic acid benzyl ester

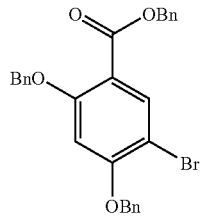 [SMILES: O=C(OCc1ccccc1)c1cc(Br)c(OCc2ccccc2)cc1OCc1ccccc1]

To a 10 L jacketed vessel, fitted with a flange lid containing stirrer, thermometer and dropping funnel, was charged acetone (2.5 L) followed by 5-bromo-2,4-dihydroxybenzoic acid (100 g, 0.43 mol) and potassium carbonate (356 g, 2.58 mol). To the stirring mixture at ambient was added benzyl bromide (185 mL, 1.55 mol) at a rate of ~20 ml/min. The mixture was heated at 60° C. for 18 h and then taken to 45° C. Water (1.5 L) was added and the mixture stirred for 30 min. The mixture was extracted with EtOAc (2×1 L) and the combined organic portions reduced in vacuo. To the residue was added $Et_2O$ (200 mL) and petroleum ether (1 L), the mixture stirred for 30 min and the solid formed collected by filtration and dried in vacuo to give the title compound (197.2 g) as a white solid.

Step 2: Synthesis of Potassium Isopropenyl Trifluoroborate

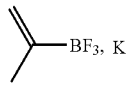

To a solution of 2-bromopropene (20 mL, 225 mmol) in anhydrous THF (250 mL) stirring under a $N_2$ atmosphere at −78° C. was added over 30 mins n-BuLi (2.5M in hexanes) (100 mL, 250 mmol) and the mixture stirred for 30 mins. To the mixture at −78° C. was slowly added triethyl borate (58 mL, 340 mmol) at a rate to ensure that the temperature of the reaction mixture did not exceed −65° C. The resulting solution was then stirred at −78° C. for 30 mins, allowed to slowly warm to ambient and stirred for a further 90 mins. Potassium hydrogen fluoride (105 g, 1.35 mol) was added to the mixture followed by water (250 mL). The mixture was stirred at ambient for 14 h and then reduced to dryness.

The procedure was repeated as above and following reduction to dryness the two residues were combined for further work-up.

To the combined residues was added acetone (800 mL), the mixture stirred for 1 h and then filtered. The solid collected was washed with acetone (200 mL) and the combined filtrates reduced in vacuo to give a solid. This solid was triturated with $Et_2O$ (250 mL) and then dried in vacuo to give the title compound (28.2 g) as a white solid.

194

Step 3: Synthesis of 2,4-bis-benzyloxy-5-isopropenyl-benzoic acid benzyl ester

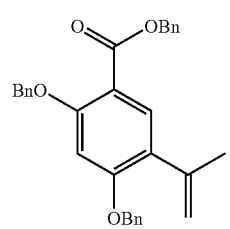 [SMILES: C=C(C)c1cc(C(=O)OCc2ccccc2)c(OCc2ccccc2)cc1OCc1ccccc1]

To a mixture of 2,4-bis-benzyloxy-5-bromo-benzoic acid benzyl ester (42.9 g, 85.7 mmol), potassium isopropenyl trifluoroborate (14.0 g, 95.2 mmol) and caesium carbonate (83.8 g, 257.1 mmol) in THF (800 mL) was added $Pd(PPh_3)_4$ (2.0 g) followed by water (150 mL). The mixture was heated at reflux for 72 h then allowed to cool to ambient. The mixture was reduced in vacuo to remove THF and then partitioned between water (500 mL) and EtOAc (300 mL). The organic portion was washed with brine, dried ($MgSO_4$), filtered and reduced in vacuo to give the title compound (40.9 g) as a brown oil.

Step 3A

Alternative Synthesis of 2,4-bis-benzyloxy-5-isopropenyl-benzoic acid benzyl ester A mixture of 2,4-bis-benzyloxy-5-bromo-benzoic acid benzyl ester (10.0 g, 20 mmol), potassium isopropenyl trifluoroborate (4.0 g, 27.2 mmol) and n-butylamine (6.0 mL, 60 mmol) in 2-propanol/water (2:1, 200 mL) was purged with $N_2$ for 5 minutes. To this mixture was added [1,1'-bis(diphenylphosphino)ferrocene]dichloropalladium(II) (816 mg, 1.09 mmol) and the mixture was heated at reflux for 20 h. The mixture was allowed to cool to ambient then diluted with water (400 mL) and extracted with EtOAc (2×300 mL). The combined organic extracts were washed with 1M aqueous HCl, brine, dried ($MgSO_4$), filtered through a plug of Celite and the filtrate reduced in vacuo to give the title compound (11.1 g) as a brown gum.

Step 4: Synthesis of 2,4-bis-benzyloxy-5-isopropenyl-benzoic acid

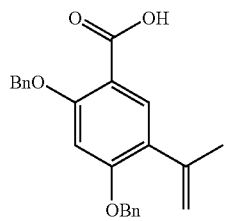

To a solution of 2,4-bis-benzyloxy-5-isopropenyl-benzoic acid benzyl ester (40.8 g, 87.9 mmol) in THF-MeOH-water (3:1:1, 300 mL total) was added lithium hydroxide (8.42 g, 352 mmol). The mixture was heated at 50° C. for 16 h, allowed to cool to ambient and then diluted with water (300 mL). The mixture was taken to pH~1 using conc. HCl (~30 mL) and then extracted with EtOAc (2×200 mL). The combined organic extracts were washed with brine, dried (MgSO$_4$), filtered and reduced in vacuo. The solid residue was taken up in P.E-MeOH (9:1, 300 mL total), the slurry stirred for 1 h at ambient and the solid collected by filtration. The solid was dried in vacuo to give the title compound (26.8 g) as an off-white solid. $^1$H NMR (400 MHz, DMSO-d$_6$) 12.30 (s, 1H), 7.61 (s, 1H), 7.53 (d, J=7.0 Hz, 2H), 7.47-7.31 (m, 8H), 6.94 (s, 1H), 5.23 (d, J=14.0 Hz, 4H), 5.08 (d, J=9.0 Hz, 2H), 2.04 (s, 3H).

Preparation B10

2,4-Bis-benzyloxy-5-isopropyl-benzoic acid

Step 1

Preparation of 1-(2-4-Bis-benzyloxy-phenyl)-ethanone

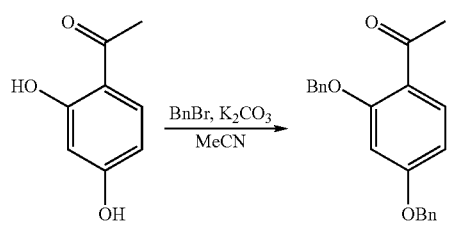

Material Inputs:

| S. No. | Item | Quantity | Eq. |
|---|---|---|---|
| 1. | 1,3 Dihydroxy acetophenone | 50 g | 1 |
| 2. | Benzyl bromide | 97 ml | 3 |
| 3. | Acetonitrile | 750 ml | 15 times |
| 4. | Potassium carbonate | 115 g | 3 |

1,3 Dihydroxy acetophenone (50 g) was placed in a 2 L single neck RB flask equipped with a reflux condenser and a guard tube. Acetonitrile (750 ml), potassium carbonate (115 g) and benzyl bromide (97 ml) were added and the mixture was heated at reflux (90° C.) for 16 hours. On completion, the acetonitrile was removed under reduced pressure. Water (200 ml) was added to the reaction mixture which was then extracted with ethyl acetate (500 ml). The organic layer was separated and dried over sodium sulphate. The solvent was removed under reduced pressure to give a residue which was washed n-hexane (600 ml) to give the product.

| Quantity of the product obtained | 105.1 g |
|---|---|
| Yield | 96.24% |
| Nature | Solid |
| Colour | Brown |

Step 2

Preparation of 2-4-Bis-benzyloxy-1-isopropenylbenzene

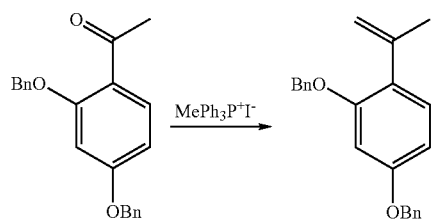 [SMILES: CC(=O)c1ccc(OCc2ccccc2)cc1OCc1ccccc1 ; C=C(C)c1ccc(OCc2ccccc2)cc1OCc1ccccc1]

Material Inputs:

| S. No. | Item | Quantity | Eq. |
|---|---|---|---|
| 1. | Compound of Step 1 | 20 g | 1 |
| 2. | n-BuLi (1.6 M) | 92.6 ml | 2.3 |
| 3. | Methyl-triphenylphosphonium iodide | 53.4 g | 2.2 |
| 4. | THF | 200 ml | 10 times |

Methyl-triphenylphosphonium iodide (53.4 g) and THF (100 ml) were introduced into a 1 L 3-neck RB flask equipped with an addition funnel and an inlet for nitrogen atmosphere and the mixture was cooled to 0° C. n-BuLi (92.6 ml) was added dropwise to the reaction mixture over a period of 15 min at 0° C. The reaction mixture was stirred for 10 min at 0° C. and further stirred at RT for 30 min. 1-(2-4-Bis-benzyloxy-phenyl)-ethanone (20 g) in THF (100 ml) was added dropwise to the reaction mixture over a period of 10 min at 0° C. and the reaction mixture was stirred overnight at RT. The progress of the reaction was monitored by TLC (10% EtOAc/n-hexane, product R$_f$~0.9). On completion, methanol (~100 ml) was added to the reaction mixture and the solvent was removed under reduced pressure to give a residue. n-Hexane (1 L) was added to the residue which was refluxed (75° C.) for 30 min. before filtering the mixture was through a Celite bed and washing the bed with n-hexane (500 ml). The solvent was removed under reduced pressure to give a residue, which was further purified by column chromatography (SiO$_2$ 2% EtOAc/n-hexane).

| Quantity of the product obtained | 12.5 g |
|---|---|
| Yield | 63.13% |
| Nature | Liquid. |
| Colour | Colorless |

Step 3

4-Isopropyl-benzene-1,3-diol

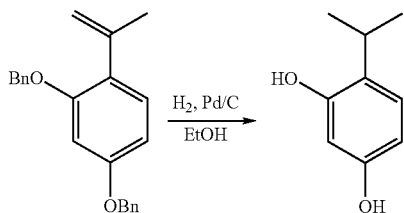

Material Inputs:

| S. No. | Item | Quantity | Eq. |
|---|---|---|---|
| 1. | 2-4-Bis-benzyloxy-1-isopropenylbenzene | 12.5 g | 1 |
| 2. | Ethanol | 125 ml | 10 times |
| 3. | 20% Palladium hydroxide | 2 g | |

To a mixture of 2-4-bis-benzyloxy-1-isopropenylbenzene (12.5 g) in ethanol (125 ml) in a 500 ml hydrogenation flask was added 20% palladium hydroxide (2 g). The reaction mixture was hydrogenated at 80 psi for 36 h. The progress of the reaction was monitored by TLC (10% EtOAc/n-hexane, product $R_f$~0.1). On completion, the reaction mixture was filtered through a bed of Celite and the bed was washed with ethanol (300 ml). The solvent was removed under reduced pressure to give a crude product, which was used as such for the next step.

| Quantity of the product obtained | 5.8 g (crude) |
|---|---|
| Nature | Solid. |
| Colour | Colourless. |

Step 4

1-(2,4-Dihydroxy-5-isopropyl-phenyl)-ethanone

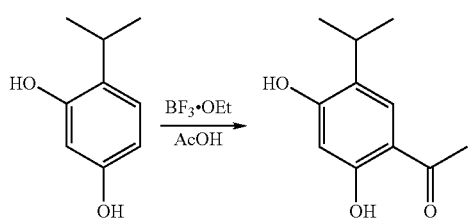

Material Inputs:

| S. No. | Item | Quantity | Eq. |
|---|---|---|---|
| 1. | 4-Isopropyl-benzene-1,3-diol | 5.8 g | 1 |
| 2. | Boron trifluoride etherate | 28.7 ml | 6 |
| 3. | Acetic acid | 4.55 ml | 2 |

4-Isopropyl-benzene-1,3-dial (5.8 g) and boron trifluoride etherate (28.7 ml) were introduced into a 250 ml single neck RB flask equipped with a reflux condenser and an inlet for nitrogen atmosphere stirred at RT for 10 min. Acetic acid (4.55 ml) was added to the reaction mixture and stirred at 90° C. for 16 h. On completion, 10% sodium acetate (300 ml) was added to the reaction mixture which was stirred at RT for 4 h before. The reaction mixture was extracted with ethyl acetate (300 ml) and washed with sat. sodium bicarbonate (100 ml) and the organic layer was dried over sodium sulphate. The reaction was monitored by TLC (10% EtOAc/n-hexane, product $R_f$~0.5). The solvent was removed under reduced pressure to give a residue, which was further purified by column chromatography (SiO$_2$, 10% EtOAc/n-hexane).

| Quantity of the product obtained | 3.2 g |
|---|---|
| Yield | 43.24% |
| Nature | Solid. |
| Colour | Colourless |

Step 5

1-(2,4-Bis-benzyloxy-5-isopropyl-phenyl)-ethanone

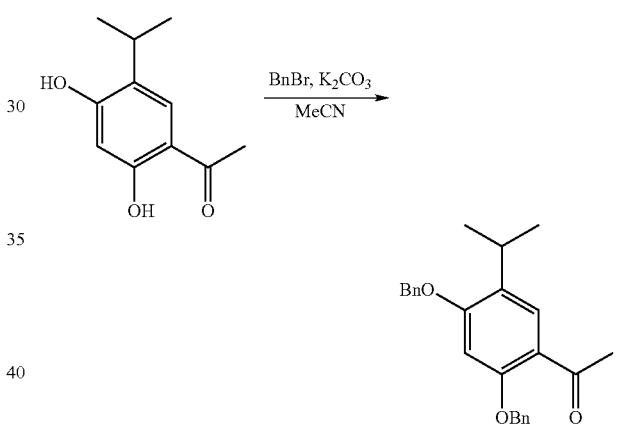

Material Inputs:

| S. No. | Item | Quantity | Eq. |
|---|---|---|---|
| 1. | 1-(2,4-Dihydroxy-5-isopropyl-phenyl)-ethanone | 3.2 g | 1 |
| 2. | Benzyl bromide | 5.89 ml | 3 |
| 3. | Potassium carbonate | 6.82 g | 3 |
| 4. | Acetonitrile | 60 ml | 20 times |

To a mixture of 1-(2,4-dihydroxy-5-isopropyl-phenyl)-ethanone (3.2 g), acetonitrile (60 ml) and potassium carbonate (10.6 g) in a 250 ml single neck RB flask equipped with a reflux condenser and a guard tube was added benzyl bromide (9.1 ml). The reaction mixture was refluxed (90° C.) for 16 h. The progress of the reaction was monitored by TLC (10% EtOAc/n-hexane, product $R_f$~0.5). On completion, acetonitrile was removed under reduced pressure. Water (100 ml) was added to the residue obtained and the resulting mixture was extracted with ethyl acetate (200 ml). The organic layer was dried over sodium sulphate. The solvent was removed under reduced pressure to give a residue to which n-hexane (150 ml) was added to give the product.

Step 6

2,4-Bis-benzyloxy-5-isopropyl-benzoic acid

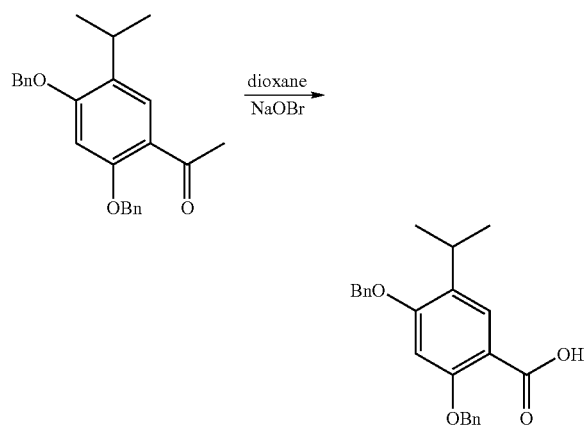

Material Inputs:

| S. No. | Item | Quantity |
|---|---|---|
| 1. | 1-(2,4-Bis-benzyloxy-5-isopropyl-phenyl)-ethanone | 7 g |
| 2. | Sodium hypobromide | 13 g in water 100 ml |
| 3. | Dioxane | 100 ml |

Procedure:

A mixture of a mixture of 1-(2,4-Bis-benzyloxy-5-isopropyl-phenyl)-ethanone (7 g) in dioxane (100 ml) in a 500 ml single neck RB flask equipped with a guard tube was cooled to 10° C. and sodium hypobromide [13 g in water (100 ml)] was added. The reaction mixture was stirred overnight at RT. The progress of the reaction was monitored by TLC (30% EtOAc/n-hexane, product $R_f$~0.5). On completion, sodium bisulphite (7 g) was added to the reaction mixture which was cooled to 0° C. The reaction mixture was then acidified with HCl (~10 ml) to pH~2, extracted with ethyl acetate (100 ml) and washed with water (25 ml). The organic layer was dried over sodium sulphate, and the solvent was removed under reduced pressure to give a residue, which was further purified by column chromatography (SiO₂, 10% EtOAc/n-hexane).

| Quantity of the product obtained | 3.4 g |
|---|---|
| Yield | 48.3% |
| Nature | Solid. |
| Colour | Colourless. |

| Quantity of the product obtained | 5.1 g |
|---|---|
| Yield | 83.6% |
| Nature | Solid. |
| Color | Colorless |

C. Synthesis of Isoindoline Intermediates

Preparation C1

Synthesis of 4,7-difluoroisoindoline

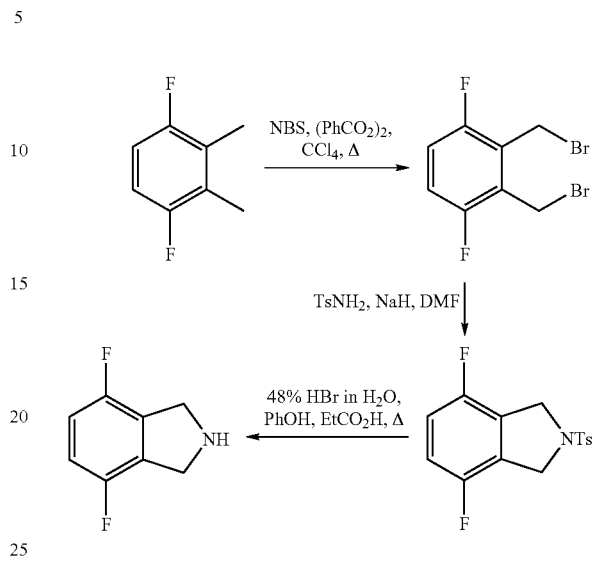

A mixture of 1,4-difluoro-2,3-dimethylbenzene (4.26 g, 30.0 mmol), N-bromosuccinimide (10.68 g, 60.0 mmol) and dibenzoyl peroxide (75 wt % in water, 120 mg) in carbon tetrachloride (50 ml) was stirred and held at reflux for 16 hours. Upon cooling to room temperature the mixture was filtered, the solids washed with carbon tetrachloride (10 ml), the organic extracts combined and the solvent removed in vacuo to afford 2,3-bis-bromomethyl-1,4-difluorobenzene (9.0 g, 100%) as a pale yellow liquid that solidified upon standing. $^1$H NMR (DMSO-$d_6$) 7.36 (2H, dd), 4.78 (4H, s).

A solution of 4-toluenesulphonamide (2.44 g, 14.28 mmol) in N,N-dimethylformamide (10 ml) was added dropwise to a vigourously stirred suspension of sodium hydride (1.2 g, 60 wt % in mineral oil, 30.0 mmol) in anhydrous N,N-dimethylformamide (60 ml). The mixture was stirred at room temperature for 1 hour, at 110° C. for 1 hour and was then cooled to 60° C. and a solution of 2,3-bis-bromomethyl-1,4-difluorobenzene (4.28 g, 14.28 mmol) in N,N-dimethylformamide (30 ml) was added dropwise. The mixture was stirred at 60° C. for 1 hour and then at room temperature for 16 hours. The solvent was removed in vacuo and the residue partitioned between dichloromethane and 1M hydrochloric acid. The organic layer was separated, washed with 5% aqueous potassium carbonate solution, the organics were separated and the solvent removed in vacuo. The residue was rinsed with diethyl ether, filtered and the solids sucked dry under reduced pressure to afford 4,7-difluoro-2-(toluene-4-sulfonyl)isoindoline (2.46 g, 56%) as a pale tan solid. $^1$H NMR (DMSO-$d_6$) 7.82 (2H, d), 7.43 (2H, d), 7.15 (2H, dd), 4.66 (4H, s), 2.36 (3H, s). MS: [M+H]$^+$ 310.

A mixture of 4,7-difluoro-2-(toluene-4-sulfonyl)isoindoline (2.36 g, 7.64 mmol), phenol (2.36 g, 25.11 mmol), 48% hydrogen bromide in water (20 ml) and propionic acid (4 ml) was stirred and held at reflux for 6 hours. Upon cooling to room temperature water (50 ml) was added and the mixture extracted with diethyl ether (2×100 ml). The aqueous layer was basified by the addition of 2M sodium hydroxide and was extracted with diethyl ether (3×100 ml). The combined extracts were evaporated to dryness in vacuo to afford 4,7-difluoroisoindoline (586 mg, 50%) as a brown oil that solidified upon standing. $^1$H NMR (DMSO-$d_6$) 7.06 (2H, dd), 4.12 (4H, s). MS: [M+H]$^+$ 156.

Preparation C2

Synthesis of 5-hydroxyisoindoline hydrobromide

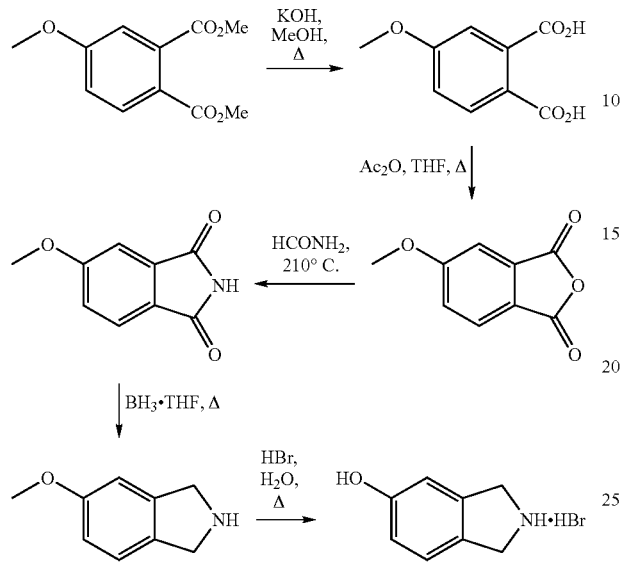

A solution of dimethyl 4-methoxyphthalate (36.75 g, 0.16 mol) in methanol (100 ml) was treated with a solution of potassium hydroxide (28.0 g, 0.5 mol) in water (50 ml) and the mixture was stirred and held at reflux for 4 hours. Upon cooling to room temperature the methanol was removed in vacuo and the mixture acidified to pH 2 or below by the addition of 5M hydrochloric acid. The solid material was filtered off, washed with water and sucked dry under reduced pressure overnight to afford 4-methoxyphthalic acid (31.8 g, 99%) as an off white solid. $^1$H NMR (DMSO-$d_6$) 12.90 (2H, br s), 7.74 (1H, d), 7.12-7.05 (2H, m), 3.84 (3H, s). MS: [M+H]$^+$ 197.

Acetic anhydride (40 ml) was added to a mixture of 4-methoxyphthalic acid (30.8 g, 0.16 mol) in anhydrous tetrahydrofuran (150 ml) and the mixture was stirred and held at reflux for 4 hours. Upon cooling to room temperature the solvent was removed in vacuo to afford 4-methoxyphthalic anhydride (27.8 g, 99%) as an off white solid. $^1$H NMR (DMSO-$d_6$) 8.02 (1H, d), 7.59 (1H, d), 7.49 (1H, dd), 3.97 (3H, s). MS: [M+H]$^+$ 179.

A mixture of 4-methoxyphthalic anhydride (27.8 g, 0.16 mol) and formamide (175 ml) was stirred and held at 210° C. for 5 hours and was then allowed to cool to room temperature overnight. The solid material was filtered off, washed sequentially with water (100 ml), 50% aqueous acetone (50 ml) and diethyl ether (200 ml) and sucked dry under reduced pressure to afford 4-methoxyphthalimide (21.3 g, 77%) as a pale yellow solid. $^1$H NMR (DMSO-$d_6$) 11.15 (1H, br s), 7.74 (1H, d), 7.33-7.28 (2H, m), 3.92 (3H, s).

A stirred solution of 4-methoxyphthalimide (21.3 g, 0.12 mol) in anhydrous tetrahydrofuran (425 ml) at 0° C. was treated dropwise with a solution of borane in tetrahydrofuran (1M, 340 ml, 0.34 mol) and the resulting mixture was stirred and held at reflux for 16 hours. The mixture was cooled to 0° C., methanol (150 ml) was added dropwise followed by 5M hydrochloric acid (150 ml) and the mixture was stirred and held at reflux for 3 hours. Upon cooling to room temperature the organic solvent was removed in vacuo, the mixture was diluted with water (750 ml) and was extracted with dichloromethane (3×750 ml). The aqueous layer was basified to pH 12 or above by the addition of 5M sodium hydroxide, extracted with dichloromethane (3×750 ml) and the combined extracts were evaporated to dryness in vacuo to afford 5-methoxyisoindoline (8.34 g, 47%) as a brown oil. $^1$H NMR (DMSO-$d_6$) 7.13 (1H, d), 6.84 (1H, d), 6.74 (1H, dd), 4.05 (2H, s), 4.01 (2H, s), 3.73 (3H, s). MS: [M+H]$^+$ 150.

5-Methoxyisoindoline (8.34 g, 55.97 mmol) in 48% aqueous hydrobromic acid (100 ml) was stirred and held at reflux for 16 hours. Upon cooling to room temperature the solvent was removed in vacuo to afford 5-hydroxyisoindoline hydrobromide (11.32 g, 93%) as a tan solid. $^1$H NMR (DMSO-$d_6$) 9.63 (1H, br s), 9.32 (2H, br s), 7.18 (1H, d), 6.79 (1H, d), 6.76 (1H, dd), 4.42 (2H, t), 4.38 (2H, t). MS: [M+H]$^+$ 136.

Preparation C3

Synthesis of 5-chloro-2,3-dihydro-1H-isoindole

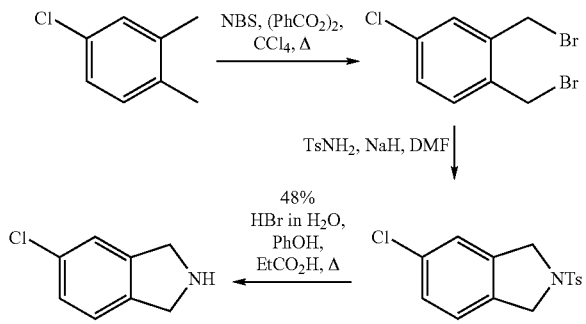

A mixture of 3,4-dimethylchlorobenzene (10 g, 71.1 mmol), N-bromosuccinimide (25 g, 142.2 mmol), and benzoyl peroxide (0.147 g, 0.6 mmol), was refluxed in 80 ml of carbon tetrachloride for 18 hours. After cooling, the insoluble material was filtered off and washed with a small amount of carbon tetrachloride. The filtrate and the washings were combined and concentrated under reduced pressure to obtain 20 g of 1,2-bis-bromomethyl-4-chloro-benzene as a pale yellow oil product as a major component.

To a suspension of 60% sodium hydride (3.0 g, 0.125 mmol) in mineral oil in 80 ml of anhydrous DMF (100 ml) was dropwise added a solution of para-toluene sulphonamide (5.6 g, 32.60 mmol) in 30 ml of DMF over 1 hour with vigorous stirring at room temperature. After the addition, the mixture was stirred for 1 hour at room temperature and another 1 hour heating at 90° C. To this mixture was added dropwise a solution of 1,2-bis-bromomethyl-4-chloro-benzene (4 g, 14.18 mmol) in 20 ml of anhydrous DMF at 60° C. and then stirred overnight at room temperature. The resultant mixture was poured onto ice and the resulting precipitate was collected by filtration. The precipitate was washed with 1N hydrochloric acid, 5% sodium carbonate and brine then dried (MgSO4), filtered and evaporated to give 2.8 g of 5-Chloro-2-(toluene-4-sulphonyl)-2,3-dihydro-1H-isoindole as a pale yellow solid. MS: [M+H]$^+$ 308

1.0 g of 2-(p-toluensulphonyl)-5-chloroisoindoline and 1.0 g of phenol were added to a mixture of 8 ml of 48% hydrobromic acid and 1.4 ml of propionic acid, and then mixture was heated at reflux for 6 hours. The resultant reaction mixture was diluted with 10 ml of water and extracted twice with 50 ml of ethyl acetate. The water layer was basified with aqueous sodium hydroxide solution and extracted with ethyl acetate three times. The extract was concentrated and the crude product was diluted with 4N HCl/dioxane and stirred for 15 minutes before evaporating the HCl and then re-evaporating with toluene three times to give 0.3 g of 5-chloro-2,3-dihydro-1H-isoindole hydrochloride as a black solid. MS: [M+H]+ 153-15

Preparation C4

Synthesis of 5-chloro-6-methoxy-2,3-dihydro-1H-isoindole

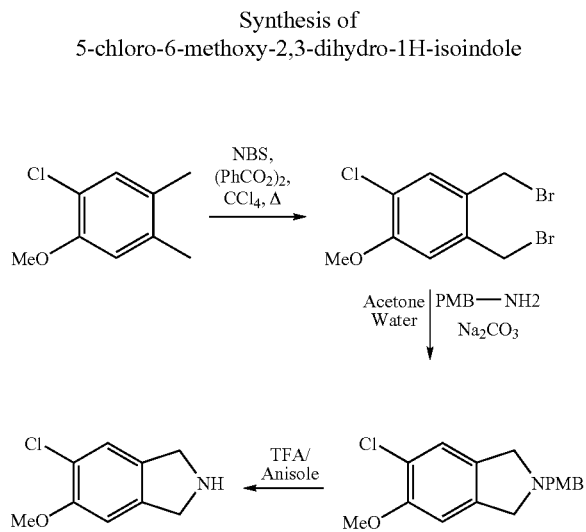

A mixture of 1-chloro-2-methoxy-4,5-dimethyl-benzene (3 g, 17.6 mmol), N-bromosuccinimide (6.3 g, 35.3 mmol), and benzoyl peroxide (0.100 g, 0.41 mmol) in carbon tetrachloride (40 ml) was heated at reflux for 18 hours. After cooling, the insoluble material was removed by filtration, washed with a small amount of carbon tetrachloride and the filtrate evaporated to give 1,2-bis-bromomethyl-4-chloro-5-methoxy-benzene as an oil product as a major component. MS: [M+H]+ 329

A solution of 4-methoxybenzylamine (2.4 g, 17.6 mmol) in acetone (110 ml) was added dropwise to a mixture of 1,2-bis-bromomethyl-4-chloro-5-methoxy-benzene (assumed theoretical, 17.6 mmol) and Na2CO3 (12 g, 114 mmol) in acetone/water (10 ml:12.5 ml) then stirred at room temperature for 2 hours and concentrated in vacuo. The crude material was dissolved in ethyl acetate and extracted with 2N HCl. The aqueous layer was neutralized with sodium carbonate, extracted with ethyl acetate (×2), dried (MgSO4) and evaporated under vacuum to give 5-chloro-6-methoxy-2-(4-methoxy-benzyl)-2,3-dihydro-1H-isoindole (0.8 g, 2.6 mmol) as a brown gum. MS: [M+H]+ 304

A solution of 5-chloro-6-methoxy-2-(4-methoxy-benzyl)-2,3-dihydro-1H-isoindole (600 mg) and anisole (0.3 ml) in trifluoroacetic acid (6 ml) was heated at 180° C. (50 W) for 40 minutes in a CEM discover microwave synthesiser. The reaction mixture was evaporated and re-evaporated with toluene. The crude material was partitioned between DCM and water, the aqueous layer washed with DCM (×3) then evaporated and re-evaporated with toluene to give 5-chloro-6-methoxy-2,3-dihydro-1H-isoindole (256 mg) as green crystals. MS: [M+H]+ 184

Preparation C5

Synthesis of 2,3-dihydro-1H-isoindol-5-ylamine trifluoroacetate

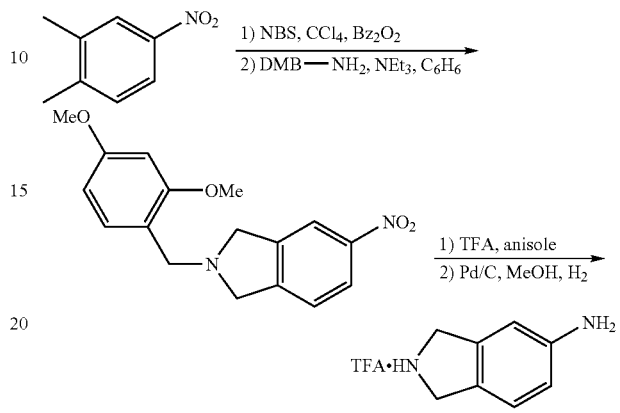

A solution of 4-nitro-o-xylene (15.1 g; 0.1 mol) in carbon tetrachloride (150 ml) was treated with N-bromosuccinimide (36 g; 0.2 mol) followed by benzoyl peroxide (1 g) then heated at reflux overnight. The reaction was allowed to cool to ambient temperature, filtered and the filtrate evaporated to give 32 g of crude 1,2-bis-bromomethyl-4-nitro-benzene as a mobile oil. The crude product was dissolved in benzene (200 ml) then treated dropwise over 30 minutes with a solution of 2,4-dimethoxybenzylamine (15 ml) and triethylamine (27.85 ml) in benzene (100 ml) then heated at 80° C. for 3 hours. The reaction was cooled, washed with water followed by saturated sodium bicarbonate. The organics were extracted with 2M HCl (2×150 ml) then combined aqueous basified with 2M NaOH and extracted with EtOAc (×2). The combined EtOAc layer was dried (MgSO4), evaporated then purified by flash column chromatography eluting with EtOAc/P.E. (1:3-1.2-1:1). Product containing fraction were combined and evaporated to give 10.15 g of 2-(2,4-dimethoxy-benzyl)-5-nitro-2,3-dihydro-1H-isoindole as a brown solid. $^1$H NMR (DMSO-$d_6$) 8.12 (2H, m), 7.50 (1H, d), 7.25 (1H, d), 6.55 (1H, d), 6.52 (1H, dd), 3.93 (4H, s), 3.80 (3H, s), 3.78 (2H, s), 3.75 (3H, s).

2-(2,4-dimethoxy-benzyl)-5-nitro-2,3-dihydro-1H-isoindole (13 g) in TFA (18 ml) was treated with anisole (6 ml) then heated in a CEM microwave synthesiser at 120° C. (30 Watts) for 20 minutes (carried out batch wise, 6 times). The reaction mixture was evaporated in vacuo and the residue partitioned between DCM and water. The water layer was separated, washed with DCM (×3) then evaporated and re-evaporated with toluene/MeOH (×3) to give 9.8 g of 5-nitro-2,3-dihydro-1H-isoindole trifluoroacetic acid salt as a beige solid. $^1$H NMR (DMSO-$d_6$) 9.85 (2H, br s), 8.32 (1H, d), 8.25 (1H, dd), 7.70 (1H, d), 4.68 (2H, s), 4.65 (2H, s).

A mixture of 5-nitro-2,3-dihydro-1H-isoindole trifluoroacetic acid salt (9.8 g) and 10% palladium on carbon (1 g) in methanol (75 ml) was hydrogenated at room temperature and pressure for 16 hours. The reaction was filtered through Celite™, the filtrate evaporated and re-evaporated with toluene to give 8.76 g of 2,3-dihydro-1H-isoindol-5-ylamine mono trifluoroacetic acid salt as a dark brown solid. $^1$H NMR (DMSO-$d_6$) 9.45 (2H, br s), 7.05 (1H, d), 6.60 (2H, m), 5.35 (2H, br s), 4.40 (2H, s), 4.30 (2H, s).

Preparation C6

Synthesis of
5-morpholin-4-ylmethyl-2,3-dihydro-1H-isoindole
ditrifluoroacetate

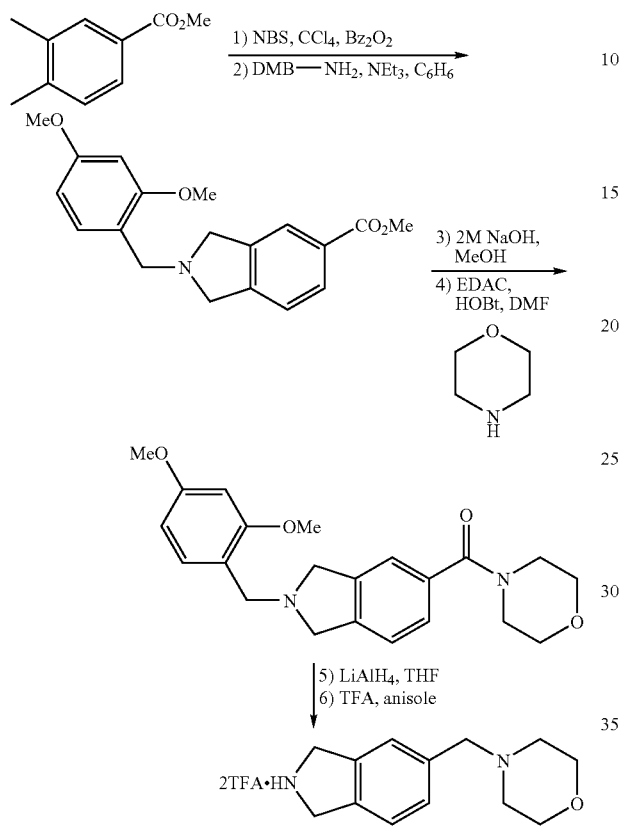

Steps 1 and 2 were carried out in a manner analogous to that described in Preparation C5 using methyl 3,4-dimethylbenzoate as the starting material.

A mixture of 2-(2,4-dimethoxybenzyl)-2,3-dihydro-1H-isoindole-5-carboxylic acid methyl ester (4.65 g; 14.2 mmol) and lithium hydroxide monohydrate (660 mg; 1.1 equiv.) in 4:1:1 THF-MeOH—H$_2$O (60 ml) was stirred at room temperature overnight. A further 170 mg of base were added and stirring continued for 7 hours. The reaction was evaporated then re-evaporated with MeOH/toluene (×2). A mixture of the crude 2-(2,4-dimethoxy-benzyl)-2,3-dihydro-1H-isoindole-5-carboxylic acid lithium salt (1.5 g; 4.7 mmol), morpholine (820 µl; 2 equiv.), EDAC (1.1 g; 1.2 equiv.) and HOBt (760 mg; 1.2 equiv.) in DMF (25 ml) was stirred at room temperature overnight then evaporated in vacuo. The residue was partitioned between EtOAc and saturated NaHCO$_3$, the EtOAc layer was separated, washed with brine, dried (MgSO$_4$) and evaporated. Purification by flash column chromatography (2% then 5% MeOH/DCM as eluant) gave 1.1 g of [2-(2,4-dimethoxybenzyl)-2,3-dihydro-1H-isoindol-5-yl]-morpholin-4-yl-methanone as a red/brown gum. $^1$H NMR (DMSO-d$_6$) 7.30-7.18 (4H, m), 6.56 (1H, d), 6.52 (1H, dd), 3.85 (4H, s), 3.78 (5H, m), 3.73 (3H, s).

A solution of [2-(2,4-dimethoxybenzyl)-2,3-dihydro-1H-isoindol-5-yl]-morpholin-4-yl-methanone (1.05 g; 2.75 mmol) in dry THF (20 ml) under a nitrogen atmosphere was treated with 1M lithium aluminum hydride solution then stirred at room temperature overnight. The reaction was quenched by the cautious addition of saturated sodium sulphate solution, then diluted with EtOAc (40 ml), filtered through Celite™ and evaporated. Purification by flash column chromatography (2% then 5% MeOH/DCM as eluant) gave 340 mg of 2-(2,4-dimethoxybenzyl)-5-morpholin-4-yl-methyl-2,3-dihydro-1H-isoindole as a pale brown gum.

A mixture of 2-(2,4-dimethoxybenzyl)-5-morpholin-4-yl-methyl-2,3-dihydro-1H-isoindole (340 mg) and anisole (350 µl) in trifluoroacetic acid (1.5 ml) was heated at 130 C in a CEM microwave synthesiser for 1 hour then evaporated and re-evaporated with toluene. The residue was partitioned between DCM and water. The water layer was separated, washed with DCM (×3) then evaporated and re-evaporated with toluene/MeOH (×3) to give 422 mg of 5-morpholin-4-ylmethyl-2,3-dihydro-1H-isoindole ditrifluoroacetate as a brown gum. $^1$H NMR (DMSO-d$_6$) 10.30 (1H, br s), 9.60 (2H, br s), 7.55-7.45 (3H, m), 4.45 (4H, s), 4.45-4.30 (2H, m), 4.20-3.88 (2H, m), 3.70-3.55 (2H, m), 3.30-3.00 (4H, m).

Preparation C7

Synthesis of
ethyl-2,3-dihydro-1H-isoindole-5-carboxylate
trifluoroacetate

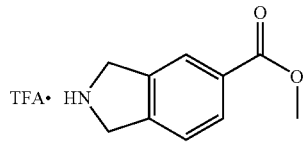

A solution of 2-(2,4-dimethoxy-benzyl)-2,3-dihydro-1H-isoindole-5-carboxylic acid methyl ester (215 mg) and anisole (200 µl) in 1 ml of TFA was heated at 140° C. for 30 minutes in a CEM discover microwave synthesiser. The reaction was partitioned between water and DCM, the water layer was separated, washed with DCM then evaporated and re-evaporated with toluene/MeOH (×2) to give 105 mg of the title compound. $^1$H NMR (DMSO-d$_6$) 9.70 (2H, br s), 8.02 (1H, s), 8.98 (1H, d), 7.57 (1H, d), 4.60 (2H, s), 4.56 (2H, s), 3.89 (3H, s).

Preparation C8

4-Hydroxy-2-(4-methoxy-benzyl)-isoindole-1,3-dione

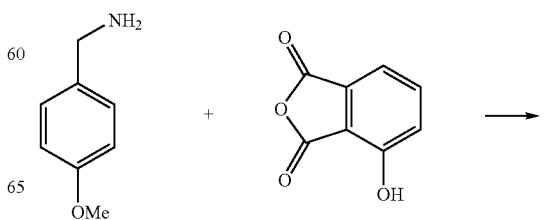

-continued

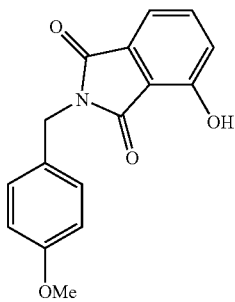

A mixture of 3-hydroxyphthalic anhydride (543 mg, 3.31 mmol), 4-methoxybenzylamine (0.43 mL, 3.31 mmol) and acetic acid (3 mL) was heated at 100° C. for 4 hours. The mixture was allowed to cool and diluted with water (20 mL). The white solid was collected by filtration, washed well with water and dried to give the title compound (760 mg, 81%). $^1$H NMR (DMSO-d$_6$) 11.03 (1H, s), 7.61 (1H, dd), 7.28 (1H, d), 7.23-7.19 (3H, m), 6.89-6.86 (2H, m), 4.63 (2H, s), 3.71 (3H, s). MS: [M−H$^+$] 282.

Preparation C9

4-Hydroxy-2-(2,4-dimethoxy-benzyl)-isoindole-1,3-dione

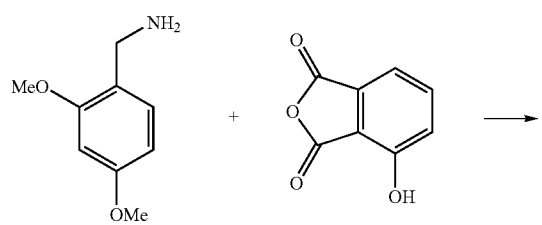

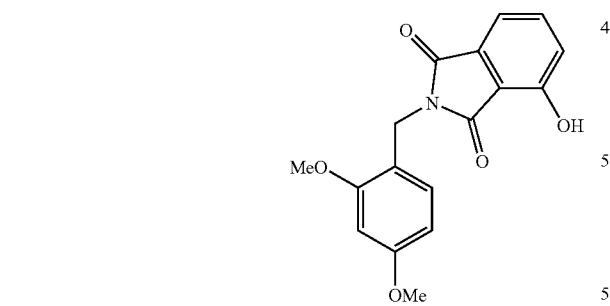

A mixture of 3-hydroxyphthalic anhydride (1.24 g, 7.6 mmol), 2,4-dimethoxybenzylamine (1.14 mL, 7.6 mmol) and acetic acid (5 mL) was heated at 80° C. for 24 hours. The mixture was allowed to cool and diluted with water (20 mL). The white solid was collected by filtration, washed well with water and dried to give the title compound (1.73 g, 73%). $^1$H NMR (DMSO-d$_6$) 11.00 (1H, s), 7.62 (1H, dd), 7.29 (1H, d), 7.21 (1H, d), 6.90 (1H, d), 6.56 (1H, d), 6.43 (1H, dd), 4.59 (2H, s), 3.79 (3H, s), 3.72 (3H, s). MS: [M−H$^+$] 314.

Preparation C10

2-(4-Methoxy-benzyl)-4-[2-(2-methoxy-ethoxy)-ethoxy]-isoindole-1,3-dione

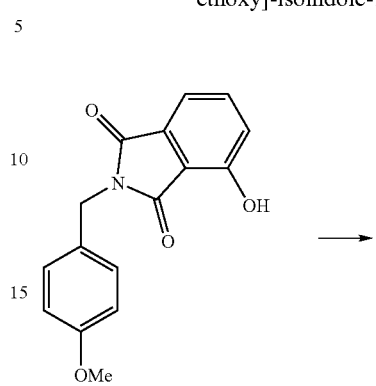

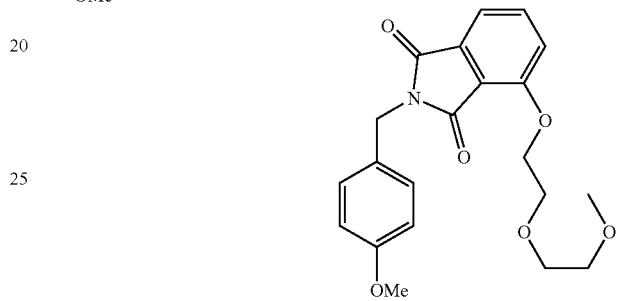

1-(2-Bromo-ethoxy)-2-methoxy-ethane (107 mg, 0.58 mmol) was added to a suspension of 4-hydroxy-2-(4-methoxy-benzyl)-isoindole-1,3-dione (150 mg, 0.53 mmol) and potassium carbonate (200 mg, 1.4 mmol) in DMF (2 mL). After 3.5 hours, a catalytic amount of potassium iodide was added. After a further 17 hours, the mixture was warmed to 60° C. After 3 hours, an additional amount of 1-(2-bromo-ethoxy)-2-methoxy-ethane (20 mg, 0.11 mmol) was added and the mixture maintained at 60° C. for a further 20 hours. The mixture was concentrated in vacuo then the residue was taken up in ethyl acetate and washed with potassium carbonate solution and brine. The organic phase was dried (MgSO$_4$) and concentrated to give the title compound as a yellow oil (149 mg, 73%). $^1$H NMR (methanol-d$_4$) 7.71 (1H, t), 7.43-7.40 (2H, m), 7.31-7.27 (2H, m), 6.87-6.83 (2H, m), 4.71 (2H, s), 4.37-4.34 (2H, m), 3.92-3.89 (2H, m), 3.77-3.74 (5H, m), 3.55-3.53 (2H, m), 3.33 (3H, s). MS: [M+H]$^+$ 386.

Preparation C11

2-(2,4-Dimethoxy-benzyl)-4-(2-dimethylamino-ethoxy)-isoindole-1,3-dione

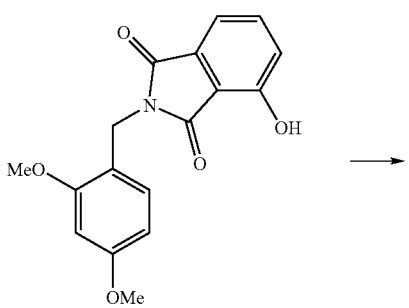

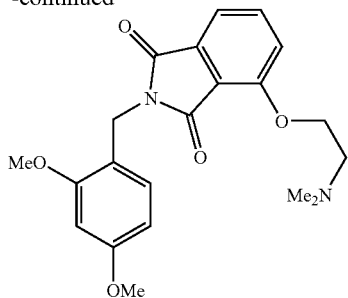

A mixture of 2-(2,4-dimethoxy-benzyl)-4-hydroxy-isoindole-1,3-dione (317 mg, 1.01 mmol), 2-dimethylaminoethyl chloride hydrochloride (160 mg, 1.11 mmol) and potassium carbonate (350 mg, 2.5 mmol) in DMF (4 mL) was heated at 60° C. for 18 hours. The mixture was concentrated in vacuo, taken up in ethyl acetate and extracted twice with 1N hydrochloric acid. The aqueous extracts were made basic with solid potassium carbonate and extracted with ethyl acetate (×2). The combined organic extracts were washed with brine, dried (MgSO$_4$) and concentrated to give the title compound (236 mg, 61%) as an off-white solid. $^1$H NMR (methanol-d$_4$) 7.73 (1H, t), 7.44-7.40 (2H, m), 7.02 (1H, d), 6.51 (1H, d), 6.42 (1H, dd), 4.72 (2H, s), 4.33 (2H, t), 3.80 (3H, s), 3.76 (3H, s), 2.87 (2H, t), 2.40 (6H, s). MS: [M+H]$^+$ 385.

Preparation C12

2-(2,4-Dimethoxy-benzyl)-4-(3-morpholin-4-yl-propoxy)-isoindole-1,3-dione

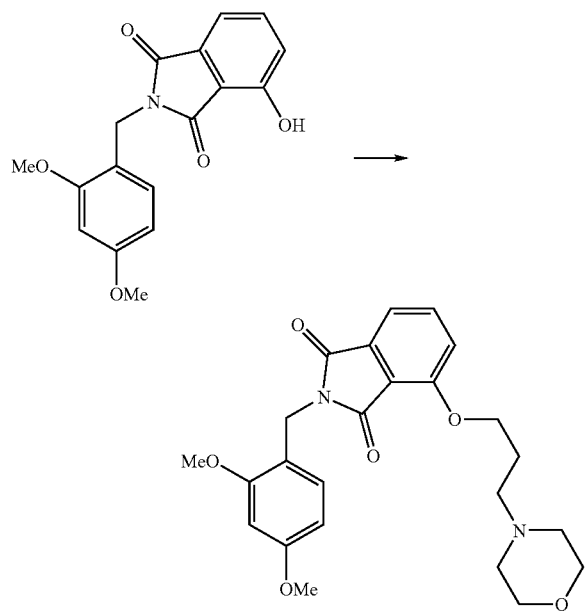

A mixture of 2-(2,4-dimethoxy-benzyl)-4-hydroxy-isoindole-1,3-dione (313 mg, 1.00 mmol), 4-(3-chloropropyl)morpholine (160 mg, 1.11 mmol) and potassium carbonate (350 mg, 2.5 mmol) in DMF (5 mL) was heated at 60° C. for 18 hours. The mixture was diluted with ethyl acetate and extracted twice with 1N hydrochloric acid. The aqueous extracts were made basic with solid potassium carbonate and extracted with ethyl acetate. The organic extract was washed with brine, dried (MgSO$_4$) and concentrated to give a yellow solid which was recrystallised from methanol/petrol then ethyl acetate/chloroform/petrol to give the title compound (298 mg, 68%) as an off-white solid. $^1$H NMR (methanol-d$_4$) 7.72 (1H, t), 7.41 (1H, d), 7.39 (1H, d), 7.02 (1H, d), 6.51 (1H, d), 6.43 (1H, dd), 4.72 (2H, s), 4.27 (2H, t), 3.81 (3H, s), 3.76 (3H, s), 3.68 (4H, t), 2.61 (2H, t), 2.50 (4H, m), 2.05 (2H, qn). MS: [M+H]$^+$ 441.

Preparation C13

2-(4-Methoxy-benzyl)-4-[2-(2-methoxy-ethoxy)-ethoxy]-2,3-dihydro-1H-isoindole

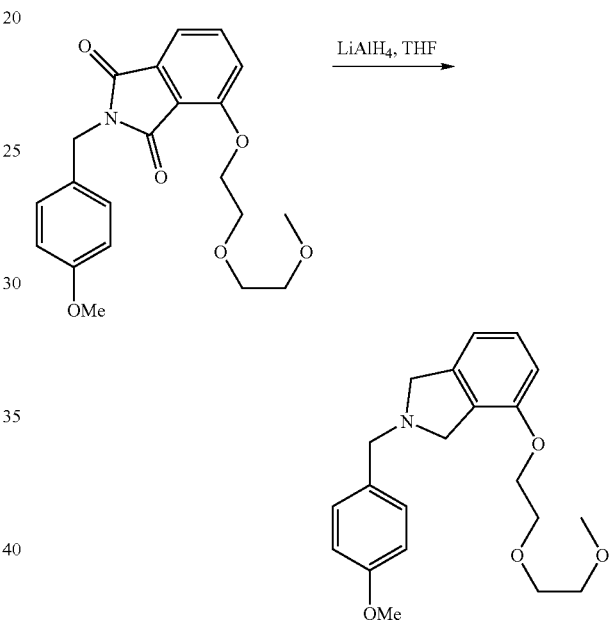

2-(4-Methoxy-benzyl)-4-[2-(2-methoxy-ethoxy)-ethoxy]-isoindole-1,3-dione (149 mg, 0.38 mmol) was treated with a 1M solution of lithium aluminum hydride in THF (5 mL, 5 mmol). The mixture was maintained at r.t. for 4 hours, 60° C. for 1 hour, then r.t. for a further 18 hours. The mixture was then cooled in ice and quenched by the dropwise addition of water (0.2 mL), 2N sodium hydroxide solution (0.4 mL) and water (0.4 mL). Magnesium sulfate was added, followed by ethyl acetate and then the mixture was stirred at r.t. for 15 minutes. The solids were removed by filtration, being well washed with ethyl acetate. Concentration of the filtrate gave a residue which was absorbed onto an SCX cartridge and washed with 5% methanol/dichloromethane then eluted with 10% 1M ammonia in methanol/dichloromethane to afford the title compound (134 mg, 97%). $^1$H NMR (methanol-d$_4$) 7.43-7.39 (2H, m), 7.27 (1H, t), 6.99-6.96 (2H, m), 6.90 (1H, d), 6.88 (1H, d), 4.33 (2H, s), 4.28 (2H, s), 4.23 (2H, s), 4.18-4.15 (2H, m), 3.85-3.79 (5H, m), 3.67-3.64 (2H, m), 3.54-3.51 (2H, m), 3.33 (3H, s). MS: [M+H]$^+$ 358.

Preparation C14

2-(2,4-Dimethoxy-benzyl)-4-(2-dimethylamino-ethoxy)-2,3-dihydro-1H-isoindole

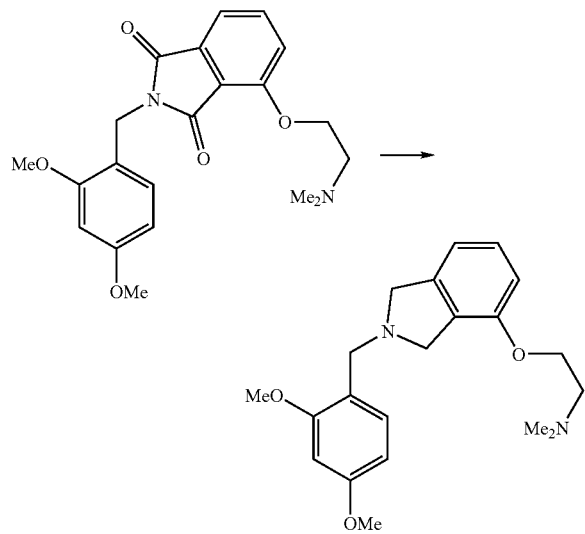

2-(2,4-Dimethoxy-benzyl)-4-(2-dimethylamino-ethoxy)-isoindole-1,3-dione (201 mg, 0.52 mmol) was treated with a 1M solution of lithium aluminum hydride in THF (5 mL, 5 mmol). After 7.5 hours at r.t. a further portion of lithium aluminum hydride solution (5 mL, 5 mmol) was added and the mixture maintained for further 18 hours. The mixture was then cooled in ice and quenched by the dropwise addition of water (0.4 mL), 2N sodium hydroxide solution (0.8 mL) and water (0.8 mL). Magnesium sulfate was added, followed by ethyl acetate and then the mixture was stirred at r.t. for 1 hour. The solids were removed by filtration, being well washed with ethyl acetate. Concentration of the filtrate gave the title compound (192 mg, 103%) as a brown oil which was carried forward without further purification. $^1$H NMR (methanol-$d_4$) 7.24 (1H, d), 7.16 (1H, t), 6.82-6.78 (2H, m), 6.55 (1H, d), 6.51 (1H, dd), 4.12 (2H, t), 3.92 (4H, s), 3.86 (2H, s), 3.82 (3H, s), 3.80 (3H, s), 2.76 (2H, t), 2.33 (6H, s). MS: [M+H]$^+$ 357.

Preparation C15

2-(2,4-Dimethoxy-benzyl)-4-(3-morpholin-4-yl-propoxy)-2,3-dihydro-1H-isoindole

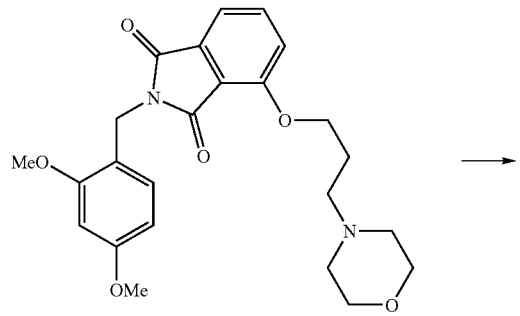

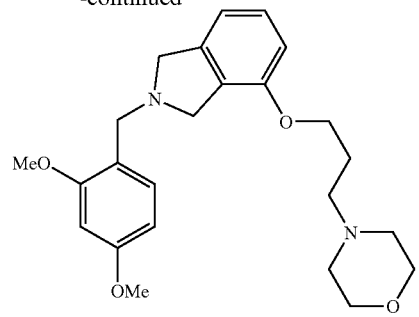

2-(2,4-Dimethoxy-benzyl)-4-(3-morpholin-4-yl-propoxy)-isoindole-1,3-dione (298 mg, 0.68 mmol) was treated with a 1M solution of lithium aluminum hydride in THF (5 mL, 5 mmol) and maintained at r.t. for 21 hours. The mixture was heated to 75° C. for 1 hour then cooled in ice and quenched by the dropwise addition of water (0.2 mL), 2N sodium hydroxide solution (0.4 mL) and water (0.4 mL). Magnesium sulfate was added, followed by ethyl acetate and then the mixture was stirred at r.t. for 1 hour. The solids were removed by filtration, being well washed with ethyl acetate. Concentration of the filtrate gave a crude product which was purified by flash chromatography on silica, eluting with 5% methanol in DCM. This afforded the title compound (233 mg, 83%) as a red oil. $^1$H NMR (methanol-$d_4$) 7.24 (1H, d), 7.15 (1H, t), 6.80 (1H, d), 6.78 (1H, d), 6.56 (1H, d), 6.52 (1H, dd), 4.05 (2H, t), 3.94 (2H, s), 3.88 (2H, s), 3.87 (2H, s), 3.83 (3H, s), 3.80 (3H, s), 3.70-3.68 (4H, m), 2.54-2.50 (2H, m), 2.49-2.47 (4H, m), 2.00-1.93 (2H, m). MS: [M+H]$^+$ 413.

Preparation C16

4-[2-(2-Methoxy-ethoxy)-ethoxy]-2,3-dihydro-1H-isoindole

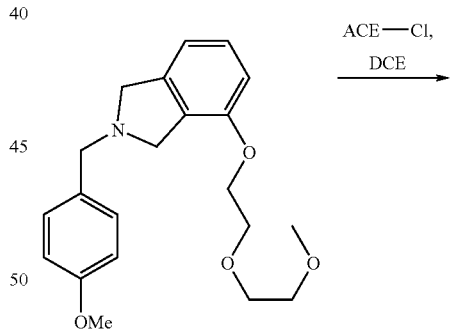

A solution of 2-(4-methoxy-benzyl)-4-[2-(2-methoxy-ethoxy)-ethoxy]-2,3-dihydro-1H-isoindole (45 mg, 0.13 mmol) in 1,2-dichloroethane (2 mL) was treated with -chloroethyl chloroformate (0.1 mL, 0.93 mmol). After 17 hours, methanol (5 mL) was added and the mixture stirred for 3 hours. The solvents were removed in vacuo to afford the title compound as a greenish-black solid, which was used without further purification. $^1$H NMR (methanol-d$_4$) 7.36 (1H, t), 6.98 (2H, d), 4.60 (2H, s), 4.57 (2H, s), 4.23-4.21 (2H, m), 3.85-3.83 (2H, m), 3.69-3.67 (2H, m), 3.57-3.54 (2H, m), 3.36 (3H, s). MS: [M+H]$^+$ 238.

Preparation C17

[2-(2,3-Dihydro-1H-isoindol-4-yloxy)-ethyl]-dimethyl-amine

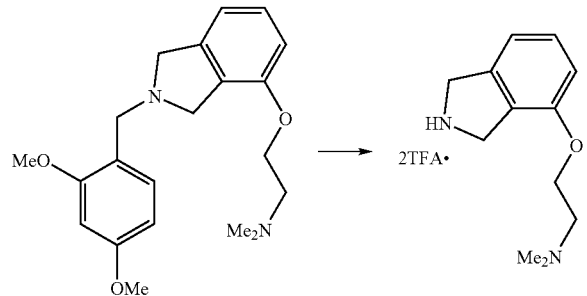 [SMILES: COc1ccc(CN2Cc3cccc(OCCN(C)C)c3C2)c(OC)c1 ; CN(C)CCOc1cccc2c1CNC2]

A solution of 2-(2,4-dimethoxy-benzyl)-4-(2-dimethylamino-ethoxy)-2,3-dihydro-1H-isoindole (170 mg, 0.48 mmol) in trifluoroacetic acid (0.5 mL) and anisole (0.5 mL) was heated at 150° C. under microwave irradiation for 10 minutes. The mixture was diluted with ethyl acetate and extracted twice with water. The combined aqueous extracts were concentrated to give the title compound as a purple oil (240 mg, including residual TFA and/or water). $^1$H NMR (methanol-d$_4$) 7.42 (1H, t), 7.07 (1H, d), 7.04 (1H, d), 4.64 (4H, br.s), 4.47-4.44 (2H, m), 3.65-3.63 (2H, m), 3.01 (6H, s). MS: [M+H]$^+$ 207.

Preparation C18

4-(3-Morpholin-4-yl-propoxy)-2,3-dihydro-1H-isoindole

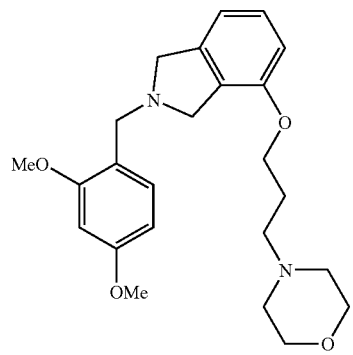

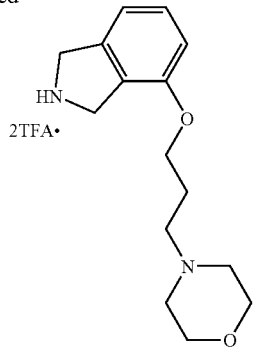

A solution of 2-(2,4-dimethoxy-benzyl)-4-(3-morpholin-4-yl-propoxy)-2,3-dihydro-1H-isoindole (233 mg, 0.56 mmol) in trifluoroacetic acid (1.0 mL) and anisole (0.5 mL) was heated at 150° C. under microwave irradiation for 10 minutes. The mixture was diluted with diethyl ether and extracted twice with water. The combined aqueous extracts were concentrated to give an oil which was dissolved in methanol and concentrated in vacuo to afford the title compound as a brown oil (348 mg, including residual TFA and/or water). $^1$H NMR (methanol-d$_4$) 7.40 (1H, t), 7.03 (1H, d), 6.99 (1H, d), 4.63 (2H, s), 4.59 (2H, s), 4.21 (2H, t), 4.14-4.04 (2H, m), 3.85-3.73 (2H, m), 3.61-3.52 (2H, m), 3.41-3.36 (2H, m), 3.25-3.13 (2H, m), 2.32-2.25 (2H, m). MS: [M+H]$^+$ 263.

Preparation C19

Synthesis of 4-bromo-2,3-dihydro-1H-isoindole trifluoroacetate

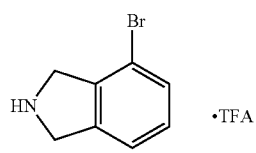

Prepared in a manner analogous to 5-nitro-2,3-dihydro-1H-isoindole (described in preparation C5). $^1$H NMR (DMSO-d$_6$) 9.73 (2H, br s), 7.60 (1H, d), 7.45 (1H, d), 7.35 (1H, t), 4.65 (2H, s), 4.55 (2H, s).

Preparation C20

Synthesis of 5-bromo-2,3-dihydro-1H-isoindole

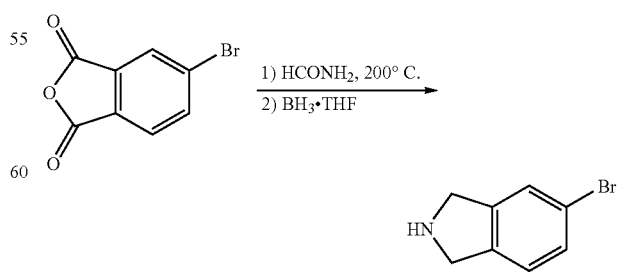

A mixture of 4-bromophthalic anhydride (25 g) in formamide (75 ml) was heated at 200° C. for 16 hours then allowed to cool to room temperature. The reaction mixture was diluted with water (200 ml), filtered, the filter cake was washed with water then diethyl ether and sucked dry to give 20.85 g of light mustard solid.

280 ml of 1M Borane-THF complex was added dropwise to a stirred solution of 4-bromophthalimide (20.85 g; 92.2 mmol) in anhydrous THF (200 ml) at 0° C. then heated at reflux overnight. The reaction was cooled to 0° C. then treated cautiously with methanol (100 ml) followed by 2M HCl (100 ml) then heated at reflux for 3 hours. The reaction mixture was cooled and the organics evaporated. The aqueous was diluted with water (100 ml) the extracted with DCM (×3). The aqueous was basified with 2M NaOH then extracted with DCM (×3). The combined DCM extracts were dried (MgSO$_4$), filtered and evaporated to give 6.99 g of 5-bromo-2,3-dihydro-1H-isoindole as a dark brown gummy solid. $^1$H NMR (DMSO-d$_6$) 7.45 (1H, s), 7.36 (1H, d), 7.20 (1H, d), 4.05 (4H, s).

Preparation C21

Synthesis of 2,3-dihydro-1H-isoindole-5-carboxylic acid methyl ester trifluoroacetate

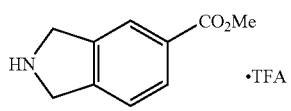

2-(2,4-Dimethoxybenzyl)-2,3-dihydro-1H-isoindole-5-carboxylic acid methyl ester (preparation C6, step 2 product) was deprotected in a manner analogous to 5-nitro-2,3-dihydro-1H-isoindole (described in preparation C5) to give the title compound. $^1$H NMR (DMSO-d$_6$) 9.70 (2H, br s), 8.00 (1H, s), 7.95 (1H, d), 7.57 (1H, d), 4.60 (4H, s), 2.88 (3H, s).

D. Synthesis of Benzylated Resorcinol Intermediates

Preparation D1

Synthesis of (2,4-bis-benzyloxy-5-isopropyl-phenyl)-[5-(2-methoxy-ethoxy)-1,3-dihydro-isoindol-2-yl]-methanone

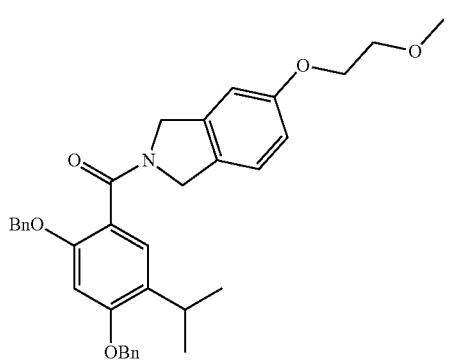 [SMILES: COCCOc1ccc2c(c1)CN(C(=O)c1cc(C(C)C)c(OCc3ccccc3)cc1OCc1ccccc1)C2]

(2,4-Bis-benzyloxy-5-isopropyl-phenyl)-(5-hydroxy-1,3-dihydro-isoindol-2-yl)-methanone (A2 from 2,4-bis-benzyloxy-5-isopropyl-benzoic acid (Preparation B10) and 5-hydroxyisoindoline) (100 mg, 0.2 mmol) and 5-hydroxyisoindoline) (100 mg, 0.2 mmol), 1-chloro-2-methoxy-ethane (23.6 mg, 0.25 mmol) and K$_2$CO$_3$ (34.5 mg, 0.25 mmol) in DMF (4 ml) were combined and stirred for 2 hours at room temperature. A further 0.25 mmol of 1-chloro-2-methoxy-ethane and K$_2$CO$_3$ was added then heated at 90° C. for 16 hours. Reaction cooled to room temperature and diluted with EtOAc then filtered. The filtrate was reduced in vacuo then purified by flash column chromatography, eluting with 100% petroleum ether to 100% ethyl acetate to afford 115 mg of the title compound as a colourless gel. MS: [M+H]$^+$ 552

Preparation D2

Synthesis of (2,4-bis-benzyloxy-5-isopropyl-phenyl)-[5-(3-morpholin-4-yl-propoxy)-1,3-dihydro-isoindol-2-yl]-methanone

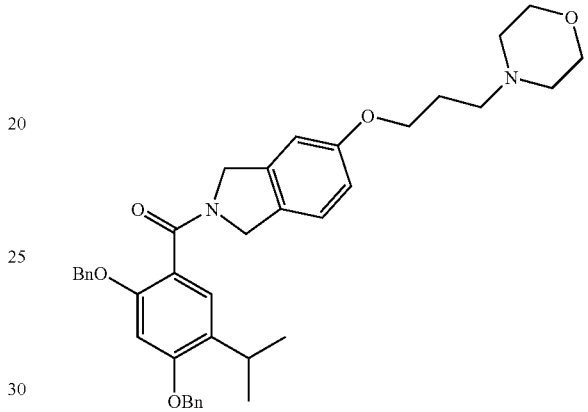

A mixture of (2,4-bis-benzyloxy-5-isopropyl-phenyl)-(5-hydroxy-1,3-dihydro-isoindol-2-yl)-methanone (100 mg, 0.2 mmol), 4-(3-chloropropyl)morpholine (82 mg, 0.5 mmol) and K$_2$CO$_3$ (104 mg, 0.75 mmol) in DMF (5 ml) was heated at 90° C. for 16 hours. The reaction mixture was diluted with EtOAc and filtered. The filtrate was reduced in vacuo and purified by flash column chromatography, eluting with 0-100% P.E./EtOAc then 0-10% MeOH/EtOAc to give the title compound as a colourless gel (90.1 mg). MS: [M+H]+ 621.

Preparation D3

Synthesis of (2,4-bis-benzyloxy-5-isopropyl-phenyl)-[5-(2-dimethylamino-ethoxy)-1,3-dihydro-isoindol-2-yl]-methanone

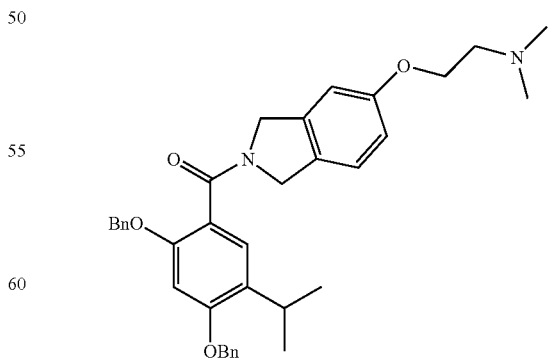

A mixture of (2,4-bis-benzyloxy-5-isopropyl-phenyl)-(5-hydroxy-1,3-dihydro-isoindol-2-yl)-methanone (100 mg, 0.2 mmol), 2-dimethylaminoethylchloride.HCl (72 mg, 0.5 mmol) and K₂CO₃ (173 mg, 1.25 mmol) in DMF (5 ml) was heated at 90° C. for 16 hours. Dilute reaction mixture with EtOAc and filtered. The reaction mixture was diluted with EtOAc and filtered. The filtrate was reduced in vacuo and purified by flash column chromatography, eluting 100% DCM then 90% DMAW 90 to give the title compound as an off white gel (79 mg). MS: [M+H]⁺ 565

Preparation D4

Synthesis of 2,4-bis-benzyloxy-5-isopropyl-benzoyl chloride

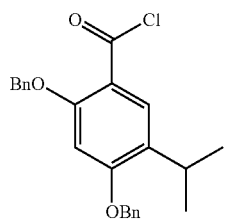 [SMILES: CC(C)c1cc(C(=O)Cl)c(OCc2ccccc2)cc1OCc1ccccc1]

2,4-Bis-benzyloxy-5-isopropyl-benzoic acid (Preparation B10) (0.2 g, 0.53 mmol) was dissolved in DCM (10 ml) and treated with oxalyl chloride (1.5 g, 12 mmol) and a catalytic amount of DMF. The reaction mixture was stirred at room temperature for 14 hours and the solvent was then removed in vacuo. The crude material was dissolved in toluene and evaporated. Crude 2,4-bis-benzyloxy-5-isopropyl-benzoyl chloride was obtained as an oil (200 mg).

Preparation D5

Synthesis of (2,4-bis-benzyloxy-5-isopropyl-phenyl)-(5-morpholin-4-yl-1,3-dihydro-isoindol-2-yl)-methanone

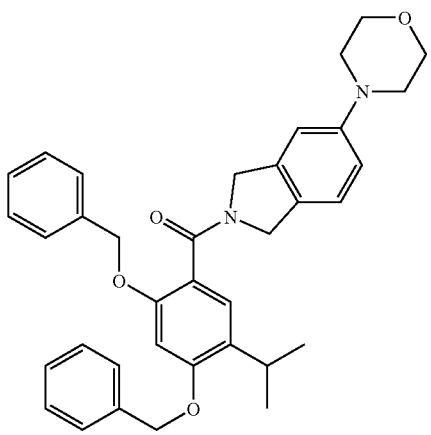 [SMILES: CC(C)c1cc(C(=O)N2Cc3ccc(N4CCOCC4)cc3C2)c(OCc2ccccc2)cc1OCc1ccccc1]

A solution of 2,4-bis-benzyloxy-5-isopropyl-benzoic acid (505 mg; 1.3 mmol) (Preparation B5), 5-nitroisoindoline, trifluoroacetate (360 mg; 1 equiv.), EDAC (300 mg; 1.2 equiv.), HOBt (210 mg; 1.2 equiv.) and NEt₃ (270 µl; 1.5 equiv.) in DMF (10 ml) was stirred at room temperature overnight then evaporated in vacuo. The residue was partitioned between EtOAc and 2M HCl, the EtOAc layer was separated, washed with saturated NaHCO₃, dried (MgSO₄) and evaporated. Purification by flash column chromatography (1:4 then 1:2 then 1:1 EtOAc/P.E. as eluant) gave 460 mg of (2,4-bis-benzyloxy-5-isopropyl-phenyl)-(5-nitro-1,3-dihydro-isoindol-2-yl)methanone. MS: [M+H]⁺ 523.

A solution of (2,4-bis-benzyloxy-5-isopropyl-phenyl)-(5-nitro-1,3-dihydro-isoindol-2-yl)methanone (460 mg; 0.88 mmol) in ethanol (25 ml) was treated with tin (II) chloride dihydrate (1 g; 5 equiv.) then heated at reflux overnight then evaporated in vacuo. The residue was partitioned between EtOAc and saturated NaHCO₃, the EtOAc layer was separated, dried (MgSO₄) and evaporated to give 380 mg of (5-amino-1,3-dihydro-isoindol-2-yl)-(2,4-bis-benzyloxy-5-isopropyl-phenyl)-methanone.

A mixture of (5-amino-1,3-dihydro-isoindol-2-yl)-(2,4-bis-benzyloxy-5-isopropyl-phenyl)-methanone (100 mg; 0.2 mmol), bis(2-chloroethyl)ether (30 µl; 1.1 equiv.), Hunigs base (125 µl; 3.5 equiv.) and tetrabutylammonium iodide (10 mg) in NMP (1 ml) was heated in a CEM microwave synthesiser at 150° C. for 30 minutes. A further 30 µl of Hunigs base and 125 µl of bis(2-chloroethyl)ether were added and heating repeated for the same time. The reaction mixture was partitioned between EtOAc and saturated NH₄Cl solution, the EtOAc layer was separated, washed with more saturated NH₄Cl solution, then brine, dried (MgSO₄) and evaporated. Purification by flash column chromatography (1:2 then 1:1 then 2:1 EtOAc/P.E. as eluant) gave 60 mg of (2,4-bis-benzyloxy-5-isopropyl-phenyl)-(5-morpholin-4-yl-1,3-dihydro-isoindol-2-yl)-methanone. MS: [M+H]⁺ 563.

Preparation D6

Synthesis of 2-(2,4-bis-benzyloxy-5-isopropyl-benzoyl)-2,3-dihydro-1H-isoindole-5-carboxylic acid

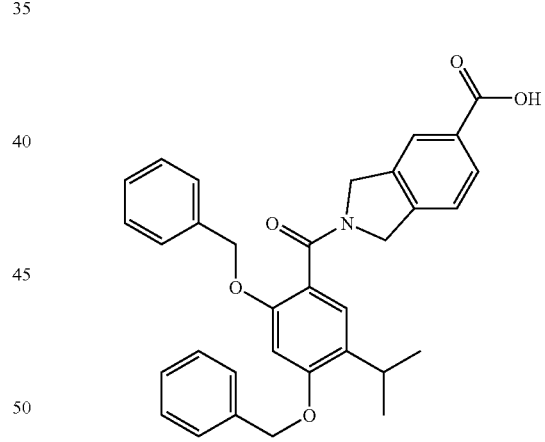

A solution of 2-(2,4-bis-benzyloxy-5-isopropyl-benzoyl)-2,3-dihydro-1H-isoindole-5-carboxylic acid methyl ester (390 mg) in methanol (10 ml) and 2M NaOH (10 ml) was heated at 50° C. for 48 hours then evaporated. The residue was acidified with 2M HCl, the solid collected by filtration, washed with water and sucked dry to give 255 mg of 2-(2,4-bis-benzyloxy-5-isopropyl-benzoyl)-2,3-dihydro-1H-isoindole-5-carboxylic acid as a white solid. [M+H]⁺ 520.

Examples

By following the methods described above, the compounds set out in the Table below were prepared.

| Example Number | Compound | Chemical Name | Method | NMR Data | MS |
|---|---|---|---|---|---|
| 1 | | (5-Chloro-2-hydroxy-phenyl)-(1,3-dihydro-isoindol-2-yl)-methanone | A1. From 5-Chloro-2-hydroxy-benzoic acid and isoindoline | $^1$H NMR (MeOH-d$_4$) 7.20-7.42 (6H, m), 6.92 (1H, d), 4.94 (2H, s), 4.74 (2H, s) | MS: [M + H]$^+$ 274 |
| 2 | | (3-tert-Butyl-4-hydroxy-phenyl)-(2,3-dihydro-indol-1-yl)-methanone | A2. From 3-tert-butyl-4-hydroxy-benzoic acid and indoline | $^1$H NMR (DMSO-d$_6$) 7.56 (2H, br m), 7.40 (1H, s), 7.33 (1H, d), 7.26 (1H, d), 7.13 (1H, t), 6.98 (1H, t), 6.85 (1H, d), 4.07 (2H, t), 3.08 (2H, t), 1.38 (9H, s) | MS: [M + H]$^+$ 296 |
| 3 | | (3-tert-Butyl-4-hydroxy-phenyl)-(3,4-dihydro-2H-quinolin-1-yl)-methanone | A2. From 3-tert-butyl-4-hydroxy-benzoic acid and 1,2,3,4-tetrahydro-quinoline | $^1$H NMR (DMSO-d$_6$) 11.05 (1H, br s), 8.17 (1H, d), 8.04 (2H, m), 7.88 (1H, d), 7.67 (1H, t), 7.54 (1H, t), 7.09 (1H, d), 3.39 (1H, m), 3.28 (1H, m), 1.40 (9H, s), 1.07 (3H, m), 0.84 (1H, m) | MS: [M + H]$^+$ 310 |
| 4 | | (3,4-Dihydro-1H-isoquinolin-2-yl)-(4-hydroxy-3-isopropyl-phenyl)-methanone | A2. From 3-isopropyl-4-hydroxy-benzoic acid and 1,2,3,4-tetrahydro-isoquinoline | $^1$ NMR (DMSO-d$_6$) 9.77 (1H, br s), 7.24 (1H, d), 7.17 (4H, s), 7.18 (1H, dd), 6.84 (1H, d), 4.68 (2H, s), 3.70 (2H, br s), 3.23 (1H, m), 2.87 (2H, m), 1.18 (6H, d) | MS: [M + H]$^+$ 296 |
| 5 | | (1,3-Dihydro-isoindol-2-yl)-(2,4-dihydroxy-5-isopropyl-phenyl)-methanone | A2 & A5. From 2,4-Bis-benzyloxy-5-isopropenyl-benzoic acid (B9) and isoindoline | $^1$H NMR (DMSO-d$_6$) 10.03 (1H, s), 9.63 (1H, s), 7.29 (4H, br m), 7.03 (1H, s), 6.40 (1H, s), 4.77 (4H, br s), 3.09 (1H, m), 1.14 (6H, d) | MS: [M + H]$^+$ 298 |

| Example Number | Compound | Chemical Name | Method | NMR Data | MS |
|---|---|---|---|---|---|
| 6 | 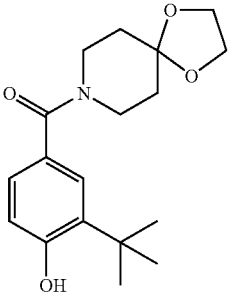 [SMILES: CC(C)(C)c1cc(C(=O)N2CCC3(CC2)OCCO3)ccc1O] | (3-tert-Butyl-4-hydroxy-phenyl)-(1,4-dioxa-8-aza-spiro[4.5]dec-8-yl)-methanone | A4. From 3-tert-butyl-4-hydroxy-benzoic acid and 4-piperidone ethylene ketal | $^1$H NMR (DMSO-$d_6$) 9.82 (1H, s), 7.22 (1H, s), 7.13 (1H, dd), 6.82 (1H, d), 3.91 (4H, s), 3.52 (4H, br m), 1.63 (4H, br m), 1.37 (9H, s) | MS: [M + H]$^+$ 320 |
| 7 | 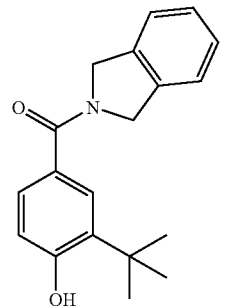 [SMILES: CC(C)(C)c1cc(C(=O)N2Cc3ccccc3C2)ccc1O] | (3-tert-Butyl-4-hydroxy-phenyl)-(1,3-dihydro-isoindol-2-yl)-methanone | A4. From 3-tert-butyl-4-hydroxy-benzoic acid and isoindoline | $^1$H NMR (DMSO-$d_6$) 9.82 (1H, s), 7.41 (1H, s), 7.38 (2H, dd), 7.29 (3H, br m), 6.82 (1H, d), 4.82 (4H, br m), 1.37 (9H, s) | MS: [M + H]$^+$ 296 |
| 8 | 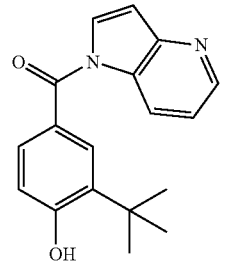 [SMILES: CC(C)(C)c1cc(C(=O)n2ccc3ncccc32)ccc1O] | (3-tert-Butyl-4-hydroxy-phenyl)-pyrrolo[3,2-b]pyridin-1-yl-methanone | A4. From 3-tert-butyl-4-hydroxy-benzoic acid and 1H-pyrrolo[3,2-b]pyridine | $^1$H NMR (DMSO-$d_6$) 8.57 (1H, dd), 8.43 (1H, d), 7.89 (1H, dd), 7.63 (1H, s), 7.56 (1H, dd), 7.35 (1H, m), 7.09 (1H, d), 6.84 (1H, dd), 1.37 (9H, s) | MS: [M + H]$^+$ 295 |
| 9 | 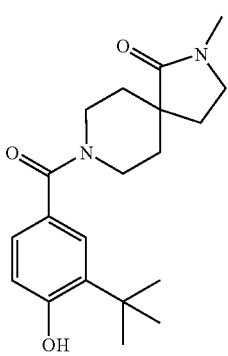 [SMILES: CN1CCC2(CCN(C(=O)c3ccc(O)c(C(C)(C)C)c3)CC2)C1=O] | 8-(3-tert-Butyl-4-hydroxy-benzoyl)-2-methyl-2,8-diaza-spiro[4.5]decan-1-one | A4. From 3-tert-butyl-4-hydroxy-benzoic acid and 4-spiro-[3-(N-methyl-2-pyrrolidinone] piperidine hydrochloride | $^1$H NMR (DMSO-$d_6$) 9.82 (1H, s), 7.22 (1H, s), 7.13 (1H, dd), 6.82 (1H, d), 3.98 (2H, br m), 3.34 (2H, s), 3.13 (2H, m), 2.71 (3H, s), 1.92 (2H, t), 1.60 (2H, m), 1.43 (2H, m), 1.37 (9H, s) | MS: [M + H]$^+$ 345 |
| 10 | 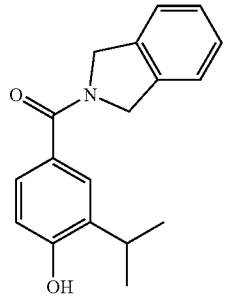 [SMILES: CC(C)c1cc(C(=O)N2Cc3ccccc3C2)ccc1O] | (1,3-Dihydro-isoindol-2-yl)-(4-hydroxy-3-isopropyl-phenyl)-methanone | A4. From 3-isopropyl-4-hydroxy-benzoic acid and isoindoline | $^1$H NMR (DMSO-$d_6$) 9.82 (1H, s), 7.4 (2H, s), 7.38 (1H, dd), 7.30 (3H, m), 6.82 (1H, d), 4.82 (4H, dd), 3.23 (1H, m), 1.23 (6H, s) | MS: [M + H]$^+$ 282 |

| Example Number | Compound | Chemical Name | Method | NMR Data | MS |
|---|---|---|---|---|---|
| 11 | | (3-tert-Butyl-4-hydroxy-phenyl)-(3,4-dihydro-1H-isoquinolin-2-yl)-methanone | A4. From 3-tert-butyl-4-hydroxy-benzoic acid and 1,2,3,4-tetrahydro isoquinoline | $^1$H NMR (DMSO-d$_6$) 7.22 (1H, s), 7.13 (5H, m), 6.82 (1H, d), 4.70 (2H, s), 3.75 (2H, br s), 2.85 (2H, t), 1.37 (9H, s) | MS: [M + H]$^+$ 310 |
| 12 | | (1,3-Dihydro-isoindol-2-yl)-(5-ethyl-2,4-di-hydroxy-phenyl)-methanone | A2, A6 and A5. From 2,4-Bis-benzyloxy-5-bromo-benzoic acid, isoindoline and potassium vinyl trifluoroborate | $^1$H NMR (MeOH-d$_4$) 7.30 (4H, s), 7.15 (1H, s), 6.38 (1H, s), 4.91 (4H, s), 2.58 (2H, q), 1.18 (3H, t) | MS: [M + H]$^+$ 284 |
| 13 | | (5-Cyclopropyl-2,4-dihydroxy-phenyl)-(1,3-dihydro-isoindol-2-yl)-methanone | A2, A6 and A5. From 2,4-Bis-benzyloxy-5-bromo-benzoic acid, isoindoline and cyclopropane boronic acid | $^1$H NMR (DMSO-d$_6$) 7.40-7.23 (4H, m), 6.73 (1H, s), 6.40 (1H, s), 4.75 (4H, br s), 1.92 (1H, m), 0.78 (2H, m), 0.53 (2H, m) | MS: [M + H]$^+$ 296 |
| 14 | | (5-sec-Butyl-2,4-dihydroxy-phenyl)-(1,3-dihydro-isoindol-2-yl)-methanone | A2, A6 and A5. From 2,4-Bis-benzyloxy-5-bromo-benzoic acid, isoindoline and 2-buten-2-yl boronic acid | $^1$H NMR (MeOH-d$_4$) 7.30 (4H, s), 7.15 (1H, s), 6.39 (1H, s), 4.92 (4H, s), 3.00 (1H, q), 1.63 (2H, m), 1.18 (3H, t), 0.88 (3H, t) | MS: [M + H]$^+$ 312 |
| 15 | | (1,3-Dihydro-isoindol-2-yl)-(3-ethoxy-4-hydroxyphenyl)-methanone | Method A4. From 3-ethoxy-4-hydroxy-benzoic acid and isoindoline | $^1$H NMR (DMSO-d$_6$) 7.45 (1H, br s), 7.30 (3H, d), 7.18 (1H, d), 7.08 (1H, dd), 6.85 (1H, d), 4.85 (4H, s), 4.10 (2H, q), 1.38 (3H, t) | MS: [M + H]$^+$ 284 |

| Example Number | Compound | Chemical Name | Method | NMR Data | MS |
|---|---|---|---|---|---|
| 16 | 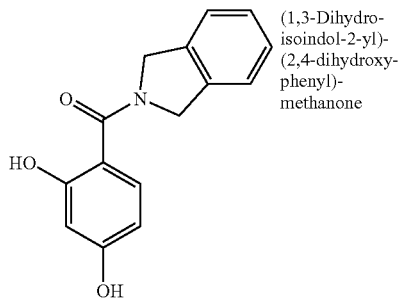 | (1,3-Dihydro-isoindol-2-yl)-(2,4-dihydroxy-phenyl)-methanone | A2 and A5. From 2,4-Bis-benzyloxy-5-bromo-benzoic acid and isoindoline | $^1$H NMR (MeOH-$d_4$) 7.30 (5H, m), 7.15 (1H, s), 6.42 (1H, s), 6.38 (1H, s), 4.93 (4H, s) | MS: [M + H]$^+$ 256 |

Example 17

Synthesis of (5-chloro-1,3-dihydro-isoindol-2-yl)-(2,4-dihydroxy-5-isopropyl-phenyl)-methanone

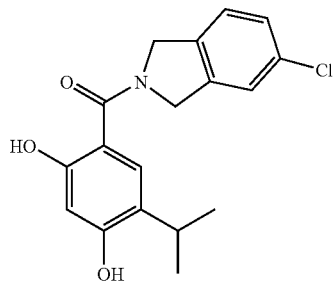 [SMILES: CC(C)c1cc(C(=O)N2Cc3ccc(Cl)cc3C2)c(O)cc1O]

A solution of 2,4-bis-benzyloxy-5-isopropyl-benzoic acid (Preparation B10) (0.451 g, 1.2 mmol), EDC (0.276 mg, 1.44 mmol), HOAt (0.196 mg, 1.44 mmol), triethylamine (0.5 ml, 3.6 mmol) and 5-chloro-2,3-dihydro-1H-isoindole (0.187 g, 1.2 mmol) (Preparation C3) in DMF (5 ml) was stirred at room temperature for 16 hours, then evaporated under vacuum. The crude material was dissolved in ethyl acetate and extracted twice with saturated NaHCO$_3$, organics washed with water three times, then evaporated under vacuum to give 0.5 g of 2,4-bis-benzyloxy-5-isopropyl-phenyl)-(5-chloro-1,3-dihydro-isoindol-2-yl)-methanone. MS: [M+H]$^+$ 512

Boron trichloride (1M in DCM) was added dropwise to a solution of 2,4-bis-benzyloxy-5-isopropyl-phenyl)-(5-chloro-1,3-dihydro-isoindol-2-yl)-methanone (0.5 g, 0.97 mmol) in dry DCM (10 ml) at 0° C. under nitrogen, then stirred for at 0° C. for 1 hour, warmed to room temperature and stirred for a further 3 hours. The reaction was quenched with ice, partitioned between DCM and water. The DCM layer was dried (MgSO$_4$), evaporated under vacuum, then purified by flash silica column chromatography eluting with 80% P.E.:EtOAc to give 0.1 g of (5-chloro-1,3-dihydro-isoindol-2-yl)-(2,4-dihydroxy-5-isopropyl-phenyl)-methanone as a white solid. MS: [M+H]$^+$ 332. $^1$H NMR (DMSO-$d_6$) 10.0 (1H, s) 9.60 (1H, s), 7.45 (1H, br s), 7.33 (2H, br s), 7.0 (1H, s), 6.4 (1H, s), 4.80 (4H, br s), 3.10 (1H, m), 1.15 (6H, d).

Example 18

Synthesis of [5-(3-amino-propoxy)-1,3-dihydro-isoindol-2-yl]-(2,4-dihydroxy-5-isopropyl-phenyl)-methanone hydrochloride

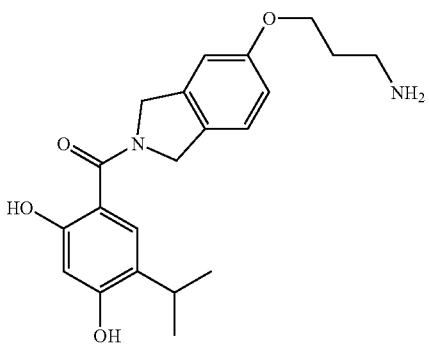 [SMILES: CC(C)c1cc(C(=O)N2Cc3ccc(OCCCN)cc3C2)c(O)cc1O]

A solution of {3-[2-(2,4-dihydroxy-5-isopropyl-benzoyl)-2,3-dihydro-1H-isoindol-5-yloxy]-propyl}-carbamic acid tert-butyl ester (Example 46) (1 g) in EtOAc (10 ml) was treated with a saturated solution of HCl in EtOAC (20 ml) then stirred at room temperature for 2 hours. The reaction mixture was evaporated and re-evaporated with ethanol (×3). The title compound was isolated as a cream foam (840 mg). 1H NMR (DMSO-d6) 10.05 (1H, br s), 9.60 (1H, s), 7.88 (3H, br s), 7.30-7.18 (1H, m), 7.05 (1H, s), 7.00-6.85 (2H, m), 6.42 (1H, s), 4.75 (2H, br s) 4.70 (2H, br s), 4.05 (2H, t), 3.10 (1H, m), 3.00-2.95 (2H, m), 2.00 (2H, tt), 1.15 (6H, d). MS: [M+H]$^+$ 371.

Example 19

(5-Bromo-2,4-dihydroxy-phenyl)-(1,3-dihydro-isoindol-2-yl)-methanone

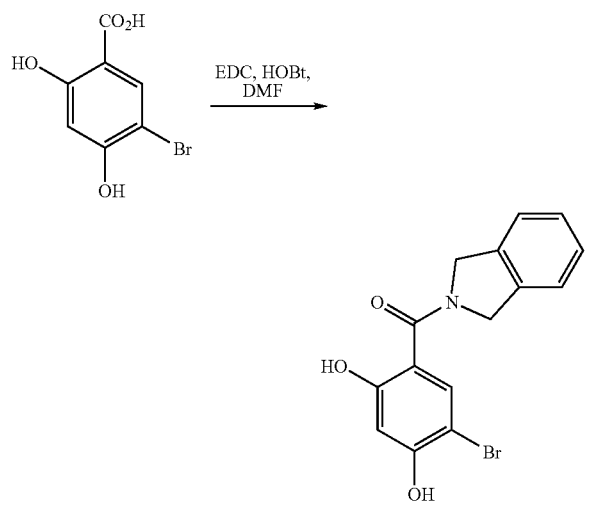

A solution of 5-bromo-2,4-dihydroxy-benzoic acid (520 mg, 2.33 mmol) in DMF (5 mL) was treated with 1-(3-dimethylaminopropyl)-3-ethylcarbodiimide hydrochloride (471 mg, 2.45 mmol) then HOBt (362 mg, 2.68 mmol). After 25 min, 2,3-dihydro-1H-isoindole (0.5 mL, 2.63 mmol) was added then the mixture was stirred at r.t. for 18 h. The solvent was removed in vacuo then the residue was taken up in ethyl acetate and washed with 1N hydrochloric acid, saturated sodium bicarbonate solution and brine then dried (MgSO$_4$) and concentrated. The residue was triturated with methanol to afford the title compound as a grey solid (328 mg, 44%). $^1$H NMR (DMSO-d$_6$) 10.45 (1H, s), 10.32 (1H, s), 7.36 (1H, br.s), 7.35 (1H, s), 7.28 (3H, br.s), 6.59 (1H, s), 4.77 (2H, br.s), 4.71 (2H, br.s). MS: [M+H]$^+$ 332/334.

Example 20

(1,3-Dihydro-isoindol-2-yl)-(2,4-dihydroxy-5-trifluoromethyl-phenyl)-methanone

20A. (2,4-Bis-benzyloxy-5-bromo-phenyl)-(1,3-dihydro-isoindol-2-yl)-methanone

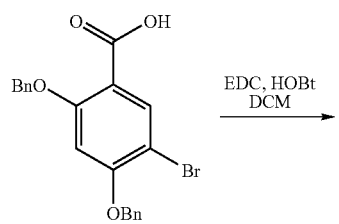

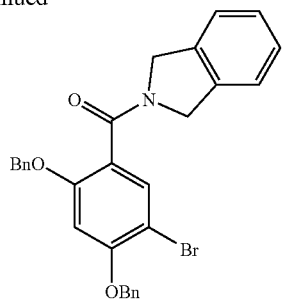

According to general method A2, 2,4-bis-benzyloxy-5-bromo-benzoic acid (1.02 g, 2.47 mmol) gave a residue which was purified by flash chromatography on silica (ethyl acetate/petrol gradient, 0-20%) to afford the title compound as a white crystalline solid (501 mg, 39%). $^1$H NMR (methanol-d$_4$) 7.52 (1H, s), 7.49-7.46 (2H, m), 7.42-7.37 (2H, m), 7.34 (t, 2H), 7.30-7.24 (4H, m), 7.23-7.20 (3H, m), 7.16 (1H, d), 6.94 (1H, s), 5.24 (2H, s), 5.16 (2H, s), 4.86 (2H, s), 4.60 (2H, s). MS: [M+H]$^+$ 514/516.

20B. (2,4-Bis-benzyloxy-5-trifluoromethyl-phenyl)-(1,3-dihydro-isoindol-2-yl)-methanone

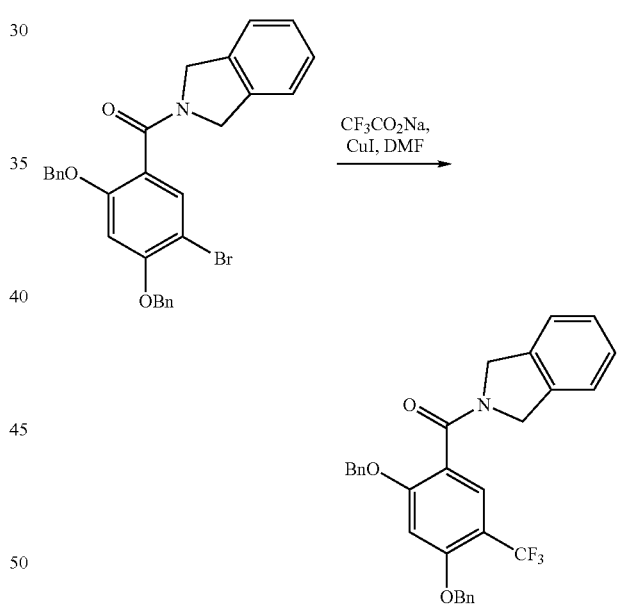

A mixture of (2,4-bis-benzyloxy-5-bromo-phenyl)-(1,3-dihydro-isoindol-2-yl)-methanone (491 mg, 0.95 mmol), sodium trifluoroacetate (649 mg, 4.8 mmol) and copper (I) iodide (364 mg, 1.91 mmol) were dried under vacuum (0.04 mbar) for 6 hours. The flask was flushed with nitrogen, DMF (5 mL) was added and the mixture heated at 150° C. for 17 hours. After cooling to r.t., the mixture was diluted with DCM (100 mL) and filtered through Celite, rinsing with DCM. The filtrate was concentrated to dryness and the residue was partially purified by flash chromatography on silica (ethyl acetate/petrol gradient, 0-20%). The purest fraction was recrystallised from methanol to afford the title compound as a white solid (140 mg, 29%). $^1$H NMR (methanol-d$_4$) 7.60 (1H, s), 7.48-7.44 (2H, m), 7.40 (2H, t), 7.37-7.21 (m, 9H), 7.17 (1H, d), 7.02 (1H, s), 5.29 (2H, s), 5.24 (2H, s), 4.88 (2H, s), 4.62 (2H, s). MS: [M+H]+ 504.

20C. (1,3-Dihydro-isoindol-2-yl)-(2,4-dihydroxy-5-trifluoromethyl-phenyl)-methanone

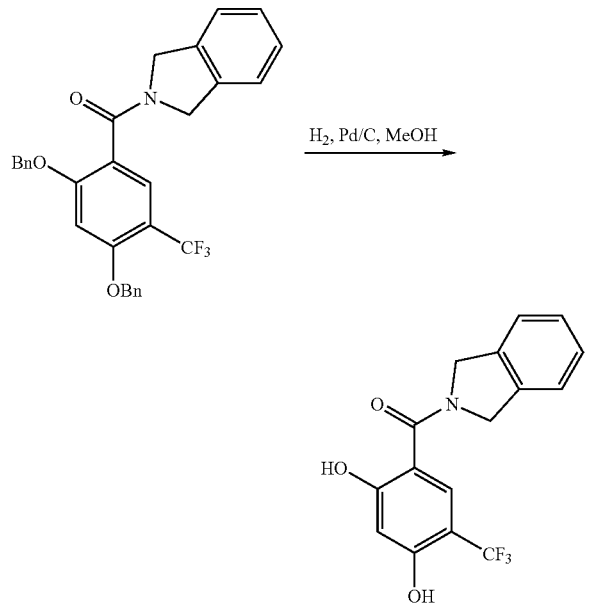

A solution of (2,4-bis-benzyloxy-5-trifluoromethyl-phenyl)-(1,3-dihydro-isoindol-2-yl)-methanone (140 mg, 0.28 mmol) in methanol (5 mL) was hydrogenated at atmospheric pressure over 10% palladium on charcoal (34 mg) for 4 hours. A further portion of catalyst was added (31 mg) and hydrogenation continued for a further 1.5 hours. The mixture was filtered through Celite, eluting with methanol, then the filtrate was concentrated in vacuo to afford the title compound as a white solid (91 mg, quant.). $^1$H NMR (DMSO-$d_6$) 10.79 (1H, s), 10.70 (1H, s), 7.40-7.35 (2H, m), 7.31-7.35 (3H, m), 6.61 (1H, s), 4.79 (2H, br.s), 4.68 (2H, br.s). MS: [M+H]+ 324.

Example 21

(2,4-Dihydroxy-5-isopropyl-phenyl)-{4-[2-(2-methoxy-ethoxy)-ethoxy]-1,3-dihydro-isoindol-2-yl}methanone

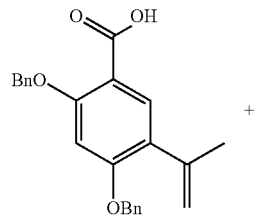
+
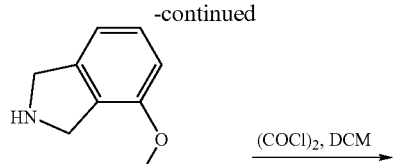

-continued

A solution of 2,4-bis-benzyloxy-5-isopropenyl-benzoic acid (96 mg, 0.26 mmol) and DMF (1 drop, cat.) in DCM (3 mL) was cooled in ice then treated with oxalyl chloride (112 L, 1.28 mmol). After 2 hours the mixture was concentrated in vacuo then azeotroped with toluene. The resulting acid chloride was dissolved in DCM (4 mL) and added to a solution of 4-[2-(2-methoxy-ethoxy)-ethoxy]-2,3-dihydro-1H-isoindole (0.26 mmol, assuming a quantitative yield from the preceding step (debenzylation procedure C16)) and triethylamine (0.20 mL, 1.4 mmol) in DCM (1 mL). After 2 hours the mixture was diluted with ethyl acetate and washed with 1N hydrochloric acid, brine, sodium bicarbonate solution and brine. The organic phase was dried (MgSO$_4$) and concentrated to give a black residue. This was partially purified by flash chromatography on silica (ethyl acetate/petrol gradient, 20-33%) to afford an impure sample of the intermediate (2,4-bis-benzyloxy-5-isopropenyl-phenyl)-{4-[2-(2-methoxy-ethoxy)-ethoxy]-1,3-dihydro-isoindol-2-yl}-methanone.

A solution of (2,4-bis-benzyloxy-5-isopropenyl-phenyl)-{4-[2-(2-methoxy-ethoxy)-ethoxy]-1,3-dihydro-isoindol-2-yl}-methanone in methanol (5 mL) was hydrogenated at atmospheric pressure over 10% palladium on charcoal (12 mg) for 3 hours. A further portion of catalyst (12 mg) was added and hydrogenation continued for a further 7 hours. The mixture was filtered through Celite, eluting with methanol, then the filtrate was concentrated in vacuo to give a residue which was purified by preparative HPLC (basic method). This afforded the title compound as a white solid (17 mg, 16% over two steps). $^1$H NMR (methanol-$d_4$) 7.25 (1H, t), 7.17 (1H, s), 6.95-6.82 (2H, m), 6.37 (1H, s), 4.89 (2H, br.s), 4.83 (overlaps with H$_2$O, br.s), 4.16 (2H, br.s), 3.82 (2H, br.s), 3.66

(2H, br.s), 3.52 (2H, br.s), 3.39-3.28 (overlaps with MeOH, m), 3.20 (1H, sept), 1.21 (6H, d). MS: [M+H]+ 416.

Example 22

(2,4-Dihydroxy-5-isopropyl-phenyl)-[4-(2-dimethylamino-ethoxy)-1,3-dihydro-isoindol-2-yl]-methanone

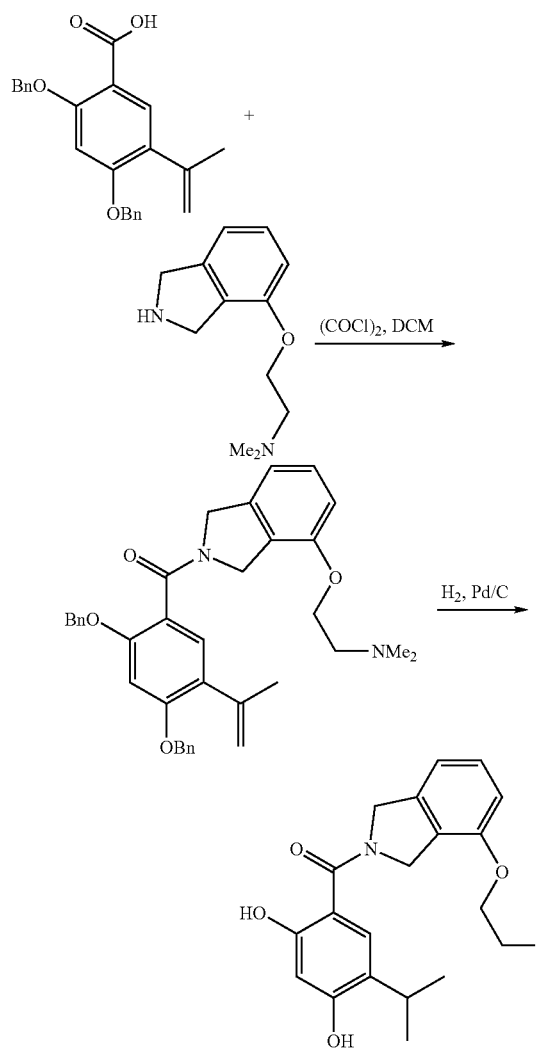

A solution of 2,4-bis-benzyloxy-5-isopropenyl-benzoic acid (189 mg, 0.50 mmol) and DMF (1 drop, cat.) in DCM (5 mL) was cooled in ice then treated with oxalyl chloride (112 L, 1.28 mmol). After 2 hours the mixture was concentrated in vacuo then azeotroped with toluene. The resulting acid chloride was dissolved in DCM (5 mL) and added to a solution of [2-(2,3-dihydro-1H-isoindol-4-yloxy)-ethyl]-dimethylamine (0.48 mmol, assuming a quantitative yield from the preceding step (C17)) and triethylamine (0.50 mL, 3.6 mmol) in DCM (3 mL). After 16 hours the mixture was diluted with ethyl acetate and washed with saturated potassium carbonate solution and brine. The organic phase was dried (MgSO4) and concentrated to give a residue which was partially purified by flash chromatography on silica (methanol/DCM gradient, 5-10% followed by 10% 2M methanolic ammonia/DCM) to afford an impure sample of the intermediate (2,4-bis-benzyloxy-5-isopropenyl-phenyl)-[4-(2-dimethylamino-ethoxy)-1,3-dihydro-isoindol-2-yl]-methanone.

A solution of (2,4-bis-benzyloxy-5-isopropenyl-phenyl)-[4-(2-dimethylamino-ethoxy)-1,3-dihydro-isoindol-2-yl]-methanone in methanol (5 mL) was hydrogenated at atmospheric pressure over 10% palladium on charcoal (40 mg) for 22 hours. The mixture was filtered through Celite, eluting with methanol, then the filtrate was concentrated in vacuo to give a residue which was purified by preparative HPLC (acidic method). This afforded the formate salt of the title compound as a white solid (9 mg, 5% over two steps). $^1$H NMR (methanol-d$_4$) 8.52 (0.7H, s), 7.29 (1H, t), 7.17 (1H, s), 6.98-6.86 (2H, m including 6.90 (1H, d)), 6.37 (1H, s), 4.89 (2H, br.s), 4.87 (2H, br.s), 4.28 (2H, br.s), 3.29-3.5 (3H, m including 3.20 (1H, sept)), 2.81-2.51 (6H, br.d), 1.21 (6H, d). MS: [M+H]+ 385.

Example 23

(2,4-Dihydroxy-5-isopropyl-phenyl)-[4-(3-morpholin-4-yl-propoxy)-1,3-dihydro-isoindol-2-yl]methanone

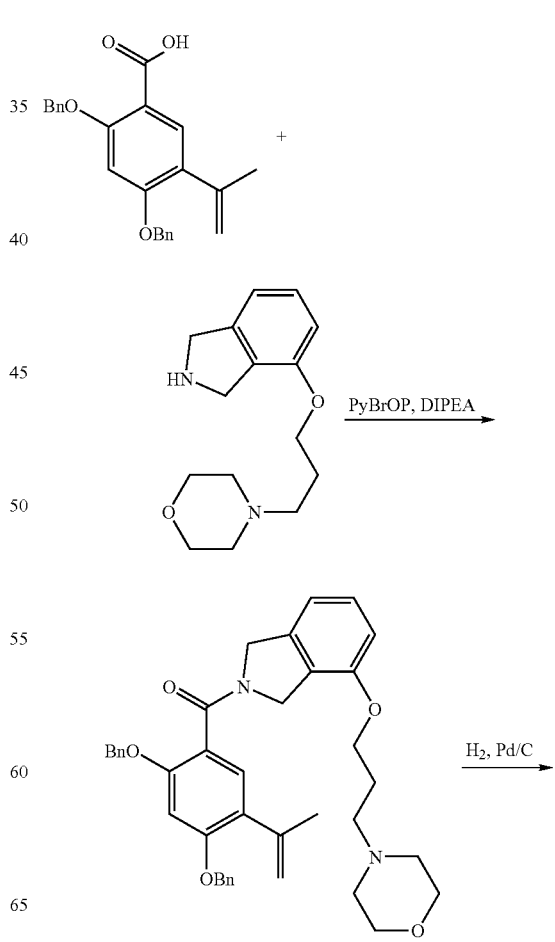

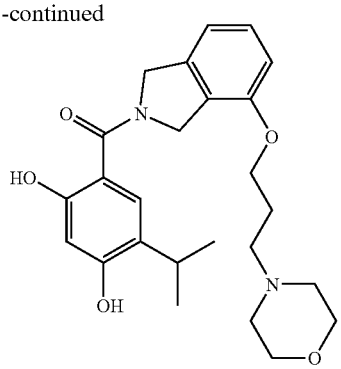

A solution of 2,4-bis-benzyloxy-5-isopropenyl-benzoic acid (210 mg, 0.56 mmol) and diisopropylethylamine (0.25 mL, 1.4 mmol) in DCM (5 mL) was treated with bromo-tris-pyrrolidino-phosphonium hexafluorophosphate (PyBrOP) (287 mg, 0.62 mmol). After 1 hour a solution of 4-(3-morpholin-4-yl-propoxy)-2,3-dihydro-1H-isoindole (0.56 mmol, assuming a quantitative yield from the preceding step (C18)) in DCM (5 mL) was added. After 4 hours the mixture was diluted with ethyl acetate and washed with water, 1N sodium hydroxide solution and brine. The organic phase was dried (MgSO$_4$) and concentrated to give a residue which was absorbed onto an SCX column. This was washed with 10% methanol/DCM then the product was eluted with 25% 2M methanolic ammonia/DCM) to afford an impure sample of the intermediate (2,4-bis-benzyloxy-5-isopropenyl-phenyl)-[4-(3-morpholin-4-yl-propoxy)-1,3-dihydro-isoindol-2-yl]-methanone.

A solution of (2,4-bis-benzyloxy-5-isopropenyl-phenyl)-[4-(3-morpholin-4-yl-propoxy)-1,3-dihydro-isoindol-2-yl]-methanone in methanol (5 mL) was hydrogenated at atmospheric pressure over 10% palladium on charcoal (45 mg) for 4 hours. The mixture was filtered through Celite, eluting with methanol, then the filtrate was concentrated in vacuo to give a residue which was purified by preparative HPLC (basic method). This afforded the title compound as a white solid (16 mg, 6% over two steps). $^1$H NMR (methanol-d$_4$) 7.24 (1H, t), 7.18 (1H, s), 6.89 (1H, d), 6.84 (1H, d), 6.37 (1H, s), 4.87 (2H, br.s), 4.78 (2H, br.s), 4.11-4.04 (2H, m), 3.72-3.66 (4H, m), 3.21 (1H, sept), 2.60-2.42 (6H, m), 2.05-1.92 (2H, m), 1.21 (6H, d). MS: [M+H]$^+$ 441.

Examples 24 to 47

By following the methods described above, the compounds of Examples 24 to 47 were prepared.

| Example Number | Compound | Chemical Name | Method | N.M.R. Data | M.S. |
| --- | --- | --- | --- | --- | --- |
| 24 | | (3-sec-Butyl-4-hydroxy-phenyl)-(1,3-dihydro-isoindol-2-yl)-methanone | A2 and A5. From (Z)-4-benzyloxy-3-(1-methyl-propenyl)-benzoic acid and isoindoline | $^1$H NMR (DMSO-d$_6$) 9.73 (1H, brs), 7.37 (1H, d), 7.32 (1H, dd), 7.30 (4H, br s), 6.86 (1H, d), 4.87 (2H, s), 4.82 (2H, s), 3.03 (1H, m), 1.63 (1H, m), 1.57 (1H, m), 1.19 (3H, d), 0.82 (3H, t) | MS: [M + H]$^+$ 296 |
| 25 | | (5-tert-Butyl-2,4-dihydroxy-phenyl)-1,3-dihydro-isoindol-2-yl)-methanone | A2 and A5. From 2,4-bis-benzyloxy-5-tert-butyl-beenzoic acid and isoquinoline | $^1$H NMR (DMSO-d$_6$) 7.34 (2H, m), 7.29 (2H, m), 7.10 (1H, s), 6.33 (1H, s), 4.83 (4H, s), 1.35 (9H, s) | MS: [M + H]$^+$ 312 |
| 26 | | 5-Chloro-2,4-dihydroxy-phenyl)-(1,3-dihydro-isoindol-2-yl)-methanone | A2 and A3. From 2,4-bis-benzyloxy-5-chloro-benzoic acid and isoindoline | $^1$H NMR (DMSO-d$_6$) 10.42 (1H, s), 10.33 (1H, s), 7.38 (2H, m), 7.30 (2H, m), 7.24 (1H, s), 6.60 (1H, s), 4.78 (2H, br s), 4.72 (2H, br s) | MS: [M + H]$^+$ 290 |

-continued

| Example Number | Compound | Chemical Name | Method | N.M.R. Data | M.S. |
|---|---|---|---|---|---|
| 27 | 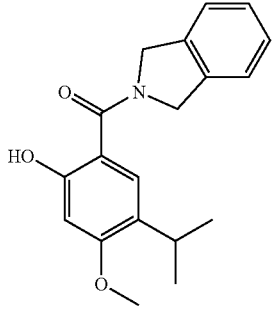 [SMILES: COc1cc(O)c(C(=O)N2Cc3ccccc3C2)cc1C(C)C] | (1,3-Dihydro-isoindol-2-yl)-(2-hydroxy-5-isopropyl-4-methoxy-phenyl)-methanone | A2, A5 & A7. From 2,4-bis-benzyloxy-5-isopropenyl-benzoic acid and isoquinoline | H NMR (DMSO-d$_6$) 10.21 (1H, br s), 7.33 (2H, br s), 7.28 (2H, br s), 7.13 (1H, s), 6.50 (1H, s), 4.80 (4H, br s), 3.79 (3H, s), 3.15 (1H, m), 1.14 (6H, d) | MS: [M + H]$^+$ 312 |
| 28 | 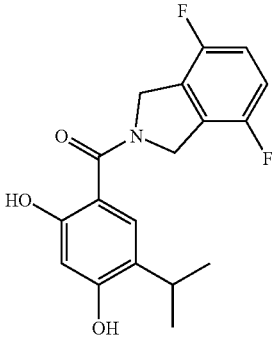 [SMILES: CC(C)c1cc(C(=O)N2Cc3c(F)ccc(F)c3C2)c(O)cc1O] | (4,7-difluoro-1,3-dihydro-isoindol-2-yl)-2,4-dihydroxy-5-isopropyl-phenyl)-methanone | A2 and A5. From 2,4-bis-benzyloxy-5-isopropenyl-benzoic acid and 4,7-difluoro-isoindoline | H NMR (DMSO-d$_6$) 9.97 (1H, br s), 9.66 (1H, br s), 7.22 (2H, dd), 7.03 (1H, s), 6.42 (1H, s), 4.84 (4H, br s), 3.10 (1H, m), 1.13 (6H, d) | MS: [M + H]$^+$ 334 |
| 29 | 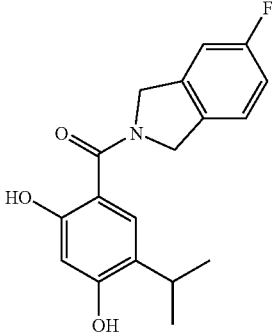 [SMILES: CC(C)c1cc(C(=O)N2Cc3ccc(F)cc3C2)c(O)cc1O] | (2,4-dihydroxy-5-isopropyl-phenyl)-(5-fluoro-1,3-dihydro-isoindol-2-yl)-methanone | A2 and A5. From 2,4-bis-benzyloxy-5-isopropenyl-benzoic acid and 5-fluoro-isoindoline [Ref. U.S. Pat. No. 5,026,856] | H NMR (DMSO-d$_6$) 10.02 (1H, br s), 9.58 (1H, s), 7.37 (1H, br m), 7.20 (1H, br m), 7.12 (1H, td), 7.04 (1H, s), 6.41 (1H, s), 4.78 (2H, br s), 4.75 (2H, br s), 3.11 (1H, m), 1.16 (6H, d) | MS: [M + H]$^+$ 316 |
| 30 | 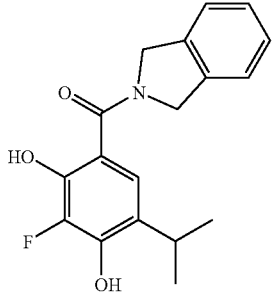 [SMILES: CC(C)c1cc(C(=O)N2Cc3ccccc3C2)c(O)c(F)c1O] | (1,3-dihydro-isoindol-2-yl)-(3-fluoro-2,4-dihydroxy-5-isopropyl-phenyl)-methanone | A8. From (1,3-dihydro-isoindol-2-yl)-(2,4-dihydroxy-5-isopropyl-phenyl)-methanone | H NMR (DMSO-d$_6$) 12.23 (1H, br s), 7.39 (1H, m), 7.35-7.25 (3H, m), 6.84 (1H, d), 5.53 (1H, s), 4.74 (2H, s), 4.59 (2H, s), 2.52 (1H, m), 1.11 (3H, d), 0.84 (3H, d); $^{19}$F NMR (DMSO-D6) 19.3 | MS: [M + H]$^+$ 316 |

-continued

| Example Number | Compound | Chemical Name | Method | N.M.R. Data | M.S. |
|---|---|---|---|---|---|
| 31 | | (1,3-dihydro-isoindol-2-yl)-(2-fluoro-4,6-dihydroxy-3-isopropyl-phenyl)-methanone | A8. From (1,3-dihydro-isoindol-2-yl)-(2,4-dihydroxy-5-isopropyl-phenyl)-methanone | H NMR (DMSO-$d_6$) 12.03 (1H, br s), 7.40-7.35 (2H, m), 7.33-7.28 (2H, m), 6.53 (1H, br d), 5.53 (1H, s), 5.07 (1H, br d), 4.98 (1H, br d), 4.79 (2H, s), 2.90 (1H, m), 1.03 (6H, m); $^{19}$F NMR (DMSO-$d_6$) 24.9 | MS: [M + H]$^+$ 316 |
| 32 | | (2,4-dihydroxy-5-isopropyl-phenyl)-(4-fluoro-1,3-dihydro-isoindol-2-yl)-methanone hydrochloride | From 2,4-bis-benzyloxy-5-isopropyl-benzoic acid (B10) and 4-fluoro-2,3-dihydro-1H-isoindole | H NMR (DMSO-$d_6$) 7.35 (2H, m), 7.20 (1H, m), 7.1 (1H, t), 7.0 (1H, s), 6.4 (1H, s), 4.80 (4H, br s), 1.20 (6H, s) | MS: [M + H]$^+$ 316 |
| 33 | | (5-chloro-6-methoxy-1,3-dihydro-iso-indol-2-yl)-2,4-dihydroxy-5-isopropyl-phenyl)-methanone | A2 and A5. From 2,4-bis-benzyloxy-5-isopropyl-benzoic acid (B10) and 5-chloro-6-methoxy-2,3-dihydro-1H-isoindole | $^1$H NMR (Me-$d_3$-OD) 7.32 (1H, s), 7.17 (1H, s), 7.05 (1H, s), 6.37 (1H, s), 4.89 (2H, s) 3.89 (3H, s), 3.36 (3H, m), 1.23 (6H, d) | MS: [M + H]$^+$ 362 |
| 34 | | (2,4-dihydroxy-5-isopropyl-phenyl)-[5-(2-methoxy-ethoxy)-1,3-dihydro-isoindol-2-yl]-methanone | A5. From (2,4-bis-benzyloxy-5-isopropyl-phenyl)-[5-(2-methoxy-ethoxy)-1,3-dihydro-isoindol-2-yl]-methanone | H NMR (DMSO-$d_6$) 10.02 (1H, s), 9.60 (1H, s), 7.22 (1H, br s), 7.03 (1H, s), 6.90 (1H, br s), 6.85 (1H, d), 6.4 (1H, s), 4.74 (4H, br d), 4.08 (2H, br s), 3.65 (2H, t), 3.18-3.03 (1H, m), 1.15 (6H, s), 3.30 (3H, s) | MS: [M + H]$^+$ 372 |

| Example Number | Compound | Chemical Name | Method | N.M.R. Data | M.S. |
|---|---|---|---|---|---|
| 35 | | (2,4-dihydroxy-5-isopropyl-phenyl)-[5-(3-morpholin-4-yl-propoxy)-1,3-dihydro-isoindol-2-yl]-methanone | A5. From (2,4-bis-benzyloxy-5-isopropyl-phenyl)-[5-(3-morpholin-4-yl-propoxy)-1,3-dihydro-isoindole-2-yl]-methanone | H NMR (DMSO-$d_6$) 10.02 (1H, s), 9.60 (1H, s), 7.22 (1H, br s), 7.03 (1H, s), 6.90 (1H, br s), 6.85 (1H, d), 6.4 (1H, s), 4.74 (4H, br d), 4.08 (2H, br s), 3.55 (4H, br s), 3.18-3.03 (1H, m), 2.40 (2H, s), 2.38 (4H, br s), 1.85 (2H, t), 1.15 (6H, s) | MS: [M + H]$^+$ 441 |
| 36 | | (2,4-dihydroxy-5-isopropyl-phenyl)-[5-(2-dimethylamino-ethoxy)-1,3-dihydro-isoindol-2-yl]-methanone | A5. From (2,4-bis-benzyloxy-5-isopropyl-phenyl)-[5-(2-dimethylamino-ethoxy)-1,3-dihydro-isoindol-2-yl]-methanone | H NMR (DMSO-$d_6$) 10.02 (1H, s), 9.60 (1H, s), 7.22 (1H, br s), 7.03 (1H, s), 6.90 (1H, br s), 6.85 (1H, d), 6.40 (1H, s), 4.74 (4H, br d), 4.08 (2H, br s), 3.18-3.03 (1H, m), 2.71 (2H, br s), 2.30 (6H, s), 1.15 (6H, s) | MS: [M + H]$^+$ 385 |
| 37 | | (2,4-dihydroxy-5-isopropyl-phenyl)-(2-oxa-5-aza-bicyclo[2.2.1]hept-5-yl)-methanone | A2 and A5. From (2,4-bis-benzyloxy-5-isopropyl-benzoic acid (Preparation B5 and 2-oxa-5-aza-bicyclo[2.2.1]-heptane | H NMR (DMSO-$d_6$) 9.64 (1H, s), 7.02 (1H, s), 6.31 (1H, s), 4.65 (2H, s), 3.78 (2H, dd), 3.31 (2H, s), 3.07 (1H, m), 1.77 (2H, m), 1.10 (6H, m) | MS: [M + H]$^+$ 278 |
| 38 | | (3,4-dihydro-1H-isoquinolin-2-yl)-(2,4-dihydroxy-5-isopropyl-phenyl)-methanone | A2 and A5. From (2,4-bis-benzyloxy-5-isopropyl-benzoic acid (Preparation B5) and 1,2,3,4-tetrahydro-isoquinoline | $^1$H NMR (Me-$d_3$-OD) 7.19 (1H, s), 7.14 (1H, br s), 7.09 (1H, br s), 7.02 (1H, s), 6.37 (1H, s), 4.75 (2H, s), 3.80 (2H, t), 3.24-3.15 (1H, m), 2.95 (2H, t), 1.19 (6H, d) | MS: [M + H]$^+$ 312 |

-continued

| Example Number | Compound | Chemical Name | Method | N.M.R. Data | M.S. |
|---|---|---|---|---|---|
| 39 | (structure) | (5-amino-1,3-dihydro-isoindol-2-yl)-2,4-dihydroxy-5-isopropyl-phenyl)-methanone | A2 & A5. From 2,4-bis-benzyloxy-5-isopropenyl-benzoic acid (Preparation B5) and 5-nitro-isoindoline. TFA (C5 but omitting hydrogenation step) | H NMR (DMSO-$d_6$) 7.05 (1H, s), 6.95-6.85 (1H, m), 6.60-6.50 (2H, m), 6.25 (1H, s), 4.6-4.5 (4H, m), 3.10 (1H, h), 1.10 (6H, d) | MS: [M + H]+ 313 |
| 40 | (structure) | (2,4-dihydroxy-5-isopropyl-phenyl)-(5-methoxy-1,3-dihydro-isoindol-2-yl)-methanone | A2 and A5. From 2,4-bis-benzyloxy-5-isopropenyl-benzoic acid (Preparation B5) and 5-methoxy-isoindoline. | H NMR (DMSO-$d_6$) 10.05 (1H, s), 9.60 (1H, s), 7.30-7.15 (1H, m), 7.05 (1H, s), 7.00-6.85 (1H, m), 6.82 (1H, d), 6.40 (1H, s), 4.75 (2H, s) 4.70 (2H, s), 3.75 (3H, s), 3.10 (1H, m), 1.13 (6H, d) | MS: [M + H] + 328 |
| 41 | (structure) | (2,4-dihydroxy-5-isopropyl-phenyl)-(5-morpholin-4-yl-1,3-dihydro-isoindol-2-yl)-methanone | A5 from (2,4-bis-benzyloxy-5-isopropenyl-phenyl)-(5-morpholin-4-yl-1,3-dihydro-isoindol-2-yl)-methanone (D5). | H NMR (DMSO-$d_6$) 9.60 (1H, br s), 7.30-7.15 (1H, m), 7.05 (1H, s), 7.00-6.90 (2H, m), 6.40 (1H, s), 4.75 (2H, s) 4.70 (2H, s), 3.75 (4H, m), 3.15-3.05 (5H, m), 1.15 (6H, d) | MS: [M + H]+ 383 |
| 42 | (structure) | (2,4-dihydroxy-5-isopropyl-phenyl)-[5-(4-methyl-piperazin-1-yl)-1,3-dihydro-isoindol-2-yl]-methanone | As for Example 41 but using bis(2-chloroethyl)-methylamine hydrochloride in step 2. | H NMR (DMSO-$d_6$) 7.30-7.15 (1H, m), 7.05 (1H, s), 6.95-6.85 (2H, m), 6.40 (1H, s), 4.70 (2H, br s) 4.65 (2H, br s), 3.15-3.05 (5H, m), 2.45 (4H, m), 2.20 (4H, s), 1.85 (3H, s), 1.15 (6H, d) | MS: [M + H]+ 396 |

-continued

| Example Number | Compound | Chemical Name | Method | N.M.R. Data | M.S. |
|---|---|---|---|---|---|
| 43 | | 2-(2,4-dihydroxy-5-isospropyl-benzoyl)-2,3-dihydro-1H-isoindole-5-carboxylic acid methyl ester | A2 and A5. From 2,4-bis-benzyloxy-5-isopropenyl-benzoic acid (Preparation B5 and 2,3-dihydro-1H-isoindole-5-carboxylic acid methyl ester. TFA (Preparation C21) | H NMR (DMSO-$d_6$) 10.05 (1H, br s), 9.60 (1H, s), 8.00-7.92 (1H, m), 7.90 (1H, s), 7.55-7.42 (1H, m), 7.05 (1H, d), 6.40 (1H, s), 4.85 (4H, br s) 3.85 (3H, s), 3.10 (1H, m), 1.13 (6H, d) | MS: [M + H]$^+$ 356 |
| 44 | | 2-(2,4-dihydroxy-5-isopropyl-benzoyl)-2,3-dihydro-1H-isoindole-5-carboxylic acid | A5, from 2-(2,4-bis-benzyloxy-5-isopropyl-benzoyl)-2,3-dihydro-1H-isoindole-5-carboxylic acid. | H NMR (DMSO-$d_6$) 12.90 (1H, br s), 10.05 (1H, br s), 9.60 (1H, s), 8.00-7.92 (1H, m), 7.90 (1H, d), 7.55-7.40 (1H, m), 7.05 (1H, d), 6.45 (1H, s), 4.85 (4H, br s) 3.10 (1H, m), 1.15 (6H, d) | MS: [M + H]$^+$ 342 |
| 45 | | (2,4-dihydroxy-5-isopropyl-phenyl)-(5-morpholin-4-ylmethyl-1,3-dihydro-isoindol-2-yl)-methanone hydrochloride | A2 and A5. From 2,4-bis-benzyloxy-5-isopropenyl-benzoic acid (Preparation B5) and 5-morpholin-4-ylmethyl-2,3-dihydro-1H-isoindole ditrifluoro-acetate (C6). | H NMR (DMSO-$d_6$) 11.03 (1H, br s), 10.05 (1H, br s), 9.78 (1H, br s), 7.60-7.38 (3H, m), 7.05 (1H, s), 6.45 (1H, s), 4.80 (4H, m), 4.33 (2H, d), 3.95-3.85 (2H, m), 3.32-3.22 (2H, m), 3.28-3.00 (5H, m), 1.15 (6H, d) | MS: [M + H]$^+$ 397 |
| 46 | | {3-[2-(2,4-dihydroxy-5-isopropyl-benzoyl)-2,3-dihydro-1H-isoindol-5-yloxy]-propyl}-carbamic acid tert-butyl ester | As for Example 34, A2 (from benzyloxy-5-isopropyl-benzoic acid (Preparation B5) and 5-hydroxy-isoindoline), alkylation using 3-(BOC-amino)propyl bromide, then A5. | H NMR (DMSO-$d_6$) 10.05 (1H, br s), 9.60 (1H, s), 7.30-7.15 (1H, m), 7.05 (1H, s), 6.98-6.80 (3H, m), 6.40 (1H, s), 4.75 (2H, br s) 4.70 (2H, br s), 3.95 (2H, s), 3.15-3.05 (3H, m), 1.80 (2H, tt), 1.37 (9H, s), 1.15 (6H, d) | MS: [M + H]$^+$ 471 |

| Example Number | Compound | Chemical Name | Method | N.M.R. Data | M.S. |
|---|---|---|---|---|---|
| 47 | 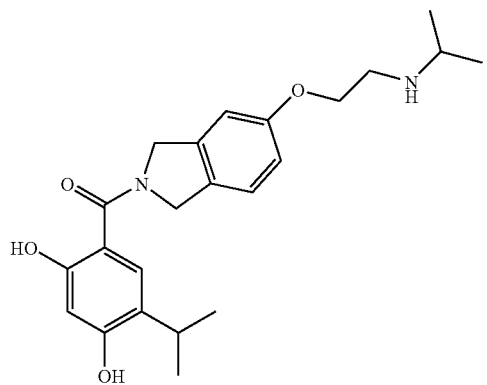 | (2,4-dihydroxy-5-isopropyl-phenyl)-(5-methyl-1,3-dihydro-isoindol-2-yl)-methanone | A2 and A5. From 2,4-bis-benzyloxy-5-isopropenyl-benzoic acid (Preparation B5) and 5-morpholin-4-ylmethyl-2,3-dihydro-1H-isoindole ditrifluoro-acetate (C6). Biproduct from Example 45. | H NMR (DMSO-$d_6$) 10.05 (1H, s), 9.60 (1H, s), 7.25-7.08 (3H, m), 7.05 (1H, s), 6.40 (1H, s), 4.75 (4H, m), 3.10 (1H, m), 2.30 (1H, s), 1.15 (6H, d) | MS: [M + H]$^+$ 312 |

Example 48

Synthesis of (2,4-dihydroxy-5-isopropyl-phenyl)-[5-(2-isopropylamino-ethoxy)-1,3-dihydro-isoindol-2-yl]-methanone

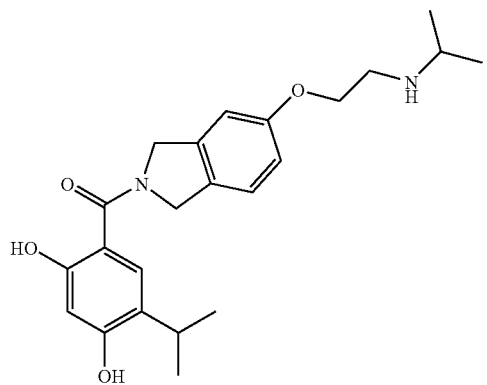 [SMILES: CC(C)NCCOc1ccc2c(c1)CN(C(=O)c1cc(C(C)C)c(O)cc1O)C2]

To a suspension of [5-(3-amino-ethoxy)-1,3-dihydro-isoindol-2-yl]-(2,4-dihydroxy-5-isopropyl-phenyl)-methanone hydrochloride (Example 57) (250 mg, 0.702 mmoles) in 1,2-dichloroethane (10 ml) was added acetone (62 µl, 0.842 mmoles), sodium triacetoxyborohydride (178 mg, 0.842 mmoles) and acetic acid (48 µl, 0.842 mmoles) and then heated at 60° C. for 24 hours. To the reaction mixture was added further acetone (52 µl, 0.702 mmoles), sodium triacetoxyborohydride (149 mg, 0.702 mmoles) and acetic acid (40 µl, 0.702 mmoles) and heated at 60° C. for a further 2 hours. The reaction mixture was then filtered and the mother liquor purified by flash chromatography [Biotage SP4: 25M, flow rate 25 ml/min, gradient 20% to 100% DMAW 90 in DCM) to give (2,4-dihydroxy-5-isopropyl-phenyl)-[5-(2-isopropylamino-ethoxy)-1,3-dihydro-isoindol-2-yl]-methanone as a light brown viscous oil (140 mg, 50%). $^1$H NMR (DMSO-d6) 10.05 (1H, br s); 9.60 (1H, br s); 7.23 (1H, br s); 7.05 (1H, s); 6.93 (1H, br s); 6.85 (1H, br d); 6.40 (1H, s); 4.70 (4H, br m); 4.00 (2H, t); 3.10 (1H, m); 2.90 (2H, t); 2.80 (1H, m); 1.15 (6H, d); 1.00 (6H, d). MS: [M+H]$^+$ 399.

Example 49

Synthesis of N-{2-[2,4-dihydroxy-5-isopropyl-benzoyl)-2,3-dihydro-1H-isoindol-5-yloxy]-ethyl}-2-morpholin-4-yl-acetamide

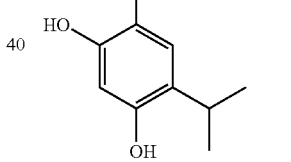

To a solution of [5-(3-amino-ethoxy)-1,3-dihydro-isoindol-2-yl]-(2,4-dihydroxy-5-isopropyl-phenyl)-methanone hydrochloride (100 mg, 0.255 mmoles) in DMF (10 ml) was added EDC (59 mg, 0.306 mmoles), HOBt (41 mg, 0.306 mmoles), morpholin-4-yl-acetic acid (37 mg, 0.255 mmoles) and triethylamine (43 µl, 0.306 mmoles) and stirred at ambient temperature for one hour. To the reaction mixture was added further EDC (20 mg, 0.104 mmoles), HOBt (14 mg, 0.104 mmoles), morpholin-4-yl-acetic acid (12 mg, 0.083 mmoles) and triethylamine (14 µl, 0.100 mmoles) and stirred at ambient temperature for a further 2 hours. Solvent removed in vacuo. The residue was purified by flash chromatography [Biotage SP4: 25S, flow rate 25 ml/min, gradient 20% DMAW 90 in DCM to 100% DMAW 90] and then by preparative HPLC to give N-{2-[2,4-dihydroxy-5-isopropyl-benzoyl)-2,3-dihydro-1H-isoindol-5-yloxy]-ethyl}-2-morpholin-4-yl-acetamide as a colourless viscous oil (40 mg, 33%). $^1$H NMR (Me-d3-OD) 7.20 (1H, br s); 7.18 (1H, s); 6.90 (2H, br m); 6.40 (1H, s); 4.10 (2H, t); 3.73 (4H, m); 3.63 (2H, t); 3.20 (1H, m); 3.18 (2H, s); 2.60 (4H, m); 1.25 (6H, d). MS: [M+H]$^+$ 484.

Example 50

Synthesis of (2,4-dihydroxy-5-isopropyl-phenyl)-[5-(4-hydroxy-1-methyl-piperidin-4-yl)-1,3-dihydro-isoindol-2-yl]-methanone

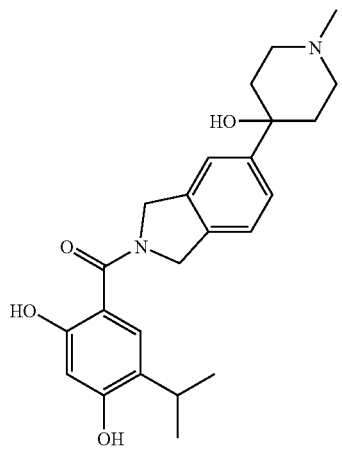 [SMILES: CC(C)c1cc(C(=O)N2Cc3ccc(C4(O)CCN(C)CC4)cc3C2)c(O)cc1O]

50A: Synthesis of 5-bromo-1,3-dihydro-isoindole-2-carboxylic acid tert-butyl ester A mixture of 5-bromo-2,3-dihydro-1H-isoindole (1.26 g; 6.4 mmol), di-tert-butyl dicarbonate (1.53 g; 1.1 equiv.) and 4-dimethylaminopyridine (catalytic amount) in DMF (20 ml) was stirred at room temperature overnight then evaporated. The residue was partitioned between EtOAc and brine, the EtOAc layer was separated, dried (MgSO$_4$) and evaporated. Purification by flash column chromatography using a Biotage SP4 (40S, 40 ml/min) eluting with 0% to 5% MeOH/DCM gave 695 mg of 5-bromo-1,3-dihydro-isoindole-2-carboxylic acid tert-butyl ester as a brown gum. $^1$H NMR (DMSO-d6) 7.55 (1H, d), 7.48 (1H, d), 7.30 (1H, dd), 4.63-4.51 (4H, m), 1.46 (9H, s).

50B. Synthesis of 5-(4-hydroxy-1-methyl-piperidin-4-yl)-1,3-dihydro-isoindole-2-carboxylic acid tert-butyl ester 0.69 ml of n-Butyl lithium (2.5M solution in hexane) was added dropwise to a stirred solution of 5-bromo-1,3-dihydro-isoindole-2-carboxylic acid tert-butyl ester (429 mg; 1.44 mmol) in anhydrous THF (10 ml) at −78° C. under an atmosphere of nitrogen. The reaction was stirred for 50 minutes then 1-methyl-4-piperidone (212 μl; 1.2 equiv.) was added and stirred at −78° C. for a further 60 minutes then warmed to room temperature. The reaction was quenched with saturated ammonium chloride solution then extracted with EtOAc. The EtOAc layer was washed with saturated NaHCO$_3$, brine, dried (MgSO$_4$) and evaporated. Purification by flash column chromatography on SiO$_2$, gradient elution from 0% to 10% 2M methanolic ammonia/DCM gave 111 mg of 5-(4-hydroxy-1-methyl-piperidin-4-yl)-1,3-dihydro-isoindole-2-carboxylic acid tert-butyl ester as a colourless oil.

50C. Synthesis of 4-(2,3-dihydro-1H-isoindol-5-yl)-1-methyl-piperidin-4-ol

A solution of 5-(4-hydroxy-1-methyl-piperidin-4-yl)-1,3-dihydro-isoindole-2-carboxylic acid tert-butyl ester (107 mg; 0.32 mmol) in THF (4 ml) was treated with concentrated hydrochloric acid (1.5 ml) then heated at reflux for 4 hours, then evaporated and re-evaporated with toluene to give 4-(2,3-dihydro-1H-isoindol-5-yl)-1-methyl-piperidin-4-ol dihydrochloride as a brown gum.

50D. Synthesis of (2,4-bis-benzyloxy-5-isopropenyl-phenyl)-[5-(4-hydroxy-1-methyl-piperidin-4yl)-1,3-dihydro-isoindol-2-yl]-methanone A solution of 2,4-bis-benzyloxy-5-isopropenyl-benzoic acid (145 mg; 1.2 equiv.) in DCM (5 ml) was treated with EDC (80 mg; 1.3 equiv.) and HOAt (66 mg; 1.5 equiv.) then stirred at room temperature for 30 minutes. This solution was then added to a mixture of 4-(2,3-dihydro-1H-isoindol-5-yl)-1-methyl-piperidin-4-ol dihydrochloride (112 mg; 0.32 mmol) and triethylamine (90 μl; 2 equiv.) in THF (5 ml) and DMF (2 ml), the reaction was then stirred at room temperature overnight. The reaction mixture was diluted with EtOAc, washed with water, 1N NaOH and brine, the EtOAc layer was separated, dried (MgSO$_4$) and evaporated. Purification by flash column chromatography on SiO$_2$, gradient elution from 0% to 5% 2M methanolic ammonia/DCM gave 104 mg of (2,4-bis-benzyloxy-5-isopropenyl-phenyl)-[5-(4-hydroxy-1-methyl-piperidin-4-yl)-1,3-dihydro-isoindol-2-yl]-methanone as a yellow glass.

50E. Synthesis of (2,4-dihydroxy-5-isopropyl-phenyl)-[5-(4-hydroxy-1-methyl-piperidin-4-yl)-1,3-dihydro-isoindol-2-yl]-methanone Hydrogenation of (2,4-bis-benzyloxy-5-isopropenyl-phenyl)-[5-(4-hydroxy-1-methyl-piperidin-4-yl)-1,3-1,3-dihydro-isoindol-2-yl]-methanone (as described in method A5) afforded 72 mg of the title compound as a cream solid. $^1$H NMR (Me-d3-OD) 7.35 (2H, m), 7.18 (1H, br m) 7.08 (1H, s), 6.25 (1H, s), 4.78 (4H, m), 3.10 (1H, m), 2.65 (2H, m), 2.45 (2H, m), 2.25 (3H, s), 2.00 (2H, m), 1.65 (2H, m), 1.10 (6H, d). MS: [M+H]$^+$ 411.

Example 51

Synthesis of (2,4-dihydroxy-5-isopropyl-phenyl)-{5-[4-(4-methyl-piperazin-1-yl)-piperidin-1-yl]-1,3-dihydro-isoindol-2-yl}-methanone

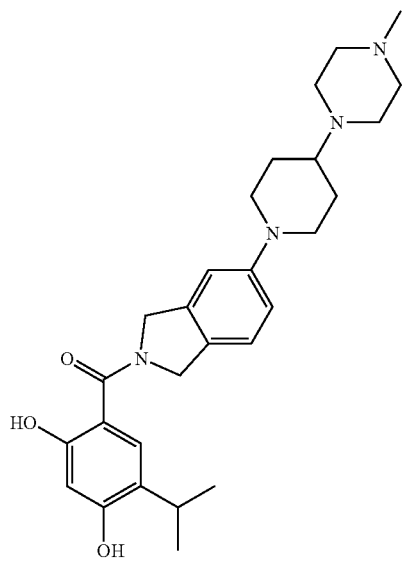 [SMILES: CC(C)c1cc(C(=O)N2Cc3ccc(N4CCC(N5CCN(C)CC5)CC4)cc3C2)c(O)cc1O]

51A. Synthesis of (2,4-bis-benzyloxy-5-isopropenyl-phenyl)-(5-bromo-1,3-dihydro-isoindol-2-yl)-methanone A solution of benzyloxy-5-isopropenyl-benzoic acid (2.85 g; 7.6 mmol), 5-bromo-2,3-dihydro-1H-isoindole (1.5 g; 1 equiv.), EDC (1.75 g; 1.2 equiv.) and HOBt (1.25 g; 1.2 equiv.) in DMF (25 ml) was stirred at room temperature overnight then evaporated. The residue was dissolved in EtOAc, washed with 2M HCl then saturated NaHCO$_3$, dried (MgSO$_4$) and evaporated. Purification using a Biotage SP4 (40S, 40 ml/min) eluting with 1:4-1:3-1:2 EtOAc/P.E. gave 2.45 g of (2,4-bis-benzyloxy-5-isopropenyl-phenyl)-(5-bromo-1,3-dihydro-isoindol-2-yl)-methanone as a light brown solid.

51B. (2,4-bis-benzyloxy-5-isopropenyl-phenyl)-{5-[4-(4-methyl-piperazin-1-yl)-piperidin-1-yl]-1,3-dihydro-isoindol-2-yl}-methanone A solution of (2,4-bis-benzyloxy-5-isopropenyl-phenyl)-(5-bromo-1,3-dihydro-isoindol-2-yl)-methanone (200 mg; 0.36 mmol) and 1-methyl-4-(piperidin-4-yl)piperazine (80 mg; 1.2 equiv.) in toluene (5 ml) was treated with (2-biphenyl)-di-tert-butylphosphine (6 mg; 5 mol %), tris(dibenzylidene)palladium(0) (10 mg; 2.5 mol %) and sodium tert-butoxide (50 mg; 1.4 equiv.) then heated at 120° C. for 30 minutes in a CEM explorer microwave synthesiser. The reaction mixture was diluted with DCM, washed with brine, dried (MgSO$_4$) and evaporated. Purification by flash column chromatography (Biotage SP4—25S, 25 ml/min) eluting with DMAW 240-120-90 followed by evaporation of product containing fractions gave 105 mg of (2,4-bis-benzyloxy-5-isopropenyl-phenyl)-{5-[4-(4-methyl-piperazin-1-yl)-piperidin-1-yl]-1,3-dihydro-isoindol-2-yl}-methanone as the acetic acid salt.

51C. (2,4-dihydroxy-5-isopropyl-phenyl)-{5-[4-(4-methyl-piperazin-1-yl)-piperidin-1-yl]-1,3-dihydro-isoindol-2-yl}-methanone hydrochloride A solution of (2,4-bis-benzyloxy-5-isopropenyl-phenyl)-{5-[4-(4-methyl-piperazin-1-yl)-piperidin-1-yl]-1,3-dihydro-isoindol-2-yl}-methanone acetic acid salt in methanol (10 ml) was treated with 10% palladium on carbon (wet), hydrogenated at room temperature and pressure overnight then filtered and evaporated. The crude compound was purified by flash column chromatograph (Biotage SP4—25S, 25 ml/min) eluting with DMAW 240-120-90-60. Product containing fractions were evaporated, treated with saturated HCl/EtOAc then evaporated and re-evaporated with methanol and dried under high vacuum at 60° C. overnight. (2,4-dihydroxy-5-isopropyl-phenyl)-{5-[4-(4-methyl-piperazin-1-yl)-piperidin-1-yl]-1,3-dihydro-isoindol-2-yl}-methanone hydrochloride was isolated as a cream solid (62 mg). $^1$H NMR (DMSO-d6) 12.40-12.00 (2H, br m), 9.75-9.55 (1H, br m), 7.45-7.05 (3H, m), 7.03 (1H, s), 6.45 (1H, s), 4.70-4.55 (4H, m), 3.85-3.65 (6H, m), 3.60-3.40 (5H, m), 3.15-3.05 (1H, m), 3.0-2.78 (5H, m), 2.30-2.20 (2H, m), 2.05-1.90 (2H, m), 1.15 (6H, d). MS: [M+H]$^+$ 479.

Example 52

Synthesis of (2,4-dihydroxy-5-isopropyl-phenyl)-[5-(4-piperazin-1-yl-phenyl)-1,3-dihydro-isoindol-2-yl]-methanone

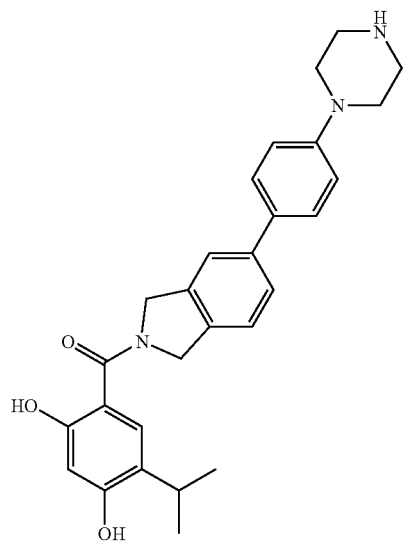 [SMILES: CC(C)c1cc(C(=O)N2Cc3ccc(-c4ccc(N5CCNCC5)cc4)cc3C2)c(O)cc1O]

52A. Synthesis of 4-{4-[2-(2,4-bis-benzyloxy-5-isopropenyl-benzoyl)-2,3-dihydro-1H-isoindol-5-yl]-phenyl}piperazine-1-carboxylic acid tert-butyl ester A mixture of (2,4-bis-benzyloxy-5-isopropenyl-phenyl)-(5-bromo-1,3-dihydro-isoindol-2-yl)-methanone (240 mg, 0.43 mmol), t-butyl-4-[4-(4,4,5,5-tetramethyl-1,3,2-dioxaborolan-2-yl)phenyl]piperazine carboxylate (210 mg, 1.25 equiv.), bis(tri-t-butylphosphine)palladium(0) (12.5 mg, 2.5 mol %) and potassium carbonate (350 mg, 6 equiv.) in toluene/water/ethanol (1 ml:1 ml:4 ml) was heated at 135° C. for 30 minutes in a CEM explorer microwave synthesiser. The reaction mixture was diluted with EtOAc, washed with saturated NaHCO$_3$, dried (MgSO$_4$) and evaporated. Purification by flash column chromatography (Biotage SP4—25S, 25 ml/min) eluting with 1:3 then 1:1 EtOAc/P.E. Evaporation of product containing fractions gave 85 mg of 4-{4-[2-(2,4-bis-benzyloxy-5-isopropenyl-benzoyl)-2,3-dihydro-1H-isoindol-5-yl]-phenyl}piperazine-1-carboxylic acid tert-butyl ester. MS: [M+H]$^+$ 736.

52B. Synthesis of (2,4-dihydroxy-5-isopropyl-phenyl)-[5-(4-piperazin-1-yl-phenyl)-1,3-dihydro-isoindol-2-yl]-methanone Hydrogenation of 4-{4-[2-(2,4-bis-benzyloxy-5-isopropenyl-benzoyl)-2,3-dihydro-1H-isoindol-5-yl]-phenyl}piperazine-1-carboxylic acid tert-butyl ester (as described in method A5), followed by BOC deprotection (as described in example 70) afforded 10 mg of the title compound as the hydrochloride salt after flash column chromatography (Biotage SP4, 25S) eluting with DMAW 240-120-90 and evaporation from saturated HCl/EtOAc. $^1$H NMR (Me-d3-OD) 7.63 (2H, d), 7.55 (2H, m) 7.45-7.30 (1H, m), 7.25 (1H, s), 7.20 (2H, d), 5.03 (4H, m), 3.55 (4H, m), 3.47 (4H, m), 3.23 (1H, m), 1.25 (6H, d). MS: [M+H]$^+$ 458.

Example 53

Synthesis of 2,4-dihydroxy-5-isopropyl-phenyl)-[5-(1-dimethylamino-2-hydroxy-ethyl)-1,3-dihydro-isoindol-2-yl]-methanone, and dihydroxy-5-isopropyl-phenyl)-[5-(2-dimethylamino-1-hydroxy-ethyl)-1,3-dihydro-isoindol-2-yl]-methanone

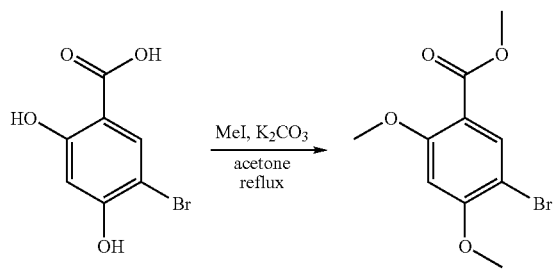

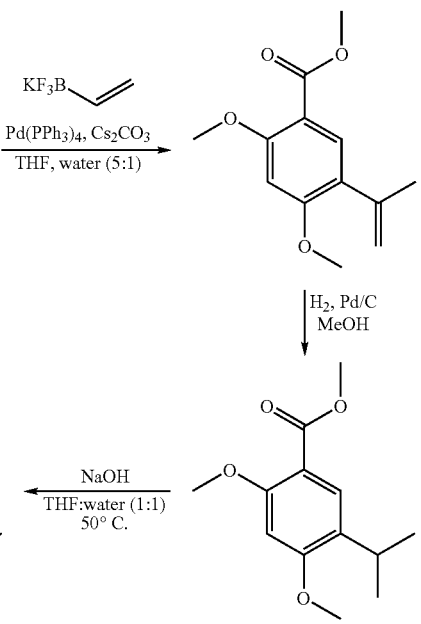

53A. Synthesis of 5-bromo-2,4-dimethoxybenzoic acid methyl ester

A solution of 5-bromo-2,4-dihydroxybenzoic acid (24.9 g, 107 mmol) in acetone (355 ml), was treated with methyl iodide (39.9 ml, 640 mmol) and $K_2CO_3$ (88 g, 640 mmol) then heated at reflux overnight. The salts were filtered off and washed with acetone. The filtrate was evaporated to dryness and the product was purified by flash column chromatography (100% DCM) to yield 5-bromo-2,4-dimethoxybenzoic acid methyl ester as a colourless solid (28 g). $^1$H NMR (Me-$d_3$-OD) 7.98 (1H, s), 6.74 (1H, s), 3.99 (3H, s), 3.94 (3H, s), 3.85 (3H, s). MS: [M+H]$^+$ 275/277.

53B. Synthesis of -isopropenyl-2,4-dimethoxy-benzoic acid methyl ester

To potassium isopropylidene trifluoroborate (4.87 g, 32.7 mmol) and 5-bromo-2,4-dimethoxybenzoic acid methyl ester (7.5 g, 27.3 mmol) in THF (195 ml) was added $Cs_2CO_3$ (26.6 g, 81.8 mmol) in water (39 ml). The reaction was degassed and Pd(PPh$_3$)$_4$ (1.58 g, 1.36 mmol) added. The reaction was heated at reflux for three days then quenched by adding water and extracted with EtOAc (×2). The combined organic layers were washed with brine, dried (MgSO$_4$), filtered and evaporated to leave an orange solid. The product was taken up in EtOAc again and the precipitate filtered. The filtrate was evaporated to dryness to yield 5-isopropenyl-2,4-dimethoxy-benzoic acid methyl ester (6.2 g). $^1$H NMR (Me-$d_3$-OD) 7.68 (1H, s), 6.66 (1H, s), 5.10-5.08 (1H, m), 5.02-5.00 (1H, m), 3.93 (3H, s), 3.92 (3H, s), 3.84 (3H, s), 2.08-2.06 (3H, m). MS: [M+H]$^+$ 237.

53C. Synthesis of 5-isopropyl-2,4-dimethoxy-benzoic acid methyl ester

A solution of 5-isopropenyl-2,4-dimethoxy-benzoic acid methyl ester (6.0 g, 25.4 mmol) in MeOH (85 ml) was shaken with 10% Pd/C under an atmosphere of H$_2$ at room temperature for 3 hours. The catalyst was filtered through GF/A paper but a little fine powder passed through. The filtrate was passed through a small pad of silica and evaporated to dryness to yield a colourless solid. The product was purified by flash column chromatography (DCM:Petrol gradient elution) to yield 5-isopropyl-2,4-dimethoxy-benzoic acid methyl ester a colourless solid (5.5 g). $^1$H NMR (Me-$d_3$-OD) 7.68 (1H, s), 6.64 (1H, s), 3.94 (3H, s), 3.91 (3H, s), 3.84 (3H, s), 3.23 (1H, sept), 1.20 (6H, d). MS: [M+H]$^+$ 239.

53D. Synthesis of 5-isopropyl-2,4-dimethoxy-benzoic acid

5-Isopropyl-2,4-dimethoxy-benzoic acid methyl ester (5.5 g, 23.1 mmol) and NaOH (1.38 g, 34.6 mmol) in THF (46 ml) and water (46 ml) was warmed to 50° C. overnight. The reaction was cooled and diluted with water and EtOAc. The aqueous layer was neutralised with HCl (1N, aq.). The product was extracted with EtOAc (×3) and the combined organic layers were washed with brine and dried over MgSO$_4$. The product was filtered and evaporated to dryness to yield 5-isopropyl-2,4-dimethoxy-benzoic acid as a pale peach solid (4.7 g). $^1$H NMR (DMSO-$d_6$) 12.1 (1H, br s), 7.62 (1H, s), 6.71 (1H, s), 3.95 (3H, s), 3.91 (3H, s), 3.19 (1H, sept), 1.18 (6H, d). MS: [M+H]$^+$ 225.

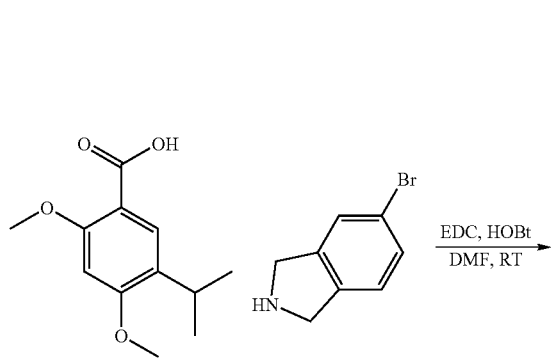
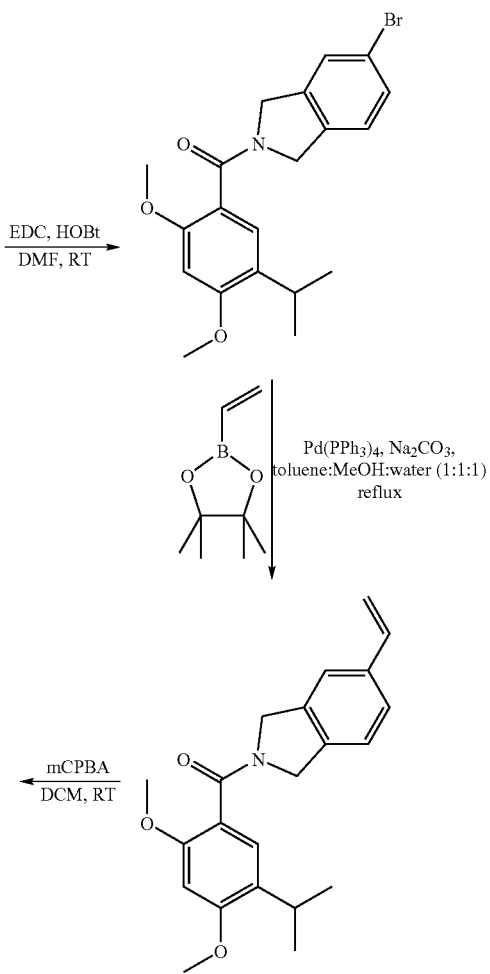

53E. Synthesis of (5-bromo-1,3-dihydro-isoindol-2-yl)-(5-isopropyl-2,4-dimethoxyphenyl)methanone To a mixture of 5-isopropyl-2,4-dimethoxybenzoic acid (2.45 g, 10.9 mmol), HOBt (1.61 g, 11.9 mmol) and EDC (1.85 g, 11.9 mmol) in anhydrous DMF (33 ml) under $N_2$ was added 5-bromo-2,3-dihydro-1H-isoindole (1.97 g, 9.95 mmol) and stirred at room temperature overnight. The reaction was quenched by diluting with NaOH (1M, aq.) and extracting the product with EtOAc (×2). The combined organic layers were washed with brine and dried over $MgSO_4$. The product was filtered and evaporated to dryness to leave a brown oil. The product was purified by flash column chromatography using gradient elution (ether/petrol) to yield (5-bromo-1,3-dihydro-isoindol-2-yl)-(5-isopropyl-2,4-dimethoxyphenyl)-methanone as a beige solid (3 g). $^1$H NMR (Me-$d_3$-OD) 7.60-7.13 (3H, m), 7.14 (1H, s), 6.71 (1H, s), 4.89 (2H, d), 4.64 (2H, d), 3.93 (3H, s), 3.90 (3H, s), 3.27 (1H, sept), 1.20 (6H, d). MS: [M+H]$^+$ 404/406.

53F. Synthesis of 5-isopropyl-2,4-dimethoxy-phenyl)-(5-vinyl-1,3-dihydro-isoindol-2-yl)-methanone To (5-bromo-1,3-dihydro-isoindol-2-yl)-(5-isopropyl-2,4-dimethoxyphenyl)methanone (2.2 g, 5.44 mmol), and 2-vinyl-4,4,5,5-tetramethyl-1,3,2-dioxaboralane (1.2 ml, 6.53 mmol) in MeOH (25 ml) and toluene (25 ml) was added $Na_2CO_3$ in water (25 ml). The reaction was degassed, $Pd(PPh_3)_4$ (0.38 g, 0.05 mmol) added then heated at 80° C. overnight. The reaction was worked up by adding water and extracting with EtOAc (×3). The combined organic layers were washed with brine and dried over $MgSO_4$. The product was filtered and evaporated to dryness then purified by flash column chromatography, gradient elution (ether:petrol) to yield 5-isopropyl-2,4-dimethoxy-phenyl)-(5-vinyl-1,3-dihydro-isoindol-2-yl)-methanone as a yellow oil (1.6 g). $^1$H NMR (Me-$d_3$-OD) 7.47-7.15 (3H, m), 7.15 (1H, s), 6.82-6.72 (1H, m), 6.71 (1H, s), 5.79 (1H, dd), 5.24 (1H, dd), 4.90 (2H, d), 4.64 (2H, d), 3.93 (3H, s), 3.91 (3H, s), 3.27 (1H, sept), 1.23 (6H, d). MS: [M+H]$^+$ 352.

53G. Synthesis of (5-isopropyl-2,4-dimethoxy-phenyl)-(5-oxiranyl-1,3-dihydro-isoindol-2-yl)-methanone To (5-isopropyl-2,4-dimethoxy-phenyl)-(5-vinyl-1,3-dihydro-isoindol-2-yl)-methanone (0.80 g, 2.28 mmol) in DCM (22 ml) was added mCPBA (0.61 g, 2.73 mmol) at 0° C. The reaction was stirred at room temperature for an hour. The reaction was diluted with NaOH (1M, aq.) and extracted the product with EtOAc. The EtOAc layer was washed with NaOH again. The organic layer was washed with brine and dried over $MgSO_4$. The product was filtered and evaporated to dryness to yield crude (5-isopropyl-2,4-dimethoxy-phenyl)-(5-oxiranyl-1,3-dihydro-isoindol-2-yl)-methanone as a very pale yellow oil. MS: [M+H]$^+$ 368.

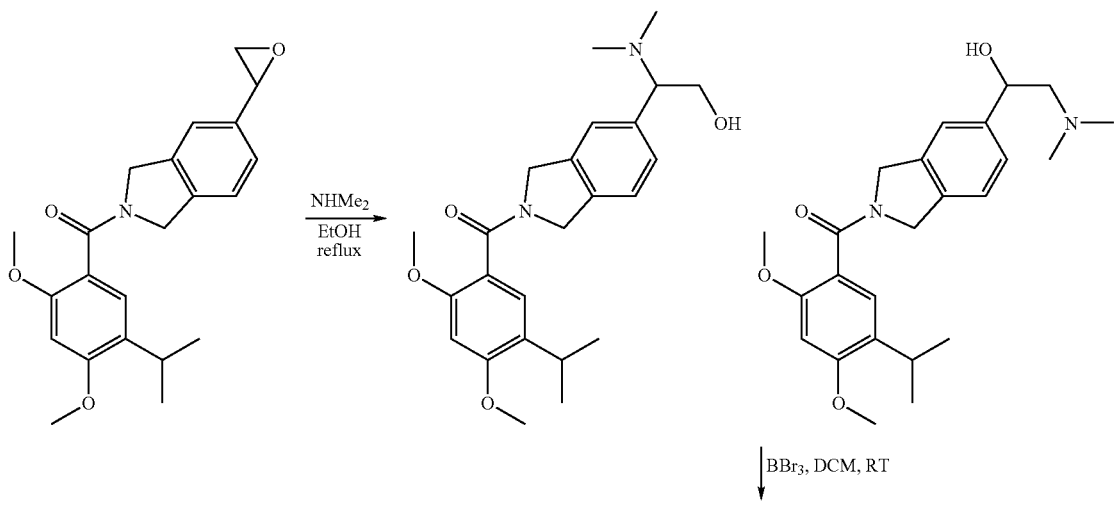

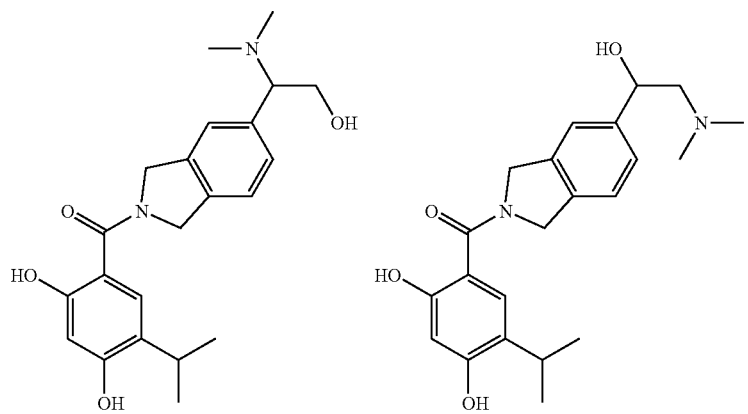

53H. Synthesis of (2,4-dihydroxy-5-isopropyl-phenyl)-[5-(1-dimethylamino-2-hydroxy-ethyl)-1,3-dihydro-isoindol-2-yl]-methanone (Compound 121H-i) and (2,4-dihydroxy-5-isopropyl-phenyl)-[5-(2-dimethylamino-1-hydroxy-ethyl)-1,3-dihydro-isoindol-2-yl]-methanone (Compound 121H-ii)

(5-Isopropyl-2,4-dimethoxy-phenyl)-(5-oxiranyl-1,3-dihydro-isoindol-2-yl)-methanone (~120 mg, crude) was dissolved in dimethylamine in EtOH (20 ml, ~33%, 5.6 M) and heated at 60° C. overnight. The reaction was evaporated to dryness and the product crudely purified by flash column chromatography MeOH:DCM (1:5) to yield impure material which was used without further purification. To a mixture of [5-(1-dimethylamino-2-hydroxy-ethyl)-1,3-dihydro-isoindol-2-yl]-(5-isopropyl-2,4-dimethoxy-phenyl)-methanone and [5-(2-dimethylamino-1-hydroxy-ethyl)-1,3-dihydro-isoindol-2-yl]-(5-isopropyl-2,4-dimethoxy-phenyl)-methanone (~100 mg) was added DCM (5 ml) and then boron tribromide (3 eq.) under $N_2$. The reaction was left to stir at room temperature until completion. The reaction was quenched with ice and diluted with water and EtOAc. The aqueous layer was extracted with EtOAc (×2). The combined organic layers were washed with brine, dried over $MgSO_4$ then filtered and evaporated to dryness, to leave a yellow residue which was purified by preparative HPLC to yield the two resorcinol isomers.

(2,4-Dihydroxy-5-isopropyl-phenyl)-[5-(1-dimethylamino-2-hydroxy-ethyl)-1,3-dihydro-isoindol-2-yl]-methanone, (Compound 121H-i) $^1$H NMR (Me-$d_3$-OD) 7.42-7.30 (3H, m), 7.19 (1H, s), 6.39 (1H, s), 4.98-4.87 (4H, m), 4.03-3.97 (1H, m), 3.94-3.86 (1H, m), 3.68 (1H, br s), 3.22 (1H, sept), 2.40 (6H, s), 1.23 (6H, d). MS: [M+H]$^+$ 384.

(2,4-Dihydroxy-5-isopropyl-phenyl)-[5-(2-dimethylamino-1-hydroxy-ethyl)-1,3-dihydro-isoindol-2-yl]-methanone, (Compound 121H-ii) $^1$H NMR (Me-$d_3$-OD) 7.39-7.25 (3H, m), 7.18 (1H, s), 6.38 (1H, s), 6.94-6.88 (5H, m), 3.22 (1H, sept), 2.77-2.68 (1H, m), 2.61-2.51 (1H, m), 2.42 (6H, s), 1.23 (6H, d). MS: [M+H]$^+$ 384.

Example 54

Synthesis of (2,4-dihydroxy-5-isopropyl-phenyl)-[5-(piperazine-1-carbonyl)-1,3-dihydro-isoindol-2-yl]-methanone hydrochloride

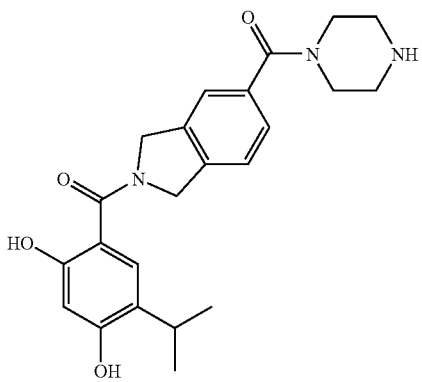 [SMILES: CC(C)c1cc(C(=O)N2Cc3ccc(C(=O)N4CCNCC4)cc3C2)c(O)cc1O]

54A. Synthesis of 4-[2-(2,4-dihydroxy-5-isopropyl-benzoyl)-2,3-dihydro-1H-isoindole-5-carbonyl]-piperazine-1-carboxylic acid tert-butyl ester A solution of 2-(2,4-bis-benzyloxy-5-isopropyl-benzoyl)-2,3-dihydro-1H-isoindole-5-carboxylic acid (Preparation D6) (0.5 g, 0.96 mmol), EDC (0.22 g, 1.15 mmol), HOBT (0.196 g, 1.15 mmol) and BOC piperazine (0.117 ml, 1.06 mmol) in DMF (10 ml) was stirred at room temperature for 48 hours, then evaporated under vacuum. The crude material was dissolved in ethyl acetate and extracted twice with saturated NaHCO$_3$, organics washed with brine, dried (MgSO$_4$), filtered then evaporated under vacuum and purified by flash column chromatography (80% EtOAc-P.E. as eluant) to give 0.5 g of 4-[2-(2,4-dihydroxy-5-isopropyl-benzoyl)-2,3-dihydro-1H-isoindole-5-carbonyl]-piperazine-1-carboxylic acid tert-butyl ester. MS: [M+H]$^+$ 688.

54B. Synthesis of (2,4-dihydroxy-5-isopropyl-phenyl)-[5-(piperazine-1-carbonyl)-1,3-dihydro-isoindol-2-yl]-methanone hydrochloride Hydrogenation as Method A5 to give (0.2 g, 0.30 mmol) 4-[2-(2,4-dihydroxy-5-isopropyl-benzoyl)-2,3-dihydro-1H-isoindole-5-carbonyl]-piperazine-1-carboxylic acid tert-butyl ester [used crude] dissolved in EtOAc then treated with saturated EtOAc/HCl, stirred at ambient for 3 hours, reaction diluted with ether, solid filtered to give 0.19 g of (2,4-dihydroxy-5-isopropyl-phenyl)-[5-(piperazine-1-carbonyl)-1,3-dihydro-isoindol-2-yl]-methanone hydrochloride. $^1$H NMR (Me-d$_3$-OD) 7.50-7.42 (3H, m), 7.18 (1H, s), 6.39 (1H, s), 5.00-4.95 (4H, br s), 3.92-3.79 (4H, br s), 3.35-3.28 (4H, br s), 3.26-3.15 (1H, m), 1.23 (6H, d). MS: [M+H]$^+$ 410.

Example 55

Synthesis of (2,4-dihydroxy-5-isopropyl-phenyl)-[5-(4-methyl-piperazin-1-ylmethyl)-1,3-dihydro-isoindol-2-yl]-methanone

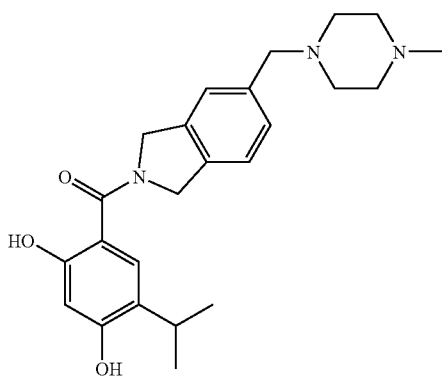 [SMILES: CC(C)c1cc(C(=O)N2Cc3ccc(CN4CCN(C)CC4)cc3C2)c(O)cc1O]

55A. Synthesis of 2-(2,4-bis-benzyloxy-5-isopropyl-benzoyl)-2,3-dihydro-1H-isoindole-5-carboxylic acid methoxy-methyl-amide A solution of 2-(2,4-bis-benzyloxy-5-isopropyl-benzoyl)-2,3-dihydro-1H-isoindole-5-carboxylic acid (Preparation D6) (1.76 g, 3.39 mmol), EDC (0.78 g, 4.06 mmol), HOBT (0.55 g, 4.06 mmol), Et$_3$N (1 ml, 6.78 mmol) and N,O-dimethylhydroxylamine hydrochloride (0.36 g, 3.72 mmol) in DMF (20 ml) was stirred at room temperature for 48 hours, then evaporated under vacuum. The crude material was dissolved in ethyl acetate and extracted twice with saturated NaHCO$_3$, organics washed with brine, dried (MgSO$_4$), filtered then evaporated to give 1.84 g of 2-(2,4-bis-benzyloxy-5-isopropyl-benzoyl)-2,3-dihydro-1H-isoindole-5-carboxylic acid methoxy-methyl-amide. MS: [M+H]$^+$ 563.

55B. Synthesis of 2-(2,4-bis-benzyloxy-5-isopropyl-benzoyl)-2,3-dihydro-1H-isoindole-5-carbaldehyde A solution of 2-(2,4-bis-benzyloxy-5-isopropyl-benzoyl)-2,3-dihydro-1H-isoindole-5-carboxylic acid methoxy-methyl-amide (0.226 g, 0.4 mmol) in THF (5 ml) cooled to 0° C., treated with 1M LiAlH$_4$/THF (0.3 ml, 0.3 mmol), stirred 1 hour, further LiAlH$_4$ (0.05 ml) added then stirred for 30 minutes. The reaction was quenched with saturated KHSO$_4$ solution, extracted with EtOAc, dried (MgSO$_4$), filtered and evaporated to give 0.2 g of 2-(2,4-bis-benzyloxy-5-isopropyl-benzoyl)-2,3-dihydro-1H-isoindole-5-carbaldehyde. MS: [M+H]$^+$ 504.

55C. Synthesis of (2,4-bis-benzyloxy-5-isopropyl-phenyl)-[5-(4-methyl-piperazin-1-ylmethyl)-1,3-dihydro-isoindol-2-yl]-methanone To a solution of 2-(2,4-bis-benzyloxy-5-isopropyl-benzoyl)-2,3-dihydro-1H-isoindole-5-carbaldehyde (0.316 g, 0.63 mmol) and n-methyl piperazine (63 mg, 0.63 mmol) in CH$_2$Cl$_2$ (10 ml) was added AcOH (38 mgs 0.63 mmol) and NaBH(OAc)$_3$ (0.28 g, 1.33 mmol), then stirred at ambient for 5 hours. The reaction was quenched with water, layers separated and aqueous washed CH$_2$Cl$_2$. The organics were combined, washed with brine, dried (MgSO$_4$), filtered and evaporated to give 0.32 g of (2,4-bis-benzyloxy-5-isopropyl-phenyl)-[5-(4-methyl-piperazin-1-ylmethyl)-1,3-dihydro-isoindol-2-yl]-methanone. MS: [M+H]$^+$ 588.

55D. Synthesis of (2,4-dihydroxy-5-isopropyl-phenyl)-[5-(4-methyl-piperazin-1-ylmethyl)-1,3-dihydro-isoindol-2-yl]-methanone Hydrogenation was carried out using Method A5 but with the addition of $K_2CO_3$ (2 equiv.) in a MeOH/$H_2O$ [9.1]. After evaporation of methanol the reaction was diluted with water, neutralised using 1M HCl and extracted with $CH_2Cl_2$ (×2). Organics dried ($MgSO_4$), filtered and evaporated under vacuum then purified by preparative HPLC to give 21 mg of (2,4-dihydroxy-5-isopropyl-phenyl)-[5-(4-methyl-piperazin-1-ylmethyl)-1,3-dihydro-isoindol-2-yl]-methanone. MS: [M+H]$^+$ 410. $^1$H NMR (Me-d$_3$-OD) 7.37-7.23 (3H, br s), 7.19 (1H, s), 6.39 (1H, s), 4.94-4.87 (4H, br s), 3.57 (2H, s), 3.27-3.16 (1H, m), 2.67-2.39 (8H, m), 2.31 (3H, s), 1.23 (6H, d).

Example 56

Synthesis of (2,4-dihydroxy-5-isopropyl-phenyl)-[4-(3-morpholin-4-yl-propoxy)-1,3-dihydro-isoindol-2-yl]methanone

56A. Synthesis of 4-hydroxyisoindoline hydrobromide

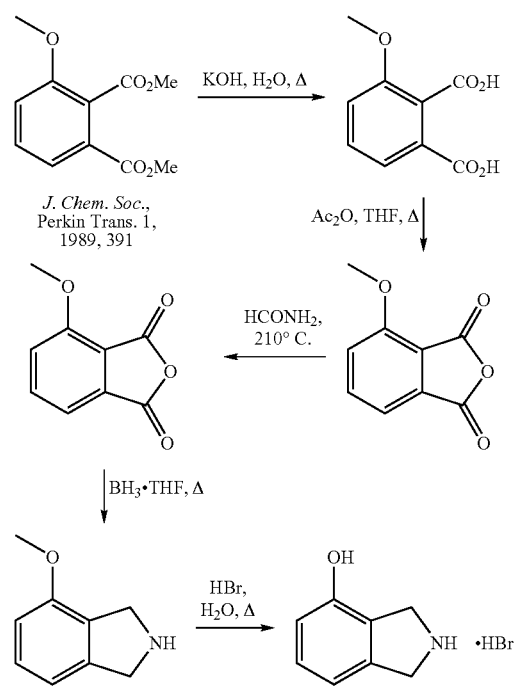

A suspension of dimethyl 3-methoxyphthalate (69.45 g, 0.31 mol) [prepared as per *J. Chem. Soc., Perkin Trans.* 1, 1989, 391] in water (300 ml) was treated with potassium hydroxide (43.7 g, 0.78 mol) and the mixture was stirred and held at reflux for 4 hours. Upon cooling to room temperature the methanol liberated during the course of the reaction was removed in vacuo, the mixture acidified to pH 2 or below by the addition of 5M hydrochloric acid and evaporated gently in vacuo to induce crystallization. The solid material was filtered off, washed with a little ice cooled water, sucked dry under reduced pressure and dried in a vacuum oven at 50° C. overnight to afford 3-methoxyphthalic acid (51.0 g, 84%) as a colourless solid. $^1$H NMR (DMSO-d$_6$) 13.05 (2H, br s), 7.48 (2H, m), 7.33 (1H, m), 3.82 (3H, s). MS: [M+H]$^+$ 197.

Acetic anhydride (70 ml) was added to a mixture of 3-methoxyphthalic acid (51.0 g, 0.26 mol) in anhydrous tetrahydrofuran (250 ml) and the mixture was stirred and held at reflux for 4 hours. Upon cooling to room temperature the solvent was removed in vacuo and the resulting solid material was dried in a vacuum oven at 50° C. overnight to afford 3-methoxyphthalic anhydride (45.9 g, 99%) as a colourless solid. $^1$H NMR (DMSO-d$_6$) 7.97 (1H, dd), 7.63 (1H, d), 7.60 (1H, d), 4.02 (3H, s). MS: [M+H]$^+$ 179.

A mixture of 3-methoxyphthalic anhydride (24.0 g, 134.8 mmol) and formamide (120 ml) was stirred and held at 210° C. for 5 hours and was then allowed to cool to room temperature overnight. Water (100 ml) was added and the solid material filtered off under reduced pressure. The crude product was washed sequentially with 50% aqueous acetone (50 ml) and diethyl ether (200 ml) and sucked dry under reduced pressure to afford 3-methoxyphthalimide (8.95 g, 37%) as an off-white solid. $^1$H NMR (DMSO-d$_6$) 11.08 (1H, br s), 7.78 (1H, dd), 7.45 (1H, d), 7.36 (1H, d), 3.93 (3H, s). MS: [M+H]$^+$ 178.

A stirred solution of 3-methoxyphthalimide (8.95 g, 50.56 mmol) in anhydrous tetrahydrofuran (200 ml) at 0° C. was treated dropwise with a solution of borane in tetrahydrofuran (1M, 150 ml, 0.15 mol) and the resulting mixture was stirred and held at reflux for 16 hours. The mixture was cooled to 0° C., methanol (60 ml) was added dropwise followed by 5M hydrochloric acid (60 ml) and the mixture was stirred and held at reflux for 4 hours. Upon cooling to room temperature the organic solvent was removed in vacuo and the mixture diluted with water (250 ml) and extracted with dichloromethane (3×250 ml). The aqueous layer was basified to pH 12 or above by the addition of 5M sodium hydroxide, extracted with dichloromethane (3×250 ml) and the combined extracts were evaporated to dryness in vacuo to afford 4-methoxyisoindoline (4.44 g, 59%) as a green oil which was used without further purification. $^1$H NMR (DMSO-d$_6$) 7.18 (1H, t), 6.83 (1H, d), 6.78 (1H, d), 4.07 (2H, s), 4.02 (2H, s), 3.78 (3H, s). MS: [M+H]$^+$ 150.

4-Methoxyisoindoline (4.4 g, 29.53 mmol) in 48% aqueous hydrobromic acid (50 ml) was stirred and held at reflux for 16 hours. Upon cooling to room temperature the solvent was removed in vacuo to afford 4-hydroxyisoindoline hydrobromide (5.0 g, 78%) as a pale orange solid. $^1$H NMR (DMSO-d$_6$) 9.95 (1H, br s), 9.37 (2H, br s), 7.19 (1H, t), 6.84 (1H, d), 6.80 (1H, d), 4.48 (2H, t), 4.40 (2H, t). MS: [M+H]$^+$ 136.

56B. Synthesis of (2,4-bis-benzyloxy-5-isopropenyl-phenyl)-(4-hydroxy-1,3-dihydro-isoindol-2-yl)-methanone

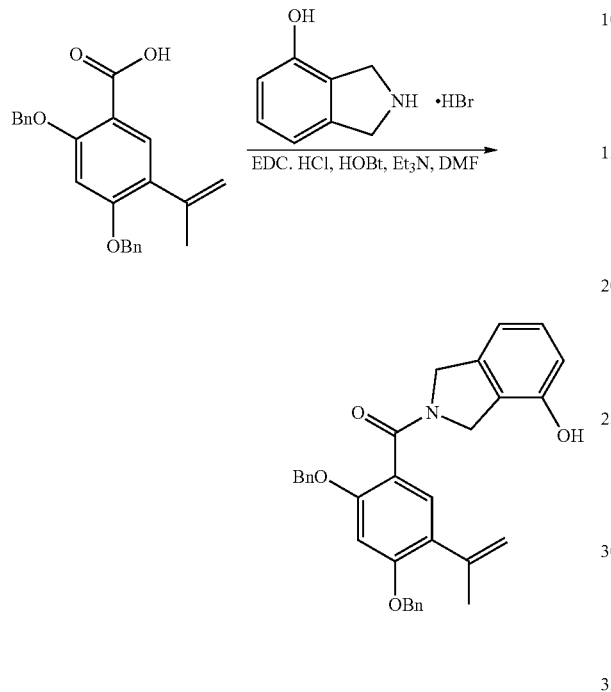

A mixture of 2,4-bis-benzyloxy-5-isopropenyl-benzoic acid (8.1 g, 21.65 mmol), 4-hydroxyisoindoline hydrobromide (4.91 g, 22.73 mmol), N-ethyl-N'-(3-dimethylaminopropyl)carbodiimide hydrochloride (5.0 g, 25.98 mmol), 1-hydroxybenzotriazole (3.5 g, 25.98 mmol) and triethylamine (6 ml, 43.3 mmol) in N,N-dimethylformamide (50 ml) was stirred at room temperature for 16 hours. The solvent was removed in vacuo and the residue was treated with a saturated aqueous solution of sodium hydrogen carbonate (200 ml). The mixture was filtered, the solid material was washed copiously with water, sucked dry under reduced pressure and dried in a vacuum oven at 50° C. overnight to afford (2,4-bis-benzyloxy-5-isopropenyl-phenyl)-(4-hydroxy-1,3-dihydro-isoindol-2-yl)-methanone (10.25 g, 96%) as a pale tan solid. $^1$H NMR (DMSO-$d_6$) (mixture of amide rotamers) 9.68 and 9.60 (1H, 2×br s), 7.45-7.25 (10H, m), 7.20-7.00 (3H, m), 6.82 and 6.72 (1H, 2×d), 6.68 (1H, m), 5.23 and 5.22 (2H, 2×s), 5.18 (2H, s), 5.11 (1H, s), 5.09 (1H, s), 4.77 and 6.67 (2H, 2×s), 4.53 and 4.44 (2H, 2×s), 2.04 (3H, s). MS: [M+H]$^+$ 492.

56C. Synthesis of (2,4-bis-benzyloxy-5-isopropenyl-phenyl)-[4-(3-morpholin-4-yl-propoxy)-1,3-dihydro-isoindol-2-yl]-methanone A mixture of (2,4-bis-benzyloxy-5-isopropenyl-phenyl)-(4-hydroxy-1,3-dihydro-isoindol-2-yl)-methanone (2 g; 4.07 mmol), 4-(3-chloropropyl)morpholine (1.66 g; 2.5 equiv.) and caesium carbonate (8.3 g; 6.25 equiv) in DMF was heated at 90° C. overnight then evaporated. The residue was dissolved in EtOAc, washed with brine, dried (MgSO$_4$) and evaporated. Purification of the crude material using a Biotage SP4 (40S, 40 ml/min), using gradient elution form 0% to 10% MeOH/EtOAc gave 1.8 g of (2,4-bis-benzyloxy-5-isopropenyl-phenyl)-[4-(3-morpholin-4-yl-propoxy)-1,3-dihydro-isoindol-2-yl]-methanone as a pale yellow gum. MS: [M+H]$^+$ 619.

56D. Synthesis of (2,4-dihydroxy-5-isopropyl-phenyl)-[4-(3-morpholin-4-yl-propoxy)-1,3-dihydro-isoindol-2-yl]methanone

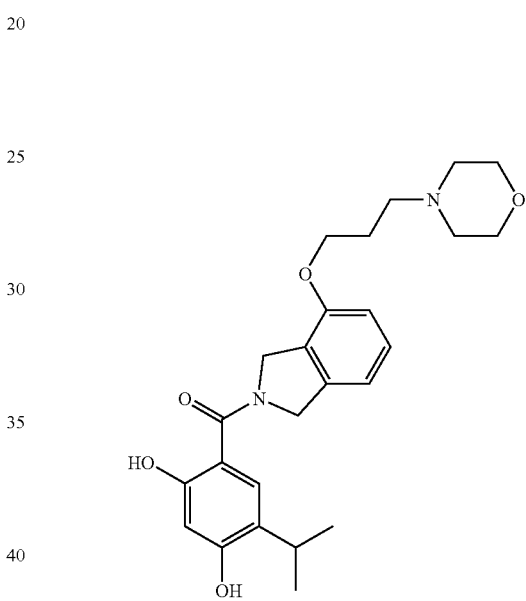

Hydrogenation of (2,4-bis-benzyloxy-5-isopropenyl-phenyl)-[4-(3-morpholin-4-yl-propoxy)-1,3-dihydro-isoindol-2-yl]-methanone (as described in method A5) followed by treatment with saturated HCl/EtOAc and trituration with hot acetone afforded 890 mg of the title compound (hydrochloride salt) as a cream solid. $^1$H NMR (DMSO-$d_6$) 10.78 (1H, br s), 10.05 (1H, br s), 9.55 (1H, br s), 7.30 (1H, t), 7.08 (1H, s) 6.98-6.90 (2H, m), 6.45 (1H, s), 4.80 (2H, s), 4.75 (2H, s), 4.15 (2H, t), 3.95 (2H, br m), 2.80 (2H, br m), 3.50-3.35 (2H, br m), 3.25 (2H, br m), 3.18-3.02 (3H, br m), 2.20 (2H, br m), 1.15 (6H, d). MS: [M+H]$^+$ 441.

Examples 57 to 74

By following the methods described above, the following compounds were prepared.

| Ex. No. | Compound | Chemical Name | Method | N.M.R. Data | M.S. |
|---|---|---|---|---|---|
| 57 | | [5-(2-Amino-ethoxy)-1,3-dihydro-isoindol-2-yl]-(2,4-dihydroxy-5-isopropyl-phenyl)-methanone | As for Example 34, A2 (from 2,4-bis-benzyloxy-5-isopropenyl-benzoic acid (Preparation B5) and 5-hydroxy-isoindoline), alkylation using 3-(BOC-amino)ethyl tosylate, then A5. Final BOC deprotection using saturated HCl/EtOAC (Example 18). | $^1$H NMR(Me-d$_3$-OD) 8.55 (1H, s), 7.30-7.20 (1H, m), 7.15 (1H, s), 7.05-6.95 (2H, m), 6.40 (1H, s), 4.95-4.80 (4H, m) 4.25 (2H, t), 3.35 (2H, t), 3.25-3.15 (1H, m), 1.25 (6H, d) | MS: [M + H]$^+$ 357 |
| 58 | | (2,4-Dihydroxy-5-isopropyl-phenyl)-(5-hydroxy-1,3-dihydro-isoindol-2-yl)-methanone | Isolated as a bi-product from synthesis of Example 57. | $^1$H NMR(Me-d$_3$-OD) 7.20 (1H, s), 7.15-7.05 (1H, m), 6.80-6.70 (2H, m), 6.40 (1H, s), 4.95-4.80 (4H, m), 3.25-3.15 (1H, m), 1.25 (6H, d) | MS: [M + H]$^+$ 314 |
| 59 | | (2,4-Dihydroxy-5-isopropyl-phenyl)-{5-[4-(2-hydroxy-ethyl)-piperazin-1-yl]-1,3-dihydro-isoindol-2-yl}-methanone | As for Example 51, using N-(2-hydroxyethyl)-piperazine in the Buchwald reaction. | $^1$H NMR (DMSO-d$_6$) 10.40 (1H, br s), 9.65 (1H, br s), 7.40-7.15 (1H, m), 7.05 (1H, s), 7.05-6.90 (2H, m), 6.45 (1H, s), 4.80-4.60 (4H, m), 3.85-3.70 (4H, m), 3.65-3.55 (2H, m), 3.25-3.05 (7H, m), 1.15 (6H, d) | MS: [M + H]$^+$ 426 |

| Ex. No. | Compound | Chemical Name | Method | N.M.R. Data | M.S. |
|---|---|---|---|---|---|
| 60 | | (2,4-Dihydroxy-5-isopropyl-phenyl)-[5-(4-morpholin-4-yl-piperidin-1-yl)-1,3-dihydro-isoindol-2-yl]-methanone | As for Example 51, using 4-morpholino-piperidine in the Buchwald reaction | $^1$H NMR (DMSO-d$_6$) 11.10 (1H, br s), 9.65 (1H, br s), 7.30-7.05 (3H, m), 7.03 (1H, s), 6.45 (1H, s), 4.80-4.65 (4H, m), 4.0-3.95 (2H, m), 3.90-3.75 (4H, m), 3.50-3.40 (2H, m), 3.40-3.30 (1H, m), 3.15-3.03 (3H, m), 2.90-2.75 (2H, m), 2.25-2.15 (2H, m), 1.95-1.80 (2H, m), 1.15 (6H, d) | MS: [M + H]$^+$ 466 |
| 61 | | (2,4-Dihydroxy-5-isopropyl-phenyl)-[5-(1-methyl-piperidin-4-ylamino)-1,3-dihydro-isoindol-2-yl]-methanone | As for Example 51, using 4-amino-1-methyl-piperidine in the Buchwald reaction. | $^1$H NMR (DMSO-d$_6$) 10.60 (1H, br s), 9.65 (1H, br s), 7.20 (1H, m), 7.03 (1H, s), 6.95-6.80 (2H, m), 6.45 (1H, s), 4.80-4.65 (4H, m), 3.45 (2H, m), 3.25 (1H, m), 3.10 (1H, m), 3.00 (2H, m), 2.70 (3H, d), 2.15-2.05 (2H, m), 1.90-1.75 (2H, m), 1.15 (6H, d) | MS: [M + H]$^+$ 410 |
| 62 | | (2,4-Dihydroxy-5-isopropyl-phenyl)-[5-(4-isopropyl-piperazin-1-yl)-1,3-dihydro-isoindol-2-yl]-methanone | As for Example 51, using i-propyl-piperazine in the Buchwald reaction. | $^1$H NMR (DMSO-d$_6$) 10.70 (1H, br s), 9.65 (1H, br s), 7.25-7.10 (1H, m), 7.05 (1H, s), 7.00-6.90 (2H, m), 6.45 (1H, s), 4.80-4.60 (4H, m), 3.80 (2H, m), 3.55-3.40 (3H, m), 3.23-3.05 (5H, m), 1.33 (6H, d), 1.15 (6H, d) | MS: [M + H]$^+$ 424 |

| Ex. No. | Compound | Chemical Name | Method | N.M.R. Data | M.S. |
|---|---|---|---|---|---|
| 63 | | (2,4-Dihydroxy-5-isopropyl-phenyl)-(5-piperazin-1-yl-1,3-dihydro-isoindol-2-yl)-methanone | As for Example 51, using Boc-piperazine in the Buchwald reaction. Boc deprotection using saturated HCl/dioxane (Example 18). | $^1$H NMR (DMSO-d$_6$) 9.70 (1H, br s), 9.25 (2H, br s), 7.23 (1H, br m), 7.05 (1H, s), 7.00-6.90 (2H, m), 6.45 (1H, s), 4.80-4.60 (4H, m), 3.35 (4H, m), 3.20 (4H, m), 3.10 (1H, m), 1.15 (6H, d) | MS: [M + H]$^+$ 382 |
| 64 | | 4-[2-(2,4-Dihydroxy-5-isopropyl-benzoyl)-2,3-dihydro-1H-isoindol-5-ylamino]-piperidine-1-carboxylic acid tert-butyl ester | As for Example 51, using 1-Boc-4-amino-piperidine in the Buchwald reaction | $^1$H NMR (Me-d$_3$-OD) 7.20 (1H, s), 7.05 (1H, m), 6.65-6.55 (2H, m), 6.35 (1H, s), 4.85-4.75 (4H, m), 4.05 (2H, m), 3.50 (1H, m), 3.20 (1H, m), 3.00 (2H, m), 2.00 (2H, m), 1.5 (9H, s), 1.30 (2H, m), (1.15 6H, d) | MS: [M + H]$^+$ 496 |
| 65 | | (2,4-dihydroxy-5-isopropyl-phenyl)-[5-(piperidin-4-ylamino)-1,3-dihydro-isoindol-2-yl]-methanone | BOC deprotection using saturated HCl/EtOAC (Example 18). | $^1$H NMR DMSO-d$_6$) 7.05 (1H, s), 7.00 (1H, m), 6.55-6.45 (2H, m), 6.40 (1H, s), 4.70-4.60 (4H, m), 3.25 (1H, m), 3.10 (1H, m), 2.95 (2H, m), 2.45 (2H, m), 1.85 (2H, m), 1.75 (3H, s), 1.20 (2H, m), 1.15 (6H, d) | MS: [M + H]$^+$ 396 |

| Ex. No. | Compound | Chemical Name | Method | N.M.R. Data | M.S. |
|---|---|---|---|---|---|
| 66 | | (2,4-dihydroxy-5-isopropyl-phenyl)-[4-(4-methyl-piperazin-1-yl)-1,3-dihydro-isoindol-2-yl]-methanone | As for Example 51, using (2,4-bis-benzyloxy-5-isopropenyl-phenyl)-(4-bromo-1,3-dihydro-isoindol-2-yl)-methanone (Prep: A2 between 2,4-bis-benzyloxy-5-isopropenyl-benzoic acid and 4-bromo-1,3-dihydro-1H-isoindoline) and N-methyl-piperazine in the Buchwald reaction. | $^1$H NMR (Me-d$_3$-OD) 7.35-7.18 (2H, m), 7.10-6.95 (2H, m), 6.95-6.85 (2H, m), 6.40 (1H, s), 4.95-4.85 (4H, m), 3.25 (1H, m), 3.20-3.05 (4H, m), 3.05-2.80 (4H, m), 2.60 (3H, m), 2.00 (3H, s), 1.25 (6H, d) | MS: [M + H]$^+$ 396 |
| 67 | | (2,4-dihydroxy-5-isopropyl-phenyl)-[4-(piperidin-4-ylamino)-1,3-dihydro-isoindol-2-yl]-methanone | As for Example 65, using 1-Boc-4-amino-piperidine in the Buchwald reaction, followed by Boc deprotection using saturated HCl/EtOAc (Example 18). | $^1$H NMR (DMSO-d$_6$) 7.05 (1H, s), 7.00 (1H, m), 6.55-6.45 (2H, m), 6.40 (1H, s), 4.70-4.60 (4H, m), 3.25 (1H, m), 3.10 (1H, m), 2.95 (2H, m), 2.45 (2H, m), 1.85 (2H, m), 1.75 (3H, s), 1.20 (2H, m), 1.15 (6H, d) | MS: [M + H]$^+$ 396 |
| 68 | | (2,4-Dihydroxy-5-isopropyl-phenyl)-(5-dimethyl-aminomethyl-1,3dihydro-isoindol-2-yl)-methanone | A2 and A5. From 2,4-bis-benzyloxy-5-isopropenyl-benzoic acid (B5, and (2,3-dihydro-1H-isoindole-5-ylmethyl)-dimethyl-amine (Preparation Al) | $^1$H NMR (Me-d$_3$-OD) 7.26-7.12 (3H, m), 7.07 (1H, s), 6.27 (1H, s), 4.85-4.77 (4H, br s), 3.40 (2H, s), 3.15-3.05 (1H, m), 2.15 (6H, s), 1.11 (6H, d) | MS: [M + H]+ 355 |

| Ex. No. | Compound | Chemical Name | Method | N.M.R. Data | M.S. |
|---|---|---|---|---|---|
| 69 | | (2,4-Dihydroxy-5-isopropyl-phenyl)-[5-(4-methyl-piperazine-1-carbonyl)-1,3-dihydro-isoindol-2-yl]-methanone | A2 and A5. From 2-(2,4-bis-benzyloxy-5-isopropyl-benzoyl)-2,3-dihydro-1H-isoindole-5-carboxylic acid (D6) and N-methyl piperazine | $^1$H NMR (Me-d$_3$-OD) 7.60-7.38 (3H, m), 7.19 (1H, s), 6.39 (1H, s), 4.96 (4H, m), 3.85-3.71 (2H, br s), 3.54-3.4 (2H, br s), 3.26-3.15 (1H, m), 2.59-2.39 (4H, br d), 2.34 (3H, s), 1.23 (6H, d) | MS: [M + H]$^+$ 424 |
| 70 | | (2,4-Dihydroxy-5-isopropyl-phenyl)-{5-[2-(2,2-dimethyl-propylamino)-ethoxy]-1,3-dihydro-isoindol-2-yl}-methanone | As for the synthesis of (2,4-dihydroxy-5-isopropyl-phenyl)-[5-(2-isopropylamino-ethoxy)-1,3-dihydro-isoindol-2-yl]-methanone except using trimethyl acetaldehyde instead of acetone. Purified by preparative HPLC. | $^1$H NMR (Me-d$_3$-OD) 7.28 (1H, br s); 7.20 (1H, s); 7.00 (2H, br m); 6.40 (1H, s); 4.35 (2H, t); 3.50 (2H, t); 3.20 (1H, m); 3.00 (2H, s); 1.23 (6H, d); 1.10 (9H s) | MS: [M + H]$^+$ 427 |
| 71 | | [5-(2-Cyclopentyl-amino-ethoxy)-1,3-dihydro-isoindol-2-yl]-(2,4-dihydroxy-5-isopropyl-phenyl)-methanone | As for the synthesis of (2,4-dihydroxy-5-isopropyl-phenyl)-[5-(2-isopropylamino-ethoxy)-1,3-dihydro-isoindole-2-yl]-methanone except using cyclopentanone instead of acetone. Purified by preparative HPCL. | $^1$H NMR (DMSO-d$_6$) 10.05 (1H, br s); 9.60 (1H, br s); 7.23 (1H, br s); 7.05 (1H, s); 6.95 (1H, br s); 6.88 (1H, br d); 6.40 (1H, s); 4.72 (4H, br m); 4.02 (2H, t); 3.10 (2H, m); 2.93 (2H, t); 1.78 (2H, m); 1.63 (2H, m); 1.48 (2H, m); 1.35 (2H, m); 1.15 (6H, d) | MS: [M + H]$^+$ 425 |
| 72 | | (2,4-Dihydroxy-5-isopropyl-phenyl)-(5-piperidin-1-ylmethyl-1,3-dihydro-isoindol-2-yl)-methanone | As for the synthesis of (2,4-dihydroxy-5-isopropyl-phenyl)-[5-(4-methyl-piperazin-1-ylmethyl)-1,3-dihydro-isoindol-2-yl]-methanone (Example 56) except using piperidine instead of N-methyl-piperazine. | $^1$H NMR (Me-d$_3$-OD) 7.35-7.24 (3H, m), 7.19 (1H, s), 6.39 (1H, s), 4.94-4.49 (4H, br s), 3.54 (2H, s), 3.27-3.18 (1H, m), 2.51-2.41 (4H, br s), 1.66-1.58 (4h br m), 1.53-1.42 (2H, br s), 1.23 (6H, d). | MS: [M + H]$^+$ 395. |

| Ex. No. | Compound | Chemical Name | Method | N.M.R. Data | M.S. |
|---|---|---|---|---|---|
| 73 | | (2,4-Dihydroxy-5-isopropyl-phenyl)-[5-(4-hydroxypiperidin-4-yl)-1,3-dihydro-isoindol-2-yl]-methanone | As for the synthesis of (2,4-dihydroxy-5-isopropyl-phenyl)-[5-(4-hydroxy-1-methyl-piperidin-4-yl)-1,3-dihydro-isoindol-2-yl]-methanone (Example 50) except using N-benzyloxy-piperidin-4-one in step 2. | $^1$H NMR (Me-d$_3$-OD) 7.47 (2H, m), 7.30 (1H, br m) 7.20 (1H, s), 6.40 (1H, s), 4.90 (4H, d), 3.22 (1H, m), 3.15 (2H, m), 2.95 (2H, m), 2.05 (2H, m), 1.75 (2H, m), 1.25 (6H, d) | MS: [M + H]$^+$ 397 |
| 74 | | (5-chloro-6-hydroxy-1,3-dihydro-isoindol-2-yl)-2,4-dihydroxy-5-isopropyl-phenyl)-methanone | Isolated as a bi-product during the preparation of Example 33. | $^1$H NMR (DMSO-d$_6$) 10.00 (1H, s), 9.58 (1H, s), 7.48-7.38 (1H, m), 7.02 (1H, s), 7.97-6.85 (1H, m), 6.40 (1H, s), 4.68 (4H, br s), 3.10 (1H, m), 1.15 (6H, d) | MS: [M + H] + 348 |

Example 75

(5-Chloro-2,4-dihydroxy-phenyl)-[5-(4-methyl-piperazin-1-yl)-1,3-dihydro-isoindol-2-yl]-methanone

75A. 5-(4-Methyl-piperazin-1-yl)-1,3-dihydro-isoindole-2-carboxylic acid tert-butyl ester

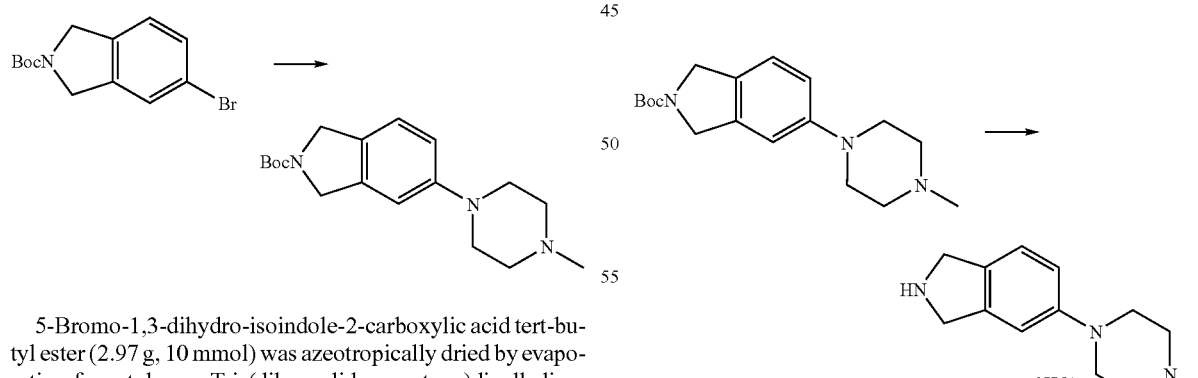

5-Bromo-1,3-dihydro-isoindole-2-carboxylic acid tert-butyl ester (2.97 g, 10 mmol) was azeotropically dried by evaporation from toluene. Tris(dibenzylideneacetone)dipalladium (0) (228 mg, 0.25 mmol), 2-(di-tert-butylphosphino)biphenyl (149 mg, 0.50 mmol) and sodium tert-butoxide (1.34 g, 13.9 mmol) were added and the flask was purged with nitrogen. Toluene (25 mL) then N-methylpiperazine (1.33 mL, 12 mmol) were added and the mixture was heated to 80° C. for 2 hours. After allowing to cool to r.t. the mixture was diluted with ether, filtered through Celite and concentrated to give a residue that was purified by flash chromatography on silica (2M methanolic ammonia/dichloromethane, 1% to 3% gradient). This afforded the title compound as a brown solid (1.45 g, 46%). $^1$H NMR (MeOH-d$_4$) 7.15 (1H, m), 6.94-6.88 (2H, m), 4.60-4.54 (4H, m), 3.20-3.17 (4H, m), 2.63-2.60 (4H, m), 2.34 (3H, s), 1.52 (9H, s). MS: [M+H]$^+$ 318.

75B. 5-(4-Methyl-piperazin-1-yl)-2,3-dihydro-1H-isoindole dihydrochloride 5-(4-Methyl-piperazin-1-yl)-1,3-dihydro-isoindole-2-carboxylic acid tert-butyl ester (247 mg, 0.78 mmol) was treated with 4M HCl in dioxane (4 mL, 4 mmol) for 24 hours. Concentration in vacuo afforded the title compound quantitatively, which was used directly in the coupling reaction. $^1$H NMR (DMSO-d$_6$) 11.13 (1H, br.s), 9.99 (2H, br.s), 7.27 (1H, d), 7.02-7.00 (2H, m), 4.43-4.37 (4H, m), 3.82-3.75 (2H, m), 3.49-3.43 (2H, m), 3.15-3.10 (4H, m), 2.79-2.78 (3H, s), 1.52 (9H, s). MS: [M+H]+ 218.

75C. (5-Chloro-2,4-dihydroxy-phenyl)-[5-(4-methyl-piperazin-1-yl)-1,3-dihydro-isoindol-2-yl]-methanone

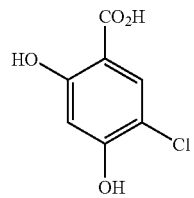

EDC, HOBt, DMF

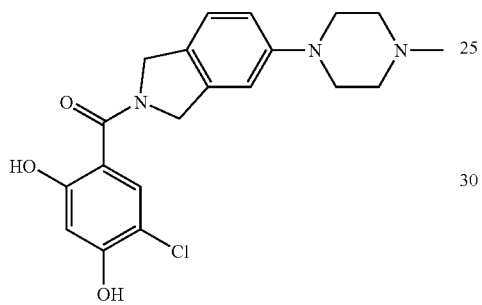

A solution of 5-chloro-2,4-dihydroxy-benzoic acid (176 mg, 0.93 mmol) in DMF (5 mL) was treated with 1-(3-dimethylaminopropyl)-3-ethylcarbodiimide hydrochloride (179 mg, 0.93 mmol) then HOBt (126 mg, 0.93 mmol). After 45 min, the solution of the activated acid was added to a mixture 5-(4-methyl-piperazin-1-yl)-2,3-dihydro-1H-isoindole dihydrochloride (290 mg, 0.78 mmol) and triethylamine (0.28 mL, 2 mmol) then the mixture was stirred at r.t. for 3 h. The solvent was removed in vacuo then the residue was partitioned between ethyl acetate and water (×3). Each extract was washed with saturated sodium bicarbonate solution and brine then dried (MgSO₄), combined and concentrated. Some insoluble material remained and this was dissolved in 1N hydrochloric acid and methanol then combined with the organic extracts. The pH was adjusted to 14 with solid sodium hydroxide and the mixture allowed to stand overnight. The pH was adjusted to 7 with 1N hydrochloric acid and the resulting precipitate was filtered off then subjected to purification by preparative HPLC to afford the title compound as a red solid. This was converted to its hydrochloride salt by treatment with 4M HCl in dioxane, concentration in vacuo and trituration with ether which gave a brown solid (91 mg, 27%). ¹H NMR (DMSO-d₆) 11.10 (1H, br.s), 10.50 (1H, br.s), 7.26-7.15 (2H, m), 7.02-6.93 (2H, m), 6.69 (1H, s), 4.72-4.61 (4H, m), 3.78-3.72 (2H, m), 3.45 (2H, br.s), 3.12 (4H, br.s), 2.78 (3H, s). MS: [M+H]+ 386/388.

Example 76

(2,4-dihydroxy-5-isopropyl-phenyl)-[5-(4-methyl-piperazin-1-yl)-1,3-di-hydro-isoindol-2-yl]-methanone 76A. Synthesis of (2,4-bis-benzyloxy-5-isopropenyl-phenyl)-(5-bromo-1,3-dihydro-isoindol-2-yl)-methanone

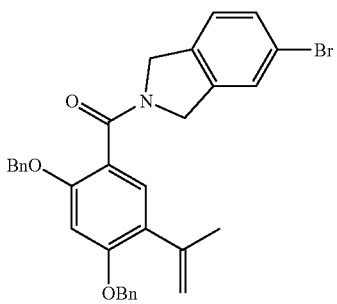 [SMILES: C=C(C)c1cc(C(=O)N2Cc3ccc(Br)cc3C2)c(OCc2ccccc2)cc1OCc1ccccc1]

Coupling of 2,4-bis-benzyloxy-5-isopropenyl-benzoic acid (5.0 g, 13.4 mmol) (Preparation B9) and 5-bromo-2,3-dihydro-1H-isoindole (Preparation C20) was completed according to method A4, using CH₂Cl₂ as the reaction solvent to give the title compound (8.34 g) as a beige solid.

76B. Synthesis of (2,4-bis-benzyloxy-5-isopropenyl-phenyl)-[5-(4-methyl-piperazin-1-yl)-1,3-dihydro-isoindol-2-yl]-methanone

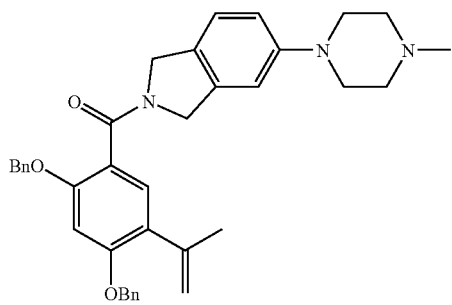 [SMILES: C=C(C)c1cc(C(=O)N2Cc3ccc(N4CCN(C)CC4)cc3C2)c(OCc2ccccc2)cc1OCc1ccccc1]

To a mixture of (2,4-bis-benzyloxy-5-isopropenyl-phenyl)-(5-bromo-1,3-dihydro-isoindol-2-yl)-methanone (8.30 g, 15.0 mmol), 2-(di-t-butylphosphino)biphenyl (223 mg, 0.75 mmol), tris(dibenzylideneacetone)dipalladium (344 mg, 0.38 mmol), sodium tert-butoxide (2.17 g, 22.5 mmol) and 1-methyl-piperazine (2.16 mL, 19.5 mmol) under a N₂ atmosphere was added anhydrous toluene (100 mL). The mixture was taken to 80° C. and heated at this temperature for 16 h. The mixture was allowed to cool to ambient temperature, diluted with ether (150 mL) and filtered through a plug of Celite, washing with ether. The filtrate was reduced in vacuo and the residue purified by column chromatography using an eluant of CH₂Cl₂-DMAW120 (1:0-0:1) to give the title compound (9.39 g) as a red gum.

76C. (2,4-dihydroxy-5-isopropyl-phenyl)-[5-(4-methyl-piperazin-1-yl)-1,3-di-hydro-isoindol-2-yl]-methanone

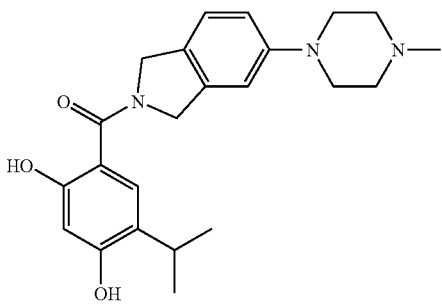 [SMILES: CC(C)c1cc(C(=O)N2Cc3ccc(N4CCN(C)CC4)cc3C2)c(O)cc1O]

A mixture of (2,4-bis-benzyloxy-5-isopropenyl-phenyl)-[5-(4-methyl-piperazin-1-yl)-1,3-dihydro-isoindol-2-yl]-methanone (8.61 g, 15.0 mmol) and 10% Pd/C (1.0 g) in methanol (200 mL) was stirred vigorously under a hydrogen atmosphere (~1 atm) for 18 h at ambient temperature. The mixture was filtered through a plug of Celite and reduced in vacuo to give a purple oil. This residue was purified by column chromatography using an eluant of DMAW120 to give the title compound as its acetate salt. This salt was taken up in MeOH (30 mL) and to the solution was added saturated HCl in EtOAc (20 mL). This mixture was stirred at ambient for 2 h and the solid formed collected by filtration and dried in vacuo to give the title compound as its hydrochloride salt (2.64 g) as a white solid.

Example 77

(5-Chloro-2,4-dihydroxy-phenyl)-[5-(4-methyl-piperazin-1-yl)-1,3-dihydro-isoindol-2-yl]-methanone

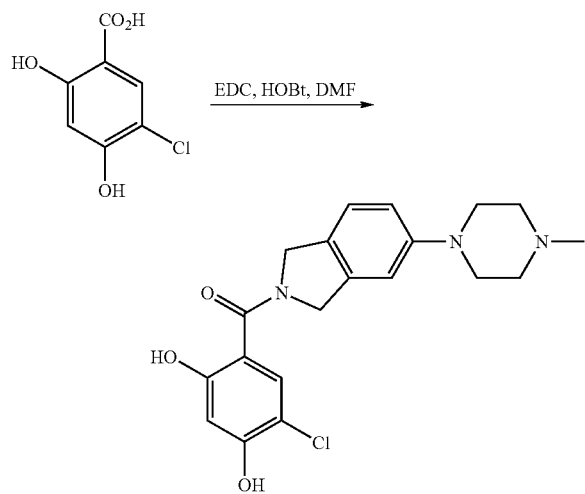

A solution of 5-chloro-2,4-dihydroxy-benzoic acid (176 mg, 0.93 mmol) in DMF (5 mL) was treated with 1-(3-dimethylaminopropyl)-3-ethylcarbodiimide hydrochloride (179 mg, 0.93 mmol) then HOBt (126 mg, 0.93 mmol). After 45 minutes, the solution of the activated acid was added to a mixture 5-(4-methyl-piperazin-1-yl)-2,3-dihydro-1H-isoindole dihydrochloride (290 mg, 0.78 mmol) and triethylamine (0.28 mL, 2 mmol) then the mixture was stirred at r.t. for 3 h. The solvent was removed in vacuo then the residue was partitioned between ethyl acetate and water (×3). Each extract was washed with saturated sodium bicarbonate solution and brine then dried (MgSO$_4$), combined and concentrated. Some insoluble material remained and this was dissolved in 1N hydrochloric acid and methanol then combined with the organic extracts. The pH was adjusted to 14 with solid sodium hydroxide and the mixture allowed to stand overnight. The pH was adjusted to 7 with 1N hydrochloric acid and the resulting precipitate was filtered off then subjected to purification by preparative HPLC to afford the title compound as a red solid. This was converted to its hydrochloride salt by treatment with 4M HCl in dioxane, concentration in vacuo and trituration with ether which gave a brown solid (91 mg, 27%). $^1$H NMR (DMSO-d$_6$) 11.10 (1H, br.s), 10.50 (1H, br.s), 7.26-7.15 (2H, m), 7.02-6.93 (2H, m), 6.69 (1H, s), 4.72-4.61 (4H, m), 3.78-3.72 (2H, m), 3.45 (2H, br.s), 3.12 (4H, br.s), 2.78 (3H, s). MS: [M+H]$^+$ 386/388.

Example 78

Alternative Synthesis of (2,4-Dihydroxy-5-isopropyl-phenyl)-[5-(4-hydroxy-1-methyl-piperidin-4-yl)-1,3-dihydro-isoindol-2-yl]-methanone

78A. 5-bromo-2-trityl-2,3-dihydro-1H-isoindole

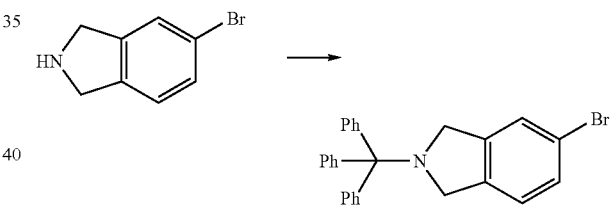

Trityl chloride (2.30 g, 8.23 mmol) was added to a solution of 5-bromo-2,3-dihydro-1H-isoindole (1.64 g, 8.23 mmol) and triethylamine (1.4 mL, 9.9 mmol) in dichloromethane (20 mL). After 18 hours the solvent was removed in vacuo, the residue taken up in ethyl acetate and washed with water (×2) and brine, dried (MgSO$_4$) and concentrated. The crude material was purified by flash chromatography on silica eluting with 1% triethylamine/10% ethyl acetate/petrol to give 5-bromo-2-trityl-2,3-dihydro-1H-isoindole as a reddish-brown solid (3.10 g, 85%). $^1$H NMR (CDCl$_3$) 7.91-7.84 (1H, m), 7.57 (6H, d), 7.45-7.41 (1H, m), 7.33-7.14 (9H, m), 6.95 (1H, d), 3.90 (2H, s), 3.86 (2H, s). MS: Ph$_3$C$^+$ 243.

78B. 1-methyl-4-(2-trityl-2,3-dihydro-1H-isoindol-5-yl)-piperidin-4-ol

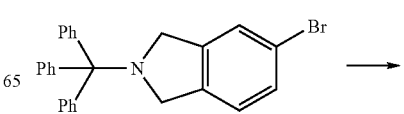

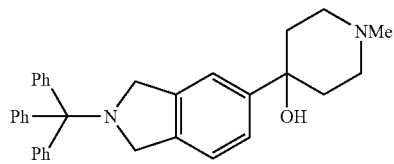

Under nitrogen, a solution of 5-bromo-2-trityl-2,3-dihydro-1H-isoindole (2.03 g, 4.6 mmol) in THF (20 mL) was cooled to −78° C. n-Butyllithium solution (2.5M in hexanes, 2.0 mL, 5 mmol) was added over 5 minutes, then after 10 minutes, 1-methyl-4-piperidone was added dropwise. After a further hour, the cooling bath was removed and the reaction quenched with sodium bicarbonate solution. The mixture was extracted with ethyl acetate then the organic phase was washed with brine, dried (MgSO$_4$) and concentrated. The residue was purified by flash chromatography on silica (gradient elution with 2M methanolic ammonia/dichloromethane, 0% to 5%) to afford 1-methyl-4-(2-trityl-2,3-dihydro-1H-isoindol-5-yl)-piperidin-4-ol as a pink foam (1.25 g, 57%). $^1$H NMR (MeOH-d$_4$) 7.56 (6H, dd), 7.28 (6H, t), 7.25-7.21 (2H, m), 7.15 (3H, t), 7.03 (1H, d), 3.92 (2H, s), 3.91 (2H, s), 2.70 (2H, d), 2.53 (2H, td), 2.33 (3H, s), 2.06 (2H, td), 1.70 (2H, d). MS: [M+H]$^+$ 475.

78C. 4-(2,3-Dihydro-1H-isoindol-5-yl)-1-methyl-piperidin-4-ol dihydrochloride

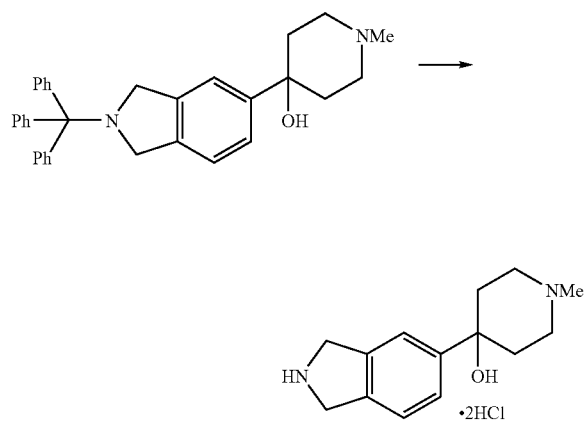 [SMILES: CN1CCC(O)(c2ccc3c(c2)CN(C(c2ccccc2)(c2ccccc2)c2ccccc2)C3)CC1 ; CN1CCC(O)(c2ccc3c(c2)CNC3)CC1 ; "·2HCl"]

A mixture of 1-methyl-4-(2-trityl-2,3-dihydro-1H-isoindol-5-yl)-piperidin-4-ol (1.42 g, 3.0 mmol), 5N hydrochloric acid (5 mL) and methanol (10 mL) was placed under nitrogen then heated to reflux for 80 minutes. After cooling, the mixture was concentrated in vacuo to remove methanol, diluted with water and washed with ethyl acetate (×2). The aqueous phase was concentrated to dryness to afford the title compound in quantitative yield as a black solid. $^1$H NMR (MeOH-d$_4$) 7.62 (1H, s), 7.57 (1H, d), 7.45 (1H, d), 4.64 (2H, s), 4.63 (2H, s), 3.49-3.46 (4H, m), 2.95 (3H, s), 2.40-2.32 (2H, m), 1.97 (2H, dd).

78D. (2,4-Bis-benzyloxy-5-isopropenyl-phenyl)-[5-(4-hydroxy-1-methyl-piperidin-4-yl)-1,3-dihydro-isoindol-2-yl]-methanone

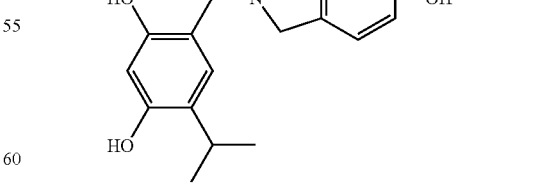

2,4-Bis-benzyloxy-5-isopropenyl-benzoic acid (1.65 g, 4.4 mmol), 1-[3-(dimethylamino)propyl]-3-ethylcarbodiimide hydrochloride (843 mg, 4.4 mmol) and 1-hydroxybenzotriazole (595 mg, 4.4 mmol) were dissolved in DMF (20 mL). After 35 minutes, the solution was added to a suspension of 4-(2,3-dihydro-1H-isoindol-5-yl)-1-methyl-piperidin-4-ol dihydrochloride (1.22 g, 4.0 mmol) in DMF (5 mL) and triethylamine (1.4 mL, 10 mmol). The mixture was stirred for 3 hours then concentrated in vacuo. The residue was taken up in ethyl acetate and washed with a mixture of water (adjusted to pH 14 with 2N sodium hydroxide solution) and brine. The aqueous phase was extracted twice further with ethyl acetate then the combined organic extracts were washed with sodium bicarbonate solution and brine, dried (MgSO$_4$) and concentrated. The crude product was purified by flash chromatography (gradient elution with 2M methanolic ammonia/dichloromethane, 2% to 10%) to afford the title compound as a brown foam (1.62 g, 69%). $^1$H NMR (methanol-d$_4$) 7.51-7.14 (14H, m), 6.85 (0.5H, s), 6.84 (0.5H, s), 5.16 (2H, s), 5.15 (2H, s), 5.10-5.08 (1H, m), 5.07-5.05 (1H, m), 4.87 (1H, s), 4.86 (1H, s), 4.61 (2H, br.s), 2.78-2.70 (2H, m), 2.57 (1H, td), 2.54 (1H, td), 2.36 (1.5H, s), 2.34 (1.5H, s), 2.16-2.05 (5H, m including 2.09 (3H, s)), 1.78-1.70 (2H, m). MS: [M+H]$^+$ 589.

78E. (2,4-Dihydroxy-5-isopropyl-phenyl)-[5-(4-hydroxy-1-methyl-piperidin-4-yl)-1,3-dihydro-isoindol-2-yl]-methanone (2,4-Bis-benzyloxy-5-isopropenyl-phenyl)-[5-(4-hydroxy-1-methyl-piperidin-4-yl)-1,3-dihydro-isoindol-2-yl]-methanone (Example 50F) (1.62 g, 2.75 mmol) was dissolved in methanol (50 mL) and hydrogenated at 50° C. over 10% palladium on charcoal using an H-cube hydrogenation apparatus, under free hydrogen conditions. Concentration afforded the title compound (1.14 g, 100%) as a yellow solid, the NMR and mass spectrometric data of which were as set out in Example 50E.

Example 79

(2,4-Dihydroxy-5-isopropyl-phenyl)-[5-(2-dimethylamino-ethoxy)-7-methyl-1,3-dihydro-isoindol-2-yl]-methanone

79A. 7-Methyl-2,3-dihydro-1H-isoindol-5-ol hydrobromide

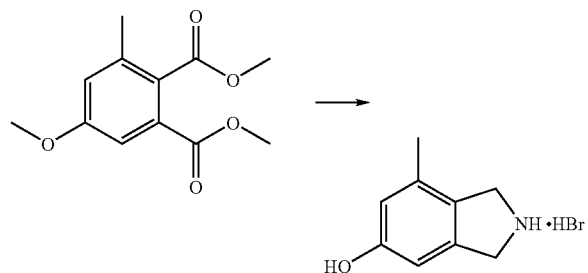

Using the method of preparation C2, 5-methoxy-3-methylphthalic acid dimethyl ester (prepared according to Tam and Coles, *Synthesis* 1988, 383) was hydrolysed to 5-methoxy-3-methyl-phthalic acid. $^1$H NMR (DMSO-d$_6$) 12.95 (2H, br.s), 7.15 (1H, d), 7.04 (1H, d), 3.80 (3H, s), 2.29 (3H, s). MS: [M−H]$^+$ 209.

5-Methoxy-3-methyl-phthalic acid was converted to 5-methoxy-3-methyl-phthalic anhydride. $^1$H NMR (DMSO-d$_6$) 7.40 (1H, d), 7.34-7.33 (1H, m), 3.94 (3H, s), 2.58 (3H, s).

5-Methoxy-3-methyl-phthalic anhydride was used to prepare 6-methoxy-4-methyl-isoindole-1,3-dione. $^1$H NMR (DMSO-d$_6$) 11.05 (1H, br.s), 7.13 (1H, d), 7.10 (1H, d), 3.88 (3H, s), 2.55 (3H, s).

Reduction of 6-methoxy-4-methyl-isoindole-1,3-dione according to the method of preparation C2 afforded 6-methoxy-4-methyl-isoindole. $^1$H NMR (DMSO-d$_6$) 6.64 (1H, s), 6.57 (1H, s), 4.05 (2H, s), 3.96 (2H, s), 3.70 (3H, s), 2.16 (3H, s). MS: [M+H]$^+$ 164.

6-Methoxy-4-methyl-isoindole was demethylated to give the title compound as its hydrobromide salt. $^1$H NMR (DMSO-d$_6$) 9.52 (1H, br.s), 9.29 (2H, br.s), 6.59 (1H, s), 6.56 (1H, s), 4.41 (2H, t), 4.34 (2H, t), 2.17 (3H, s).

79B. (2,4-Bis-benzyloxy-5-isopropenyl-phenyl)-(5-hydroxy-7-methyl-1,3-dihydro-isoindol-2-yl)-methanone

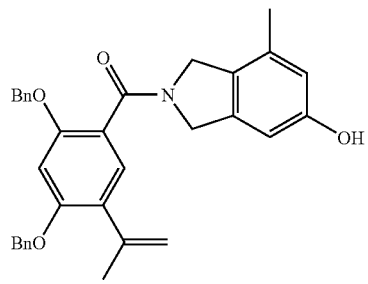 [SMILES: C=C(C)c1cc(C(=O)N2Cc3cc(O)cc(C)c3C2)c(OCc2ccccc2)cc1OCc1ccccc1]

2,4-Bis-benzyloxy-5-isopropenyl-benzoic acid (248 mg, 0.66 mmol), 1-[3-(dimethylamino)propyl)]-3-ethylcarbodiimide hydrochloride (127 mg, 0.66 mmol) and 1-hydroxybenzotriazole (89 mg, 0.66 mmol) were dissolved in DMF (5 mL). After 20 minutes, 7-methyl-2,3-dihydro-1H-isoindol-5-ol hydrobromide (152 mg, 0.66 mmol) and triethylamine (0.14 mL, 0.99 mmol) were added. After a further 3.5 hours the mixture was concentrated in vacuo and the residue was treated with 1N hydrochloric acid and ethyl acetate. The aqueous phase was removed, brine was added and the title compound was collected by filtration as a grey solid (168 mg, 57%). $^1$H NMR (DMSO-d$_6$) 9.30 (0.47H, s), 9.24 (0.53H, s), 7.48-7.25 (10H, m), 7.09 (0.47H, s), 7.08 (0.53H, s), 6.99 (0.47H, s), 6.98 (0.53H, s), 6.56 (0.47H, s), 6.50 (0.53H, s), 6.48 (0.47H, s), 6.44 (0.53H, s), 5.24 (0.47H, s), 5.22 (0.53, s), 5.18 (2H, s), 5.10-5.07 (2H, m), 4.70 (0.47H, s), 4.61 (0.53H, s), 4.46 (0.47H, s), 4.36 (0.53H, s), 2.17 (1.41H, s), 2.04 (3H, s), 1.99 (1.59H, s). MS: [M+H]$^+$ 506.

79B. (2,4-Bis-benzyloxy-5-isopropenyl-phenyl)-[5-(2-dimethylamino-ethoxy)-7-methyl-1,3-dihydro-isoindol-2-yl]-methanone

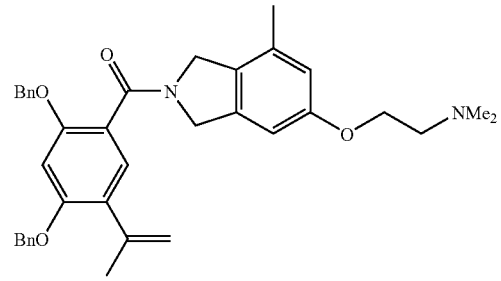 [SMILES: C=C(C)c1cc(C(=O)N2Cc3cc(OCCN(C)C)cc(C)c3C2)c(OCc2ccccc2)cc1OCc1ccccc1]

A mixture of (2,4-bis-benzyloxy-5-isopropenyl-phenyl)-(5-hydroxy-7-methyl-1,3-dihydro-isoindol-2-yl)-methanone (164 mg, 0.32 mmol), potassium carbonate (112 mg, 0.81 mmol) and 2-(dimethylamino)ethyl chloride hydrochloride (93 mg, 0.64 mmol) in DMF (5 mL) was heated at 60° C. for 17 hours then 90° C. for 6 hours. Further portions of potassium carbonate (112 mg, 0.81 mmol) and 2-(dimethylamino)ethyl chloride hydrochloride (93 mg, 0.64 mmol) were added and the mixture maintained at 60° C. for 72 hours and finally, a further 24 hours at 90° C. The mixture was concentrated in vacuo then the residue was partitioned between ethyl acetate and 0.5N aqueous sodium hydroxide. The organic phase was washed with brine (×2), dried (MgSO$_4$) and concentrated to give a residue which was purified by preparative HPLC (acidic method) to afford the title compound as a formate salt (37 mg, 20%). $^1$H NMR (MeOH-d$_4$) 8.51 (1H, br.s), 7.43-7.27 (7H, m), 7.24-7.20 (3H, m), 7.17 (0.5H, s), 7.16 (0.5H, s), 6.85 (0.5H, s), 6.84 (0.5H, s), 6.81 (0.5H, s), 6.77 (0.5H, s), 6.74 (0.5H, s), 6.62 (0.5H, s), 5.16 (1H, s), 5.14 (3H, s), 5.09 (1H, m), 5.06 (1H, m), 4.83 (1H, s), 4.74 (1H, s), 4.60 (1H, s), 4.48 (1H, s), 4.28 (1H, t), 4.23 (1H, t), 3.41 (1H, t), 3.37 (1H, t), 2.84 (3H, s), 2.81 (3H, s), 2.27 (1.5H, s), 2.09 (3H, s), 2.07 (1.5H, s). MS: [M+H]$^+$ 577.

79C. (2,4-Dihydroxy-5-isopropyl-phenyl)-[5-(2-dimethylamino-ethoxy)-7-methyl-1,3-dihydro-isoindol-2-yl]-methanone

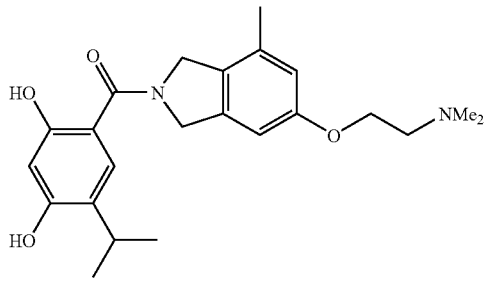 [SMILES: Cc1cc(OCCN(C)C)cc2c1CN(C(=O)c1cc(C(C)C)c(O)cc1O)C2]

(2,4-Bis-benzyloxy-5-isopropenyl-phenyl)-[5-(2-dimethylamino-ethoxy)-1,3-dihydro-isoindol-2-yl]-methanone (37 mg, 0.06 mmol) was hydrogenated in methanol at 50° C. over 10% palladium on charcoal using an H-cube hydrogenation apparatus, under free hydrogen conditions. The product was purified by preparative HPLC (basic method) to give the title compound as an off-white solid (9 mg, 35%). $^1$H NMR (MeOH-d$_4$) 7.18 (1H, s), 6.77-6.65 (2H, br.m), 6.37 (1H, s), 4.85 (water obscuring CH$_2$), 4.77 (2H, s), 4.08 (2H, t), 3.20 (1H, sept), 2.81 (2H, t), 2.39 (6H, s), 2.22 (3H, br.s), 1.21 (6H, d). MS: [M+H]$^+$ 399.

Example 80

(2,4-Dihydroxy-5-isopropyl-phenyl)-[5-(4-methyl-piperazin-1-ylmethyl)-1,3-dihydro-isoindol-2-yl]-methanone

Step 1

4-Acetoxy-2-hydroxy-benzoic acid methyl ester

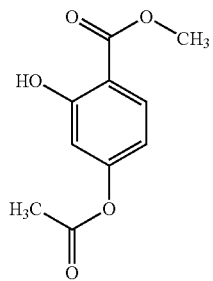

Resorcinol methyl ester (50 g, 0.298 mol) and N,N-dimethyl-4-aminopyridine (0.27 g, 0.0022 mol, 0.74 mol %) were added to toluene 0.2 L followed by acetic anhydride (30 mL, 0.318 mol). The solution was heated to 50° C. for 2 h. The solvent was removed by evaporation at 50° C. to a small volume and the residue was azeotroped once with toluene. To the residual oil was immediately added toluene (100 mL) whilst still warm and the solution used for Step 2 without further purification.

Step 2

5-Acetyl-2,4-dihydroxy-benzoic acid methyl ester

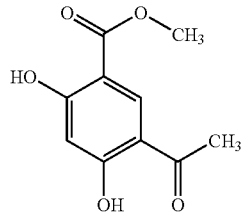

The toluene solution from Step 1 was cooled in an ice bath under N$_2$ and triflic acid (26 mL) added slowly over 30 min. On stirring a fine white solid was formed which dissolved on stirring for 16 h at RT to give a yellow solution. To the solution was added acetyl chloride (2 mL) and the solution stirred at RT for a further 1 h. This solution was cannulated into a stirred cooled (0° C.) solution of EtOAc (600 mL) and NaOAc.3H$_2$O (40 g) dissolved in water (400 mL). The organic phase was washed with water (twice, 200 mL), saturated brine and was evaporated to a small volume without drying. The residue was azeotroped with heptane (twice, 100 mL) and heptane (100 mL) was added and the crystalline solid removed by filtration, washed well on sinter with heptane and dried to give 49.5 g (79%).

Final Purification of Combined Batches

The combined batches of solid (96.3 g) was heated to boiling with 10% IPA/heptane (250 mL) then cooled to RT and finally to 0° C., filtered and the residue dried 72 h (oil pump) to give (88.04 g, 91.5%), pure by hplc, tlc and NMR.
$^1$H NMR (DMSO-d$_6$) 12.58 (1H, s), 11.22 (1H, s), 8.33 (1H, s), 6.45 (1H, s), 3.90 (3H, s), 2.62 (3H, s).

Step 3

5-Acetyl-2,4-dihydroxy-benzoic acid methyl ester (Alternative procedure)

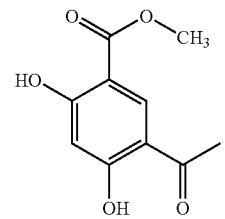

Resorcinol methyl ester (50 g, 0.298 mol) and Amberlyst 15 resin (40 g) were suspended in toluene 150 mL (under a nitrogen atmosphere) and the solution was heated in an oil bath at 70° C. (internal temp 56° C.). Acetyl chloride (22 mL, 308 mmol) was added in 5 mL portions over 30 mins giving evolution of gaseous HCl (which was scrubbed by passing the nitrogen stream through aqueous NaOH). The solution was stirred at 70° C. for 4.5 h then heated in an oil bath temp (internal temperature 96° C.) for 3.5 h. The solution was cooled to 50° C. and EtOAc (100 mL) was added and the solution filtered whilst at this temperature. The residual resin was washed with EtOAc (50 mL) and the combined filtrates were concentrated to slurry of crystalline solid (total weight of 128 g for solid plus solvent). To the slurry was added heptane (100 mL) and after 10 mins at RT the solid was removed by filtration. The residue was washed with heptane:toluene (2:1, 60 mL) then with petroleum ether by 40-60° C. and dried in vacuo to give crop 1 29 g (46.4%) (NMR showed 3% of material resulting from saponification of the methyl ester).

The filtrate was evaporated to a small volume and 20% EtOAc in heptane (100 mL) was added. After standing at RT 16 h a second crop of 4.75 g (7.6%) was obtained (NMR identical to crop 1).

Step 4

5-Acetyl-2,4-bis-benzyloxy-benzoic acid methyl ester

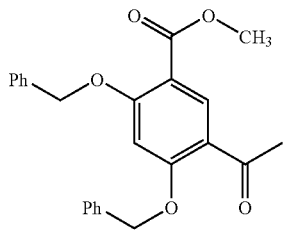 [SMILES: COC(=O)c1cc(C(C)=O)c(OCc2ccccc2)cc1OCc1ccccc1]

Benzyl bromide (70 ml, 0.59 mol) was added to a stirred mixture of methyl 5-acetyl-2,4-dihydroxybenzoate (60.7 g, 0.29 mol) and anhydrous potassium carbonate (87.8 g, 0.64 mol) in acetonitrile (800 ml) and the mixture was stirred and held at reflux for 16 hours. Upon cooling to room temperature the mixture was poured onto water (3 L) and stirred vigorously for 2 hours. The solids were collected by filtration, rinsed with water (2 L), sucked dry under reduced pressure and dried to constant mass in a vacuum oven at 60° C. overnight to afford methyl 5-acetyl-2,4-benzyloxybenzoate (112.1 g, 99%) as a cream solid. $^1$H NMR (DMSO-$d_6$) 8.21 (1H, s), 7.55 (4H, m), 7.43 (4H, m), 7.37 (2H, m), 7.04 (1H, s), 5.38 (4H, s), 3.79 (3H, s), 2.48 (3H, s). MS: [M+H]$^+$ 391.

Step 5

2,4-Bis-benzyloxy-5-isopropenyl-benzoic acid methyl ester

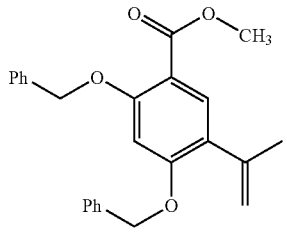 [SMILES: C=C(C)c1cc(C(=O)OC)c(OCc2ccccc2)cc1OCc1ccccc1]

Potassium tert-butoxide (29.1 g, 0.26 mol) was added to a stirred suspension of methyltriphenylphosphonium bromide (92.8 g, 0.26 mol) in anhydrous tetrahydrofuran (1 L) and the mixture was stirred at room temperature for 10 minutes whereupon methyl 5-acetyl-2,4-bis-benzyloxybenzoate (78.0 g, 0.2 mol) was added and the mixture stirred at room temperature for a further 30 minutes. Methanol (100 ml) was added to quench excess phosphorus ylide and the solvent was removed in vacuo to afford an orange oil that crystallized on standing. The residue was recrystallized from methanol (330 ml). The solids were collected by suction filtration, washed with methanol (50 ml) and sucked dry under reduced pressure to afford methyl 2,4-bis-benzyloxy-5-isopropenyl-benzoate as pale yellow needles. The mother liquor deposited a second crop of material upon standing overnight (combined yield: 56.55 g, 73%) $^1$H NMR (DMSO-$d_6$) 7.59 (1H, s), 7.52 (2H, d), 7.64-7.32 (8H, m), 6.97 (1H, s), 5.28 (2H, s), 5.22 (2H, s), 5.09 (1H, s), 5.04 (1H, s), 3.76 (3H, s), 2.02 (3H, s). MS: [M+H]$^+$ 389.

A further crop of the ester could be obtained as follows. The crystallization residues were evaporated to dryness in vacuo and the oily solid was treated with 5% ethyl acetate in heptane (250 ml). Ethyl acetate was added in small portions to the vigourously stirred mixture until the residue deposited a large quantity of solid triphenylphosphine oxide. The solids were removed by filtration and the filtrate evaporated to dryness in vacuo to afford an orange oil. Recrystallization from methanol (as described above) afforded further methyl 2,4-bis-benzyloxy-5-isopropenyl-benzoate as a pale yellow crystalline solid (total yield 85-90%).

Step 6

2,4-Bis-benzyloxy-5-isopropenyl-benzoic acid

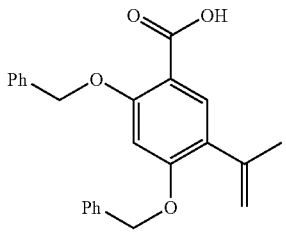 [SMILES: C=C(C)c1cc(C(=O)O)c(OCc2ccccc2)cc1OCc1ccccc1]

Potassium hydroxide (10.96 g, 0.19 mmol) was added to a stirred suspension of methyl 2,4-bis-benzyloxy-5-isopropenyl-benzoate (61.0 g, 0.16 mol) in methanol (750 ml) and water (250 ml) and the mixture was stirred and held at reflux for 16 hours. Upon cooling the organic solvent was removed in vacuo and the mixture acidified to pH 2 or below by the addition of 2M hydrochloric acid (200 ml). The mixture was diluted with water (2 L) and extracted with ethyl acetate (2 L), the organic layer was separated and the solvent removed in vacuo to afford 2,4-bis-benzyloxy-5-isopropenyl-benzoic acid (58.8 g, 100%) as a colourless solid. $^1$H NMR (DMSO-$d_6$) 7.52 (2H, d), 7.47-7.29 (9H, m), 6.82 (1H, s), 5.20 (2H, s), 5.17 (2H, s), 5.06 (1H, s), 5.04 (1H, s), 2.03 (3H, s). MS: [M+H]$^+$ 375.

Step 7

Di-prop-2-ynyl-carbamic acid benzyl ester

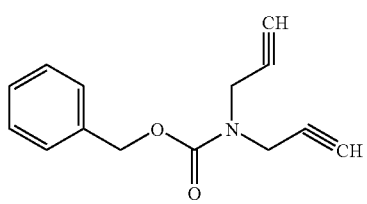 [SMILES: C#CCN(CC#C)C(=O)OCc1ccccc1]

To a cooled (0° C.) solution of dipropargylamine (46.7 g, 502 mmol) in EtOAc (200 mL) and 10% aqueous $K_2CO_3$ (700 mL, 507 mmol) was slowly added a solution of N-(benzyloxycarbonyloxy)succinimide (125 g, 502 mmol) in EtOAc (500 mL) over 20 mins. The solution was stirred at 0° C. for 2 h then at RT 16 h. The phases were separated and the organic phase was washed with 10% aqueous $K_2CO_3$ (700 mL, 507 mmol) and then with saturated brine (500 mL) and was diluted to 1000 mL with EtOAc to give a 0.5M solution.

Step 8

5-Hydroxymethyl-1,3-dihydro-isoindole-2-carboxylic acid benzyl ester

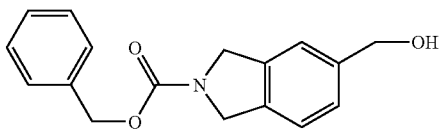 [SMILES: O=C(OCc1ccccc1)N1Cc2ccc(CO)cc2C1]

A solution of propargyl alcohol (26.4 mL, 424 mmol) in toluene (120 mL) was degassed. The 0.5M-diyne solution above (440 mL, 220 mmol) was evaporated and the residue dissolved in toluene (80 mL). This protected diyne solution and Wilkinson's catalyst (2.26 g, 2.44 mmol, 1.11% were added in 14 equal portions over a 2 h period with constant monitoring of the internal temperature such that the temperature remained 50-100° C. The solution was allowed to cool to 50° C. over 30 min when the solution was evaporated (to remove excess propargyl alcohol). The residue was heated with toluene (500 mL) and charcoal (Darco 4-12 mesh, 20 g) at 100° C. for 30 min and then filtered hot through a bed of Celite and the brown solution was evaporated. The residue was dissolve in EtOAc (400 mL) at 80° C. when silica gel (chromatography grade 65 g) was added and heating continued for 20 mins. The solution was filtered whilst hot and then evaporated (with seeding) to give a pale brown solid. 10% EtOAc/heptane (v/v, 100 mL) was added and the solid removed by filtration. The solid was washed on the sinter with heptane (100 mL) and the dried (50° C., oil pump, 16 h) to give the title compound 59.0 g (95%). 1H NMR (400 MHz, Me-d3-OD): 7.51-7.16 (m, 8H), 5.21 (s, 2H), 4.74 (s, 2H), 4.70 (s, 2H), 4.61 (s, 2H).

Step 9

5-Methanesulfonyloxymethyl-1,3-dihydro-isoindole-2-carboxylic acid benzyl ester

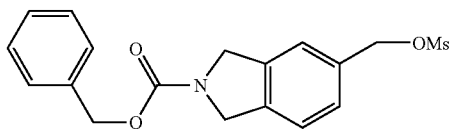 [SMILES: CS(=O)(=O)OCc1ccc2c(c1)CN(C(=O)OCc1ccccc1)C2]

To a solution of 5-hydroxymethyl-1,3-dihydro-isoindole-2-carboxylic acid benzyl ester (65.75 g, 0.232 mol) in THF (470 mL) and EtOAc (770 mL) was added $Et_3N$ (39 mL, 0.28 mol). The solution was cooled in an ice-bath and a solution of methanesulphonyl chloride (19 mL, 0.245 mol) dissolved in EtOAc (50 mL) was added (so that the internal temp <12° C.). After stirring for 2 h in the ice-bath further additions of methanesulphonyl chloride (1.9 mL and 0.95 mL) and $Et_3N$ (3.9 mL) were made (so that by tlc there was no remaining starting material after a further 1 h of stirring). $NaHCO_3$ (550 mL) was added and the solution stirred for 20 mins then saturated brine (200 mL) was added and the phases were separated. The organic phase was dried ($MgSO_4$) and evaporated with seeding to give a damp solid which was used in the next step without thorough drying.

Step 10

5-(4-Methyl-piperazin-1-ylmethyl)-1,3-dihydro-isoindole-2-carboxylic acid benzyl ester dihydrochloride salt

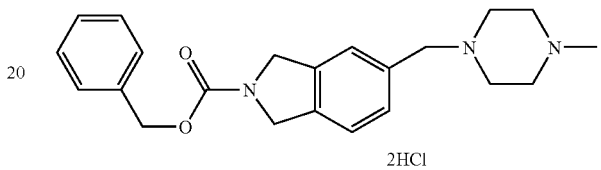

2HCl

The solid from Step 9 (assume 0.232 mol) was dissolved in acetone (700 mL) and this solution was added over 45 mins to a cooled (internal temp 15-17° C.) suspension of $K_2CO_3$ (48 g) and N-methylpiperazine (50 mL, 0.45 mol) in acetone (330 mL). The suspension was stirred at 15° C. for 3 h (complete removal of starting material by tlc) when the solution was evaporated to a small volume and the residue partition between EtOAc (1000 mL) and a mixture of water (500 mL) and saturated brine (50 mL). The organic phase was washed with a mixture of water (500 mL) and saturated brine (150 mL) and finally washed with saturated brine (300 mL). The solution was dried ($MgSO_4$) and filtered and to this solution was added 1M-HCl in MeOH (430 mL, 0.43 mol). The suspension was cooled (0° C. for 30 mins) and the solid removed by filtration which was washed with EtOAc and then heptane on the sinter and the solid dried (oil-pump, RT 72 h) to give crop 1 of the title compound 66.34 g (65%) as a colourless solid. 1H NMR (400 MHz, Me-d3-OD): 7.64-7.51 (m, 2H), 7.51-7.29 (m, 6H), 5.23 (s, 2H), 4.79 (dd, J=16.2, 6.1 Hz, 4H), 4.49 (s, 2H), 3.66 (s, 8H), 3.03 (s, 3H).

Alternative Step 10A 5-(4-Methyl-piperazin-1-ylmethyl)-1,3-dihydro-isoindole-2-carboxylic acid benzyl ester dihydrochloride

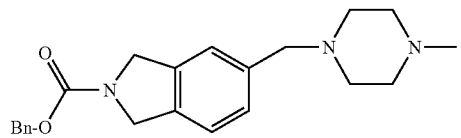

Step 10A can be used as an alternative route to replace steps 9 and 10 above.

To a suspension of manganese dioxide (15.5 g, 178 mmol) in DCM (100 mL) was added 5-hydroxymethyl-1,3-dihydro-isoindole-2-carboxylic acid benzyl ester (3.35 g, 11.8 mmol) and after 6 h stirring at RT a further addition of manganese dioxide (5 g, 57 mmol) was made. After a further 1 h stirring at RT Celite (7 g) was added and the solution was filtered through a bed of Celite™ giving a clear pale yellow solution. The Celite™ was washed with DCM and the volume of the combined organic solution adjusted to 100 mL by evaporation. N-Methylpiperazine (1.31 mL, 11.8 mmol) and acetic acid (0.68 mL) were added followed by sodium triacetoxyborohydride (4.98 g, 23.5 mmol). The yellow solution was stirred 16 h giving a colourless solution. To the solution was added 2M-HCl (10 mL, 20 mmol) giving an effervescence. After 30 min water (10 mL) and $K_2CO_3$ (5.5 g, 39.8 mmol) were added and the organic phase was dried ($Na_2SO_4$). After filtration 4M-HCl in dioxan (6 mL) was added with stirring and the suspension was evaporated to dryness. The residue was dissolved in MeOH with warming and after evaporation the solid was washed on a sinter with EtOAc then petrol (bp 40-60° C.) followed by drying in vacuo at 50° C. to give the title compound 3.61 g (70%). 1H NMR (400 MHz, Me-d3-OD): 7.65-7.51 (2H, m), 7.51-7.27 (6H, m), 5.23 (2H, s), 4.83-4.69 (4H, m), 4.49 (2H, s), 3.66 (8H, d), 3.03 (3H, s)

Step 11

5-(4-Methyl-piperazin-1-ylmethyl)-2,3-dihydro-1H-isoindole

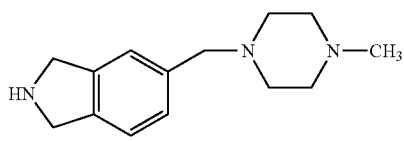

To 5-(4-Methyl-piperazin-1-ylmethyl)-1,3-dihydro-isoindole-2-carboxylic acid benzyl ester dihydrochloride salt (Step 10, 59.8 g, 136.7 mmol) was added EtOAc (400 mL) and 10% aqueous $K_2CO_3$ (400 mL). The organic phase was washed with saturated brine (200 mL) and then dried ($MgSO_4$). The solution was filtered and was evaporated to an oil (which crystallised on standing with petroleum ether (bp 40-60° C.)). The solid was dried in vacuo to give a colourless solid: 48.8 g (133.5 mmol).

A portion of the solid (24.4 g, 66.8 mmol) was dissolved in MeOH (170 mL) and after degassing the solution and purging with nitrogen 10% Pd/C (1.22 g) was added and the mixture hydrogenated at 1 atmosphere for 2.5 h. The solution was filtered and the solution evaporated and the residue was azeotroped twice with toluene at 30-40° C. The residue was dissolved in DMF (92 mL) and the solution was immediately degassed and purged with $N_2$.

(NB The product at this stage is sensitive to air and darkens on contact with oxygen. The DMF solution was used immediately but can be stored by degassing and storing under an atmosphere of $N_2$)

Step 12

(2,4-Bis-benzyloxy-5-isopropenyl-phenyl)-[5-(4-methyl-piperazin-1-ylmethyl)-1,3-dihydro-isoindol-2-yl]-methanone

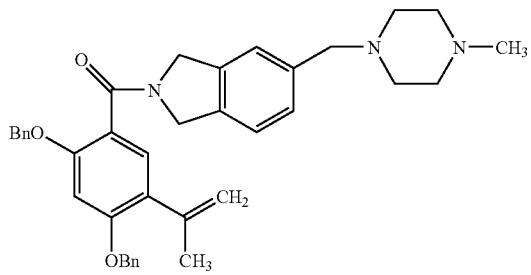 [SMILES: C=C(C)c1cc(C(=O)N2Cc3ccc(CN4CCN(C)CC4)cc3C2)c(OCc2ccccc2)cc1OCc1ccccc1]

A solution of the resorcinol acid (Step 6, 23.7 g, 63.4 mmol) and 1-hydroxybenzotriazole (10.21 g, 66.7 mmol) were dissolved in DMF (92 mL) and to this solution was added N-ethyl-N'-(3-dimethylaminopropyl)carbodiimide hydrochloride (12.8 g, 66.8 mmol). The solution was stirred at RT for 40 mins and this solution was added to the solution of the amine from Step 11 (66.8 mmol) together with DMF (5 mL) washings. The solution was degassed and the solution stirred at RT for 16 h. To the solution was added 10% $K_2CO_3$ (500 mL) and EtOAc (500 mL) and the organic phase was washed sequentially with 10% $K_2CO_3$ (500 mL), water (4×100 mL) and saturated brine (200 mL). The solution was evaporated to a small volume and 20% EtOAc in heptane (250 mL) was added and stored at 0° C. The solid which had formed was removed by filtration, washed with heptane twice and was dried in vacuo to give the title compound 35.05 g (94.4%). 1H NMR (400 MHz, Me-d3-OD): 7.49-7.10 (m, 14H), 6.86 (d, J=2.5 Hz, 1H), 5.17 (d, J=2.5 Hz, 4H), 5.09 (d, J=11.3 Hz, 2H), 4.88 (s, 2H), 4.63 (s, 2H), 3.54 (d, J=16.0 Hz, 2H), 2.50 (s, 7H), 2.28 (d, J=7.6 Hz, 3H), 2.11 (s, 3H).

Step 13

(2,4-Dihydroxy-5-isopropyl-phenyl)-[5-(4-methyl-piperazin-1-ylmethyl)-1,3-dihydro-isoindol-2-yl]-methanone

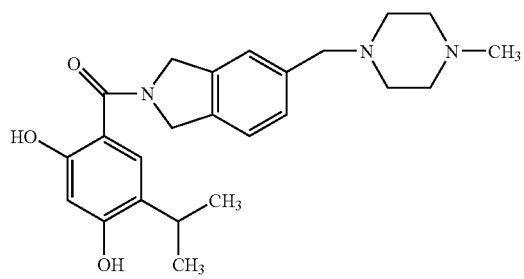 [SMILES: CC(C)c1cc(C(=O)N2Cc3ccc(CN4CCN(C)CC4)cc3C2)c(O)cc1O]

The product from Step 12 (4.7 g) was dissolved in 1:1 MeOH/water (98 mL) and after purging with $N_2$ 10% Pd/C and $K_2CO_3$ (2.38 g, 17.2 mmol) were added and the suspension was hydrogenated for 16 h under an atmosphere of $H_2$. The solution was filtered and the solvent evaporated. To the residue was added aqueous 2M-HCl (40 mL) and the solution was washed with 1:1 EtOAc/petrol (40 mL×2) and then the pH adjusted to pH 8.5 by addition of NaOH and EtOAc (50 mL) added. The solution was heated to 60° C. and the aqueous phase removed. The hot organic phase was washed with water (30 mL) and then evaporated to a small volume (ca. 5 mL) and allowed to stand at RT 16 h with seeding. To the crystalline material was added 1:1 EtOAc/petrol (10 mL) and the mixture was filtered and dried to give the title compound as the free base 1.76 g. 1H NMR (400 MHz, Me-d3-OD): 7.29 (s, 3H), 7.19 (s, 1H), 6.39 (s, 1H), 4.91 (s, 4H), 3.56 (s, 2H), 3.28-3.15 (m, 1H), 2.53 (s, 8H), 2.31 (s, 3H), 1.23 (d, J=6.9 Hz, 7H).

Optional Step 14

Purification of (2,4-Dihydroxy-5-isopropyl-phenyl)-[5-(4-methyl-piperazin-1-ylmethyl)-1,3-dihydro-isoindol-2-yl]-methanone In some batches of product, the title compound (X=H in the formula) can contain small amounts of the impurity 2,4-Dihydroxy-5-(2-hydroxyprop-2-yl)-phenyl)-[5-(4-methyl-piperazin-1-ylmethyl)-1,3-dihydro-isoindol-2-yl]-methanone (X=OH in the formula). The impurities can be removed by the following method.

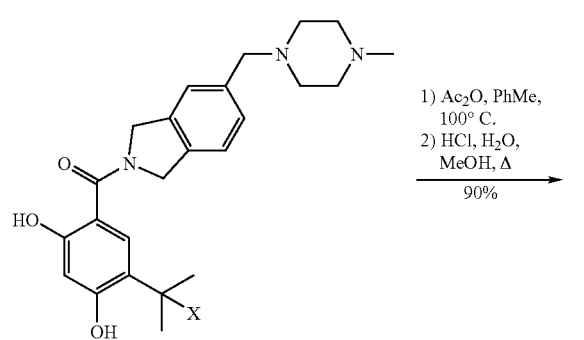

X = H and OH

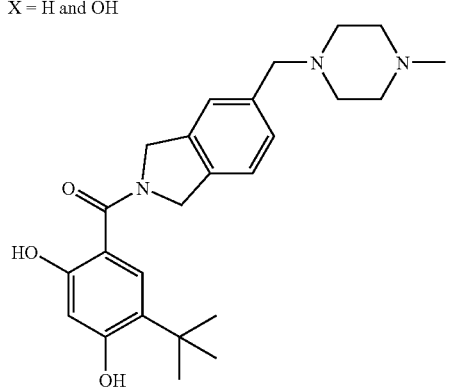

Acetic anhydride (1.04 ml, 11.0 mmol) was added to a stirred suspension of impure 2-(2,4-dihydroxy-5-isopropyl-benzoyl)-5-(4-methylpiperazin-1-ylmethyl)-1,3-dihydroisoindole (2.05 g, 5.0 mmol) in toluene (20 ml) and the resulting mixture was stirred and held at 100° C. for 16 hours. Upon cooling to room temperature the solvent was removed in vacuo to afford a brown oil which was dissolved in methanol (20 ml). Concentrated hydrochloric acid (1 ml) was added and the mixture was stirred and held at reflux for 5 hours. Upon cooling to room temperature, the organic solvent and volatile material were removed in vacuo and the aqueous residue was diluted with water (25 ml) and basified to pH 8 with vigourous stirring by the careful addition of 10% aqueous potassium carbonate solution. 50% Ethyl acetate in heptane (50 ml) was added and the mixture was stirred vigourously at room temperature for 16 hours. The solid material was collected by suction filtration, rinsed with 50% ethyl acetate in heptane (50 ml), sucked dry under reduced pressure and dried overnight in a vacuum oven at 50° C. to afford 2-(2,4-dihydroxy-5-isopropylbenzoyl)-5-(4-methylpiperazin-1-ylmethyl)-1,3-dihydroisoindole (1.85 g, 90%) as an off-white solid. $^1$H NMR (DMSO-$d_6$) 10.07 (1H, br s), 9.60 (1H, br s), 7.24 (3H, m), 7.06 (1H, s), 6.40 (1H, s), 4.76 (4H, br s), 3.44 (2H, s), 3.10 (1H, m), 2.32 (8H, m), 2.14 (3H, s), 1.15 (6H, d). MS: [M+H]$^+$ 410.

Example 81

(2,4-Dihydroxy-5-isopropyl-phenyl)-[5-(4-methyl-piperazin-1-ylmethyl)-1,3-dihydro-isoindol-2-yl]-methanone Example 81 describes a synthetic route containing essentially the same process steps as the route described in Example 80 but wherein the process conditions are more suited to larger scale reactions.

Step 1

4-Acetoxy-2-hydroxy-benzoic acid methyl ester

To a heated solution (50° C.) of resorcinol methyl ester (16.5 Kg, 98.1 mol) and N,N-dimethyl-4-aminopyridine (89.1 g, 0.73 mol, 7.4 mol %) in toluene (66 L) was slowly added (over 2 h) acetic anhydride (9.9 L, 104.9 mol). The solution was heated to 50° C. for a further 1.5 h and then the solvent was removed by evaporation at 50° C. to a small volume and the residue was azeotroped once with toluene. To the residual oil was immediately added toluene (33 L) whilst still warm and the solution used for Step 2 without further purification.

Step 2

5-Acetyl-2,4-dihydroxy-benzoic acid methyl ester

The toluene solution from Step 1 was cooled in an ice bath under $N_2$ and triflic acid (9.44 L) added slowly over 3 h. On stirring a fine white solid was formed which dissolved on warming to RT over 20 h and then stirring at RT for 37 h to give a yellow solution. To the solution was added acetyl chloride (726 mL) and the solution stirred at RT for a further 1 h. This solution was cannulated into a stirred cooled (0° C.) solution of EtOAc (217.8 L) and NaOAc.3H$_2$O (14.52 Kg) dissolved in water (145 L). The organic phase was washed with saturated brine (twice, 72.6 L), and was evaporated to 5.5 Kg. Toluene:Isopropanol (2:3) was added and the crystalline solid removed by filtration and dried to give 12.6 Kg (61% over 2 steps), mp 124-126° C.

Step 3

5-Acetyl-2,4-bis-benzyloxy-benzoic acid methyl ester

To a stirred solution of benzyl bromide (16.14 L, 136 mol) and anhydrous potassium carbonate (20.25 Kg, 147.6 mol) in acetonitrile (184.5 L) was added methyl 5-acetyl-2,4-dihydroxybenzoate (14 Kg, 66.6 mol, step 2) in 6 portions over 5 h. The mixture was stirred and held at reflux for 20 hours, cooled to room temperature the mixture was poured onto water (682 L) and stirred vigorously for 2 hours. The solids were collected by centrifugation and dried under reduced pressure to constant mass in a vacuum oven at 60° C. overnight to afford methyl 5-acetyl-2,4-bis-benzyloxybenzoate (23.5 Kg, 97.3%) as a cream solid mp 114-115° C.

Step 4

2,4-Bis-benzyloxy-5-isopropenyl-benzoic acid methyl ester

A solution of potassium tert-butoxide (6.72 Kg, 60.1 mol) in anhydrous THF (60 L) was added over 3 h to a stirred suspension of methyltriphenylphosphonium bromide (21.43 Kg, 60.1 mol) and methyl 5-acetyl-2,4-bis-benzyloxybenzoate (21.3 Kg, 54.6 mol, step 3) in anhydrous tetrahydrofuran (213 L) at 15° C. The mixture was stirred at 15° C. for 70 mins and the warmed to 20° C. over 60 mins. Methanol (27.3 L) was added to quench excess phosphorus ylide and the solvent was concentrated in vacuo followed by addition of EtOAc and water. The organic phase was treated with activated charcoal, filtered and evaporated to a small volume. The residue was crystallised from boiling MeOH and the solids were collected by suction filtration, washed with methanol and dried under reduced pressure to afford methyl 2,4-bis-benzyloxy-5-isopropenyl-benzoate 18.1 Kg (85%) as pale yellow needles mp 92-94° C. (99.6% pure by hplc).

Step 5

2,4-Bis-benzyloxy-5-isopropenyl-benzoic acid

Potassium hydroxide (0.527 Kg, 9.4 mol) was added to a stirred suspension of methyl 2,4-bis-benzyloxy-5-isopropenyl-benzoate (3.1 Kg, 8 mol, step 4) in methanol (18.6 L) and water (12.4 L) and the mixture was stirred and held at reflux for 3 hours. The methanol was removed under partial vacuum from the vessel, and to the remaining solution was added toluene (62 L). The solution was heated to 40° C. and to the mixture was added conc HCl (1.36 L). The biphasic mixture is heated to 50° C. and the phases separated. The organic phase was washed with water (31 L) at 50° C. and the organic phase was evaporated under reduced pressure to give 2,4-bis-benzyloxy-5-isopropenyl-benzoic acid 2.851 Kg (95% yield) as a colourless solid.

Step 6

Di-prop-2-ynyl-carbamic acid benzyl ester

To a cooled (5° C.) solution of $K_2CO_3$ (4 Kg, 29.0 mol) in water (17.5 L) and toluene (12.5 L) was added dipropargylamine (2.50 Kg, 26.88 mol). Benzyloxychloroformate (4.8 Kg, 28.14 mol) was added at a rate such that T<10° C. The solution was stirred at 5° C. for 10 mins and then allowed to warm to RT. The aqueous phase was separated and the organic phase was washed with 0.2M HCl (12.5 L), sat $NaHCO_3$ (13.5 L) and brine (17 L) and the resultant solution used in step 7 (assayed to contain 6.23 Kg, 102% based on an evaporated portion).

Step 7

5-Hydroxymethyl-1,3-dihydro-isoindole-2-carboxylic acid benzyl ester

A solution of propargyl alcohol (2.11 Kg, 37.7 mol) in toluene (32.48 L) was degassed and heated to 55° C. The solution of di-prop-2-ynyl-carbamic acid benzyl ester (4.06 Kg, 17.86 mol, step 6) in toluene and Wilkinsons catalyst (0.162 Kg) were added in 10 equal portions such that temperature <65° C. (the exotherm was allowed to subside before the next addition was made). The solution was then stirred at 55° C. for 1 h and then cooled to 20° C. DCM (8.12 L) was added and the mixture was concentrated to a small volume. Toluene (8 L) was added and the solution evaporated to constant weight giving the title compound 5.72 Kg (113%).

Step 8

5-Methanesulfonyloxymethyl-1,3-dihydro-isoindole-2-carboxylic acid benzyl ester

To a cooled solution (5° C.) of 5-hydroxymethyl-1,3-dihydro-isoindole-2-carboxylic acid benzyl ester (11 Kg, 38.8 mol, step 7) and $Et_3N$ (7.04 L, 50.6 mol) in DCM (55 L) was added methanesulphonyl chloride (2.97 L, 38.4 mol) so that the internal temp <10° C. After stirring for 0.5 h at 5° C. the solution was used below in step 9.

Step 9

5-(4-Methyl-piperazin-1-ylmethyl)-1,3-dihydro-isoindole-2-carboxylic acid benzyl ester dihydrochloride salt

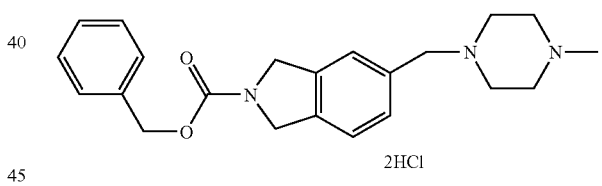

2HCl

The solid from Step 8 (assume 0.232 mol) was dissolved in acetone (700 mL) and this solution was added over 45 mins to a cooled (internal temp 15-17° C.) suspension of $K_2CO_3$ (48 g) and N-methylpiperazine (50 mL, 0.45 mol) in acetone (330 mL). The suspension was stirred at 15° C. for 3 h (complete removal of starting material by tlc) when the solution was evaporated to a small volume and the residue partition between EtOAc (1000 mL) and a mixture of water (500 mL) and saturated brine (50 mL). The organic phase was washed with a mixture of water (500 mL) and saturated brine (150 mL) and finally washed with saturated brine (300 mL). The solution was dried ($MgSO_4$) and filtered and to this solution was added 1M-HCl in MeOH (430 mL, 0.43 mol). The suspension was cooled (0° C. for 30 mins) and the solid removed by filtration which was washed with EtOAc and then heptane on the sinter and the solid dried (oil-pump, RT 72 h) to give crop 1 of the title compound 66.34 g (65%) as a colourless solid. 1H NMR (400 MHz, Me-d3-OD): 7.64-7.51 (m, 2H), 7.51-7.29 (m, 6H), 5.23 (s, 2H), 4.79 (dd, J=16.2, 6.1 Hz, 4H), 4.49 (s, 2H), 3.66 (s, 8H), 3.03 (s, 3H).

Step 9

5-(4-Methyl-piperazin-1-ylmethyl)-1,3-dihydro-isoindole-2-carboxylic acid benzyl ester DCM (33 L) and N-methylpiperazine (21.45 L, 193.4 mol) were stirred at 25° C. and the solution from step 8 added over a minimum of 30 mins such that temperature 20-30° C. After stirring the solution for a further 30 mins water (55 L) was added and the organic phase was washed with water (2×55 L). The product was extracted into 0.8M HCl (66 L) and the layers separated. The aqueous phase was washed with DCM (55 L) and then basified with 2M NaOH to pH 10-11 and the product was extracted into EtOAc (2×55 L). The combined organic phase were filtered to remove solids and the evaporated followed by azeotroping with toluene and drying to constant weight to give the title compound, 6.63 kg (47% yield, 98% pure by hplc).

Step 10

5-(4-Methyl-piperazin-1-ylmethyl)-2,3-dihydro-1H-isoindole

To a degassed solution of 5-(4-Methyl-piperazin-1-ylmethyl)-1,3-dihydro-isoindole-2-carboxylic acid benzyl ester (Step 9, 1.3 Kg, 3.55 mol) dissolved in EtOH (13 L) was added 10% Pd/C (0.065 Kg). Hydrogen was passed through the mixture at 30° C. for 4 h or until complete by NMR. The solution was then stirred for 1 h under an atmosphere of $N_2$ and then filtered to remove the catalyst through a GF/F filter followed by filtration through a Cuno filter. The filtrate was evaporated to a small volume, azeotroped with toluene (3.9 L) and dried to constant weight yielding the title compound as a red/black oily solid (0.78 Kg) which was stored under nitrogen until required.

Step 11

(2,4-Bis-benzyloxy-5-isopropenyl-phenyl)-[5-(4-methyl-piperazin-1-ylmethyl)-1,3-dihydro-isoindol-2-yl]-methanone 1,1'-Carbonyldiimidazole (4.82 Kg, 29.8 mol) was added to a solution of 2,4-bis-benzyloxy-5-isopropenyl-benzoic acid (10.58 Kg, 28.3 mol, step 5) in DMF (21.2 L) at 25° C. After 20 mins at 25° C. a solution of 5-(4-Methyl-piperazin-1-ylmethyl)-2,3-dihydro-1H-isoindole (7.2 Kg, 31.1 mol, step 10) in DMF (7.2 L) maintaining a temperature below 35° C. and the solution stirred at 25° C. for a minimum of 12 h. The solid which had formed was removed by filtration, washed with isopropyl acetate (2×21.6 L) and dried at 35° C. to constant weight to give the title compound 8.7 Kg (77% yield, purity by hplc 97.5%).

Step 12

(2,4-Dihydroxy-5-isopropyl-phenyl)-[5-(4-methyl-piperazin-1-ylmethyl)-1,3-dihydro-isoindol-2-yl]-methanone The product from Step 11 (0.9 Kg, 1.53 mol) was dissolved in isopropanol (6.8 L) and water (1.04 L) and after purging with $N_2$ 10% Pd/C (90 g) and $K_2CO_3$ (0.212 Kg, 1.53 mol) were added and the suspension was hydrogenated for 60 to 70 mins under an 3 Barr pressure of $H_2$. The solution was diluted with water (0.5 L) and filtered. To the filtrate was added aqueous HCl (30% hydrochloric acid, 0.85 Kg diluted with water 5.42 Kg) and the solution was concentrated at 60° C. under vacuum (removing 10 L isopropanol). Water (0.45 L) was added to the solution and concentration continued (until a further 10 L isopropanol had been removed). The aqueous phase was washed with EtOAc (4.61 L), diluted with acetonitrile (4.06 L) and neutralised to pH 7.5-8.5 by addition of conc ammonia solution (0.35 Kg). The suspension was stirred for 2.5 h and then the solid was removed by filtration. The residue was washed with acetonitrile (2×0.8 L) and dried at 40° C. to constant weight to give the title compound 588 g (94% yield).

Example 82

Alternative Synthesis of 5-(4-Methyl-piperazin-1-ylmethyl)-2,3-dihydro-1H-isoindole

82A. Synthesis of 1-methyl-4-prop-2-ynyl-piperazine

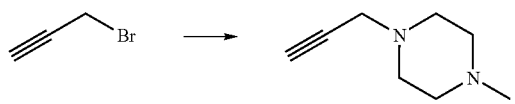

To 1-methylpiperazine (37.7 ml, 337 mmol) and $K_2CO_3$ (46.6 g, 337 mmol) in acetone (380 ml) was added propargyl bromide (25 ml, 225 mmol, 80% in toluene) in acetone (70 ml) dropwise at 0° C. under $N_2$. The internal temperature of the reaction was kept <10° C. The reaction was stirred at room temperature for 3 hours. The reaction was filtered, and the salts were washed with small portions of acetone (×2). The filtrates were combined evaporated to concentration (gently). To the residue was added water and the product was extracted with DCM (×3). The combined organic layers were washed with brine and dried over $MgSO_4$. The product was filtered and evaporated to dryness to yield 1-methyl-4-prop-2-ynyl-piperazine as a yellow oil.

82B. Synthesis of 5-(4-Methyl-piperazin-1-ylmethyl)-1,3-dihydro-isoindole-2-carboxylic acid tert-butyl ester

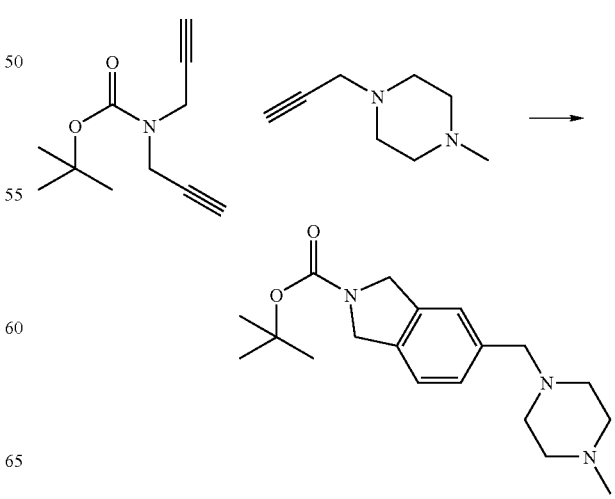

A solution of N-boc-dipropargylamine (36.3 ml, 226 mmol, 86% pure) in EtOAc (30 ml) was made up and degassed by bubbling through N₂, in a separating funnel. Tris(triphenylphosphine)rhodium(I) chloride (1.39 g, 1.50 mmol, 1 mol %) was added to pre-degassed EtOAc (15 ml) in a second separating funnel. (NB CpRu(COD)Cl) can also be used as an alternative catalyst).

In the main reactor flask, 1-propargyl-4-methylpiperazine (32.3 ml, 150 mmol, 90% pure) was diluted with EtOAc (75 ml) and was degassed by bubbling N₂ through the mixture The mixture was cooled in a ice-water bath and then the tris(triphenylphosphine)rhodium(I) chloride (1.39 g, 1 mol %) in EtOAc was added. Slow addition of N-boc-dipropargylamine/EtOAc was undertaken to yield a mild exotherm. The internal temperature rose to 25° C. and remained at this temperature. After addition was approximately one third complete (~45 minutes), the exotherm tailed off (despite the continual slow addition of N-boc-dipropargylamine/EtOAc). Another portion of tris(triphenylphosphine)rhodium(I) chloride catalyst (1.39 g, 1 mol %) in EtOAc (15 ml, pre-degassed) was made up and added very slowly to the reaction. After a couple of minutes a new exotherm started and grew to 30° C. The reaction temperature was cooled gently by the addition of a small amount of ice to the water bath. Once the exotherm began to subside, slow addition of N-boc-dipropargylamine/EtOAc was continued. The entire addition was carried out over a 2 hour period. The reaction mixture was then left at room temperature overnight before diluting with EtOAc and washing with NH₄Cl (x2) (aqueous, saturated) to remove excess 1-propargyl-4-methylpiperazine. The mixture was diluted with a small amount of water to dissolve the salts. The organic layer was washed with water, brine and dried over MgSO₄. The product was filtered and evaporated to dryness to leave a brown oil.

To the oil residue obtained was added n-heptane. The oil/heptane was left to stand (~10 minutes) until a red precipitate formed. The precipitate was filtered and washed with fresh n-heptane (x2). The filtrates were dried to yield the product as a red oil.

The desired product was further purified by forming the toluenesulphonic acid (TsOH) salt. Thus, the crude product was taken up in MeOH (20 ml) and the TsOH.H₂O (1 eq to estimated purity by NMR) was added. The solution was evaporated to dryness, and then dissolved in toluene (x1) and re-evaporated. The resulting product was taken up in ether. After a few minutes, a precipitate and solution formed. The precipitate was filtered and washed with more ether (x2) until the filtrate was colourless. The yellow solid was dried to yield the product as the TsOH salt. MS: [M+H]⁺ 332.

82C. Synthesis of 5-(4-Methyl-piperazin-1-ylmethyl)-2,3-dihydro-1H-isoindole

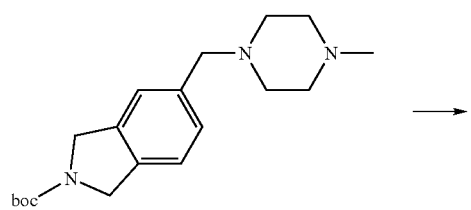

→

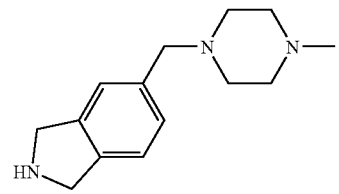

The isoindoline tosylate salt was taken up in DCM (0.3 M) and TFA (12 eq.) added slowly at 0° C. The reaction was stirred overnight at room temperature. The reaction was evaporated to dryness and then with toluene/MeOH (x3) to yield the product as a mixture of acid addition salts. MS: [M+H]⁺ 232.

The compound of Example 82C can be used in the method of Example 80 Step 12.

Example 83

Alternative Synthesis of 5-hydroxymethyl-1,3-dihydro-isoindole-2-carboxylic acid benzyl ester 83A. Methyl 2-benzyl-2,3-dihydro-1H-isoindole-5-carboxylate

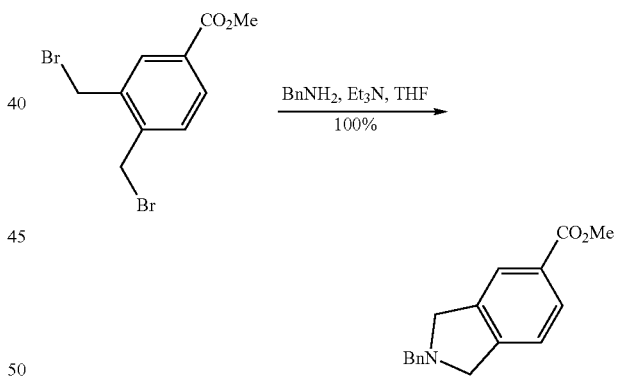

Benzylamine (3.21 g, 30.0 mmol) in anhydrous tetrahydrofuran (25 ml) was added to a stirred mixture of methyl 3,4-bis-(bromomethyl)benzoate (9.66 g, 30.0 mmol) (obtained from Fluorochem) and triethylamine (9 ml, 64.7 mmol) in anhydrous tetrahydrofuran (50 ml) and the resulting mixture was stirred at room temperature for 3 hours. The solvent was removed in vacuo at 40° C. and the residue partitioned between ethyl acetate (100 ml) and water (100 ml). The organic layer was washed with a further portion of water (100 ml), separated and the solvent removed in vacuo at 40° C. to afford methyl 2-benzyl-2,3-dihydro-1H-isoindole-5-carboxylate as a pale orange solid that was used immediately without further purification as described below. ¹H

83B. (2-Benzyl-2,3-dihydro-1H-isoindol-5-yl)-methanol

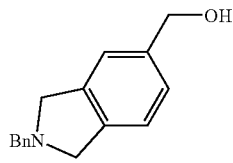

Methyl 2-benzyl-2,3-dihydro-1H-isoindole-5-carboxylate (from above) was dissolved in anhydrous tetrahydrofuran (75 ml) and added dropwise over 15 minutes to a rapidly stirred suspension of lithium aluminum hydride (1.71 g, 45.0 mmol) in anhydrous tetrahydrofuran (75 ml). The mixture was stirred at room temperature for 2 hours whereupon excess lithium aluminum hydride was destroyed by the slow dropwise addition of 1M sodium sulphate solution (12 ml). The solids were removed by filtration, rinsed with ethyl acetate (2×50 ml) and sucked dry. The solvent was removed in vacuo to afford (2-benzyl-2,3-dihydro-1H-isoindol-5-yl)-methanol (7.15 g, 99%) as a tan solid. $^1$H NMR (DMSO-$d_6$) 7.40-7.30 (4H, m), 7.28 (1H, m), 7.17-7.10 (3H, m), 5.10 (1H, t), 4.47 (2H, d), 3.85 (2H, s), 3.82 (2H, s), 3.80 (2H, s). MS: $[M+H]^+$ 240.

83C. (2,3-Dihydro-1H-isoindol-5-yl)-methanol

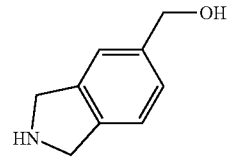

10% Palladium on activated carbon (200 mg) was added to a solution of (2-benzyl-2,3-dihydro-1H-isoindol-5-yl)-methanol (2.39 g, 10.0 mmol) in ethanol (60 ml) and the resulting mixture was placed in a Parr apparatus, heated to 50° C. and shaken under a hydrogen atmosphere at 60 psi for 30 hours. Upon cooling to room temperature the mixture was filtered under gravity, the solids were rinsed with ethanol (2×10 ml) and the solvent removed in vacuo to afford (2,3-dihydro-1H-isoindol-5-yl)-methanol (1.49 g, 100%) as an off-white solid. $^1$H NMR (DMSO-$d_6$) 7.20 (1H, s), 7.18 (1H, d), 7.12 (1H, d), 5.10 (1H, br s), 4.46 (2H, s), 4.05 (4H, s). MS: $[M+H]^+$ 150.

83D. 5-Hydroxymethyl-1,3-dihydro-isoindole-2-carboxylic acid benzyl ester

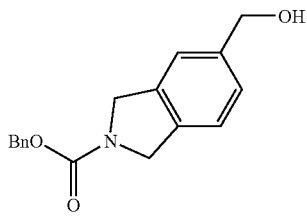 [SMILES: O=C(OCc1ccccc1)N1Cc2ccc(CO)cc2C1]

A mixture of (2,3-dihydro-1H-isoindol-5-yl)-methanol (1.34 g, 9.0 mmol) in anhydrous tetrahydrofuran (50 ml) was warmed gently to aid dissolution and allowed to cool to room temperature. Triethylamine (1.5 ml, 10.8 mmol) was added and the stirred mixture was treated dropwise with benzyl chloroformate (1.35 ml, 9.5 mmol) and stirred at room temperature for 3 hours. The solvent was removed in vacuo and the residue partitioned between ethyl acetate (30 ml) and 2M hydrochloric acid (30 ml). The organic layer was washed with water (30 ml), separated and the solvent removed in vacuo to afford a pink oil that solidified upon standing. The solids were triturated with 10% ethyl acetate in hexane (10 ml), filtered, rinsed with heptane (10 ml) and sucked dry to afford the title compound (2.5 g, 98%) as a pale pink solid. $^1$H NMR (DMSO-$d_6$) 7.45-7.21 (8H, m), 5.20 (1H, t), 5.17 (2H, s), 4.71 (2H, br s), 4.64 (2H, br s), 4.50 (2H, d). MS: $[M+H]^+$ 284.

The title compound can be used in Step 9 of Example 80.

Example 84

Crystal Structure Studies

The compound of formula (1) has the structure:

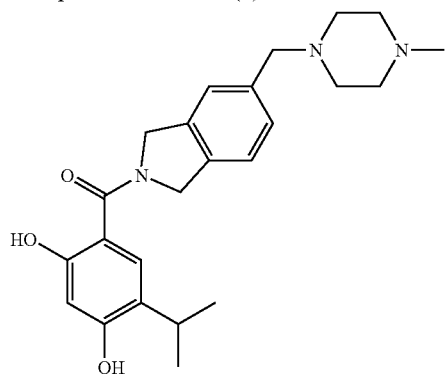

(1)

The compound of formula (1) and its salts exist in a number of different crystalline forms. These have been identified and characterised using the methods described below.

General Methods

Single Crystal Diffraction Methodology

Crystallographic data were collected at room temperature (20° C.) using synchrotron radiation ($\lambda$=0.775 Å) from ESRF ID23.1 beamline equipped with $\phi$ goniometer and an ADSC Quantum 315 CCD detector. Images were collected in two $\phi$ scans with $\phi$=0-180° and $\Delta\phi$=1°, one with high radiation dose and one with low dose. Detector to crystal distance was 110 mm. Data collection was controlled by ProDC software and images were processed and scaled by Dtrek.

The crystal structures were solved using direct methods implemented in SHELXS-97 and refined by SHELXL-97. Hydrogen atoms were generated on geometrical grounds while the location of heteroatom bound hydrogen atoms was confirmed by inspection of Fo-Fc difference maps. The positional and thermal parameters of hydrogen atoms were constricted to ride on corresponding non-hydrogen atoms. The thermal motion of non-hydrogen atoms was modeled by anisotropic thermal factors.

Powder Diffraction Methodology

Samples for X-ray powder diffraction (XRPD) data collection were gently ground by marble mortar and loaded into a crystallographic capillary (from Hampton Research, Quartz or Glass Type 10, 0.4 or 0.7 mm diameter). Diffraction patterns were collected at room temperature using CuK$\alpha$ radiation ($\lambda$=1.5418 Å) from a Rigaku rotating anode RU3HR, Osmic blue confocal optics, ¼ c goniometer and a Rigaku HTC image plate detector. 2D Images were collected while spinning $\phi$ axis with a detector to crystal distance of 250 mm. Data collection was controlled by CrystalClear software and 2D images were converted to 1D plot (2$\theta$ vs. Intensity) by Datasqueeze (intensity averaged over the azimuthal angle 0<χ<360° for 2θ range 3-30° in 0.02° steps). In house program AstexXRP was used for manipulation and visualisation of 1D XRPD patterns.

Determination of Salt Stoichiometry by Titration Experiments

In the following examples, where they relate to salts and the stoichiometry of the salt is given, the stoichiometry was determined using the following titration method.

A solution (KCl/HCl solution) of 150 mM KCl and 20 mM HCl was freshly prepared for each batch of titration experiments. An aliquot of 1 ml of the solution was titrated and the potentiometric titration curve thus produced was used as the control curve. All titrations were performed at 25° C. and with 300 mM KOH in 2 μl steps using a Mettler Toledo MP220 pH meter. Electrode potential readings for 4 standard buffers were recorded before and after daily batch of measurement. Samples of Compound (1) salts of (1-3 mg) were dissolved in 1 ml of KCl/HCl solution and titrated with vigorous stirring using a small magnetic stirrer. The recorded electrode potentials were converted into pH values using a calibration curve from the 4 standard buffers. Sample and control titration data were processed to produce a Bjerrum plot in the pH range 2-12. The Bjerrum plot calculation and analysis method is described in the review "Physicochemical Profiling (Solubility, Permeability and Charge State)", A. Avdeef (Current Topics in Medicinal Chemistry 2001, p 277-351).

The stoichiometry of the Compound (1) salts was deduced from the starting nH (number of protons at pH=2), (i.e. free base starts with −2 protons, mono-salt with −1 protons (Compound $(1)^+$ acid$^-$)), while double salts (Compound $(1)^{2+}$ acid$^{2-}$ or Compound $(1)^{2+}$ 2* acid$^-$) start at nH=0.

Compound (1) L-Lactate 1:1 Salt Crystal Forms (84A) Compound (1) L-Lactate—Form FL1

The L-Lactate salt form FL1 was prepared as described in Example 2 above.

Form FL1 is stable in air and at 40° C. and 75% RH for at least one month. The XRPD pattern for form FL1 is shown in FIG. 4 and the main peaks are listed in Table EX84A.

TABLE EX84A

Main XRPD peaks for Compound (1) Lactate - Form FL1

| 2θ/° | d/Å | I/% |
|---|---|---|
| 6.18 | 14.30 | 15 |
| 6.53 | 13.52 | 50 |
| 8.39 | 10.54 | 19 |
| 11.08 | 7.98 | 7 |
| 13.10 | 6.75 | 85 |
| 14.13 | 6.26 | 33 |
| 14.40 | 6.15 | 23 |
| 15.21 | 5.82 | 4 |
| 16.21 | 5.46 | 6 |
| 16.81 | 5.27 | 100 |
| 17.22 | 5.15 | 45 |
| 18.65 | 4.75 | 23 |
| 19.52 | 4.54 | 33 |
| 19.82 | 4.48 | 34 |
| 20.49 | 4.33 | 7 |
| 20.76 | 4.27 | 13 |
| 21.13 | 4.20 | 17 |
| 22.02 | 4.03 | 12 |
| 22.33 | 3.98 | 44 |
| 22.84 | 3.89 | 40 |
| 23.09 | 3.85 | 25 |
| 23.94 | 3.71 | 14 |
| 25.19 | 3.53 | 7 |

TABLE EX84A-continued

Main XRPD peaks for Compound (1) Lactate - Form FL1

| 2θ/° | d/Å | I/% |
|---|---|---|
| 26.41 | 3.37 | 14 |
| 26.95 | 3.31 | 5 |
| 27.81 | 3.21 | 14 |

(84B) Compound (1) L-Lactate—Form FL2

Form FL2 was observed in precipitation experiments of methanol solutions of form FL1. Single crystal X-ray analysis showed that form FL2 is hydrated. It is nominally a trihydrate because there are 3 crystal water positions in the asymmetric unit, but they are not 100% occupied at room temperature and laboratory humidity. A saturated solution of form FL1 in methanol:water 9:1 was prepared at room temperature. Slow precipitation with approximately 4 volumes of acetone gave form FL2 which is stable in air. The XRPD pattern for form FL2 is shown in FIG. 5 and the main peaks are listed in Table EX84B(i) below. A crystal packing diagram is shown in FIG. 6 and the atom coordinates are listed in Table EX84B(ii) below.

TABLE EX84B(i)

Main XRPD peaks for Compound (1) Lactate salt - form FL2

| 2θ/° | d/Å | I/% |
|---|---|---|
| 8.03 | 11.00 | 29 |
| 10.71 | 8.26 | 53 |
| 11.98 | 7.38 | 90 |
| 13.13 | 6.74 | 49 |
| 15.39 | 5.75 | 29 |
| 16.09 | 5.50 | 32 |
| 16.61 | 5.33 | 42 |
| 17.26 | 5.13 | 37 |
| 18.17 | 4.88 | 20 |
| 18.82 | 4.71 | 56 |
| 20.40 | 4.35 | 40 |
| 21.01 | 4.22 | 49 |
| 21.53 | 4.12 | 27 |
| 22.34 | 3.98 | 100 |
| 22.56 | 3.94 | 73 |
| 23.71 | 3.75 | 82 |
| 24.30 | 3.66 | 8 |
| 24.65 | 3.61 | 12 |
| 26.56 | 3.35 | 13 |
| 27.70 | 3.22 | 21 |
| 28.29 | 3.15 | 16 |

TABLE EX84B(ii)

Unit cell parameters and coordinates in cif format for crystal structure of Compound (1) Lactate salt - form FL2 space group: P2$_1$
unit cell at 293K with a, b, c & β having 5% s.u.:
a = 5.8
b = 16.6
c = 14.9
beta = 98
alpha = gamma = 90
Coordinates in cif format:
loop_
_atom_site_label
_atom_site_type_symbol
_atom_site_fract_x
_atom_site_fract_y
_atom_site_fract_z

TABLE EX84B(ii)-continued

Unit cell parameters and coordinates in cif format for crystal structure of Compound (1) Lactate salt - form FL2

_atom_site_U_iso_or_equiv
_atom_site_adp_type
_atom_site_occupancy
_atom_site_symmetry_multiplicity
_atom_site_calc_flag
_atom_site_refinement_flags
_atom_site_disorder_assembly
_atom_site_disorder_group
C1 C −0.643(2) 1.1037(6) 0.6763(7) 0.097(3) Uani 1 1 d . . .
H1A H −0.6995 1.0577 0.6395 0.117 Uiso 1 1 calc . . .
H1B H −0.5231 1.1308 0.6484 0.117 Uiso 1 1 calc . . .
N2 N −0.5563(16) 1.0791(5) 0.7694(6) 0.096(2) Uani 1 1 d . . .
C3 C −0.692(2) 1.1148(8) 0.8352(8) 0.124(4) Uani 1 1 d . . .
H3A H −0.7713 1.0734 0.8651 0.148 Uiso 1 1 calc . . .
H3B H −0.5925 1.1454 0.8805 0.148 Uiso 1 1 calc . . .
C4 C −0.8553(19) 1.1667(7) 0.7825(7) 0.094(3) Uani 1 1 d . . .
C5 C −0.8393(19) 1.1609(6) 0.6900(7) 0.092(3) Uani 1 1 d . . .
C6 C −1.036(2) 1.2141(8) 0.8083(8) 0.110(3) Uani 1 1 d . . .
H6 H −1.0636 1.2139 0.8682 0.132 Uiso 1 1 calc . . .
C7 C −1.172(2) 1.2611(8) 0.7456(8) 0.105(3) Uani 1 1 d . . .
C8 C −1.145(2) 1.2560(8) 0.6564(9) 0.111(3) Uani 1 1 d . . .
H8 H −1.2387 1.2867 0.6138 0.133 Uiso 1 1 calc . . .
C9 C −0.979(2) 1.2053(9) 0.6287(7) 0.109(3) Uani 1 1 d . . .
H9 H −0.9640 1.2017 0.5677 0.130 Uiso 1 1 calc . . .
C10 C −1.3561(18) 1.3173(8) 0.7739(9) 0.106(3) Uani 1 1 d . . .
H10A H −1.4455 1.3402 0.7202 0.127 Uiso 1 1 calc . . .
H10B H −1.4617 1.2864 0.8055 0.127 Uiso 1 1 calc . . .
N11 N −1.2550(14) 1.3836(6) 0.8332(6) 0.096(2) Uani 1 1 d . . .
C12 C −1.1136(17) 1.4353(6) 0.7839(7) 0.091(3) Uani 1 1 d . . .
H12A H −1.2098 1.4591 0.7324 0.109 Uiso 1 1 calc . . .
H12B H −0.9935 1.4035 0.7615 0.109 Uiso 1 1 calc . . .
C13 C −1.0015(17) 1.5021(7) 0.8462(8) 0.100(3) Uani 1 1 d . . .
H13A H −0.8991 1.4783 0.8961 0.121 Uiso 1 1 calc . . .
H13B H −0.9092 1.5368 0.8128 0.121 Uiso 1 1 calc . . .
N14 N −1.1853(15) 1.5509(5) 0.8822(6) 0.094(2) Uani 1 1 d . . .
H14 H −1.2741 1.5755 0.8352 0.113 Uiso 1 1 calc . . .
C15 C −1.3350(18) 1.4966(7) 0.9279(7) 0.095(3) Uani 1 1 d . . .
H15A H −1.4599 1.5276 0.9479 0.114 Uiso 1 1 calc . . .
H15B H −1.2441 1.4730 0.9808 0.114 Uiso 1 1 calc . . .
C16 C −1.4358(17) 1.4308(7) 0.8658(8) 0.098(3) Uani 1 1 d . . .
H16A H −1.5310 1.3959 0.8977 0.117 Uiso 1 1 calc . . .
H16B H −1.5346 1.4542 0.8148 0.117 Uiso 1 1 calc . . .
C17 C −1.068(2) 1.6140(9) 0.9439(9) 0.119(4) Uani 1 1 d . . .
H17A H −1.1835 1.6447 0.9694 0.178 Uiso 1 1 calc . . .
H17B H −0.9807 1.6492 0.9103 0.178 Uiso 1 1 calc . . .
H17C H −0.9658 1.5886 0.9916 0.178 Uiso 1 1 calc . . .
C18 C −0.382(2) 1.0287(9) 0.7999(8) 0.113(4) Uani 1 1 d . . .
C19 O −0.345(2) 1.0216(8) 0.8837(6) 0.156(4) Uani 1 1 d . . .
C20 C −0.228(2) 0.9847(6) 0.7418(7) 0.096(3) Uani 1 1 d . . .
C21 C −0.069(3) 0.9286(9) 0.7863(9) 0.119(4) Uani 1 1 d . . .
C22 C 0.064(2) 0.8867(9) 0.7367(9) 0.114(4) Uani 1 1 d . . .
H22 H 0.1812 0.8547 0.7669 0.137 Uiso 1 1 calc . . .
C23 C 0.038(2) 0.8879(7) 0.6447(8) 0.097(3) Uani 1 1 d . . .
C24 C −0.1201(18) 0.9425(7) 0.5972(8) 0.096(3) Uani 1 1 d . B .
C25 C −0.253(2) 0.9882(7) 0.6463(8) 0.100(3) Uani 1 1 d . . .
H25 H −0.3632 1.0228 0.6160 0.120 Uiso 1 1 calc . . .
O26 O −0.036(2) 0.9229(9) 0.8775(6) 0.169(5) Uani 1 1 d . . .
H26 H −0.1427 0.9456 0.8980 0.253 Uiso 1 1 calc R . .
O27 O 0.1658(15) 0.8404(5) 0.5948(6) 0.118(3) Uani 1 1 d . . .
H27 H 0.2091 0.7999 0.6238 0.176 Uiso 1 1 calc R . .
C28 C −0.141(4) 0.9478(11) 0.4948(10) 0.138(6) Uani 1 1 d . . .
H28 H −0.0894 0.8953 0.4750 0.166 Uiso 1 1 calc . A 1
C29 C −0.029(11) 1.004(4) 0.449(3) 0.24(3) Uani 0.58(6) 1 d P B 1
H29A H −0.0741 0.9976 0.3847 0.363 Uiso 0.58 1 calc P B 1
H29B H 0.1361 0.9972 0.4628 0.363 Uiso 0.58 1 calc P B 1
H29C H −0.0703 1.0575 0.4662 0.363 Uiso 0.58 1 calc P B 1
C30 C −0.417(7) 0.950(3) 0.4621(19) 0.159(19) Uani 0.58(6) 1 d P B 1
H30A H −0.4911 0.9083 0.4918 0.239 Uiso 0.58 1 calc P B 1
H30B H −0.4462 0.9424 0.3978 0.239 Uiso 0.58 1 calc P B 1
H30C H −0.4773 1.0016 0.4772 0.239 Uiso 0.58 1 calc P B 1
C29 C −0.156(11) 1.040(2) 0.465(2) 0.14(2) Uani 0.42(6) 1 d P B 2
H29D H −0.0071 1.0655 0.4814 0.215 Uiso 0.42 1 calc P B 2
H29E H −0.2703 1.0675 0.4943 0.215 Uiso 0.42 1 calc P B 2
H29F H −0.1983 1.0438 0.4003 0.215 Uiso 0.42 1 calc P B 2
C30 C −0.295(12) 0.897(4) 0.446(2) 0.150(19) Uani 0.42(6) 1 d P B 2
H30D H −0.3403 0.9185 0.3870 0.224 Uiso 0.42 1 calc P B 2
H30E H −0.4300 0.8910 0.4766 0.224 Uiso 0.42 1 calc P B 2
H30F H −0.2234 0.8451 0.4418 0.224 Uiso 0.42 1 calc P B 2
O1L O −1.5549(12) 1.6174(6) 0.7786(6) 0.124(3) Uani 1 1 d . . .
O2L O −1.7419(12) 1.7087(6) 0.6890(7) 0.125(3) Uani 1 1 d . . .
C1L C −1.5569(17) 1.6742(7) 0.7238(8) 0.098(3) Uani 1 1 d . . .
C2L C −1.3365(17) 1.6989(8) 0.6926(9) 0.108(4) Uani 1 1 d . . .
H2L H −1.3065 1.7549 0.7117 0.129 Uiso 1 1 calc . . .
C3L C −1.355(2) 1.6971(12) 0.5917(11) 0.143(5) Uani 1 1 d . . .
H3L1 H −1.2130 1.7162 0.5734 0.214 Uiso 1 1 calc . . .
H3L2 H −1.4813 1.7312 0.5662 0.214 Uiso 1 1 calc . . .
H3L3 H −1.3842 1.6429 0.5706 0.214 Uiso 1 1 calc . . .
O3L O −1.1538(13) 1.6538(7) 0.7316(8) 0.150(4) Uani 1 1 d . . .
H3L H −1.0243 1.6711 0.7191 0.224 Uiso 1 1 d . . .
O1W O −0.448(6) 1.237(6) 1.045(2) 0.45(5) Uani 0.78(6) 1 d P . .
O2W O −0.021(15) 0.8037(17) 0.9990(19) 0.74(7) Uani 1 1 d . . .
O3W O −0.35(3) 0.773(9) 0.953(15) 0.77(8) Uani 0.22(6) 1 d P . .

(84C) Compound (1) L-Lactate—Form FL3

Form FL3 was observed in precipitation experiments of THF solutions of form FL1. Form FL3 transforms in air into form FL1. A saturated solution of form FL1 in THF was prepared at room temperature. Slow precipitation with approximately 4 volumes of heptane gave form FL3. The XRPD pattern of a fresh sample of form FL3 is shown in FIG. 7 and the main peaks are listed in Table EX84C(i) below. A sample of FL3 was dried in air for 2 days after which XRPD analysis showed that conversion to form FL1 had occurred.

TABLE EX84C(ii)

Main XRPD peaks for Compound (1) Lactate salt - form FL3

| 2θ/° | d/Å | I/% |
|---|---|---|
| 5.53 | 15.98 | 100 |
| 8.36 | 10.56 | 5 |
| 11.07 | 7.98 | 41 |
| 13.16 | 6.72 | 12 |
| 13.85 | 6.39 | 8 |
| 16.69 | 5.31 | 39 |
| 17.17 | 5.16 | 21 |
| 18.00 | 4.92 | 49 |
| 18.49 | 4.80 | 11 |
| 19.28 | 4.60 | 14 |
| 19.79 | 4.48 | 5 |
| 20.34 | 4.36 | 7 |
| 21.05 | 4.22 | 21 |
| 21.47 | 4.14 | 7 |
| 21.93 | 4.05 | 4 |
| 22.47 | 3.95 | 16 |
| 22.84 | 3.89 | 23 |
| 24.56 | 3.62 | 4 |
| 26.28 | 3.39 | 6 |
| 27.06 | 3.29 | 3 |
| 27.47 | 3.24 | 3 |
| 29.11 | 3.07 | 6 |

Biological Activity

Example 85

Isothermal Titration Calorimetry

The ability of the compounds for use in the combinations of the invention to bind to human Hsp90 proteins was determined using isothermal titration calorimetry.

Isothermal titration calorimetry (ITC) experiments were performed with a VP-ITC titration calorimeter (Microcal Inc., Northampton, Mass., USA). Cloning, expression, and purification of the Human Hsp90α N-terminal domain were performed according to published methods (Jez, J. M. et al, Chem Biol. 2003 April; 10(4):361-8.) Solutions of the human Hsp90α N-terminal domain and compound were prepared in a buffer comprising 25 mM Tris, 100 mM NaCl, 1 mM $MgCl_2$, 1 mM TCEP, 5% DMSO, pH 7.4. All solutions were filtered and degassed prior to a titration being carried out. The enthalpy change resulting from each injection of ligand was obtained through integration of the calorimetric signal. Data were analysed using Origin 7.0 (Microcal Software Inc., Northampton, Mass.). Heats of dilution were estimated using the final injections of each individual titration and subtracted before data fitting. Different ITC experimental formats were employed in order to obtain compound dissociation constants (Kd's) over a wide range of affinities. For weakly binding compounds a low c-value ITC method was used (Turnbull W. B. & Daranas A. H. J. Am. Chem. Soc. 2003 Dec. 3; 125(48): 14859-66) in which the protein was present at 10-20 µM in the calorimetric cell and the compound concentration was 1-20 mM in the injection syringe. In this type of experiment the stoichiometry parameter (N) was locked at 1 for data fitting. For Kd's in the 20-0.004 µM range the experiment was configured such that the binding site concentration divided by the Kd (c-value) was between 5 and 1000. For the majority of these experiments the protein concentration in the calorimetric cell was in the range 4-100 µM and the ligand concentration in the injection syringe ranged from 50-1500 µM. In rare cases where compound solubility was limiting, the compound solution was placed in the calorimetric cell and titrated with protein from the injection syringe, maintaining a c-value between 5 and 1000. Competition ITC experiments were used to access Kd's <4 nM by performing the titration in the presence of a weaker binding competitor according to the method described in Sigurskjold B. W. Anal Biochem. 2000 Jan. 15; 277(2):260-6.

The compounds of examples 5, 10, 11, 12, 13, 14, 16, 17, 18, 19, 21, 22, 23, 25, 26, 27, 28, 29, 32, 33, 34, 35, 36, 37, 38, 39, 40, 41, 42, 43, 44, 45, 48, 49, 50, 51, 52, 53, 54, 55, 59, 60, 61, 62, 63, 65, 66, 67, 68, 69, 70, 71, 72, 73, 74 and 75 were tested and were found to have $K_d$ values of less than 1 micromolar.

The compounds of examples 5, 10, 12, 13, 14, 16, 17, 18, 19, 21, 22, 23, 25, 26, 27, 28, 29, 32, 33, 34, 35, 36, 37, 38, 39, 40, 41, 42, 43, 44, 45, 48, 49, 50, 51, 53, 54, 55, 59, 60, 61, 62, 63, 65, 66, 67, 68, 69, 70, 71, 72, 73, 74 and 75 have $K_d$ values of less than 0.1 micromolar and most of these compounds have $K_d$ values of less than 0.01 micromolar.

Example 86

Anti-Proliferative Activity

The anti-proliferative activities of compounds for use in the combinations of the invention can be determined by measuring the ability of the compounds to inhibition of cell growth in a number of cell lines such as the human colon cancer cell line HCT116. Inhibition of cell growth is measured using the Alamar Blue assay (Nociari, M. M, Shalev, A., Benias, P., Russo, C. Journal of Immunological Methods 1998, 213, 157-167). The method is based on the ability of viable cells to reduce resazurin to its fluorescent product resorufin. For each proliferation assay cells are plated onto 96 well plates and allowed to recover for 16 hours prior to the addition of inhibitor compounds for a further 72 hours. At the end of the incubation period 10% (v/v) Alamar Blue is added and incubated for a further 6 hours prior to determination of fluorescent product at 535 nM ex/590 nM em. In the case of the non-proliferating cell assay cells are maintained at confluence for 96 hour prior to the addition of inhibitor compounds for a further 72 hours. The number of viable cells is determined by Alamar Blue assay as before. Cell lines can be obtained from the ECACC (European Collection of cell Cultures).

The compounds of examples 5, 12, 13, 14, 17, 18, 19, 21, 22, 23, 25, 28, 29, 32, 33, 34, 35, 36, 37, 38, 39, 40, 41, 42, 43, 45, 48, 49, 50, 51, 52, 53, 54, 55, 59, 60, 61, 62, 63, 65, 66, 67, 68, 69, 70, 71, 72, 74 and 75 were tested and were found to have $IC_{50}$ values of less than 1 micromolar against the HCT116 cell line.

Pharmaceutical Formulations

Example 87

(i) Tablet Formulation

A tablet composition containing a compound of the formula (I) is prepared by mixing 50 mg of the compound with 197 mg of lactose (BP) as diluent, and 3 mg magnesium stearate as a lubricant and compressing to form a tablet in known manner.

(ii) Capsule Formulation

A capsule formulation is prepared by mixing 100 mg of a compound of the formula (I) with 100 mg lactose and filling the resulting mixture into standard opaque hard gelatin capsules.

(iii) Injectable Formulation I

A parenteral composition for administration by injection can be prepared by dissolving a compound of the formula (I) (e.g. in a salt form) in water containing 10% propylene glycol to give a concentration of active compound of 1.5% by weight. The solution is then sterilised by filtration, filled into an ampoule and sealed.

(iv) Injectable Formulation II

A parenteral composition for injection is prepared by dissolving in water a compound of the formula (I) (e.g. in salt form) (2 mg/ml) and mannitol (50 mg/ml), sterile filtering the solution and filling into sealable 1 ml vials or ampoules.

v) Injectable Formulation III

A formulation for i.v. delivery by injection or infusion can be prepared by dissolving the compound of formula (I) (e.g. in a salt form) in water at 20 mg/ml. The vial is then sealed and sterilised by autoclaving.

vi) Injectable Formulation IV

A formulation for i.v. delivery by injection or infusion can be prepared by dissolving the compound of formula (I) (e.g. in a salt form) in water containing a buffer (e.g. 0.2 M acetate pH 4.6) at 20 mg/ml. The vial is then sealed and sterilised by autoclaving.

(vii) Subcutaneous Injection Formulation

A composition for sub-cutaneous administration is prepared by mixing a compound of the formula (I) with pharmaceutical grade corn oil to give a concentration of 5 mg/ml. The composition is sterilised and filled into a suitable container.

viii) Lyophilised Formulation

Aliquots of formulated compound of formula (I) are put into 50 ml vials and lyophilized. During lyophilisation, the compositions are frozen using a one-step freezing protocol at (−45° C.). The temperature is raised to −10° C. for annealing, then lowered to freezing at −45° C., followed by primary drying at +25° C. for approximately 3400 minutes, followed by a secondary drying with increased steps if temperature to 50° C. The pressure during primary and secondary drying is set at 80 millitor.

Compounds are added concurrently for 96 hours. Following a total of 96 hours compound incubation, cells are fixed with ice-cold 10% (w/v) trichloroacetic acid for 1 hour on ice and then washed four times with $dH_2O$ using a plate washer (Labsystems Wellwash Ascent) and air-dried. Cells are then stained with 0.4% (w/v) Sulforhodamine B (Sigma) in 1% acetic acid for 20 min at room temperature and then washed four times with 1% (v/v) acetic acid and air-dried before the addition of 10 mM Tris buffer to solubilise the dye. Colourmetric product is quantified by reading at Abs490 nm on a Wallac Victor$^2$ plate reader (1420 multilabel counter, Perkin Elmer Life Sciences). The $IC_{50}$ for Compound II in the presence of varying doses of Compound I is determined. Synergy is determined when the $IC_{50}$ shifts down in the presence of sub-effective doses of Compound I. Additivity is determined when the response to Compound II and Compound I together results in an effect equivalent to the sum of the two compounds individually. Antagonistic effects are defined as those causing the $IC_{50}$ to shift upwards, i.e. those where the response to the two compounds is less than the sum of the effect of the two compounds individually.

| | Conc | Compound I | | | | | | Compound I | | | | | |
|---|---|---|---|---|---|---|---|---|---|---|---|---|---|
| | | a | b | c | d | e | Control | a | b | c | d | e | Control |
| Compound II | a | | | | | | | | | | | | |
| | b | | | | | | | | | | | | |
| | c | | | | | | | | | | | | |
| | d | | | | | | | | | | | | |
| | e | | | | | | | | | | | | |
| | f | | | | | | | | | | | | |
| | g | | | | | | | | | | | | |
| | Control | | | | | | | | | | | | |

Example 88

Assay for Therapeutic Efficacy

The effect of a compound of formula (I) (Compound I) in combination with one or more ancillary compounds (Compound II) is assessed using the following technique:

$IC_{50}$ Shift Assay

Cells from human cells lines (e.g. HCT116, U87MG, A549) are seeded onto 96-well tissue culture plates at a concentration of $2.5 \times 10^3$, $6.0 \times 10^3$, or $4.0 \times 10^3$ cells/well respectively. Cells are allowed to recover for 48 hours prior to addition of compound(s) or vehicle control (0.35% DMSO) as follows:

Example 89

General Method for the Assessment of the Effect of Combination

The effect of the compound (2,4-dihydroxy-5-isopropyl-phenyl)-[5-(4-methyl-piperazin-1-ylmethyl)-1,3-dihydro-isoindol-2-yl]-methanone ("Compound I") in combination with any ancillary compound (Compounds II-IV) can be assessed using the following technique:

1. Combination Screen Assay

Human colon carcinoma cell line HCT 116 (ECACC No. 91091005) cells are seeded onto 96-well tissue culture plates at a concentration of $2 \times 10^4$ cells/ml and 200 μl per well. Cells are allowed to recover overnight prior to addition of compound(s) or vehicle control (0.2% DMSO) as follows;

|  | 3x IC₅₀ | IC₅₀ | 0.3x IC₅₀ | 3x IC₅₀ | IC₅₀ | 0.3x IC₅₀ | 3x IC₅₀ | IC₅₀ | 0.3x IC₅₀ | DMSO CTLs |
|---|---|---|---|---|---|---|---|---|---|---|
| Compound I 0.3x IC₅₀ | | | | | | | | | | |
| Compound I IC₅₀ | | | | | | | | | | |
| Compound I 3x IC₅₀ | | | | | | | | | | |
|  | Compound II | | | Compound III | | | Compound IV | | | |

Compounds are added according to one of the following schedules;
a) Concurrent for 72 hours.
b) Compound I for 24 hours, followed by the addition of Compound II, III or IV for a further 48 hours.
c) Compound II, III or IV for 24 hours, followed by the addition of Compound I for a further 48 hours.

Following a total of 72 hours compound incubation, Alamar Blue™ is added to a final concentration of 10% (v/v) and incubated at 37° C. for 6 hours. Fluorescent product is quantified by reading at d535/25x (excitation) and d590/20m (emission) on a Fusion Reader (Perkin Elmer).

The fluorescence as a percentage of vehicle control (0.2% DMSO) is determined for cell samples treated with Compound II, III or IV, in the presence of varying concentrations of Compound I. The data are analysed using the method of multiplicity which assumes that each individual agent demonstrates a linear dose response curve. This assumption allows for the generation of a theoretical curve, termed the line of multiplicity, that represents the expected additive response.

Additivity is determined when the response to Compounds II, III or IV and Compound I together resulted in an effect approximately equivalent to the theoretical line of multiplicity calculated from the product of the two compounds individually. Synergy is determined when the observed response to the combined agents is greater than the theoretical line of multiplicity. Antagonism is determined when the observed response to the combined agents is less than the theoretical line of multiplicity.

EQUIVALENTS

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

The invention claimed is:

1. A combination comprising (2,4-dihydroxy-5-isopropyl-phenyl)-[5-(4-methyl-piperazin-1-ylmethyl)-1,3-dihydro-isoindol-2-yl]-methanone or a salt, solvate or tautomer thereof; and an ancillary compound which is 4-(2,6-dichloro-benzoylamino)-1H-pyrazole-3-carboxylic acid piperidin-4-ylamide; or a salt or tautomer or N-oxide or solvate thereof.

2. A combination according to claim 1 wherein the (2,4-dihydroxy-5-isopropyl-phenyl)-[5-(4-methyl-piperazin-1-ylmethyl)-1,3-dihydro-isoindol-2-yl]-methanone is in the form of an L-lactate.

3. A combination according to claim 1 wherein the ancillary compound 4-(2,6-dichloro-benzoylamino)-1H-pyrazole-3-carboxylic acid piperidin-4-ylamide; or salt or tautomer or N-oxide or solvate thereof; and the compound (2,4-dihydroxy-5-isopropyl-phenyl)-[5-(4-methyl-piperazin-1-ylmethyl)-1,3-dihydro-isoindol-2-yl]-methanone or salt, solvate or tautomer thereof are:
(a) physically associated; or
(b) in admixture; or
(c) chemically/physicochemically linked; or
(d) chemically/physicochemically co-packaged; or
(e) unmixed but co-packaged or co-presented.

4. The combination according to claim 1 wherein the ancillary compound is:
i. a methanesulphonic acid salt of 4-(2,6-dichlorobenzoylamino)-1H-pyrazole-3-carboxylic acid piperidin-4-ylamide.

* * * * *